United States Patent
Jo et al.

(10) Patent No.: US 7,074,819 B2
(45) Date of Patent: Jul. 11, 2006

(54) BENZOPYRAN OR THIOBENZOPYRAN DERIVATIVES

(75) Inventors: Jae Chon Jo, Incheon (KR); Hyun Suk Lim, Suwon (KR); Jong Min Kim, Suwon (KR); Ju Su Kim, Ansan (KR); Kazumi Morikawa, Mishima (KR); Yoshitake Kanbe, Gotemba (KR); Myung Hwa Kim, Gotemba (KR); Masahiro Nishimoto, Mishima (KR)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 427 days.

(21) Appl. No.: 10/640,696

(22) Filed: Aug. 12, 2003

(65) Prior Publication Data

US 2004/0102479 A1    May 27, 2004

Related U.S. Application Data

(62) Division of application No. 09/719,608, filed as application No. PCT/KR99/00300 on Jun. 14, 1999, now Pat. No. 6,645,951.

(30) Foreign Application Priority Data

Jun. 13, 1998  (KR) ............................... 1998/22212

(51) Int. Cl.
*A61K 31/38* (2006.01)
*C07D 335/04* (2006.01)

(52) U.S. Cl. .......................................... 514/432; 549/23
(58) Field of Classification Search ................ 514/432; 549/23
See application file for complete search history.

(56) References Cited

U.S. PATENT DOCUMENTS

| 3,535,344 | A |  | 10/1970 | Irmscher et al. |
|---|---|---|---|---|
| 3,755,372 | A |  | 8/1973 | Irmscher et al. |
| 4,376,123 | A |  | 3/1983 | Hausberg et al. |
| 4,508,732 | A |  | 4/1985 | Hausberg et al. |
| 4,780,478 | A |  | 10/1988 | Hausberg et al. |
| 5,919,817 | A |  | 7/1999 | Jacobsen et al. |
| 5,985,306 | A |  | 11/1999 | Jacobsen et al. |
| 6,005,003 | A |  | 12/1999 | Nique |
| 6,043,269 | A |  | 3/2000 | Jacobsen et al. |
| 6,316,494 | B1 |  | 11/2001 | Jacobsen et al. |
| 6,677,460 | B1 | * | 1/2004 | Nakamura et al. ....... 548/364.4 |
| 6,680,332 | B1 | * | 1/2004 | Konkoy et al. ............. 514/337 |
| 6,806,288 | B1 | * | 10/2004 | Hartman et al. ............ 514/434 |
| 6,812,225 | B1 | * | 11/2004 | Pierson et al. ............. 514/183 |
| 6,916,831 | B1 | * | 7/2005 | Lee et al. ................... 514/320 |
| 2001/0046489 | A1 |  | 11/2001 | Habener et al. |

FOREIGN PATENT DOCUMENTS

| DE | 29 50 135 | 6/1981 |
|---|---|---|
| JP | 60-178815 | 9/1985 |
| WO | WO 95/03293 | 2/1995 |

OTHER PUBLICATIONS

C. Pelissero et al., "The Estrogenic Activity of Certain Phytoestrogens in the Siberian Sturgeon," J. Steroid Biochem. Mol. Biol. 1991, pp. 293-299.
H. Llyod Davies et al., "The Effects of Diet on the Metabolism in Sheep of the Tritiated Isoflavones Formononetin and Biochanin A," Aust. J. Agric. Res., 1990, pp. 157-163.
C. Deschamps-Vallet et al., "Tetrahedron Letters," 1984, pp. 3993-3996.
H. Meier et al., "Cycloaddition von Benzothiet an 4- substitute Styrole," Chem. Ber., 1989, pp. 1545-1550.
A. Arnoldi et al., "A Simple Synthesis of 2-Substituted 1-Benzothiophenes and 3-Substituted 2H-1-Benzothiophenes," pp. 119-123, 1988.
D. Gopel et al., "A Novel two-step Synthesis of 3-Phenly-2H-1-benzopyrans," Indian J. Chem., Sect. B, 1987, p. 401.
C. Burali et al., "Synthesis and anti-rhinovirus activity of halogen-substituted isoflavenes and isoflavans," Eur. J. Med. Chem., 1987, pp. 119-123.

(Continued)

*Primary Examiner*—Deborah C. Lambkin
(74) *Attorney, Agent, or Firm*—Peter F. Corless; John B. Alexander; Edwards Angell Palmer & Dodge LLP

(57) ABSTRACT

The present invention relates to a novel benzopyran or thiobenzopyran derivative represented by formula (1): pharmaceutically acceptable salt or stereoisomer thereof, in which X, $R_1$, $R_2$, $R_3$, $R_4$ and A are defined as described in the specification, and to a process for preparation thereof and a pharmaceutical composition having anti-estrogenic activity which contains the compound (1) as an active component.

13 Claims, No Drawings

OTHER PUBLICATIONS

F.M. Dean et al., "The Enamine Route to 2-Morpholinoisoflav-3-ene," J. Chem. Soc. PErkin Trans. 1, 1982, pp. 1193-1196.

3,4-dihydro-3-phenyl-2H-1-benzopyran-7-ol, sodium salt C.A. No. 79131-01-4, 1991.

* cited by examiner

BENZOPYRAN OR THIOBENZOPYRAN DERIVATIVES

This application is a division of application Ser. No. 09/719,608, filed Jul. 16, 2001, now U.S. Pat. No. 6,645,951, which is a 371 of PCT/KR99/00300, filed Jun. 14, 1999.

TECHNICAL FIELD

The present invention relates to a novel benzopyran or thiobenzopyran derivative having anti-estrogenic activity. More specifically, the present invention relates to a novel benzopyran or thiobenzopyran derivative represented by the following formula (1):

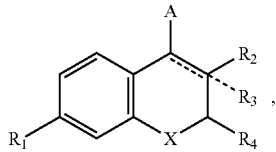

(1)

pharmaceutically acceptable salt or stereoisomer thereof, in which

X represents O or S, $R_1$ represents hydrogen, hydroxy, or —$OR_6$ (wherein $R_6$ represents acyl or alkyl), $R_2$ represents phenyl which is optionally substituted by one or more substituents selected from a group consisting of hydroxy, lower alkyl, halogen, nitro, hydroxymethyl, carboxy, alkoxycarbonyl, —$OR_6$ (wherein $R_6$ represents acyl or alkyl) and amino which is optionally substituted by one or two lower alkyl; or represents 5- or 6-membered unsaturated heterocycle containing nitrogen, oxygen or sulfur as the hetero atom, $R_3$ represents hydrogen or lower alkyl, provided that $R_3$ does not exist when ----- is a double bond (wherein ----- represents a single bond or a double bond), $R_4$ represents hydrogen or lower alkyl, A represents hydrogen; hydroxyalkyl; carboxyalkyl; carboxyvinylphenyl; pyrrole substituted by carboxyvinylbenzyl; or represents a group selected from the following formulae (a) to (l);

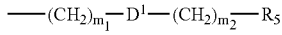
(a)

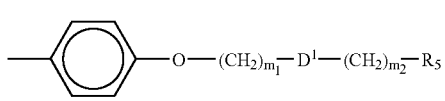
(b)

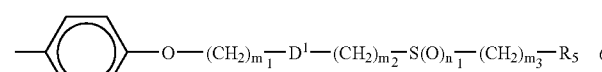
(c)

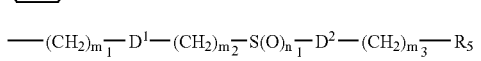
(d)

(e)

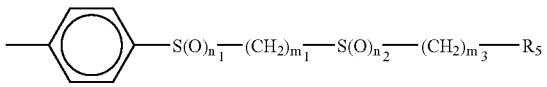
(f)

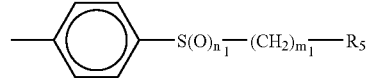
(g)

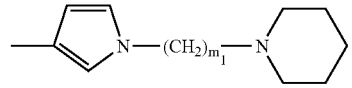
(h)

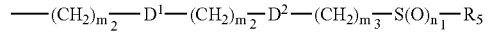
(i)

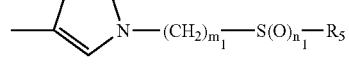
(j)

(k)

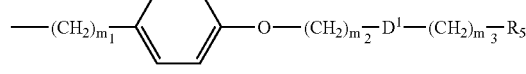
(l)

in the above formulae (a) to (l)

$m_1$ to $m_3$ independently of one another represent an integer of 0 to 15, $n_1$ to $n_2$ independently of one another represent an integer of 0, 1 or 2, $R_5$ represents cyano; alkyl; halogenoalkyl; alkoxy; hydroxy; carboxy; alkoxycarbonyl; carbamoyl; monoalkylamino; phenyl which is optionally substituted by one or more substituents selected from a group consisting of straight-chain or branched alkyl, carboxy and cyano; piperidinyl which is optionally substituted by one or more substituents selected from a group consisting of carboxy, alkyl and alkoxycarbonyl; cyclohexyl which is optionally substituted by carboxy; imidazolyl; dialkylamino; or piperidinyl oxide, $D^1$ and $D^2$ independently of one another represent a direct bond, or a group selected from the following:

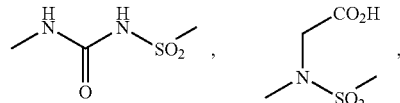

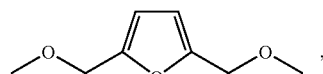

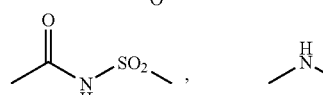

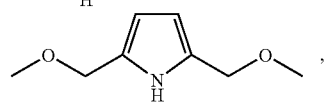

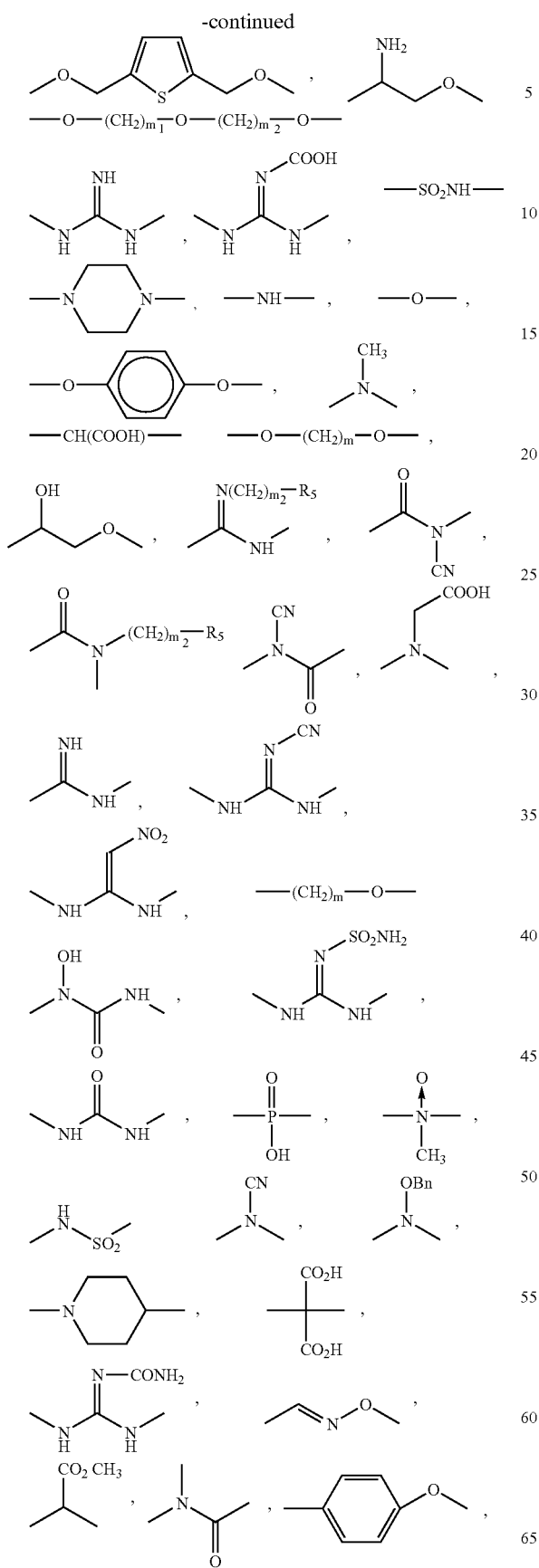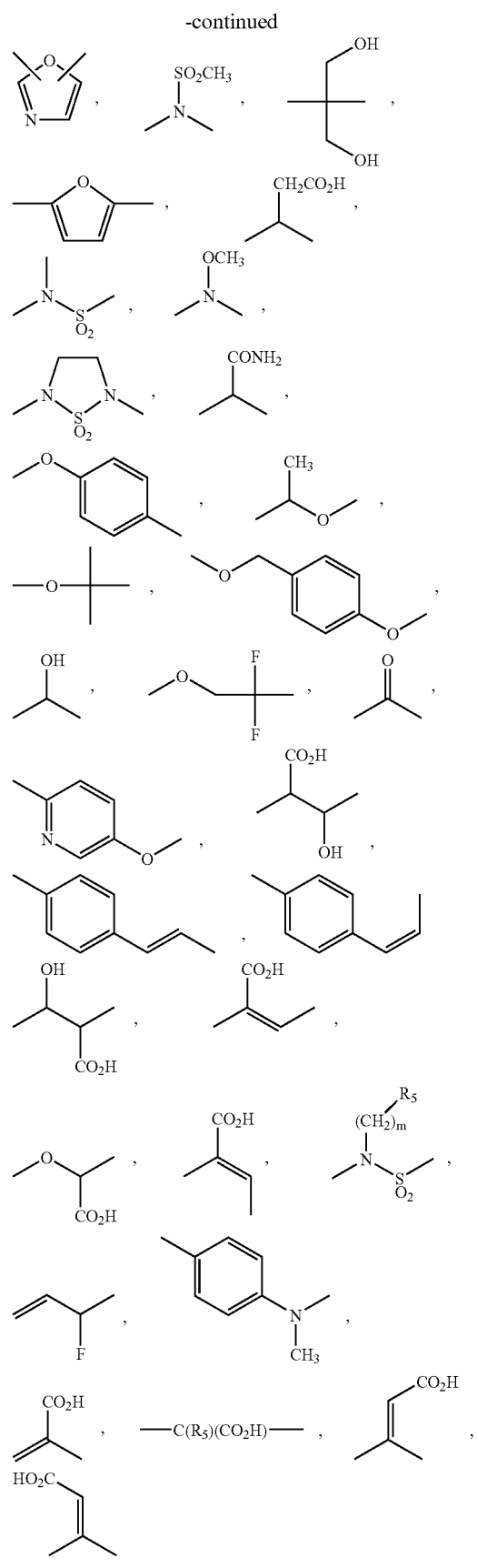

wherein m, $m_1$ and $m_2$ independently of one another represent an integer of 0 to 15, and $R_5$ is defined as previously described, and to a process for preparation thereof and a pharmaceutical composition having anti-estrogenic activity which contains the compound (1) as an active component.

BACKGROUND ART

In treating diseases caused by the abnormal tissue growth depending on a certain sexual steroidal hormone such as estrogen, it is very important to significantly inhibit, if possible, to completely remove the effect induced by said sexual steroidal hormone. For this purpose, it is desirable to block the receptor site which can be stimulated by sexual steroidal hormone and further, to reduce the level of sexual steroidal hormone capable of acting on said receptor site. For instance, as a substitution or combined therapy, administration of anti-estrogenic agents to limit the production of estrogen to the amount less than required to activate the receptor site may be used. However, prior methods for blocking the estrogen production could not sufficiently inhibit the effect induced through estrogen receptor. Practically, even when estrogen is completely absent, some of the receptors may be activated. Accordingly, it was considered that antagonists for estrogen can provide better therapeutic effect in comparison to the method for blocking only the production of sexual steroidal hormone. Thus, numerous anti-estrogenic compounds have been developed. For example, many patent publications including U.S. Pat. Nos. 4,760,061, 4,732,912, 4,904,661, 5,395,842 and WO 96/22092, etc. disclose various anti-estrogenic compounds. However, prior antagonists have sometimes insufficient affinity to the receptors. In some cases, moreover, they can combine to the receptor but act themselves as agonists, and therefore, activate rather than block the receptor. For example, Tamoxifen has been most widely used as an anti-estrogenic agent. However, it has a disadvantage that it exhibits estrogenic activity in some organs (see, M. Harper and A. Walpole, J. Reprod. Fertil., 1967, 13, 101). Therefore, it is required to develop the anti-estrogenic compound which has substantially or completely no agonistic effect and can effectively block the estrogenic receptor.

In addition, it has been known that 7α-substituted derivatives of estradiol, for example, 7α-$(CH_2)_{10}$CONMeBu derivative, exhibit anti-estrogenic activity (see, EP Appl. 0138504, U.S. Pat. No. 4,659,516). Further, estradiol derivative having —$(CH_2)_9SOC_5H_6F_5$ substituent has also been disclosed (see, Wakeling et al., Cancer Res., 1991, 51, 3867) as steroidal anti-estrogenic agent without agonistic effect.

Non-steroidal anti-estrogenic drug without agonistic effect has been first reported by Wakeling et al. in 1987 (see, A. Wakeling and J. Bowler, J. Endocrinol., 1987, 112, R7). Meanwhile, U.S. Pat. No. 4,904,661 (ICI, Great Britain) discloses a phenol derivative having anti-estrogenic activity. This phenol derivative generally has a tetrahydronaphthalene structure and includes, typically, the following compounds:

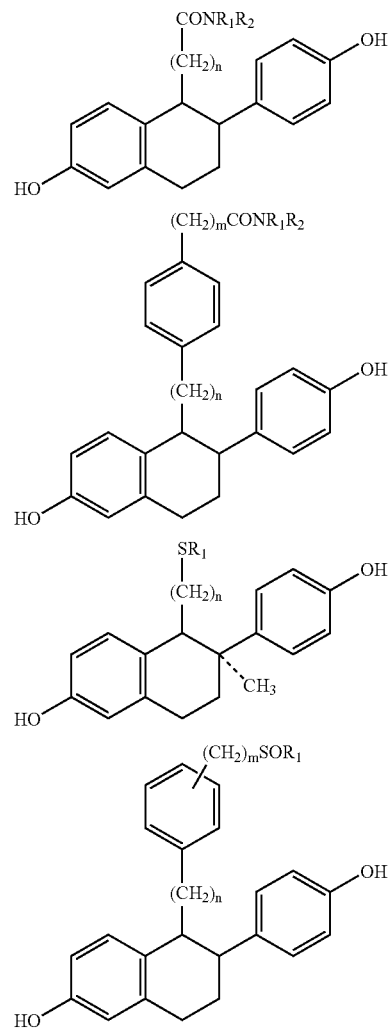

As other non-steroidal anti-estrogenic compounds, WO 93/10741 discloses a benzopyran derivative having amino-ethoxyphenyl substituent (Endorecherche), of which the typical compound is EM-343 having the following structure:

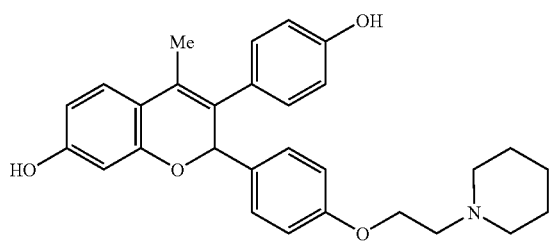

Accordingly, the present inventors have researched the anti-estrogenic activity of compounds having various structures. As a result, we have identified that the benzopyran or thiobenzopyran derivatives represented by formula (1), as defined above, can exhibit a good anti-estrogenic activity without agonistic activity, to be expected no undesirable side effect and thus, completed the present invention.

DISCLOSURE OF THE INVENTION

Therefore, the present invention relates to a novel benzopyran or thiobenzopyran derivative represented by the following formula (1):

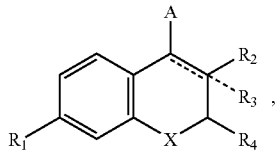
(1)

pharmaceutically acceptable salt or stereoisomer thereof, in which

X represents O or S, $R_1$ represents hydrogen, hydroxy, or —$OR_6$ (wherein $R_6$ represents acyl or alkyl), $R_2$ represents phenyl which is optionally substituted by one or more substituents selected from a group consisting of hydroxy, lower alkyl, halogen, nitro, hydroxymethyl, carboxy, alkoxycarbonyl, —$OR_6$ (wherein $R_6$ represents acyl or alkyl) and amino which is optionally substituted by one or two lower alkyl; or represents 5- or 6-membered unsaturated heterocycle containing nitrogen, oxygen or sulfur as the hetero atom, $R_3$ represents hydrogen or lower alkyl, provided that $R_3$ does not exist when ----- is a double bond (wherein ----- represents a single bond or a double bond), $R_4$ represents hydrogen or lower alkyl, A represents hydrogen; hydroxyalkyl; carboxyalkyl; carboxyvinylphenyl; pyrrole substituted by carboxyvinylbenzyl; or represents a group selected from the following formulae (a) to (l);

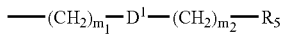
(a)

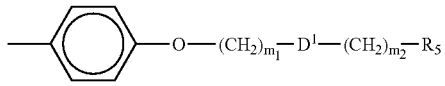
(b)

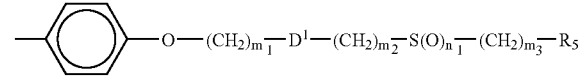
(c)

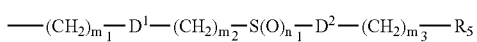
(d)

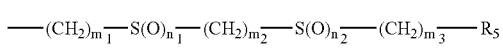
(e)

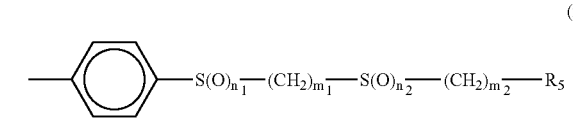
(f)

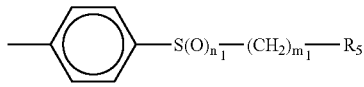
(g)

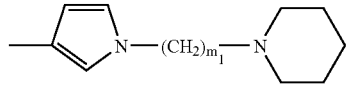
(h)

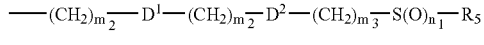
(i)

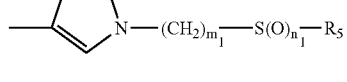
(j)

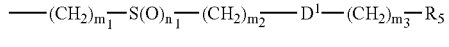
(k)

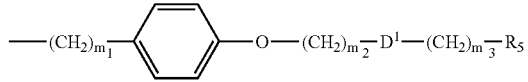
(l)

in the above formulae (a) to (l)

$m_1$ to $m_3$ independently of one another represent an integer of 0 to 15, $n_1$ to $n_2$ independently of one another represent an integer of 0, 1 or 2, $R_5$ represents cyano; alkyl; halogenoalkyl; alkoxy; hydroxy; carboxy; alkoxycarbonyl; carbamoyl; monoalkylamino; phenyl which is optionally substituted by one or more substituents selected from a group consisting of straight-chain or branched alkyl, carboxy and cyano; piperidinyl which is optionally substituted by one or more substituents selected from a group consisting of carboxy, alkyl and alkoxycarbonyl; cyclohexyl which is optionally substituted by carboxy; imidazolyl; dialkylamino; or piperidinyl oxide, $D^1$ and $D^2$ independently of one another represent a direct bond, or a group selected from the following:

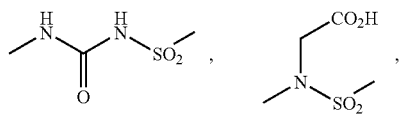

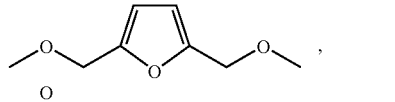

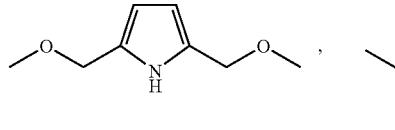

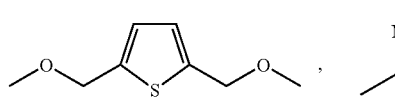

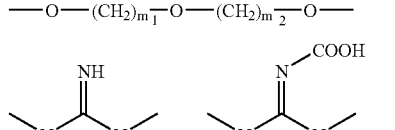

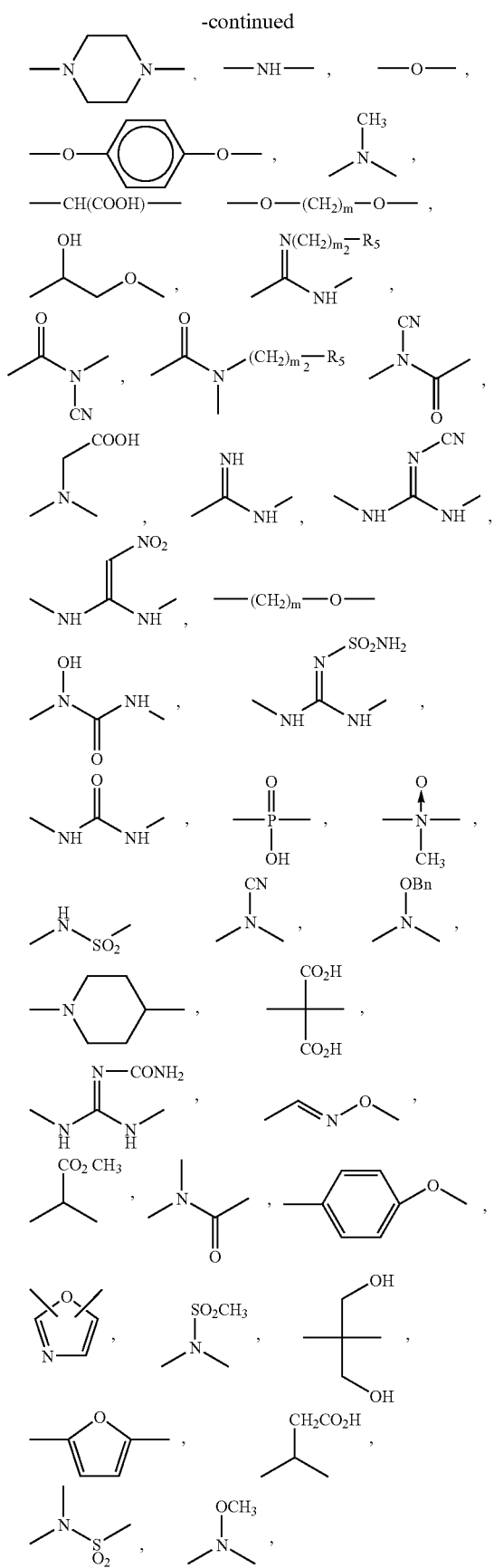
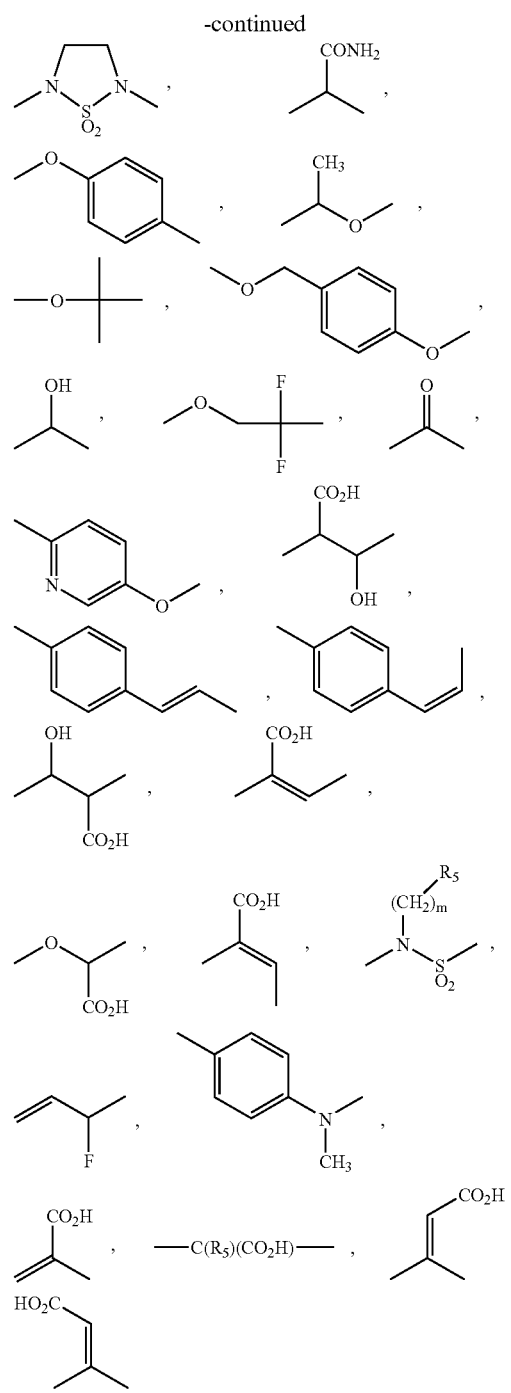

wherein m, $m_1$ and $m_2$ independently of one another represent an integer of 0 to 15, and $R_5$ is defined as previously described.

In addition, the present invention also relates to processes for preparing the benzopyran or thiobenzopyran derivative of formula (1).

Further, the present invention relates to a pharmaceutical composition having anti-estrogenic activity, which contains the compound of formula (1) as an active component.

BEST MODE FOR CARRYING OUT THE INVENTION

In the present specification, the term "lower alkyl" denotes straight-chain or branched saturated hydrocarbon radicals having 1 to 6, preferable 1 to 4, carbon aoms; the term "halogenoalkyl" denotes straight-chain or branched saturated hydrocarbon radicals having halogen atoms such as fluorine, chlorine, bromine, etc., preferably fluorine atom; and the term "alkyl" denotes straight-chain or branched saturated hydrocarbon radicals having 1 to 12 carbon atoms including lower alkyl as defined above.

The compound of formula (1) according to the present invention can form a pharmaceutically acceptable salt. Such salt includes a salt with pharmaceutically acceptable acids such as asparagic acid, gluconic acid, hydrochloric acid, p-toluenesulfonic acid or citric acid, etc., a salt with bases such as pyridine or ammonia, etc., and a salt with acids or bases which are generally known and conventionally used in the technical field to which the benzopyran or thiobenzopyran derivative pertains. These pharmaceutically acceptable salts can be prepared according to a conventional conversion method.

In the compound of formula (1) wherein the bond between 3- and 4-positions of benzopyran or thiobenzopyran ring is a single bond, the two carbon atoms of 3- and 4-positions of the ring can be asymmetric, and thus the compound of formula (1) can exist as a pure stereoisomer such as enantiomer of R or S, diastereomer, etc., or a mixture thereof including racemate. Therefore, the present invention also includes each of these stereoisomers and their mixtures.

Among the novel compound of formula (1) according to the present invention, the preferred compounds include those wherein X represents O or S,
$R_1$ represents hydroxy,
$R_2$ represents phenyl which is optionally substituted by one or more substituents selected from a group consisting of hydroxy, lower alkyl and halogen; or represents 6-membered unsaturated heterocycle containing nitrogen as the hetero atom,
$R_3$ represents lower alkyl, provided that $R_3$ does not exist when ----- is a double bond,
$R_4$ represents hydrogen,
A represents a group selected from the following formulae (a) to (e), (k) and (l);

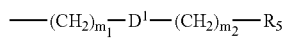 (a)

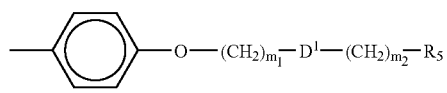 (b)

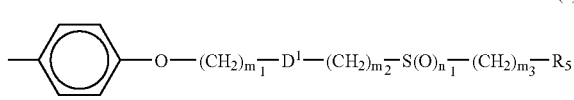 (c)

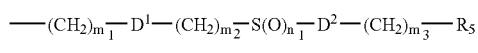 (d)

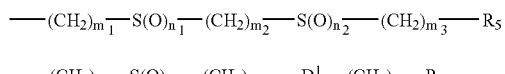 (e)

—(CH₂)$_{m_1}$—S(O)$_{n_1}$—(CH₂)$_{m_2}$—S(O)$_{n_2}$—(CH₂)$_{m_3}$—R₅ (k)

—(CH₂)$_{m_1}$—S(O)$_{n_1}$—(CH₂)$_{m_2}$—D¹—(CH₂)$_{m_3}$—R₅

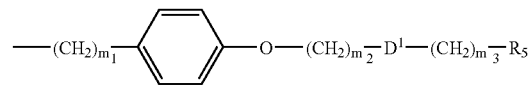 (l)

in the above formulae (a) to (e), (k) and (l)
$m_1$ to $m_3$ independently of one another represent an integer of 0 to 15,
$n_1$ to $n_2$ independently of one another represent an integer of 0, 1 or 2,
$R_5$ represents alkyl; halogenoalkyl; alkoxy; hydroxy; carboxy; phenyl which is optionally substituted by one or two straight-chain or branched alkyl; or dialkylamino,
$D^1$ and $D^2$ independently of one another represent a direct bond, or a group selected from the following:

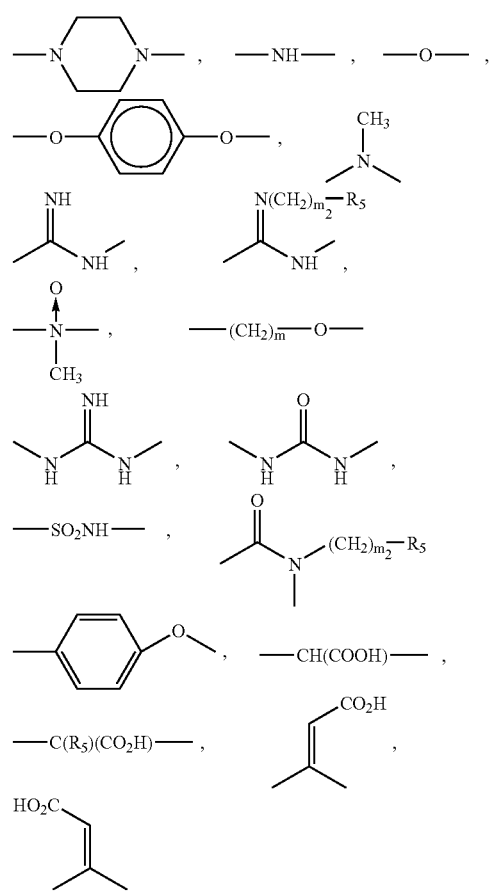

wherein
$m_1$ and $m_2$ independently of one another represent an integer of 0 to 15, and
$R_5$ is defined as previously described.

As specific example of the compound of formula (1) according to the present invention, the following compounds can be mentioned.

7-hydroxy-3-(4-hydroxyphenyl)-3-methyl-4-{9-[4-(4,4,5,5,5-pentafluoropentyl)piperazinyl]nonyl}chroman;

(3RS,4RS)-7-hydroxy-4-[(11-imino-11-N-butylamino)undecyl]-3-(4-hydroxyphenyl)-3-methylchroman;

(3RS,4RS)-7-hydroxy-4-[(11-N-butylimino-11-N-butylamino)undecyl]-3-(4-hydroxyphenyl)-3-methylchroman;

(3RS,4SR)-7-hydroxy-4-{4-{2-{4-{[3,5-bis(t-butyl)phenyl]methyl}piperazinyl}ethoxy}-phenyl}-3-(4-hydroxyphenyl)-3-methylchroman;

(3RS,4RS)-7-hydroxy-3-(4-hydroxyphenyl)-4-{5-[N-methyl-N-3-(4,4,5,5,5-pentafluoropentylthio)-propylamino]pentyl}-3-methylchroman;

4-{4-{2-[2-(4,4,5,5,5-pentafluoropentylsulfinyl)ethoxy]ethoxy}phenyl}-7-hydroxy-3-(4-hydroxyphenyl)-2H-chromene;

(3RS,4RS)-4-[9-(3-dimethylaminopropylsulfinyl)nonyl]-7-hydroxy-3-(4-hydroxyphenyl)-3-methylthiochroman;

(3RS,4RS)-4-[9-(N-4,4,5,5,5-pentafluoropentylaminosulfonylamino)nonyl]-7-hydroxy-3-(4-hydroxyphenyl)-3-methylchroman;

6-{(3RS,4RS)-{9-[7-hydroxy-3-(4-hydroxyphenyl)-3-methylthiochroman-4-yl]nonylsulfinyl}hexanoic acid;

(3RS,4RS)-7-hydroxy-3-(4-hydroxyphenyl)-3-methyl-4-{9-[2-(2-methoxyethoxy)ethylsulfinyl]nonyl}thiochroman;

(3RS,4RS)-7-hydroxy-3-(4-hydroxyphenyl)-3-methyl-4-{9-[2-(2-hydroxyethoxy)ethylsulfinyl]nonyl}thiochroman;

(3RS,4RS)-7-hydroxy-3-(2-methylphenyl)-3-methyl-4-[9-(4,4,5,5,5-pentafluoropentyl)sulfinylnonyl]thiochroman;

(3RS,4RS)-7-hydroxy-3-methyl-4-[9-(4,4,5,5,5-pentafluoropentylsulfinyl)nonyl]-3-(4-pyridyl)chroman;

(3RS,4RS)-7-hydroxy-3-(4-hydroxyphenyl)-3-methyl-4-[9-(4,4,5,5,5-pentafluoropentylsulfonylamino)nonyl]thiochroman;

(3RS,4RS)-3-(4-fluorophenyl)-7-hydroxy-3-methyl-4-[9-(4,4,5,5,5-pentafluoropentylsulfinyl)nonyl]thiochroman;

(3RS,4RS)-3-(3-fluorophenyl)-7-hydroxy-3-methyl-4-[9-(4,4,5,5,5-pentafluoropentylsulfinyl)nonyl]thiochroman;

(3RS,4RS)-7-hydroxy-3-(4-hydroxyphenyl)-3-methyl-4-{3-[N-5-(4,4,5,5,5-pentafluoropentylsulfinyl)pentylamino]propyl}chroman;

(3RS,4RS)-7-hydroxy-3-(4-hydroxyphenyl)-3-methyl-4-[9-(N-methyl-N-4,4,5,5,5-pentafluoropentyl)aminononyl]chroman;

N-methyl-N-(4,4,5,5,5-pentafluoropentyl)-9-[(3RS,4RS)-7-hydroxy-3-(4-hydroxyphenyl)-3-methylchroman-4-yl]nonylamine N-oxide;

(3RS,4RS)-7-hydroxy-3-(4-hydroxyphenyl)-3-methyl-4-{3-{4-[2-(4,4,5,5,5-pentafluoropentylsulfinyl)ethoxy]phenoxy}propyl}thiochroman;

(3RS,4RS)-7-hydroxy-3-(4-hydroxyphenyl)-3-methyl-4-[4-oxa-9-(4,4,5,5,5-pentafluoropentylsulfinyl)nonyl]thiochroman;

(3RS,4RS)-7-hydroxy-3-(4-hydroxyphenyl)-3-methyl-4-[9-(4,4,5,5,5-pentafluoropentylaminosulfonyl)nonyl]chroman;

(3'RS,4'RS)-10-[7-hydroxy-3-(4-hydroxyphenyl)-3-methylthiochroman-4-yl]-2-(4,4,5,5,5-pentafluoropentyl)decanoic acid;

(3'RS,4'RS)-{8-[7-hydroxy-3-(4-hyroxyphenyl)-3-methylthiochroman-4-yl]octyl}-(4,4,5,5,5-pentafluoropentyl)methane-1,1-dicarboxylic acid;

methyl-(3'RS,4'RS)-10-[7-hydroxy-3-(4-hydroxyphenyl)-3-methylthiochroman-4-yl]-2-(4,4,5,5,5-pentafluoropentyl)decanoate;

(3'RS,4'RS)-2-{8-[7-hydroxy-3-(4-hydroxyphenyl)-3-methylthiochroman-4-yl]octyl}-2-(4,4,5,5,5-pentafluoropentyl)propane-1,3-diol;

(3RS,4RS)-7-hydroxy-3-(4-hydroxyphenyl)-3-methyl-4-(9-(2-aza-2-carbonyl-1-(4,4,5,5,5-pentafluoropentylamino)ethenyl)aminononyl)thiochroman;

(3RS,4RS)-7-hydroxy-3-(4-hydroxyphenyl)-3-methyl-4-(9-(1-((4,4,5,5,5-pentafluoropentyl)amino)-2-nitroethenyl)amino)nonyl)thiochroman;

(3RS,4RS)-7-hydroxy-3-(4-hydroxyphenyl)-3-methyl-4-[8-(4,4,5,5,5-pentafluoropentylsulfonylamino)octyl]chroman;

(3RS,4RS)-7-hydroxy-3-(4-(hydroxyphenyl)-3-methyl-4-[4-(4-piperidyl-butyloxy)phenyl]chroman;

(3RS,4RS)-7-hydroxy-3-methyl-3-(4-hydroxyphenyl)-4-(4-(3-(2-(4,4,5,5,5-pentafluoropentylsulfinyl)ethoxy)-(R)-2-hydroxypropyloxy)phenyl)chroman;

(3RS,4RS)-7-hydroxy-3-(4-hydroxyphenyl)-3-methyl-4-{[4-(4,4,5,5,5-pentafluoropentylsulfinyl)butyloxy]butyl}chroman;

(3RS,4RS)-7-hydroxy-3-(4-hydroxyphenyl)-3-methyl-4-{5-{N-methyl-N-[3-(4,4,5,5,5-pentafluoropentyl)sulfiny]propyl}aminopentyl}chroman;

(3RS,4RS)-7-hydroxy-3-(4-hydroxyphenyl)-3-methyl-4-{5-{N-methyl-N-oxo-N-[3-(4,4,5,5,5-pentafluoropentyl)sulfiny]propyl}aminopentyl}chroman;

(3'RS,4'RS)-2-(4-(7-hydroxy)-3-(4-hydroxyphenyl)-3-methylchroman-4-yl)butyl-6-(4-(4,4,5,5,5-pentafluoropentyl)sulfinyl)hexanoic acid;

(3RS,4RS)-7-hydroxy-3-(4-hydroxyphenyl)-3-methyl-4-[9-(N-cyano-N-pentylcarbonyl)aminononyl]thiochroman;

(3RS,4RS)-7-hydroxy-3-(4-(hydroxyphenyl)-3-methyl-4-[5-oxa-9-(4,4,5,5,5-pentafluoropentylsulfonylamino)nonyl]chroman;

(3'RS,4'RS)-6,6,7,7,7-pentafluoro-2-(2-(4-(4-(7-hydroxy-3-(4-hydroxyphenyl)-3-methylchroman-4-yl)butyl)phenyloxy)ethyl)heptanoic acid;

(3RS,4RS)-4-allyl-7-methoxy-3-(4-methoxyphenyl)-3-methylthiochroman;

(3RS,4RS)-7-hydroxy-3-(4-hydroxyphenyl)-3-methyl-4-{9-[2-(2,2,2-trifluoroethoxy)ethylsulfinyl]nonyl}thiochroman;

(3'RS,4'RS)-8-[7-hydroxy-3-(4-hydroxyphenyl)-3-methylthiochroman-4-yl]octanoic acid;

(3'RS,4'RS)-6-[7-hydroxy-3-(4-hydroxyphenyl)-3-methylthiochroman-4-yl]hexanoic acid;

(3'RS,4'RS)-7-[7-hydroxy-3-(4-hydroxyphenyl)-3-methylthiochroman-4-yl]heptanoic acid;

(3RS,4RS)-4-[4,7-dioxa-9-(4,4,5,5,5-pentafluoropentylsulfinyl)nonyl]-7-hydroxy-3-(4-hydroxyphenyl)-3-methylthiochroman;

(3RS,4RS)-7-hydroxy-3-(4-hydroxyphenyl)-3-methyl-4-[6-oxa-9-(4,4,5,5,5-pentafluoropentylsulfinyl)nonyl]thiochroman;

(3RS,4RS)-7-hydroxy-3-(4-hydroxyphenyl)-3-methyl-4-[7-oxa-9-(4,4,5,5,5-pentafluoropentylsulfinyl)nonyl]thiochroman;

(3RS,4RS)-7-hydroxy-3-(4-hydroxyphenyl)-3-methyl-4-[5-oxa-9-(4,4,5,5,5-pentafluoropentylsulfinyl)nonyl]thiochroman;

(3'RS,4'RS)-9-[7-hydroxy-3-(4-hydroxyphenyl)-3-methylthiochroman-4-yl]nonanoic acid;

(3'RS,4'RS)-10-[7-hydroxy-3-(4-hydroxyphenyl)-3-methylthiochroman-4-yl]decanoic acid;

(E)-3-[7-hydroxy-3-(4-hydoxyphenyl)-2H-chromen-4-yl]phenylacrylic acid;

(3'RS,4'RS)-(E)-3-[7-hydroxy-3-(4-hydoxyphenyl)thiochroman-4-yl]phenylacrylic acid;

(3RS,4RS)-4-[9-(4-cyanobutylsulfinyl)nonyl]-7-hydroxy-3-(4-hydroxyphenyl)-3-methylthiochroman;

(3'RS,4'RS)-4-{7-hydroxy-3-methyl-4-[9-(4,4,5,5,5-pentafluoropentylsulfinyl)nonyl]chroman-3-yl}benzoic acid;

(3'RS,4'RS)-4-{7-hydroxy-3-methyl-4-[9-(4,4,5,5,5-pentafluoropentylsulfinyl)nonyl]chroman-3-yl}benzyl alcohol;

(3RS,4RS)-7-hydroxy-3-(4-hydroxyphenyl)-3-methyl-4-{3-[3-(4,4,5,5,5-pentafluoropentylsulfinyl)propylphenoxy]-1-propyl}chroman;

(3RS,4RS)-7-hydroxy-3-(4-hydroxyphenyl)-3-methyl-4-{3-[3-(4,4,5,5,5-pentafluoropentylsulfonyl)propylphenoxy]-1-propyl}chroman;

(3RS,4RS)-7-hydroxy-3-(4-hydroxyphenyl)-3-methyl-4-{4-[4-(4,4,5,5,5-pentafluoropentylsulfinylethyloxy)phenyl]-1-butyl}chroman;

(3RS,4RS)-7-hydroxy-3-(4-hydroxyphenyl)-3-methyl-4-{4-[4-(4,4,5,5,5-pentafluoropentylsulfonyl-ethyloxy)phenyl]-1-butyl}chroman;

(3'RS,4'RS)-1-[7-hydroxy-4-(4-hydroxyphenyl)-3-methylchroman-4-yl]-14,14,15,15,15-pentafluoropentadecan-10-ol;

(3RS,4RS)-7-hydroxy-3-methyl-4-[9-(4,4,5,5,5-pentafluoropentylsulfinyl)nonyl]-3-(3-pyridyl)chroman;

(3RS,4RS)-7-hydroxy-3-(4-hydroxyphenyl)-4-[9-(4,4,5,5,5-pentafluoropentylsulfinyl)nonyl]chroman;

(3RS,4RS)-7-hydroxy-3-(4-hydroxyphenyl)-4-(9-oxo-14,14,15,15,15-pentafluoro)pentadecyl-3-methylchroman;

(3RS,4RS)-7-hydroxy-3-(4-hydroxyphenyl)-4-(9-hydroxy-10-hydroxycarbonyl-14,14,15,15,15-pentafluoro)pentadecyl-3-methylchroman;

(3RS,4RS)-7-hydroxy-4-[(10-ethoxycarbonyl-14,14,15,15,15-pentafluoro)pentadec-9-enyl]-3-(4-hydroxyphenyl)-3-methylchroman;

1,1,1,2,2-pentafluoro-14-[(3RS,4RS)-7-hydroxy-3-(4-hydroxyphenyl)-3-methylchroman-4-yl]-5-pentadecanone;

(E)-6,6,7,7,7-pentafluoro-2-{9-[(3RS,4RS)-7-hydroxy-3-(4-hydroxyphenyl)-3-methylchroman-4-yl]nonyl}-2-heptenoic acid;

(3RS,4RS)-7-hydroxy-3-(4-hydroxyphenyl)-3-methyl-4-[9-(4,4,5,5,5-pentafluoropentylsulfonylamino)nonyl]chroman;

(3RS,4RS)-(E)-3-{4-[7-hydroxy-3-(4-hydroxyphenyl)thiochroman-4-yl]phenyl}propenoic acid (3RS,4RS)-(E)-3-{4-[7-hydroxy-3-(4-hydroxyphenyl)thiochroman-4-yl]phenyl}propenoic acid (3'RS,4'RS)-(E)-3-{4-[7-hydroxy-3-(4-hydroxyphenyl)-3-methylthiochroman-4-yl]phenyl}propenoic acid (3'RS,4'RS)-N-[2-(4,4,5,5,5-pentafluoropentylsulfinyl)]ethyl-4-{4-[7-hydroxy-3-(4-hydryoxyphenyl)-3-methylchroman-4-yl]butyl}phenyl-N-methylamino;

6-{4-[(3RS,4RS)-7-hydroxy-3-(4-hydroxyphenyl)-3-methylchroman-4-yl]phenoxy}-2-(4,4,5,5,5-pentafluoropentyl)hexanoic acid;

7-{4-[(3RS,4RS)-7-hydroxy-3-(4-hydroxyphenyl)-3-methylchroman-4-yl]phenoxy}-2-(4,4,5,5,5-pentafluoropentyl)heptanoic acid;

8-{4-[(3RS,4RS)-7-hydroxy-3-(4-hydroxyphenyl)-3-methylchroman-4-yl]phenoxy}-2-(4,4,5,5,5-pentafluoropentyl)octanoic acid;

9-{4-[(3RS,4RS)-7-hydroxy-3-(4-hydroxyphenyl)-3-methylchroman-4-yl]phenoxy}-2-(4,4,5,5,5-pentafluoropentyl)nonanoic acid;

(3RS,4RS)-9-(7-hydroxy-3-(4-hydroxyphenyl)-3-methylchroman-4-yl-2-(4,4,5,5,5-pentafluoropentyl)nonanoic acid;

(3RS,4RS)-9-(7-hydroxy-3-(4-hydroxyphenyl)-3-thiochroman-4-yl-2-(4,4,5,5,5-pentafluoropentyl)nonanoic acid;

(3RS,4RS)-7-hydroxy-3-(4-hydroxyphenyl)-4-{[11-carboxyl-11-(4,4,5,5,5-pentafluoropentyl)]undecyl}-3-methylthiochroman;

(3RS,4RS)-10-[7-hydroxy-3-(4-hydroxyphenyl)-3-methylchroman-4-yl]-2-(4,4,5,5,5-pentafluoropentyl)decanoic acid;

9-{4-[(3RS,4RS)-7-hydroxy-3-(4-hydroxyphenyl)-3-methylthiochroman-4-yl]phenoxy}-2-(4,4,5,5,5-pentafluoropentyl)nonanoic acid;

8-{4-[(3RS,4RS)-7-hydroxy-3-(4-hydroxyphenyl)-3-methylthiochroman-4-yl]phenoxy}-2-(4,4,5,5,5-pentafluoropentyl)octanoic acid;

7-{4-[(3RS,4RS)-7-hydroxy-3-(4-hydroxyphenyl)-3-methylthiochroman-4-yl]phenoxy}-2-(4,4,5,5,5-pentafluoropentyl)heptanoic acid;

6-{4-[(3RS,4RS)-7-hydroxy-3-(4-hydroxyphenyl)-3-methylthiochroman-4-yl]phenoxy}-2-(4,4,5,5,5-pentafluoropentyl)hexanoic acid;

5-{4-[(3RS,4RS)-7-hydroxy-3-(4-hydroxyphenyl)-3-methylchroman-4-yl]phenoxy}-2-(4,4,5,5,5-pentafluoropentyl)pentanoic acid;

5-{4-[(3RS,4RS)-7-hydroxy-3-(4-hydroxyphenyl)-3-methylthiochroman-4-yl]phenoxy}-2-(4,4,5,5,5-pentafluoropentyl)pentanoic acid;

(3'RS,4'RS)-11-[7-hydroxy-3-(4-hydroxyphenyl)-3-methylthiochroman-4-yl]-2-(4,4,5,5,5-pentafluoropentyl)undecanoic acid;

(3'RS,4'RS)-11-[7-hydroxy-3-(4-hydroxyphenyl)-3-methylchroman-4-yl]-2-(4,4,5,5,5-pentafluoropentyl)undecanoic acid;

(3'RS,4'RS)-12-[7-hydroxy-3-(4-hydroxyphenyl)-3-methylthiochroman-4-yl]-2-(4,4,5,5,5-pentafluoropentyl)dodecanoic acid;

(3'RS,4'RS)-12-[7-hydroxy-3-(4-hydroxyphenyl)-3-methylchroman-4-yl]-2-(4,4,5,5,5-pentafluoropentyl)dodecanoic acid;

(3'RS,4'RS)-9-[7-hydroxy-3-(4-hydroxyphenyl)-3-methylthiochroman-4-yl]-2-(4,4,5,5,5-pentafluoropentyl)nonanoic acid;

(3'RS,4'RS)-9-[7-hydroxy-3-(4-hydroxyphenyl)-3-methylchroman-4-yl]-2-(4,4,5,5,5-pentafluoropentyl)nonanoic acid;

(3'RS,4'RS)-10-[7-hydroxy-3-(4-hydroxyphenyl)-3-methylchroman-4-yl]-2-(4,4,5,5,5-pentafluoropentyl)decanoic acid;

(3'RS,4'RS)-10-[7-hydroxy-3-(4-hydroxyphenyl)-3-methylthiochroman-4-yl]-2-(4,4,5,5,5-pentafluoropentyl)decanoic acid;

(3'RS,4'RS)-10-[7-hydroxy-3-(4-hydroxyphenyl)-3-methylchroman-4-yl]-2-(3,3,4,4,4-pentafluorobutyl)decanoic acid;

(3'RS,4'RS)-10-[7-hydroxy-3-(4-hydroxyphenyl)-3-methylthiochroman-4-yl]-2-(3,3,4,4,4-pentafluorobutyl)decanoic acid;

(3'RS,4'RS)-10-[7-hydroxy-3-(4-hydroxyphenyl)-3-methylchroman-4-yl]-2-(5,5,6,6,6-pentafluorohexyl)decanoic acid;

(3'RS,4'RS)-10-[7-hydroxy-3-(4-hydroxyphenyl)-3-methylthiochroman-4-yl]-2-(5,5,6,6,6-pentafluorohexyl)decanoic acid;

(3'RS,4'RS)-10-[7-hydroxy-3-(4-hydroxyphenyl)-3-methylchroman-4-yl]-2-(6,6,7,7,7-pentafluoroheptyl)decanoic acid;

(3'RS,4'RS)-10-[7-hydroxy-3-(4-hydroxyphenyl)-3-methylthiochroman-4-yl]-2-(6,6,7,7,7-pentafluoroheptyl)decanoic acid;

(3'RS,4'RS)-11-[7-hydroxy-3-(4-hydroxyphenyl)-3-methylchroman-4-yl]-2-(3,3,4,4,4-pentafluorobutyl)undecanoic acid;

(3'RS,4'RS)-11-[7-hydroxy-3-(4-hydroxyphenyl)-3-methylthiochroman-4-yl]-2-(3,3,4,4,4-pentafluorobutyl)undecanoic acid;
(3'RS,4'RS)-11-[7-hydroxy-3-(4-hydroxyphenyl)-3-methylchroman-4-yl]-2-(5,5,6,6,6-pentafluorohexyl)undecanoic acid;
(3'RS,4'RS)-11-[7-hydroxy-3-(4-hydroxyphenyl)-3-methylthiochroman-4-yl]-2-(5,5,6,6,6-pentafluorohexyl)undecanoic acid;
(3'RS,4'RS)-11-[7-hydroxy-3-(4-hydroxyphenyl)-3-methylchroman-4-yl]-2-(6,6,7,7,7-pentafluoroheptyl)undecanoic acid;
(3'RS,4'RS)-11-[7-hydroxy-3-(4-hydroxyphenyl)-3-methylthiochroman-4-yl]-2-(6,6,7,7,7-pentafluoroheptyl)undecanoic acid;
(3'RS,4'RS)-11-[7-hydroxy-3-(4-hydroxyphenyl)-3-methylthiochroman-4-yl]-2-methyl-2-(4,4,5,5,5-pentafluoropentyl)undecanoic acid;
(3'RS,4'RS)-11-[7-hydroxy-3-(4-hydroxyphenyl)-3-methylchroman-4-yl]-2-methyl-2-(4,4,5,5,5-pentafluoropentyl)undecanoic acid;
(3'RS,4'RS)-10-[7-hydroxy-3-(4-hydroxyphenyl)-3-methylthiochroman-4-yl]-2-methyl-2-(4,4,5,5,5-pentafluoropentyl)decanoic acid;
(3'RS,4'RS)-10-[7-hydroxy-3-(4-hydroxyphenyl)-3-methylchroman-4-yl]-2-methyl-2-(4,4,5,5,5-pentafluoropentyl)decanoic acid;
(3'RS,4'RS)-11-[7-hydroxy-3-(4-hydroxyphenyl)-3-methylthiochroman-4-yl]-2-ethyl-2-(4,4,5,5,5-pentafluoropentyl)undecanoic acid;
(3'RS,4'RS)-11-[7-hydroxy-3-(4-hydroxyphenyl)-3-methylchroman-4-yl]-2-ethyl-2-(4,4,5,5,5-pentafluoropentyl)undecanoic acid;
(3'RS,4'RS)-10-[7-hydroxy-3-(4-hydroxyphenyl)-3-methylthiochroman-4-yl]-2-ethyl-2-(4,4,5,5,5-pentafluoropentyl)decanoic acid;
(3'RS,4'RS)-10-[7-hydroxy-3-(4-hydroxyphenyl)-3-methylchroman-4-yl]-2-ethyl-2-(4,4,5,5,5-pentafluoropentyl)decanoic acid;
(3'RS,4'RS)-11-[7-hydroxy-3-(4-hydroxyphenyl)-3-methylchroman-4-yl]-2-methyl-2-(5,5,6,6,6-pentafluorohexyl)undecanoic acid;
(3'RS,4'RS)-11-[7-hydroxy-3-(4-hydroxyphenyl)-3-methylthiochroman-4-yl]-2-methyl-2-(5,5,6,6,6-pentafluorohexyl)undecanoic acid;
(3'RS,4'RS)-11-[7-hydroxy-3-(4-hydroxyphenyl)-3-methylchroman-4-yl]-2-methyl-2-(6,6,7,7,7-pentafluoroheptyl)undecanoic acid;
(3'RS,4'RS)-11-[7-hydroxy-3-(4-hydroxyphenyl)-3-methylthiochroman-4-yl]-2-methyl-2-(6,6,7,7,7-pentafluoroheptyl)undecanoic acid;
(3'RS,4'RS)-11-[7-hydroxy-3-(4-hydroxyphenyl)-3-methylchroman-4-yl]-2-ethyl-2-(5,5,6,6,6-pentafluorohexyl)undecanoic acid;
(3'RS,4'RS)-11-[7-hydroxy-3-(4-hydroxyphenyl)-3-methylthiochroman-4-yl]-2-ethyl-2-(5,5,6,6,6-pentafluorohexyl)undecanoic acid;
(3'RS,4'RS)-11-[7-hydroxy-3-(4-hydroxyphenyl)-3-methylchroman-4-yl]-2-ethyl-2-(6,6,7,7,7-pentafluoroheptyl)undecanoic acid;
(3'RS,4'RS)-11-[7-hydroxy-3-(4-hydroxyphenyl)-3-methylthiochroman-4-yl]-2-ethyl-2-(6,6,7,7,7-pentafluoroheptyl)undecanoic acid;
(3'RS,4'RS)-10-[7-hydroxy-3-(4-hydroxyphenyl)-3-methylchroman-4-yl]-2-methyl-2-(5,5,6,6,6-pentafluorohexyl)decanoic acid;
(3'RS,4'RS)-10-[7-hydroxy-3-(4-hydroxyphenyl)-3-methylthiochroman-4-yl]-2-methyl-2-(5,5,6,6,6-pentafluorohexyl)decanoic acid;
(3'RS,4'RS)-10-[7-hydroxy-3-(4-hydroxyphenyl)-3-methylchroman-4-yl]-2-methyl-2-(6,6,7,7,7-pentafluoroheptyl)decanoic acid;
(3'RS,4'RS)-10-[7-hydroxy-3-(4-hydroxyphenyl)-3-methylthiochroman-4-yl]-2-methyl-2-(6,6,7,7,7-pentafluoroheptyl)decanoic acid;
(3'RS,4'RS)-10-[7-hydroxy-3-(4-hydroxyphenyl)-3-methylchroman-4-yl]-2-ethyl-2-(5,5,6,6,6-pentafluorohexyl)decanoic acid;
(3'RS,4'RS)-10-[7-hydroxy-3-(4-hydroxyphenyl)-3-methylthiochroman-4-yl]-2-ethyl-2-(5,5,6,6,6-pentafluorohexyl)decanoic acid;
(3'RS,4'RS)-10-[7-hydroxy-3-(4-hydroxyphenyl)-3-methylchroman-4-yl]-2-ethyl-2-(6,6,7,7,7-pentafluoroheptyl)decanoic acid; or
(3'RS,4'RS)-10-[7-hydroxy-3-(4-hydroxyphenyl)-3-methylthiochroman-4-yl]-2-ethyl-2-(6,6,7,7,7-pentafluoroheptyl)decanoic acid.

The present invention also provides the following processes I to V for preparing the compound of formula (1) as defined above.

[Process I]

First, the compound of formula (1) wherein A represents hydrogen, that is a compound of formula (2):

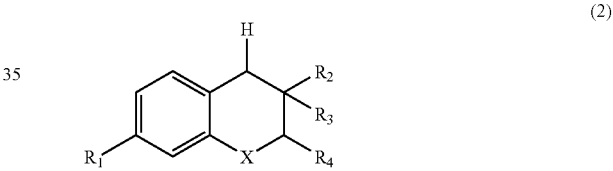

wherein X, $R_1$, $R_2$, $R_3$ and $R_4$ are defined as previously described, can be prepared by the reduction of the ketone of formula (3):

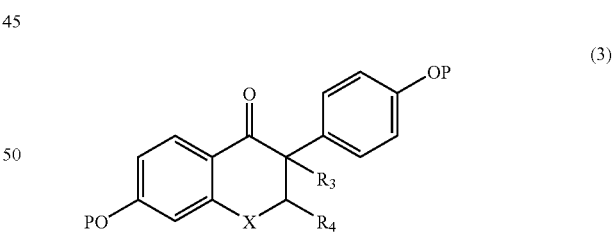

wherein X, $R_3$ and $R_4$ are defined as previously described, and P represents a hydroxy-protecting group.

In the following processes for preparing the compound of formula (1) according to the present invention including the process for preparing the compound of formula (1) wherein A represents hydrogen, suitable hydroxy-protecting groups and leaving groups which have been conventionally used in the technical field to which the present invention pertains or which can be easily selected by a person skilled in the art may be used. Preferably, methoxymethyl or t-butyldimethylsilyl as the hydroxy-protecting group and tosyloxy, mesyloxy, halo or acetyi as the leaving group can be mentioned.

Further, if not specifically mentioned, any organic solvents which do not adversely affect the reaction can be used as the solvent in the processes according to the present invention. These solvents may be used under anhydrous condition if such a condition is required due to the nature of the reaction, Only the solvents particularly appropriate are mentioned for the respective reaction steps in the present specification, The reactions may be carried out under cooling to warming or heating, and the reaction temperature and time are organically combined together to contribute to the reaction completion.

[Process II]

The compound of formula (1) wherein A represents hydroxyalkyl, that is a compound of formula (4):

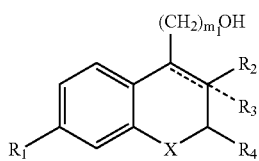
(4)

wherein X, $R_1$, $R_2$, $R_3$, $R_4$ and $m_1$ are defined as previously described, can be prepared using the same procedure described in International Patent Appln No. PCT/KR97/00265.

[Process III]

The compound of formula (1) wherein A represents carboxyalkyl, that is a compound of formula (5):

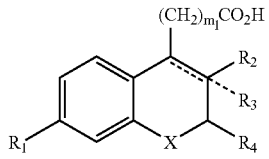
(5)

wherein X, $R_1$, $R_2$, $R_3$, $R_4$ and $m_1$ are defined as previously described, can be prepared by a process characterized in that
(a) the compound of formula (6):

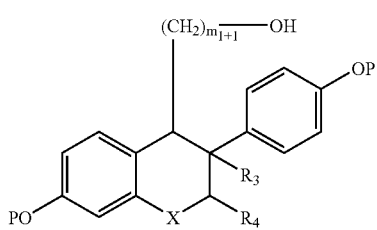
(6)

wherein X, $R_3$, $R_4$, $m_1$ and P are defined as previously described, is oxidized and deprotected to produce a compound of formula (5a):

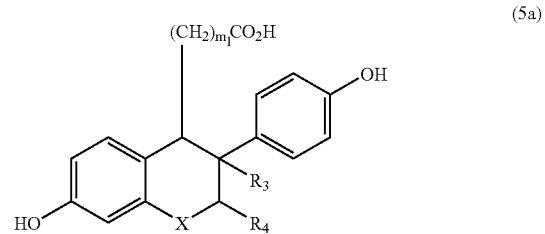
(5a)

wherein X, $R_3$, $R_4$ and $m_1$ are defined as previously described, or
(b) the compound of formula (7):

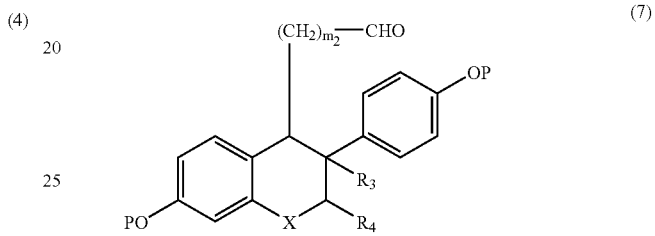
(7)

wherein X, $R_3$, $R_4$, $m_2$ and P are defined as previously described, is reacted with a Wittig reagent and the resulting compound is hydrogenated and deprotected to produce a compound of formula (5a):

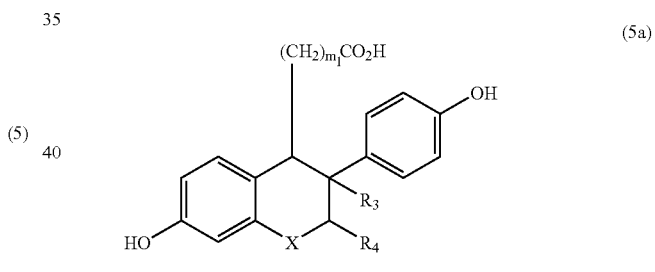
(5a)

wherein X, $R_3$, $R_4$ and $m_1$ are defined as previously described.

[Process IV]

The compound of formula (1) wherein A represents carboxyvinylphenyl, that is a compound of formula (8):

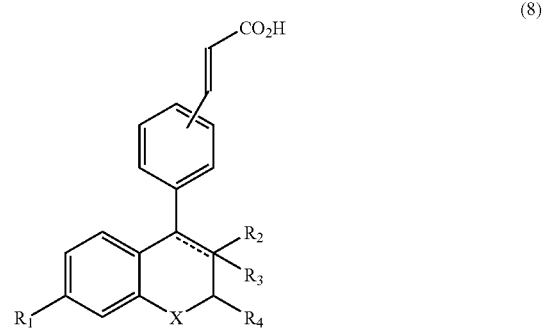
(8)

wherein X, $R_1$, $R_2$, $R_3$ and $R_4$ are defined as previously described, can be prepared by a process characterized in that a compound of formula (9):

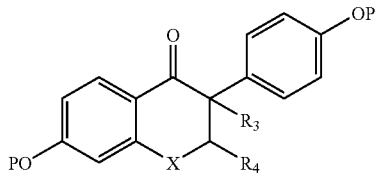
(9)

wherein X, $R_3$, $R_4$ and P are defined as previously described, is reacted with a compound of formula (10):

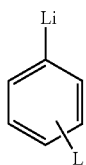
(10)

wherein L represents acetal or nitrile or protected-hydroxymethyl group, and the resulting compound is deprotected or hydrogenated or dehydrated or oxidized to produce a compound of formula (11):

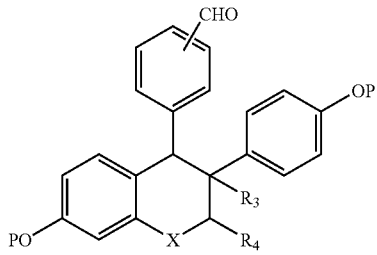
(11)

wherein X, $R_3$, $R_4$ and P are defined as previously described, and the resulting compound of formula (11) is reacted with malonic acid derivative and is deprotected to produce a compound of formula (12):

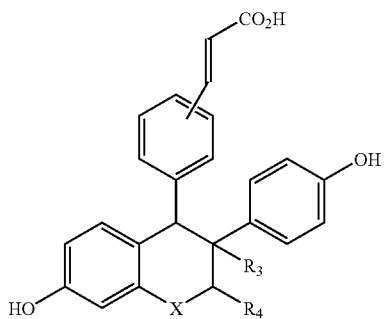
(12)

wherein X, $R_3$ and $R_4$ are defined as previously described.

[Process V]

(Method A)

The compound of formula (1) wherein A represents group (a), that is a compound of formula (1a):

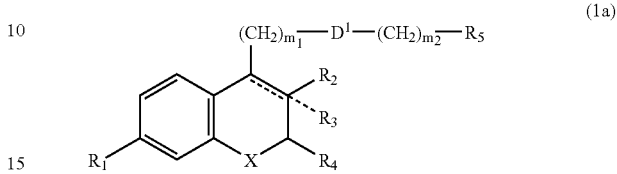
(1a)

wherein X, $R_1$, $R_2$, $R_3$, $R_4$, $R_5$, $m_1$, $m_2$ and $D^1$ are defined as previously described, can be prepared by a process characterized in that
a compound of formula (13):

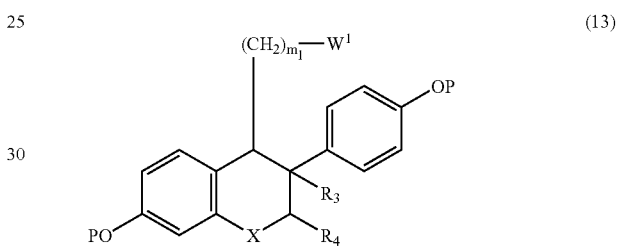
(13)

wherein X, $R_3$, $R_4$, $m_1$ and P are defined as previously described, and $W^1$ represents a leaving group, is reacted with a compound of formula (14):

$$D^1H_2 \qquad (14)$$

wherein $D^1$ is defined as previously described, to produce a compound of formula (15):

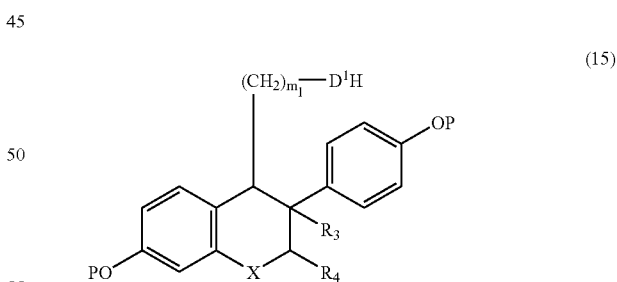
(15)

wherein X, $R_3$, $R_4$, $D^1$, $m_1$ and P are defined as previously described, the resulting compound of formula (15) is reacted with a compound of formula (16):

$$W^2-(CH_2)_{m_2}-R_5 \qquad (16)$$

wherein $R_5$ and $m_2$ are defined as previously described, and $W^2$ represents a leaving group such as acyl, hydrogen, etc., and then deprotected to produce a compound of formula (1aa):

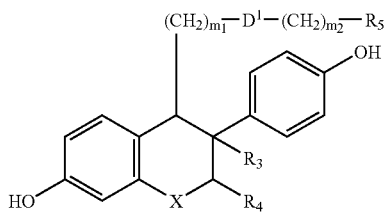

wherein X, $R_3$, $R_4$, $R_5$, $m_1$, $m_2$ and $D^1$ are defined as previously described, or (b) the compound of formula (13) is reacted with sodium cyanide to produce a compound of formula (17):

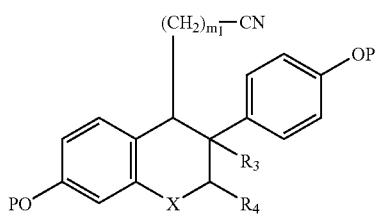

wherein X, $R_3$, $R_4$, $m_1$ and P are defined as previously described, the resulting compound of formula (17) is reacted with a compound of formula (18):

wherein $R_5$ and $m_2$ are defined as previously described, in the presence of a Lewis acid to produce a compound of formula (1ab) or (1ac):

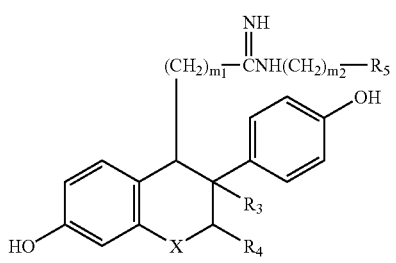

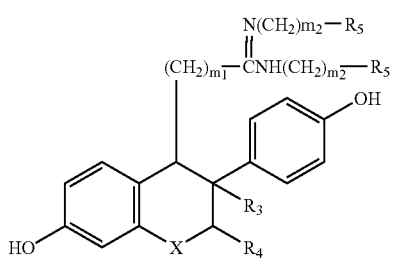

wherein X, $R_3$, $R_4$, $R_5$, $m_1$ and $m_2$ are defined as previously described.

In the method A(a) for preparing the compound of formula (1a), the coupling step of the compound (13) and (14) may be carried out in a solvent. As the preferable solvent, one or more selected from a group consisting of dioxane, methanol, ethanol, diethylether, tetrahydrofuran, dimethylsulfoxide, methylene chloride, dimethylformamide, chloroform, ethyl acetate, acetonitrile and acetone can be used. This reaction may be carried out optionally in the presence of one or more inorganic or organic bases selected from a group consisting of potassium carbonate, potassium hydroxide, sodium hydroxide, sodium methoxide, sodium ethoxide, triethylamine and cesium carbonate. The reaction may be suitably proceeded under the reflux temperature of the solvent used or room temperature if appropriate, under ice-cooling.

The compound of formula (15) resulted from the coupling of compounds (13) and (14) is reacted with the compound of formula (16) and then deprotected to produce the compound of formula (1aa). This reaction can be carried out in one or more solvents selected from a group consisting of acetone, toluene, dimethylformamide, acetonitrile, dimethylsulfoxide and methylene chloride, optionally in the presence of a base such as potassium carbonate, triethylamine, sodium ethoxide, etc. The deprotection reaction may be carried out according to a conventional method such as hydrolysis in the presence of acid or base, and reduction, etc. Preferably, the deprotection is achieved in the presence of one or more hydrolyzing agents selected from a group consisting of borontribromide, hydrochloric acid, hydrobromic acid, hydrofluoric acid, pyridinium-p-toluenesulfonate and sulfuric acid, or in the presence of one or more reducing agents selected from a group consisting of $Pd(OH)_2/C$ under hydrogen, Pd/C and diisobutylaluminum hydride (DIBAL). This reaction can be carried out under a low temperature to warming, preferably carried out by starting at a low temperature of $-78°$ C. and then warming to room temperature. While, the compound of formula (1aa) thus produced may be further oxidized using metachloroperbenzoic acid (mCPBA) in a solvent such as chloroform.

In the method A(b), the compound of formula (13) is first reacted with sodium cyanide to produce the compound of formula (17). In this reaction, one or more solvents selected from dimethylsulfoxide, acetonitrile and dimethylformamide can be used. The compound (17) thus produced is reacted with the compound of formula (18) in the presence of a Lewis acid to give the compound of formula (1ab) or (1ac). As the Lewis acid which can be used, $AlCl_3$, $BF_3 \cdot Et_2O$, $SnCl_4$, $ZnI_2$ or $FeCl_3$ can be mentioned, and as the solvent one or more selected from xylene, benzene and toluene can be mentioned. Preferably, the reaction is proceeded at the reflux temperature of the solvent used for 1 to 20 hours.

(Method A-1)

The compound of formula (1a) wherein $R_1$, $R_2$, $R_3$, $R_4$ and $D^1$ represent —OH, —$C_6H_4$ (OH), -Me, H and (—CH($CO_2H$)—) respectively may typically be synthesized by the following methods.

Method A-1a

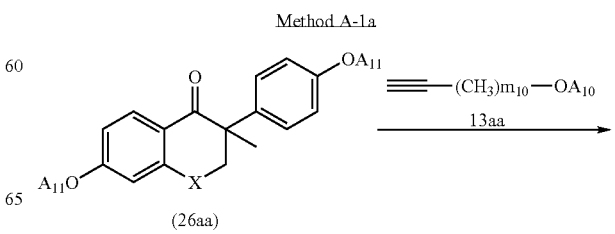

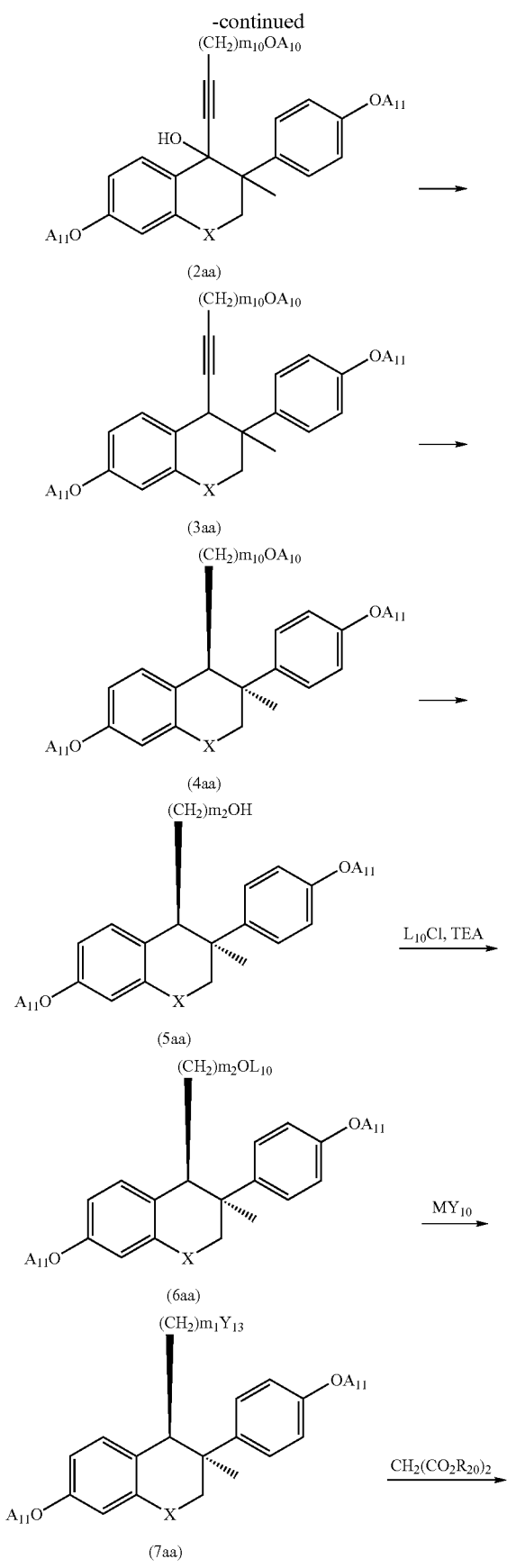
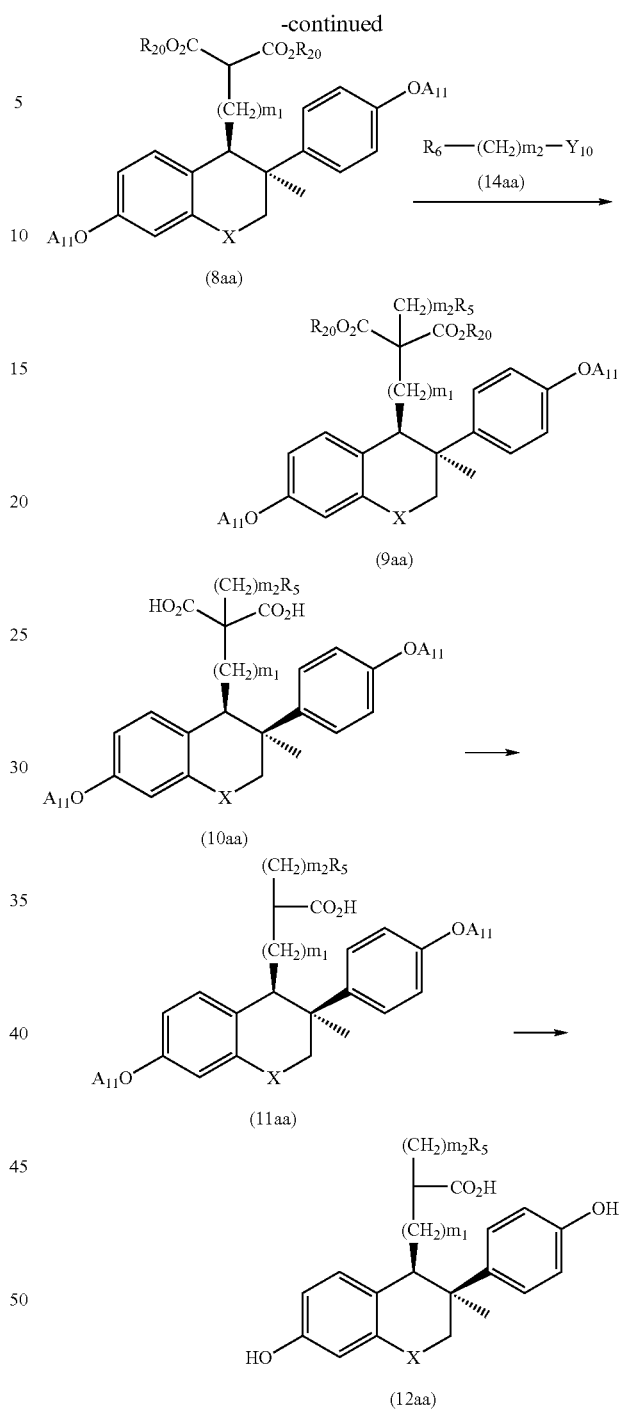

wherein X, $R_5$, $m_1$ and $m_2$ are defined as previously described; $A_{10}$ and $A_{11}$ are protecting group such as t-butyldimethylsilyl, triisopropylsilyl, triethylsilyl, t-butyldiphenylsilyl, methoxymethyl, tetrahydropyranyl, methyl, etc.; $L_{10}$ is a leaving group such as methanesulfonyl, p-toluenesulfonyl, etc.; M is a metal such as Li, Na, K, etc.; $Y_{10}$ is a halogen such as Cl, Br, I, etc.; $R_{20}$ is alkyl group such as methyl, ethyl, etc.; and $m_{10}$ is an integer of 0 to 12.

The compound (12aa) may be synthesized in the following manner.

The compund represented by the formula (26aa) is reacted with acetylene (13aa) in the presence of base such as n-buthyllithium, sec-buthyllithium, sodium hydride, in a solvent inert to the reaction such as tetrahydrofuran, dioxane, dichloromethane, chloroform, preferably in tetrahydrfuran or dioxane, at the temperature between −78° C. and the boiling point of the reaction mixture, preferably at −78° C. through room temperature, to yield the compound represented by the formula (2aa).

The compound represented by the formula (2aa) is reduced by sodium cyanoborohydride in the presence of Lewis acid such as zinc iodide, in a solvent inert to the reaction such as tetrahydrofuran, dioxane, dichloromethane, dichloroethane or chloroform, preferably in dichloroethane at the temperature between −78° C. and the boiling point of the reaction mixture, preferably at 0° C. through room temperature, to yield the compound represented by the formula (3aa).

The compound represented by the formula (3aa) is hydrogenated with a catalyst such as palladium on activated carbon, palladium hydroxide, platinum oxide, in a solvent inert to the reaction such as methanol, ethanol, ethyl acetate, tetrahydrofuran, dioxane, dichloromethane, dichloroethane, chloroform, preferably in tetrahydrofuran, ethyl acetate at the temperature between room temperature and the boiling point of the reaction mixture, preferably at room temperature, optionally in the presence of sodium hydrogen carbonate, to yield the compound represented by the formula (4aa). The compound represented by the formula (4aa) is also obtained from the compound represented by the formula (2aa) directly by hydrogenation reaction with a catalyst such as palladium on activated carbon, palladium hydroxide or platinum oxide, in a solvent inert to the reaction such as methanol, ethanol, ethyl acetate, tetrahydrofuran, dioxane, dichloromethane, dichloroethane or chloroform, preferably in tetrahydrofuran, ethyl acetate at the temperature between room temperature and the boiling point of the reaction mixture, preferably at room temperature.

The compound represented by the formula (4aa) is treated with tetrabuthylammonium fluoride or cesium fluoride or hydrogen fluoride-pyridine in a solvent inert to the reaction such as tetrahydrofuran, dioxane, dichloromethane, dichloroethane or chloroform, preferably in tetrahydrofuran, at the temperature between room temperature and the boiling point of the reaction mixture, preferably at room temperature to yield the compound represented by the formula (5aa).

The compound represented by the formula (5aa) is treated with methanesulfonyl chloride or p-toluenesulfonylchloride in the presence of an organic base such as triethylamine or pyridine in a solvent inert to the reaction such as tetrahydrofuran, dioxane, dichloromethane, dichloroethane or chloroform, preferably in dichloromethane, at the temperature between room temperature and the boiling point of the reaction mixture, preferably at room temperature to yield the compound represented by the formula (6aa).

The compound represented by the formula (6aa) is treated with metalhalide such as sodium iodide or potassium iodide in a solvent inert to the reaction such as acetone, tetrahydrofuran, dioxane, dichloromethane, dichloroethane or chloroform, preferably in dichloromethane, at the temperature between room temperature and the boiling point of the reaction mixture, preferably at the boiling point of the reaction mixture, to yield the compound represented by the formula (7aa).

The compound represented by the formula (7aa) is reacted with malonate such as diethyl malonate or dimethyl malonate in the presence of a base such as sodium hydride, sodium hydroxide or potassium t-butoxide, in a solvent inert to the reaction such as tetrahydrofuran, dioxane, dichloromethane, dichloroethane or chloroform, preferably in tetrahydrofuran, at the temperature between room temperature and the boiling point of the reaction mixture to yield the compound represented by the formula (8aa). The compound represented by the formula (8aa) is also obtained from the compound represented by the formula (6aa) directly by the reaction with malonate such as diethyl malonate or dimethyl malonate in the presence of a base such as sodium hydride, sodium hydroxide or potassium t-butoxide, in a solvent inert to the reaction such as tetrahydrofuran, dioxane, dichloromethane, dichloroethane or chloroform, preferably in tetrahydrofuran, at the temperature between room temperature and the boiling point of the reaction mixture.

The compound represented by the formula (8aa) is reacted with alkylhalide as the compound represented by the fomula (14aa) in the presence of a base such as sodium hydride, sodium hydroxide or potassium t-butoxide in a solvent inert to the reaction such as tetrahydrofuran, dioxane, dichloromethane, dichloroethane or chloroform, preferably in tetrahydrofuran, at the temperature between room temperature and the boiling point of the reaction mixture to yield the compound represented by the formula (9aa).

The compound represented by the formula (9aa) is treated with sodium hydroxide or potassium hydroxide in a solvent such as water, ethanol, methanol, a mixture of water-ethanol or a mixture of water-methanol at the temperature between room temperature and the boiling point of the reaction mixture, preferably at the boiling point of the reaction mixture to yield the compound represented by the formula (10aa).

The compound represented by the formula (10aa) is heated at 50° C. to the boiling point of the reaction mixture in a solvent such as dimethylsulfoxide, dimethylformamide, benzene, toluene, xylene, dioxane or tetrahydrofuran, optionally in the presence of an acid such as hydrogen chloride, sulfuric acid or p-toluenesulfonic acid, to yield the compound represented by the formula (11aa).

The compound represented by the formula (11aa) is treated with an acid, such as hydrogen chloride, sulfuric acid, hydrogen bromide, hydrogen pyridinium chloride, boron tribromide at the temperature between −78° C. and the boiling point of the reaction mixture to yield the compound represented by the formula (12aa).

Method A-1b

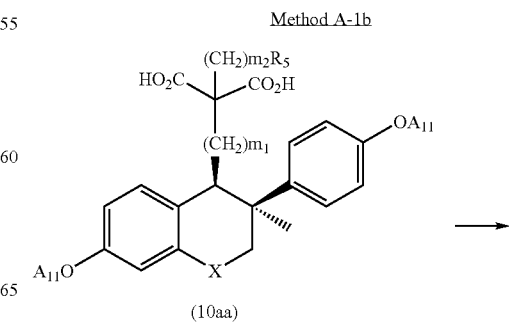

(10aa)

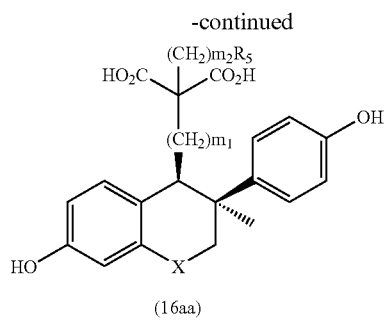

(16aa)

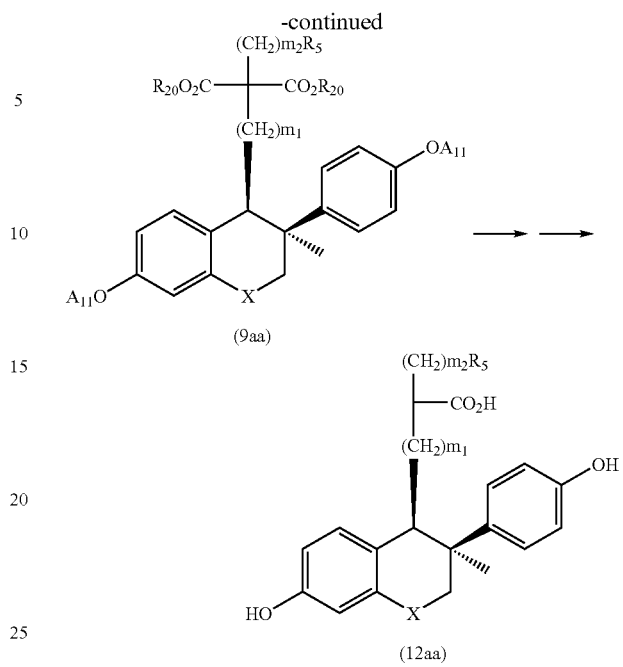

(9aa)

(12aa)

(12aa)

wherein X, $R_5$, $m_1$, $m_2$ and $A_{11}$ are defined as previously described.

The compound (12aa) may be synthesized in the following manner.

The compound represented by the formula (10aa) is treated with an acid, such as hydrogen chloride, sulfuric acid, hydrogen bromide, hydrogen pyridinium chloride or boron tribromide at the temperature between −78° C. and the boiling point of the reaction mixture to yield the compound represented by the formula (16aa).

The compound represented by the formula (16aa) is heated at 50° C. to the boiling point of the reaction mixture in a solvent such as dimethylsulfoxide, dimethylformamide, benzene, toluene, xylene, dioxane or tetrahydrofuran, optionally in the presence of an acid such as hydrogen chloride, sulfuric acid or p-toluenesulfonic acid, to yield the compound represented by the formula (12aa).

wherein X, $R_5$, $R_{20}$, $Y_{10}$, $A_{11}$, $m_1$ and $m_2$ are defined as previously described.

The compound represented by the formula (25aa) is reacted with malonate such as diethyl malonate or dimethyl malonate in the presence of a base such as sodium hydride, sodium hydroxide or potassium t-butoxide, in a solvent inert to the reaction such as tetrahydrofuran, dioxane, dichloromethane, dichloroethane or chloroform, preferably in tetrahydrofuran, at the temperature between −78° C. and the boiling point of the reaction mixture to yield the compound represented by the formula (15aa).

The compound represented by the formula (15aa) is reacted with the compound represented by the formula (7aa) in the presence of a base such as sodium hydride, sodium hydroxide or potassium t-butoxide in a solvent inert to the reaction such as tetrahydrofuran, dioxane, dichloromethane, dichloroethane or chloroform, preferably in tetrahydrofuran, at the temperature between −78° C. and the boiling point of the reaction mixture to yield the compound represented by the formula (9aa).

The compound represented by the formula (9aa) is converted to the compound represented by the formula (12aa) according to the previously described method.

Method A-1c

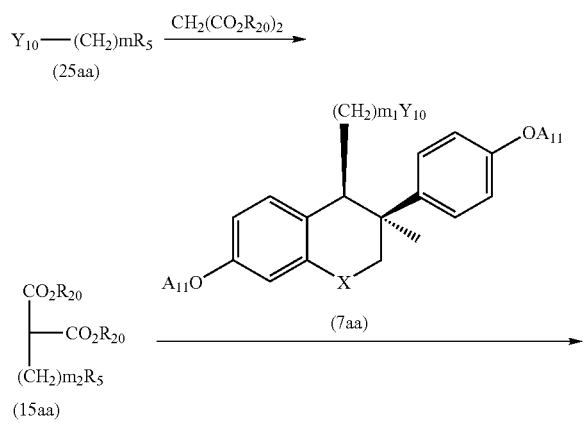

Method A-1d

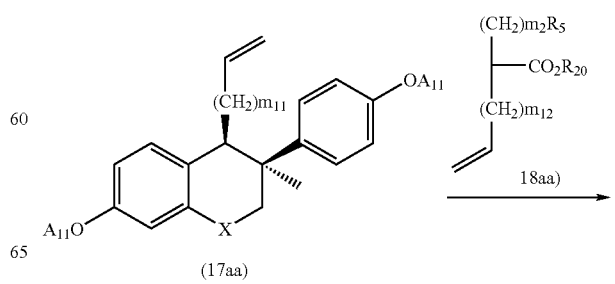

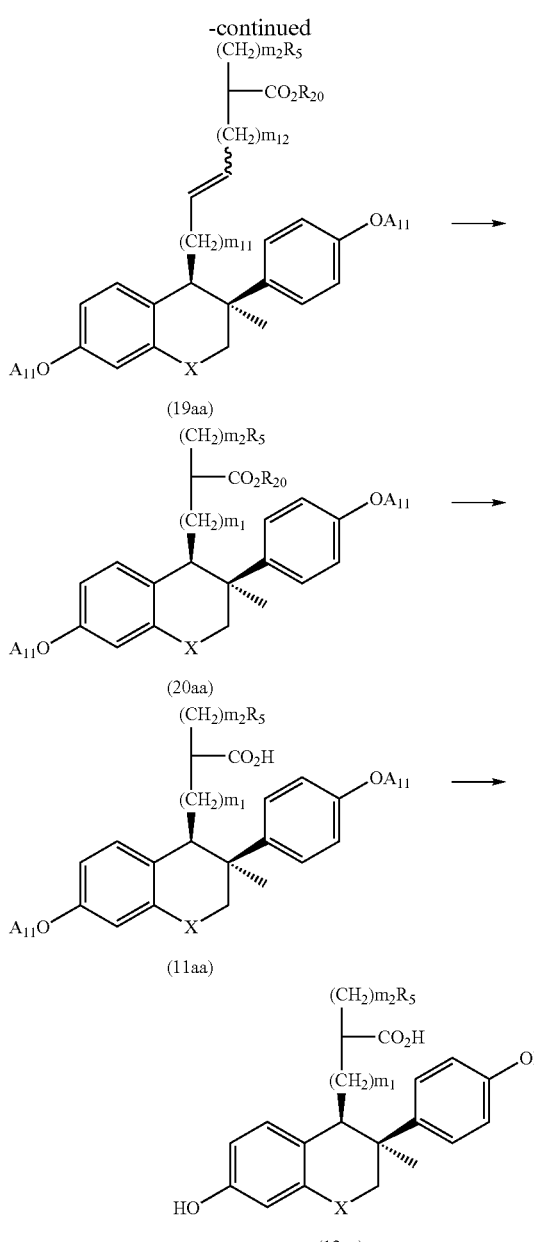

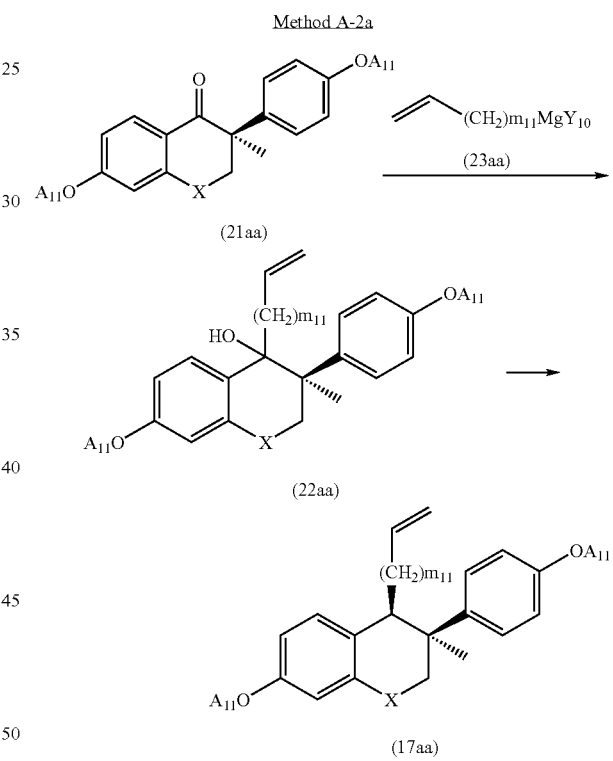

wherein X, $R_5$, $R_{20}$, $A_{11}$, $m_1$ and $m_2$ are defined as previously described; $m_{11}$ and $m_{12}$ are an integer of 0 to 10.

The compound (12aa) may be synthesized in the following manner.

The compound represented by the formula (17aa) is reacted with the compound represented by the formula (18aa) in the presence of a catalyst such as benzylidene-bis (tricyclohexylphosphine)dichlororuthenium in a solvent such as methylene chloride, chloroform, benzene, toluene, xylene, dioxane, tetrahydrofuran, dimethylsulfoxide or dimethylformamide at the temperature between −78° C. and the boiling point of the reaction mixture to, preferably at the boiling point of the reaction mixture, yield the compound represented by the formula (19aa)

The compound represented by the formula (19aa) is hydrogenated with a catalyst such as palladium on activated carbon, palladium hydroxide, platinum oxide or Wilkinson's catalyst in a solvent inert to the reaction such as methanol, ethanol, ethyl acetate, tetrahydrofuran, dioxane, dichloromethane, dichloroethane, chloroform or benzene at the temperature between room temperature and the boiling point of the reaction mixture, preferably at room temperature to yield the compound represented by the formula (20aa).

The compound represented by the formula (20aa) is treated with sodium hydroxide or potassium hydroxide in a solvent such as water, ethanol, methanol, a mixture of water-ethanol or a mixture of water-methanol at the temperature between room temperature and the boiling point of the reaction mixture, preferably at the boiling point of the reaction mixture to yield the compound represented by the formula (11aa).

The compound represented by the formula (11aa) is converted to the compound represented by the formula (12aa) according to the previously described method.

(Method A-2)

The compound of formula (17aa) may typically be synthesized by the following methods.

wherein X, $A_{11}$, $m_{11}$ and $Y_{10}$ are defined as previously described.

The compound (17aa) may be synthesized in the following manner.

The compound represented by the formula (21aa) is reacted with the Grignard reagent represented by the formula (23aa) in a solvent inert to the reaction such as diethyl ether, benzene, toluene, xylene, dioxane or tetrahydrofuran at the temperature between −78° C. and the boiling point of the reaction mixture, to yield the compound represented by the formula (22aa).

The compund represented by the formula (22aa) is reduced by sodium cyanoborohydride in the presence of Lewis acid such as zinc iodide, or by triethylsilane in the presence of an acid such as trifluoroacetic acid, in a solvent inert to the reaction such as tetrahydrofuran, dioxane, dichloromethane, dichloroethane or chloroform, preferably in dichloroethane at the temperature between −78° C. and the boiling point of the reaction mixture, preferably at 0° C. through room temperature, to yield the compound represented by the formula (17aa).

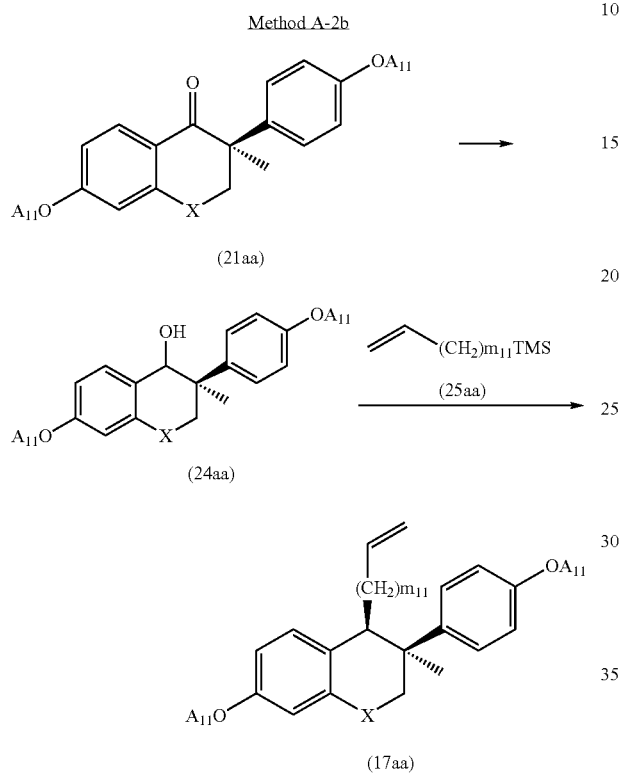

wherein X, $A_{11}$ and $m_{11}$ are defined as previously described.

The compound (17aa) may be synthesized in the following manner.

The compound represented by the formula (21aa) is reduced by a reagent such as sodium borohydride or lithium aluminum hydride in a solvent inert to the reaction such as tetrahydrofuran, dioxane, dichloromethane, dichloroethane, or chloroform at the temperature between −78° C. and the boiling point of the reaction mixture, preferably at the temperature between 0° C. and room temperature, to yield the compound represented by the formula (24aa).

The compound represented by the formula (24aa) is reacted with the compound represented by the formula (25aa) in the presence of a Lewis acid such as zinc iodide or boron trifluoride diethyl etherate in a solvent inert to the reaction such as tetrahydrofuran, dioxane, dichloromethane, dichloroethane, or chloroform at the temperature between −78° C. and the boiling point of the reaction mixture to yield the compound represented by the formula (17aa).

The above compound (17aa) is novel.

(Method B)

The compound of formula (1) wherein A represents group (b), that is a compound of formula (1b):

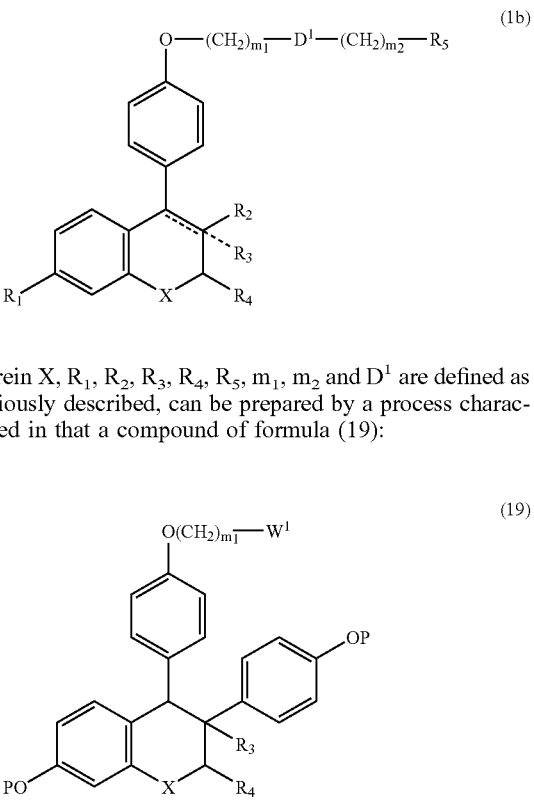

wherein X, $R_1$, $R_2$, $R_3$, $R_4$, $R_5$, $m_1$, $m_2$ and $D^1$ are defined as previously described, can be prepared by a process characterized in that a compound of formula (19):

wherein X, $R_3$, $R_4$, $m_1$, $W^1$ and P are defined as previously described, is reacted with a compound of formula (20):

$$HD^1\text{-}(CH_2)_{m_2}\text{—}R_5 \quad (20)$$

wherein $R_5$, $m_2$ and $D^1$ are defined as previously described, and then deprotected to produce a compound of formula (1ba):

wherein X, $R_3$, $R_4$, $R_5$, $m_1$, $m_2$ and $D^1$ are defined as previously described.

The reaction of the compound (19) with (20) is preferably carried out in one or more solvents selected from acetone, dimethylformamide, methylene chloride and chloroform at the reflux temperature of the solvent used. In addition, a base such as potassium carbonate, tetra-n-butylammonium iodide, tetra-n-butylammonium fluoride, tetra-n-butylammonium bromide, etc. may be used to more facilitate the reaction.

(Method C)

The compound of formula (1) wherein A represents group (c), that is a compound of formula (1c):

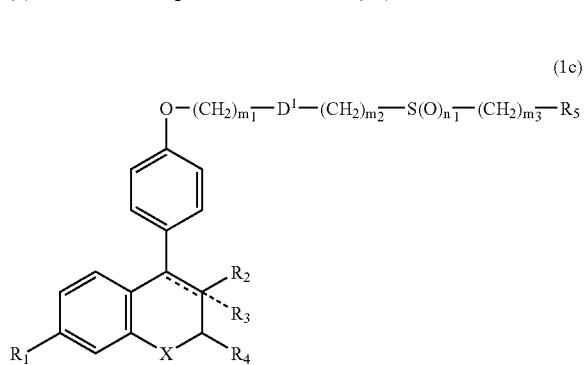

(1c)

wherein X, $R_1$, $R_2$, $R_3$, $R_4$, $R_5$, $m_1$, $m_2$, $m_3$, $n_1$ and $D^1$ are defined as previously described, can be prepared by a process characterized in that a compound of formula (21):

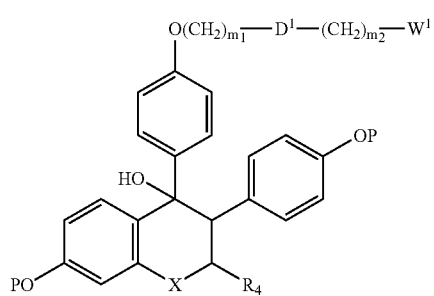

(21)

wherein X, $R_4$, $m_1$, $m_2$, $D^1$, $W^1$ and P are defined as previously described, is reacted with a compound of formula (22):

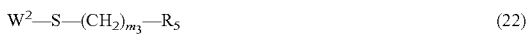

(22)

wherein $R_5$, $m_3$ and $W^2$ are defined as previously described, to produce a compound of formula (23):

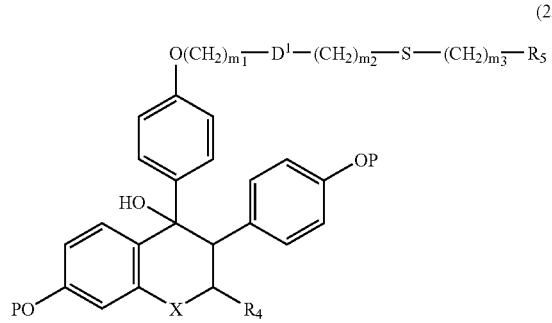

(23)

wherein X, $R_4$, $R_5$, $m_1$, $m_2$, $m_3$, $D^1$ and P are defined as previously described, the resulting compound of formula (23) is deprotected and dehydrated to produce a compound of formula (24):

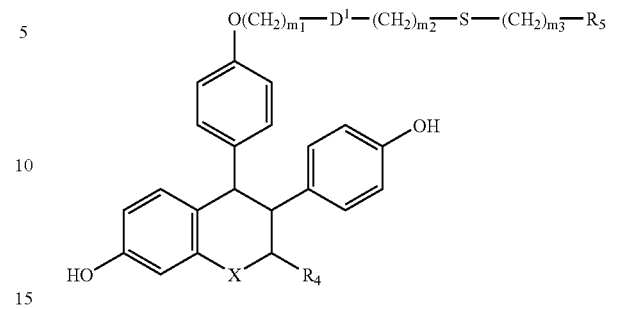

(24)

wherein X, $R_4$, $R_5$, $m_1$, $m_2$, $m_3$ and $D^1$ are defined as previously described, which is then oxidized to produce a compound of formula (1ca):

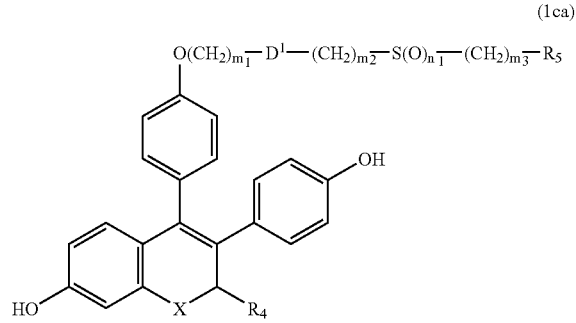

(1ca)

wherein X, $R_4$, $R_5$, $m_1$, $m_2$, $m_3$ and $D^1$ are defined as previously described, and $n_1'$ represents 1 or 2.

The compound of formula (21) is reacted with the compound of formula (22) in one or more solvents selected from methanol, ethanol and acetonitrile and optionally in the presence of one or more bases selected from sodium hydroxide, sodium ethoxide and sodium methoxide under warming for 1 to 20 hours to produce the coupling product of formula (23). Deprotection and dehydration reactions are subjected to the resulting compound of formula (23) to prepare the compound of formula (24). The deprotection and dehydration reaction may be carried out by applying the reaction conditions which are generally used for this purpose. This reaction is preferably carried out by refluxing under argon in the presence of a salt such as pyridinium p-toluenesulfonate.

The desired compound of formula (1ca) is produced by oxidizing the compound of formula (24). The oxidation reaction can be carried out under the condition selected from the various possible conditions based on the structure and nature of the compound to be oxidized. Generally, the oxidation is carried out in one or more solvents selected from methanol, water, chloroform, tetrahydrofuran, dioxane, ethanol and methylene chloride in the presence of one or more oxidizing agents selected from sodium periodate ($NaIO_4$), metachloroperbenzoic acid, hydrogen peroxide and Oxone® (monopersulfate compound; DuPont product). Hereinafter, the oxidation reactions for the other compounds having different structures can be explained in the same manner.

(Method D)

The compound of formula (1) wherein A represents group (d), that is a compound of formula (1d):

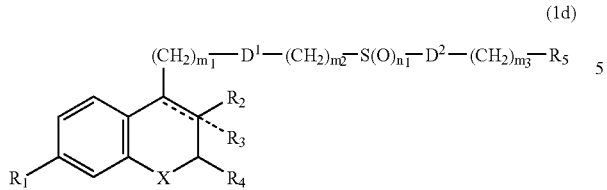
(1d)

wherein X, $R_1$, $R_2$, $R_3$, $R_4$, $R_5$, $m_1$, $m_2$, $m_3$, $n_1$, $D^1$ and $D^2$ are defined as previously described, can be preparedt by a process characterized in that
(a) the compound of formula (13):

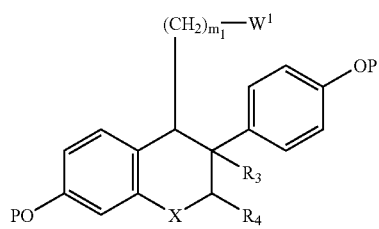
(13)

wherein X, $R_3$, $R_4$, $m_1$, P and $W^1$ are defined as previously described, is reacted with a compound of formula (25):

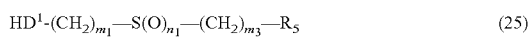
(25)

wherein $R_5$, $m_2$, $m_3$, $n_1$ and $D^1$ are defined as previously described, and then deprotected to produce a compound of formula (1da):

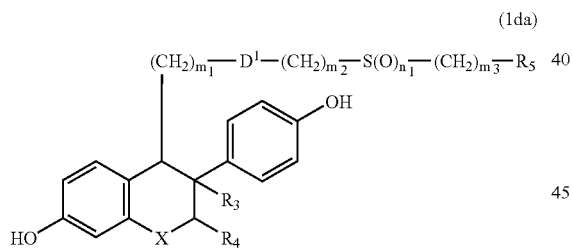
(1da)

wherein X $R_3$, $R_4$, $R_5$, $m_1$, $m_2$, $m_3$, $n_1$ and $D^1$ are defined as previously described,
(b) the compound of formula (15):

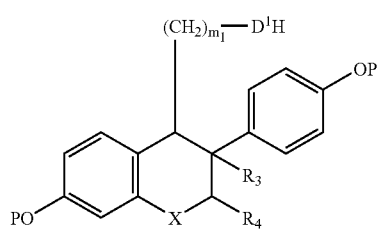
(15)

wherein X, $R_3$, $R_4$, $D^1$, $m_1$ and P are defined as previously described, is reacted with a compound of formula (26):

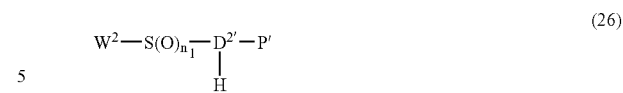
(26)

wherein $n_1$ and $W^2$ are defined as previously described, P' represents a hydroxy-protecting group, and $D^{2'}$ is the same with $D^2$, provided that 1 or 2 hydrogen atoms are excluded therefrom, to produce a compound of formula (27):

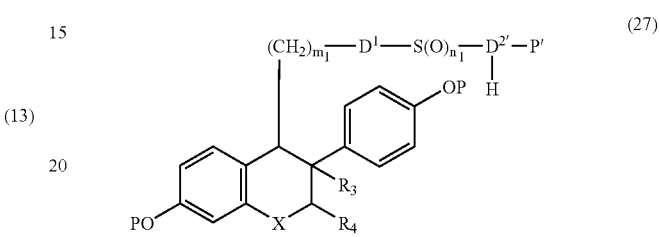
(27)

wherein X, $R_3$, $R_4$, $m_1$, $n_1$, $D^1$, $D^{2'}$, P and P' are defined as previously described, the resulting compound of formula (27) is condensed with a compound of formula (28):

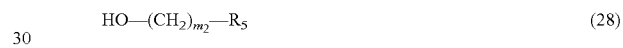
(28)

wherein $R_5$ and $m_2$ are defined as previously described, and then deprotected to produce a compound of formula (1db):

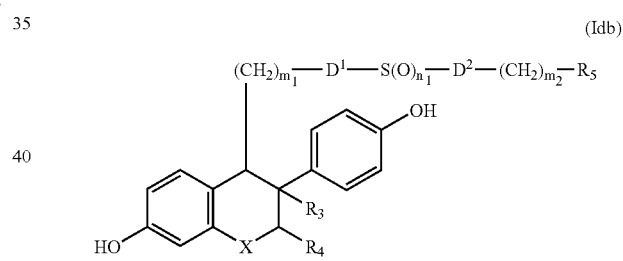
(1db)

wherein X, $R_3$, $R_4$, $R_5$, $m_1$, $m_2$, $n_1$, $D^1$ and $D^2$ are defined as previously described,
(c) the compound of formula (13) is reacted with a compound of formula (29):

(29)

wherein $R_5$, $m_3$, $D^2$ and $W^2$ are defined as previously described, to produce a compound of formula (30):

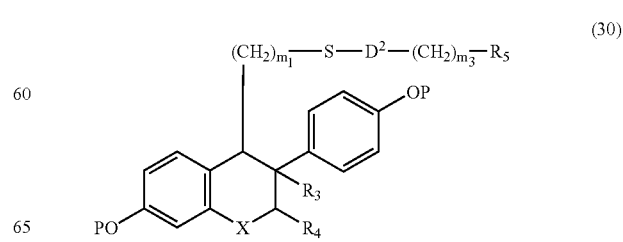
(30)

wherein X, $R_3$, $P_4$, $R_5$, $m_1$, $m_3$, $D^2$ and P are defined as previously described, the resulting compound of formula (30) is then deprotected and oxidized to produce a compound of formula (1dc):

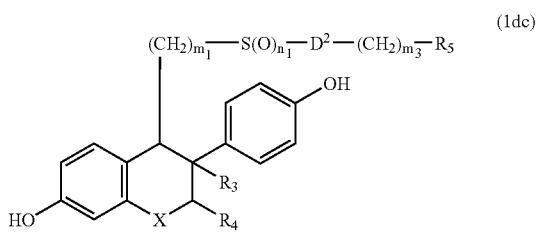
(1dc)

wherein X, $R_3$, $R_4$, $R_5$, $m_1$, $m_3$, $n_1'$ and $D^2$ are defined as previously described, (d) the compound of formula (13) is reacted with a compound of formula (29a):

(29a)

wherein $m_3$, $D^2$, P' and $W^2$ are defined as previously described, and $R_5'$ is the same with $R_5$, provided that 1 or 2 hydrogen atoms are excluded therefrom, to produce a compound of formula (30a):

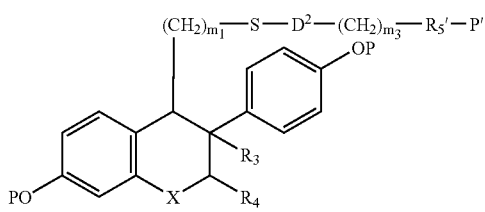
(30a)

wherein X, $R_3$, $R_4$, $R_5'$, $m_1$, $m_3$, $D^2$, P and P' are defined as previously described, the resulting compound of formula (30a) is then deprotected and oxidized to produce the compound of formula (1dc), (e) the compound of formula (13) is reacted with sodium azide and then reduced to produce a compound of formula (31):

(31)

wherein X, $R_3$, $R_4$, $m_1$ and P are defined as previously described, the resulting compound of formula (31) is reacted with a compound of formula (32):

(32)

wherein $R_5$, $m_3$ and $W^2$ are defined as previously described, and then deprotected to produce a compound of formula (1dd):

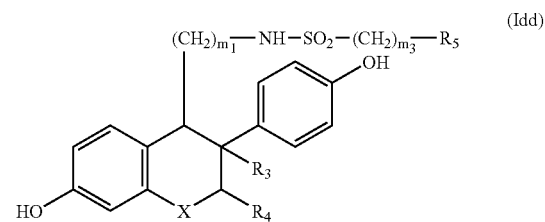
(1dd)

wherein X, $R_3$, $R_4$, $R_5$, $m_1$ and $m_3$ are defined as previously described, (f) the compound of formula (31) is reacted with a compound of formula (32a):

(32a)

wherein $R_5$, $m_3$ and $n_1$ are defined as previously described, and $m_2'$ equals $m_2-1$, and then deprotected to produce a compound of formula (1de):

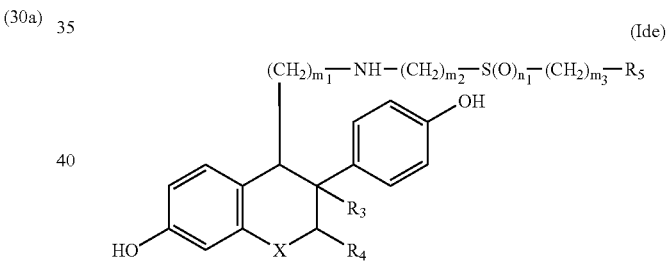
(1de)

wherein X, $R_3$, $R_4$, $R_5$, $m_1$, $m_2$, $m_3$ and $n_1$ are defined as previously described, (g) a compound of formula (33):

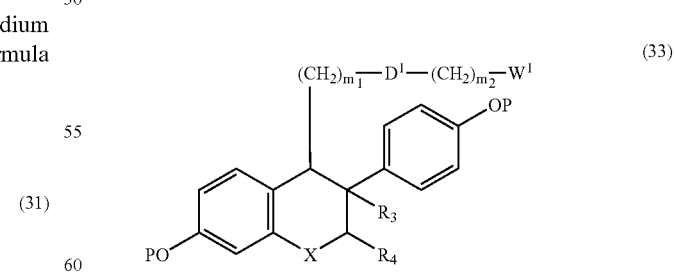
(33)

wherein X, $R_3$, $R_4$, $m_1$, $m_2$, $D^1$, $W^1$ and P are defined as previously described, is reacted with the compound of formula (22):

(22)

wherein $R_5$, $m_3$ and $W^2$ are defined as previously described, to produce a compound of formula (34):

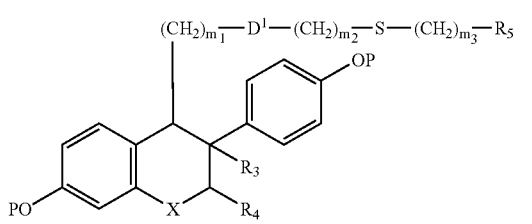

(34)

wherein X, $R_3$, $R_4$, $R_5$, $m_1$, $m_2$, $m_3$, $D^1$ and P are defined as previously described, the resulting compound of formula (34) is then deprotected and oxidized to produce a compound of formula (1df):

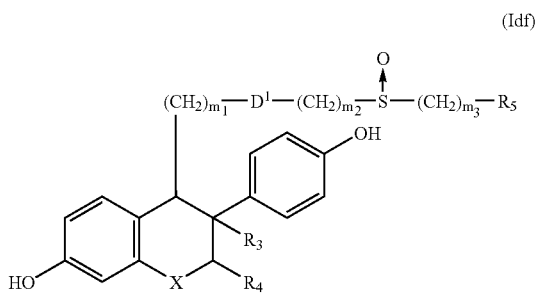

(1df)

wherein X, $R_3$, $R_4$, $R_5$, $m_1$, $m_2$, $m_3$ and $D^1$ are defined as previously described, or (h) a compound of formula (35):

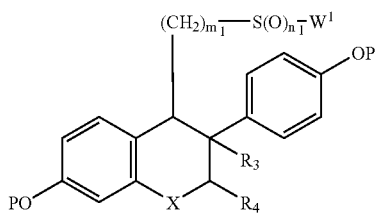

(35)

wherein X, $R_3$, $R_4$, $m_1$, $n_1$, $W^1$ and P are defined as previously described, is reacted with a compound of formula (36):

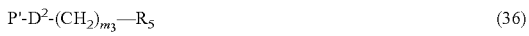

P'-$D^2$-$(CH_2)_{m_3}$-$R_5$ (36)

wherein $R_5$, $m_3$, $D^2$ and P' are defined as previously described, and then deprotected to produce a compound of formula (1dg):

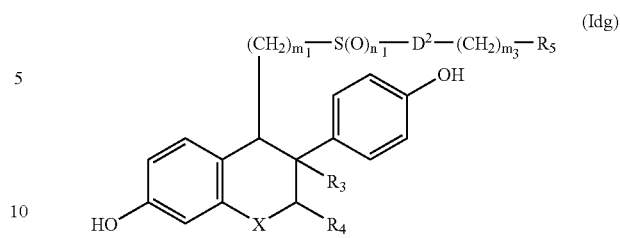

(1dg)

wherein X, $R_3$, $R_4$, $R_5$, $m_1$, $m_3$, $n_1$ and $D^2$ are defined as previously described.

The above methods D(a) to D(h) will be explained more in detail in due order hereinafter.

In the method D(a), the compound of formula (13) is coupled with the compound of formula (25) and then deprotected to produce the compound of formula (1da). The reaction conditions explained for the preparation of the compound of formula (1aa) can be referred to in this coupling and deprotection reaction.

In the method D(b), the compound of formula (27) is prepared by reacting the compound of formula (15) with the compound of formula (26) in a solvent such as methylene chloride in the presence of one or more organic bases selected from triethylamine, pyridine, diisopropylamine and dimethylethylamine under a low temperature. The compound of formula (27) thus prepared is condensed with the compound of formula (28) and then deprotected to produce the desired compound of formula (1 db). The condensation reaction may be carried out optionally in one or more solvents selected from methylene chloride, tetrahydrofuran, acetonitrile and dimethylformamide, and in the presence of a condensing agent such as triphenylphosphine, diethylazodicarboxylate, etc.

In the methods D(c) and D(d), the compound of formula (13) is coupled with the compound of formula (29) or (29a), respectively, to produce the compound of formula (30) or (30a), and the resulting compound (30) or (30a) is then deprotected and oxidized to produce the desired compound of formula (1dc). The optimum reaction condition for the structure of the compound to be reacted can be established by referring to the process for preparing the compound of formula (1aa) for the coupling and deprotection reaction, and referring to the process for preparing the compound of formula (1ca) for the oxidation reaction, respectively.

In the method D(e), the compound of formula (13) is first reacted with sodium azide, and then reduced to produce the amine compound of formula (31). The reaction with sodium azide is preferably carried out in one or more solvents selected from dimethylformamide, acetonitrile, methylene chloride, chloroform and tetrahydrofuran and optionally under nitrogen. The reduction is also carried out using a reducing agent such as Pd/C or Pd(OH)$_2$/C under hydrogen in one or more solvents selected from methanol, ethanol, ethyl acetate and methylene chloride. The amine compound of formula (31) thus obtained is coupled with the compound of formula (32) and then deprotected to produce the desired compound of formula (1dd). The reaction conditions explained for the preparation of the compound of formula (1aa) can be referred to in this coupling and deprotection reaction.

In the method D(f) for preparing the compound of formula (1de), the compound of formula (31) prepared in the above method D(e) is used as the starting material. That is, the compound of formula (31) is coupled with the aldehyde compound of formula (32a) and then deprotected to produce the compound of formula (1de). Here, the coupling reaction with the aldehyde compound is preferably carried out in the presence of a reducing agent such as sodium cyanoborohydride in one or more solvents selected from methanol, methylene chloride, diethylether and dichloroethane. Also, the reaction conditions explained for the preparation of the compound of formula (1aa) can be referred to in this deprotection reaction.

In the method D(g), the compound of formula (33) is first coupled with the compound of formula (22) to produce the compound of formula (34), and the resulting compound (34) is subjected to deprotection and oxidation reaction to produce the desired compound of formula (1df). Here, the optimum reaction condition for the compound to be reacted can be established by referring to the process for preparing the compound of formula (1aa) for the coupling and deprotection reaction, and referring to the process for preparing the compound of formula (1ca) for the oxidation reaction, respectively.

In the method D(h), the compound of formula (35) is first coupled with the compound of formula (36) and then deprotected to produce the desired compound of formula (1dg). Here, the optimum reaction condition for the compound to be reacted can be established by referring to the process for preparing the compound of formula (1aa) for the coupling and deprotection reaction.

(Method E)

The compound of formula (1) wherein A represents group (e), that is a compound of formula (1e):

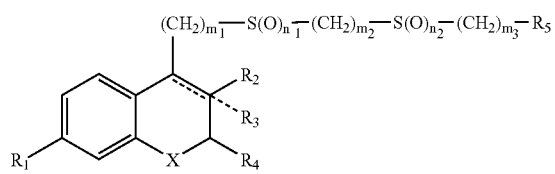

(1e)

wherein X, $R_1$, $R_2$, $R_3$, $R_4$, $R_5$, $m_1$, $m_2$, $m_1$, $n_1$ and $n_2$ are defined as previously described, can be prepared by a process characterized in that a compound of formula (13):

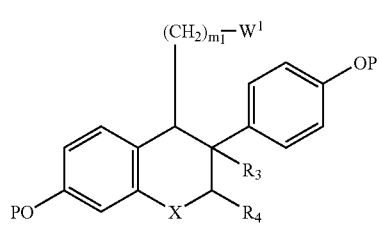

(13)

wherein X, $R_3$, $R_4$, $m_1$, P and $W^1$ are defined as previously described, is reacted with a compound of formula (37):

$$W^3S-(CH_2)_{m_2}-S(O)_{n_2}-(CH_2)_{m_3}-R_4 \quad (37)$$

wherein $R_5$, $m_2$, $m_3$ and $n_2$ are defined as previously described and $W^3$ represents acyl group, and the resulting compound is then deprotected and oxidized to produce a compound of formula (1ea):

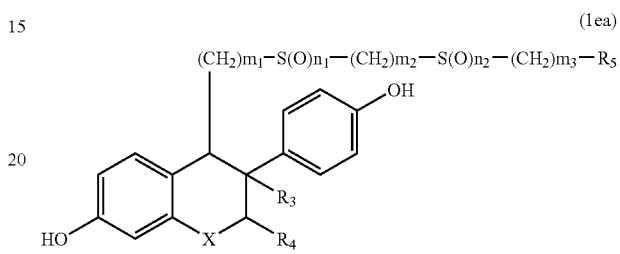

(1ea)

wherein X, $R_3$, $R_4$, $R_5$, $m_1$, $m_2$, $m_3$, $n_1$ and $n_2$ are defined as previously described.

The reaction of the compound (13) and (37) can be carried out in one or more solvents selected from methanol, ethanol and acetonitrile and optically in the presence of one or more bases selected from sodium hydroxide, sodium ethoxide and sodium methoxide under warming for 1 to 20 hours. The deprotection can be carried out using a conventional method such as hydrolysis in the presence of acid or base. Preferably, the deprotection is achieved in the presence of one or more hydrolyzing agents selected from a group consisting of borontribromide, hydrochloric acid, hydrobromic acid and pyridinium-p-toluenesulfonate The oxidation can be carried out under the condition selected from the various conditions based on the structure and nature of the compound. Generally, the oxidation is carried out in one or more solvents selected from methanol, water, chloroform, tetrahydrofuran, dioxane, ethanol and methylene chloride in the presence of one or more oxidizing agents selected from sodium periodate, metachloroperbenzoic acid, hydrogen peroxide and Oxone® (monopersulfate compound; DuPont product).

(Method F)

The compound of formula (1) wherein A represents group (f), that is a compound of formula (1f):

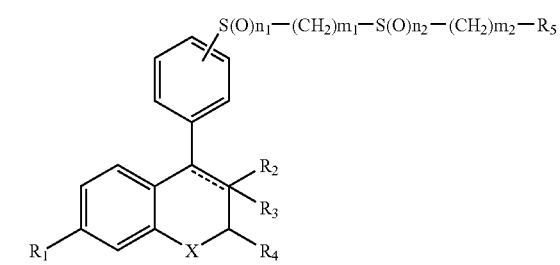

(1f)

wherein X, $R_1R_2$, $R_3$, $R_4$, $R_5$, $m_1$, $m_2$, $n_1$ and $n_2$ are defined as previously described, can be prepared by a process characterized in that a compound of formula (38):

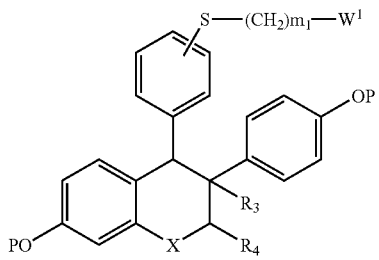

(38)

wherein X, $R_3$, $R_4$, $m_1$, P and $W^1$ are defined as previously described, is reacted with a compound of formula (39):

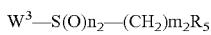

(39)

wherein $R_5$, $m_2$ and $W^3$ are defined as previously described, and the resulting compound is then deprotected and oxidized to produce a compound of formula (1fa):

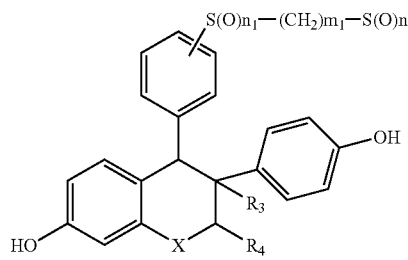

(1fa)

wherein X, $R_3$, $R_4$, $R_5$, $m_1$, $m_2$, $n_1$, and $n_2$ are defined as previously described.

The reaction of the compound (38) and (39) can be carried out in one or more solvents selected from methanol, ethanol and acetonitrile and optically in the presence of one or more bases selected from sodium hydroxide, sodium ethoxide and sodium methoxide under warming for 1 to 20 hours. The deprotection can be carried out using a conventional method such as hydrolysis in the presence of acid or base. Preferably, the deprotection is achieved in the presence of one or more hydrolyzing agents selected from a group consisting of borontribromide, hydrochloric acid, hydrobromic acid and pyridinium-p-toluenesulfonate. The oxidation can be carried out under the condition selected from the various conditions based on the structure and nature of the compound. Generally, the oxidation is carried out in one or more solvents selected from methanol, water, chloroform, tetrahydrofuran, dioxane, ethanol and methylene chloride in the presence of one or more oxidizing agents selected from sodium periodate, metachloroperbenzoic acid, hydrogen peroxide and Oxone® (monopersulfate compound; DuPont product).

(Meth d G)

The compound of formula (1) wherein A represents group (g), that is a compound of formula (1g):

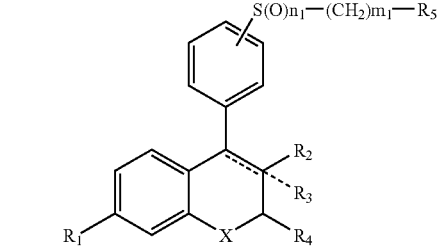

(1g)

wherein X, $R_1$, $R_2$, $R_3$, $R_4$, $R_5$, $m_1$ and $n_1$ are defined as previously described, can be prepared by a process characterized in that a compound of formula (38):

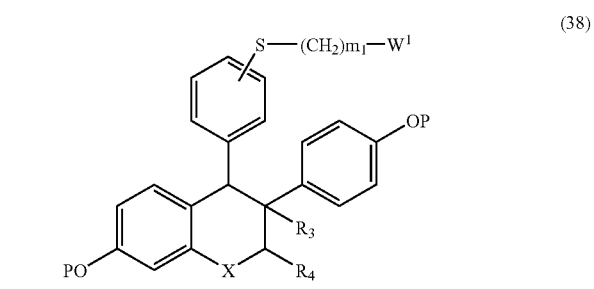

(38)

wherein X, $R_3$, $R_4$, $m_1$, P, and $W^1$ are defined as previously described, is reacted with a compound of formula (40):

(40)

wherein $R_5$ is defined as previously described, $W^4$ represents hydrogen, and the resulting compound is then deprotected to produce a compound of formula (1ga):

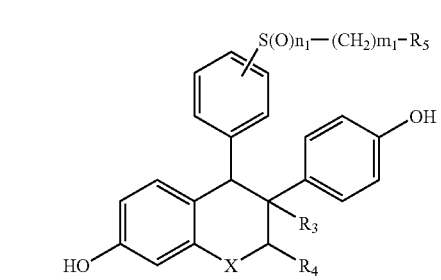

(1ga)

wherein X, $R_3$, $R_4$, $R_5$, $m_1$ and $n_1$ are defined as previously described.

The reaction of the compound (38) and (40) can be carried out in one or more solvents selected from methanol, ethanol and acetonitrile under refluxing for 1 to 48 hours. The deprotection can be carried out using a conventional method such as hydrolysis in the presence of acid or base. Preferably, the deprotection is achieved in the presence of one or more hydrolyzing agents selected from a group consisting of borontribromide, hydrochloric acid, hydrobromic acid and pyridinium-p-toluenesulfonate.

(Method H)

The compound of formula (1) wherein A represents group (h), that is a compound of formula (1h):

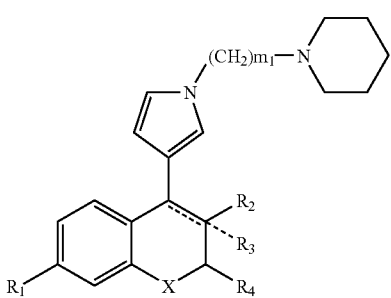

(1h)

wherein X, $R_1$, $R_2$, $R_3$, $R_4$ and $m_1$ are defined as previously described, can be prepared by a process characterized in that a compound of formula (41):

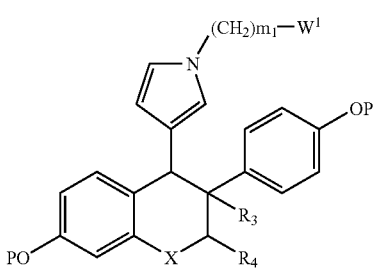

(41)

wherein X, $R_3$, $R_4$, $m_1$, P and $W^1$ are defined as previously described, is reacted with a compound of formula (42):

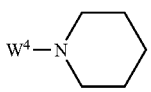

(42)

wherein $W^4$ is defined as previously described, and the resulting compound is then deprotected to produce a compound of formula (1ha):

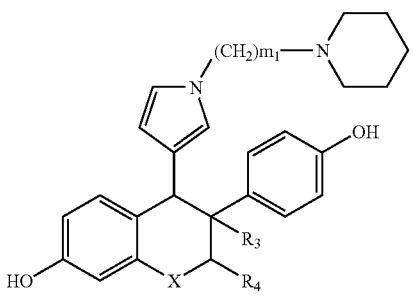

(1ha)

wherein X, $R_3$, $R_4$ and $m_1$ are defined as previously described.

The reaction of the compound (41) and (42) can be carried out in one or more solvents selected from methanol, ethanol and acetonitrile under refluxing for 1 to 48 hours. The deprotection can be carried out using a conventional method such as hydrolysis in the presence of acid or base. Preferably, the deprotection is achieved in the presence of one or more hydrolyzing agents selected from a group consisting of borontribromide, hydrochloric acid, hydrobromic acid and pyridinium-p-toluenesulfonate.

(Method I)

The compound of formula (1) wherein A represents group (i), that is a compound of formula (1i):

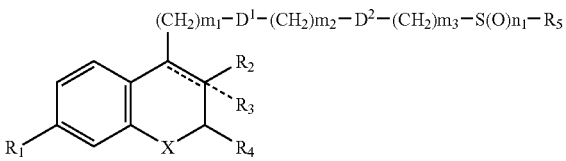

(1i)

wherein X, $R_1$, $R_2$, $R_3$, $R_4$, $R_5$, $D^1$, $D^2$, $m_1$, $m_2$, $m_3$ and $n_1$ are defined as previously described, can be prepared according to the similar procedure as Method D.

(Method J)

The compound of formula (1) wherein A represents group (j), that is a compound of formula (1j):

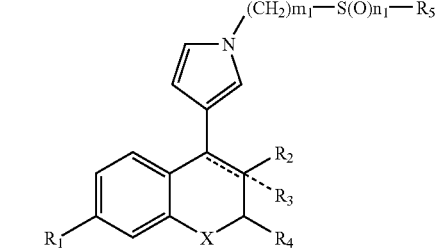

(1j)

wherein X, $R_1$, $R_2$, $R_3$, $R_4$, $R_5$, $m_1$ and $n_1$ are defined as previously described, can be prepared by a process characterized in that a compound of formula (41):

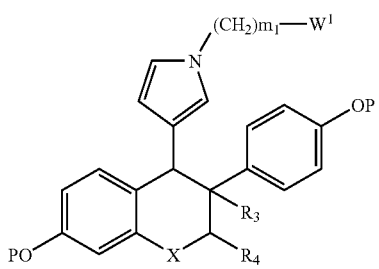

(41)

wherein X, $R_3$, $R_4$, $m_1$, P and $W^1$ are defined as previously described, is reacted with a compound of formula (43):

$$W^3-S(O)n_1-R_5 \qquad (43)$$

wherein $R_5$, $n_1$ and $W^3$ are defined as previously described, and the resulting compound is then deprotected and oxidized to produce a compound of formula (1ja):

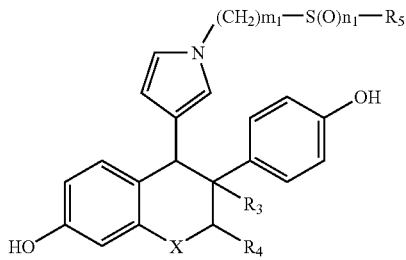

(1ja)

wherein X, $R_3$, $R_4$, $R_5$, $m_1$ and $n_1$ are defined as previously described.

The reaction of the compound (41) and (43) can be carried out in one or more solvents selected from methanol, ethanol and acetonitrile and optically in the presence of one or more bases selected from sodium hydroxide, sodium ethoxide and sodium methoxide under warming for 1 to 20 hours. The deprotection can be carried out using a conventional method such as hydrolysis in the presence of acid or base. Preferably, the deprotection is achieved in the presence of one or more hydrolyzing agents selected from a group consisting of borontribromide, hydrochloric acid, hydrobromic acid and pyridinium-p-toluenesulfonate. The oxidation can be carried out under the condition selected from the various conditions based on the structure and nature of the compound. Generally, the oxidation is carried out in one or more solvents selected from methanol, water, chloroform, tetrahydrofuran, dioxane, ethanol and methylene, chloride in the presence of one or more oxidizing agents selected from sodium periodate, metachloroperbenzoic acid, hydrogen peroxide and Oxone® (monopersulfate compound; DuPont product).

(Method K)

The compound of formula (1) wherein A represents group (k), that is a compound of formula (1k):

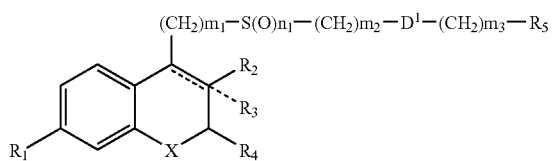

(1k)

wherein X, $R_1$, $R_2$, $R_3$, $R_4$, $R_5$, $m_1$, $m_2$, $n_1$ and and $D^1$ are defined as previously described, can be prepared by a process characterized in that a compound of formula (13):

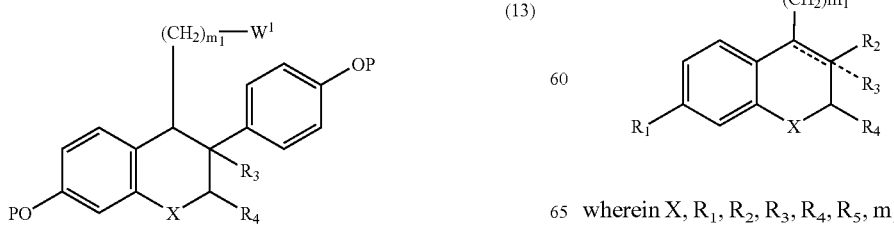

(13)

wherein X, $R_3$, $R_4$, $m_1$, P and $W^1$ are defined as previously described, is reacted with a compound of formula (44):

$$W^3S—(CH_2)m_2-D^1-(CH_2)m_3—R_5 \qquad (44)$$

wherein $R_5$, $m_2$, $m_3$, $W^3$ and $D^1$ are defined as previously described, and the resulting compound is then deprotected and oxidized to produce a compound of formula (1ka):

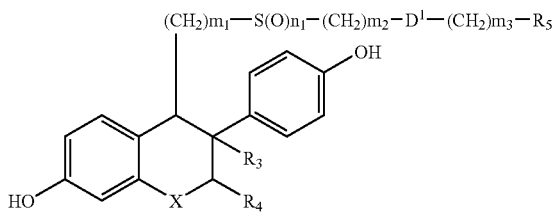

(1ka)

wherein X, $R_3$, $R_4$, $R_5$, $m_1$, $m_2$, $m_3$, $n_1$ and $D^1$ are defined as previously described.

The reaction of the compound (13) and (44) can be carried out in one or more solvents selected from methanol, ethanol and acetonitrile and optically in the presence of one or more bases selected from sodium hydroxide, sodium ethoxide and sodium methoxide under warming for 1 to 20 hours. The deprotection can be carried out using a conventional method such as hydrolysis in the presence of acid or base. Preferably, the deprotection is achieved in the presence of one or more hydrolyzing agents selected from a group consisting of borontribromide, hydrochloric acid, hydrobromic acid and pyridinium-p-toluenesulfonate. The oxidation can be carried out under the condition selected from the various conditions based on the structure and nature of the compound. Generally, the oxidation is carried out in one or more solvents selected from methanol, water, chloroform, tetrahydrofuran, dioxane, ethanol and methylene chloride in the presence of one or more oxidizing agents selected from sodium periodate, metachloroperbenzoic acid, hydrogen peroxide and Oxone® (monopersulfate compound; DuPont product).

(Method L)

The compound of formula (1) wherein A represents group (l), that is a compound of formula (1l):

(1l)

wherein X, $R_1$, $R_2$, $R_3$, $R_4$, $R_5$, $m_1$, $m_2$, $m_3$ and $D^1$ are defined as previously described, can be prepared by a process characterized in that a compound of formula (45):

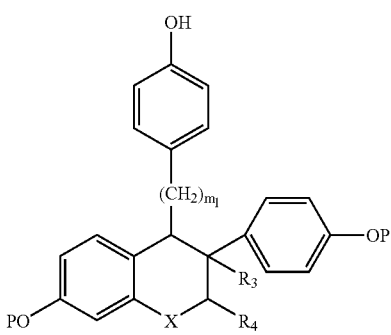
(45)

wherein X, $R_3$, $R_4$, $m_1$ and P are defined as previously described, is reacted with a compound of formula (46):

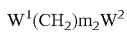
$W^1(CH_2)_{m_2}W^2$ (46)

wherein $m_2$, $W^1$ and $W^2$ are defined as previously described, to produce a compound of formula (47):

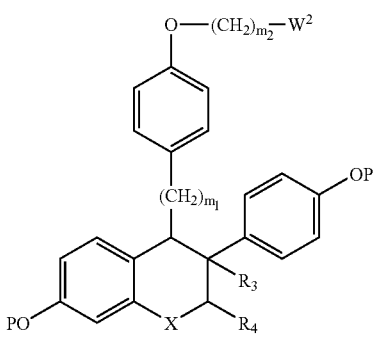
(47)

wherein X, $R_3$, $R_4$, $m_1$, $m_2$, $W^2$ and P are defined as previously described, the resulting compound of formula (47) is reacted with a compound of formula (14):

$D^1H_2$ (14)

wherein $D^1$ is defined as previously described, to produce a compound of formula (48):

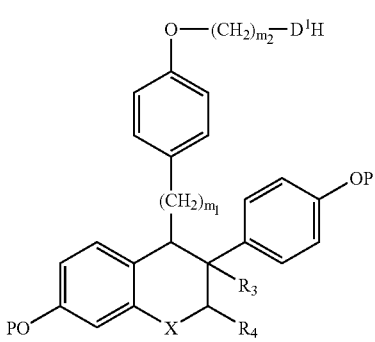
(48)

wherein X, $R_3$, $R_4$, $m_1$, $m_2$, $D^1$ and P are defined as previously described, the resulting compound of formula (48) is reacted with a compound of formula (16a):

$W^5-(CH_2)_{m_3}-R_5$ (16a)

wherein $R_5$ and $m_3$ are defined as previously described, and $W^5$ represents a leaving group and then deprotected to produce a compound of formula (11a):

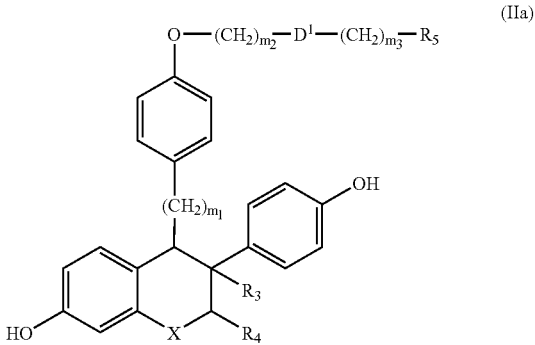
(IIa)

wherein X, $R_3$, $R_4$, $R_5$, $m_1$, $m_2$, $m_3$ and $D^1$ are defined as previously described.

The coupling step of the compound (45) and (46) may be carried out in a solvent. As the preferable solvent, one or more selected from a group consisting of dioxane, methanol, ethanol, diethylether, tetrahydrofuran, dimethylsulfoxide, methylene chloride, dimethylformamide, chloroform, ethyl acetate, acetonitrile and acetone can be used. This reaction may be carried out optionally in the presence of one or more inorganic or organic bases selected from a group consisting of potassium carbonate, potassium hydroxide, sodium hydroxide, sodium methoxide, sodium ethoxide, triethylamine and cesium carbonate. The reaction may be suitably proceeded under the reflux temperature of the solvent used or room temperature, if appropriate, under ice-cooling.

The coupling step of the compound (47) and (14) in a solvent. As the preferable solvent, one or more selected from a group consisting of dioxane, methanol, ethanol, diethylether, tetrahydrofuran, dimethylsulfoxide, methylene chloride, dimethylformamide, chloroform, ethyl acetate, acetonitrile and acetone can be used. This reaction may be carried out optionally in the presence of one or more inorganic or organic bases selected from a group consisting of potassium carbonate, potassium hydroxide, sodium hydroxide, sodium methoxide, sodium ethoxide, triethylamine and cesium carbonate. The reaction may be suitably proceeded under the reflux temperature of the solvent used or room temperature, if appropriate, under ice-cooling.

The coupling step of the compound (48) and (16a) in a solvent. As the preferable solvent, one or more selected from a group consisting of dioxane, methanol, ethanol, diethylether, tetrahydrofuran, dimethylsulfoxide, methylene chloride, dimethylformamide, chloroform, ethyl acetate, acetonitrile and acetone can be used. This reaction may be carried out optionally in the presence of one or more inorganic or organic bases selected from a group consisting of potassium carbonate, potassium hydroxide, sodium hydroxide, sodium methoxide, sodium ethoxide, triethylamine and cesium carbonate. The reaction may be suitably proceeded under the reflux temperature of the solvent used or room temperature, if appropriate, under ice-cooling.and then deprotected to produce the compound of formula (11a). This reaction can be carried out in one or more solvents selected from a group consisting of acetone, toluene, dimethylformamide, acetonitrile, dimethylsulfoxide and methylene chloride, optionally in the presence of a base such as potassium carbonate, triethylamine, sodium ethoxide, etc. The deprotection reaction may be carried out according to a conventional method such as hydrolysis in the presence of acid or base, reduction, etc. Preferably, the deprotection is achieved in the presence of one or more hydrolyzing agents selected from a group consisting of borontribromide, hydrochloric acid, hydrobromic acid, hydrofluoric acid, pyridinium-p-toluenesulfonate and sulfuric acid, or in the presence of one or more reducing agents selected from a group consisting of Pd(OH)$_2$/C under hydrogen, Pd/C and diisobutylaluminum hydride (DIBAL). This reaction can be carried out under a low temperature to warmning, preferably carried out by starting at a low temperature of −78° C. and then warming to room temperature. While, the compound of formula (1aa) thus produced may be further oxidized using metachloroperbenzoic acid (mCPBA) in a solvent such as chloroform.

The desired compounds obtained in each processes may be separated and purified using the conventional methods such as column chromatography, recrystallization, etc.

The above processes I to V according to the present invention will be more specifically explained through the following examples.

As stated above, the compound of formula (1) prepared according to the process of the present invention as mentioned above has a good anti-estrogenic activity and, therefore, can be used for the treatment of estrogen-related diseases including anovular infertility, breast cancer, endometrial cancer, uterine cancer, ovarian cancer, endometriosis, endometfial fibroma, benign prostate hypertrophy, premature, menstrual disorder, etc.

Therefore, the present invention relates to an anti-estrogenic pharmaceutical composition containing the compound of formula (1) as an active component.

When the anti-estrogenic pharmaceutical composition containing the compound of the present invention as an active component is used for clinical purpose, it can be formulated into a conventional preparation in the pharmaceutical field, for example, preparation for oral administration such as tablet, capsule, troche, solution, suspension, etc., or injectable preparation such as injectable solution or suspension, ready-to-use injectable dry powder which can be reconstituted with distilled water for injection when it is injected, etc., by combining with a carrier conventionally used in the pharmaceutical field.

Suitable carrier which can be used in the composition of the present invention includes those conventionally used in the pharmaceutical field, for example, binder, lubricant, disintegrant, excipient, solubilizer, dispersing agent, stabilizing agent, suspending agent, coloring agent, perfume, etc. for oral preparation; and preservative, pain alleviating agent, solubilizing agent, stabilizing agent, etc. for injectable preparation. The pharmaceutical preparation thus prepared can be administered orally or parenterally, for example, intravenously, subcutaneously or intraperitoneally. In addition, in order to prevent the active component from the decomposition with gastric acid, the oral preparation can be administered together with an antacid or in the enteric-coated form of the solid preparation such as tablet.

The dosage of the benzopyran or thiobenzopyran derivative of formula (1) according to the present invention for human being can be suitably determined depending on absorption, inactivation and secretion of the active ingredient in the human body, age, sex and condition of subject patient, kinds and severity of disease to be treated. It is generally suitable to administer the compound of formula (1) in an amount of 1 to 500 mg, preferably 5 to 200, per day for adult patient.

The present invention is more specifically explained by the following examples. However, it should be understood that the present invention is not limited to these examples in any manner.

EXAMPLE 1

Synthesis of 7-hydroxy-3-(4-hydroxyphenyl)-3-methyl-4-{9-[4-(4,4,5,5,5-pentafluoropentyl)piperazinyl]nonyl}chroman Step 1) Synthesis of 7-(methoxymethoxy)-3-(4-methoxymethoxyphenyl)-4-(9-piperazinylnonyl)-3-methylchroman

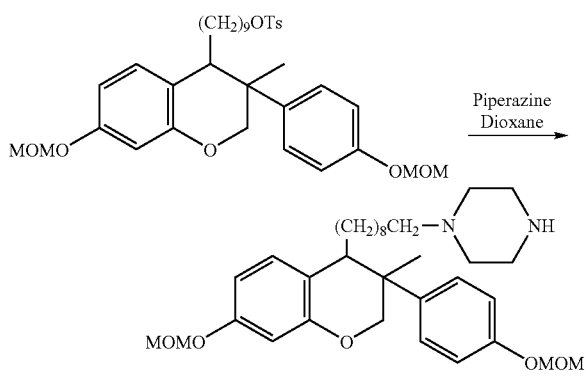

9-{7-(Methoxymethoxy)-3-[4-(methoxymethoxy)phenyl]-3-methylchroman-4-yl}nonyl 4-methylbenzenesulfonate (540 mg, 0.843 mmol) and piperazine (2.2 g, 25.5 mmol) were dissolved in dioxane and then the mixture was refluxed for 2 hours. The mixture was cooled down to room temperature, basified to pH 13 using 5N-NaOH, and then extracted with ethyl acetate. The organic layer was dried over anhydrous magnesium sulfate and filtered, and the organic solvent was removed under reduced pressure. The concentrate was subjected to column chromatography (methanol) to give 380 mg (yield: 81%, (3RS,4RS):(3RS, 4SR)=5:4) of the title compound as a white solid.

$^1$H NMR (300 MHz, CDCl$_3$, (3RS,4RS)-compound) δ: 0.99 (s, 3H), 1.19 (brs, 14H), 1.38 (brs, 2H), 2.19 (t, 2H), 2.3 (brs, 4H), 2.79 (brs, 4H), 2.98 (m, 1H), 3.39 (s, 6H), 3.83 (d, 1H), 4.11 (d, 1H), 5.05 (d, 4H), 6.48 (d, 2H), 6.80–6.95 (m, 3H), 7.48 (d, 2H)

Step 2) Synthesis of 7-(methoxymethoxy)-3-(4-methoxymethoxyphenyl)-4-{9-[4-(4,4,5,5,5-pentafluoropentyl)piperazinyl]nonyl}-3-methylchroman

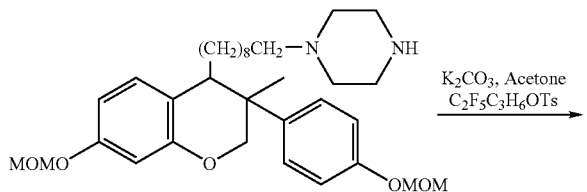

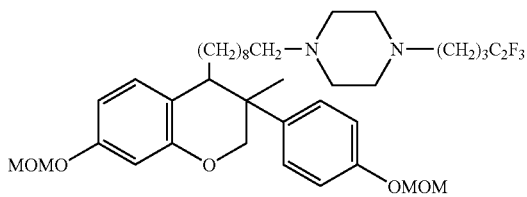

7-(Methoxymethoxy)-3-(4-methoxymethoxyphenyl)-4-(9-piperazinylnonyl)-3-methylchroman (380 mg, 0.685 mmol), $K_2CO_3$ (190 mg, 1.375 mmol) and 4,4,5,5,5-pentafluoropentyl-4-methylbenzenesulfonate (460 mg, 1.384 mmol) were refluxed under acetone for 15 hours. After the mixture was cooled down to room temperature, water was added thereto, and the resulting mixture was extracted with ethyl acetate. The organic layer was dried over anhydrous magnesium sulfate, filtered, and the organic solvent was removed under reduced pressure. The concentrate was subjected to column chromatography (n-hexane:ethyl acetate=4:1) to give 238 mg (yield: 48%) of the title compound as a white solid.

$^1$H NMR (300 MHz, $CDCl_3$, (3RS,4RS)-compound) δ: 0.82–1.30 (m, 19H), 1.4 (brs, 4H), 2.3 (m, 6H), 3.05 (m, 1H), 3.31 (s, 2H), 3.37 (s, 6H), 3.40 (s, 2H), 3.43 (brs, 2H), 3.86 (d, 1H), 4.13–4.21 (m, 1H), 5.1 (m, 4H), 6.4–6.5 (m, 2H), 6.94–6.85 (m, 3H), 7.20 (d, 2H)

Step 3) Synthesis of 7-hydroxy-3-(4-hydroxyphenyl)-3-methyl-4-{9-[4-(4,4,5,5,5-pentafluoropentyl)piperazinyl]nonyl}chroman

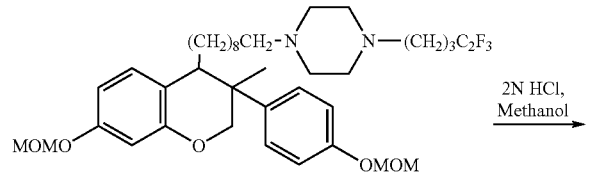

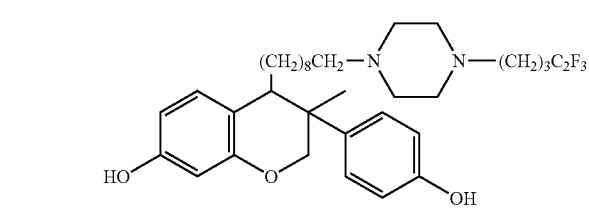

7-(Methoxymethoxy)-3-(4-methoxymethoxyphenyl)-4-{9-[4-(4,4,5,5,5-pentafluoropentyl)piperazinyl]nonyl}-3-methylchroman (210 mg, 0.294 mmol) was dissolved in 2N-HCl solution in methanol, and the mixture was stirred at 50° C. for 1 hour. The mixture was cooled down to room temperature, adjusted to pH=9 using aqueous NaHCO solution, and then extracted with ethyl acetate. The organic layer was dried over anhydrous magnesium sulfate, filtered, and the organic solvent was removed under reduced pressure. The concentrate was subjected to column chromatography (n-hexane:ethyl acetate=1:1) to give 162 mg (yield: 88%. (3RS,4RS):(3RS,4SR)=8:5) of the title compound as a white solid.

$^1$H NMR (300 MHz, $CDCl_3$, (3RS,4RS)-compound) δ: 0.8–1.2 (brs, 19H), 1.36 (brs, 4H), 1.86–2.1 (m, 2H), 2.30 (m, 4H), 2.48 (brs, 7H), 4.12 (d, 1H), 4.39 (d, 1H), 6.23 (s, 1H), 6.26 (m, 1H), 6.64 (m, 3H), 6.69 (m, 2H)

EXAMPLE 2

Synthesis of (3RS,4RS)-7-hydroxy-4-[(11-imino-11-N-butylamino)undecyl]-3-(4-hydroxyphenyl)-3-methylchroman and (3RS,4RS)-7-hydroxy-4-[(11-N-butylimino-11-N-butylamino)undecyl]-3-(4-hydroxyphenyl)-3-methylchroman Step 1) Synthesis of (3RS,4RS)-4-(10-cyanodecyl)-7-(methoxymethoxy)-3-[4-(methoxymethoxy)phenyl]-3-methylchroman

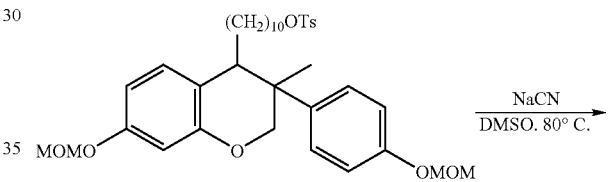

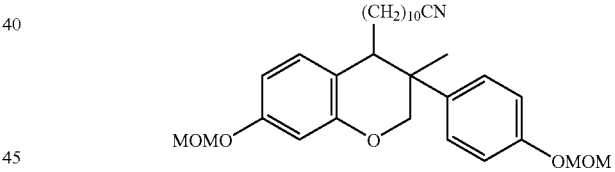

(3RS,4RS)-4-[10-(4-Methylbenzenesulfonyldecyl]-7-(methoxymethoxy)-3-[4-(methoxymethoxy)phenyl]-3-methylchroman (233 mg, 0.37 mmol) and NaCN (54.7 mg, 1.1 mmol) were dissolved in DMSO (5 ml) and the resulting mixture was stirred at 80° C. for 10 hours. After the mixture was cooled down to room temperature, water was added thereto, and the reaction mixture was extracted with ethyl acetate. The organic layer was dried over anhydrous magnesium sulfate, filtered, and the organic solvent was removed under reduced pressure. The concentrate was subjected to column chromatography (n-hexane:ethyl acetate=8:1) to give 128 mg (yield: 68%) of the title compound as a colorless oil.

$^1$H NMR (300 MHz, $CDCl_3$) δ: 0.87–1.37 (m, 18H), 1.35 (q, 3H), 2.23 (t, 2H), 2.56 (m, 1H), 3.42 (d, 6H), 4.19 (dd, 1H), 4.46 (dd, 1H), 5.01 (d, 4H), 6.46 (m, 2H), 6.82 (dd, 1H), 6.91 (d, 2H), 7.01 (d, 2H)

Step 2) Synthesis of (3RS,4RS)-7-hydroxy-4-[(11-imino-11-N-butylamino)undecyl]-3-(4-hydroxyphenyl)-3-methylchroman(I) and (3RS,4RS)-7-hydroxy-4-[(11-N-butyl-imino-11-N-butylamino)undecyl]-3-(4-hydroxyphenyl)-3-methylchroman(II)

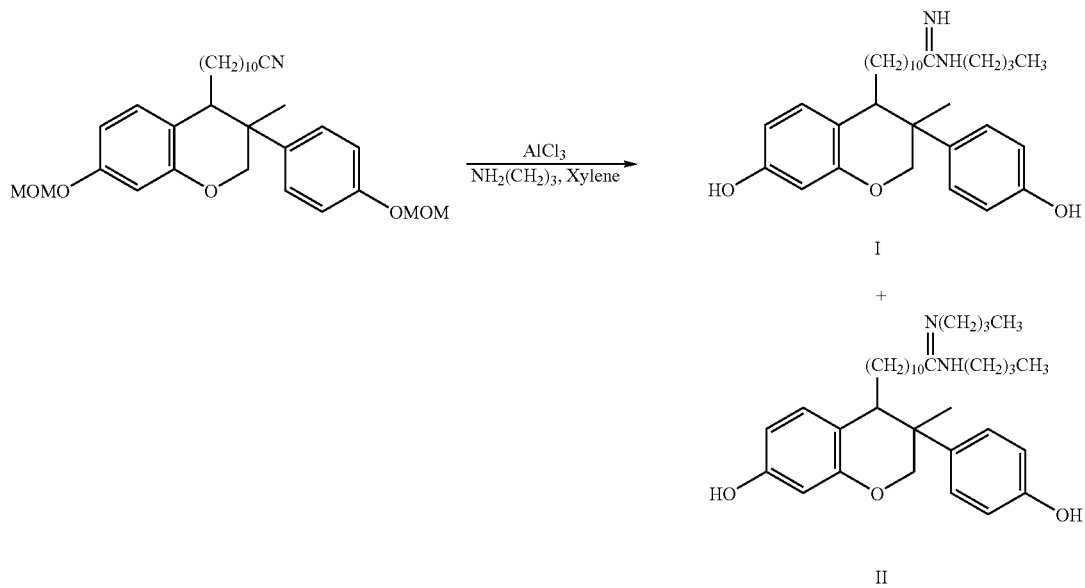

(3RS,4RS)-4-(10-Cyanodecyl)-7-(methoxymethoxy)-3-[4-(methoxymethoxy)phenyl]-3-methylchroman (70 mg, 0.14 mmol) and AlCl$_3$ (73.2 mg, 0.56 mmol) were dissolved in xylene (3 mL), butylamine (61.4 mg, 0.84 mmol) was added dropwise thereto, and the resulting mixture was refluxed for 1.5 hour. The mixture was cooled down to normal temperature, water was added thereto, and the reaction mixture was extracted with ethyl acetate. The organic layer was dried over anhydrous magnesium sulfate, filtered, and the organic solvent was removed under reduced pressure. The concentrate was subjected to base silica gel column chromatography (ethyl acetate:ethanol=5:1) to give the compound I (19 mg, yield 27%) and the compound 11 (30.8 mg, yield 40%).

<Compound I>

$^1$H NMR (300 MHz, CD$_3$OD) δ: 0.8 (t, 3H), 0.82–1.7 (m, 23H), 2.23 (t, 2H), 2:52 (m, 1H), 2.92 (broad), 3.15 (t, 2H), 4.06 (dd, 1H), 4.37 (dd, 1H), 6.16 (m, 2H), 6.43–6.72 (m, 3H), 6.89 (dd, 2H)

<Compound II>

$^1$H NMR (300 MHz, CD3OD) δ: 0.84 (t, 6H), 0.84–1.73 (m, 26H), 2.3 (t, 2H), 2.55 (m, 1H), 3.2 (t, 4H), 4.1 (dd, 1H), 4.39 (dd, 1H), 6.21 (m, 2H), 6.43–6.72 (m, 3H), 6.89 (dd, 2H)

EXAMPLE 3

Synthesis of (3RS,4SR)-7-hydroxy-4-{4-{2-{4-{[3,5-bis(t-butyl)phenyl]methyl}piperazinyl}ethoxy}phenyl}-3-(4-hydroxyphenyl)-3-methylchroman Step 1) Synthesis of 3,5-bis(t-butyl)-1-(bromomethyl)benzene

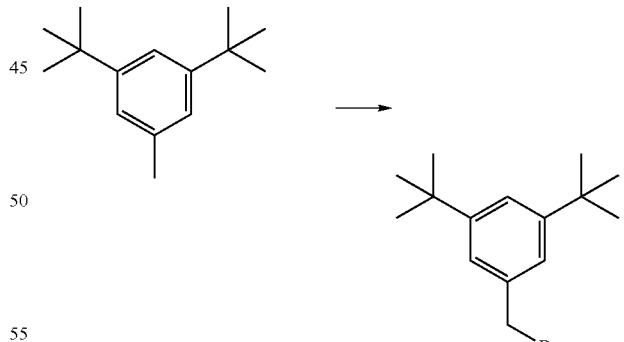

3,5-Bis(t-butyl)-1-methylbenzene (200 mg, 0.98 mmol) was dissolved in carbon tetrachloride (4 ml), and then N-bromosuccinimide (192 mg, 1.08 mmol) and AIBN (α,α'-azabisisobutyronitrile) (2 mg) were added thereto. The mixture was heated under reflux and stirred for 5 hours. The filtrate obtained from the filtration of the reaction mixture was evaporated under reduced pressure to give 170 mg (yield: 61%) of a pale yellow oil.

$^1$H-NMR (300 MHz CDCl$_3$) δ: 1.30 (s, 18H), 4.52 (s, 2H), 7.21 (s, 2H), 7.38 (s, 1H)

Step 2) Synthesis of t-butyl 4-{[3,5-bis(t-butyl)phenyl]methyl}piperazine carboxylate

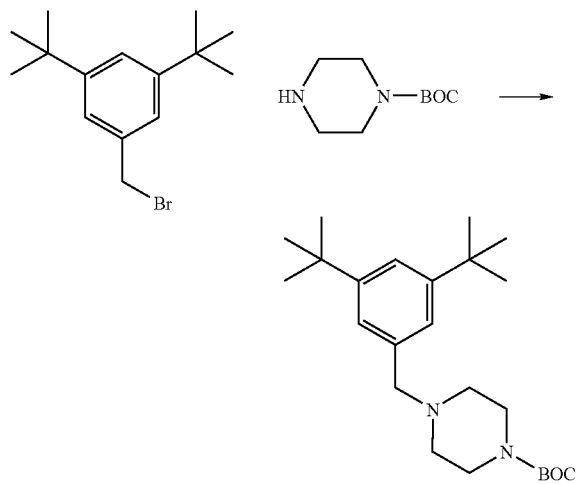

3,5-Bis(t-butyl)-1-(bromomethyl)benzene (170 mg, 0.60 mmol), t-butyl piperazine carboxylate (102 mg, 0.55 mmol) and potassium carbonate (151 mg, 1.10 mmol) were dissolved in a solvent mixture of acetone (2 ml) and DMF (0.2 ml), and the mixture was stirred overnight while heated under reflux. The reaction mixture was extracted with ethyl acetate, dried over sodium sulfate, and then the filtrate was evaporated under reduced pressure. The concentrate was subjected to silica gel column chromatography (n-hexane:ethyl acetate=4:1) to give 120 mg (yield: 56%) of the title compound as a white solid.

$^1$H-NMR (300 MHz, CDCl$_3$) δ: 1.31 (s, 18H), 1.42 (s, 9H), 2.46 (t, 4H), 3.38 (t, 4H), 3.49 (s, 2H), 7.11 (s, 2H), 7.27 (s, 1H)

Step 3) Synthesis of {[3,5-bis(t-butyl)phenyl]methyl}piperazinedihydro chloride

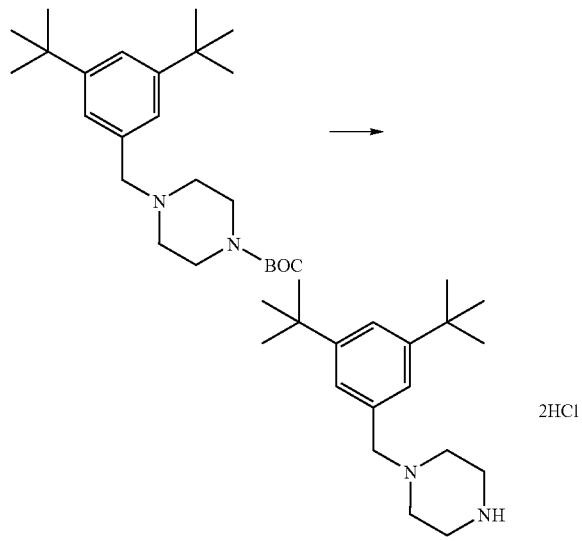

t-Butyl 4-{[3,5-bis(t-butyl)phenyl]methyl}piperazinecarboxylate (1.88 g, 4.84 mmol) was dissolved in dichloromethane (20 ml), 4N-HCl (1,4-dioxane solution) (10 ml) was added dropwise thereto at 0° C., and the mixture was stirred at room temperature for 2 hours. The reaction solution was evaporated under reduced pressure to give 2.15 g (yield: 100%) of the title compound as a white solid.

$^1$H-NMR (300 MHz, CD$_3$OD) δ: 1.38 (s, 18H), 3.56–3.64 (m, 8H), 4.45 (s, 2H), 7.50 (s, 2H), 7.61 (s, 1H)

Step 4) Synthesis of (3RS,4SR)-4-[4-(t-butyldimethylsilyloxy)phenyl]-7-(methoxy-methoxy)-3-[4-(methoxymethoxy)phenyl]-3-methylchroman

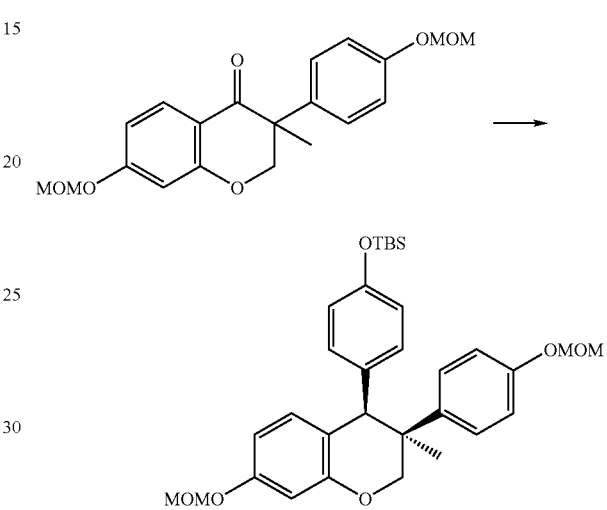

Magnesium (909 mg, 37.39 mmol) and iodine (10 mg) were introduced into a 250 ml flask saturated with argon. 2 ml of a solution wherein 1-bromo-4-(t-butyldimethylsilyloxy) benzene (8.06 g, 28.05 mmol) was dissolved in dry tetrahydrofuran (35 ml) was added portionwise thereto, and the mixture was heated. After the brown color disappeared, the remaining sblution (33 ml) was slowly added portionwise thereto again under reflux condition. After the mixture was heated under reflux for 2 hours, 7-(methoxymethoxy)-3-[4-(methoxymethoxy)phenyl]-3-methylchroman-4-one (6.7 g, 18.69 mmol) dissolved in dry tetrahydrofuran (35 ml) was slowly added portionwise at room temperature, and the resulting mixture was stirred under reflux for 2 hours. The reaction mixture was treated with ice water, extracted with ethyl acetate, washed with saline solution, dried over sodium sulfate, and then filtered. The filtrate was evaporated under reduced pressure and the concentrate thus obtained was subjected to silica gel column chromatography (n-hexane:ethyl acetate=8:1) to give 7.4g of a colorless oil. This oil was dissolved in 1,2-dichloroethane (150 ml) zine iodide (6.25 g, 19.58 mmol) and sodium cyanoborohydride (5.74 g, 91.34 mmol) were added thereto at 0° C., and the resulting mixture was stirred for 10 minutes. The mixture was stirred at room temperature for further 1 hour, treated with water, and extracted with dichloromethane. The extract was washed with saline solution, dried over sodium sulfate, and filtered. The filtrate was evaporated under reduced pressure and the concentrate thus obtained was subjected to silica gel column chromatography (n-hexane:ethyl acetate=16:1) to give 2.19 g (yield. 21%) of a colorless oil.

¹H-NMR (300 MHz, CDCl₃) δ: 0.01 (s, 6H), 0.83 (s, 9H), 1.38 (s, 3H), 3.37 (s, 6H), 3.78 (s, 1H), 3.90 (dd, 1H), 4.48 (dd, 1H), 5.06 (s, 4H), 6.33 (m, 4H), 6.44 (dd, 1H), 6.56 (t, 1H), 6.70 (m, 5H)

Step 5) Synthesis of (3RS,4SR)-4-[4-(2-chloroethoxy)phenyl]-7-(methoxymethoxy)-3-[4-(methoxymethoxy)phenyl]-3-methylchroman ¹H-NMR (300 MHz, CDCl₃) δ: 1.51 (s, 3H), 3.46 (s, 3H), 3.51 (s, 3H), 3.74 (t, 2H), 3.91 (s, 1H), 4.02 (d, 1H), 4.03–4.13 (m, 2H), 4.58 (d, 1H), 5.12 (s, 2H), 5.15 (s, 2H), 6.50 6.88 (m, 11H)

Step 6) Synthesis of (3RS,4SR)-4-{4-{2-{4-{[3,5-bis(t-butyl)phenyl)methyl]piperazinyl}ethoxy}phenyl}-7-(methoxymethoxy)-3-[4-(methoxymethoxy)phenyl]-3-methyl-chroman

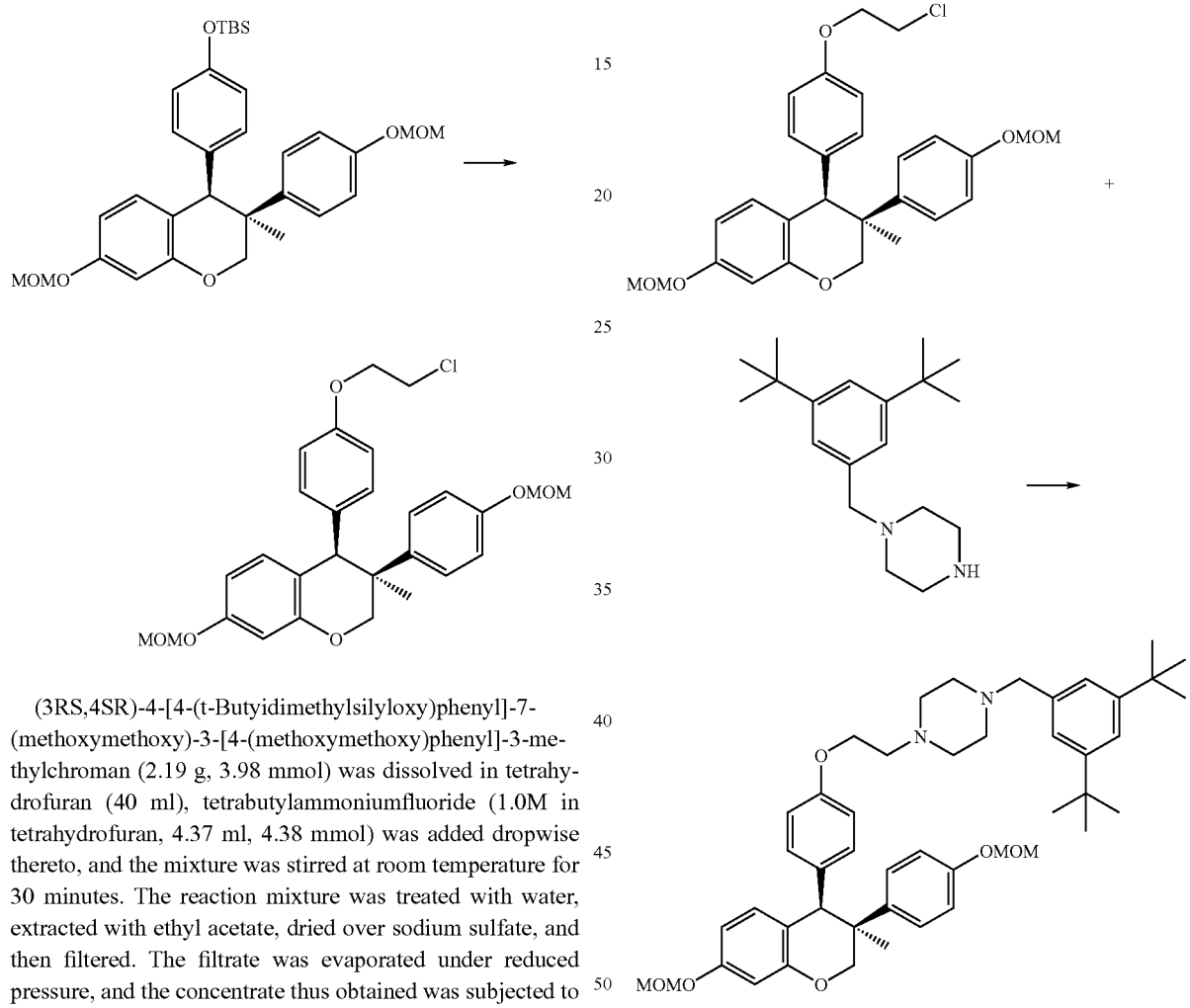

(3RS,4SR)-4-[4-(t-Butyidimethylsilyloxy)phenyl]-7-(methoxymethoxy)-3-[4-(methoxymethoxy)phenyl]-3-methylchroman (2.19 g, 3.98 mmol) was dissolved in tetrahydrofuran (40 ml), tetrabutylammoniumfluoride (1.0M in tetrahydrofuran, 4.37 ml, 4.38 mmol) was added dropwise thereto, and the mixture was stirred at room temperature for 30 minutes. The reaction mixture was treated with water, extracted with ethyl acetate, dried over sodium sulfate, and then filtered. The filtrate was evaporated under reduced pressure, and the concentrate thus obtained was subjected to silica gel column chromatography (n-hexane:ethyl acetate=4:1) to give 1.7 g of a foamy oil. (3RS,4SR)-4-(4-Hydroxyphenyl)-7-(methoxymethoxy)-3-[4-(methoxymethoxy)phenyl]-3-methylchroman (140 mg, 0.32 mmol) thus obtained was dissolved in a solvent mixture of 1,4-dioxane (3 ml) and water (0.5 ml), sodium hydroxide (38 mg, 0.96 mmol) and 1-bromo-2-chloroethane (0.13 ml, 1.60 mmol) were added thereto, and the mixture was stirred while heated under reflux for 2 days. The reaction solution was extracted with ethyl acetate, dried over sodium sulfate, and filtered. The filtrate was evaporated under reduced pressure, and the concentrate thus obtained was subjected to silica gel column chromatography (n-hexane:ethyl acetate=8:1) to give 95 mg (yield: 59%) of a sticky oil.

(3RS,4SR)-4-[4-(2-Chloroethoxy)phenyl]-7-(methoxymethoxy)-3-[4-(methoxymethoxy)phenyl]-3-methylchroman (210 mg, 0.42 mmol) and {(3,5-bis(t-butyl)phenyl]methyl}piperazine (243 mg, 0.84 mmol) were dissolved in a solvent mixture of acetone (4 ml) and DMF (0.4 ml). To the mixture potassium carbonate (116 mg, 0.84 mmol) and tetrabutylammonium iodide (16 mg, 0.04 mmol) added were, and the mixture was stirred while heated under reflux for 3 days. The reaction solution was extracted with ethyl acetate, dried over sodium sulfate, and filtered. The filtrate was evaporated under reduced pressure, and the concentrate thus obtained was subjected to silica gel column chromatography (n-hexane:ethyl acetate=4:1) to give 160 mg (yield: 51%) of a white foamy solid.

$^1$H-NMR (300 MHz, CDCl$_3$) δ: 1.32 (s, 18H), 1.49 (s, 3H), 2.47–2.62 (m, 8H), 2.75 (t, 2H), 3.46 (s, 3H), 3.51 (s, 3H), 3.53 (s, 2H), 3.92 (s, 1H), 3.94–4.02 (m, 3H), 4.57 (d, 1H), 5.09 (s, 2H), 5.14 (s, 2H), 6.47–7.28 (m, 14H)

Step 7) Synthesis of (3RS,4SR)-4-{4-{2-{4-{[3,5-bis(t-butyl)phenyl]methyl}piperazinyl}ethoxy}phenyl}-7-hydroxy-3-(4-hydroxyphenyl)-3-methylchroman

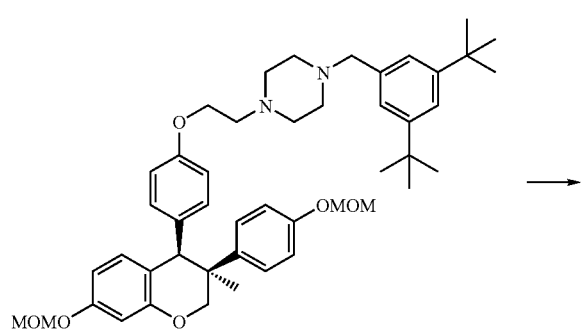

-continued

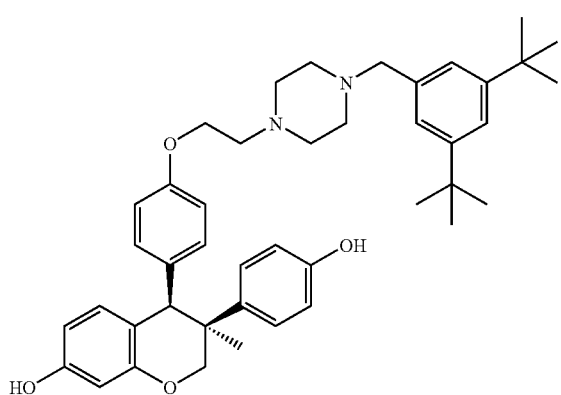

(3RS,4SR)-4-{4-{2-{4-{[3,5-Bis(t-butyl)phenyl]methyl}piperazinyl}ethoxy}phenyl}-7-(methoxymethoxy)-3-[4-(methoxymethoxy)phenyl]-3-methylchroman (150 mg, 0.21 mmol) was dissolved in methanol (1.5 ml), 6N-HCl (2 ml) was added portionwise thereto, and the mixture was stirred at 50–60° C. for 2 hours. The reaction solution was diluted with dichloromethane, which was then basified with saturated sodium bicarbonate solution. This solution was washed with water, dried over sodium sulfate, and filtered. The filtrate was evaporated under reduced pressure, and the concentrate thus obtained was subjected to silica gel column chromatography (dichloromethane:methanol=40:1) to give 75 mg (yield: 54%) of a pale yellow solid.

$^1$H-NMR (300 MHz, CD$_3$OD) δ: 1.38 (s, 18H), 1.53 (s, 3H), 2.54–2.72 (m, 8H), 2.80 (t, 2H), 3.62 (5, 2H), 3.98–4.07 (m. 4H), 4.62 (d, 1H), 6.82–7.44 (m, 14H)

Mass (ESI): 663 (M+1)

EXAMPLE 4

Synthesis of (3RS,4RS)-7-hydroxy-3-(4-hydroxyphenyl)-4-{5-[N-methyl-N-3-(4,4,5,5,5-pentafluoropentylthio)propylamino]pentyl}-3-methylchroman Step 1) Synthesis of (3RS,4RS)-4-(5-hydroxypentyl)-7-methoxy-3-(4-methoxyphenyl)-3-methyl-chroman

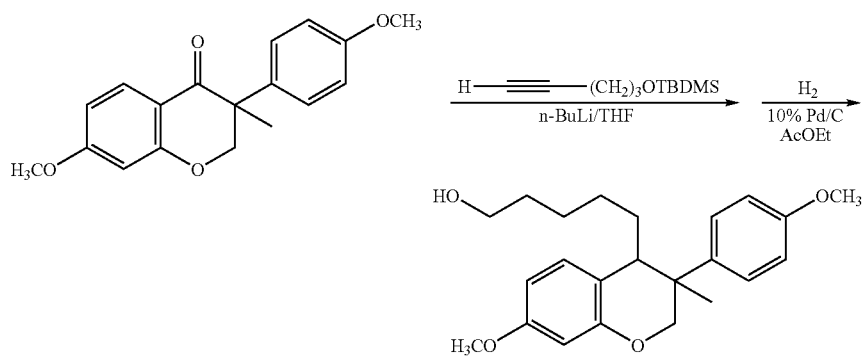

5-(t-Butyldimethylsilyloxy)pent-1-yne (1.15 g, 5.8 mmol) was dissolved in dry tetrahydrofuran (40 ml) under argon atmosphere, which was then cooled down to −78° C. 2.5M n-Butyllithium (n-BuLi) (2.3 ml, 5.8 mmol) was slowly added dropwise thereto, and the resulting mixture was stirred for 30 minutes. 7-Methoxy-3-(4-methoxyphenyl)-3-methylchroman-4-one (860 mg, 2.9 mmol) dissolved in dry tetrahydrofuran (10 ml) was added dropwise thereto, which was slowly warmed to room temperature. Water was added to the reaction solution to stop the reaction, and then the reaction solution was extracted with ethyl acetate. The organic layer thus separated was dried over magnesium sulfate and concentrated to give 2.2 g of a white solid. This solid was dissolved in ethyl acetate (60 ml), and then 10% Pd/C (0.7 g) was added dropwise thereto. The reaction solution was stirred under hydrogen for 15 hours, filtered, and concentrated. The residue was subjected to silica gel column chromatography (n-hexane:ethyl acetate=4:1→1:1) to give the title compound (430 mg, yield from the two steps 40%) as a colorless oil.

Step 2) Synthesis of (3RS,4RS)-7-methoxy-3-(4-methoxyphenyl)-4-[5-(p-toluene-sulfonyloxy)pentyl]-3-methylchroman

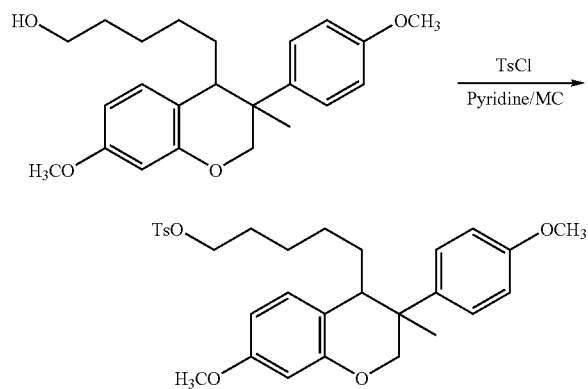

(3RS,4RS)-4-(5-Hydroxypentyl)-7-methoxy-3-(4-methoxyphenyl)-3-methylchroman (430 mg, 1.2 mmol) was dissolved in a solvent mixture of pyridine (12 ml) and dichloromethane (4 ml), which was then cooled down to 0° C. p-Toluenesulfonylchloride (460 mg, 2.3 mmol) was added dropwise thereto, and the mixture was stirred at room temperature for 3 hours. Water was then added, and the organ layer was extracted with ethyl acetate. The organic extract was washed with 2N hydrochloric acid solution, dried over magnesium sulfate, and concentrated. The residue was subjected to silica gel column chromatography (n-hexane:ethyl acetate=4:1) to give the title compound (315 mg, yield 53%) as a colorless oil.

$^1$H-NMR (300 MHz CDCl$_3$) δ: 7.70 (d, 2H), 7.28 (d, 2H), 7.08 (d, 2H), 6.85 (m, 3H), 6.44 (m, 1H), 6.40 (m, 1H), 4.50 (d, 1H), 4.25 (dd, 1H), 3.87 (t, 2H), 3.82 (s, 3H), 3.75 (s, 3H), 2.58 (m, 1H), 2.41 (s, 3H), 1.05–1.55 (m, 8H)

Step 3) Synthesis of (3RS,4RS)-7-methoxy-3-(4-methoxyphenyl)-4-{5-[N-methyl-N-3-(4,4,5,5,5-pentafluoropentylthio)-propylamino]pentyl}-3-methylchroman

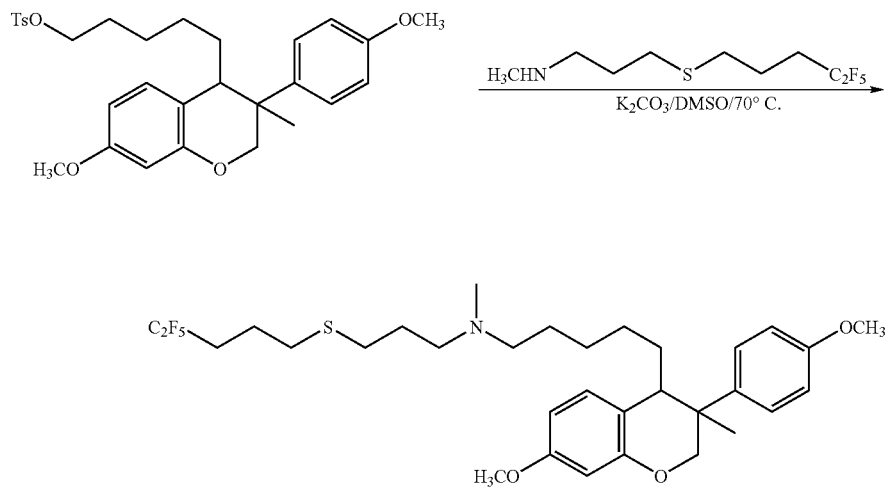

(3RS,4RS)-7-Methoxy-3-(4-methoxyphenyl)-4-[5-(p-toluenesulfonyloxypentyl]-3-methylchroman (0.31 g, 0.6 mmol), 3-(N-methylamino)-1-(4,4,5,5,5-pentafluoropentylthio) propane (0.6 mmol) and K$_2$CO$_3$ (0.25 g, 0.18 mmol) were dissolved in DMSO (7 ml), and the mixture was stirred at 70–80° C. After 1 hour the mixture was cooled down to normal temperature, and water was added thereto to stop the reaction. The reaction solution was extracted with ethyl acetate, washed with water and saturated aqueous sodium chloride solution, dried over anhydrous magnesium sulfate, and subjected to silica gel column chromatography (n-hexane:ethyl acetate, 8:1→4:1) to give the title compound (150 mg, yield 47%) as a colorless oil.

$^1$H-NMR (300 MHz, CDCl$_3$) δ: 7.12 (d, 2H), 6.86 (m, 3H), 6.38–6.45 (m, 2H), 4.50 (d, 1H), 4.24 (dd, 1H), 3.91 (t, 2H), 3.80 (s, 3H), 3.76 (s, 3H), 3.31 (br, 2H), 2.82 (br, 3H), 2.40–2.72 (m, 5H) 2.12 (m, 2H), 1.70–1.91 (m, 4H), 1.10–1.62 (m, 9H)

Step 4) Synthesis of (3RS,4RS)-7-hydroxy-3-(4-hydroxyphenyl)-4-{5-[N-methyl-N-3-(4,4,5,5,5-pentafluoropentylthio)-propylamino]pentyl}-3-methylchroman

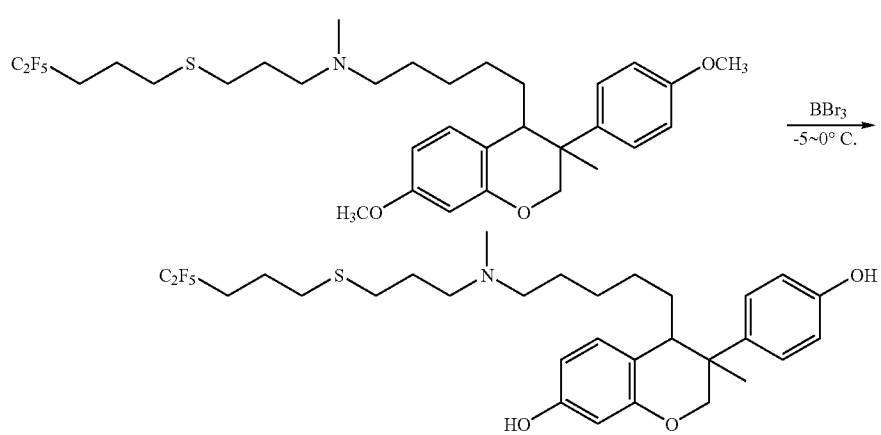

(3RS,4RS)-7-Methoxy-3-(4-(methoxyphenyl)-{5-[N-methyl-N-3(4,4,5,5,5-pentafluoropentylthio)propylamino]pentyl}-3-methylchroman (150 mg, 0.24 mmol) was dissolved in dry dichloromethane (5 ml) under argon atmosphere, which was cooled down to −78° C. Then, BBr$_3$ (1M methylene chloride solution, 1.75 ml, 1.44 mmol) was slowly added dropwise thereto. The resulting mixture was stirred at −50° C. for 6 hours, water was added thereto, and then the mixture was extracted with ethyl acetate. The organic layer separated after extraction was washed with water and saturated aqueous sodium chloride solution, dried over anhydrous magnesium sulfate, and subjected to silica gel column chromatography (n-hexane:ethyl acetate=4:1) to give the title compound (68 mg, yield 49%) as a colorless oil.

Mass=655(M+2Na)

$^1$H-NMR (300 MHz, acetone d$_6$) δ: 7.20 (d, 2H), 6.96 (d, 1H), 6.84 (d, 2H), 6.41 (dd, 1H), 6.38 (d, 1H), 4.50 (d, 1H), 4.23 (dd, 1H), 3.95 (t, 2H), 3.37 (t, 2H) 2.88 (s, 3H), 2.84 (m, 1H), 2.70 (t, 2H), 2.55 (t, 2H) 2.26 (m, 2H) 1.78–2.10 (m, 4H), 1.05–1.45 (m, 9H)

EXAMPLE 5

Synthesis of 4-{4-{2-[2-(4,4,5,5,5-pentafluoropentylsulfinyl)ethoxy]ethoxy}phenyl}-7-hydroxy-3-(4-hydroxyphenyl)-2H-chromene Step 1) Synthesis of 4-hydroxy-4-{4-[2-(2-chloroethoxy)ethoxy]phenyl}-7-(methoxymethoxy)-3-[4-(methoxymethoxy)phenyl]chroman

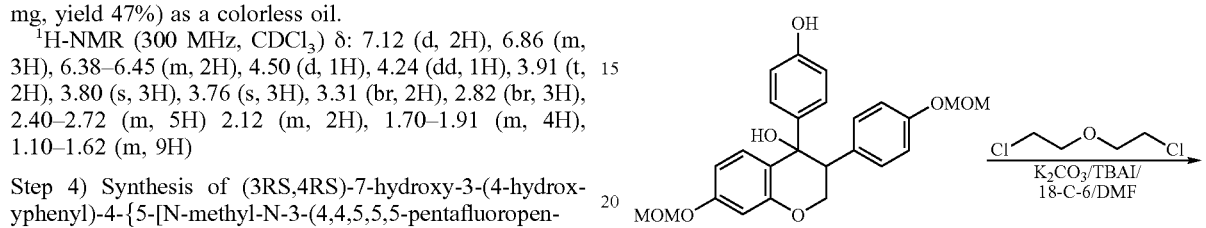

-continued

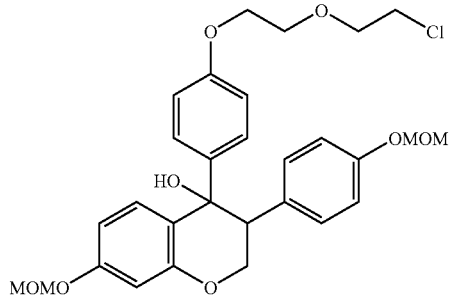

4-Hydroxy-4-(4-hydroxyphenyl)-7-(methoxymethoxy)-3-[4-(methoxymethoxy)phenyl]chroman (770 mg, 1.4 mmol), bis-(2-chloroethyl)ether (810 mg, 5.7 mmol), potassium carbonate (782 mg, 5.7 mmol) and 18-crown-6(132 mg, 0.49 mmol) were dissolved in dry N,N-dimethylformamide (10 mL) under argon atmosphere, which was then stirred at 100° C. for 2.5 hours. The reaction solution was cooled down to normal temperature, water was added thereto, and the mixture was extracted with ethyl acetate. The organic extract was dried over anhydrous magnesium sulfate and concentrated under reduced pressure. The residue was subjected to flash column chromatography (n-hexane:ethyl acetate=2:1) to give the title compound (0.71 g, yield 35%) as a red oil.

¹H-NMR (300 MHz, CDCl₃) δ: 7.06 (d, 2H), 6.83–6.73 (m, 7H), 6.61 (d, 1H), 6.52 (dd, 1H), 5.13 (s, 2H), 5.08 (s, 2H), 4.66 (t, 1H), 4.26 (dd, 1H), 4.11 (t, 2H), 3.83 (t, 2H), 3.79 (t, 2H), 3.63 (t, 2H), 3.45 (s, 3H), 3.41 (s, 3H), 3.39 (dd, 1H)

Step 2) Synthesis of 4-{4-[2-(2-iodoethoxy)ethoxy]phenyl}4-hydroxy-7-(methoxymethoxy)-3-(4-(methoxymethoxy)phenyl)chroman

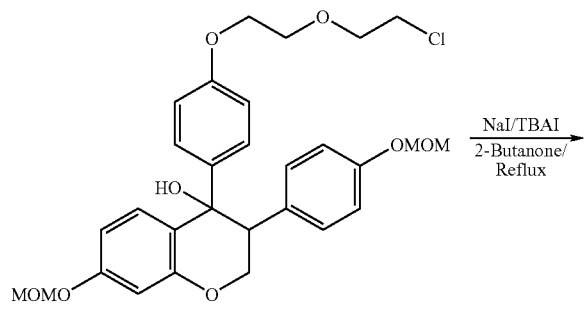

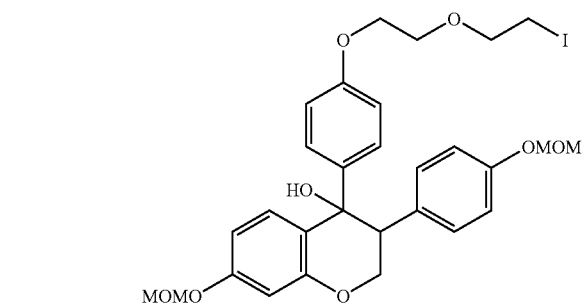

4-Hydroxy-4-{4-[2-(2-chloroethoxy)ethoxy]phenyl}-7-(methoxymethoxy)-3-[4-(methoxymethoxy)phenyl]chroman (490 mg, 0.9 mmol) was dissolved in 2-butanone (30 ml) under argon atmosphere. Then, sodium iodide (1.4 g, 9.3 mmol) and tetrabutylammonium iodide (1.6 g, 4.5 mmol) were added thereto, and the mixture was refluxed for 16 hours. The reaction solution was cooled down to normal temperature, concentrated, and diluted with ethyl acetate. Then, in order to eliminate the resulting NaCl and the excess sodium iodide and tetrabutylammonium iodide, the solution was filtered. The filtrate was concentrated under reduced pressure, and the residue was subjected to flash column chromatography (n-hexane:ethyl acetate=4:1→2:1) to give the title compound (527 mg, yield 90%) which is pale yellow and sticky.

Mass [M−H₂O]⁺=619

Step 3) Synthesis of 4-hydroxy-4-{4-{2-[2-(4,4,5,5,5-pentafluoropentylthio)ethoxy]ethoxy}phenyl}-7-(methoxymethoxy)-3-[4-(methoxymethoxy)phenyl]chroman

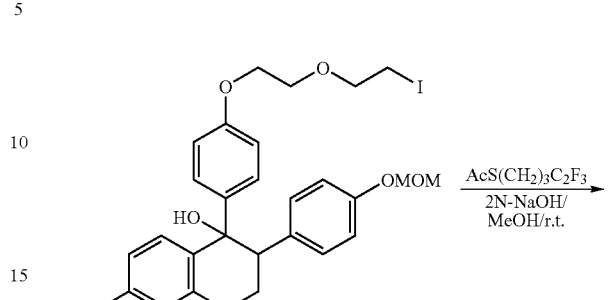

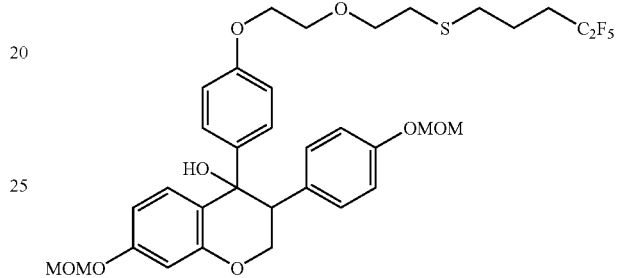

1-(4,4,5,5,5-Pentafluoropentylthio)acetate (67 mg, 4.15 mmol) was dissolved in MeOH (25 ml). 2N-NaOH (5 ml) was added thereto, and the mixture was stirred at room temperature for 30 minutes. 4-{4-[2-(2-Iodoethoxy)ethoxy]phenyl}-4-hydroxy-7-(methoxymethoxy)-3-[4-(methoxymethoxyphenyl]chroman (527 mg, 0.83 mmol) dissolved in MeOH (25 ml) was added thereto, which was then stirred at 60° C. for 20 hours. The reaction solution was cooled down to room temperature, water was added, and the resulting mixture was extracted with ethyl acetate. The organic extract was dried over anhydrous magnesium sulfate, and concentrated under reduced pressure. The residue was subjected to flash column chromatography (n-hexane: ethyl acetate=4:1→2:1) to give the title compound (565 mg, yield 97%) as a colorless oil.

¹H-NMR (300 MHz, CDCl₃) δ: 7.05 (d, 2H), 6.82–6.71 (m, 7H), 6.61 (d, 1H), 6.49 (dd, 1H), 5.14 (s, 2H), 5.08 (s, 2H), 4.67 (t, 1H), 4.23 (dd, 1H), 4.07 (t, 2H), 3.76 (t, 2H), 3.67 (t, 2H)

Step 4) Synthesis of 7-hydroxy-4-{4-{2-[2-(4,4,5,5,5-pentafluoropentylthio)ethoxy]ethoxy}phenyl}-3-(4-hydroxyphenyl)-2H-chromene

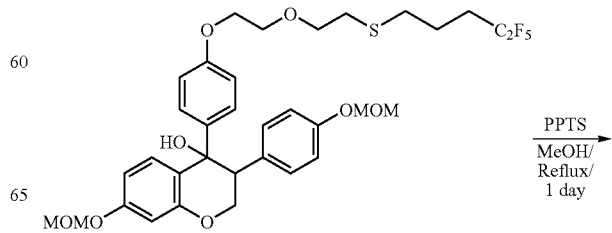

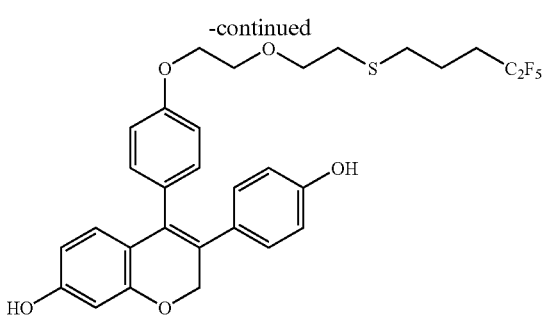

4-Hydroxy-4-{4-{2-[2-(4,4,5,5,5-pentafluoropentylthio)ethoxy]ethoxy)}phenyl}-7-(methoxymethoxy)-3-[4-(methoxymethoxy)phenyl]chroman-4-ol (540 mg, 0.77 mmol) was dissolved in methanol (40 mg) under argon atmosphere. Pyridinium p-toluenesulfonate (1.94 g, 7.72 mmol) was added thereto, which was then vigorously refluxed for 10 hours. The reaction solution was cooled down to room temperature, concentrated under reduced pressure, and diluted with ethyl acetate (40 ml). This solution was stirred at room temperature for 30 minutes, filtered, and the filtrate was concentrated. The residue was subjected to flash column chromatography (n-hexane:ethyl acetate=2:1) to give the pale yellow oilic title compound (359 mg, yield 78%).

$^1$H-NMR (300 MHz, CDCl$_3$) δ: 7.01 (d, 2H), 6.82 (m, 4H), 6.68 (d, 1H), 6.59 (d, 2H), 6.40 (d, 1H), 6.28 (dd, 1H), 5.01 (s, 2H), 4.09 (t, 2H), 3.82 (t, 2H), 3.71 (t, 2H), 2.71 (t, 2H), 2.64 (t, 2H), 2.16 (m, 2H), 1.90 (m, 2H)

Step 5) Synthesis of 4-{4-{2-[2-(4,4,5,5,5-pentafluoropentylthio)ethoxy]ethoxy}phenyl}-7-hydroxy-3-(4-hydroxyphenyl)-2H-chromene

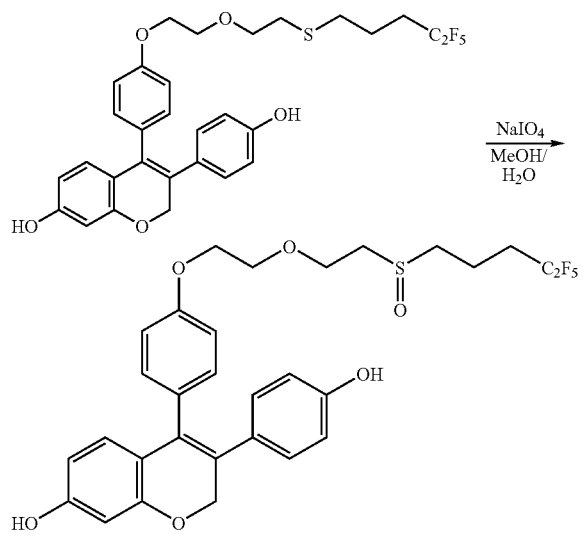

4-Hydroxy-4-{4-{2-[2-(4,4,5,5,5-pentafluoropentylthio)ethoxy]ethoxy}phenyl}-3-(4-hydroxyphenyl)-2H-chromene (359 mg, 0.06 mmol) was dissolved in MeOH (40 ml). Water (4.6 ml) and sodium periodate (193 mg, 0.90 mmol) were added thereto, and then the mixture was stirred under the atmosphere of normal temperature for 14 hours. The reaction solution was filtered, and the filtrate was concentrated. The residue was extracted with ethyl acetate, dried over anhydrous magnesium sulfate, and subjected to flash column chromatography (ethanol:ethyl acetate=1:19) to give the title compound (219 mg, yield 60%) as a yellow foamy solid.

$^1$H-NMR (300 MHz, CD$_3$OD) δ: 7.02 (d, 2H), 6.84 (m, 4H), 6.58 (d, 1H), 6.51 (d, 2H), 6.31 (d, 1H), 6.22 (dd, 1H), 4.93 (s, 2H), 4.13 (t, 2H), 3.97 (t, 2H), 3.82 (t, 2H), 3.12 (m, 1H), 3.02 (m, 1H), 2.91 (m, 2H), 2.81 (m, 2H), 2.05 (m, 2H)

EXAMPLE 6

Synthesis of (3RS,4RS)-4-]9-(3-dimethylaminopropylsulfinyl)nonyl]-7-hydroxy-3-(4-hydroxyphenyl)-3-methylthiochroman Step 1) Synthesis of 4-[9-(t-butyldimethylsilyloxy)-1-nonynyl]-4-hydroxy-7-methoxy-3-(4-methoxyphenyl)-3-methylthiochroman

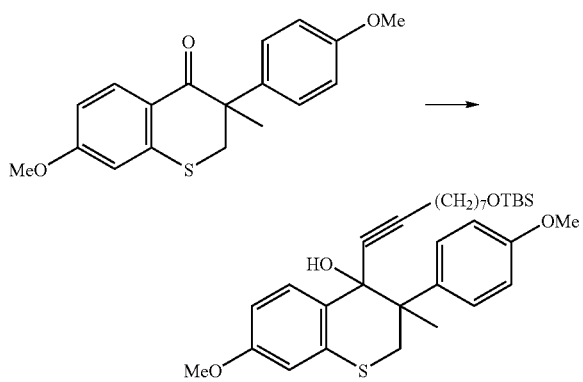

To a solution of 9-(t-butyldimethylsilyloxy)-1-nonyne (12 g, 47.15 mmol) in dry tetrahydrofuran (150 ml) was added dropwise n-butyl lithium (25.5ml, 42.43 mmol, 1.66 mole/l in tetrahydrofuran) at −78° C., which was then stirred at −20° C. for 1 hour. Then, to this reaction mixture was added 7-methoxy-3-(4-methoxyphenyl)-3-methylthiochroman-4-one (3 g, 9.54 mmol) dissolved in tetrahydrofuran at the same temperature for 30 minutes, and the resulting mixture was stirred at −10° C. for 24 hours. After the reaction was completed, saturated ammonium chloride solution was added to the reaction solution, and the mixture was extracted with ethyl acetate. The extract was dried over anhydrous magnesium sulfate and concentrated under reduced pressure. The residue was subjected to column chromatography (n-hexane:ethyl acetate=9:1) to stoichiometrically give the title compound (5.40 g) as a colorless oil.

$^1$H-NMR (270 MHz, CDCl$_3$) δ: 7.86 (d, J=8.5 Hz, 1H, Ar—H), 7.59 (d, J=8.9 Hz 2H, Ar—H), 6.87 (d, J=8.9 Hz, 2H, Ar—H), 6.63 (m, 2H, Ar—H), 4.25 (d, J=12.6 Hz, 2H, C2-H), 3.81 (s, 3H, OCH$_3$), 3.77 (s, 3H, OCH$_3$), 3.59 (t, J=6.6 Hz, 2H, CH$_2$-OTBS), 2.70 (d, 12.6 Hz, 1H, C2-H), 2.18 (t, J=6.6 Hz, 3H, propargyl-CH$_2$ and OH), 1.48 (s, 3H, C3-CH$_3$), 1.36 (m, 10H, alkyl-H), 0.89 (s, 9H, t-butyl-H), 0.04 (s, 6H, 2×CH$_3$)-

Step 2) Synthesis of 4-[9-(t-butyldimethylsilyloxy)-1-nonynyl]-7-methoxy-3-(4-methoxyphenyl)-3-methylthiochroman

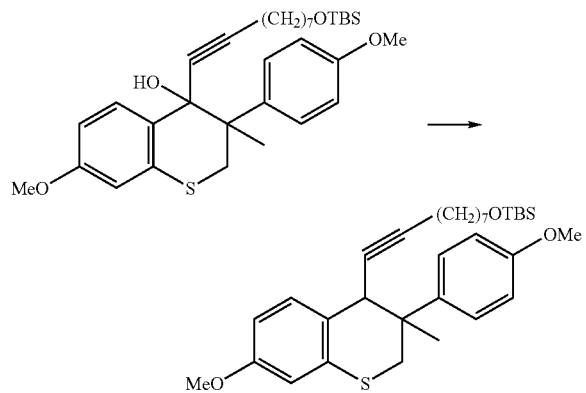

To a solution of 4-[9-(t-butyldimethylsilyloxy)-1-nonynyl]-4-hydroxy-7-methoxy-3-(4-methoxyphenyl)-3-methylthiochroman (5.40 g, 9.49 mmol) in 1,2-dichloroethane (150 ml) were added zinc iodide (4.54 g, 14.23 mmol) and sodium cyanoborohydride (4.47 g, 71.17 mmol), which was then stirred at room temperature for 12 hours. After the reaction was completed, water was added to the reaction mixture, and the resulting mixture was extracted with ethyl acetate. The extract was dried over anhydrous magnesium sulfate, and concentrated under reduced pressure. The residue was subjected to flash chromatography on silica gel (n-hexane:ethyl acetate=9:1) to give the title compound (2.64 g, yield 50%, 3RS/4RS:3RS/4SR=6:1) as a colorless oil.

$^1$H-NMR (270 MHz, CDCl$_3$, 3RS,4RS-compound) δ: 7.25 (m, 3H, Ar—H), 6.82 (d, J=8.9 Hz, 2H, Ar—H), 6.68 (m, 2H, Ar—H), 3.78 (s, 3H, OCH$_3$), 3.76 (s, 3H, OCH$_3$), 3.72 (s, 1H, C4-H), 3.76 (d, J=12.2 Hz, 1H, C2-H), 3.58 (t, J=6.6 Hz, 2H, CH$_2$-OTBS), 2.99 (d, J=12.2 Hz, 1H, C2-H), 2.02 (m, 2H, propargyl-CH2), 1.44 (s, 3H, C3-CH$_3$), 1.20 (m, 10H, alkyl-H), 0.89 (s, 9H, t-butyl-H), 0.05 (s, 6H, 2×CH$_3$)

Step 3) Synthesis of 4-[9-(t-butyldimethylsilyloxy)nonyl]-7-methoxy-3-(4-methoxyphenyl)-3-methylthiochroman

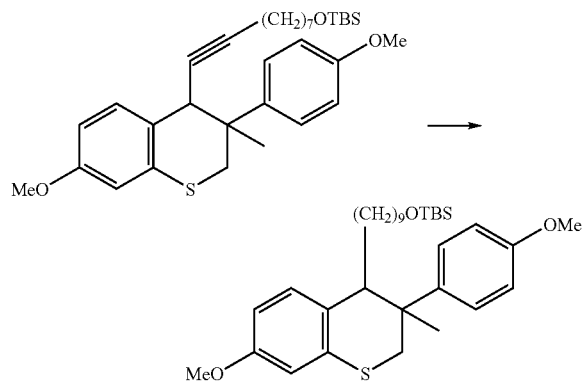

To a solution of 4-[9-(t-butyldimethylsilyloxy)-1-nonynyl]-7-methoxy-3-(4-methoxyphenyl)-3-methylthiochroman (2.64 g, 4.77 mmol) in methanol (150 ml) and tetrahydrofuran (15 mg) was added 10% Pd-C (850 mg), which was then stirred at room temperature under hydrogen (atmospheric pressure) for 1 day. Ethyl acetate was added to the reaction solution. The resulting solution was filtered, extracted several times with ethyl acetate, and concentrated under reduced pressure to remove the organic solvent. Hydrogenation reaction was repeated three times under the same condition. After the organic solvent was removed, the residue was subjected to flash chromatography on silica gel (n-hexane:ethyl acetate=9:1) to give the title compound (2.20 g, yield 83%) as a colorless oil.

$^1$H-NMR (270 MHz, CDCl$_3$, 3RS,4RS-compound) δ: 7.28 (d, J=8.9 Hz, 2H, Ar—H), 6.91 (m, 3H, Ar—H), 6.72 (d, J=2.3 Hz, 1H, C8-H), 6.58 (dd, J=8.6 and 2.3 Hz, 1H, C6-H), 3.82 (s, 3H, OCH$_3$), 3.78 (s, 3H, OCH$_3$), 3.64 (d, J=11.5 Hz, 1H, C2-H), 3.56 (t, J=6.6 Hz, 2H, CH$_2$-OTBS), 2.98 (d, J=11.5 Hz, 1H, C2-H), 2.71 (brt, 1H, C4-H), 1.48–1.17 (m, 19H, C3-CH$_3$ and alkyl-H), 0.88 (s, 9H, t-butyl-H), 0.03 (s, 6H, 2×CH$_3$)

Step 4) Synthesis of 4-(9-hydroxynonyl)-7-methoxy-3-(4-methoxyphenyl)-3-methylthiochroman

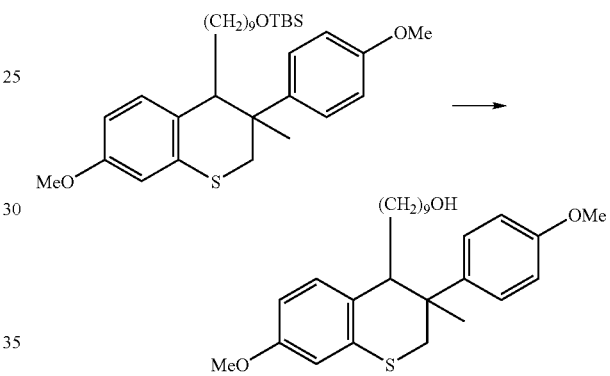

4-[9-(t-Butyldimethylsilyloxy)nonyl]-7-methoxy-3-(4-methoxyphenyl)-3-methylthiochroman (2.2 g, 3.95 mmol) was dissolved in tetrahydrofuran (150 ml), and 3N-HCl (11 ml) was added thereto. The reaction mixture was stirred at room temperature for 140 minutes. After the reaction was completed, water was added to the reaction solution, and the resulting mixture was extracted with ethyl acetate. The extract was dried over anhydrous magnesium sulfate, and concentrated under reduced pressure. The residue was subjected to flash chromatography on silica gel (n-hexane:ethyl acetate=8:2 and 1:1) to give the title compound (1.61 g, yield 92%) as a white solid.

$^1$H-NMR (270 MHz, CDCl$_3$, 3RS,4RS-compound) δ: 7.29 (d, J=8.9 Hz, 2H, Ar—H), 6.91 (m, 3H, Ar—H), 6.71 (m, 1H, Ar—H), 6.58 (m, 1H, Ar—H), 3.82 (s, 3H, OCH$_3$), 3.78 (s, 3H, OCH$_3$), 3.68 (m, 4H, CH$_2$—OH and C2-CH$_2$), 2.98 (d, J=11.6 Hz, 1H, C2-H), 2.78 (brt, 1H, C4-H), 1.56–1.08 (m, 19H, C3-CH$_3$ and alkyl-H).

Step 5) Synthesis of 4-(9-methanesulfonyloxynonyl)-7-methoxy-3-(4-methoxy-phenyl)-3-methylthiochroman

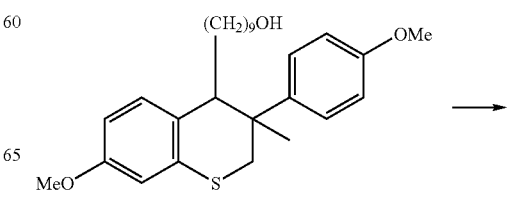

-continued

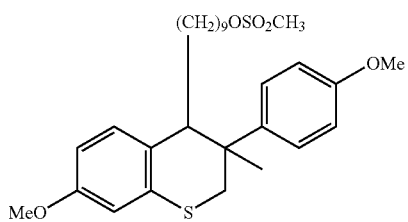

4-(9-Hydroxynonyl)-7-methoxy-3-(4-methoxyphenyl)-3-methyl thiochroman (882 mg, 1.99 mmol) was dissolved in dichloromethane (60 ml) and triethylamine (1.38 ml, 9.96 mmol), to which was added methanesulfonylchloride (0.77 ml, 9.96 mmol). The reaction mixture was stirred at room temperature for 40 minutes. After the reaction was completed, water was added to the reaction solution, and the resulting mixture was extracted with ethyl acetate. The organic layer was washed with water and saturated sodium chloride solution, and dried over anhydrous magnesium sulfate. The residue was subjected to flash chromatography on silica gel (n-hexane:ethyl acetate=7:3) to give the title compound (0.74 g, yield 72%) as a colorless oil.

$^1$H-NMR (270 MHz, CDCl$_3$, 3RS,4RS-compound) δ: 7.29 (d, J=8.9 Hz, 2H, Ar—H), 6.91 (m, 3H, Ar—H), 6.70 (d, J=2.3 Hz, 1H, C8-H), 6.58 (dd, J=8.5 and 2.3 Hz, 1H, Ar—H), 4.18 (t, J=6.6 Hz, 2H, OCH$_2$), 3.82 (s, 3H, OCH$_3$), 3.78 (s, 3H, OCH$_3$), 3.64 (d, J=11.3 Hz, 1H, C2-H), 2.99 (s, 3H, OSO$_2$CH$_3$), 2.97 (brd, J=not separated, 1H, C2-H), 2.78 (brs, 1H, C4-H), 1.63 (m, 3H, alkyl-H), 1.37–1.08 (m, 16H, C3-CH$_3$ and alkyl-H)

Step 6) Synthesis of 3-dimethylaminopropan-1-thiolacetate

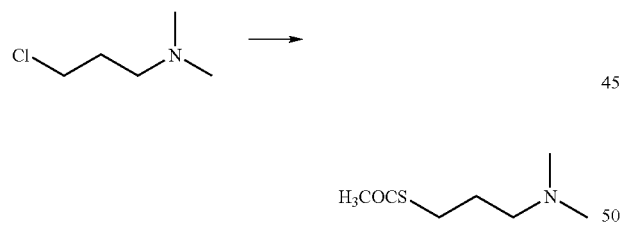

To a solution of 3-dimethylaminopropyl chloride (1.77 g, 14.5 mmol) in acetone (40 ml) was added potassium thioacetate (3.64 g, 31.87 mmol), and the mixture was stirred at room temperature for 2 days. After the reaction was completed, the reaction mixture was filtered through a filter paper and washed three times with diethyl ether. The organic solution was combined and concentrated under reduced pressure to give the title compound (1.50 g, yield 64%) as a yellow oil. This compound thus obtained was used in the next reaction without further purification.

$^1$H-NMR (270 MHz, CDCl$_3$) δ: 2.89 (t, J=7.2 Hz, 2H, C$_1$-CH$_2$), 2.40 (t, J=7.3, 2H, C3-CH$_2$), 2.32 (s, 3H, SCOCH$_3$), 2.27 (s, 6H, N(CH$_3$$_2$), 1.78 (quin, J=7.2 and 7.5 Hz, 2H, C2-CH$_2$)

Step 7) Synthesis of 4-[9-(3-dimethylaminopropylthio)nonyl]-7-methoxy-3-(4-methoxyphenyl)-3-methylthiochroman

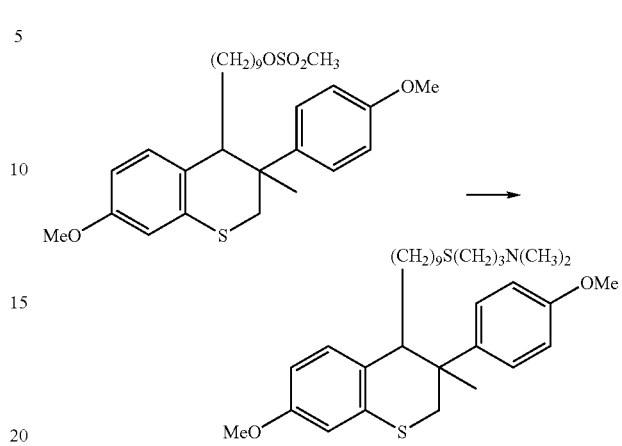

To a solution of 3-dimethylaminopropyl-1-thiolacetate (596 mg, 3.69 mmol) in methanol (20 ml) was added 1M sodium methoxide (3.21 ml), and the resulting mixture was stirred at room temperature for 90 minutes. Then, 4-(9-methanesulfonyloxynonyl)-7-methoxy-3-(4-methoxyphenyl)-3-methylthiochroman (290 mg, 0.566 mmol) dissolved in dry tetrahydrofuran (10 ml) was added dropwise thereto at room temperature. The reaction mixture was stirred overnight. After the reaction was completed, water was added to the reaction solution, and the resulting mixture was extracted with ethyl acetate. The organic layer was washed with water and saturated sodium chloride solution, and dried over anhydrous magnesium sulfate. The residue was concentrated under reduced pressure to give the title compound (300 mg, crude product, stoichiometric yield) as an oil. This compound was used in the next reaction without further purification.

$^1$H-NMR (270 MHz, CDCl$_3$, 3RS,4RS-compound) δ: 7.27 (d, J=8.9 Hz, 2H, Ar—H), 6.91 (m, 3H, Ar—H), 6.72 (d, J=2.3 Hz, 1H, C8-H), 6.58 (dd, J=8.2 and 2.3 Hz, 1H, C6-H), 3.82 (s, 3H, OCH$_3$), 3.77 (s, 3H, OCH$_3$), 3.64 (d, J=119 Hz, 1H. C2-H), 2.97 (d, J=11.9 Hz, 1H, C2-H), 2.72 (t, J=7.2 Hz, 2H, SCH$_2$), 2.50 (m. 3H, C4-H and SCH$_2$), 2.34 (t, 2H, J=6.6 Hz, N—CH$_2$), 2.22 (s, 6H, 2×NCH$_3$), 1.85 (m, 2H, SCH$_2$CH2CH$_2$N), 1.75 (m, 2H, alkyl-H), 1.48–0.98 (m, 17H, C3-CH$_3$, and alkyl-H)

Step 8) Synthesis of 7-hydroxy-3-(4-hydroxyphenyl)-3-methyl-4-[9-(3-dimethylaminopropylthio)nonyl]thiochroman

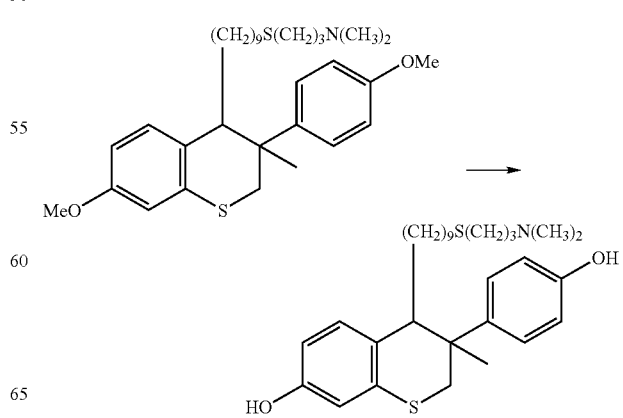

A mixture of 7-methoxy-3-(4-methoxyphenyl)-3-methyl-4-[9-(3-dimethylaminopropylthio)nonyl]thiochroman (50 mg, 0.09 mmol), hydrobromic acid (0.13 ml, 48% aqueous solution) and acetic acid (0.15 ml) was heated for 8 hours. After the reaction was completed, water was added to the reaction solution, and the resulting mixture was extracted with ethyl acetate. The organic layer was washed with saturated sodium bicarbonate solution and water, and dried over anhydrous magnesium sulfate. The residue was concentrated under reduced pressure to give the title compound (60 ml, crude product) as a colorless oil. This compound thus obtained was used in the next reaction without further purification.

$^1$H-NMR (270 MHz, CDCl$_3$, 3RS,4RS-compound) δ: 7.23 (d, J=8.9 Hz, 2H, Ar—H), 6.85 (d, J=8.2 Hz, 1H, C5-H), 6.76 (d, J=8.6 Hz, 2H, Ar—H), 6.61 (d, J=2.3 Hz, 1H, C8-H), 6.50 (dd, J=8.2 and 2.3 Hz, 1H, C6-H), 4.96 (brs, 1H, OH), 4.92 (brs, 1H, OH), 3.64 (d, J=11.9 Hz, 1H, C2-H), 2.97 (d, J=11.9 Hz, 1H, C2-H), 2.71 (t, 3=6.6 Hz, 2H, SCH$_2$), 2.46 (m, 3H, C4-H and SCH$_2$), 2.34 (t, 2H, J=7.6 Hz, N—CH$_2$), 2.24 (s, 6H, 2×NCH$_3$), 1.86 (m, 2H, SCH$_2$CH$_2$CH$_2$N), 1.42–0.96 (m, 19H, C3-CH$_3$ and alkyl-H)

Step 9) Synthesis of (3RS,4RS)-4-[9-(3-dimethylaminopropylsulfinyl)nonyl]-7-hydroxy-3-(4-hydroxyphenyl)-3-methylthiochroman

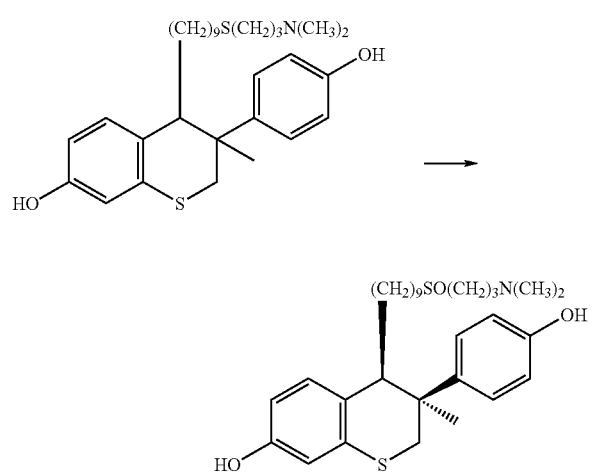

Methanol (7 ml) and water (1.5 ml) were added to a mixture of 7-hydroxy-3-(4-hydroxyphenyl)-3-methyl-4-[9-(3-dimethylaminopropylthio)nonyl]room temperature for 4 hours. To the reaction mixture were added absolute methanol and a small quantity of anhydrous magnesium sulfate, which was then filtered through a filter paper. Then, the filtrate was concentrated under reduced pressure to remove the solvent. The crude product thus obtained was subjected to amino silica gel plate (ethyl acetate:methanol=10:0.5) to give the title compound (26 mg, yield from the two steps 54%) as a white solid.

$^1$H-NMR (270 MHz, CD$_3$OD, 3RS,4RS-compound) δ: 7.08 (d, J=8.6 Hz, 2H, Ar—H), 6.66 (m, 3H, Ar—H), 6.43 (d, J=2.3 Hz, 1H, C8-H), 6.31 (dd, J=8.2 and 2.3 Hz, 1H, C6-H), 3.51 (d, J=11.6 Hz, 1H, C2-H), 2.83 (d, J=11.6 Hz, 1H, C2-H), 2.67 (m, 5H, C4-H and 2×S(O)CH$_2$), 2.42 (t, J=7.2 Hz, 2H, N—CH$_2$), 2.20 (s, 6H, 2×NCH$_3$), 1.89 (m, 2H, SCH$_2$CH$_2$CH$_2$N), 1.65–0.95 (m, 19H, C3-CH$_3$ and alkyl-H)

EXAMPLE 7

Synthesis of (3RS,4RS)-4-]9-(N-4,4,5,5,5-pentafluoropentylaminosulfonylamino)nonyl]-7-hydroxy-3-(4-hydroxyphenyl)-3-methylchroman Step 1) Synthesis of 4-[9(t-butyldimethylsilyloxy)-1-nonynyl]-4-hydroxy-7-methoxymethoxy-3-(4-methoxymethoxyphenyl)-3-methylchroman

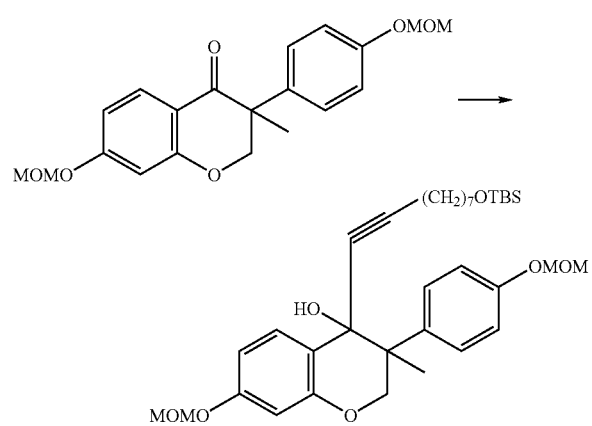

9-(t-Butyl dimethylsilyloxy)-1-nonyne (7.1 g, 27.9 mmol) was dissolved in dry tetrahydrofuran (70 mL) under argon atmosphere, which was then cooled down to –78° C. n-Butyllithium (15.1 ml, 25.1 mmol, 1.66 mol/l solution in tetrahydrofuran) was slowly added dropwise thereto, and the mixture was stirred at –20° C. for 80 minutes. To this mixture was added dropwise 7-methoxymethoxy-3-(4-methoxymethoxyphenyl)-3-methylchroman-4-one (2.0 g, 5.58 mmol) dissolved in dry tetrahydrofuran (15 mL) at –20° C., and the resulting reaction mixture was stirred at the same temperature for 3 hours, and then stirred at –10° C. overnight. The reaction was quenched with water, and the reaction solution was extracted with ethyl acetate. The organic layer was washed with water and saturated sodium chloride solution, dried over anhydrous magnesium sulfate, and concentrated. The residue was subjected to flash chromatography on silica gel (n-hexane:ethyl acetate=9:1) to give the title compound (3.37 g, yield 99%) as a colorless oil.

$^1$H-NMR (270 MHz, CDCl$_3$) δ: 7.65 (d, J=8.6 Hz, 1H, CS—H), 7.47 (d, J=8.9 Hz, 2H, Ar—H), 7.04 (d, 1=8.9 Hz, 2H, Ar—H), 6.66 (dd, 8.6 and 2.3 Hz, 1H, C6-H), 6.55 (d, J=2.3 Hz, 1H, C8-H), 5.19 (s, 2H, OCH$_2$OCH$_3$), 4.90 (d, J=10.6 Hz, 1H, C2-H), 4.06 (d, J=10.6 Hz, 1H, C2-H), 3.60 (t, J=6.6 Hz, 2H, CH$_2$-OTBS), 3.49 (s, 3H, OCH$_2$OCH$_3$), 3.47 (s, 3H, OCH$_2$OCH$_3$), 2.26 (t, J=6.9 Hz, 2H, propargyl-CH$_2$), 2.06 (s, 1H, OH), 1.50 (s, 3H, C3-CH$_3$), 1.58–1.23 (m, 10H, alkyl-H), 0.89 (s, 9H, t-butyl-H), 0.04 (s, 6H, 2×CH$_3$)

Step 2) Synthesis of 4-[9-(t-butyldimethylsilyloxy)-1-nonynyl]-7-methoxymethoxy-3-(4-methoxymethoxyphenyl)-3-methylchroman

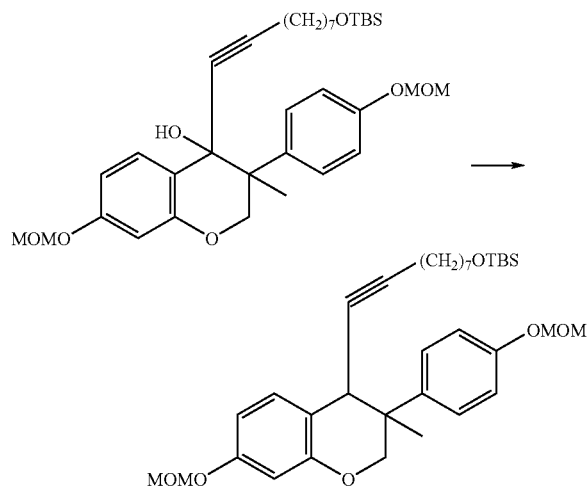

To a solution of 4-[9-(t-butyldimethylsilyloxy)-1-nonynyl]-4-hydroxy-7-methoxymethoxy-3-(4-methoxymethoxyphenyl)-3-methylchroman (3.10 g, 5.06 mmol) in 1,2-dichloroethane (200 ml) were added zinc iodide (2.42 g, 7.59 mmol) and sodium cyanoborohydride (2.23 g, 35.42 mmol), which was then stirred at room temperature for 8 hours. After the reaction was completed, water was added to the reaction mixture, and the resulting mixture was extracted with ethyl acetate. The extract was dried over anhydrous magnesium sulfate, and concentrated under reduced pressure. The residue was subjected to flash chromatography on silica gel (n-hexane:ethyl acetate=9:1) to give the title compound (1.50 g, yield 50%, 3RS/4RS:3RS14SR=6:1) as a colorless oil.

$^1$H-NMR (270 MHz, CDCl$_3$, 3RS,4RS-compound) δ: 7.27. (m, 3H, Ar—H), 6.94 (d, J=8.9 Hz, 2H, Ar—H), 6.61 (dd, J=8.3 and 2.3 Hz, 1H, C6-H), 6.51 (d, J=2.3 Hz, 1H, C8-H), 5.14 (s, 2H, OCH$_2$OCH$_3$), 5.12 (s, 2H, OCH$_2$—OCH$_3$), 4.49 (d, J=10.6 Hz, 1H, C2-H), 4.16 (d, J=10.6 Hz, 1H, C2-H), 3.89 (brs, 1H, C4-H), 3.58 (t, J=6.6 Hz, 2H, CH$_2$-OTBS), 3.47 (s, 3H, OCH$_2$OCH$_3$), 3.46 (s, 3H, OCH$_2$OCH$_3$), 2.03 (m, 2H, propargyl-CH2), 1.37 (s, 3H, C3-CH$_3$), 1.42–0.93 (m, 10H, alkyl-H), 0.89 (s, 9H, t-butyl-H), 0.05 (s, 6I4, 2×CH$_3$)

Step 3) Synthesis of 4-[9-(t-butyldimethylsilyloxy)nonyl]-7-methoxymethoxy-3-(4-methoxymethoxyphenyl)-3-methylchroman

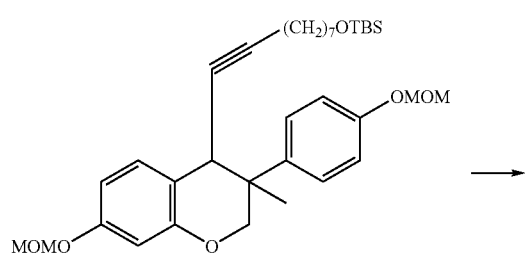

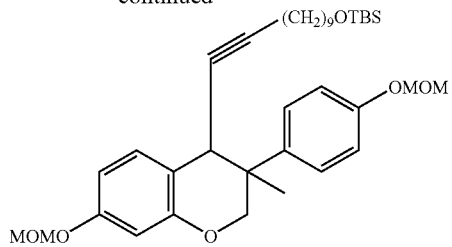

To a solution of 4-[9-(t-butyldimethylsilyloxy)-1-nonynyl]-7-methoxymethoxy-3-(4-methoxymethoxyphenyl)-3-methylchroman (150 g, 2.51 mmol) in methanol (100 ml) and tetrahydrofuran (10 ml) was added 10% Pd—C (570 mg), which was then stirred at room temperature under hydrogen (atmospheric pressure) for 1 day. Ethyl acetate was added to the reaction solution, which was then filtered, extracted several times with ethyl acetate, and concentrated under reduced pressure to give the title compound (134 g, yield 89%, 3RS:4RS:3RS/4SR=6:1) as a colorless oil.

$^1$H-NMR (270 MHz, CDCl$_3$, 3RS,4RS-compound) δ: 7.13 (d, J=8.9 Hz, 2H, Ar—H), 7.02 (d, J=8.9 Hz, 2H, Ar—H), 6.95 (dd, J=8.6 and 2.3 Hz, 1H, C6-H), 6.57 (m, 2H, Ar—H), 5.17 (s, 2H, OCH$_2$OCH$_3$), 5.14 (s, 2H, OCH$_2$OCH$_3$), 4.52 (d, J=10.6 Hz, 1H, C2-H), 4.25 (d, J=10.6 Hz, 1H, C2-H), 3.57 (t, J=6.6 Hz, 2H, CH$_2$-OTBS), 3.50 (s, 3H, OCH$_2$OCH$_3$), 3.49 (s, 3H, OCH$_2$OCH$_3$) 2.65 (brs, 1H, C4-H), 1.54–1.09 (m, 19H, C3-CH$_3$ and alkyl-H), 0.88 (s, 9H, t-butyl-H), 0.03 (s, 6H, 2×CH$_3$)

Step 4) Synthesis of 4-(9-hydroxynonyl)-7-methoxymethoxy-3-(4-methoxymethoxyphenyl)-3-methylchroman

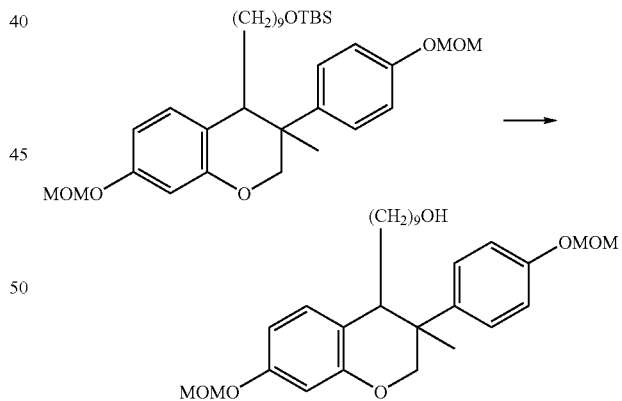

4-[9-(t-Butyldimethylsilyloxy)nonyl]-7-methoxymethoxy-3-(4-methoxymethoxyphenyl)-3-methylchroman (1.34 g, 2.23 mmol) was dissolved in ethanol (70 ml), and pyridinium ptoluenesulfonate (426 mg, 1.70 mmol) was added thereto. The reaction mixture was stirred at room temperature for 10 hours, water was added, and the resulting mixture was extracted with ethyl acetate. The organic layer was separated, dried over anhydrous magnesium sulfate, and concentrated under reduced pressure. The residue was subjected to flash chromatography on silica gel (n-hexane:ethyl acetate=7:3 and 1:1) to give the title compound (831 mg, yield 77%) as a colorless oil. In this reaction, 247 mg (18%) of the unreacted starting compound was recovered.

¹H-NMR (270 MHz, CDCl₃, 3RS,4RS-compound) δ: 7.12 (d, J=8.9 Hz, 2H, Ar—H), 7.02 (d, J=8.9 Hz, 2H, Ar—H), 6.95 (dd, J=8.6 and 2.3 Hz, 1H, C6-H), 6.57 (m, 2H, Ar—H), 5.18 (s, 2H, OC$\underline{H}_2$OCH₃), 5.14 (s, 2H, OC$\underline{H}_2$—OCH₃), 4.52 (d, J=10.6 Hz, 1H, C2-H), 4.25 (d, J=10.6 Hz, 1H, C2-H), 3.50 (s, 3H, OCH₂OC$\underline{H}_3$), 3.49 (s, 3H, OCH₂OC$\underline{H}_3$), 3.47 (t, J=not separated, 2H, C$\underline{H}_2$—OH), 2.63 (brs, 1H, C4-H), 1.57–1.06 (m, 19H, C3-CH₃ and alkyl-H)

Step 5) Synthesis of 4-(9-methanesulfonyloxynonyl)-7-methoxymethoxy-3-(4-methoxymethoxyphenyl)-3-methylchroman

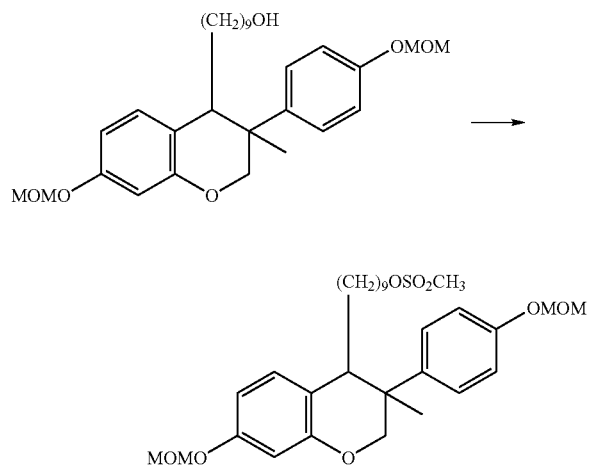

4-(9-Hydroxynonyl)-7-methoxymethoxy-3-(4-methoxymethoxyphenyl)-3-methylchroman (435 mg, 0.89 mmol) was dissolved in dichloromethane (30 ml), to which were added triethylamine (0.62 ml, 4.47 mmol) and methanesulfonyl chloride (0.34 ml, 4.47 mmol). The reaction mixture was stirred at room temperature for 30 minutes. After the reaction was completed, water was added to the reaction solution, and the resulting mixture was extracted with ethyl acetate. The organic layer was washed with water and saturated sodium chloride solution, dried over anhydrous magnesium sulfate, and concentrated. The residue was subjected to flash chromatography on silica gel (n-hexane:ethyl acetate-7:3) to give the title compound (0.49 g, yield 97%) as a colorless oil.

¹H-NMR (270 MHz, CDCl₃, 3RS,4RS-compound) δ: 7.12 (d, 3=8.9 Hz, 2H, Ar—H), 7.02 (d, J=8.9 Hz, 2H, Ar—H), 6.95 (dd, J=8.6 and 2.3 Hz, 1H, C6-H), 6.58 (m, 2H, Ar—H), 5.16 (s, 2H, OC$\underline{H}_2$), 5.13 (s, 2H, OC$\underline{H}_2$OCH₃), 4.56 (d, J=10.6 Hz, 1H, C2-H), 4.23 (d, J=10.6 Hz, 1H, C2-H), 4.19 (t, J=6.6 Hz, OCH₂), 3.50 (s, 3H, OCH₂OC$\underline{H}_3$), 3.49 (s, 3H, OCH₂OC$\underline{H}_3$), 2.99 (s, 3H, OSO₂CH₃), 2.65 (brs, 1H, C4-H), 1.61 (m, 3H, alkyl-H), 1.42–1.02 (m, 16H, C3-CH₃ and alkyl-H)

Step 6) Synthesis of 4-(9-azidononyl)-7-methoxymethoxy-3-(4-methoxymethoxyphenyl)-3-methylchroman

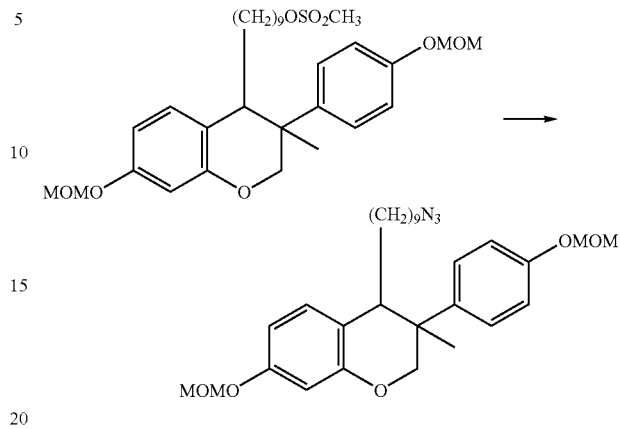

To a solution of 4-(9-methanesulfonyloxynonyl)-7-methoxymethoxy-3-(4-methoxymethoxyphenyl-3-methylchroman (499 mg, 0.966 mmol) in N,N-dimethyl-formamide (8 ml) was added sodium azide (281 mg, 4.33 mmol), which was then stirred at 50° C. for 2 hours. After the reaction was completed, water was added to the reaction solution, and the resulting mixture was extracted with ethyl acetate. The organic layer was washed with water and saturated sodium chloride solution, dried over anhydrous magnesium sulfate, and concentrated. The residue was subjected to flash chromatography on silica gel (n-hexane:ethyl acetate=7:3) to give the title compound (411 mg, yield 93%) as a white solid.

¹H-NMR (270 MHz, CDCl₃, 3RS,4RS-compound) δ: 7.13 (d, J=8.9 Hz, 2H, Ar—H), 7.02 (d, J=8.9 Hz, 2H, Ar—H), 6.95 (dd, J=8.6 and 2.3 Hz, 1H, C6-H), 6.56 (m, 2H, Ar—H), 5.18 (s, 2H, OC$\underline{H}_2$OCH₃), 5.14 (s, 2H, OC$\underline{H}_2$OCH₃), 4.52 (d, J=10.5 Hz, 1H, C2-H), 4.25 (d, J=10.6 Hz, 1H, C2-H), 3.50 (s, 3H, OCH₂OC$\underline{H}_3$), 3.49 (s, 3H, OCH₂OC$\underline{H}_3$), 3.22 (t, J=6.9 Hz, 2H, CH₂N₂), 2.62 (brs, 1H, C4-H), 1.55–1.02 (m, 19H, C3-CH₃ and alkyl-H)

Step 7) Synthesis of 4-(9-aminononyl)-7-methoxymethoxy-3-(4-methoxymethoxyphenyl)-3-methylchroman

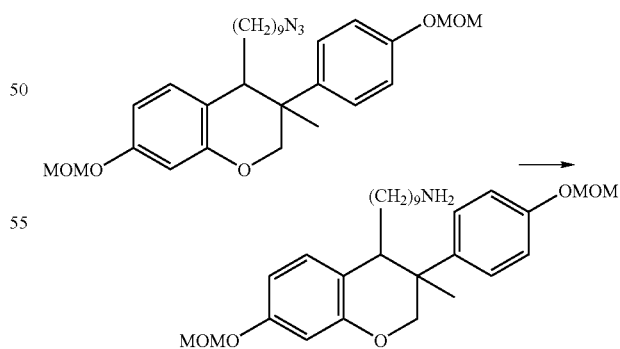

To a solution of 4-(9-azidononyl)-7-methoxymethoxy-3-(4-methoxymethoxyphenyl)-3-methylchroman (411 mg, 0.80 mmol) in methanol (100 ml) was added 10% Pd—C (100 mg), which was then stirred overnight at room temperature under hydrogen (atmospheric pressure). The resulting mixture was filtered through cellite and concentrated under reduced pressure to give the title compound (391 mg, stoichiometric yield) as a white solid.

$^1$H-NMR (270 MHz, CDCl$_3$, 3RS,4RS-compound) δ: 7.13 (d, J=8.9 Hz, 2H, Ar—H), 7.02 (d, J=8.9 Hz, 2H, Ar—H), 6.94 (m, 1H, Ar—H), 6.55 (m, 2H, Ar—H), 5.17 (s, 2H, OCH$_2$OCH$_3$), 5.14 (s, 2H, OCH$_2$OCH$_3$), 4.52 (d, J=10.5 Hz, 1H, C2-H), 4.25 (d, J=10.6 Hz, 1H, C2-H), 3.49 (s, 3H, OCH$_2$OCH$_3$), 3.48 (s, 3H, OCH$_2$OCH$_3$), 2.65 (t J=6.6 Hz, 2H, CH$_2$NH$_2$), 2.62 (brs, 1H, C4-H), 1.39–1.06 (m, 19H, C$_3$-CH$_3$ and alkyl-H).

Step 8) Synthesis of 4-[9-(N-t-butyloxycarbonylaminosulfonylamino)nonyl]-7-methoxymethoxy-3-(4-methoxymethoxyphenyl)-3-methylchroman

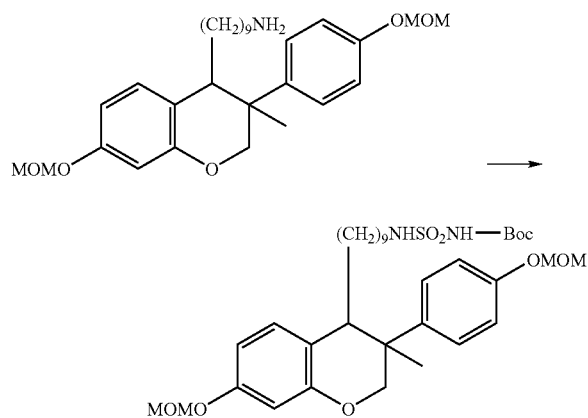

To a solution of chlorosulfonylisocyanate (25 µl, 0.292 mmol) in dichloromethane (1 ml) was added t-butanol (27 µl, 0.292 mmol) at −38° C. for 10 minutes, which was then stirred for 2.5 hours. Then, the reaction mixture was cooled down to −78° C., 4-(9-aminononyl)-7-methoxymethoxy-3-(4-methoxymethoxyphenyl)-3-methylchroman (118 mg, 0.243 mmol) dissolved in triethylamine (50 µl, 0.364 mmol) and dichloromethane (1 ml) was slowly added thereto, and the resulting mixture was stirred overnight at room temperature. After the reaction was completed, saturated ammonium chloride solution was added to the reaction solution, and the resulting solution was extracted with ethyl acetate. The organic layer was washed with diluted hydrochloride solution, water and saturated sodium chloride solution, and dried over anhydrous magnesium sulfate. The residue was subjected to preparative TLC (chloroform:methanol=10:1) to give the title compound (57 mg, yield 36%) as a white solid.

$^1$H-NMR (270 MHz, CDCl$_3$, 3RS,4RS-compound) δ: 7.13 (d, J=8.9 Hz, 2H, Ar—H), 7.02 (d, J=8.9 Hz, 2H, Ar—H), 6.94 (dd, J=8.6 and 2.3 Hz, 1H, C6-H), 6.56 (m, 2H, Ar—H), 5.18 (s, 2H, OCH$_2$OCH$_3$), 5.14 (s, 2H, OCH$_2$OCH$_3$), 4.52 (d, J=10.3 Hz, 1H, C2-H), 4.25 (d, J=10.3 Hz, 1H, C2-H), 3.50 (s, 3H, OCH$_2$OCH$_3$), 3.49 (s, 3H, OCH$_2$OCH$_3$), 3.01 (t, J=6.2 Hz, 2H, CH$_2$—NHSO$_2$NH), 2.63 (brs, 1H, C4-H), 1.48 (s, 9H, t-butyl-H), 1.28–1.05 (m, 19H, C3-CH$_3$ and alkyl-H)

Step 9) Synthesis of 4-[9-(N-t-butyloxycarbonyl-N-4,4,5,5,5-pentafluoropentylaminosulfonylamino)nonyl]-7-methoxymethoxy-3-(4-methoxymethoxyphenyl)-3-methylchroman

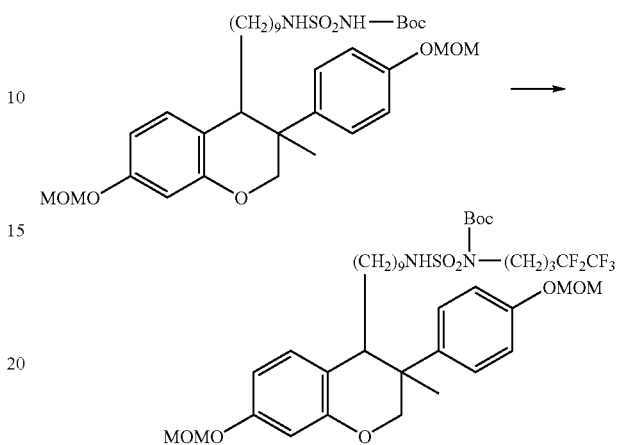

To a solution of 4-[9-(N-t-butyloxycarbonylaminosulfonylamino)nonyl]-7-methoxymethoxy-3-(4-methoxymethoxyphenyl)-3-methylchroman (5 7 mg, 0.088 mmol) in dichloromethane (2 ml) were added 4,4,5,5,5-pentafluoropentyl alcohol (15.6 mg, 0.088 mmol) and triphenylphosphine (23 mg, 0.088 mmol) at room temperature. Diethyl azodicarboxylate in dichloromethane (1 ml) was added dropwise to the reaction mixture at the same temperature until the color of the reaction solution turned to yellow, which was then stirred overnight. After the reaction was completed, the organic solvent was evaporated under reduced pressure. The crude product thus obtained was subjected to preparative TLC (n-hexane:ethyl acetate=8:2) to give the title compound (47 mg, yield 67%) as a white solid.

$^1$H-NMR (270 MHz, CDCl$_3$, 3RS,4RS-compound) δ: 7.13 (d, J=8.9 Hz, 2H, Ar—H), 7.02 (d, J=8.9 Hz, 2H, Ar—H), 6.94 (m, 1H, Ar—H), 6.56 (m, 2H, Ar—H), 5.18 (s, 2H, OCH$_2$OCH$_3$), 5.14 (s, 2H, OCH$_2$OCH$_3$), 4.52 (d, J=10.2 Hz, 1H, C2-H), 4.25 (d, J=10.2 Hz, 1H, C2-H), 3.73 (t, J=6.5 Hz, 2H, CH$_2$—N-Boc), 3.50 (s, 3H, OCH$_2$OCH$_3$), 3.49 (s, 3H, OCH$_2$OCH$_3$), 2.91 (t, J=6.9 Hz, 2H, CH$_2$—NHSO$_2$NH), 2.62 (brs, 1H, C4-H), 1.94 (m, 4H, alkyl-H), 1.52 (s, 9H, t-butyl-H), 1.24–1.09 (m, 19H, C3-CH$_3$, and alkyl-H)

Step 10) Synthesis of (3RS,4RS)-4-[9-(N-4,4,5,5,5-pentafluoropentylaminosulfonylamino)nonyl]-7-hydroxy-3-(4-hydroxyphenyl)-3-methylchroman

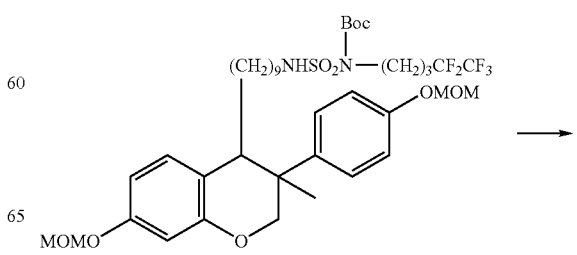

-continued

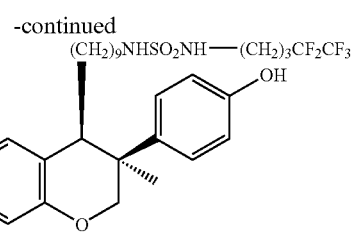

To a solution of ethyl 6-bromohexanoate (2.23 g, 10 mmol) in polyethyleneglycol 400(20 mL) was added potassium thioacetate (1.14 g, 10 mmol) at room temperature, which was then stirred overnight. Water was added to the reaction solution, and the resulting solution was extracted with ethyl acetate. The extract was dried over anhydrous magnesium sulfate, and concentrated under reduced pressure to give the title compound (2.17 g, yield 94%) as a yellow oil. This product thus obtained was used in the next reaction without further purification.

$^1$H-NMR (270 MHz, CDCl$_3$, 3RS,4RS-compound) δ: 7.07 (d, J=8.6 Hz, 2H, Ar—H), 6.90 (d, J=7.9 Hz, 1H, Ar—H), 6.38 (d, 1=8.6 Hz, 2H, Ar—H), 6.37 (m, 2H, Ar—H), 5.27 (s, 1H, OH), 5.77 (s, 1H, OH), 4.50 (d, J=10.6 Hz, 1H, C2-H), 4.21 (m, 3H, C2-H and 2×NH), 3.15 (dd, 1=6.6 Hz, 2H, CH$_2$—NH), 2.61 (brs, 1H, C4-H), 2.09 (m, 2H, alkyl-H), 1.87 (s, 2H, alkyl-H), 1.49–1.06 (m, 19H, C3-CH$_3$ and alkyl-H)

EXAMPLE 8

Synthesis of 6-[(3RS,4RS){9-[7-hydroxy-3-(4-hydroxyphenyl)-3-methylthiochroman-4-yl]nonylsulfinyl}hexanoic acid Step 1) Synthesis of 5-ethoxycarbonylpentan-1-thio]acetate

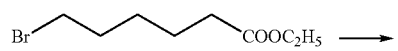

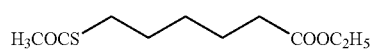

To a solution of ethyl 6-bromohexanoate acid ethylester (2.23 g, 10 mmol) in polyethyleneglycol 400 (20 ml) was added potassium thioacetate (1.14 g, 10 mmol) at room temperature, which was then stirred overnight. Water was added to the reaction solution, and the resulting solution was extracted with ethyl acetate. The extract was dried over anhydrous magnesium sulfate, and concentrated under reduced pressure to give the title compound (2.17 g, yield 94%) as a yellow oil. This product thus obtained was used in the next reaction without further purification.

$^1$H-NMR (270 MHz, CDCl$_3$) δ: 4.06 (q, J=7.2 Hz, 2H, COOC$\underline{H}_2$CH$_3$). 2.82 (dd, J=7.1 and 7.4 Hz, 2H, C1-CH$_2$), 2.25 (s, 3H, SCOCH$_3$), 2.21 (t, 2H, CH$_2$), 1.52 (m, 4H, 2×CH$_2$), 1.34 (m, 2H, CH$_2$), 1.19 (t, J=7.2 Hz, 3H, COOCH$_2$C$\underline{H}_3$)

Step 2) Synthesis of {9-[7-methoxy-3-(4-methoxyphenyl)-3-methyl]thiochroman-4-yl}nonylthio-6-hexanoic acid

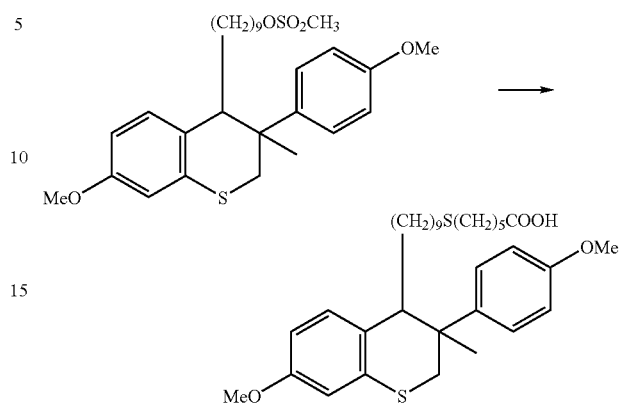

To a solution of 5-ethoxycarbonylpentan-1-thiolacetate (807 mg, 3.47 mmol) in ethanol (20 ml) was added 2N sodium hydroxide solution at room temperature, which was then stirred for 40 minutes. Then, 4-(9-methanesulfonyloxynonyl)-7-methoxy-3-(4-methoxyphenyl)-3-methylthiochrom an (362 mg, 0.695 mmol) dissolved in dry tetrahydrofuran (12 ml) was added dropwise thereto at room temperature, and the resulting mixture was stirred overnight at room temperature. After the reaction was completed, the reaction mixture was acidified with 1N-HCl and extracted with ethyl acetate. The organic layer was washed with water, dried over anhydrous magnesium sulfate, and concentrated under reduced pressure. The concentrate was subjected to preparative TLC (n-hexane:ethyl acetate=1:1) to give the title compound (350 mg, yield 88%) as a white solid.

$^1$H-NMR (270 MHz, CDCl$_3$, 3RS,4RS-compound) δ: 7.29 (d, J=8.9 Hz, 2H, Ar—H), 6.91 (m, 3H, Ar—H), 6.73 (d, J=2.3 Hz, 1H, thiochroman C8-H), 6.58 (dd, J=8.2 and 2.3 Hz, 1H, thiochroman C6-H), 3.82 (s, 3H, OCH$_3$), 3.77 (s, 3H, OCH$_3$), 3.64 (d, J=11.6 Hz, 1H, thiochroman C2-H), 2.98 (d, J=11.6 Hz, 1H, thiochroman C2-H), 2.72 (brs, 1H, thiochroman C4-H), 2.47 (m, 4H, 2×SCH$_2$), 2.35 (t, J=7.2 Hz, 2H, CH$_2$CO), 1.62–0.99 (m, 25H, thiochroman C3-CH$_3$ and alkyl-H)

Step 3) Synthesis of (3RS,4RS)-{9-[7-hydroxy-3-(4-hydroxyphenyl)-3-methyl]thiochroman-4-yl}nonylthio-6-hexanoic acid

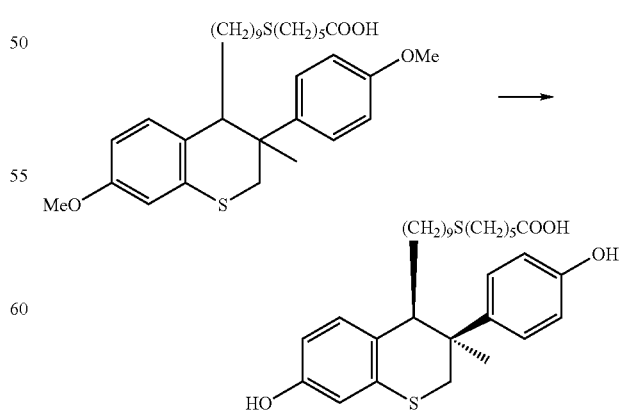

{9-[7-Methoxy-3-(4-methoxyphenyl)-3-methyl]thiochroman-4-yl}nonylthio-6-hexanoic acid (350 mg, 0.61 mmol)

was dissolved in dichloromethane (30 ml), and boron tribromide (2.63 ml, 1.0 mol/l solution in dichloromethane) was added thereto at −78 C. The reaction mixture was stirred at the same temperature for 1 hour, and further stirred at room temperature for about 8 hours. After the reaction was completed, water was added to the reaction mixture, which was then extracted with ethyl acetate. The organic layer was washed with water, dried over anhydrous magnesium sulfate, and concentrated under reduced pressure. The concentrate was subjected to preparative TLC (chloroform:methanol=10:1) to give the title compound (230 mg, yield 69%) as a white solid.

$^1$H-NMR (270 MHz, CDCl$_3$, 3RS,4RS-compound) δ: 7.24 (d, J=8.6 Hz, 2H, Ar—H), 6.85 (m, 3H, Ar—H), 6.67 (d, J=2.7 Hz, 1H, thiochroman C8-H), 6.50 (dd, J=8.8 and 2.7 Hz, 1H, thiochroman C6-H), 3.62 (d, J=11.5 Hz, 1H, thiochroman C2-H), 2.95 (d, J=11.5 Hz, 1H, thiochroman C2-H), 2.69 (brs, 1H, thiochroman C4-H), 2.49 (m, 4H, 2×SCH$_2$), 2.37 (t, J=7.2 Hz, 2H, CH$_2$CO), 1.69–1.05 (m, 25H, thiochroman C3-CH$_3$ and alkyl-H)

Step 4) Synthesis of 6-{(3RS,4RS)-{9-[7-hydroxy-3-(4-hydroxyphenyl)-3-methylthiochroman-4-yl]-nonylsulfinyl}-hexanoic acid

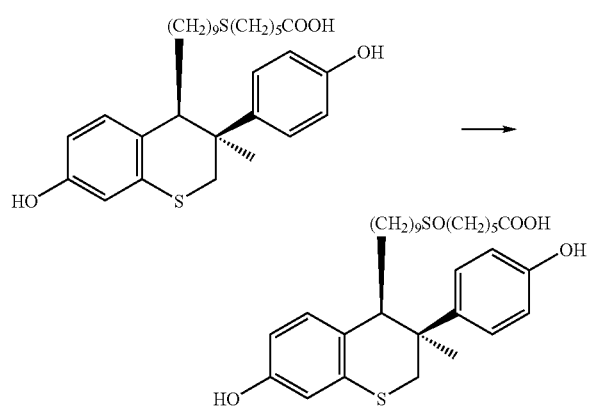

To a solution of (3RS,4RS)-{9-[7-hydroxy-3-(4-hydroxyphenyl)-3-methyl]thiochroman-4-yl}-nonylthio-6-hexanoic acid (1.65 mg, 0.30 mmol) in methanol (10 ml) and tetrahydrofuran (30 mg) was slowly added Oxone® (monopersulfate compound; DuPont product) (186 mg, 0.30 mmol) dissolved in water (1 ml), which was then stirred at the same temperature for 10 minutes. After water was added thereto, the reaction solution was extracted with ethyl acetate. The extract was concentrated under reduced pressure, and subjected to preparative TLC (chloroform:methanol=10:1) to give the title compound (94 mg, yield 55%) as a white solid.

$^1$H-NMR (270 MHz, CD$_3$OD, 3RS,4RS-compound) δ: 7.16 (d, J=8.9 Hz, 2H, Ar—H), 6.78 (d, J=8.2 Hz, 1H, thiochroman C5-H), 6.69 (d, J=8.9 Hz, 2H, Ar—H), 6.47 (d, J=2.3 Hz, 1H, thiochroman C8-H), 6.35 (dd, 3=8.2 and 2.3 Hz, 1H, thiochroman C6-H), 3.53 (d, J=11.5 Hz, 1H, thiochroman C2-H), 2.85 (d, J=11.5 Hz, 1H, thiochroman C2-H), 2.68 (m, 5H, thiochroman C4-H and 2×SCOCH$_2$), 2.12 (t, J=7.3 Hz, 2H, COCH$_2$), 1.81–0.99 (m, 25H, thiochroman C3-CH$_3$ and alkyl-H)

EXAMPLE 9

Synthesis of (3RS,4RS)-7-hydroxy-3-(4-hydroxyphenyl)-3-methyl-4-[9-(2-(2-methoxyethoxy)ethylsulfinyl]nonyl}thiochroman Step 1) Synthesis of 2-(2-methoxyethoxy)ethyl p-toluenesulfonate

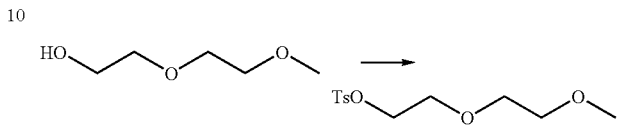

To a solution of diethylene glycol monomethylether (12 g, 100 mmol) in pyridine (70 ml) was added p-toluenesulfonyl chloride (22.8 g, 120 mmol) at 0° C., which was then stirred at room temperature for 2 hours. Water was added thereto, and the mixture was extracted with diethyl ether. The extracted organic layer was washed with 0.5N-HCl, water and saturated sodium bicarbonate solution, and dried over anhydrous magnesium sulfate. The organic solvent was removed under reduced pressure to give the title compound (27 g, stoichiometric yield) as a yellow oil. The compound thus obtained was used in the next reaction without further purification.

$^1$H-NMR (270 MHz, CDCl$_3$) δ: 3.54 (m, 6H, 3×OCH$_2$), 3.35 (s, 3H, OCH$_3$), 3.07 (t, J=6.2 Hz, 2H, SCH$_2$), 2.31 (s, 3H, SCOCH$_3$)

Step 2) Synthesis of 2-(2-methoxyethoxy)ethyl thioacetate

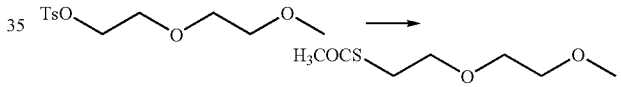

The title compound was prepared from 2-(2-methoxyethoxy)ethyl p-toluenesulfonate according to the same procedure as Step 1 of Example 8.

$^1$H-NMR (270 MHz, CDCl$_3$) δ: 7.78 (d, J=8.0 Hz, 2H, Ar—H), 7.32 (d, J=7.7 Hz, 2H, Ar—H), 4.15 (dd, J=5.0 and 4.1 Hz, 2H, OCH$_2$), 3.67 (dd, J=5.5 and 4.1 Hz, 2H, OCH$_2$), 3.56 (m, 2H, OCH$_2$), 3.46 (m, 2H, OCH$_2$), 3.33 (s, 3H, OCH$_3$), 2.43 (s, 3H, CH$_3$)

Step 3) Synthesis of 7-hydroxy-3-(4-hydroxyphenyl)-3-methylthiochroman-4-one

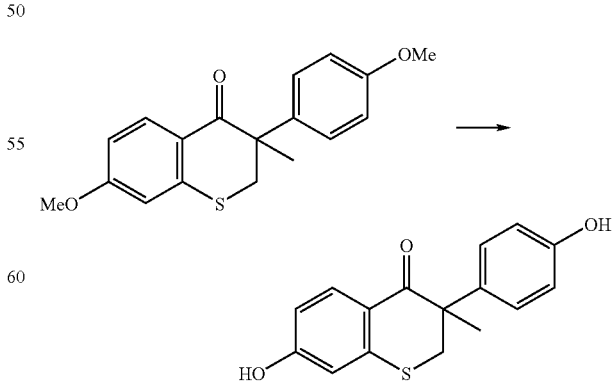

To a solution of 7-methoxy-3-(4-methoxyphenyl)-3-methylthiochroman-4-one (2.27 g, 7.22 mmol) in acetic acid (75 ml) was added 48% aqueous HBr solution (75 mg), which was then heated under reflux for 1 day. The reaction mixture was extracted with diethyl ether. The organic layer was washed with saturated sodium bicarbonate solution and saturated saline solution, dried over anhydrous magnesium sulfate, and concentrated. Then, the residue was subjected to flash chromatography on silica gel (n-hexane:ethyl acetate=7:3 and 1:1) to give the title compound (1.92 g, yield 92%).

$^1$H-NMR (270 MHz, CDCl$_3$) δ: 8.12 (d, J=8.6 Hz, 1H, C5-H), 7.07 (d, J=8.6 Hz, 2H, Ar—H), 6.75 (d, J=8.6 Hz, 2H, Ar—H), 6.63 (d, J=8.6 and 2.3 Hz, 1H, C6-H), 6.56 (d, J=2.3 Hz, 1H, C8-H), 3.41 (s, 2H, C2-CH2), 1.26 (s, 3H, C3-CH$_3$)

Step 4) Synthesis of 7-methoxymethoxy-3-(4-methoxymethoxyphenyl)-3-methylthiochroman-4-one

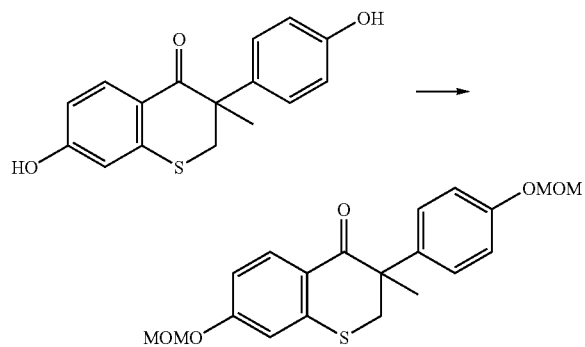

To a solution of 7-hydroxy-3-(4-hydroxyphenyl)-3-methylthiochroman-4-one (1.92 g, 6.7 mmol) in dry acetone (200 ml) were added potassium carbonate (8.34 g, 60.42 mmol) and methoxymethyl chloride (3.04 ml, 40.28 mmol), which was then heated for 8 hours. Water was added thereto, and the resulting solution was extracted with ethyl acetate. Then, the organic layer was washed with water and saturated sodium chloride solution, dried over anhydrous magnesium sulfate, and concentrated under reduced pressure. The residue was subjected to flash chromatography on silica gel (n-hexane:ethyl acetate=7:3 and 1:1) to give the title compound (2.50 g, yield 99%).

$^1$H-NMR (270 MHz, CDCl$_3$) δ: 8.17 (d, J=8.9 Hz, 1H, C5-H), 7.14 (d, J=8.3 Hz, 2H, Ar—H), 6.95 (d, J=8.6 Hz, 2H, Ar—H), 6.80 (d, J=8.9 and 2.6 Hz, 1H, C6-H), 6.75 (d, J=2.3 Hz, 1H, C8-H), 5.24 (s, 2H, OC$\underline{H_2}$OCH$_3$), 5.15 (s, 2H, OC$\underline{H_2}$OCH$_3$), 3.48 (s, 2H, C2-CH2), 3.45 (s, 3H, OCH$_2$O C$\underline{H_3}$), 3.44 (s, 3H, OCH$_2$OC$\underline{H_3}$), 1.57 (s, 3H, C3-CH$_3$)

Step 5) Synthesis of 4-[9-(t-butyldimethylsilyloxy)-1-nonynyl]4-hydroxy-7-methoxymethoxy-3-(4-methoxymethoxyphenyl)-3-methylthiochroman

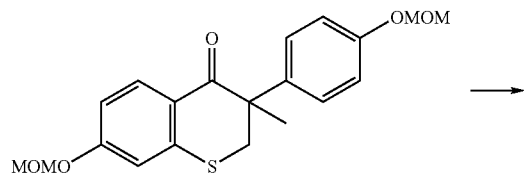

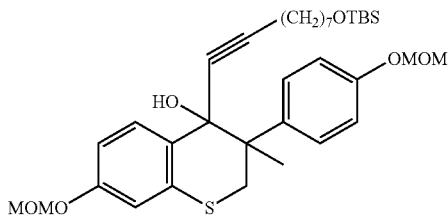

The title compound was prepared from 7-methoxymethoxy-3-(4-methoxy-methoxyphenyl}-3-methylthiochroman-4-one according to the same procedure as Step 1 of Example 6.

$^1$H-NMR (270 MHz, CDCl$_3$) δ: 7.86 (d, J=8.9 Hz, 1H, C5-H), 7.59 (d, J=8.9 Hz, 2H, Ar—H), 7.01 (d, J=8.9 Hz, 2H, Ar—H), 6.82 (d, J=2.3 Hz, 1H, C8-H), 6.75 (dd, J=8.9 and 2.4 Hz, 1H, C6-H), 5.18 (s, 2H, OC$\underline{H_2}$OCH$_3$), 5.14 (s, 2H, OC$\underline{H_2}$OCH$_3$), 4.25 (d, J=12.6 Hz, 1H, C2-H), 3.56 (t, 1=6.6 Hz, 2H, CH$_2$-OTBS), 3.48 (s, 31, OCH$_2$OC$\underline{H_3}$), 3.46 (s, 3H, OCH$_2$OC$\underline{H_3}$), 2.69 (d, J=12.6 Hz, 1H, C2-H), 2.18 (m, 3H, OH and propargyl-CH$_2$), 1.58 (s, 3H, C3-CH$_3$), 1.57–1.29 (m, 10H, alkyl-H), 0.89 (s, 9H, t-butyl-H), 0.04 (s, 6H, 2×CH$_3$)

Step 6) Synthesis of 4-[9-(t-butyldimethylsilyloxy)-1-nonynyl]-7-methoxymethoxy-3-(4-methoxymethoxyphenyl)-3-methylthiochroman

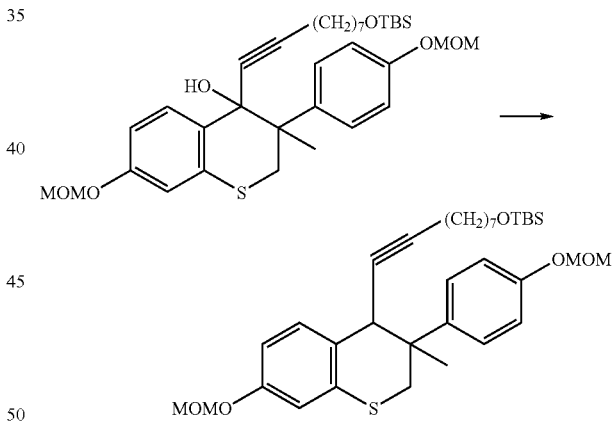

The title compound was prepared from 4-[9-(t-butyldimethylsilyloxy)-1-nonynyl]4-hydroxy-7-methoxymethoxy-3-(4-methoxymethoxyphenyl)-3-methylthiochroman according to the same procedure as Step 2 of Example 6.

$^1$H-NMR (270 MHz, CDCl$_3$, 3RS,4RS-compound) δ: 7.43 (m, 3H, Ar—H), 6.97 (d, J=8.9 Hz, 2H, Ar—H), 6.84 (d, J=2.3 Hz, 1H, C8-H), 6.73 (dd, J=8.9 and 2.3 Hz, 1h, C6-H), 5.15 (s, 2H, OC$\underline{H_2}$OCH$_3$), 5.12 (s, 2H, OC$\underline{H_2}$OCH$_3$), 3.77 (brs, 1H, C4-H), 3.65 (d, J=12.2 Hz, 1H, C2-H), 3.59 (t, J=6.6 Hz, 2H, CH$_2$-OTBS), 3.52 (s, 3H, OCH$_2$OC$\underline{H_3}$), 3.51 (s, 3H, OCH$_2$OC$\underline{H_3}$), 2.99 (d, J=12.2 Hz, 1H, C2-H), 2.04 (t, J=6.6 Hz, 2H, propargyl-CH$_2$), 1.55 (s, 3H, C3-CH$_3$), 1.49–1.25 (m, 10H, alkyl-H), 0.89 (s, 9H, t-butyl-H), 0.04 (s, 6H, 2×CH$_3$)

Step 7) Synthesis of 4-(9-hydroxynonyl)-7-methoxymethoxy-3-(4-methoxymethoxyphenyl)-3-methylthiochroman

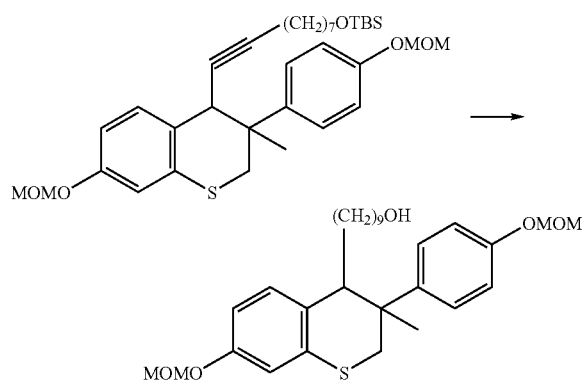

4-[9-(t-Butyldimethylsilyloxy)-1-nonynyl]-7-methoxymethoxy-3-(4-methoxymethoxyphenyl)-3-methylthiochroman (1.43 g, 2.27 mmol) was dissolved in ethanol (100 ml) and tetrahydrofuran (10 ml), and 20% palladium hydroxide on carbon (500 mg) which had been washed with ethanol was added thereto. The reaction solution was stirred for 1 day under hydrogen (atmospheric pressure). Ethyl acetate was added to the reaction mixture, which was then filtered and concentrated. The concentrate was dissolved in dichloromethane (50 ml) and 1N-sodium hydroxide (2 ml), and tetra-n-butylammonium chloride (556 mg, 2 mmol) was added thereto at room temperature. To the reaction mixture was added dropwise methoxymethyl chloride (0.22 ml, 3 mmol) at the same temperature, which was then stirred for 2 hours. Water was added, and the resulting solution was extracted with ethyl acetate. Then, the organic layer was washed with water and saturated sodium chloride solution, dried over anhydrous magnesium sulfate, and concentrated under reduced pressure. The residue was subjected to flash chromatography on silica gel (n-hexane:ethyl acetate=1:1) to give the title compound (855 mg, yield 75%) as a white solid.

$^1$H-NMR (270 MHz, CDCl$_3$, 3RS,4RS-compound) δ: 7.27 (d, J=8.9 Hz, 2H, Ar—H), 7.02 (d, J=8.6 Hz, 2H, Ar—H), 6.92 (d, J=8.3 Hz, 1H, C5-H), 6.87 (d, J=2.3 Hz, 1H, C8-H), 6.68 (dd, J=8.3 and 2.3 Hz, 1H, C6-H), 5.18 (s, 2H, OC$\underline{H}_2$OCH$_3$), 5.13 (s, 2H, OC$\underline{H}_2$OCH$_3$), 3.60 (m, 3H, C2-H and C$\underline{H}_2$OH), 3.49 (s, 3H, OCH$_2$OC$\underline{H}_3$), 3.48 (s, 3H, OCH$_2$OC$\underline{H}_3$), 2.98 (d, J=12.2 Hz, 1H, C2-H), 2.78 (brs, 1H, C4-H), 1.56–1.08 (m, 19H, C3-CH$_3$ and alkyl-H)

Step 8) Synthesis of 4-(9-methanesulfonyloxynonyl)-7-methoxymethoxy-3-(4-methoxymethoxyphenyl)-3-methylthiochroman

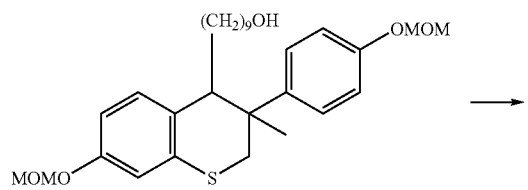

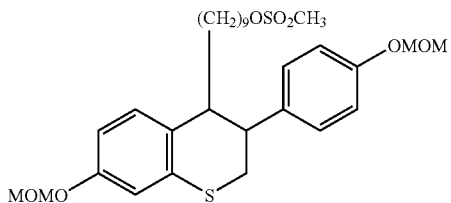

The title compound was prepared from 4-(9-hydroxynonyl)-7-methoxymethoxy-3-(4-methoxymethoxyphenyl)-3-methylthiochroman according to the same procedure as Step 5 of Example 6.

$^1$H-NMR (270 MHz, CDCl$_3$, 3RS,4RS-compound) δ: 7.27 (d, J=8.9 Hz, 2H, Ar—H), 7.01 (d, J=8.6 Hz, 2H, Ar—H), 6.91 (d, J=8.2 Hz, 1H, C5-H), 6.86 (d, J=2.3 Hz, 1H, C8-H), 6.67 (dd, J=8.2 and 2.3 Hz, 1H, C6-H), 5.17 (s, 2H, OC$\underline{H}_2$OCH$_3$), 5.12 (s, 2H, OC$\underline{H}_2$OC$\underline{H}_3$), 4.17 (t, J=6.6 Hz, 2H, OCH$_2$), 3.61 (d, J=11.5 Hz, 1H, C2-H), 3.48 (s, 3H, OCH$_2$C$\underline{H}_3$), 3.47 (s, 3H, OCH$_2$OC$\underline{H}_3$), 2.97 (m, 4H, C2-H and OSO$_2$CH$_3$), 2.78 (brs, 1H, C4-H), 1.67 (m, 3H, alkyl-H), 1.34–1.06 (m, 16H, C3-CH$_3$ and alkyl-H)

Step 9) Synthesis of 7-methoxymethoxy-3-(4-methoxymethoxyphenyl)-3-methyl-4-{9-[2-(2-methoxyethoxy)ethylthio]nonyl}thiochroman

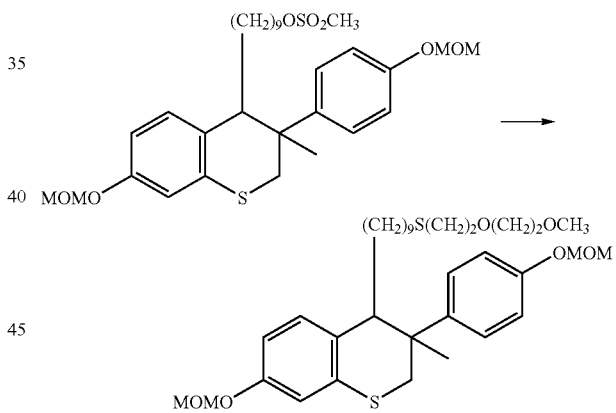

The title compound was prepared from 4-(9-methanesulfonyloxynonyl)-7-methoxymethoxy-3-(4-methoxymethoxyphenyl)-3-methylthiochroman and 2,2-methoxyethoxy)ethyl thiolacetate according to the same procedure as Step 7 of Example 6.

$^1$H-NMR (270 MHz, CDCl$_3$, 3RS,4RS-compound) δ: 7.28 (d, J=8.9 Hz, 2H, Ar—H), 7.02 (d, J=8.9 Hz, 2H, Ar—H), 6.91 (d, J=8.3 Hz, 1H, C5-H), 6.87 (d, J=2.3 Hz, 1H, C8-H), 6.67 (dd, J=8.3 and 2.3 Hz, 1H, C6-H), 5.18 (s, 2H, OC$\underline{H}_2$OCH$_3$), 5.14 (s, 2H, OC$\underline{H}_2$OCH$_3$), 3.58 (m, 7H, C2-H and 3×OCH$_2$), 3.49 (s, 3H, OCH$_2$OC$\underline{H}_3$), 3.48 (s, 3H, OCH$_2$OC$\underline{H}_3$), 3.37 (s, 3H, OCH$_3$), 2.97 (d, J=11.8 Hz, 1H, C2-H), 2.70 (m, 3H, C4-H and SCH$_2$), 2.50 (t, J=6.6 Hz, 2H, SCH$_2$), 1.56 (m, 3H, alkyl-H), 1.35–1.05 (m, 16H, C3-CH$_3$ and alkyl-H)

Step 10) Synthesis of (3RS,4RS)-7-hydroxy-3-(4-hydroxyphenyl)-3-methyl-4-{9-[2-(2-methoxyethoxy)ethylthio]nonyl}thiochroman

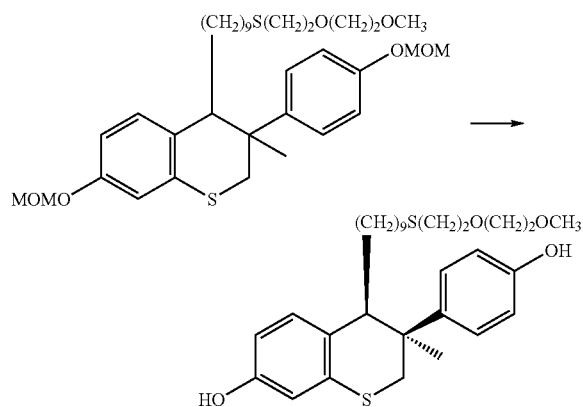

To a solution of 7-methoxymethoxy-3-(4-methoxymethoxyphenyl)-3-methyl-4-{9-[2-(2-methoxyethoxy)ethylthio]nonyl}thiochroman (68 mg, 0.109 mmol) in isopropanol (5.5 ml) and tetrahydrofuran (0.9 ml) was added 5N-HCl (1.47 ml) at room temperature, which was stirred for 2 days. Water was added thereto, and the resulting solution was extracted with ethyl acetate. Then, the organic layer was washed with water and saturated sodium chloride solution, dried over anhydrous magnesium sulfate, and concentrated under reduced pressure. The residue was subjected to flash chromatography on silica gel (n-hexane:ethyl acetate=1:1) to give the title compound (43 mg, yield 74%) as a white solid.

$^1$H-NMR (270 MHz, CDCl$_3$, 3RS,4RS-compound) δ: 7.29 (d, J=8.9 Hz, 2H, Ar—H), 6.70 (m, 3H, Ar—H), 6.72 (d, J=2.3 Hz, 1H, C8-H), 6.54 (dd, J=8.2 and 2.3Hz, 1H, C6-H). 5.70 (s, 1H, OH), 5.37 (s, H, OH), 3.66 (m, 7H, C2-H and 3×OCH$_2$), 3.44 (s, 3H, OCH$_3$), 2.99 (d, J=11.5 Hz, 1H, C2-H), 2.76 (m, 3H, C4-H and SCH$_2$), 2.56 (t, J=6.6 Hz, 2H, SCH$_2$), 1.53 (m, 3H, alkyl-H), 1.33–1.09 (m, 16H, C3-CH$_3$ and alkyl-H)

Step 11) Synthesis of (3RS,4RS)-7-hydroxy-3-(4-hydroxyphenyl)-3-methyl-4-{9-[2-(2-methoxyethoxy)ethylsulfinyl]nonyl}thiochroman

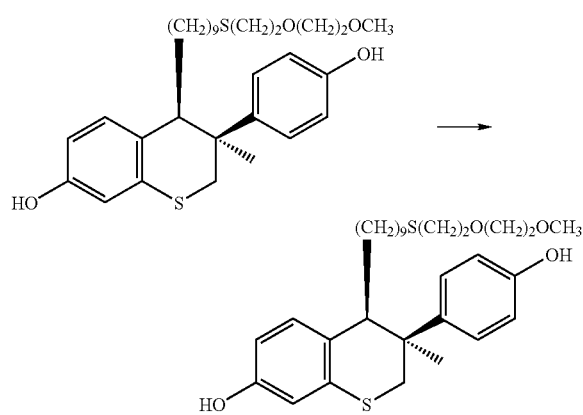

The title compound was prepared from (3RS,4RS)-7-hydroxy-3-(4-hydroxyphenyl)-3-methyl-4-{9-[2-(2-methoxyethoxy)ethylthio]nonyl}thiochroman according to the same procedure as Step 4 of Exampel 8.

$^1$H-NMR (270 MHz, CDCl$_3$, 3RS,4RS-compound) δ: 7.62 (s, 1H, OH, diastereomer A), 7.21 (d, J=8.9 Hz, 2H, Ar—H), 7.15 (s, 1H, OH, diastereomer A), 6.85 (m, 3H, Ar—H), 6.67 (d, J=2.3 Hz, 1H, C8-H), 6.50 (m, 1H, C6-H), 5.70 (s, 1H, OH, diastereomer B), 5.43 (s, 1H, OH, diastereomer B), 3.95 (m, 2H, OCH$_2$), 3.62 (m, 5H, C2-H and 2×OCH$_2$), 3.39 (s, 3H, OCH$_3$), 2.87 (m, 6H, C2-H, C4-H and 2×SOCH$_2$), 1.72 (m, 3H, alkyl-H), 1.49–1.02 (m, 16H, C3-CH$_3$ and alkyl-H)

EXAMPLE 10

Synthesis of (3RS,4RS)-7-hydroxy-3-(4-hydroxyphenyl)-3-methyl-4-{9-[2-(2-hydroxyethoxy)ethylsulfinyl]nonyl}thiochroman Step 1) Synthesis of 2-[2-(t-butyldimethylsilyloxy)ethoxy]ethyl chloride

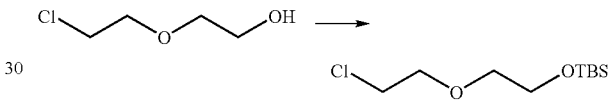

To a solution of ethylene glycol mono-2-chloroethyl ether (6.2 g, 50 mmol) in acetonitrile (150 mg) were added imidazole (6.77 g, 99.54 mmol) and t-butyldimethylsilyl chloride (11.25 g, 74.65 mmol) at room temperature. The reaction mixture was stirred overnight at the same temperature. After the reaction was completed, the mixture was filtered through a filter paper, and concentrated under reduced pressure. Then, the concentrate was subjected to flash chromatography on silica gel (n-hexane:ethyl acetate=9:1) to give the title compound (11.0 g, yield 92%) as a colorless oil.

$^1$H-NMR (270 MHz, CDCl$_3$) δ: 3.86 and 3.63 (m, 8H, CH$_2$Cl and 3×OCH$_2$), 0.89 (s, 9H, t-butyl-H), 0.06 (s, 6H, 2×CH$_3$)

Step 2) Synthesis of 2-[2-(t-butyldimethylsilyloxy)ethoxy]ethyl thioacetate

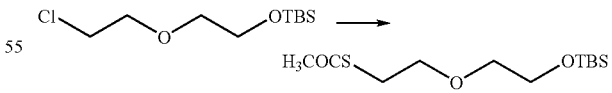

The title compound was prepared from 2-[2-(t-butyldimethylsilyloxy)ethoxy]ethyl chloride according to the same procedure as Step 1 of Example 8.

$^1$H-NMR (270 MHz, CDCl$_3$) δ: 3:74 (dd, J=5.3 and 5.0 Hz, 2H, OCH$_2$), 3.60 (dd, J=6.6 and 6.3 Hz, 2H, OCH$_2$), 3.52 (dd, J=5.3 and 4.9 Hz, 2H, OCH$_2$), 3.08 (dd, J=6.2 and 6.6 Hz, 2H, SCH$_2$), 2.33 (s, 3H, SCOCH$_3$), 0.89 (s, 9H, t-butyl-H), 0.06 (s, 6H, 2×CH$_3$)

Step 3) Synthesis of 7-methoxymethoxy-3-(4-methoxymethoxyphenyl)-3-methyl-4-{9-[2-(2-t-butyldimethylsilyloxyethoxy)ethylthio]nonyl}thiochroman

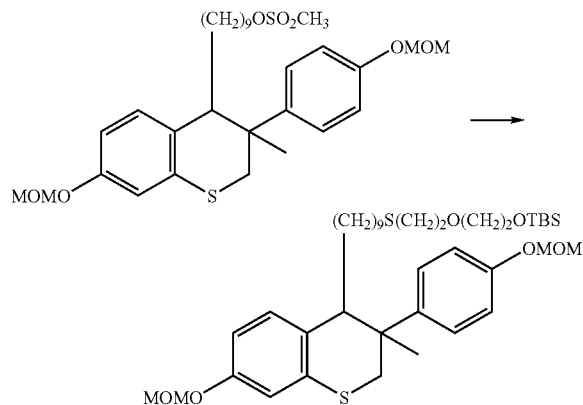

The title compound was prepared from 4-(9-methanesulfonyloxynonyl)-7-methoxymethoxy-3-(4-methoxymethoxyphenyl)-3-methylthiochroman and 2-[2-(t-butyldimethylsilyloxy)ethoxy]ethyl thioacetate according to the same procedure as Step 7 of Example 6.

$^1$H-NMR (270 MHz, CDCl$_3$, 3RS,4RS-compound) δ: 7.28 (d, J=8.9 Hz, 2H, Ar—H), 7.02 (d, J=8.9 Hz, 2H, Ar—H), 6.88 (d, J=8.3 Hz, 1H, C5-H), 6.86 (d, J=2.3 Hz, 1H, C8-H), 6.66 (dd, J=8.3 and 2.3 Hz, 1H, C6-H), 5.18 (s, 2H, OC$\underline{H}_2$OCH$_3$), 5.13 (s, 2H, OC$\underline{H}_2$OCH$_3$), 3.64 (m, 7H, C2-H and 3×OCH$_2$), 3.49 (s, 3H, OCH$_2$OC$\underline{H}_3$), 3.48 (s, 3H, OCH$_2$OC$\underline{H}_3$), 2.98 (d, J=11.8 Hz, 1H, C2-H), 2.68 (m, 3H, C4-H and SCH$_2$), 2.50 (t, J=6.6 Hz, 2H, SCH$_2$), 1.62–1.08 (m, 19H, C3-CH$_3$ and alkyl-H), 0.89 (s, 9H, t-butyl-H), 0.06 (s, 6H, 2×CH$_3$)

Step 4) Synthesis of (3RS,4RS)-7-hydroxy-3-(4-hydroxyphenyl)-3-methyl-4-{9-[2-(2-hydroxyethoxy)ethylthio]nonyl}thiochroman

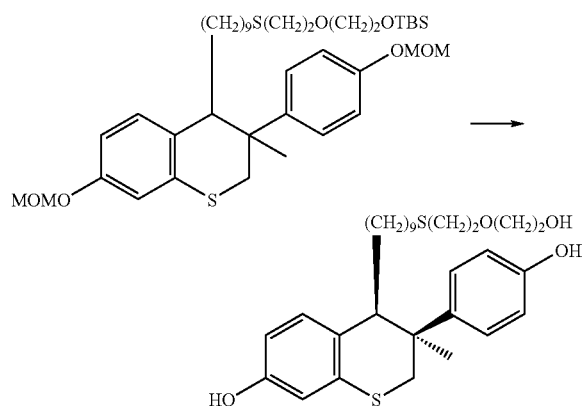

The title compound was prepared from 7-methoxymethoxy-3-(4-methoxymethoxyphenyl)-3-methyl-4-{9-[2-2-(t-butyldimethylsilyloxyethoxy)ethylthio]nonyl}thiochroman according to the same procedure as Step 10 of Example 9.

$^1$H-NMR (270 MHz, CDCl$_3$, 3RS,4RS-compound) δ: 7.23 (d, J=8.9 Hz, 2H, Ar—H), 6.85 (m, 3H, Ar—H), 6.67 (d, J=2.3 Hz, 1H, C8-H), 6.50 (dd, J=8.2 and 2.3 Hz, 1H, C6-H), 5.83 (s, 1H, OH), 5.39 (s, 1H, OH), 3.67 (m, 7H, C2-H and 3×OCH$_2$), 2.94 (d, J=11.5 Hz, 1H, C2-H), 2.72 (m, 3H, C4-H and SCH$_2$), 2.54 (t, J=6.6 Hz, 2H, SCH$_2$), 1.53 (m, 3H, alkyl-H), 1.28–1.08 (m, 16H, C3-CH$_3$ and alkyl-H)

Step 5) Synthesis of (3RS,4RS)-7-hydroxy-3-(4-hydroxyphenyl)-3-methyl-4-{9-[2-(2-hydroxyethoxy)ethylsulfinyl]nonyl}thiochroman

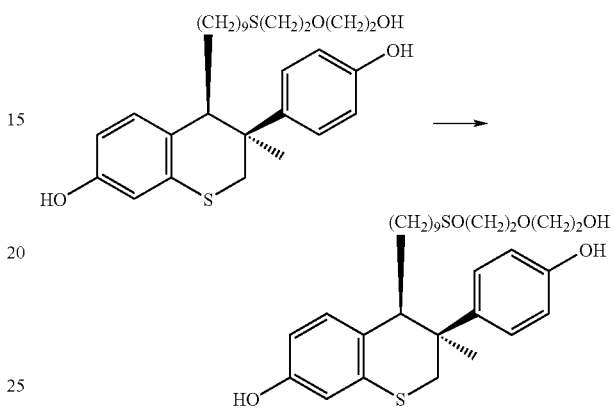

The title compound was prepared from (3RS,4RS)-7-hydroxy-3-(4-hydroxyphenyl)-3-methyl 4-{9-[2-(2-hydroxyethoxy)ethylthio]nonyl}thiochroman according to the same procedure as Step 4 of Example 8.

$^1$H-NMR (270 MHz, CD$_3$CD, 3RS,4RS-compound) δ: 7.17 (d, J=8.9 Hz, 2H, Ar—H), 6.77 (d, J=8.2 Hz, 1H, C5-H), 6.69 (d, J=8.9 Hz, 2H, Ar—H), 6.48 (d, J=2.3 Hz, 1H, C8-H), 6.36 (dd, J=8.2 and 2.3 Hz, 1H, C6-H), 3.81 (m, 2H, OCH$_2$), 3.58 (m, 3H, C2-H and OCH$_2$), 3.49 (m, 2H, OCH$_2$), 2.88 (m, 6H, C2-H, C4-H and 2×S(O)CH$_2$), 1.63 (m, 3H, alkyl-H), 1.40–1.04 (m, 16H, C3-CH$_3$ and alkyl-H)

EXAMPLE 11

Synthesis of (3RS,4RS)-7-hydroxy-3-(2-methylphenyl)-3-methyl-4-[9-(4,4,5,5-pentafluoropentyl)sulfinylnonyl]thiochroman Step 1) Synthesis of 7-methoxy-3-(2-methylphenyl)-3-methylthiochroman-4-one

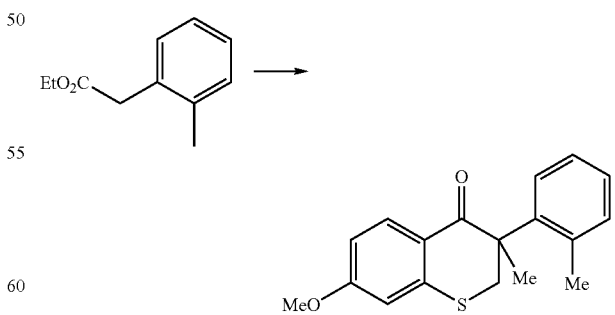

The title compound was prepared using ethyl 2-methylphenylacetate according to the same procedure described in International Patent Appln. No. PCT/KR97/00265.

$^1$H-NMR (270 MHz, CDCl$_3$) δ: 8.17 (d, 1H, J=8.9 Hz, C5-H), 7.44–7.34 (m, 1H, Ar—H), 7.24–7.12 (m, 3H), 6.75

(dd, 1H, J=8.9 Hz and 2.6 Hz, Ar—H), 6.70 (d, 1H, J=2.3 Hz, C8-H), 3.90 (d, 1H, J=14.2 Hz), 3.84 (3H, s, OCH₃), 2.78 (d, 1H, J=14.2 Hz), 2.22 (s, 3H, Ar—CH₃), 1.81 (s, 3H, C3-CH₃)

Step 2) Synthesis of (3RS,4RS)-7-hydroxy-3-(2-methylphenyl)-3-methyl-4-[9-(4,4,5,5,5-pentafluoropentyl)sulfinylnonyl]thiochroman

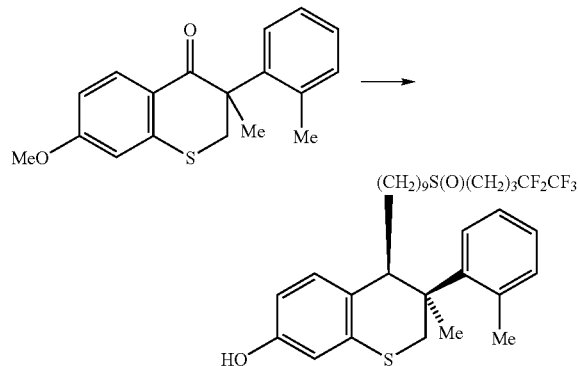

The title compound was prepared from 7-methoxy-3-(2-methylphenyl)-3-methylthiochroman-4-one according to the same procedure described in International Patent Appln. No. PCT/KR97/00265.

EI-MS 604 (M+)

¹H-NMR (270 MHz, CDCl₃) δ: 7.30–7.12 (m, 4H, Ar—H), 6.87 (d, 1H, J=8.3 Hz, Ar—H), 6.69 (dd, 1H, J=2.3, 2.3 Hz, C8-H), 6.62 (s, 1H, OH), 6.56–6.50 (m, 1H, Ar—H), 3.80 (d, 1H, J=7.9 Hz, C2-H), 3.19 (d, 1H, J=7.9 Hz), 3.10–2.92 (1H, m, C4-H), 2.86–2.68 (m, 2H), 2.62 (s, 3H, Ar—CH₃), 2.40–2.10 (m, 4H), 1.76–1.60 (m, 2H), 1.36 (s, 3H, C3-CH₃), 1.36–1.00 (m, 16H)

EXAMPLE 12

Synthesis of (3RS,4RS)-7-hydroxy-3-methyl-4-[9-(4,4,5,5,5-pentafluoropentylsulfinyl)nonyl]-3-(4-pyridyl)chroman Step 1) Synthesis of 2-hydroxy-4-methoxy-2-(4-pyridyl) acetophenone

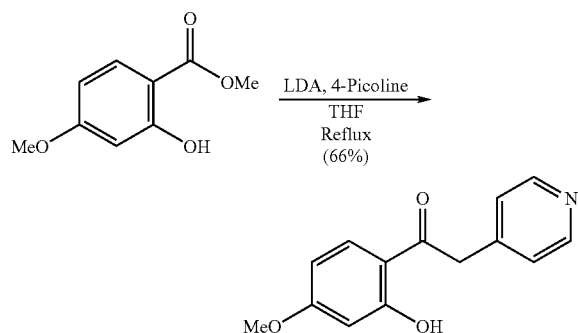

To a solution of lithium diisopropylamide (LDA) (2.0 mol/l, 35.2 ml, 70.4 mmol) in tetrahydrofuran (15 ml) was added dropwise a solution of 4-picoline (3.28 g, 3.52 mmol) in tetrahydrofuran (15 ml) under ice-cooling, which was then stirred for 30 minutes. Then, a solution of methyl 4-methoxysalicylate (4.0 g, 22 mmol) in tetrahydrofuran (20 ml) was added dropwise thereto, and the resulting mixture was heated under reflux for 3 hours. After the reaction was completed, the reaction solution was neutralized under ice-cooling using saturated aqueous NH₄Cl solution, extracted with ethyl acetate, and washed with water and saturated saline solution. The organic layer was dried over magnesium sulfate, and the solvent was removed under reduced pressure. The residue was subjected to silica gel column chromatography (n-hexane:ethyl acetate=1:2) to give 2-hydroxy-4-methoxy-2-(4-pyridyl)acetophenone (3.51 g, yield 66%).

EI-MS : 243 (M+)

¹H-NMR (270 MHz, CDCl₃) δ: 12.53 (s, 1H, ArOH), 8.58 (d, 2H, J=5.6 Hz, pyridyl), 7.68 (d, 1H, J=8.6 Hz, Ar—H), 7.21 (d, 2H, J=5.6 Hz, pyridyl), 6.48 (d, 1H, J=2.3 Hz, Ar—H), 6.45 (s, 1H, Ar—H), 4.22 (s, 2H, C(O)CH₂), 3.85 (s, 1H, OCH₃)

Step 2) Synthesis of 7-methoxy-3-(4-pyridyl)chroman-4-one

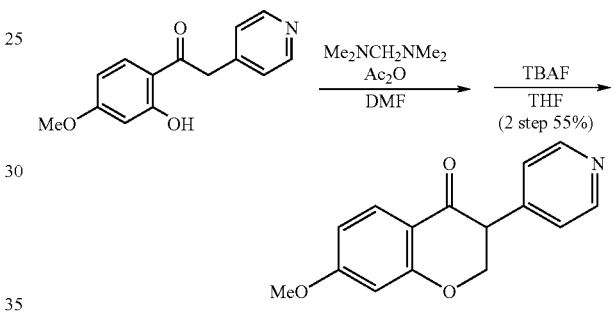

To a solution of 2-hydroxy-4-methoxy-2-(4-pyridyl)acetophenone (3.51 g, 14.4 mmol) in tetrahydrofuran (30 ml) were added under ice-cooling dry acetate (2.72 ml, 28.8 mmol) and a solution of N,N,N',N'-tetramethyl-diaminomethane (1.96 ml, 14.4 mmol) in DMF (10 ml), which was then stirred for 30 minutes. After the reaction was completed, the reaction solution was neutralized under ice-cooling using saturated aqueous NaHCO₃ solution, extracted with ethyl acetate, and washed with saturated saline solution. The organic layer was dried over magnesium sulfate, and the solvent was removed under reduced pressure. The residue was dissolved in tetrahydrofuran (20 mg), tetra-n-butylammonium fluoride (11.0 mmol/g, 0.144 mg, 0.144 mmol) was added thereto under ice-cooling, and the resulting mixture was stirred at room temperature for 1 hour. After the reaction was completed, saturated aqueous NH₄Cl solution was added to the reaction solution, which was then extracted with ethyl acetate and washed with saturated saline solution. The organic layer was dried over magnesium sulfate, and the solvent was removed under reduced pressure. The residue was subjected to silica gel column chromatography (n-hexane:ethyl acetate=1:2) to give 7-methoxy-3-(4-pyridyl)chroman-4-one (2.02 g, yield 55%).

EI-MS: 255(M+)

¹H-NMR (270 MHz, CDCl₃) δ: 8.57 (d, 2H, J=6.3 Hz, pyridyl), 7.89 (d, 1H, J=8.9 Hz, Ar—H), 7.24 (d, 2H, J=6.3 Hz, pyridyl), 6.63 (dd, 1H, J=2.3, 6.9 Hz, Ar—H), 6.46 (d, 1H, J=2.3 Hz, C8-H), 4.69 (d, 2H, J=6.3 Hz, C2-H), 3.89 (t, 1H, J=6.3 Hz, C3-H), 3.86 (s, 3H, OCH3)

Step 3) Synthesis of 7-methoxy-3-methyl-3-(4-pyridyl)chroman-4-one

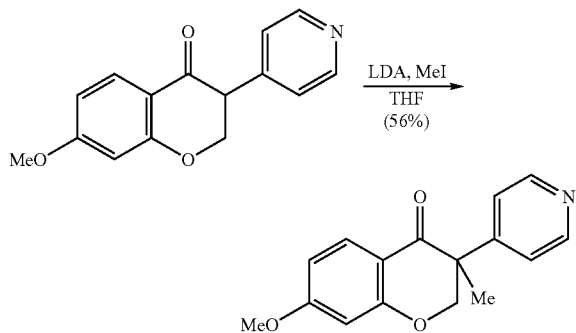

To a solution of LDA (2.0 mol/l, 0.863 ml, 1.73 mmol) in tetrahydrofuran (1.5 ml) was added at −78° C. a solution of 7-methoxy-3-(4-pyridyl)chroman-4-one (220 mg, 0.863 mmol) in tetrahydrofuran (2 ml), which was then stirred for 30 minutes. Iodomethane (0.537 ml, 8.63 mmol) was added to -the reaclion solution, which was warmed to −10° C. and stirred for 3 hours. After the reaction was completed, the reaction solution was neutralized under ice-cooling using saturated aqueous NH$_4$Cl solution, extracted with ethyl acetate, and washed with saturated saline solution. The organic layer was dried over magnesium sulfate, and the solvent was removed under reduced pressure. The residue was subjected to silica gel column chromatography (n-hexane:ethyl acetate=1:2) to give 7-methoxy-3-methyl-3-(4-pyridyl)chroman-4-one (131 mg, yield 56%).

$^1$H-NMR (270 MHz, CDCl$_3$) δ: 8.54 (dd, 2H, J=3.3, 6.3 Hz, pyridyl), 7.87 (d, 1H, J=8.9 Hz, Ar—H), 7.33 (dd, 2H, J=3.3, 6.3 Hz, pyridyl), 6.59 (dd, 1H, J=2.3 Hz, 8.9 Hz, Ar—H), 6.35 (d, 1H, J=2.3 Hz, C8-H), 4.85 (d, 1H, J=12.2 Hz, C2-H), 4.38 (d, 1H, J=12.2 Hz, C2-H), 3.81 (s, 3H, OCH$_3$), 1.48 (s, 3H, C3-CH$_3$)

Step 4) Synthesis of 4-[9-(t-butyldimethylsilyloxy)-1-nonynyl]-4-hydroxy-7-methoxy-3-methyl-3-(4-pyridyl)chroman

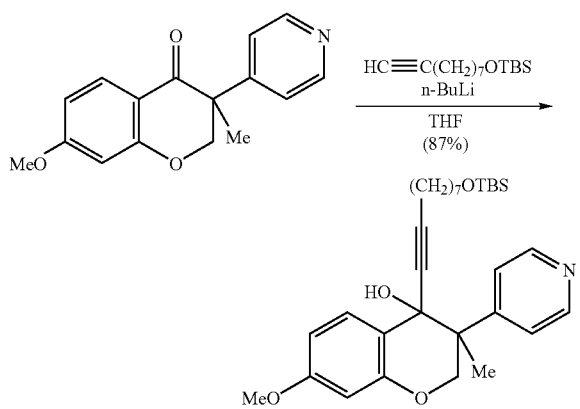

To a solution of an acetylene (525 mg, 1.94 mmol, separately synthesized) in tetrahydrofuran (5 ml) was added at −78° C. n-BuLi (1.59 mol/l, 1.02 ml, 1.62 mmol), which was then adjusted to −50° C. and stirred for 30 minutes. A solution of 7-methoxy-3-methyl-3-(4-pyridyl)chroman-4-one (290 mg, 1.08 mmol) in tetrahydrofuran (3 ml) was added thereto, and the resulting solution was adjusted to −10° C., and then stirred for 4 hours. After the reaction was completed, the reaction solution was neutralized under ice-cooling using saturated aqueous NH$_4$Cl solution, extracted with ethyl acetate, and washed with saturated saline solution. The organic layer was dried over magnesium sulfate, and the solvent was removed under reduced pressure. The residue was subjected to silica gel column chromatography (n-hexane:ethyl acetate=3:1) to give 4-[9-(t-butyldimethylsilyloxy)-1-nonynyl]-4-hydroxy-7-methoxy-3-methyl-3-(4-pyridyl)chroman (509 mg, yield 87%).

$^1$H-NMR (270 MHz, CDCl$_3$) δ: 8.54 (d, 2H, J=5.3 Hz, pyridyl), 7.64 (d, 1H, J=8.9 Hz, Ar—H), 7.46 (d, 2H, J=5.3 Hz, pyridyl), 6.58 (dd, 1H, J=2.6, 8.9 Hz, Ar—H), 6.41 (d, 1H, J=2.6 Hz, C8-H), 4.92 (d, 1H, J=10.2 Hz, C2-H), 4.09 (d, 1H, J=10.2 Hz, C2-H), 3.80 (s, 3H, OCH$_3$), 3.60 (t, 2H, J=6.4 Hz, C$\underline{H}_2$OTBS), 2.29 (t, 2H, J=6.9 Hz, C$\underline{H}_2$-acetylene), 1.60–1.24 (m, 10H), 1.50 (s, 3H, C3-CH$_3$), 0.89 (s, 9H, SiBu-t), 0.04 (s, 6H, SiCH$_3$×2)

Step 5) Synthesis of 4-(9-hydroxynonyl)-7-methoxy-3-methyl-3-(4-pyridyl) Chroman

To a solution of 4-[9-(t-butyldimethylsilyloxy)-1-nonynyl]4-hydroxy-7-methoxy-3-methyl-3-(4-pyridyl)chroman (471 mg, 0.874 mmol) in 1,2-dichloroethane (6 ml) were added under ice-cooling ZnI$_2$ (558 mg, 1.75 mmol) and NaBH$_3$CN (384 mg, 6.12 mmol), which was then stirred at room temperature for 3 hours. After the reaction was completed, water was added, and the resulting mixture was extracted with chloroform and washed with saturated saline solution. The organic layer was dried over magnesium sulfate, and the solvent was removed under reduced pressure. The residue thus obtained was subjected to silica gel column chromatography (n-hexane:ethyl acetate=3:1) to give a mixture containing 4-[9-(t-butyldimethylsilyloxy)-1-nonynyl]-7-methoxy-3-methyl-3-(4-pyridyl)chroman This mixture was dissolved in ethyl acetate (5 ml), Pd(OH)$_2$(150 mg) was added thereto, and the resulting mixture was stirred overnight at room temperature under hydrogen. After the reaction was completed, the solvent was removed under reduced pressure. The residue was dissolved in EtOH (5 ml), Pd(OH)$_2$ (150 ml) was added thereto, then the mixture was stirred at 60° C. under hydrogen atmosphere for 3 days. After the reaction was completed, the reaction solution was filtered and the filtrate was concentrated under reduced pressure. The residue was subjected to silica gel column chromatography (chloroform:methanol=10:1) to give 4-(9-hydroxynonyl)-7-methoxy-3-methyl-3-(4-pyridyl)chroman (108 mg, yield 31%).

$^1$H-NMR (270 MHz, CDCl$_3$) δ: 8.59 (d, 10/9H, J=5.9 Hz, pyridyl), 8.49 (d, 8/9H, J=5.6 Hz, pyridyl), 7.31 (d, 8/9H, J=5.6 Hz, pyridyl), 7.16 (d, 10/9H, J=5.9 Hz, Ar—H), 6.96 (d, 5/9H, J=8.6 Hz, pyridyl), 6.93 (d, 4/9H, J=8.6 Hz, Ar—H), 6.48 (dd, 5/9H, J=2.6, 8.6 Hz, Ar—H), 6.43 (d, 5/9H, J=2.6 Hz, C8-H), 6.39 (dd, 4/9H, J=2.6, 8.6 Hz, Ar—H), 6.32 (d, 4/9H, J=2.6 Hz, C8-H), 4.54 (d, 5/9H, J=10.6 Hz, C2-H), 4.31 (d, 4/9H, J=10.6 Hz, C2-H), 4.27 (d, 5/9H, J=10.6 Hz, C2-H), 4.04 (d, 4/9H, J=10.6 Hz, C2-H), 3.79 (s, 10/3H, OCH$_3$), 3.73 (s, 8/3H, OCH$_3$), 3.64 (t, 8/9H, J=6.3 Hz, C$\underline{H_2}$OH), 3.62 (t, 10/9H, J=6.3 Hz, C$\underline{H_2}$OH), 3.04–2.96 (m, 4/9H, C3-H), 2.72–2.64 (m, 5/9H, C3-H), 1.62–1.44 (m, 2H); 1.42–1.04 (m, 16H), 1.28 (s, 5/3H, C3-CH$_3$), 1.25 (s, 4/3H, C3-CH$_3$)

Step 6) Synthesis of 4-(9-methanesulfonyloxynonyl)-7-methoxy-3-methyl-3-(4-pyridyl)chroman

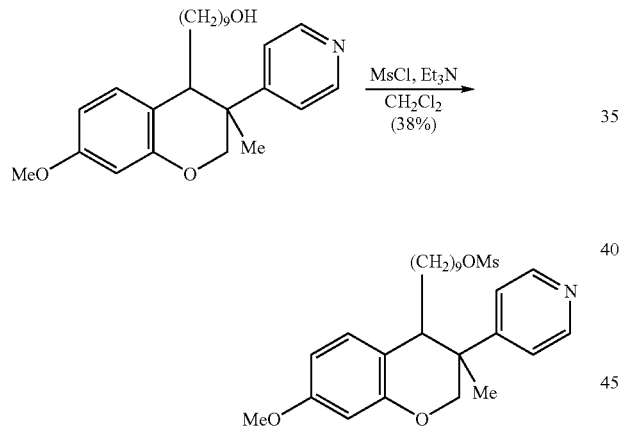

To a solution of 4-(9-hydroxynonyl)-7-methoxy-3-methyl-3-(4-pyridyl)chroman (108 mg, 0.272 mmol) in methylene chloride (2 mL) were added under ice-cooling triethylamine (0.057 mL, 0.41 mmol) and methanesulfonyl chloride (0.032 ml, 0.41 mmol), which was then stirred for 30 minutes. After the reaction was completed, saturated aqueous NH$_4$Cl solution was added, the resulting mixture was then extracted with methylene chloride and washed with saturated saline solution. The organic layer was dried over magnesium sulfate, and the solvent was removed under reduced pressure. The residue was subjected to silica gel column chromatography (n-hexane:ethyl acetate=1:1) to give 4-(9-methanesulfonyloxynonyl)-7-methoxy-3-methyl-3-(4-pyridyl)chroman (492 mg, yield 38%).

EI-MS: 475(M+)

$^1$H-NMR (270 MHz, CDCl$_3$) δ: 8.58 (d, 10/9H, J=5.9 Hz, pyridyl), 8.48 (d, 8/9H, J=5.9 Hz, pyridyl), 7.29 (d, 8/9H, J=5.9 Hz, pyridyl), 7.15 (d, 10/9H, J=5.9 Hz, pyridyl), 6.96 (d, 5/9H, J=8.6 Hz, Ar—H), 6.91 (d, 4/9H, J=8.6 Hz, Ar—H), 6.48 (dd, 5/9H, J=2.3, 8.6 Hz, Ar—H), 6.43 (d, 5/9H, J=2.3 Hz, C8-H), 6.40 (dd, 4/9H, J=2.3, 8.6 Hz, Ar—H), 6.31 (d, 4/9H, J=2.3 Hz, C8-H), 4.54 (d, 5/9H, J=10.5 Hz, C2-H), 4.31 (d, 4/9H, J=10.5 Hz, C2-H), 4.27 (d, 5/9H, J=10.5 Hz, C2-H), 4.22 (t, 8/9H, J=6.6 Hz, C$\underline{H_2}$OH), 4.20 (t, 10/9H, J=6.6 Hz, C$\underline{H_2}$OH), 4.06 (d, 4/9H, J=10.5 Hz, C2-H), 3.79 (s, 10/3H, OCH$_3$), 3.72 (s, 8/3H, OCH$_3$), 3.00 (s, 8/3H, CH$_3$SO2), 2.99 (s, 10/3H, CH$_3$SO$_2$), 2.72–2.66 (m, 5/9H, C3-H), 2.62–2.56 (m, 4/9H, C3-H), 1.80–160 (m, 2H), 1.44–1.04 (m, 16H), 1.28 (s, 5/3H, C3-CH$_3$), 1.26 (s, 4/3H, C3-CH$_3$)

Step 7) Synthesis of (3RS,4RS)-7-methoxy-3-methyl-4-[9-(4,4,5,5,5-pentafluoropentylthio)nonyl]-3-(4-pyridyl)chroman

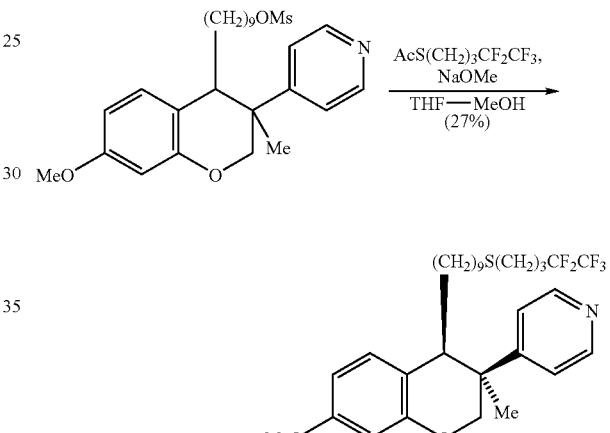

To a solution of 4,4,5,5,5-pentafluoropentythioacetate (47.7 mg, 0.202 mmol, separately synthesized) in tetrahydrofuran (1 ml) was added under nitrogen NaOMe (0.992 mmol/l, 0.183 ml, 0.182 mmol), which was then stirred for 15 minutes. A solution of 4-(9-methanesulfonyloxynonyl)-7-methoxy-3-methyl-3-(4-pyridyl)chroman (48.0 ml, 0.101 mmol) in tetrahydrofuran (1 ml) was added to the reaction solution, and the mixture was stirred overnight. After the reaction was completed, saturated aqueous NH$_4$Cl solution was added, the resulting mixture was then extracted with ethyl acetate and washed with saturated saline solution. The organic layer was dried over magnesium sulfate, and the solvent was removed under reduced pressure. The residue was subjected to silica gel column chromatography (n-hexane:ethyl acetate=1:1) to give (3RS,4RS)-7-methoxy-3-methyl-4-[9-(4,4,5,5,5-pentafluoropentylthio)nonyl]-3-(4-pyridyl)chroman (15.5 mg, yield 27%).

$^1$H-NMR (270 MHz, CDCl$_3$) δ: 8.39 (d, 2H, J=5.9 Hz, pyridyl), 7.14 (d, 2H, J=5.9 Hz, pyridyl), 6.96 (d, 1H, J=8.3 Hz, Ar—H), 6.49 (dd, 1H, J=2.3, 8.3 Hz, Ar—H), 6.43 (d, 1H, J=2.3 Hz, C8-H), 4.54 (d, 1H, J=10.6 Hz, C2-H), 4.27 (dd, 1H, J=1.6, 10.6 Hz, C2-H), 3.79 (s, 3H, OCH$_3$), 2.74–2.66 (m, 1H, C4-H), 2.58 (t, 2H, J=6.9 Hz), 2.48 (t, 2H, J=7.3 Hz), 2.18–2.06 (m, 2H), 1.96–1.80 (m, 2H), 1.60–1.46 (m, 2H), 1.28 (s, 3H, C3-CH₃), 1.40–1.04 (m, 14H)

Step 8) Synthesis of (3RS,4RS)-7-hydroxy-3-methyl-4[9-(4,4,5,5,5-pentafluoropentylthio)nonyl]-3-(4-pyridyl)chroman

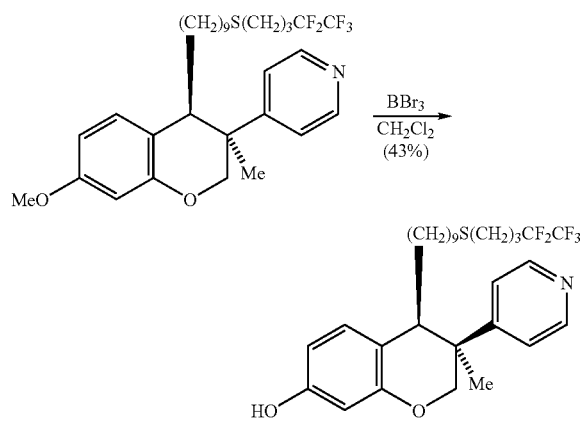

To a solution of (3RS,4RS)-7-methoxy-3-methyl-4-[9-(4,4,5,5,5-pentafluoropentylthio)nonyl]-3-(4-pyridyl)chroman (15.2 mg, 0.0265 mmol) in methylene chloride (1 ml) was added at −78° C. BBr₃ (1.0 mol/l, 0.080 ml), which was then slowly warmed, and stirred for 2 hours under ice-cooling. After the reaction was completed saturated aqueous NaHCO₃, solution was added under ice-cooling, the resulting mixture was then extracted with chloroform and washed with saturated saline solution. The organic layer was dried over magnesium sulfate, and the solvent was removed under reduced pressure. The residue was subjected to silica gel column chromatography (n-hexane:ethyl acetate=1:1) to give (3RS,4RS)-7-hydroxy-3-methyl-4-[9-(4,4,5,5,5-pentafluoropentylthio)nonyl]-3-(4-pyridyl)chroman (6.3 mg, yield 43%).

¹H-NMR (270 MHz, CDCl₃) δ: 8.59 (d, 2H, J=5.9 Hz, pyridyl), 7.16 (d, 2H, J=5.9Iz, pyridyl), 6.91 (d, 1H, J=8.3 Hz, Ar—H), 6.42 (dd, 1H, J=2.3, 8.3 Hz, Ar—H), 6.39 (d, 1H, J=2.3 Hz, C8-H), 4.53 (d, 1H, J=10.2 Hz, C2-H), 4.26 (d, 1H, J=10.2 Hz, C3-H), 2.74–2.66 (m, 1H, C4-H), 2.58 (t, 2H, J=6.9 Hz), 2.48 (t, 2H, J=7.3 Hz), 2.18–2.02 (m, 2H), 1.96–1.80 (m, 2H), 1.60–1.46 (m, 2H), 1.28 (s, 3H, C3CH₃), 1.40–1.04 (m, 14H)

Step 9) Synthesis of (3RS,4RS)-7-hydroxy-3-methyl-4-[9-(4,4,5,5,5-pentafluoropentylsulfinyl)nonyl]-3-(4-pyridyl)chroman

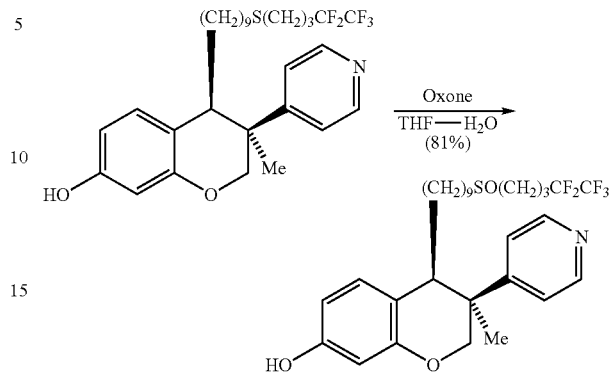

To a solution of (3RS,4RS)-7-hydroxy-3-methyl-4-[9-(4,4,5,5,5-pentafluoropentylthio)nonyl]-3-(4-pyridyl)chroman (6.1 mg, 0.011 mmol) in tetrahydrofuran (0.5 ml) was added under ice-cooling a solution of Oxone® (monopersulfate compound; DuPont product) (3.4 mg, 0.0055 mmol) in water (0.5 ml), which was then stirred for 5 hours. After the reaction was completed, the reaction solution was extracted with ethyl acetate and washed with saturated saline solution. The organic layer was dried over magnesium sulfate, and the solvent was removed under reduced pressure. The residue was subjected to silica gel column chromatography (ethyl acetate) to give (3RS,4RS)-7-hydroxy-3-methyl-4-[9-(4,4,5,5,5-pentafluoropentylsulfinyl)nonyl]-3-(4-pyridyl)chroman (5.1 mg, yield 81%).

EI-MS: 575(M+)

¹H-NMR (270 MHz, CDCl₃) δ: 8.58 (d, 2H, J=5.9 Hz, pyridyl), 7.1 6 (d, 2H, J=5.9 Hz, pyridyl), 6.90 (d, 1H, J=8.2 Hz, Ar—H), 6.43 (dd, 11H, J=2.3, 8.2 Hz, Ar—H), 6.39 (d, 1H, J=2.3 Hz, C8-H), 4.54 (d, 1H, J=10.6 Hz, C2-H), 4.26 (d, 1H, J=10.6 Hz, C2-H), 2.94–2.54 (m, 5H), 2.36–2.10 (m, 4H), 1.80–1.54 (m, 2H), 1.28 (s, 3H, C3-CH₃), 1.44–1.04 (m, 14H)

EXAMPLE 13

Synthesis of (3RS,4RS)-7-hydroxy-3-(4-hydroxyphenyl)-3-methyl-4-[9-(4,4,5,5,5-pentafluoropentylsulfonylamino)nonyl]thiochroman Step 1) Synthesis of 4,4,5,5,5-pentafluoropentylsulfonyl chloride

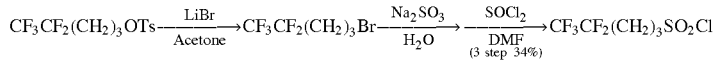

To a solution of 1,1,1,2,2-pentafluoro-5-p-toluenesulfonyloxypentane (11.0 g, 3.0 mmol) in acetone (10 nm) was added LiBr (523 mg, 6.02 mmol), which was then heated under reflux for 4 hours. After the reaction solution was filtered, the solvent was removed under reduced pressure. The residue thus obtained was dissolved in water (10 ml), $Na_2SO_3$ (759 mg, 6.02 mmol) was added thereto, and the resulting mixture was heated under reflux for 17 hours. After the reaction was completed, to the residue which was obtained by removing the solvent under reduced pressure was added EtOH. This mixture was filtered while hot, and the filtrate was concentrated under reduced pressure. The residue was dissolved in benzene (5 ml), DMF (0.5 ml) and thionyl chloride (0.383 ml, 5.25 mmol) were added thereto, and the mixture was heated under reflux overnight. After the reaction was completed, saturated aqueous $NaHCO_3$ solution was added. The resulting mixture was then extracted with methylene chloride and washed with saturated saline solution. The organic layer was dried over magnesium sulfate, and the solvent was removed under reduced pressure. The residue was subjected to silica gel column chromatography (n-hexane:ethyl acetate=10:1) to give 4,4,5,5,5-pentafluoropentylsulfonyl chloride (267 mg, yield 34%).

$^1$H-NMR (300 MHz, $CDCl_3$) δ: 3.77 (t, 2H, J=6.6 Hz, C$\underline{H}_2SO_2Cl$), 2.48–2.24 (m, 4H)

Step 2) Synthesis of 7-methoxy-3-(4-methoxyphenyl)-3-methyl-4-[9-(4,4,5,5,5-pentafluoropentylsulfonylamino)nonyl]thiochroman solution was filtered, the residue obtained by removing the solvent under reduced pressure was dissolved in methylene chloride (2 ml). 4,4,5,5,5-penta-fluoropentylsulfonylchloride (155 mg, 0.595 mmol) and triethylamine (0.1 ml) were added thereto under ice-cooling, which was then stirred for 10 minutes. After the reaction was completed, saturated aqueous $NaHCO_3$ solution was added. The resulting mixture was then extracted with methylene chloride and washed with saturated saline solution. The organic layer was dried over magnesium sulfate, and the solvent was removed under reduced pressure. The residue was subjected to silica gel column chromatography (n-hexane:ethyl acetate=8:1) to give 7-methoxy-3-(4-methoxyphenyl)-3-methyl-4-[9-(4,4,5,5,5-pentafluoropentylsulfonylamino)nonyl]thiochroman (126 mg, yield 65%).

$^1$H-NMR (270 MHz, $CDCl_3$) δ: 7.29 (d, 2H, J=8.8 Hz, Ar—H), 6.93 (d, 2H, J=8.8 Hz, Ar—H), 6.90 (d, 1H, J=6.9 Hz, Ar—H), 6.73 (d, 1H, J=2.7 Hz, C8-H), 6.58 (dd, 1H, J=2.7, 6.9 Hz, Ar—H), 4.20–4.10 (m, 1H, NH), 3.83, 3.78 (respectively s, respectively 3H, OC$\underline{H}_3$×2), 3.64 (d, 1H, J=11.8 Hz, C2-H), 3.12–3.04 (m, 4H, C$\underline{H}$NHSO$_2$C$\underline{H}_2$), 3.00 (d, 1H, J=11.8 Hz, C2-H), 2.76–2.70 (m, 1H, C4-H), 2.36–2.06 (m, 4H, C$\underline{H}_2$C$\underline{H}_2$CF$_2$CF$_3$), 1.58–1.44 (m, 2H, C$\underline{H}_2$CH$_2$NH), 1.17 (s, 1H, C3-CH$_3$), 1.30–1.00 (m, 14H)

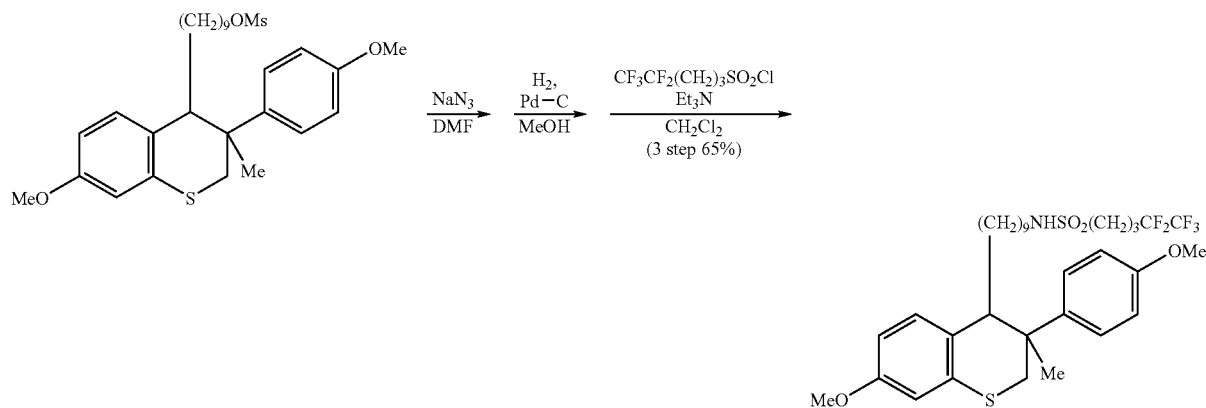

To a solution of a mesylate (152 mg, 0.292 mmol, separately synthesized) in DMF (1 ml) was added under nitrogen $NaN_3$ (25.5 mg, 0.392 mmol), which was then stirred overnight at room temperature. After the reaction was completed, water was added under ice-cooling. The resulting mixture was extracted with ethyl acetate, and washed with saturated saline solution. The organic layer was dried over magnesium sulfate, and then the residue which was obtained by removing the solvent under reduced pressure was dissolved in MeOH (1 ml). Pd—C (40 mg) was added to this solution, and the resulting mixture was stirred under hydrogen overnight at room temperature. After the reaction Step 3) Synthesis of (3RS,4RS)-7-hydyoxy-3-(4-hydroxyphenyl)-3-methyl-4-[9-(4,4,5,5,5-pentafluoropentylsulfonylamino)nonyl]thiochroman

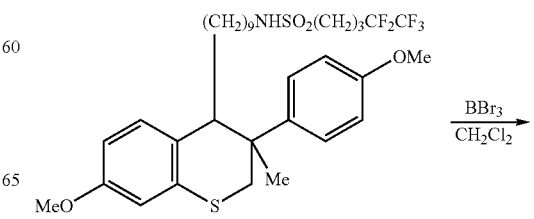

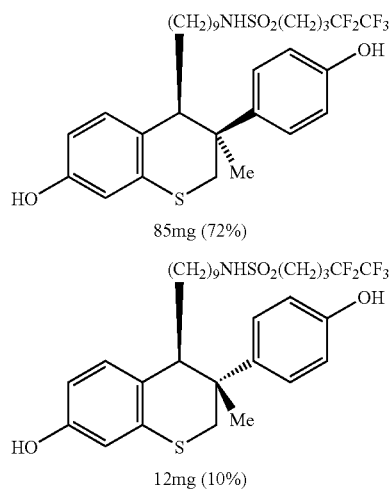

85mg (72%)

12mg (10%)

To a solution of 7-methoxy-3-(4-methoxyphenyl)-3-methyl-4-[9-(4,4,5,5,5-pentafluoropentylsulfonylamino)nonyl]thiochroman (124 mg, 0.186 mmol) in methylene chloride (1 ml) was added at −78° C. BBr$_3$ (1.0 mol/l, 1.12 ml), which was then slowly warmed over 3 hours. After the reaction was completed, saturated aqueous NaHCO$_3$ solution was added at 0° C. The resulting mixture was then extracted with methylene chloride and washed with saturated saline solution. The organic layer was dried over magnesium sulfate, and the solvent was removed under reduced pressure. The residue was subjected to silica gel column chromatography (n-hexane:ethyl acetate=1:2) to give (3RS,4RS)-7-hydroxy-3-(4-hydroxyphenyl)-3-methyl-4-[9-(4,4,5,5,5-pentafluoropentylsulfonylamino)nonyl]thiochroman (85.0 mg, yield 72%) and trans form thereof (12.0 mg, yield 10%).

$^1$H-NMR (270 MHz, CDCl$_3$) δ: 7.24 (d, 2H, J=8.5 Hz, Ar—H), 6.88 (d, 1H, J=8.3 Hz, Ar—H), 6.84 (d, 2H, J=8.5 Hz, Ar—H), 6.67 (d, 1H, J=2.7 Hz, C8-H), 6.51 (dd, 1H, J=2.7, 8.3 Hz, Ar—H), 5.28 (s, 1H, OH), 4.86 (s, 1H, OH), 4.32–4.26 (m, 1H, NH), 3.63 (d, 1H, J=11.5 Hz, C2-H), 3.16–3.06 (m, 4H, C<u>H$_2$</u>NHSO$_2$C<u>H$_2$</u>), 2.96 (d, 1H, J=11.5 Hz, C2-H), 2.72–2.66 (m, 1H, C4-H), 2.36–2.10 (m, 4H, C<u>H$_2$</u>C<u>H$_2$</u>CF$_2$CF$_3$), 1.58–1.44 (m, 2H, C<u>H$_2$</u>CH$_2$NH), 1.17 (s, 1H, C3-CH$_3$), 1.30–1.00 (m, 14H)

EXAMPLE 14

Synthesis of (3RS,4RS)-3-(4-fluorophenyl)-7-hydroxy-3-methyl-4-[9-(4,4,5,5,5-pentafluoropentylsulfinyl)nonyl]thiochroman Step 1) Synthesis of 3-(4-fluorophenyl)-7-methoxy-3-methylthiochroman-4-one

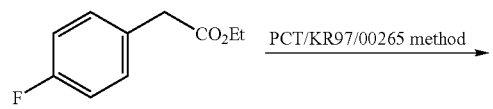

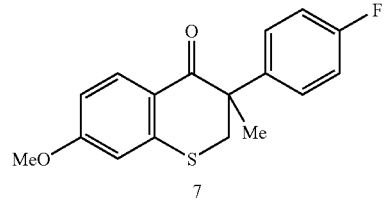

3-(4-fluorophenyl)-7-methoxy-3-methylthiochroman-4-one was prepared from ethyl 4-fluorophenylacetate according to the same procedure described in International Patent Appln. No. PCT/KR97/00265.

$^1$H-NMR (270 MHz, CDCl$_3$) δ: 8.17 (1H, d, J=9 Hz, C5-H), 7.19 (2H, m, Ar—H), 6.98 (2H, m, Ar—H), 6.71 (1H, dd, J=9 and 2 Hz, C&H), 6.58 (1H, d, J=2 Hz, C8-H), 3.78 (3H, s, OCH$_3$), 3.44 (2H, d, J=5 Hz, C2-H), 1.59 (3H, s, C3-CH$_3$)

Step 2) Synthesis of 4-[9-(t-butyldimethylsilyloxy)-1-nonynyl]-3-(4-fluorophenyl)-4-hydroxy-7-methoxy-3-methylthiochroman

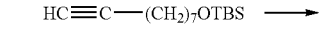

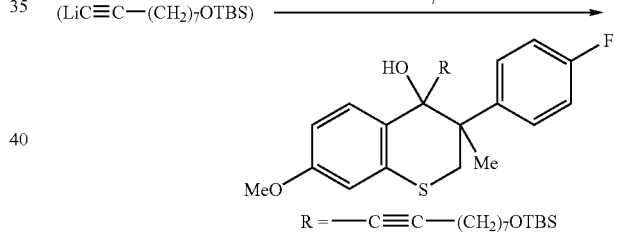

An alkyne compound (3.81 g, 15 mmol) separately prepared was dissolved in dry tetrahydrofuran (30 ml) and cooled down to −20° C. under argon. To this solution was added dropwise n-butyllithium (1.66 mol/l solution in hexane, 8.4 ml, 14 mmol), and the resulting mixture was stirred at −20° C. to —10° C. for 1 hour. Then, 3-(4-fluorophenyl)-7-methoxy-3-methylthiochroman-4-one (0.50 g, 5 mmol) dissolved in tetrahydrofuran (20 ml) was added dropwise thereto, and the mixture was stirred at −10° C. to 0° C. for 3 hours. After the reaction was completed, the mixture was poured to ice-water and extracted with ethyl acetate. The organic layer was dried over anhydrous magnesium sulfate, and concentrated under reduced pressure to give the crude product. This crude product was subjected to silica gel column chromatography (n-hexane:ethyl acetate=20:1) to give 4-[9-(t-butyldimethylsilyloxy)-1-nonynyl]-3-(4-fluorophenyl)-4-hydroxy-7-methoxy-3-methylthiochroman (1.78 g, yield 64%).

$^1$H-NMR (270 MHz, CDCl$_3$) δ: 7.84 (1H, d, J=8 Hz, C5-H), 7.66 (2H, m, Ar—H), 7.01 (2H, m, Ar—H), 6.66–6.61 (2H, m, C6-H and C8-H), 4.23 (1H, d, J=13 Hz, C2-H), 3.78 (3H, s, OCH$_3$), 3.60 (2H, t, J=6 Hz, CH$_2$OTBS), 2.73 (1H, d, J=13 Hz, C2-H), 2.17 (3H, t, J=7 Hz, CH$_2$C≡C and OH), 1.58 (3H, s, C3-CH$_3$), 1.50–1.28 (10H, m, alkyl-H), 0.90 (9H, s, t-butyl-H), 0.05 (6H, s, Si(CH$_3$)$_2$)

Step 3) Synthesis of 4-(9-hydroxynonyl)-3-(4-fluorophenyl)-7-methoxy-3-methylthiochroman

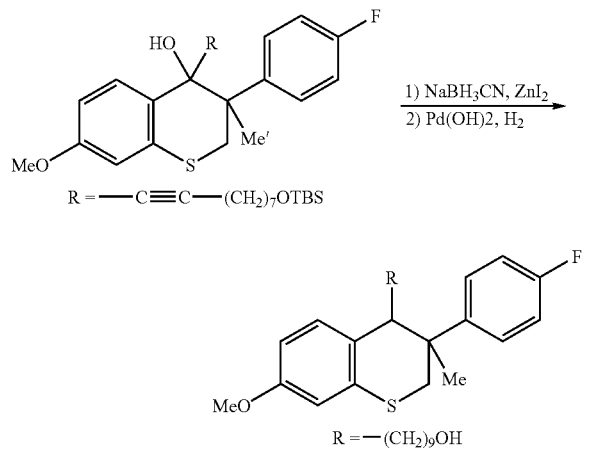

To a solution of 4-[9-(t-butyldimethylsilyloxy)-1-nonynyl]-3-(4-fluorophenyl)-4-hydroxy-7-methoxy-3-methylthiochroman (0.55 g, 0.99 mmol) in 1,2-dichloroethane (30 ml) were added zinc iodide(II) (0.35 g) and sodium cyanoborohydride (0.30 g), which was then stirred at 0° C. for 4 hours. After the reaction was completed, water was poured thereto, and the mixture was extracted with chloroform. The organic layer was dried over anhydrous magnesium sulfate and concentrated under reduced pressure to give a crude product. This crude product was subjected to silica gel column chromatography (n-hexane:ethyl acetate=10:1) to give 4-[9-(t-butyldimethylsilyloxy)-1-nonynyl]-3-(4-fluorophenyl)-7-methoxy-3-methylthiochroman (374 mg, yield 70%). This product thus obtained (374 mg) was dissolved in a solvent mixture of ethanol (30 ml) and tetrahydrofuran (10 ml), 20% palladium hydroxide carbon (0.16 g) washed with the reaction solvent was added, and the mixture was stirred under hydrogen at room temperature for 20 hours. The reaction solution was filtered through a cellite to remove the palladium carbon, and the filtrate was concentrated under reduced pressure to give the crude product. This crude product thus obtained was subjected to silica gel column chromatography (n-hexane:ethyl acetate-5:1) to give 4-(9-hydroxynonyl)-3-(4-fluorophenyl)-7-methoxy-3-methylthiochroman (a mixture of (3RS,4RS) and (3RS,4SR), (3RS,4RS)/(3RS,4SR)=about 6/1) (220 mg, yield 74%).

$^1$H-NMR (270 MHz, CDCl$_3$, (3RS,4RS)) δ: 7.35 (2H, m, Ar—H), 7.06 (2H, m, Ar—H), 6.93 (1H, d, J=9 Hz, C5=H), 6.73 (1H, d, J=2 Hz, C8-H), 6.59 (1H, dd, J=9 and 2 Hz, C6H), 3.78 (3H, s, OCCH$_3$), 3.66–3.59 (4H, m, C2-H and —CH$_2$OH), 2.98 (1H, d, J=12 Hz, C2-H), 2.73 (1H, brs, C4-H), 1.19 (3H, s, C$_3$-CH$_3$), 1.54–1.05 (16H, m, alkyl-H)

Step 4) Synthesis of 3-(4-fluorophenyl)-4-(9-methanesulfonyloxynonyl)-7-methoxy-3-methylthiochroman

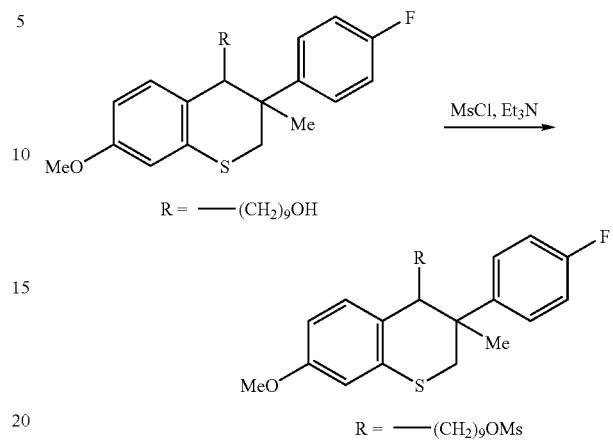

4-(9-Hydroxynonyl)-3-(4-fluorophenyl)-7-methoxy-3-methylthiochroman (0.41 g, 0.95 mmol) was dissolved in dichloromethane (50 ml), methanesulfonyl chloride (0.44 g) and triethylamine (0.41 g) were added thereto, and the mixture was stirred at room temperature for 1 hour. After the reaction was completed, water was poured thereto, and the mixture was extracted with chloroform (50 ml). The organic layer was dried over anhydrous magnesium sulfate and concentrated under reduced pressure to give a crude product. This crude product thus obtained was subjected to silica gel column chromatography (n-hexane:ethyl acetate=3:1) to give 3-(4-fluorophenyl)-4-(9-methanesulfonyloxynonyl)-7-methoxy-3-methylthiochroman (a mixture of (3RS,4RS) and (3RS, 4SR), (3RS,4RS)/(3RS,4SR)=about 6/1) (480 mg, yield 99%).

$^1$H-NMR (270 MHz, CDCl$_3$, (3RS,4RS)) δ: 7.35 (2H, m, Ar—H), 7.06 (2H, m, Ar—H), 6.93 (1H, d, J=9 Hz, C5=H), 6.73 (1H, d, J=3 Hz, C8-H), 6.59 (1H, dd, J=9 and 3 Hz, C6-H), 4.19 (2H, t, J=7 Hz, —CH$_2$OMs), 3.78 (3H, s, OCH$_3$), 3.68–3.63 (1H, m, C2-H), 2.99 (4H, m, —SO$_2$CH$_3$ and C2-H), 2.72 (1H, brs, C4-H), 1.19 (3H, s, C3-CH$_3$), 1.72–1.07 (16H, mn, alkyl-H)

Step 5) Synthesis of 3-(4-fluorophenyl)-7-methoxy-3-methyl-4-[9-(4,4,5,5,5-pentafluoropentylthio)nonyl]thiochroman

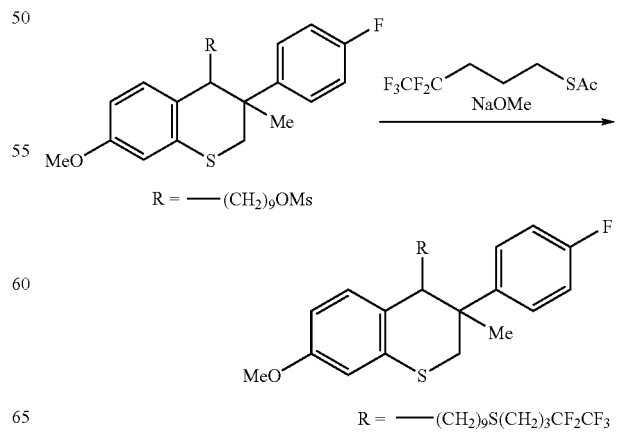

A thioacetate (1.37 g, 5.8 mmol, separately prepared) was dissolved in methanol (10 mL), sodium methoxide (5.3 mL, 5.3 mmol, 1 mol/L in MeOH) was added thereto, and the mixture was stirred at room temperature for 1 hour. Then, 3-(4-fluorophenyl)-4-(9-methanesulfonyloxynonyl)-7-methoxy-3-methylthiochrom (0.48 g, 0.95 mmol) dissolved in tetrahydrofuran (10 mL) was added dropwise thereto, which was stirred at room temperature for 18 hours. After the reaction was completed, the reaction solution was neutralized by 50% aqueous acetic acid solution, water was poured thereto, and the mixture was extracted with ethyl acetate. The organic layer was dried over anhydrous magnesium sulfate and concentrated under reduced pressure to give a crude product. This crude product thus obtained was subjected to silica gel column chromatography (n-hexane: ethyl acetate=30:1) to give 3-(4-fluorophenyl)-7-methoxy-3-methyl-4-[9-(4,4,5,5,5-pentafluoropentylthio)nonyl]methylthiochroman (a mixture of (3RS,4RS) and (3RS,4SR), (3RS,4RS)/(3RS,4SR)=about 6/1) (678 mg, stoichiometric yield).

$^1$H-NMR (270 MHz, CDCl$_3$, (3RS,4RS)) δ: 7.34 (2H, m, Ar—H), 7.05 (2H, m, Ar—H), 6.93 (1H, d, J=8 Hz, C5-H), 6.73 (1H, d, J=2 Hz, C8-H), 6.59 (1H, dd, J=8 and 2 Hz, C6-H), 3.78 (3H, s, OCH:.), 3.64 (1H, d, J=12 Hz, C2-H), 2.98 (1H, d, J=12 Hz, C2-H), 2.72 (1H, brs, C4-H), 2.57 (2H, t, J=7 Hz, CH$_2$—S—), 2.47 (2H, t, 1=7 Hz, CH$_2$—S—), 2.30–1.84 (4H, m, —CH$_2$CH$_2$CF$_2$CF$_3$), 1.55 (2H, m, —CH$_2$CH$_2$S—CH$_2$)$_3$ CF$_2$CF$_3$), 1.19 (3H, s, C3-CH$_3$), 1.39–1.05 (14H, m, alkyl-H)

Step 6) Synthesis of (3RS,4RS)-3-(4-fluorophenyl)-7-hydroxy-3-methyl-4-[9-(4,4,5,5,5-pentafluoropentylthio)nonyl]thiochroman

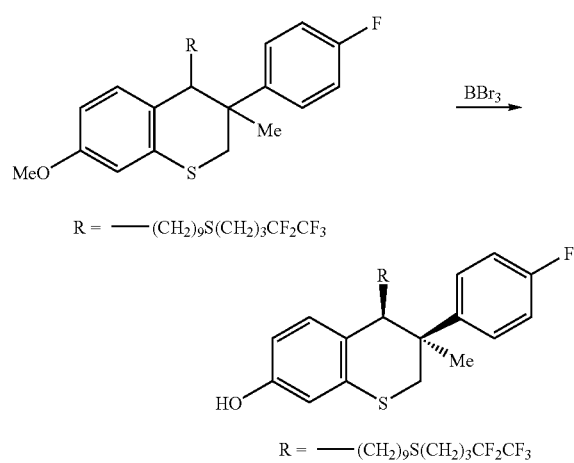

3-(4-Fluorophenyl)-7-methoxy-3-methyl-4-[9-(4,4,5,5,5-pentafluoropentylthio)nonyl]thiochroman (678 mg, 1.1 mmol) was dissolved in dry dichloro methane (40 mL), which was then cooled down to −78° C. under argon. To this solution was added dropwise BBr$_3$(1.0 mol/l solution in dichloromethane, 3.5 mL, 3.5 mmol), and the reaction mixture was warmed to room temperature over 12 hours. After the reaction was completed, the mixture was poured into ice-water and extracted with chloroform. The organic layer was dried over anhydrous magnesium sulfate, concentrated under reduced pressure to give a crude product. The crude product thus obtained was subjected to column chromatography (n-hexane:ethyl acetate=10:1, Lobar column) to purify the cis form, and thus (3RS,4RS)-3-(4-fluorophenyl)-7-hydroxy-3-methyl-4-[9-(4,4,5,5,5-pentafluoropentylthio)nonyl]thiochroman (107 mg, yield 19%) was given.

$^1$H-NMR (270 MHz, CDCl$_3$, (3RS,4RS)) δ: 7.34 (2H, m, Ar—H), 7.06 (2H, m, Ar—H), 6.89 (1H, d, J=8 Hz, C5-H), 6.68 (1H, d, J=3 Hz, C8-H), 6.51 (1H, dd, J=8 and 3 Hz, C6-H), 3.64 (1H, d, J=12 Hz, C2-H), 2.98 (1H, d, J=12 Hz, C2-H), 2–72 (1H, d, J=8 Hz, C4-H), 2.58 (2H, t, J=7 Hz, CHrS—), 2.48 (2H, t, J=7 Hz, CH$_2$—S—), 2.20–2.07 (2H, m, —CH$_2$CF$_2$CF$_3$), 1.93–1.85 (2H, m, —CH$_2$CH$_2$CF$_2$CF$_3$), 1.56–1.47 (2H, m, —CH$_2$CH$_2$—S—(CH$_2$)$_3$CF$_2$CF$_3$), 1.19 (3H, s, C$_3$-CH$_3$), 1.39–1.00 (14H, m, alklyl-H)

Step 7) Synthesis of (3RS,4RS)-344-fluorophenyl)-7-hydroxy-3-methyl-4-[9-(4,4,5,5,5-pentafluoropentylsulfinyl)nonyl]thiochroman

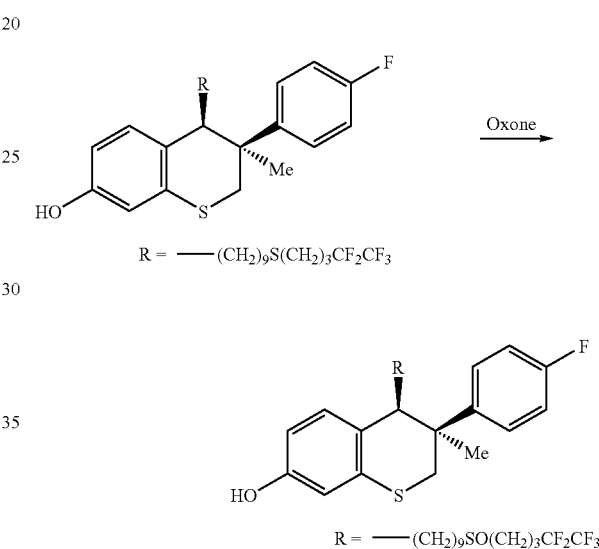

To a solution of (3RS,4RS)-3-(4-fluorophenyl)-7-hydroxy-3-methyl-4-[9-(4,4,5,5,5-pentafluoropentylthio)nonyl]thiochroman (107 mg, 0.18 mmol) in tetrahydrofuran (8 ml) was added Oxone® (monopersulfate compound; DuPont product) (60 mg, 0.1 0 mmol), which was then stirred at 0° C. for 5 minutes. Water (0.5 ml) was added thereto, and the resulting mixture was stirred at 0° C. for 1 hour. The reaction solution was poured into water, and extracted with ethyl acetate. The organic layer was dried over anhydrous magnesium sulfate, and concentrated under reduced pressure to give a crude product. The crude product thus obtained was subjected to silica gel column chromatography (n-hexane:ethyl acetate=2:1) to give (3RS,4RS)-3-(4-fluorophenyl)-7-hydroxy-3-methyl-4-[9-(4,4,5,5,5-pentafluoropentylsulfinyl)nonyl]thiochroman (73 mg, yield 66%).

$^1$H-NMR (270 MHz, CDCl$_3$, (3RS,4RS)) δ: 7.34 (2H, m, Ar—H), 7.05 (2H, m, Ar—H), 6.87 (1H, d, J=8 Hz, C5=H), 6.70–6.67 (2H, m, C8-H and OH), 6.58–6.52 (2H, m, C6-H and OH), 3.64 (1H, d, J=12 Hz, C2-H), 2.97 (1H, d, J=12 Hz, C2-H), 2.82–2.54 (5H, m, CH$_2$—S—CH$_2$, and C4-H), 2.29–2.13 (4H, m, —CH—CH$_2$CF$_2$CF$_3$), 1.68 (2H, m, —CH$_2$CH$_2$—SO—(CH$_2$)$_3$CF$_2$CF$_3$), 1.19 (3H, s, C3-CH$_3$), 1.39–1.05 (14H, m, alkyl-H)

EXAMPLE 15

Synthesis of (3RS,4RS)-3-(3-fluorophenyl)-7-hydroxy-3-methyl-4-[9-(4,4,5,5,5-pentanuoropentylsulfinyl)nonyl]thiochroman Step 1) Synthesis of 3-(3-fluorophenyl)-7-methoxy-3-methylthiochroman-4-one

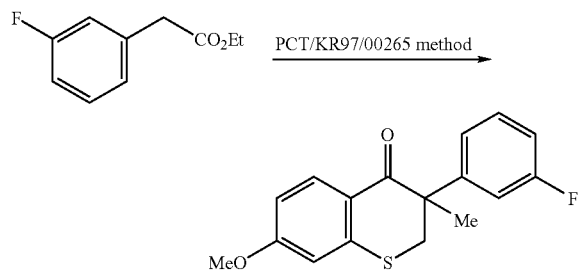

3-(3-Fluorophenyl)-7-methoxy-3-methylthiochroman-4-one was prepared from ethyl 3-fluorophenylacetate according to the same procedure described in International Patent Appln. No. PCT/KR97/00265.

$^1$H-NMR (270 MHz, CDCl$_3$) δ: 8.18 (1H, d, J=9 Hz, C5—H), 7.30–7.22 (1H, m, Ar—H), 7.00–6.91 (3H, m, Ar—H), 6.72 (1H, dd, J=9 and 2 Hz, C6-H), 6.59 (1H, d, J=2 Hz, C8-H), 3.80 (3H, s, OCH$_3$), 3.45 (2H, d, I=4 Hz, C2-H), 1.61 (3H, s, C3-CH$_3$)

Step 2) Synthesis of (3RS,4RS)-3-(3-fluorophenyl)-7-hydroxy-3-methyl-4-[9-(4,4,5,5,5-pentafluoropentylsulfinyl)nonyl]thiochroman

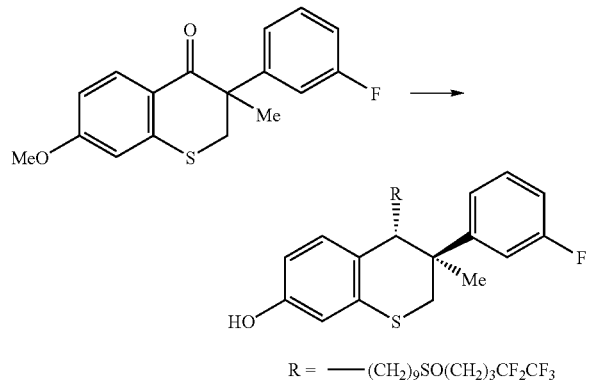

(3RS,4RS)-3-(3-Fluorophenyl)-7-hydroxy-3-methyl-4-[9-(4,4,5,5,5-pentafluoropentylsulfinyl)nonyl]thiochroman was prepared from 3-(3-fluorophenyl)-7-methoxy-3-methylthiochroman-4-one according to the same procedure as Steps 2 to 7 of Example 14

$^1$H-NMR (270 MHz CDCl$_3$, (3RS,4RS)) δ: 7 37–6.53 (8H, m, Ar—H and OH), 3.63 (1H, d, J=12 Hz, C2-H). 2.96 (1H, d, J=12 Hz, C2-H), 2.78–2.54 (5H, m, CH$_2$—S—CH$_2$, and C4-H), 2.40–2.18 (4H, m, —CH$_2$CH$_2$CF$_2$CF$_3$), 1.68 (2H, m, —CH$_2$CH$_2$—SO—CH$_2$)$_3$CF$_2$CF$_3$), 1.19 (3H, s, C3-CH$_3$), 1.50–0.88 (14H, m, alkyl-H)

EXAMPLE 16

Synthesis of (3RS,4RS)-7-hydroxy-3-(4-hydroxyphenyl)-3-methyl-4-{3-[N-5-(4,4,5,5,5-pentafluoropentylsulfinyl)pentylamino]propyl}chroman Step 1) Synthesis of 4,4,5,5,5-pentafluoropentyl thioacetate

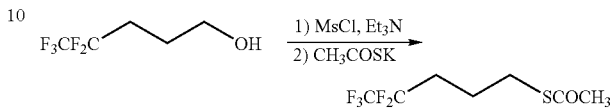

To a solution of 4,4,5,5,5-pentafluoropentanol (23.2 g, 130 mmol) in dry dichloromethane (100 ml) were added dropwise at 0° C. triethylamine (27 g, 267 mmol) and methanesulfonylchloride (30 g, 262 mmol), which was then warmed to room temperature over 12 hours. After the reaction was completed, the mixture was poured into ice-water, and extracted with chloroform. The organic layer was dried over anhydrous magnesium sulfate, and concentrated under reduced pressure to give a crude product (33.9 g). This crude product thus obtained was then dissolved in acetone (500 ml), potassium thioacetate (18 g, 158 mmol) was added thereto at room temperature, and the resulting mixture was stirred for 12 hours. The precipitate was filtered, and the filtrate was concentrated under reduced pressure to give a crude product. This crude product thus obtained was subjected to silica gel column chromatography (n-hexane:ethyl acetate=20:1) to give 4,4,5,5,5-pentafluoropentylthioacetate (15.8 g, yield 51%).

$^1$H-NMR (270 MHz, CDCl$_3$) δ: 2.94 (2H, t, J=7 Hz, CH$_2$SAc), 2.34 (3H, s, COCH$_3$), 2.20–1.80 (4H, m, alkyl-H)

Step 2) Synthesis of 5,5-imethoxy-1-(4,4,5,5,5-pentafluoropentylthio)pentane

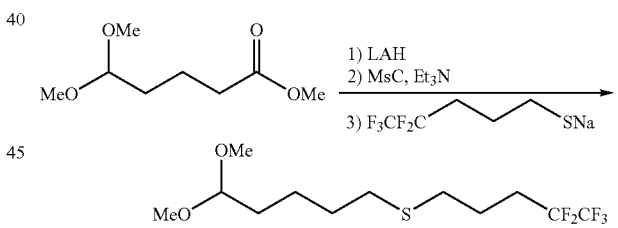

To a suspension of LAH (0.4 g, 11 mmol) in tetrahydrofuran (20 ml) was added dropwise at 0° C. methyl 5,5-dimethoxyvalerate (3.5 g, 20 mmol) dissolved in tetrahydrofuran (30 ml), which was then stirred for 2 hours. After the reaction was completed, the mixture was poured into ice-water (50 ml) and then extracted with ether. The organic layer was dried over anhydrous magnesium sulfate, and concentrated under reduced pressure to give a crude product. This crude product thus obtained was subjected to silica gel column chromatography (n-hexane:ethyl acetate-2:1) to give 5,5-dimethoxypentanol (1.02 g, yield 34%). Methanesulfonylchloride (3.2 g, 28 mmol) and triethylamine (3.0 g, 30 mmol) dissolved in dichloromethane (50 ml) were added thereto, and the mixture was stirred at room temperature for 1 hour. After the reaction was completed, the reaction mixture was poured into water and extracted with chloroform. The organic layer was dried over anhydrous magnesium sulfate, and concentrated under reduced pressure to give a crude product (2.36 g). While, 4,4,5,5,5-pentafluoropentyl thioacetate (5.7 g, 24 mmol) prepared in Step 1 was dissolved in methanol (10 ml), sodium methoxide (23 mg, 23 mmol, 11.0 mol/l) was added thereto, and the resulting mixture was stirred at room temperature for 1 hour. To this solution was added dropwise the crude product prepared above (0.90 g) dissolved in tetrahydrofuran (10 ml), which was then stirred at room temperature for 5 hours. After the reaction was completed, the reaction mixture was poured into water and extracted with ether. The organic layer was dried over anhydrous magnesium sulfate, and concentrated under reduced pressure to give a crude product. This crude product thus obtained was subjected to silica gel column chromatography (n-hexane:ethyl acetate=20:1) to give 5,5-dimethoxy-1-(4,4,5,5,5-pentafluoropentylthio)pentane (460 mg).

$^1$H-NMR (270 MHz CDCl$_3$) δ: 4.35 (1H, t, J=6 Hz, C$\underline{H}$(OCH$_3$)$_2$), 3.31 (6H, s, CH(OC$\underline{H_3}$)$_2$), 2.61–2.48 (4H, m, C$\underline{H_2}$—S—C$\underline{H_2}$), 2.30–2.05 (2H, m, —C$\underline{H_2}$CF$_2$CF$_3$), 1.93–1.82 (2H, C$\underline{H_2}$CH$_2$CF$_2$CF$_3$), 1.70–1.40 (6H, m, C$\underline{H_2}$C$\underline{H_2}$CH(OCH$_3$)$_2$)

Step 3) Synthesis of 5,5-dimethoxy-1-(4,4,5,5,5-pentafluoropentylsulfinyl)pentane

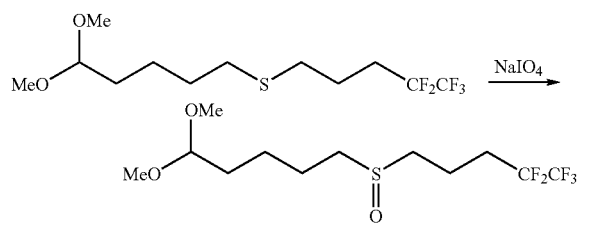

To a solution of 5,5-dimethoxy-1-(4,4,5,5,5-pentafluoropentylthio)pentane (460 mg, 1.4 mmol) in methanol (10 mg) were added sodium periodate (420 mg, 2.0 mmol) dissolved in water (8 ml) and methanol (5 ml), and the resulting mixture was stirred at room temperature for 2 hours. After the reaction was completed, the reaction solution was poured into water and extracted with ethyl acetate. The organic layer was dried over anhydrous magnesium sulfate, and concentrated under reduced pressure to give a crude product. This crude product thus obtained was subjected to silica gel column chromatography (n-hexane:ethyl acetate=2:1) to give 5,5-dimethoxy-1-(4,4,5,5,5-pentafluoropentylsulfinyl)pentane (365 mg, yield 76%).

$^1$H-NMR (270 MHz, CDCl$_3$) δ: 4.35 (1H, t, J=5 Hz, C$\underline{H}$(OCH$_3$)$_2$), 3.31 (6H, s, CH(OC$\underline{H_3}$)$_2$), 2.80–2.60 (4H, m, C$\underline{H_2}$—SO—C$\underline{H_2}$), 2.30–2.10 (4H, m, —C$\underline{H_2}$C$\underline{H_2}$CF$_2$CF$_3$), 1.85–1.45 (6H, m, C$\underline{H_2}$C$\underline{H_2}$CH$_2$CH(OCH$_3$)$_2$)

Step 4) Synthesis of 5-(4,4,5,5,5-pentafluoropentylsulfinyl)pentanal

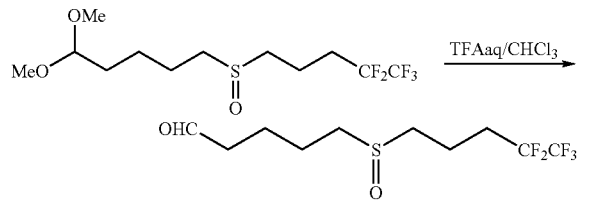

5,5-Dimethoxy-1-(4,4,5,5,5-pentafluoropentylsulfinyl)pentane (355 mg, 0.10 mmol) was dissolved in chloroform (2 ml), 50% TFA aqueous solution (2 ml) was added thereto at room temperature, and the resulting mixture was then stirred for 2 hours. After the reaction was completed, the reaction solution was poured into water and extracted with chloroform. The organic layer was dried over anhydrous magnesium sulfate, and concentrated under reduced pressure to give a crude product. This crude product thus obtained was subjected to silica gel column chromatography (n-hexane:ethyl acetate=2:1→1:1-ethyl acetate) to give 5-(4,4,5,5,5-pentafluoropentylsulfinyl)pentanal (28 mg, yield 93%).

$^1$H-NMR (270 MHz, CDCl$_3$) δ: 9.79 (1H, s, C$\underline{H}$O), 2.98–2.54 (6H, m, C$\underline{H_2}$—SO—C$\underline{H_2}$ and C$\underline{H_2}$CHO), 2.38–2.17 (4H, m, —C$\underline{H_2}$C$\underline{H_2}$CF$_2$CF$_3$), 1.82 (4H, m, C$\underline{H_2}$C$\underline{H_2}$CH$_2$CHO)

Step 5) Synthesis of 4-[3-(t-butyldimethylsilyloxy)-1-propynyl]-4-hydroxy-7-methoxymethoxy-3-(4-methoxymethoxyphenyl)-3-methylchroman

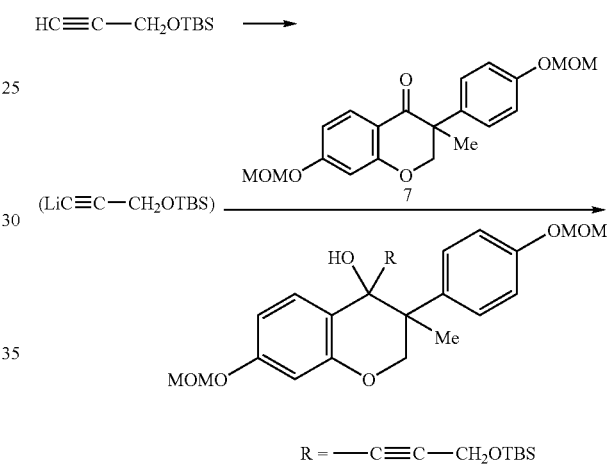

An alkyne compound (1.5 g, 8.8 mmol, separately prepared) was dissolved in dry tetrahydrofuran (20 mg), which was then cooled down to −20° C. under argon. To this solution was added dropwise n-butyllithium (1.66 mol/l solution in hexane, 4.8 ml, 8.0 mmol), and the mixture was stirred at −20° C. to −10° C. for 1 hour. Then, a solution of the chromanone derivative (7) (1.0 g, 2.8 mmol) dissolved in dry tetrahydrofuran (20 ml) was added dropwise, and the mixture was stirred at −10C to 0° C. for 1 hour. After the reaction was completed, the reaction mixture was poured into ice-water and extracted with ether. The organic layer was dried over anhydrous magnesium sulfate, and concentrated under reduced pressure to give a crude product. This crude product thus obtained was subjected to silica gel column chromatography (n-hexane:ethyl acetate=5:1) to give 4-[3-(t-butyidimethylsilyloxy)-1-propynyl]-4-hydroxy-7-methoxymethoxy-3-(4-methoxymethoxyphenyl)-3-methylchroman (1.26 g, yield 85%).

$^1$H-NMR (270 MHz, CDCl$_3$) δ: 7.65 (1H, d, J=9 Hz, C5-H), 7.50 (2H, d, J=9 Hz, Ar—H), 7.05 (2H, d, J=9 Hz, Ar—H), 6.66 (1H, dd, J=9 and 2 Hz, C6-H), 6.57 (1H, d, J=2 Hz, C8-H), 5.18 (2H, s, —OC$\underline{H_2}$OCH$_3$), 5.15 (2H, s, —OC$\underline{H_2}$OCH$_3$), 4.89 (1H, d, J=11 Hz, C2-H), 4.40 (2H, s, —C$\underline{H_2}$OTBS), 7.23–4.05 (1H, m, C2-H), 3.48 (3H, s, —OCH$_3$), 3.47 (3H, s, —OCH$_3$), 1.52 (3H, s, C3-CH$_3$), 0.92 (9H, s, t-butyl-H), 0.10 (6H, s, Si(C$\underline{H_3}$)$_2$)

Step 6) Synthesis of 4-[3-(t-butyldimethylsilyloxy)-1-pro-pynyl-3-(7-methoxymethoxy-3-(4-methoxymethoxyphe-nyl)-3-methylchroman

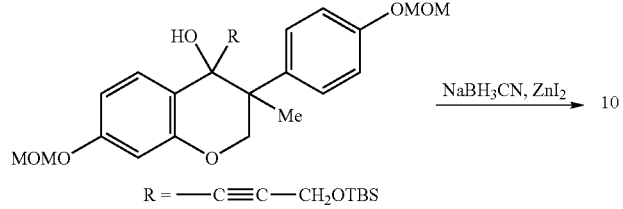

To a solution of 4-[3-(t-butyldimethylsilyloxy)-1-propy-nyl}-4-hydroxy-7-methoxymethoxy-3-(4-methoxymethox-yphenyl)-3-methylchroman (1.26 g, 2.4 mmol) in 1,2-dichloroethane (80 ml) were added zinc iodide(II) (1.1 g) and sodium cyanoborohydride (1.1 g), which was then stirred at room temperature for 1 hour.

After the reaction was completed, the reaction mixture was poured into water and extracted with chloroform. The organic layer was dried over anhydrous magnesium sulfate, and concentrated under reduced pressure to give a crude product. This crude product thus obtained was subjected to silica gel column chromatography (n-hexane:ethyl acetate=5:1) to give 4-[3-(t-butyidimethylsilyloxy)-1-propy-nyl]-7-methoxymethoxy-3-(4-methoxymethoxyphenyl)-3-methylchroman (a mixture of (3RS,4RS) and (3RS,4SR), (3RS,4RS)/(3RS,4SR)=about 6/1) (0.72 g, yield 59%).

$^1$H-NMR (270 MHz, CDCl$_3$, (3RS,4RS)) δ: 7.35–6.51 (7H, m, Ar—H), 5.14 (2H, s, —OCH$_2$O), 5.13 (2H, s, —OCH$_2$O), 4.49 (1H, d, J=11 Hz, C2-H), 4.23–3.90 (4H, m, C2-H, —CH$_2$OTBS and C4-H), 3.47 (6H; s, (OCH$_3$)×2), 1.38 (3H, s, C3-CH$_3$), 0.83 (9H, s, t-butyl-H), 0.03 (6H, s, Si(CH$_3$)$_2$)

Step 7) Synthesis of 4-(3-hydroxypropyl)-7-meth-oxymethoxy-3-(4-methoxymethoxyphenyl)-3-methylchro-man

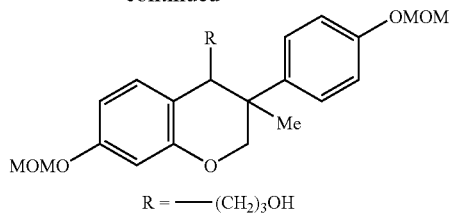

4-[3-(t-Butyldimethylsilyloxy)-1-propynyl]-7-meth-oxymethoxy-3{(4-methoxymethoxyphenyl)-3-methylchro-man (560 mg, 1.1 mmol) was dissolved in methanol (60 ml) and tetrahydrofuran (10 ml), 10% palladium on carbon (0.23 g) was added thereto, and the resulting mixture was stirred at room temperature under hydrogen for 20 hours. The reaction solution was filtered through cellite and concentrated under reduced pressure to give a crude product. This crude product thus obtained was crudely purified using silica gel column chromatography (n-hexane:ethyl acetate=10:1) to give 4-[3-(t-butyldimethylsilyloxy)propyl]-7-meth-oxymethoxy-3-(4-methoxymethoxyphenyl)-3-methylchro-man (0.44 g, yield 82%). This crude compound thus obtained (0.44 g) was dissolved in methanol (20 ml), PPTS (pyridinium p-toluenesulfonate) (0.40 g) was added thereto, and the mixture was stirred at room temperature for 3 hours. After the reaction was completed, the reaction mixture was concentrated under reduced pressure to give a crude product. This crude product was poured into water and extracted with ethyl acetate. The organic layer was dried over anhydrous magnesium sulfate, and concentrated under reduced pressure to give a crude product. This crude product thus obtained was subjected to silica gel column chromatography (n-hexane:ethyl acetate=2:1) to give 4-(3-hydroxypropyl)-7-methoxymethoxy-3-(4-methoxymethoxyphenyl)-3-methylchro man (a mixture of (3RS,4RS) and (3RS,4SR), (3RS, 4RS)/(3RS, 4SR)=about 6/1) (0.28 g, yield 82%).

$^1$H-NMR (270 MHz, CDCl$_3$, (3RS,4RS)) δ: 7.16–6.94 (5H, m, Ar—H), 6.58–6.51 (2H, m, Ar—H), 5.18 (2H, s, —OCH$_2$O), 5.14 (2H, s, —OCH$_2$O), 4.54 (1H, d, J=11 Hz, C2-H), 4.27 (1H, d, J=11 Hz, C2-H), 3.49–3.41 (8H, m, (OCH$_3$)×2 and CH$_2$OH), 2.68 (1H, brs, C4-H), 1.26 (3H, s, C3-CH$_3$), 1.56–1.06 (4H, m, alkyl-H)

Step 8) Synthesis of (3RS,4RS)-4-(3-azidopropyl)-7-meth-oxymethoxy-3-(4-methoxymethoxyphenyl)-3-methylchro-man

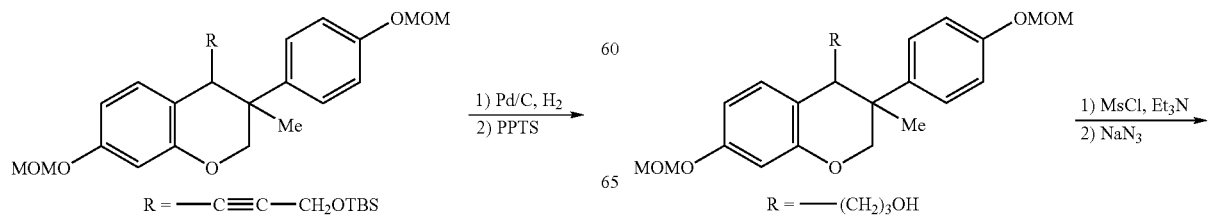

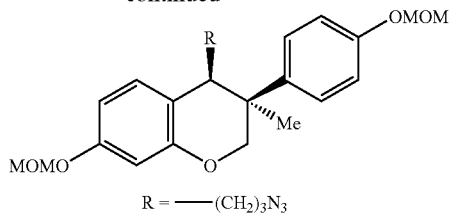

R = ——(CH$_2$)$_3$N$_3$ 4-(3-Hydroxypropyl)-7-methoxymethoxy-3-(4-methoxymethoxyphenyl)-3-methylchroman (280 mg, 0.70 mmol) was dissolved in dichloromethane (50 ml), methanesulfonylchloride (0.32 g) and triethylamine (0.30 g) were added thereto, and the mixture was stirred at room temperature for 1 hour After the reaction was completed, the reaction mixture was poured into water and extracted with chloroform. The organic layer was dried over anhydrous magnesium sulfate, and concentrated under reduced pressure to give a crude product. This crude product thus obtained was subjected to silica gel column chromatography (n-hexane: ethyl acetate=3:1) to give 4-(3-methanesulfonyloxypropyl)-7-methoxymethoxy-3-(4-methoxymethoxyphenyl)-3-methylchroman (a mixture of (3RS,4RS) and (3RS,4SR), (3RS,4RS)/(3RS,4SR)=about 6/1) (350 mg, stoichiometric yield). Then, to a solution of the product (0.59 g, 1.2 mmol) in DMF (15 ml) was added sodium azide (0.14 g), and the mixture was stirred at 60° C. for 2 hours. After the reaction was completed, the reaction mixture was poured into water and extracted with ether. The organic layer was dried over anhydrous magnesium sulfate, and concentrated under reduced pressure to give a crude product. This crude product thus obtained was subjected to preparative TLC (n-hexane/ethyl acetate=10/1 for twice, 5/1 for twice) to produce (3RS,4RS)-4-(3-azidopropyl)-7-methoxymethoxy-3-(4-methoxymethoxyphenyl)-3-m ethylchroman (220 mg, yield 42%).

$^1$H-NMR (270 MHz, CDCl$_3$, (3RS,4RS)) δ: 7.14 (2H, d, J=9 Hz, Ar—H), 7.04 (2H, d, J=9 Hz, Ar—H), 6.95–6.91 (1H, m, Ar—H), 6.59 6.57 (2H, m, Ar—H), 5.18 (2H, s, OCH$_2$O), 5.15 (2H, s, OCH$_2$O), 4.52 (1H, d, J=11 Hz, C2-H), 4.29 (1H, d, J=11 Hz, C2-H), 3.49 (6H, s, (OCH$_3$)×2), 3.03 (2H, t, J=7 Hz, CH$_2$N$_3$), 2.67 (1H, brs, C4-H), 1.19 (3H, s, C3-CH$_3$), 1.57–1.10 (4H, m, alkyl-H)

Step 9) Synthesis of (3RS,4RS)-4-(3-aminopropyl)-7-methoxymethoxy-3-(4-methoxymethoxyphenyl)-3-methylchroman

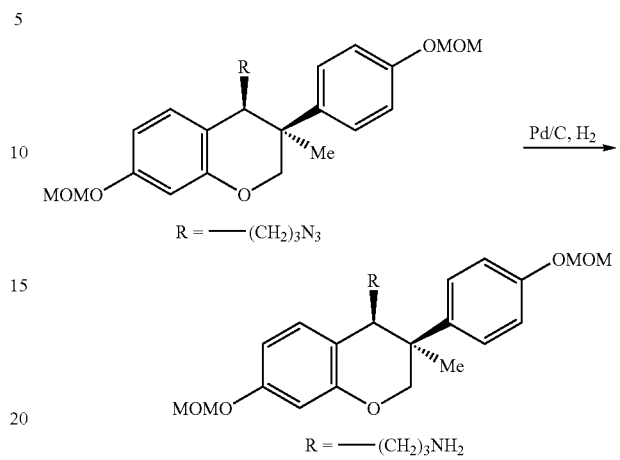

(3RS,4RS)-4-(3-Azidopropyl)7-methoxymethoxy-3-(4-methoxymethoxyphenyl)-3-methylchroman (170 mg, 4.0 mmol) was dissolved in methanol (20 ml) and tetrahydrofuran (5 ml), 10% palladium on carbon (50 mg) was added to this solution, which was then stirred at room temperature under hydrogen for 12 hours. The reaction solution was filtered through cellite and concentrated under reduced pressure to give a crude product. This crude product thus obtained was subjected to silica gel column chromatography (chloroform:methanol:ammonia water=10:1:0.1) to give (3RS,4RS)-4-(3-aminopropyl)-7-methoxymethoxy-3-(4-methoxymethoxyphenyl)-3-methylchroman (116 mg, yield 73%).

$^1$H-NMR (270 MHz, CDCl$_3$, (3RS,4RS)) δ: 7.13 (2H, d, J=9 Hz, Ar—H), 7.02 (2H, d, J=9 Hz, Ar—H), 6.96–6.93 (1H, m, Ar—H), 6.57 (2H, brs, Ar—H), 5.17 (2H, s, OCH$_2$O), 5.14 (2H, s, OCH$_2$O), 4.53 (1H, d, J=10 Hz, C2-H), 4.27 (1H, d, J=10 Hz, C2-H), 3.49 (6H, s, (OCH$_3$)×2), 2.66 (1H, brs, C4-H), 2.60–2.35 (2H, m, CH$_2$NH$_2$), 1.25 (3H, s, C3-CH$_3$), 1.60–1.00 (4H, m, alkyl-H)

Step 10) Synthesis of (3RS,4RS)-7-methoxymethoxy-3-(4-methoxymethoxyphenyl)-3-methyl-4-(3-N-5-(4,4,5,5,5-pentafluoropentylsulfinyl)pentylamino]propyl}chroman

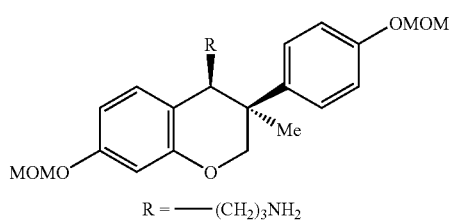

R = ——(CH$_2$)$_3$NH$_2$

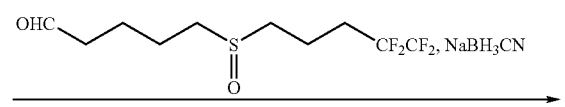

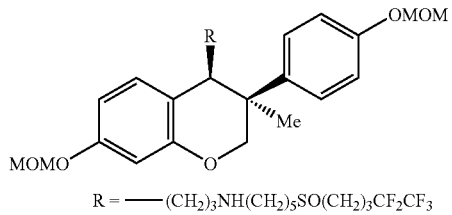

To a solution of (3RS,4RS)-4-(3-aminopropyl)-7-methoxymethoxy-3-(4-methoxymethoxyphenyl)-3-methylchroman (80 mg, 0.20 mmol) and 5-(4,4,5,5,5-pentafluoropentylsulfinyl)pentanal (80 mg, 0.19 mmol) in methanol (5 ml) was added a solution of sodium cyanoborohydride (12 mg, 0.19 mmol) in methanol (5 ml), which was then stirred at 0 for 2 hours. The reaction solution was poured into water and extracted with chloroform. The organic layer was dried over anhydrous magnesium sulfate, and concentrated under reduced pressure to give a crude product. This crude product thus obtained was subjected to preparative TLC on silica gel using chloroform/methanol/ammonia water (7/1/0.1) as a mobile phase to give (3RS,4RS)-7-methoxymethoxy-3-(4-methoxymethoxyphenyl)-3-methyl-4-{3-[N-5-(4,4,5,5,5-pentafluoropentylsulfinyl)pe ntylamino]propyl}chroman (38 mg, yield 28%).

$^1$H-NMR (270 MHz, CDCl$_3$, (3RS,4RS)) δ: 7.14–6.95 (5H, m, Ar—H), 6.56–6.54 (2H, m, Ar—H), 5.17 (2H, s, —OC$\underline{H}_2$OCH$_3$), 5.12 (2H, s, —OC$\underline{H}_2$OCH$_3$), 4:51 (1H, d, J=11 Hz, C2-H), 4.25 (1H, d, J=11 Hz, C2-H), 3.49 (3H, s, —OCH$_3$), 3.47 (3H, s, —OCH$_3$), 2.73–2.45 (9H, m, C$\underline{H}_2$—SO—C$\underline{H}_2$, C$\underline{H}_2$NHC$\underline{H}_2$ and C4-H), 2.41–2.08 (4H, m, —C$\underline{H}_2$C$\underline{H}_2$CF$_2$CF$_3$), 1.25 (3H, s, C3-CH$_3$), 1.79–1.10 (10H, m, alkyl-H)

Step 11) Synthesis of (3RS,4RS)-7-hydroxy-3-(4-hydroxyphenyl)-3-methyl-4-(3-[N-5-(4,4,5,5,5-pentafluoropentyl-sulfinyl)pentylamino]propyl}chroman

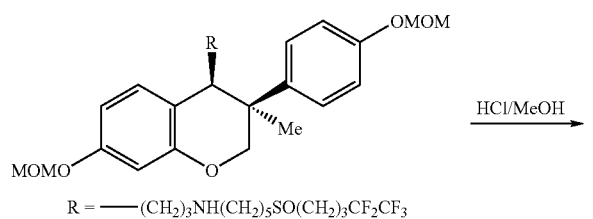

(3RS,4RS)-7-Methoxymethoxy-3-(4-methoxymethoxyphenyl)-3-methyl-4-{3-[N-5-(4,4,5,5,5-pentafluoropentylsulfinyl)pentylamminopropyl}chroman (38 mg, 0.056 mmol) was dissolved in hydrochloric acid/methanol (3 ml), which was then stirred at room temperature for 2 days. This reaction solution was basified using ammonia water, and concentrated under reduced pressure to give a crude product This crude product thus obtained was subjected to preparative TLC on aminosilica gel using chloroform/methanol (5/1) as a mobile phase to give (3RS,4RS)-7-hydroxy-3-(4-hydroxyphenyl)-3-methyl-4-{3-N-5S4,4,5,5,5-pentafluoropentylsulfinyl)pentylamino]propyl) chroman (27 mg, yield 82%).

$^1$H-NMR (270 MHz, CD$_3$OD, (3RS,4RS)), δ: 7.05 (2H, d, J=9Ht, Ar—H), 6.85–6.71 (3H, m, Ar—H), 6.23–6.19 (2H, m, Ar—H), 4.46 (1H, d, J=10 Hz, C2-H), 4.16 (1H, d, J=10 Hz, C2-H), 2.86–2.60 (5H, m, C$\underline{H}_2$—SO—C$\underline{H}_2$ and C4-H), 2.40–2.27 (6H, m, —C$\underline{H}_2$CF$_2$CF$_3$ and C$\underline{H}_2$—NH—C$\underline{H}_2$), 2.05–1.99 (2H, m, —C$\underline{H}_2$CH$_2$CF$_2$CF$_3$), 1.12 (3H, s, C3-CH$_3$), 1.66–1.09 (10H, m, alkyl-H)

EXAMPLE 17

Synthesis of (3RS,4RS)-7-hydroxy-3-(4-hydroxyphenyl)-3-methyl-4-[9-(N-methyl-N-4,4,5,5,5-pentafluoropentyl)aminononyl]chroman Step 1) Synthesis of 4-[9-(t-butyldimethylsilyloxy)-1-nonynyl]4-hydroxy-7-methoxymethoxy-3-(4-methoxymethoxyphenyl)-3-methylchroman

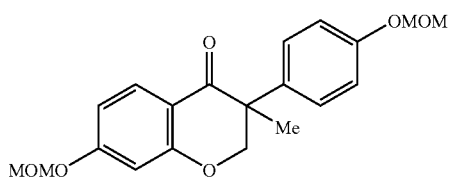

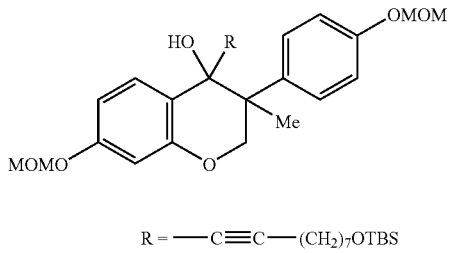

R = —C≡C—(CH₂)₇OTBS

An alkyne compound (2.0 g, 7.8 mmol, separately prepared) was dissolved in dry tetrahydrofuran (15 ml), which was then cooled down to −20° C. under argon. n-Butyllithium (1.66 mol/l solution in hexane, 4.2 ml, 7.0 mmol) was added dropwise to this solution, and the mixture was stirred at −20° C. to −10° C. for 1 hour. Then, the chromanone derivative (0.75 g, 2.1 mmol) dissolved in dry tetrahydrofuran (20 ml) was added dropwise thereto, which was stirred at −10° C. to 0° C. for 1 hour. After the reaction was completed, the reaction mixture was poured into ice-water and extracted with ether. The organic layer was dried over anhydrous magnesium sulfate, and concentrated under reduced pressure to give a crude product. This crude product thus obtained was subjected to silica gel column chromatography (n-hexane:ethyl acetate=5:1) to give 4-[9-(t-butyldimethylsilyloxy)-1-nonynyl-4-hydroxy-7-methoxymethoxy-3-(4-methoxymethoxyphenyl)-3-methylchroman (1.16 g, yield 90%).

$^1$H-NMR (270 MHz, CDCl$_3$) δ: 7.66 (1H, d, J=9 Hz, C5-H), 7.48 (2H, d, J=9 Hz, Ar—H), 7.05 (2H, d, J=9 Hz, Ar—H), 6.67 (1H, dd, J=9 and 2 Hz, C6-H), 6.56 (1H, d, J=2 Hz, C8-H), 5.19 (2H, s, —OCH$_2$OCH$_3$), 5.16 (2H, s, —OCH$_2$OCH$_3$), 4.91 (1H, d, J=11 Hz, C2-H), 4.60 (1H, d, J=11 Hz, C2-H), 3.60 (2H, t, J=7 Hz, —CH$_2$OTBS), 3.50 (3H, s, —OCH$_3$), 3.47 (3H, s, —OCH$_3$), 2.27 (2H, t, J=7 Hz, —CH$_2$C≡C), 1.51 (3H, s, C3-CH$_3$), 1.60–1.34 (10H, m, alkyl-H), 0.89 (9H, s, t-butyl-H), 0.05 (6H, s, Si(CH$_3$)$_2$)

Step 2) Synthesis of 4-[9-(t-butyldimethylsilyloxy)-nonyl]-7-methoxymethoxy-3-(4-methoxymethoxyphenyl)-3-methylchroman

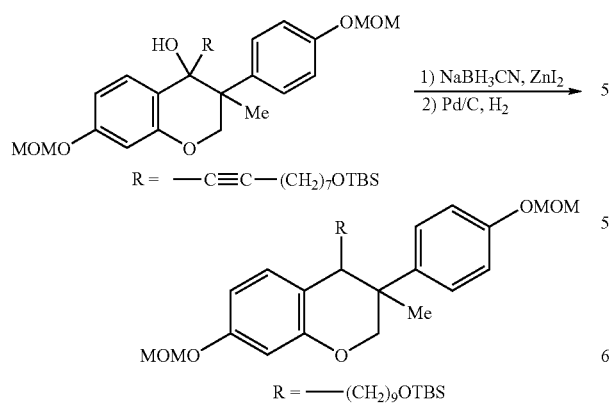

To a solution of 4-[9-(t-butyldimethylsilyloxy)-1-nonynyl]4-hydroxy-7-methoxymethoxy-3-(4-methoxymethoxyphenyl)-3-methylchroman (116 g, 1.9 mmol) in 1,2-dichloroethane (50 ml) were added zinc iodide(II) (0.7 g) and sodium cyanoborohydride (0.6 g), which was then stirred at room temperature for 4 hours. After the reaction was completed, the reaction mixture was poured into water and extracted with chloroform. The organic layer was dried over anhydrous magnesium sulfate, and concentrated under reduced pressure to give a crude product. This crude product thus obtained was subjected to silica gel column chromatography (n-hexane:ethyl acetate=5:1) to give 4-[9-(t-butyldimethylsilyloxy)-1-nonynyl]-7-methoxymethoxy-3-(4-methoxymethoxyphenyl)-3-methylchroman (a mixture of (3RS,4RS) and (3RS,4SR), (3RS,4RS)/(3RS,4SR)=about 6/1) (590 mg, yield 52%). Then, this compound thus obtained was dissolved in methanol (50 ml) and tetrahydrofuran (10 ml), 10% palladium on carbon (0.23%) was added thereto, and the resulting mixture was stirred at room temperature under hydrogen for 20 hours. The reaction solution was filtered through cellite and concentrated under reduced pressure to give 4-(9-(t-butyldimethylsilyloxy)-nonyl)-7-methoxymethoxy-3-(4-methoxymethoxyphenyl)-3-methylchroman (crude product, 640 mg, stoichiometric yield, a mixture of (3RS,4RS) and (3RS,4SR), (3RS,4RS)/(3RS,4SR)=about 6/1).

$^1$H-NMR (270 MHz, CDCl$_3$) δ: 7.22–6.55 (7H, m, Ar—H), 5.18 (2H, s, —OCH$_2$OCH$_3$), 5.15 (2H, s, —OCH$_2$OCH$_3$), 4.52 (1H, d, J=10 Hz, C2-H), 4.25 (1H, d, J=10 Hz, C2-H), 3.59–3.46 (8H, m, —(OCH$_3$)×2, and CH$_2$OTBS), 2.65 (1H, brs, C4-H), 1.47–1.07 (16H, m, alkyl-H), 1.25 (3H, s, C3-CH$_3$), 0.89 (9H, s, t-butyl-H), 0.05 (6H, s, Si(CH$_3$)$_2$)

Step 3) Synthesis of (3RS,4RS)A-(9-methanesulfonyloxynonyl)-7-methoxymethoxy-3-(4-methoxymethoxyphenyl)-3-methylchroman

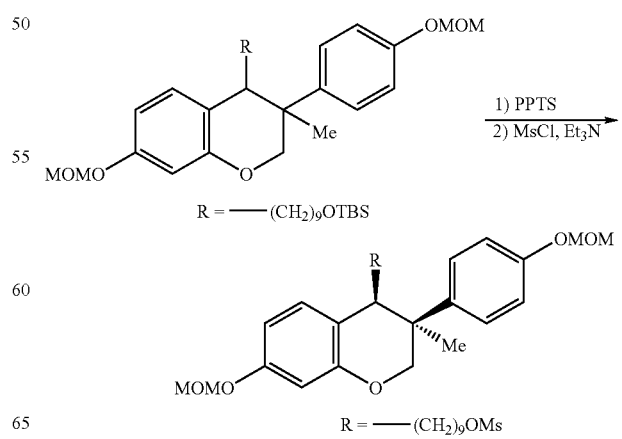

4-[9-(t-Butyldimethylsilyloxy)-nonyl]-7-methoxymethoxy-3-(4-methoxymethoxyphenyl)-3-methylchroman (0.62 g, 11.0 mmol) was dissolved in methanol (30 ml), PPTS (0.70 g) was added thereto, and the mixture was stirred at room temperature for 4 hours. After the reaction was completed, the reaction mixture was concentrated under reduced pressure. The residue was poured into water and extracted with ethyl acetate. The organic layer was dried over anhydrous magnesium sulfate, and concentrated under reduced pressure to give a crude product. This crude product thus obtained was subjected to silica gel column chromatography (n-hexane:ethyl acetate=2:1) to give 4-(9-hydroxynonyl)-7-methoxymethoxy-3-(4-methoxymethoxyphenyl)-3-methylchroman (a mixture of (3RS,4RS) and (3RS,4SR), (3RS,4RS)/(3RS,4SR)=about 6/1, 370 mg, yield 77%). This compound thus obtained was dissolved in dichloromethane (20 ml), methanesulfonylchloride (0.40 g) and triethylamine (0.38 g) were added thereto, and the mixture was stirred at room temperature for 1 hour. After the reaction was completed, the reaction mixture was poured into water and extracted with chloroform. The organic layer was dried over anhydrous magnesium sulfate, and concentrated under reduced pressure to give a crude product. This crude product thus obtained was subjected to preparative TLC using n-hexane/ethyl acetate (5/1 for 6 times) to produce (3RS,4RS)-4-(9-methanesulfonyloxynonyl)-7-methoxymethoxy-3-(4-methoxymethoxyphenyl)-3-methylchroman (241 mg, yield 56%).

¹H-NMR (270 MHz, CDCl₃) δ: 7.13 (2H, d, J=9 Hz, Ar—H), 7.03 (2H, d, J=9 Hz, Ar—H), 6.96–6.93 (1H, m, Ar—H), 6.58–6.55 (2H, m, Ar—H), 5.18 (2H, s, —OCH₂OCH₃), 5.15 (2H, s, —OCH₂OCH₃), 4.52 (1H, d, J=10 Hz, C2-H), 4.23–4.17 (3H, m, C2-H and CH₂OMs), 3.50 (6H, m, —(OCH₃)×2), 2.99 (3H, s, —OSO₂CH₃), 2.65 (1H, brs, C4-H), 1.71 (2H, m, —CH₂CH₂OMs), 1.25 (3H, s, C3-CH₃), 1.34–1.11 (14H, m, alkyl-H)

Step 4) Synthesis of (3RS,4RS)-7-methoxymethoxy-3-(4-methoxymethoxyphenyl)-3-methyl-4-[9-(methylamino)-nonyl]chroman

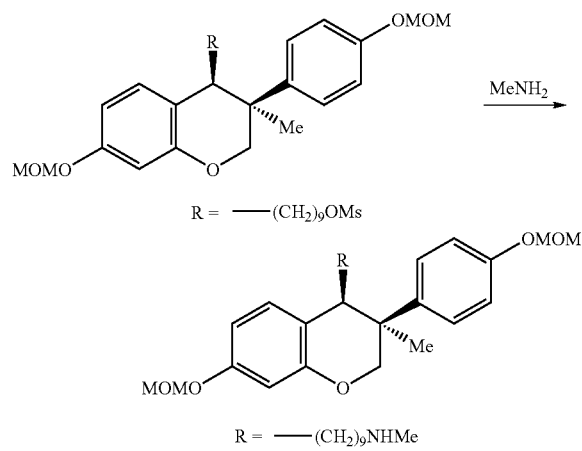

To (3RS,4RS)-4-(9-methanesulfonyloxynonyl)-7-methoxymethoxy-3-(4-methoxymethoxyphenyl)-3-methylchroman (241 mg, 0.43 mmol) was added a solution of 40% monomethylamine in methanol (40 ml), which was then stirred at room temperature for 24 hours. After the reaction was completed, the mixture was concentrated under reduced pressure. The residue was poured into 10% aqueous potassium carbonate solution, and extracted with chloroform. The organic layer was dried over anhydrous magnesium sulfate, and concentrated under reduced pressure to give (3RS,4RS)-7-methoxymethoxy-3-(4-methoxy-methoxyphenyl)-3-methyl-4-[9-(methylamino)-nonyl]chroman (191 mg, yield 90%).

¹H-NMR (270 MHz, CDCl₃) δ: 7.13 (2H, d, J=9 Hz, Ar—H), 7.02 (2H, d, J=9 Hz, Ar—H), 6.96–6.93 (1H, m, Ar—H), 6.57–6.55 (2H, m, Ar—H), 5.18 (2H, s, —OCH₂OCH₃), 5.15 (2H, s, —OCH₂OCH₃), 4.52 (1H, d, J=11 Hz, C2-H), 4.25 (1H, d, J=11 Hz, C2-H), 3.49 (6H, s, —(OCH₃)×2), 2.64 (1H, brs, C4-H), 2.53 (2H, t, J=7 Hz, —CH₂NHCH₃), 2.42 (3H, s, —NHCH₃), 1.23 (3H, s, C3-CH₃), 1.46–1.11 (16H, m, alkyl-H)

Step 5) Synthesis of (3RS,4RS)-7-methoxymethoxy-3-(4-methoxymethoxyphenyl)-3-methyl-4-[9-(N-methyl-N-4,4,5,5,5-pentafluoropentyl)-aminononyl]chroman

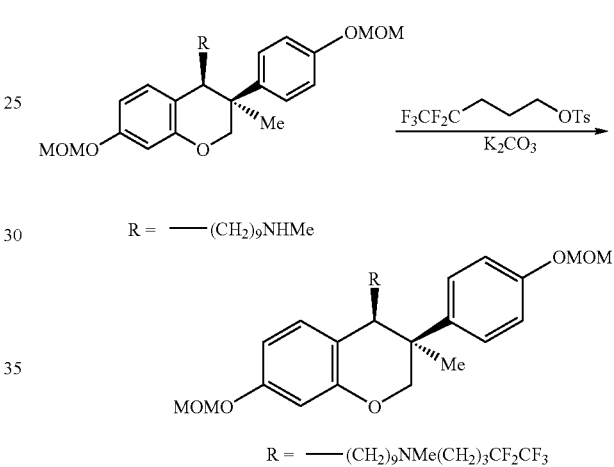

(3RS,4RS)-7-Methoxymethoxy-3-(4-methoxymethoxyphenyl)-3-methyl-4-[9-(methylamino)-nonyl]chroman (73 mg, 0.14 mmol), 4,4,5,5,5-pentafluoropentyl-1-(p-toluenesulfonyloxy)pentane (180 mg, 0.54 mmol, separately prepared) and potassium carbonate (75 mg, 0.54 mmol) were dissolved in toluene, which was then stirred at 120° C. for 4 days. The reaction solution was concentrated under reduced pressure, water was poured into the residue, and the mixture was extracted with chloroform. The organic layer was dried over anhydrous magnesium sulfate, and concentrated under reduced pressure to give a crude product. This crude product thus obtained was subjected to preparative TLC on silica gel using chloroform/methanol (20/1) as a mobile phase to give (3RS,4RS)-7-methoxymethoxy-3-(4-methoxymethoxyphenyl)-3-methyl-4-[9-(N-methyl-N-4,4,5,5,5-pentafluoropentyl)-aminononyl]chroman (80 mg, yield 88%).

¹H-NMR (270 MHz, CDCl₃) δ: 7.13 (2d, J=9 Hz, Ar—H), 7.02 (2H, d, J=9 Hz, Ar—H), 6.97–6.93 (1H, m, Ar—H), 6.59 (2H, brs, Ar—H), 5.18 (2H, s, —OCH₂OCH₃), 5.15 (2H, s, —OCH₂OCH₃), 4.53 (1H, d, J=10 Hz, C2-H), 4.26 (1H, d, J=10 Hz, C2-H), 3.50 (6H, s, —(OCH₃)×2), 2.65 (1H, brs, C4-H), 2.40–2.27 (4H, m, —CH₂NMeCH₂—), 2.19 (3H, s, —NCH₃), 2.14–1.97 (2H, m, —CH₂CF₂CF₃), 1.25 (3H, s, C3-CH₃), 1.76–1.11 (18H, m, alkyl-H)

Step 6) Synthesis of (3RS,4RS)-7-hydroxy-3-(4-hydroxyphenyl)-3-methyl-4-[9-(N-methyl-N-4,4,5,5,5-pentafluoropentyl)-aminononyl]chroman

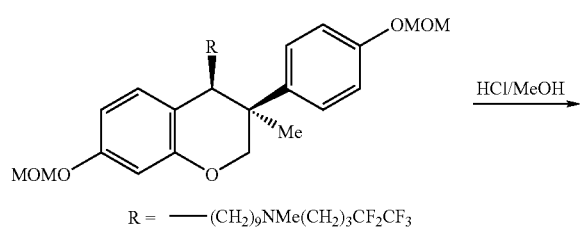

R = ——(CH₂)₉NMe(CH₂)₃CF₂CF₃

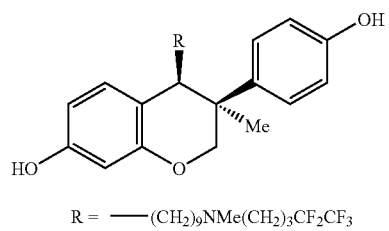

R = ——(CH₂)₉NMe(CH₂)₃CF₂CF₃

5% Hydrochloric acid/methanol (20 ml) was added to (3RS,4RS)-7-methoxymethoxy-3-(4-methoxymethoxyphenyl)-3-methyl-4-[9-(N-methyl-N-4,4,5,5,5-pentafluoropentyl)-aminononyl]chroman (85 mg, 0.13 mmol), which was then stirred at room temperature for 12 hours. After the reaction was completed, the reaction solution was concentrated under reduced pressure to give a crude product. This crude product thus obtained was subjected to preparative TLC on silica gel using chloroform/methanol (10/1) as a mobile phase to give (3RS,4RS)-7-hydroxy-3-(4-hydroxyphenyl)-3-methyl-4-[9-(N-methyl-N-4,4,5,5,5-pentafluoropentyl)-aminononyl]chroman (66 mg, yield 90%).

¹H-NMR (270 MHz, CD₃OD, (3RS,4RS)) δ; 7.08 (2H, d, J=9 Hz, Ar—H), 6.85 (1H, d, J=8 Hz, C5-H), 6.77 (2H, d, J=9 Hz, Ar—H), 6.30 (1H, dd, J=8 and 2 Hz, C6-H), 6.24 (1H, d, J=2 Hz, C8-H), 4.49 (1H, d, J=11 Hz, C2-H), 4.20 (1H, d, J=11 Hz, C2-H), 2.62 (1H, brs, C4-H), 2.50–2.35 (4H, m, —CH₂NMeCH₂), 2.25 (3H, s, —NCH₃), 2.17–2.11 (2H, m, —CH₂CF₂CF₃), 1.82–1.73 (2H, m, —CH₂CH₂CF₂CF₃), 1.45–1.09 (16H, m, alkyl-H), 1.20 (3H, s, C3-CH₃)

EXAMPLE 18

Synthesis of N-methyl-N-(4,4,5,5,5-pentafluorpentyl)-9-[(3RS,4RS)-7-hydroxy-(3-(4-hydroxyphenyl)-3-methylchroman-4-yl]nonylamine N-oxide

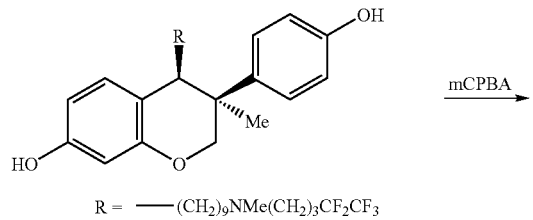

R = ——(CH₂)₉NMe(CH₂)₃CF₂CF₃

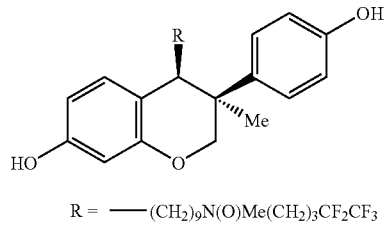

R = ——(CH₂)₉N(O)Me(CH₂)₃CF₂CF₃

To a solution of (3RS,4RS)-7-hydroxy-3-(4-hydroxyphenyl)-3-methyl-4-[9-(N-methyl-N-4,4,5,5,5-pentafluoropentyl)-aminonoyl]chroman (66 mg, 0.12 mmol) in chloroform was added at 0° C. mCPBA (30 mg, 0.12 mmol, 70%), which was then stirred for 3 hours. After the reaction was completed, the reaction solution was basified by adding ammonia water and concentrated under reduced pressure to give a crude product. This crude product thus obtained was subjected to preparative TLC on silica gel using chloroform/methanol (10/1) as a mobile phase to give N-methyl-N-(4,4,5,5,5-pentafluoropentyl)-9-[(3RS,4RS)-7-hydroxy-3-(4-hydroxyphenyl)-3-methylchroman-4-yl]nonylamine N-oxide (53 mg, yield 78%).

¹H-NMR (270 MHz, CD₃OD, (3RS,4RS)) δ: 7.10–7.07 (2H, m, Ar—H), 6.85 (1H, d, J=8 Hz, C5-H), 6.78 (2H, d, J=9 Hz, Ar—H), 6.30 (11H, dd, J=9 and 2 Hz, C6-H), 6.24 (1H, d, J=2 Hz, C8-H), 4.49 (1H, d, J=10 Hz, C2-H), 4.20 (1H, d, J=10 Hz, C2-H), 3.29–3.16 (4H, m, —CH₂N(O)MeCH₂), 3.06 (3H, s, —N(O)CH₃), 2.62 (1H, brs, C4-H), 2.32–2.10 (4H, m, —CH₂CH₂CF₂CF₃), 1.77–1.70 (2H, m, —CH₂CH₂N(O)Me(CH₂)₃ CF₂CF₃), 1.27–1.00 (14H, m, alkyl-H), 1.20 (3H, s, C3-CH₃)

EXAMPLE 19

Synthesis of (3RS,4RS)-7-hydroxy-3-(4-hydroxyphenyl)-3-methyl-4-{3-{4-[2-(4,4,5,5,5-pentafluoropentylsulfinyl)ethoxy]phenoxy}propyl}thiochroman Step 1) Synthesis of 4-(2-t-butyldimethylsilyloxy)ethoxyphenol

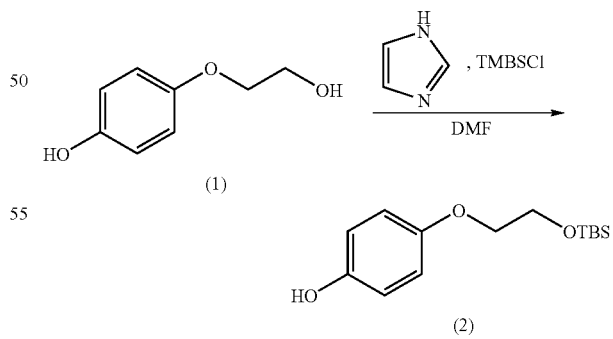

2-(4-Hydroxyphenoxy)-ethanol (1) (500 mg, 3.2 mmol) was dissolved in DMF (15 ml), which was then cooled down to 0° C. Imidazole (221 mg, 3.2 mmol) and TBSCl (489 mg, 3.2 mmol) were added thereto, and the mixture was stirred for 1 hour Water was added thereto, and the mixture was extracted with ethyl acetate. The organic layer was dried over anhydrous magensium sulfate, concentrated under reduced pressure, and subjected to silica gel column chromatography to give 4-(2-t-butyldimethylsilyloxy)ethoxyphenol (2) (778 mg, yield 89%) as a colorless oily substance.

$^1$H NMR (270 MHz, CDCl$_3$) δ: 6.85–6.70 (4H, m), 4.7–4.6 (1H, brs), 4.0–3.9 (4H, m), 0.91 (9H, s), 0.10 (6H, s)

Step 2) Synthesis of 3-[4-(2-t-butyldimethylsilyloxyethoxy)phenoxy]-1-propane

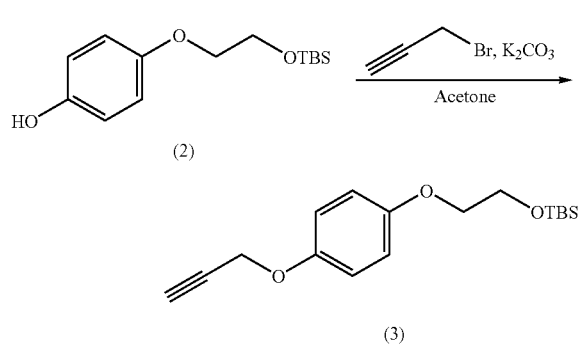

4-(2-t-Butyldimethylsilyloxy)ethoxyphenol (2) (268 mg, 1.0 mmol) prepared in Step 1) was dissolved in acetone (5 ml), potassium carbonate (166 mg, 1.2 mmol) and propargyl bromide (163 mg, 1.1 mmol) were added thereto, and the mixture was heated under reflux for 20 hours. The reaction solution was cooled, and the precipitate was separated by filtration. The filtrate was diluted with ether and washed with 10% aqueous sodium hydroxide solution. The ether layer was acidified with diluted hydrochloric acid and extracted with chloroform. The organic layer was dried over anhydrous magnesium sulfate, concentrated, and subjected to silica gel column chromatography to give 3-[4-(2-t-butyldimethylsilyloxyethoxy)phenoxy]-1-propyne (3) (237 mg, yield 78%) as a yellow oily substance.

$^1$H NMR (270 MHz, CDCl$_3$) δ: 6.95–6.80 (4H, m), 4.64 (2H, d, J=2.3 Hz), 4.05–3.90 (4H, m), 2:50 (1H, t, J=2.3 Hz), 0.91 (9H, s), 0.10 (6H, s)

Step 3) Synthesis of 4-[{3-[4-(2-t-butyldimethylsilyloxyethoxy)phenoxy]-1-propynyl}-4-hydroxy-7-methoxymethoxy-3-[4-(methoxymethoxy)phenyl]-3-methylthiochroman

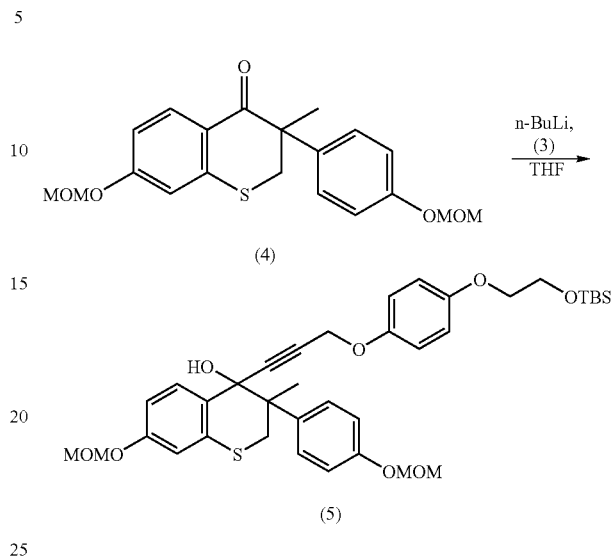

The alkyne compound (3) prepared in Step 2 (1.61 g, 5.3 mmol) was dissolved in dry tetrahydrofuran (15 ml), which was then cooled down to −78° C. n-Butyllithium (1.59 mol/l, 2.97 mg, 4.7 mmol) was added dropwise thereto, and the mixture was warmed to −10C and stirred for 1 hour. To this reaction solution was added dropwise the separately synthesized ketone compound (4) (655 mg, 1.8 mmol) dissolved in dry tetrahydrofuran (15 ml), which was then stirred for 3 hours. Water was added, and the mixture was extracted with ethyl acetate. The organic layer was dried over anhydrous magnesium sulfate, concentrated, and subjected to silica gel column chromatography to give 4-{3-[4-(2-t-butyldimethylsilyloxyethoxy)phenoxy]-1-propynyl}-4-hydroxy-7-methoxymethoxy-3-[4-(methoxymethoxy)phenyl]-3-methylthiochroman (5) (938 mg, yield 79%) as a brown oily-substance.

$^1$H NMR (270 MHz, CDCl$_3$) δ: 7.71 (2H, d, J=8.9 Hz), 7.49 (2H, d, J=8.9 Hz), 6.95 (2H, d, J=8.9 Hz), 6.90–6.80 (5H, m), 6.70 (2H, dd, J=8–6 Hz, 1.6 Hz), 5.17 (3H, s), 5.14 (3H, s), 2.33 (2H, s), 4.21 (1H, J=12.5 Hz), 4.05–3.90 (4H, m), 3.49 (3H, s), 3.46 (3H, s), 2.65 (2H, d, J=12.5 Hz), 2.23 (1H, s), 1.53 (3H, s), 0.91 (9H, s), 0.10 (6H, s)

Step 4) Synthesis of 4-{3-[4-(2-t-butyldimethylsilyloxyethoxy)phenoxy]-1-propynyl}-7-methoxymethoxy-3-[4-(methoxymethoxy)phenyl]-3-methylthiochroman

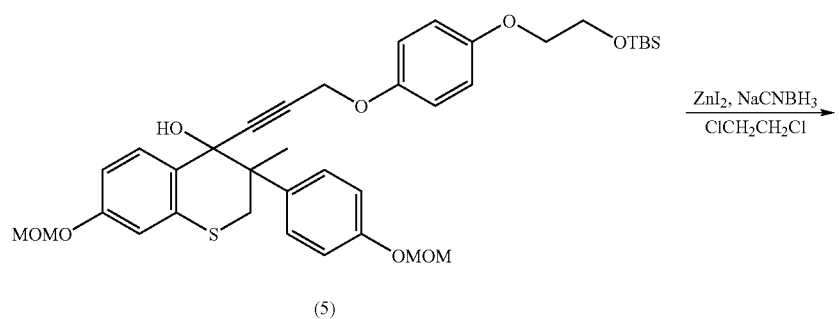

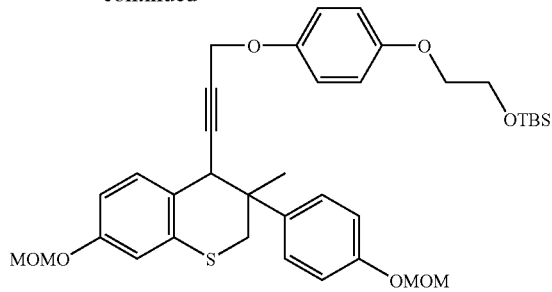

(6)

4-{3-[4-(2-t-Butyldimethylsilyloxyethoxy)phenoxy]-1-propynyl}-4-hydroxy-7-methoxymethoxy-3-[4-(methoxymethoxy)phenyl]-3-methylthiochroman (5) prepared in Step 3 (916 mg, 1.4 mmol) was dissolved in 1,2-dichloroethane (13.5 ml), zinc iodide (644 mg, 2 mmol) and sodium cyanoborohydride (634 mg, 10 mmol) were added, and the resulting mixture was stirred at room temperature for 1 day and stirred at 40° C. for further 3 hours. Water was added thereto, and the mixture was extracted with ethyl acetate. The organic layer was dried over anhydrous magnesium sulfate, concentrated, and subjected to silica gel column chromatography to give 4-{3-[4-(2-t-butyldimethylsilyloxyethoxy)phenoxy]-1-propynyl}-7-methoxymethoxy-3-[4-(methoxymethoxy)phenyl]-3-methylthiochroman (6) (408 mg, yield 46%) as a yellow oily substance.

$^1$H NMR (270 MHz, CDCl$_3$) δ: 7.22 (2H, d, J=8.6 Hz), 7.16 (2H, d, J=8.6 Hz), 6.92 (2H, d, J=8.9 Hz), 6.82–6.68 (5H, m), 5.15 (2H, s), 5.13 (2H, s), 4.49 (2H, d, J=1.65), 4.02–3.9 (4H, m), 3.82 (1H, s), 3.83 (1H, s), 3.59 (1H, d, J=12.5 Hz), 3.47 (3H, s), 3.46 (3H, s), 2.92 (1H, s), 1.41 (3H, s), 0.92 (9H, s), 0.10 (6H, s)

Step 5) Synthesis of 4-{3-[4-(2-hydroxyethoxy)phenoxy]propyl}-7-methoxymethoxy-3-[4-(methoxymethoxy)phenyl]-3-methylthiochroman

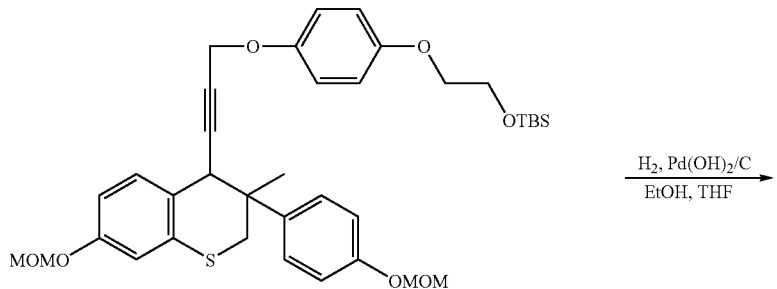

(6)

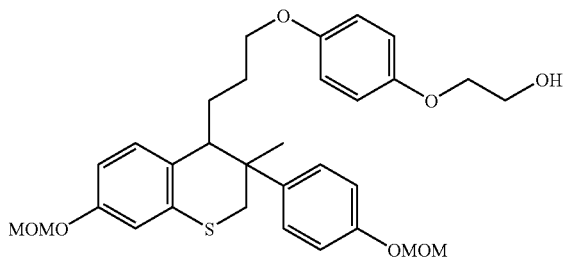

(7)

4-{3-[4-(2-t-Butyldimethylsilyloxyethoxy)phenoxy]-1-propynyl}-7-methoxymethoxy-3-[4-(methoxymethoxy)phenyl]-3-methylthiochroman (6) prepared in Step 4 (408 mg) was dissolved in a solvent mixture of ethanol (6 ml) and tetrahydrofuran (2 ml), 20% palladium hydroxide/carbon (130 mg) washed with ethanol was added, and the resulting mixture was stirred under hydrogen for 17 hours. The reaction solution was filtered through cellite, concentrated, and subjected to silica gel column chromatography to give 4-(3-[4-(2-hydroxyethoxy)phenoxy]propyl}-7-methoxymethoxy-3-[4-(methoxymethoxy)phenyl]-3-methylthiochroman (7) (241 mg, yield 71%) as a yellow oily substance.

$^1$H NMR (270 MHz, CDCl$_3$) δ: 7.28 (2H, d, J=10 Hz), 7.02–6.64 (9H, m), 5.18 (2H, s), 5.15 (2H, s), 4.1–3.96 (2H, m), 3.96–3.9 (2H, m), 3.7–3.6 (2H, m), 3.5 (3H, s), 3.49 (3H, s), 3.42 (1H, d, J=3.6 Hz), 3.0 (1H, d, J=12 Hz), 2.82 (1H, d, J=9.6 Hz), 1.65–1.5 (2H, m), 1.4–1.19 (5H, m)

Step 6) Synthesis of 4-{3-[4-(2-methanesulfonyloxyethoxy)phenoxy]propyl}-7-methoxymethoxy-3-[4-(methoxymethoxy)phenyl]-3-methylthiochroman

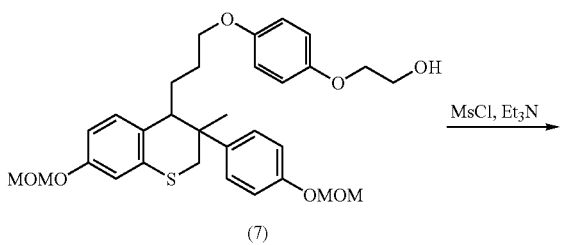

(7)

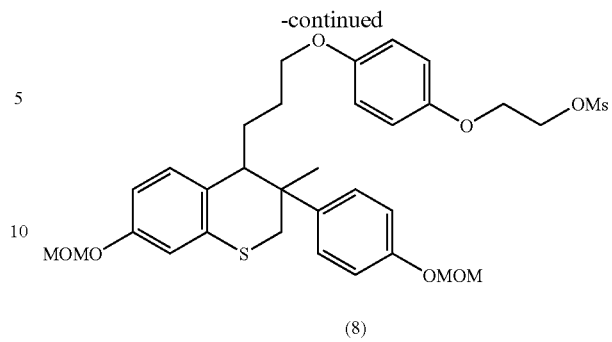

(8)

4-{3-[4-(2-Hydroxyethoxy)phenoxy]propyl}-7-methoxymethoxy-3-[4-(methoxymethoxy)phenyl]-3-methylthiochroman (7) prepared in Step 5 (45.6 mg, 0.082 mmol) was dissolved in CH$_2$Cl$_2$ (0.4 ml), which was then cooled down to 0° C. Triethylamine (23 μl, 0.17 mmol) and methanesulfonylchloride (16 μl, 0.21 mmol) were added thereto, and the mixture was stirred for 30 minutes. Saturated aqueous ammonium chloride solution was added, and the resulting mixture was extracted with ethyl acetate. The organic layer was dried over anhydrous magnesium sulfate, concentrated, and subjected to silica gel column chromatography to give 4-{3-[4-(2-methanesulfonyloxyethoxy)phenoxy]propyl}-7-methoxymethoxy-3-[4-(methoxymethoxy)phenyl]-3-methylthiochroman (8) (49.2 mg, yield 95%) as a colorless oily substance.

$^1$H NMR (270 MHz, CDCl$_3$) δ: 7.8 (2H, d, J=11 Hz), 7.0–6.6 (9H, m), 5.18 (3H, s), 5.14 (3H, s), 4.6–4.5 (2H, m), 4.2–4.](2H, m), 3.7–3.6 (2H, m), 3.50 (3H, s), 3.49 (3H, s), 3.42 (1H, d, J=3.3 Hz), 3.08 (3H, s), 3.08 (1H, d, J=2.6 Hz), 2.83 (1H, d, J=7.6 Hz), 1.65–1.5 (2H, m), 1.3–1.19 (5H, m)

Step 7) Synthesis of (3RS,4RS) and (3RS,4SR)-7-methoxymethoxy-3-[4-(methoxymethoxy)phenyl]-3-methyl-4-{3-{4-[2-(4,4,5,5,5-pentafluoropentylthio)ethoxy]phenoxy}propyl}thiochroman

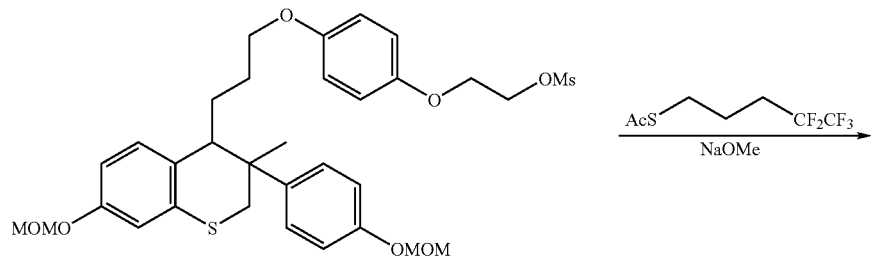

(8)

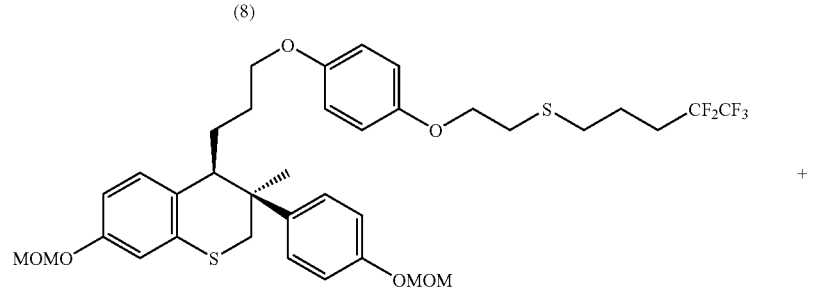

(9)

+

-continued

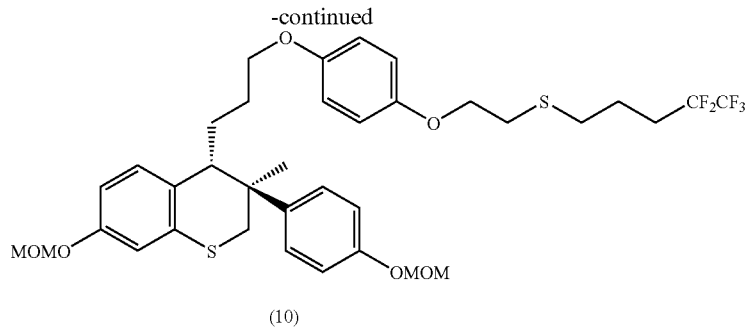

(10)

Pentafluoropentyl-thioacetate separately prepared (504 mg, 2.1 mmol) was dissolved in absolute methanol (1 mL), 1N sodium methoxide (2 mL) was added, and the resulting mixture was stirred for 1 hour. To this reaction solution was added dropwise 4-{3-[4-(2-methanesulfonyloxyethoxy)phenoxy]propyl}-7-methoxymethoxy-3-[4-(methoxymethoxy)phenyl]-3-methylthiochroman (8) prepared in Step 6(270 mg, 0.43 mmol) dissolved in dry tetrahydrofuran (1 mL), which was then stirred for 20 hours. Saturated aqueous ammonium chloride solution was added, and the resulting mixture was extracted with ethyl acetate. The organic layer was dried over anhydrous magnesium sulfate, concentrated, and subjected to silica gel column chromatography and preparative TLC to give (3RS,4RS)-7-methoxymethoxy-3-[4-(methoxymethoxy)phenyl]-3-methyl-4-{3-{4-[2-(4,4,5,5,5-pentafluoropentylthio)ethoxy]phenoxy}propyl}thiochroman (9) (167 mg, yield 54%) as a yellow oily substance and (3RS,4RS)-7-methoxymethoxy-3-[4-(methoxymethoxy)phenyl]-3-methyl-4-{3-{4-[2-(4,4,5,5,5-pentafluoropentylthio)ethoxy]phenoxy}propyl}thiochroman (10) (42 mg, yield 13%) as a yellow oily substance.

$^1$H NMR (270 MHz, CDCl$_3$, 3RS,4RS-compound) δ: 7.28 (2H, d, J=8.8 Hz), 6.99 (3H, dd, J=8.9 Hz, 8.6 Hz), 6.89 (1H, d, J=2.3 Hz), 6.76 (2H, d, J=8.9 Hz), 6.72 (1H, d, J=2.3 Hz), 6.65 (2H, d, J=9.2 Hz), 5.18 (2H, s), 5.14 (2H, s), 4.07 (2H, t, J=6.6 Hz), 3.7–3.6 (3H, m), 3.66 (3H, s), 3.62 (3H, s), 3.0 (1H, d, J=11.6 Hz), 2.9–2.8 (3H, m), 2.7 (2H, t, J=7.1 Hz), 2.3–2.1 (2H, m), 2.0–1.9 (2H, m), 1.7–1.5 (2H, m), 1.4–1.2 (2, m), 1.19 (3H, s)

$^1$H NMR (270 MHz, CDCl$_3$, 3RS,4SR-compound) δ: 7.3 (2H, d, J=8.9 Hz), 6.85–6.78 (7H, m), 6.7 (1H, d, J=2.0 Hz), 6.53 (2H, dd, J=8.3 Hz, 8.6 Hz), 5.08 (2H, s), 5.04 (2H, s), 4.09 (2H, t, J=6.6 Hz), 3.92–3.8 (2H, m), 3.43 (3H, s), 3.42 (3H, s), 3.27 (1H, d, J=13 Hz), 3.23 (1H, d, J=13 Hz), 3.0 (1H, d), 2.88 (2H, t, J=6.9 Hz), 2.71 (2H, t, J=6.9 Hz), 2.3–2.1 (2H, m), 2.0–1.9 (2H, m), 1.8–1.5 (4H, m), 1.39 (3H, s)

Step 8) Synthesis of (3RS,4RS)-7-hydroxy-3-(4-hydroxyphenyl)-3-methyl-4-{3-{4-[2-(4,4,5,5,5-pentafluoropentylthio)ethoxy]phenoxy}propyl}thiochroman

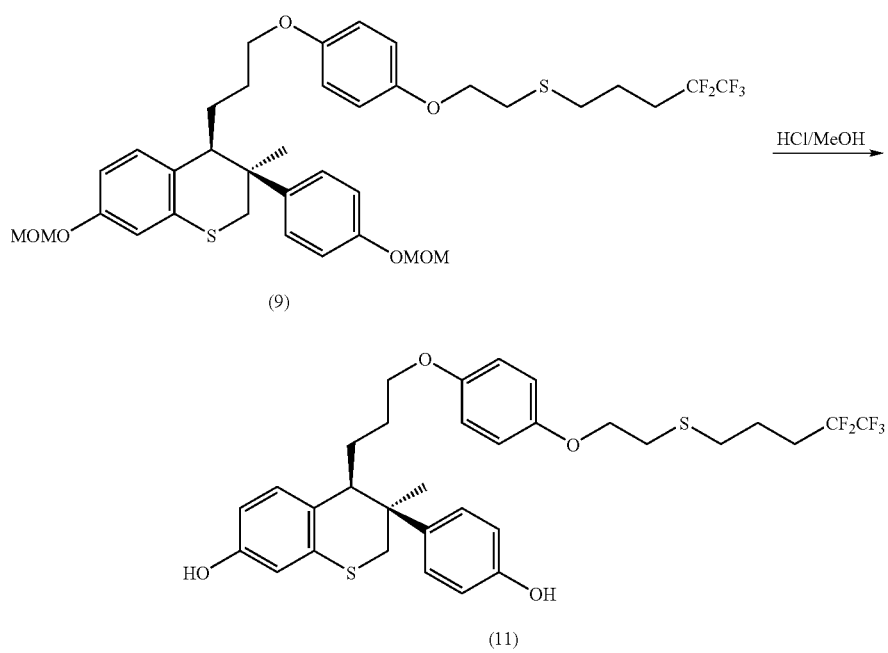

(3RS,4RS)-7-Methoxymethoxy-3-[4-(methoxymethoxy)phenyl]-3-methyl-4-{3-{4-[2-(4,4,5,5,5-pentafluoropentylthio)ethoxy]phenoxy}propyl}thiochroman (9) prepared in Step 7 (144 mg, 0.2 mmol) was dissolved in hydrochloric acid/methanol (1 ml) and tetrahydrofuran (0.1 ml), which was then stirred at room temperature for 4 days. Saturated aqueous sodium hydrogen carbonate solution was added to the reaction solution, and the resulting mixture was extracted with ethyl acetate and chloroform. The organic layer was dried over anhydrous magnesium sulfate, concentrated, and subjected to silica gel column chromatography to give (3RS,4RS)-7-hydroxy-3-(4-hydroxyphenyl)-3-methyl-4-{3-{4-[2-(4,4,5,5,5-pentafluoropentylthio)ethoxy]phenoxy}propyl}thiochroman (11) (110 mg, yield 87%) as a yellow oily substance.

$^1$H NMR (270 MHz, CDCl$_3$) δ: 7.22 (2H, d, J=9.6 Hz), 6.91 (1H, d, J=7.9 Hz), 6.50 (1H, dd, J=8.3 Hz, 2.6 Hz), 5.0 (2H, brs), 4.08 (2H, t, J=6.6 Hz), 3.8–3.6 (3H, m), 2.98 (1H, d, J=11.5 Hz), 2.87 (2H, t, J=6.6 Hz), 2.78 (1H, d, J=9.2 Hz), 2.70 (2H, t, J=6.9 Hz), 2.3–2.1 (2H, m), 2.0–2.9 (2H, m), 1.7–1.5 (21, m), 1.4–1.2 (2H, m), 1.18 (3H, s)

Step 9) Synthesis of (3RS,4RS)-7-hydroxy-3-(4-hydroxyphenyl)-3-methyl-4-{3-(4-[2-(4,4,5,5,5-pentafluoropentylsulfinyl)ethoxy]phenoxy}propyl}thiochroman the reaction solution and the resulting mixture was extracted with ethyl acetate. The organic layer was dried over anhydrous magnesium sulfate, concentrated, and subjected to silica gel column chromatography to give (3RS,4RS)-7-hydroxy-3-(4-hydroxyphenyl)-3-methyl-4-{3-{4-[2-(4,4,5,5,5-pentafluoropentylsulfinyl)ethoxy]phenoxy}propyl}thiochroman (12) (64.5 mg, yield 57%) as a colorless foamy substance.

$^1$H NMR (270 MHz, CDCl$_3$) δ: 7.10 (2H, d, J=8.6 Hz), 7.8–7.65 (8H, m), 6.58 (1H, d, J=8.9 Hz), 6.43 (1H, m), 6.26 (1H, d, J=20.8 Hz), 4.5–4.3 (2H, m), 3.8–3.7 (2H, m), 3.72 (1H, d, J=4.6 Hz), 3.3–2.9 (5H, m), 2.67 (1H, d, J=8.8 Hz), 2.4–2.16 (4H, m), 1.62–1.4 (2H, m), 1.35–1.2 (2H, m), 1.12 (3H, s)

FAB-MS 659 (M+1)

EXAMPLE 20

Synthesis of (3RS,4RS)-7-hydroxy-3-(4-hydroxyphenyl)-3-methyl-4-[4-oxa-9-(4,4,5,5,5-pentafluoropentylsulfinyl)nonyl]thiochroman Step 1) Synthesis of 9-(t-butyldimethylsilyloxy)-4-oxa-1-nonyne

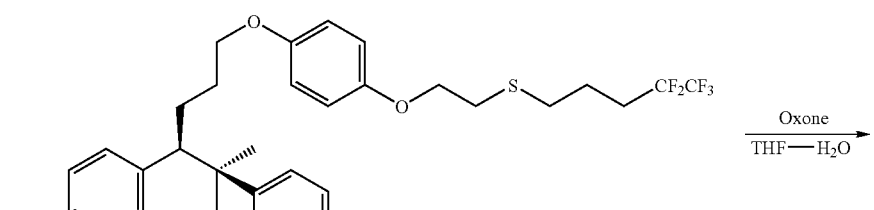

(11)

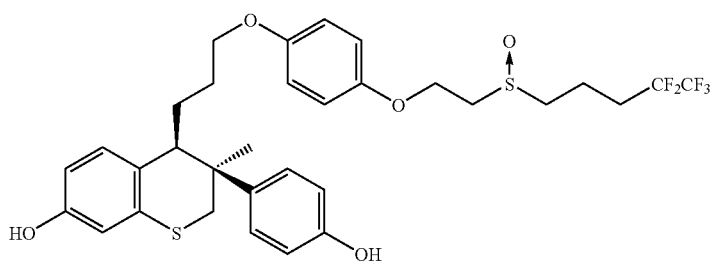

(12)

(3RS,4RS)-7-Hydroxy-3-(4-hydroxyphenyl)-3-methyl-4-{3-{4-[2-(4,4,5,5,5-pentafluoropentylthio)ethoxy]phenoxy}propyl}thiochroman (11) prepared in Step 8 (110 mg, 0.17 mmol) was dissolved in tetrahydrofuran (5 ml), which was then cooled down to 0° C. Oxone® (monopersulfate compound; DuPont product) (63 mg, 0.1 mmol) and water (3 drops) were added thereto, and the resulting mixture was stirred for 1 hour. Water (2 drops was further added, and the mixture was stirred for 1 hour. Water was added to

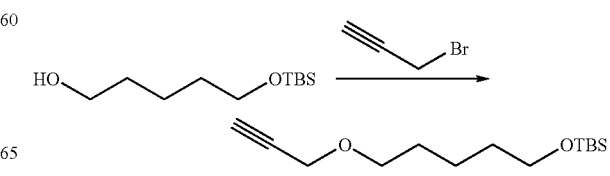

To a solution of alcohol compound (2.96 g, 13.6 mmol, separately prepared), in dry tetrahydrofuran (100 mg) was added sodium hydride (597 mg, 60% in oil, 14.9 mmol) at room temperature. After stirring for 30 minutes, propargyl bromide (4.04 g, 80% in toluene, 27.2 mmol) was added, and resulting the mixture was warmed to 50° C. and stirred for 6 hours. After the reaction was completed, ice-water was added, and the mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane: ethyl acetate=6.1) to give the title compound (3.23 g, yield 93%).

$^1$H-NMR (270 MHz, CDCl$_3$) δ: 4.13 (d, 2H, J=2.31 Hz), 3.61 (t, 2H, J=6.3 Hz), 3.51 (t, 2H. J=6.6 Hz), 2.41 (t, 1H, J=2.3 Hz), 1.67–1.51 (m, 4H), 1.49–1.36 (m, 2H), 0.89 (s, 9H), 0.04 (s, 6H)

Step 2) Synthesis of 4-[9-(t-butyldimethylsilyloxy)-4-oxa-1-nonynyl]4-hydroxy-7-methoxy-3-(4-methoxyphenyl)-3-methylthiochroman

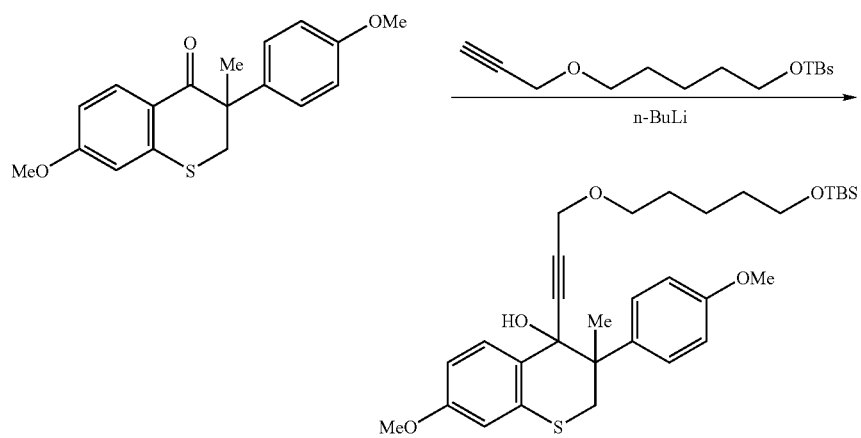

An alkyne compound separately prepared (1.02 g, 3.98 mmol) was dissolved in dry tetrahydrofuran (10 mL), which was then cooled down to −70° C. under hydrogen. n-Butyllithium (1.61M, 2.4 mL, 3.81 mmol) was added dropwise to this solution, and the mixture was warmed to −40° C. and stirred for 10 minutes. Then, the thiochromanone derivative (630 mg, 2.01 mmol) dissolved in dry tetrahydrofuran (10 mL) was added dropwise thereto, and the resulting mixture was warmed to room temperature over 4 hours. After the reaction was completed, ice-water was added, and the mixture was extracted with ethyl acetate. The organic layer was washed with saturated saline solution, dried over anhydrous sodium sulfate, and filtered. The organic solvent was removed—under reduced pressure to give a crude product. This crude product thus obtained was subjected to silica gel column chromatography (n-hexane:ethyl acetate=4:1) to give the title compound (1.1 g, yield 96%).

$^1$H-NMR (270 MHz, CDCl$_3$) δ: 7.82 (d, 1H, J=8.6 Hz), 7.61 (d, 2H, J=8.9 Hz), 6.88 (d, 2H, J=8.9 Hz), 6.68–6.62 (m, 2H), 4.24 (d, 1H, J=12.2 Hz), 4.14 (s, 2H), 3.81 (s, 3H), 3.78 (s, 3H), 3.60 (t, 2H, J=6.6 Hz), 3.37 (t, 2H, J=6.6 Hz), 2.71 (d, 1H, J=12.2 Hz), 2.26 (s, 1H), 1.58–1.48 (m, 7H), 1.41–1.32 (m, 2H), 0.89 (s, 9H), 0.04 (s, 6H)

Step 3) Synthesis of (3RS,4RS) and (3RS,4SR)-4-[9-(t-butyldimethylsilyloxy)-4-oxa-1-nonynyl]-7-methoxy-3-(4-methoxyphenyl)-3-methylthiochroman

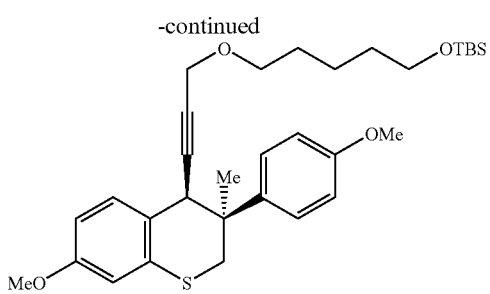

To a solution of alcohol compound (1.0 g, 1.75 mmol) in 1,2-dichloroethane (30 ml) were added sequentially sodium cyanoborohydride (880 mg, 14 mmol) and zinc iodide (1.1 g, 3.5 mmol) at room temperature. The mixture was stirred at room temperature for 30 minutes at the same condition. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane: ethyl acetate=4:1) to give the title compound [575 mg, yield 59%; (3RS,4RS):(3RS,4SR)=4:1].

$^1$H-NMR (270 MHz, CDCl$_3$; 3RS,4RS) δ: 7.31 (d, 2H, J=8.9 Hz), 7.23 (d, 1H, J=8.3 Hz), 6.83 (d, 2H, J=8.9 Hz), 6.69 (d, 1H, J=2.3 Hz), 6.62 (dd, 1H, J=8.3 Hz and 2.3 Hz), 3.99 (d, 2H, J=2.0 Hz), 3.89 (s, 1H), 3.78 (s, 3H), 3.77 (s, 3H), 3.68 (d, 1H, J=12.2 Hz), 3.58 (t, 2H, J=6.5 Hz), 3.16 (t, 2H, J=6.3 Hz), 3.01 (d, 1H, J=12.2 Hz), 1.50–1.30 (m, 9H), 0.89 (s, 9H), 0.05 (s, 6H)

Step 4) Synthesis of (3RS,4RS) and (3RS,4SR)-4-[9-(t-butyldimethylsilyloxy)-4-oxanonyl]-7-methoxy-3-(4-methoxyphenyl)-3-methylthiochroman

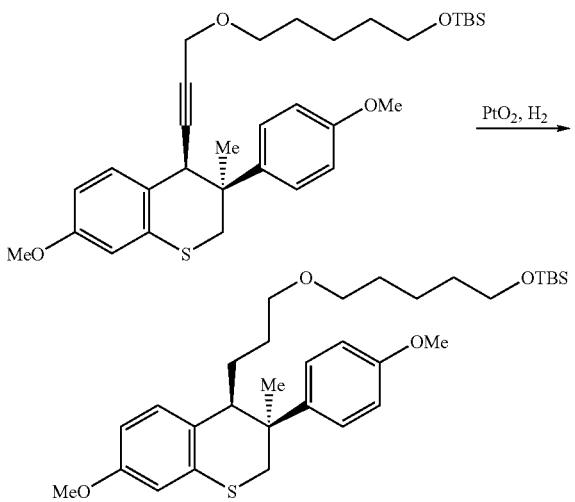

The alkyne compound above (575 mg, 1.04 mmol) was dissolved in ethyl acetate (10 ml), platinum oxide (273 mg, 1.04 mmol) was added, and the resulting mixture was stirred at room temperature under hydrogen for 20 hours. The reaction solution was concentrated and filtered through silica gel to give the title compound [550 mg, yield 95%; (3RS,4RS):(3RS,4SR)=4:1] as a crude product.

$^1$H-NMR (270 MHz, CDCl$_3$; 3RS,4RS) δ: 7.29 (d, 2H, J=8.9 Hz), 6.95 (d, 1H, J=8.2 Hz), 6.89 (d, 2H, J=8.9 Hz), 6.72 (d, 1H, J=2.6 Hz), 6.57 (dd, 1H, J=8.2 Hz and 2.6 Hz), 3.82 (s, 3H), 3.77 (s, 3H), 3.63 (d, 1H, J=11.6 Hz), 3.57 (t, 2H, J=6.6 Hz), 3.21 (t, 2H, J=6.6 Hz), 3.14 (t, 2H, J=6.6 Hz), 2.99 (d, 1H, J=11.6 Hz), 2.77–2.76 (m, 1H), 1.52–1.21 (m, 8H), 1.18 (s, 3H), 0.88 (s, 9H), 0.03 (s, 6H)

Step 5) Synthesis of (3RS,4RS) and (3RS,4SR)-4-{-(9-hydroxy-4-oxanonyl)-7-methoxy-3-(4-methoxyphenyl)-3-methylthiochroman

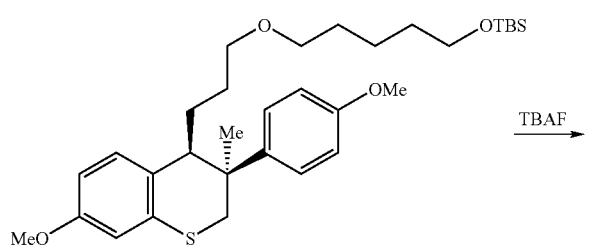

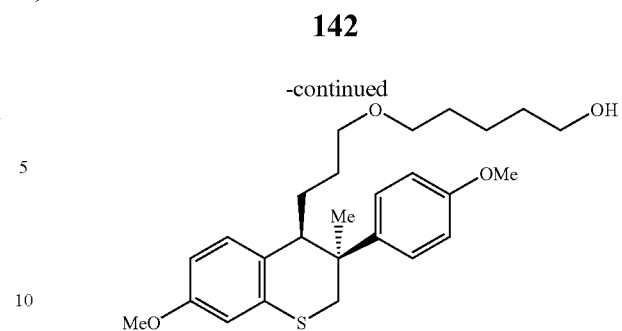

The compound protected by TBS (550 mg, 0.99 mmol) was dissolved in tetrahydrofuran (10 ml), and tetran-butylammonium fluoride (TBAF, 20 ml, 1.0M solution in tetrahydrofuran) was added thereto at 0° C. The mixture was stirred at room temperature for 1 hour, and stirred at 50° C. for further 2 hours. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane:ethyl acetate=1:1) to give the title compound [380 mg, yield 87%; (3RS,4RS):(3RS,4SR)=4:1].

$^1$H-NMR (270 MHz, CDCl$_3$; 3RS,4RS) δ: 7.29 (d, 2H, J=8.9 Hz), 6.94 (d, 1H, J=8.3 Hz), 6.90 (d, 2H, J=8.9 Hz), 6.73 (d, 1H, J=2.3 Hz), 6.57 (dd, 1H, J=8.3 Hz and 2.3 Hz), 3.82 (s, 3H), 3.78 (s, 3H), 3.64 (d, 1H, J=11.9 Hz), 3.60 (t, 2H, J=6.3 Hz), 3.22 (t, 2H, J=6.6 Hz), 3.16 (t, 2H, J=6.6 Hz), 3.00 (d, 1H, J=11.9 Hz), 2.78–2.75 (m, 1H), 1.56–1.26 (m, 11H), 1.18 (s, 3H)

Step 6) Synthesis of (3RS,4RS) and (3RS,4SR)-4-(9-methanesulfonyloxy-4-oxanonyl)-7-methoxy-3-(4-methoxyphenyl)-3-methylthiochroman

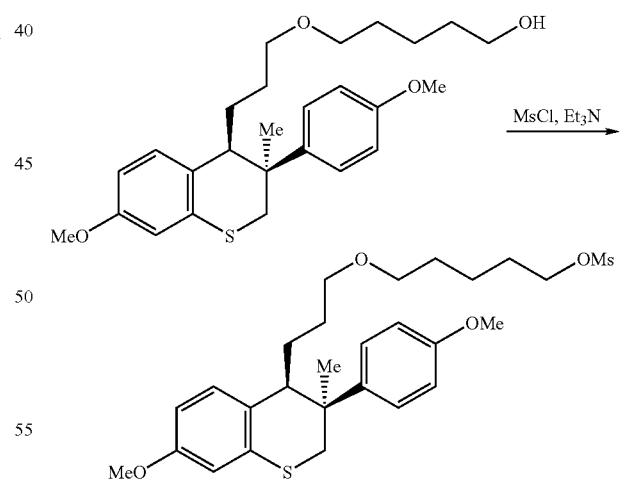

An alcohol compound (380 mg, 0.86 mmol) was dissolved in dichloromethane (10 ml), and triethylamine (174 mg, 1.72 mmol) and methanesulfonylchloride (100 ml, 128 mmol) were sequentially added thereto at 0° C. The mixture was stirred at the same temperature for 10 minutes. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane: ethyl acetate=1:1) to give the title compound [420 mg, yield 94%; (3RS,4RS):(3RS,4SR)=4:1].

$^1$H-NMR (270 MHz, CDCl$_3$; 3RS,4RS) δ: 7.29 (d, 2H, J=8.9 Hz), 6.95 (d, 1H, J=8.6 Hz), 6.90 (d, 2H, J=8.9 Hz), 6.73 (d, 1H, J=2.7 Hz), 6.57 (dd; 1H, J=8.6 Hz and 2.7 Hz), 4.19 (t, 2H, J=6.6 Hz), 3.82 (s, 3H), 3.78 (s, 3H), 3.64 (d, 1H, J=11.9 Hz), 3.22 (t, 2H, J=6.7 Hz), 3.14 (t, 2H, J=6.3 Hz), 3.00 (d, 1H, J=11.9 Hz), 2.99 (s, 3H), 2.79–2.75 (m, 1H), 1.83–1.71 (m, 2H), 1.65–1.31 (m, 8H), 1.18 (s, 3H)

Step 7) Synthesis of (3RS,4RS) and (3RS,4SR)-7-methoxy-3-(4-methoxyphenyl)-3-methyl-4-[4-oxa-9-(4,4,5,5,5-pentafluoropentylthio)nonyl]thiochroman

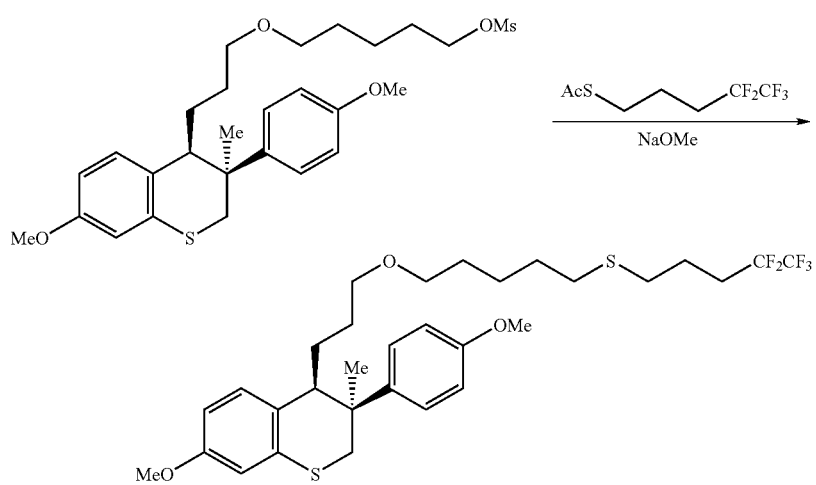

To a solution of thioacetate separately prepared (328 mg, 1.39 mmol) in methanol (5 ml) was added sodium methoxide (1.3 ml, 11.0M solution in methanol, 1.32 mmol) at room temperature. The mixture was stirred for 15 minutes, and a solution of mesylate (340 mg, 0.65 mmol) in tetrahydrofuran (5 ml) was added thereto. This mixture was stirred at room temperature for 2 days. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane:ethyl acetate=4:1) to give the title compound [405 mg, Stoichiometric yield, (3RS,4RS):(3RS,4SR) =4:1].

$^1$H-NMR (270 MHz, CDCl$_3$; 3RS,4RS) δ: 7.29 (d, 2H, J=8.9 Hz), 6.95 (d, 1H, J=8.6 Hz), 6.90 (d, 2H, J=8.9 Hz), 6.72 (d, 1H, J=2.3 Hz), 6.57 (dd, 1H, J=8.6 Hz and 2.3 Hz), 3.82 (s, 3H), 3.78 (s, 3H), 3.63 (d, 1H, J=11.6 Hz), 3.22 (t, 2H, J=6.6 Hz), 3.16 (t, 2H, J=6.6 Hz), 3.00 (d, 1H, J=11.6 Hz), 2.75 (t, 1H, J=6.9 Hz), 2.57 (t, 2H, J=7:0 Hz), 2.47 (t, 2H, J=6.9 Hz), 2.19–2.01 (m, 2H), 1.92–1.81 (m, 2H), 1.60–1.31 (m, 10H), 1.18 (s, 3H)

Step 8) Synthesis of (3RS,4RS)-7-hydroxy-3-(4-hydroxyphenyl)-3-methyl-4-[4-oxa-9-(4,4,5,5,5-pentafluoropentylthio)nonyl]thiochroman

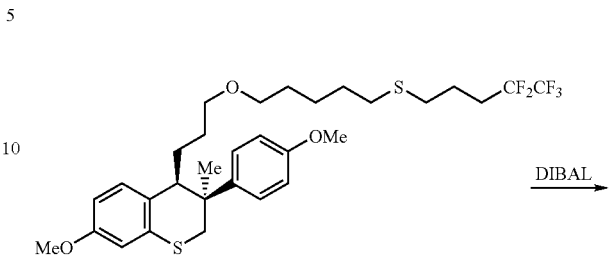

-continued

Thioether (253 mg, 0.41 mmol) was added to DIBAL-H solution (8.2 ml, 1.0M solution in toluene, 8.16 mmol), which was then heated under reflux for 10 hours. After the reaction was completed, water was added, and then diluted hydrochloric acid was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to high pressure silica gel column chromatography (n-hexane:ethyl acetate=2:1) to give the title compound (175 mg, yield 72%).

$^1$H-NMR (270 MHz, CDCl$_3$) δ: 7.24 (d, 2H, J=8.6 Hz), 6.89 (d, 1H, J=8.2 Hz), 6.82 (d, 2H, J=8.6 Hz), 6.66 (d, 1H, J=2.3 Hz), 6.48 (dd, 1H, J=7.9 and 2.3 Hz), 4.87 (brs, 1H), 4.68 (brs, 1H), 3.62 (d, 1H, J=11.5 Hz), 3.21 (t, 2H, J=6.3 Hz), 3.17 (t, 2H, J=6.6 Hz), 2.97 (d, 1H, J=11.5 Hz), 2.74 (d, 1H, J=11.2 Hz), 2.59 (t, 2H, J=6.9 Hz), 2.49 (t, 2H, J=7.3 Hz), 2.20–2.07 (m, 2H), 1.93–1.82 (m, 2H), 1.60–1.26 (m, 10H), 1.18 (s, 3H)

Step 9) Synthesis of (3RS,4RS)-7-hydroxy-3-(4-hydroxyphenyl)-3-methyl-4-[4-oxa-9-(4,4,5,5,5-pentafluoropentylsulfinyl)nonyl]thiochroman

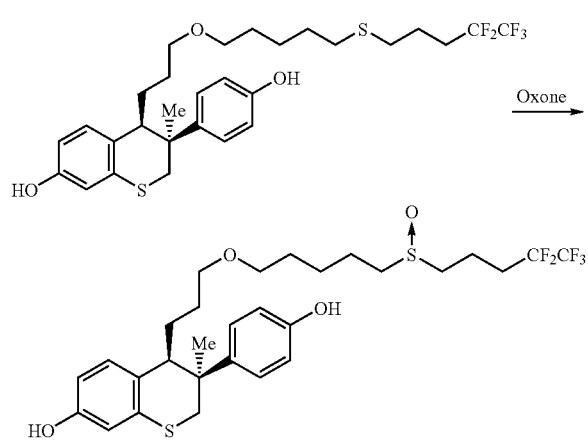

To a solution of thioether (163 mg, 0.28 mmol) in tetrahydrofuran (2 mg) was added Oxone® (monopersulfate compound; DuPont product) (85 mg, 0.14 mmol) at 0° C. Water (50 µl) was added thereto at the same temperature, which was then stirred for 2 hours. After the reaction was completed, the mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane:ethyl acetate=1:1) to give the title compound (99 mg, yield 59%).

$^1$H-NMR (270 MHz, CDCl$_3$) δ: 7.58 (br, 1H), 7.22 (d, 2H, J=8.6 Hz), 6.86 (d, 1H, J=8.3 Hz), 6.84 (d, 2H, J=8.6 Hz), 6.68 (d, 1H, J=2.3 Hz), 6.49 (dd, 1H, J=8.3 and 2.3 Hz), 5.46 (br, 1H), 3.67 (dd, 1H, J=12.6 and 12.2 Hz), 3.32–2.63 (m, 10H), 2.32–2.17 (m, 4H), 1.81–1.70 (m, 2H), 1.35–1.18 (m, 11H)

EXAMPLE 21

Synthesis of (3RS,4RS)-7-hydroxy-3-(4-hydroxyphenyl)-3-methyl-4-[9-(4,4,5,5,5-pentafluoropentylaminosulfonyl)nonyl]chroman Step 1) Synthesis of 4-(9-acetylthiononyl)-7-methoxymethoxy-3-(4-methoxymethoxyphenyl)-3-methylchroman

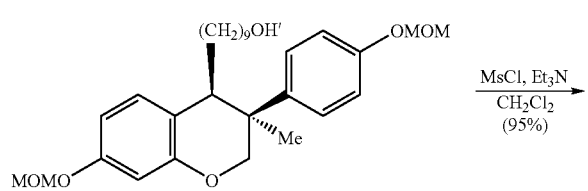

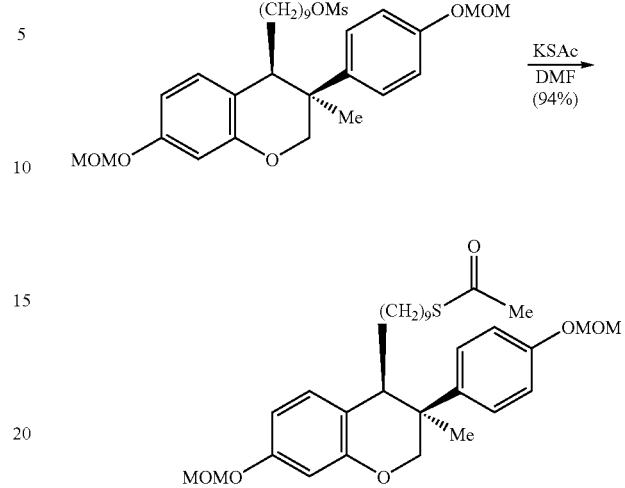

Alcohol compound separately prepared (115 mg, 0.236 mmol) was dissolved in methylene chloride (1 ml) and ice-cooled. Then, triethylamine (0.036 ml, 0.26 mmol) and MsCl (0.020 ml, 0.26 mmol) were added dropwise thereto, which was then stirred for 20 minutes. After the reaction was completed, the mixture was ice-cooled, and then saturated saline solution was added thereto. The resulting mixture was extracted with methylene chloride and washed with saturated saline solution. The organic layer was dried over anhydrous magnesium sulfate and concentrated under reduced pressure. The residue thus obtained was subjected to silica gel column chromatography (n-hexane:ethyl acetate=2:1) to give 4-(9-methanesulfonyloxynonyl)-7-methoxymethoxy-3-(4-methoxymethoxyphenyl)-3-methylchroman (126 mg, yield 95%). Thus obtained 4-(9-methanesulfonyloxynonyl)-7-methoxymethoxy-3-(4-methoxymethoxyphenyl)-3-methylchroman (126 mg, 0.222 mmol) was dissolved in DMF (1 ml), KSAc (27.9 mg, 0.244 mmol) was added dropwise thereto, and the resulting mixture was stirred at 40° C. for 2 hours. After the reaction was completed, water was added thereto. The resulting mixture was extracted with ethyl acetate and washed with saturated saline solution. The organic layer was dried over magnesium sulfate and concentrated under reduced pressure. The residue thus obtained was subjected to silica gel column chromatography (n-hexane:ethyl acetate=2:1) to give 4-(9-acetylthiononyl)-7-methoxymethoxy-3-(4-methoxymethoxyphenyl)-3-methylchroman (114 mg, yield 94%).

$^1$H-NMR (270 MHz, CDCl$_3$) δ: 7.13 (d, 2H, J=8.9 Hz, Ar—H), 7.02 (d, 2H, J=8.9 Hz, Ar—H), 7.00–6.92 (m, 1H, Ar—H), 6.60–6.54 (m, 2H, Ar—H), 5.18, 5.15 (respectively s, respectively 2H, OCH$_2$O), 4.52 (d, 1H, J=10.6 Hz, C2-H), 4.26 (d, 1H, J=10.6 Hz, C2-H), 3.50, 3.49 (respectively s, respectively 3H, OCH$_3$), 2.84 (t 2H, J=7.3 Hz, CH$_2$SAc), 2.31 (s, 3H, C(O)CH$_3$) 2.68–2.60 (m, 1H, C4-H), 1.25 (s, 1H, C3-CH$_3$), 1.30–1.00 (m, 16H)

Step 2) Synthesis of 4,4,5,5,5-pentafluoropentylcarbamic acid t-butylester

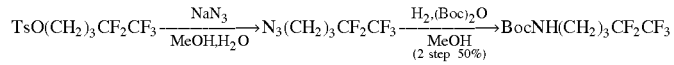

1,1,1,2,2-Pentafluoro-5-p-toluenesulfonyloxypentane (4.00 mg, 12.0 mmol) was dissolved in methanol (40 ml), NaN$_3$ (936 mg, 14.4 mmol) dissolved in water (10 ml) was added thereto, and the mixture was stirred overnight at 60° C. After the reaction was completed, the reaction mixture was extracted with chloroform and washed with saturated saline solution. The organic layer was dried over magnesium sulfate and concentrated under reduced pressure. The residue was dissolved in methanol (40 ml), (Boc)$_2$O (2.62 g, 12.0 mmol) and Pd—C (800 mg) were added thereto, and then the mixture was stirred overnight under hydrogen. After the reaction was completed, the mixture was filtered, and the filtrate was concentrated under reduced pressure. The residue was subjected to silica gel column chromatography (n-hexane:ethyl acetate=4:1) to give 4,4,5,5,5-pentafluoropentylcarbamic acid t-butylester (1.12 g, yield 50%).

$^1$H-NMR (300 MHz, CDCl$_3$) δ: 4.55 (brs, 1H, NH), 4.12 (q, 2H, J=7.2 Hz, CH$_2$NH), 2.18–1.96 (m, 2H, CF$_2$CH$_2$), 1.84–1.72 (m, 2H), 1.45 (s, 9H, t-Bu)

Step 3) Synthesis of 7-methoxymethoxy-3-(4-methoxymethoxyphenyl)-3-methyl-4-[9-(4,4,5,5,5-pentafluoropentylaminosulfonyl)nonyl]chroman N-chlorosuccinimide (39.3 mg, 0.294 mmol) was added, and the resulting mixture was stirred for 15 minutes. After the reaction was completed, saturated aqueous NAHCO$_3$ solution was added thereto. The mixture was extracted with methylene chloride and washed with saturated saline solution. The organic layer was dried over magnesium sulfate and concentrated under reduced pressure to give a mixture containing 4-(9-chlorosulfonylnonyl)-7-methoxymethoxy-3-(4-methoxymethoxyphenyl)-3-methylchroman. 4,4,5,5,5-Pentafluoropentylcarbamic acid t-butylester (61.8 mg, 0.221 mmol) was dissolved in methylene chloride (1 ml), TFA (1 ml) was added dropwise thereto, and the mixture was stirred at room temperature for 15 minutes. After the reaction was completed, the solvent was removed under reduced pressure. The residue thus obtained was dissolved in methylene chloride (1 ml) and cooled. To this solution was added a mixture containing triethylamine (0.051 ml, 0.37 mmol) and 4-(9-chlorosulfonylnonyl)-7-methoxymethoxy-3-(4-methoxymethoxyphenyl)-3-methylchroman dissolved in methylene chloride (1 ml), which was then stirred for 1 hour. After the reaction was completed, the organic layer was dried over magnesium sulfate and concentrated under reduced pressure. The residue thus obtained was subjected to silica gel column chromatography (n-hexane:ethyl acetate=1:1) to give 7-methoxymethoxy-3-(4-methoxymethoxyphenyl)-3-methyl-4-[9-(4,4,5,5,5-pentafluoropentylaminosulfonyl)nonyl]chroman (8.0 mg, yield 16%).

$^1$H-NMR (270 MHz, CDCl$_3$) δ: 7.13 (d, 2H, J=8.6 Hz, Ar—H), 7.02 (d, 2H, J=8.6 Hz, Ar—H), 7.00–6.92 (m, 1H, Ar—H), 6.60–6.54 (m, 2H, Ar—H), 5.18, 5.15 (respectively s, respectively 2H, OCH$_2$O), 4.52 (d, 1H, J=10.6 Hz, C2-H), 4.26 (d, 1H, J=10.6 Hz, C2-H), 3.49 (s, 6H, OCH$_3$×2), 3.44–3.30 (m, 2H), 3.28–3.14 (m, 2H), 2.68–2.60 (m, 1H, C4-H), 2.22–1.96 (m, 2H), 1.90–1.52 (m, 4H), 1.24 (s, 1H, C3-CH$_3$), 1.30–1.00 (m, 14H)

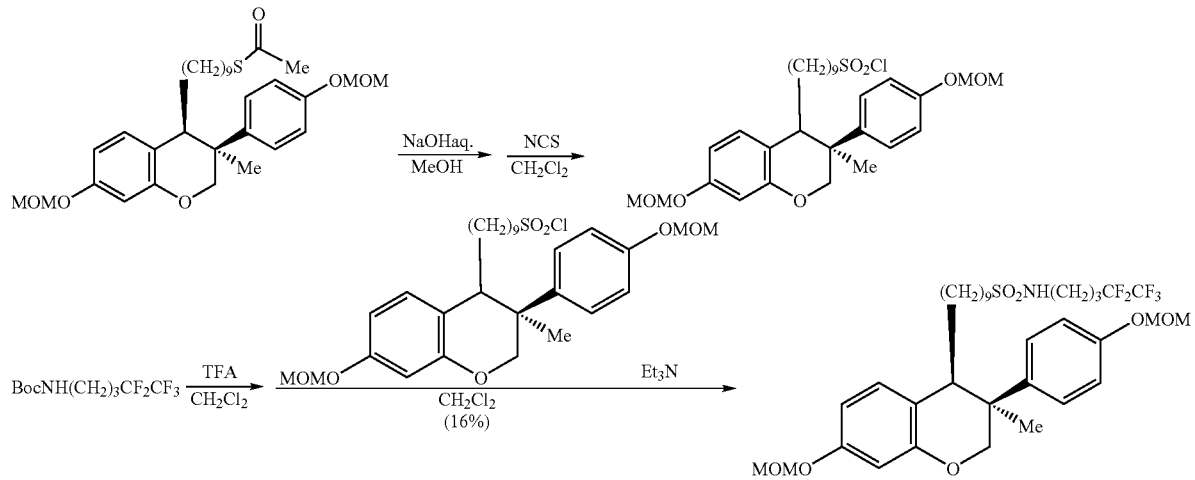

4-(9-Acetylthiononyl)-7-methoxymethoxy-3-(4-methoxymethoxyphenyl)-3-methylchroman (40.0 mg, 0.0735 mmol) was dissolved in methanol (1 ml) under nitrogen, 2N—NaOH (0.5 ml) was added dropwise thereto, and the mixture was stirred at room temperature for 30 minutes. After the reaction was completed, the reaction mixture was cooled, and 2N-HCl aqueous solution was poured thereinto. This solution was extracted with chloroform and washed with saturated saline solution. The organic layer was dried over magnesium sulfate and concentrated under reduced pressure. The residue thus obtained was added to a solvent mixture of methylene chloride (1 ml) and water (0.5 ml), Step 4) Synthesis of (3RS,4RS)-7-hydroxy-3-(4-hydroxyphenyl)-3-methyl-4-[9-(4,4,5,5,5-pentafluoropentylaminosulfonyl)nonyl]chroman

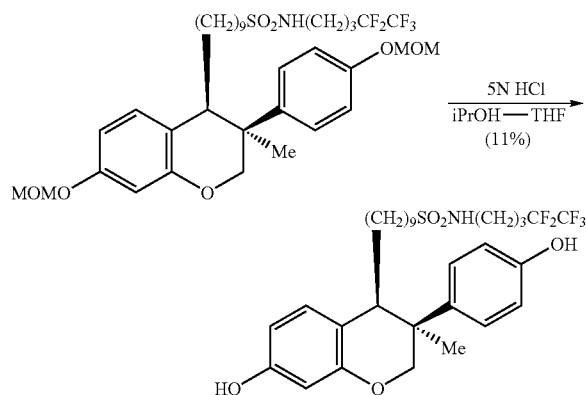

7-Methoxymethoxy-3-(4-methoxymethoxyphenyl)-3-methyl-4-[9-(4,4,5,5,5-pentafluoropentylaminosulfonyl)nonyl]chroman (8.0 mg, 0.0113 mmol) was dissolved in a solvent mixture of THF (0.2 ml) and isopropanol (0.2 ml), 5N-HCl aqueous solution (0.6 ml) was added dropwise thereto, and the mixture was stirred at room temperature for 3 days. After the reaction was completed, the mixture was cooled, and then saturated aqueous NaHCO$_3$ solution was added thereto. The resulting mixture was extracted with chloroform and washed with saturated saline solution. The organic layer was dried over magnesium sulfate and concentrated under reduced pressure. The residue thus obtained was subjected to silica gel column chromatography (n-hexane:ethyl acetate=1:1) to give (3RS,4RS)-7-hydroxy-3-(4-hydroxyphenyl)-3-methyl-4-[9-(4,4,5,5,5-pentafluoropentylaminosulfonyl)nonyl]chroman (0.78 mg, yield 11%).

$^1$H-NMR (270 MHz, CDCl$_3$) δ: 7.08 (d, 2H, J=8.3 Hz, Ar—H), 6.90–6.80 (m, 1H, Ar—H), 6.83 (d, 2H, J=8.3 Hz, Ar—H), 6.40–6.34 (m, 2H, Ar—H), 5.23, 4.72 (respectively s, respectively 1H, OH), 4.51 (d, 1H, J=10.2 Hz, C2-H), 4.24 (d, 1H, J=10.2 Hz, C2-H), 3.30–3.18 (m, 2H, NHC$\underline{H}_2$), 3.00 (t, 2H, J=7.6 Hz, C$\underline{H}_2$SO$_2$), 2.64–2.56 (m, 1H, C4-H), 2.24–2.00 (m, 2H), 1.94–1.62 (m, 4H), 1.25 (s, 1H, C3-CH$_3$), 1.40–1.00 (m, 14H)

EXAMPLE 22

Synthesis of (3'RS,4'RS)-10-[7-hydroxy-3-(4-hydroxyphenyl)-3-methyltbiochroman-4-yl]-2-(4,4,5,5,5-pentafluoropentyl)decanoic acid Step 1) Synthesis of 6-bromo-1-(t-butyldimethylsilyloxy)hexane

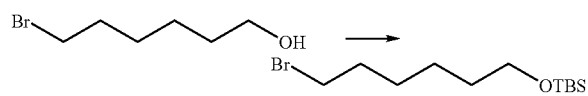

6-Bromo-1-hexanol (20 g, 110.42 mmol) was dissolved in dry tetrahydrofuran (700 ml) and cooled to 0° C. under argon atmosphere, to which were added imidazole (15 g, 220.84 mmol) and t-butyldimethylsilyl chloride (33 g, 220.84 mmol) and the resulting solution was stirred overnight. After the reaction was completed, the mixture was poured in ice-water and extracted with ethyl acetate. The organic solvent was dried over anhydrous magnesium sulfate and concentrated under reduced pressure. This crude product was purified by column chromatography on silica gel, eluting with ethyl acetate:n-hexane=1:40. After removal of the solvent, 30 g of the title compound was obtained as colorless oil. (yield: 92.4%)

$^1$H-NMR (300 MHz, CDCl$_3$) δ: 3.61 (t, 2H, 3=6.4 Hz), 3.41 (t, 2H, J=7.2 Hz), 1.87 (m, 2H), 1.56~1.30 (m, 6H), 0.89 (s, 9H), 0.05 (s, 6H)

Step 2) Synthesis of 8-(t-butyldimethylsilyloxy)-1-octyne

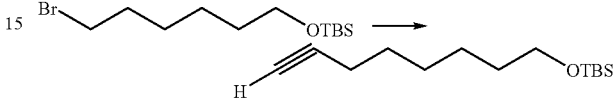

6-Bromo-1-(t-butyldimethylsilyloxy)hexane (20 g, 110.42 mmol) was dissolved in dry dimethyl sulfoxide (500 ml) and tetrahydrofuran (50 ml) and cooled to 0° C. under argon atmosphere, to which was added lithium acetylide ethylene diamine complex (28.0 g, 304.74 mmol) and the resulting solution was stirred for 1 day at 4° C. After the reaction was completed, the mixture was poured in ice-water and extracted with ethyl ether. The organic solvent was dried over anhydrous magnesium sulfate and concentrated under reduced pressure. This crude product was purified by column chromatography on silica gel, eluting with ethyl acetate:n-hexane=1:40. After removal of the solvent, 18 g of the title compound was obtained as colorless oil. (yield: 73.8%)

$^1$H-NMR (300 MHz, CDCl$_3$) δ: 3.59 (t, 2H, J=6.4 Hz), 2.15 (m, 2H), 1.90 (t, 1H, J=2.4 Hz), 1.55~1.30 (m, 8H), 0.88 (s, 9H), 0.05 (s, 6H)

Step 3) Synthesis of 4-[8-(t-Butyldimethylsilyloxy)-1-octynyl]-4-hydroxy-7-methoxy-3-(4-methoxyphenyl}3-methylthiochroman

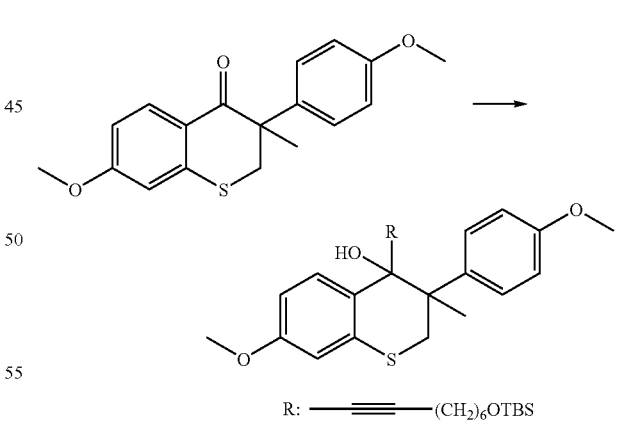

8-(t-Butyldimethylsilyloxy)-1-octyne (12 g, 49.9 mmol) was dissolved in dry tetrahydrofuran (150 ml) under argon atmosphere and then cooled to −78C. 2.5M n-Butyllithium (18 ml, 44.9 mmol) was added dropwise thereto, and the mixture was warmed to −10° C. and stirred for 1 hour and then cooled to −78° C. 7-Methoxy-3-(4-methoxyphenyl)-3-methylthiochroman-4-one (860 mg,2.9 mmol) was added portionwise and then warmed to room temperature and stirred for 1.5 hour. The mixture was quenched by water. The reaction solvent was evaporated off, then the residue was dissolved in ethyl acetate, which was washed with water. The organic solvent was dried over anhydrous magnesium sulfate and removed by evaporation under vacuum. This product was purified by column chromatography on silica gel, eluting with 10% ethyl acetate in n-hexane. After removal of the solvent, 14 g of the title compound was obtained as colorless oil. (yield: 99.3%)

$^1$H NMR (300 MHz, CDCl$_3$) δ: 7.83 (d, 1H, J=8.7 Hz), 7.57 (d, 2H, J=8.7 Hz), 6.85 (d, 2H, J=9.0 Hz), 6.65 (m, 2H), 4.23 (d, 1H, J=12.4 Hz), 3.79 (s, 3H), 3.76 (s, 3H), 3.57 (t, 2H, J=6.4 Hz), 2.69 (d, 1H, J=12.4 Hz), 2.15 (m, 2H), 1.50 (m, 8H), 0.87 (s, 9H), 0.02 (s, 6H)

Step 4) Synthesis of (3RS,4RS)-4-[8-(t-Butyldimethylsilyloxy)-1-octyl]-7-methoxy-3-(4-methoxyphenyl)-3-methylthiochroman

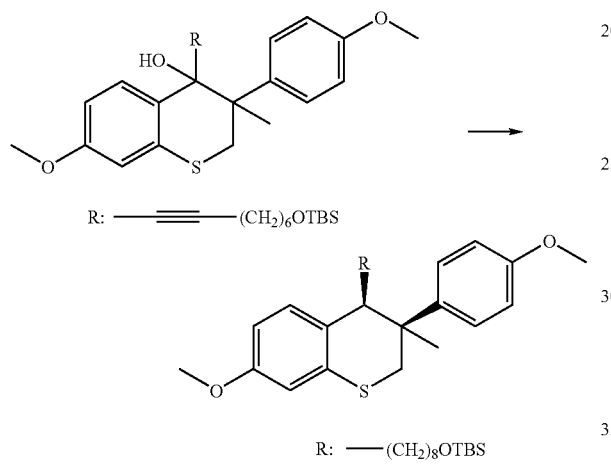

4-[8-(t-Butyldimethylsilyloxy)-1-octynyl]-4-hydroxy-7-methoxy-3-(4-methoxyphenyl)-3-methylthiochroman (14 g, 25.2 mmol) was dissolved in 1,2-dichloroethane (300 mL) and cooled to 0° C. Zinc iodide(II) (24.2 g, 75.69 mmol) and sodium cyanoborohydride (9.51 g, 151.38 mmol) was sequentially added and slowly warmed to room temperature and stirred for 2 hours. After the reaction was completed, the reaction solvent was removed under reduced pressure. The residue was poured into water and extracted with ethyl acetate. The organic layer was dried over anhydrous magnesium sulfate and removed by evaporation under vacuum. This product was purified by column chromatography on silica gel, eluting with 10% ethyl acetate in n-hexane. After removal of the solvent, crude 11 g of the title compound was obtained as pale yellow oil. (yield: 79.5%) Then, this compound thus obtained (11 g) was dissolved in tetrahydrofuran (300 mL). 0.2N NaHCO$_3$(300 mL) and 10% palladium on carbon (3 g) was added and stirred for 2 day under hydrogen (atmospheric pressure). The reaction mixture was filtered through cellite and concentrated under reduced pressure. The residue was dissolved in ethyl acetate, which was washed with water and brine. The organic solvent was dried over anhydrous magnesium sulfate and removed by evaporation under vacuum. This product was purified by column chromatography on silica gel, eluting with ethyl acetate:n-hexane=1:40. After removal of the solvent, 5.6 g of the title compound was obtained as colorless oil. (yield: 50.5%).

$^1$H NMR (300 MHz, CDCl$_3$, 3RS,4RS-compound) δ: 7.27 (d, 2H, J=9.0 Hz), 6.90 (m, 3H), 6.70 (d, 1H, J=2.6 Hz), 6.56 (dd, 1H, J=2.6, 8.7 Hz), 3.79 (s, 3H), 3.76 (s, 3H), 3.62 (d, 1H, J=11.7 Hz), 3.53 (t, 2H, J=6.4 Hz), 2.96 (d, 1H, J=12.7 Hz), 2.70 (bd, 1H), 1.40 (m, 2H), 1.15 (s, 3H), 1.20–0.90 (m, 12H), 0.86 (s, 9H), 0.01 (s, 6H)

Step 5) Synthesis of (3RS,4RS)-4-(8-hydroxyoctyl)-7-methoxy-3-(4-methoxyphenyl)-3-methylthiochroman

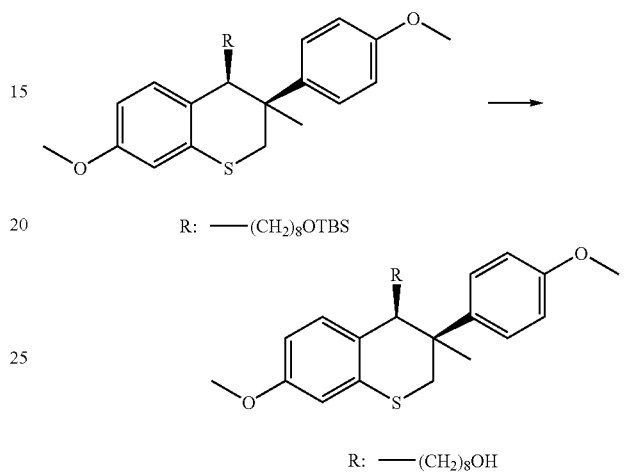

(3RS,4RS)-4-[8-(t-Butyldimethylsilyloxy)-1-octyl]-7-methoxy-3-(4-methoxyphenyl)-3-methylthiochroman (4.5 g, 8.29 mmol) was dissolved in tetrahydrofuran (100 ml), and cooled to 0°. To this solution was added tetrabutylammonium fluoride (16.6 ml, 16.58 mmol), and the reaction mixture was stirred at room temperature for 2 hours. The solvent was removed by evaporation under reduced pressure and the residue was dissolved in ethyl acetate, which was washed with water. The organic layer was separated, dried over anhydrous magnesium sulfate, and concentrated under reduced pressure. The product was purified by column chromatography on silica gel, eluting with 30% ethyl acetate in n-hexane to afford 3.3 g of the title compound as a pale yellow oil. (yield: 93.0%)

$^1$H-NMR (300 MHz, CDCl$_3$, 3RS,4RS-compound) δ: 7.27 (d, 2H, J=8.7 Hz), 6.90 (m, 3H), 6.70 (d, 1H, J=2.6 Hz), 6.56 (dd, 1H, J=2.6, 8.7 Hz), 3.80 (s, 3H), 3.76 (s, 3H), 3.67 (d, 1H, J=13.2 Hz), 3.53 (t, 2H, J=6.4 Hz), 2.96 (d, 1H, J=11.7 Hz), 2.71 (bd, 1H), 1.16 (s, 3H), 1.30–1.07 (m, 14H)

Step 6) Synthesis of (3RS,4RS)-4-(8-methanesulfonyloxyoctyl)-7-methoxy-3-(4-methoxy-phenyl)-3-methylthiochroman

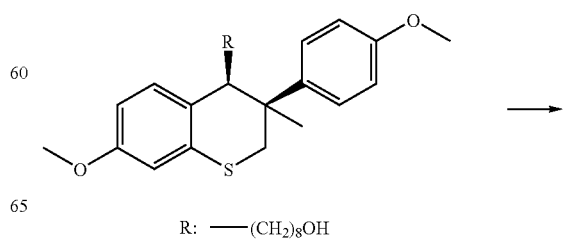

-continued

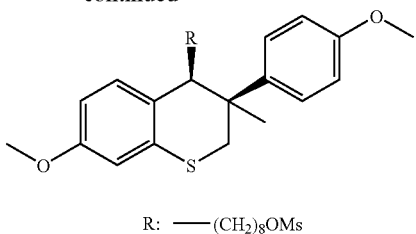

R: ——(CH₂)₈OMs (3RS,4RS)-4-(8-hydroxyoctyl)-7-methoxy-3-(4-methoxyphenyl)-3-methylthiochroman (3.25 g, 7.58 mmol) was dissolved in dichloromethane (100 ml), to which were added triethylamine (1.59 ml, 11.37 mmol) and methanesulfonyl chloride (0.88 ml, 11 37 mmol). The reaction mixture was stirred at room temperature for 1 hour. After the reaction was completed, water was added to the reaction solution, and the resulting mixture was extracted with methylene chloride. The organic layer was washed with 1M HCl solution, water and saturated sodium chloride solution, dried over anhydrous magnesium sulfate, and concentrated. The product was purified by column chromatography on silica gel, eluting with 30% ethyl acetate in n-hexane to afford 3.75 g of the title compound as a pale yellow oil. (yield: 97.7%)

¹H-NMR (300 MHz, CDCl₃) δ: 7.27 (d, 2H, J=9.0 Hz), 6.90 (m, 3H), 6.70 (d, 1H, J=2.6 Hz), 6.56 (dd, 1H, J=2.6, 8.3 Hz), 4.15 (t, 2H, J=6.4 Hz), 3.80 (s, 3H), 3.76 (s, 3H), 3.62 (d, 1H, J=11.7 Hz), 2.97 (d, 1H, J=11.7 Hz), 2.96 (s, 3H), 2.71 (bd, 1H), 1.60 (m, 2H), 1.15 (s, 3H), 1.20~0.96 (m, 12H)

Step 7) Synthesis of (3RS,4RS)-4 (8-iodooctyl)-7-methoxy-3-(4-methoxyphenyl)-3-methylthiochroman

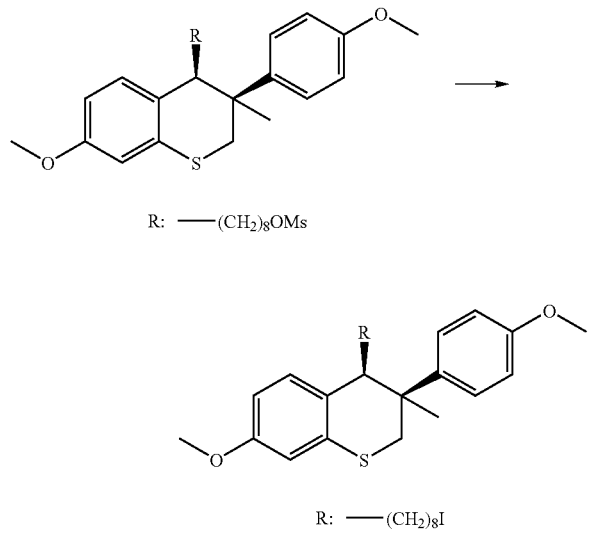

(3RS,4RS)—(8-methanesulfonyloxyoctyl)-7-methoxy-3-(4-methoxyphenyl)-3-methylthiochroman (3.75 g, 7.40 mmol) was dissolved in acetone (70 ml). To the reaction solution was added sodium iodide (3.33 g, 22.20 mmol). The reaction mixture was heated at reflux temperature, with stirring, for 4 hours and then allowed to cool to ambient temperature, then concentrated under reduced pressure in order to remove acetone. The residue was dissolved in ethyl acetate and filtrated. The organic layer was washed with 1% Na₂S₂O₃ solution, water and brine dried over anhydrous magnesium sulfate, and removed by evaporation under vacuum. This product was purified by column chromatography on silica gel, eluting with 10% ethyl acetate in n-hexane to afford 3.73 g of the title compound as a colorless oil. (yield: 93.6%)

¹H-NMR (300 MHz, CDCl₃, 3RS,4RS-compound) δ: 7.27 (d, 2H, J=8.7 Hz), 6.90 (m, 3H), 6.72 (d, 1H, J=2.6 Hz), 6.56 (dd, 1H, J=2.6, 8.7 Hz), 3.81 (s, 3H), 3.76 (s, 3H), 3.63 (d, 1H, J=11.7 Hz), 3.12 (t, 2H, J=6.8 Hz), 2.96 (d, 1H, J=11.7 Hz), 2.70 (bd, 1H), 1.70 (m, 2H), 1.16 (s, 3H), 1.28~1.00 (m, 14H)

Step 8) Synthesis of (Methylsulfonyl)oxy(4,4,5,5,5-pentafluoropentyl)

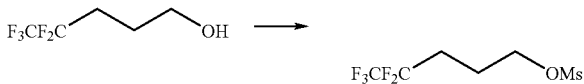

4,4,5,5,5-Pentafluoropentanol (25 g, 0.132 mol) was dissolved in dichloromethane (50 mg) and cooled to 0° C., to which were added triethylamine (46 me, 0.330 mol) and methanesulfonyl chloride (20.4 md, 0.264 mol). The reaction mixture was stirred at, room temperature for 3 hour. After the reaction was completed, water was added to the reaction solution, and the resulting mixture was extracted with dichlorornethane. The organic layer was washed with 1M HCl solution, water and saturated sodium chloride solution, dried over anhydrous magnesium sulfate, and concentrated. The product was purified by column chromatography on silica gel, eluting with 50% ethyl acetate in n-hexane to afford 34 g of the title compound as a pale yellow oil. (yield: quantitative)

¹H-NMR (300 MHz, CDCl₃) δ: 4.30 (t, 2H), 3.05 (s, 3H), 2.30–2.05 (m, 4H)

Step 9) Synthesis of 1,1,1,2,2-Pentafluoro-5-iodopentane

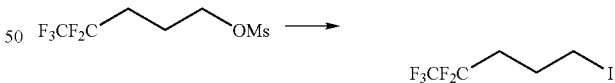

(Methylsulfonyl)oxy(4,4,5,5,5-pentafluoropentyl)(20 g, 0.781 mol) was dissolved in acetone (200 ml). To the reaction solution was added sodium iodide (35.1 g, 2:154 mol). The reaction mixture was stirred at reflux overnight and then allowed to cool to ambient temperature, then filtrated and concentrated under reduced pressure. The residue was dissolved in ethyl ether and filtered. The organic layer was washed with water and brine, dried over anhydrous magnesium sulfate, and removed by evaporation under reduced pressure to afford 21.1 g of the title compound as a colorless oil. (yield 93.4%)

¹H-NMR (300 MHz, CDCl₃) δ: 3.22 (t, 2H, J=6.8 Hz), 2.28–2.10 (m, 4H)

Step 10) Synthesis of diethyl 2-(4,4,5,5,5-pentafluoropentyl)propane-1,3-dioate

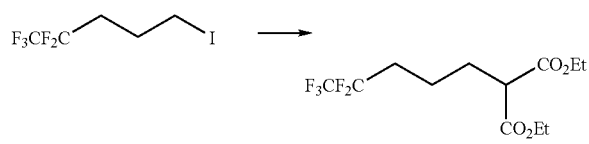

To a solution of sodium hydride (60%) (3.90 g, 96.07 mol) in tetrahydrofuran (160 ml) was added dropwise a solution of diethyl malonate (16.6 ml, 110.85 mol) under ice-cooling, which was then stirred for 30 minutes. Then, 1,1,1,2,2-Pentafluoro-5-iodopentane (21 g, 73.9 mol) was added dropwise thereto, and reaction mixture was warmed to room temperature, with stirring, for overnight. After the reaction was completed, the reaction was quenched with water, extracted with ethyl acetate. The organic layer was washed with water and brine, dried over anhydrous magnesium sulfate, and removed by evaporation under reduced pressure. This product was purified by column chromatography on silica gel, eluting with dichloromethane:n-hexane=1:3 to afford 18.3 g of the title compound as a colorless oil. (yield: 78.4%)

$^1$H-NMR (300 MHz, CDCl$_3$) δ: 4.22 (q, 4H, J=7.1 Hz), 3.35 (t, 1H, J=6.0 Hz), 2.15~1.93 (m, 4H), 1.67 (m, 2H), 1.28 (t, 6H, J=7.1 Hz)

Step 11) Synthesis of (3'RS,4'RS) diethyl 2-{8-[7-methoxy-3-(4-methoxyphenyl)-3-methylthiochroman-4-yl]octyl}-2-(4,4,5,5,5-pentafluoropentyl)propane-1,3-dioate

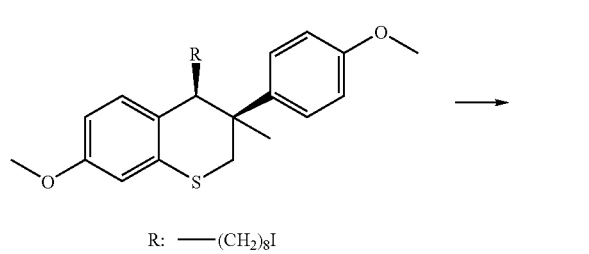

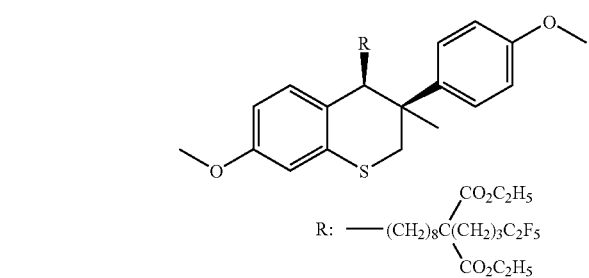

To a solution of sodium hydride (60%) (312 mg, 7.799 mmol) in tetrahydrofuran (14 ml) was added dropwise a solution of 2-(4,4,5,5,5-pentafluoropentyl)propane-1,3-dioate (2.38 g, 7.428 mmol) in tetrahydrofuran (8 ml) under ice-cooling, which was then stirred for 1 hour. Then, a solution of (3RS,4RS)-4-(8-iodooctyl)-7-methoxy-3-(4-methoxyphenyl)-3-methyl-thiochroman (2.0 g, 3.714 mmol) in tetrahydrofuran (8 ml) was added dropwise thereto, and reaction mixture was warmed to room temperature, with stirring, for 2 days. After the reaction was completed, the reaction was quenched with water, extracted with ethyl acetate. The organic layer was washed with water and brine, dried over anhydrous magnesium sulfate, and removed by evaporation under vacuum. This product was purified by column chromatography on silica gel, eluting with ethyl acetate:n-hexane=1:4→1:1 to afford 2.60 g of the title compound as a colorless oil. (yield: 95.9%)

$^1$H-NMR (300 MHz, CDCl$_3$) δ: 7.26 (d, 2H, J=8.7 Hz), 6.89 (m, 3H), 6.70 (d, 1H, J=2.6 Hz), 6.56 (dd, 1H, J=2.6, 8.3 Hz), 4.15 (q, 4H, J=7.1 Hz), 3.80 (s, 3H), 3.76 (s, 3H), 3.62 (d, 1H, J=11.7 Hz), 2.96 (d, 1H, J=11.7 Hz), 2.70 (bd, 1H), 2.00 (m, 2H), 1.87 (m, 4H), 1.48 (m, 2H), 1.15 (s, 3H), 1.20~0.96 (m, 12H)

Step 12) Synthesis of (3'RS,4'RS)-{8-[7-methoxy-3-(4-methoxyphenyl)-3-methylthiochroman-4-yl]octyl}(4,4,5,5,5-pentafluoropentyl)methane-1,1-dicarboxylic acid

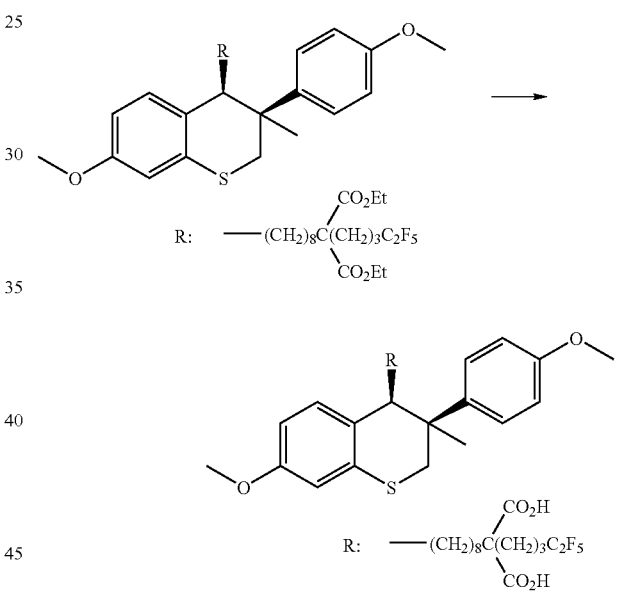

To a solution of (3RS,4RS)-4-(8-iodooctanyl)-7-methoxy-3-(4-methoxyphenyl)-3-methylthiochroman (2.6 g, 3.557 mmol) in ethyl alcohol (40 ml) was added a solution of potassium hydroxide (7.8 g, 142.30 mmol) in water (20 ml). The resulting mixture was heated under reflux for overnight. The residue, left after removal of ethyl alcohol, was dissolved in water and the mixture was extracted with ethyl acetate. The organic layer was washed with water and brine, dried over anhydrous magnesium sulfate, and removed by evaporation under vacuum to afford 2.30 g of the title compound as a white foam. (yield: quantitative)

$^1$H-NMR (300 MHz, CDCl$_3$) δ: 7.28 (d, 2H, J=8.7 Hz), 6.90 (m, 3H), 6.71 (d, 1H, J=2.6 Hz), 6.57 (dd, 1H, J=2.6, 8.3 Hz), 3.82 (s, 3H), 3.77 (s, 3H), 3.62 (d, 1H, J=11.7 Hz), 2.97 (d, 1H, J=11.7 Hz), 2.70 (bd, 1H), 2.07 (m, 4H), 1.87 (m, 2H), 1.56 (m, 2H), 1.15 (s, 3H), 1.13~1.00 (m, 14H)

Step 13) Synthesis of (3'RS,4'RS)-10-[7-methoxy-3-(4-methoxyphenyl)-3-methylthiochroman-4-yl]-2-(4,4,5,5,5-pentafluoropentyl)decanoic acid

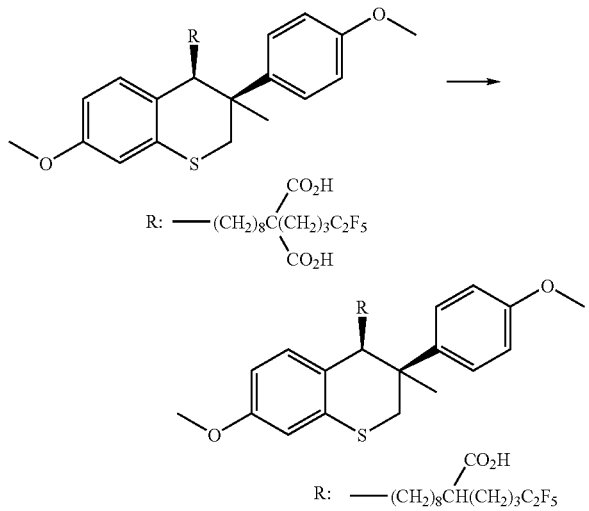

To a solution of (3'RS,4'RS)-{8-[7-methoxy-3-(4-methoxyphenyl)-3-methylthiochroman-4-yl]octyl}(4,4,5,5,5-pentafluoropentyl)methane-1,1-dicarboxylic acid (2.0 g, 3.093 mol) in dimethyl sulfoxide (20 ml) was heated under 130–140° C. for 4 hours. The reaction mixture was dissolved in ethyl acetate and washed with water (20 ml×4) and brine (20 ml×2), dried over anhydrous magnesium sulfate. This product was purified by column chromatography on silica gel, eluting with ethyl acetate:n-hexane=1:9→1:5→1:1 to afford 1.60 g of the title compound as a white foam (yield: 82.1%)

$^1$H-NMR (300 MHz, CDCl$_3$) δ: 7.27 (d, 2H, J=8.7 Hz), 6.90 (m, 3H), 6.70 (d, 1H, J=2.6 Hz), 6.56 (dd, 1H, J=2.6, 8.3 Hz), 3.80 (s, 3H), 3.76 (s, 3H), 3.62 (d, 1H, J=11.7 Hz), 2.96 (d, 1H, J=11.7 Hz), 2.70 (bd, 1H), 2.34 (m, 1H), 2.06 (m, 2H), 1.70~1.40 (m, 6H), 1.15 (s, 3H), 1.20–1.00 (m, 14H)

Step 14) Synthesis of (3'RS,4'RS)-10-[7-hydroxy-3-(4-hydroxyphenyl)-3-methylthiochroman-4-yl-4-yl]-2-(4,4,5,5,5-pentafluoropentyl)decanoic acid

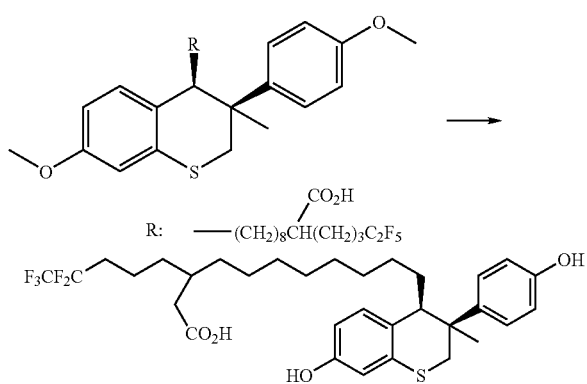

The solution of (3'RS,4'RS)-10-[7-methoxy-3-(4-methoxyphenyl)-3-methylthiochroman-4-yl]-2-(4,4,5,5,5-pentafluoropentyl)decanoic acid (1.3 g, 2.061 mmol) in dry dichloromethane (30 ml) was cooled to −78° C. under argon atmosphere. To this solution was added dropwise boron tribromide (1.0 mol/l solution in dichloromethane, 12.4 ml, 12.366 mmol) for 10 min and the resulting solution was stirred for 1 hours and then warmed to −5C, and stirred for 1 hour. After the reaction was completed, the mixture was poured in ice-water and extracted with dichloromethane. The organic solvent was dried over anhydrous magnesium sulfate and concentrated under vacuum. This crude product was purified by column chromatography on silica gel, eluting with ethyl acetate:n-hexane=1:5→1:3→2:3. After removal of the solvent, 1.1 g of the title compound was obtained as white foam. (yield: 88.7%, HPLC=94%)

$^1$H-NMR (300 MHz, CDCl$_3$) δ: 7.1 6 (d, 2H, J=8.7 Hz), 6.75 (m, 3H), 6.60 (d, 1H, J=2.4 Hz), 6.56 (dd, 1H, J=8.2, 2.4 Hz), 3.55 (d, 1H, J=11.5 Hz), 2.88 (d, 1H, J=11.5 Hz), 2.62 (bd, 1H), 2.33 (m, 1H), 1.94 (m, 2H), 1.70~1.40 (m, 6H), 1.10 (s, 3H), 1.10~1.00 (m, 14H)

Mass (ESI): 625 [M+Na], 603 [M+1]

EXAMPLE 23

Synthesis of (3'RS,4'RS)-{8-[7-hydroxy-3-(4-hyroxyphenyl)-3-methylthiochroman-4-yl]octyl}(4,4,5,5,5-pentafluoropentyl)methane-1,1-dicarboxylic acid Step 1) Synthesis of (3'RS,4'RS)-{8-[7-hydroxy-3-(4-hydroxyphenyl)-3-methylthiochroman-4-yl]octyl}(4,4,5,5,5-pentafluoropentyl)methane-1,1-dicarboxylic acid

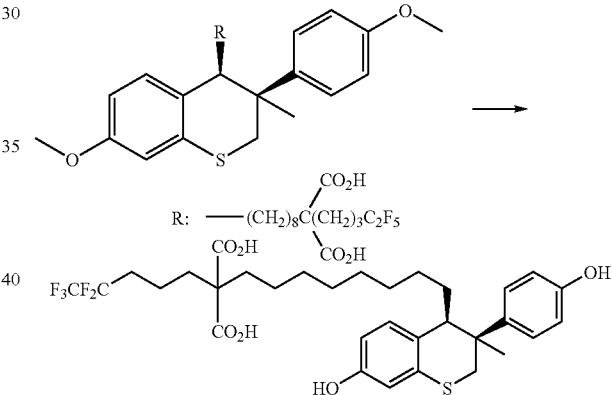

The solution of (3RS,4RS)-{8-[7-methoxy-3-(4-methoxyphenyl)-3-methylthiochroman-4-yl]octyl}(4,4,5,5,5-pentafluoropentyl)methane-1,1-dicarboxylic acid (170 mg, 0.252 mmol) in dry dichloromethane (30 ml) was cooled to 0° C. under argon atmosphere. To this solution was added dropwise boron tribromide (1.0 mol/l solution in dichloromethane, 0.52 ml, 0.59 mmol) and stirred for 1 hour. After the reaction was completed, the mixture was poured in ice-water and extracted with dichloromethane. The organic solvent was dried over anhydrous magnesium sulfate and concentrated under reduced pressure. This crude product was purified by column chromatography on silica gel, eluting, with 15% methanol in dichloromethane. After removal of the solvent, 120 mg of the title compound was obtained as white foam. (yield: 73.0%)

$^1$H-NMR (300 MHz, CDCl$_3$) δ: 7.27 (d, 2H, J=9.0 Hz), 6.88 (d, 1H, J=8.3 Hz), 6.81 (d, 1H, J=8.7 Hz), 6.60 (d, 1H, J=2.6 Hz), 6.48 (dd, 1H, J=8.3, 2.6 Hz), 3.64 (d, 1H, J=11.7 Hz), 2.99 (d, 1H, J=11.7 Hz), 2.77 (bd, 1H), 2.10 (m, 1H), 1.85 (m, 2H), 1.75 (bs, 2H), 1.53 (m, 2H), 1.16 (s, 3H), 1.10~1.00 (m, 14H)

Mass (ESI): 647 [M+1]

EXAMPLE 24

Synthesis of methyl (3'RS,4'RS) 10-[7-hydroxy-3-(4-hydroxyphenyl)-3-methylthiochroman-4-yl]-2-(4,4,5,5,pentafluoropentyl)decanoate Step 1) Synthesis of methyl (3'RS,4'RS)-10-[7-hydroxy-3-(4-hydooxyphenyl)-3-methylthiochroman-4-yl]-2-(4,4,5,5,5-pentafluoropentyl)decanoate

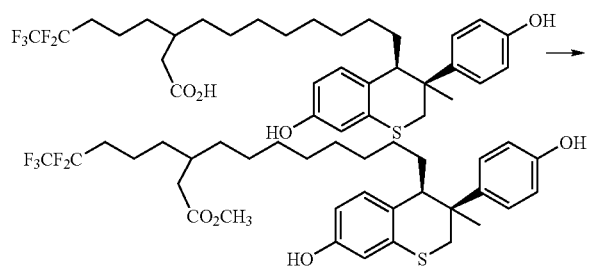

The solution of (3'RS,4'RS)-10-[7-hydroxy-3-(4-hydroxyphenyl)-3methylthiochroman-4-yl]-2-(4,4,5,5,5-pentafluoropentyl)decanoic acid (100 mg, 0.166 mmol) in dry diethyl ether (2 ml) was cooled to 0° C. under argon atmosphere. To this solution was added dropwise diazo methane (ca. 1.0 mol/l solution in diethyl ether, 2 ml) and the resulting solution was stirred for 10 minutes and then quenched by acetic acid. The residue, left after removal of acetic acid and diethyl ether, was extracted with ethyl acetate. The organic layer was washed with water and brine, dried over anhydrous magnesium sulfate and concentrated under reduced pressure. This crude product was purified by column chromatography on silica gel, eluting with ethyl acetate:n-hexane=1:3. After removal of the solvent, 80 mg of the title compound was obtained as white foam. (yield: 78.4%)

$^1$H-NMR (300 MHz, CDCl$_3$) δ: 7.21 (d, 2H, J=8.7 Hz), 6.83 (m, 3H), 6.66 (d, 1H, J=2.3 Hz), 6.56 (dd, 1H, J=7.2, 2.3 Hz), 5.86 (d, 1H, J=7.9 Hz), 5.28 (d, 1H, J=7.5 Hz), 3.70 (s, 3H), 3.61 (d, 1H, J=11.7 Hz), 2.93 (d, 1H, J=11.7 Hz), 2.67 (bd, 1H), 2.37 (m, 1H), 2.00 (m, 2H), 1.69~1.30 (m, 6H), 1.16 (s, 3H), 1.13~1.00 (m, 14H)

Mass (ESI): 617 [M+1]

EXAMPLE 25

Synthesis of (3'RS,4'RS)-2-{8-[7-hydroxy-3-(4-hydroxyphenyl)-3-methylthiochroman-4-yl]octyl)-2-(4,4,5,5-pentafluoropentyl)propane-1,3-diol Step 1) Synthesis of (3'RS,4'RS) dimethyl 2-{8-[7-methoxy-3-(4-methoxyphenyl)-3-methylthiochroman-4-yl 3-octyl}-2-(4,4,5,5,5-pentafluoropentyl)propane-1,3-dioate

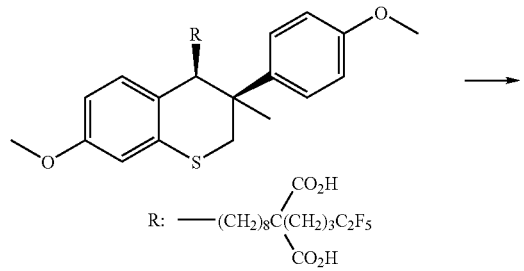

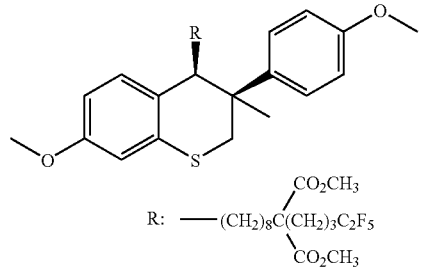

To a solution of (3'RS,4'RS)-{8-[7-methoxy-3-(4-methoxyphenyl)-3-methylthiochroman-4-yl]octyl)}(4,4,5,5,5-pentafluoropentyl)methane-1,1-dicarboxylic acid (150 mg, 0.222 mmol) in dimethylformamide (5 ml) was added powdered potassium carbonate (320 mg, 2.220 mmol) and iodomethane (0.14 ml, 2.220 mmol) and stirred for overnight at room temperature. The reaction mixture was dissolved in ethyl acetate (300 ml) and washed with water (20 ml×4) and brine (20 ml×2), dried over anhydrous magnesium sulfate. This product was purified by column chromatography on silica gel, eluting with ethyl acetate:n-hexane=1:5 to afford 145 mg of the title compound as a white foam. (yield: 93.0%)

$^1$H-NMR (300 MHz, CDCl$_3$) δ: 7.27 (d, 2H, J=9.0 Hz), 6.90 (m, 3H), 6.70 (d, 1H, J=2.6 Hz), 6.56 (dd, 1H, J=2.6, 8.3 Hz), 3.80 (s, 3H), 3.76 (s, 3H), 3.69 (s, 6H), 3.62 (d, 1H, J=11.7 Hz), 2.96 (d, 1H, J=11.7 Hz), 2.66 (bd, 1H), 2.00 (m, 2H), 1.87 (m, 2H), 1.73 (m, 2H), 1.48 (m, 2H), 1.16 (s, 3H), 1.21~1.06 (m, 14H)

Step 2) Synthesis of (3'RS,4'RS)-2-{8-[7-methoxy-3-(4-methoxyphenyl)-3-methylthiochroman-4-yl]octyl}-2-(4,4,5,5,5-pentafluoropentyl)propane-1,3-diol

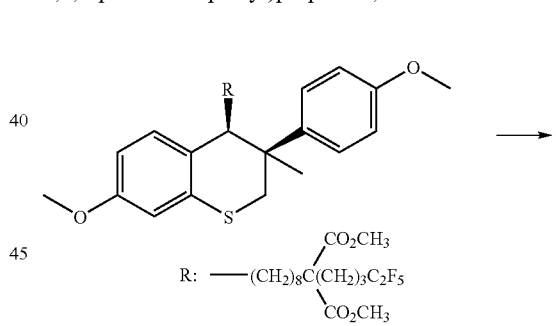

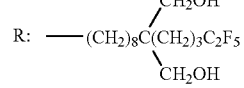

To a solution of (3'RS,4'RS) dimethyl 2-{8-[7-methoxy-3-(4-methoxyphenyl)-3-methylthiochroman-4-yl]octyl}-2-(4,4,5,5,5-pentafluoropentyl)propane-1,3-dioate (135 mg, 0.192 mmol) in tetrahydrofuran (5 ml) was added powdered lithium aluminum hydride (14.6 mg, 0.384 mmol) and stirred for 1 hour at room temperature and then quenched by ethyl acetate. The residue, left after removal of tetrahydrofuran, was extracted with ethyl acetate. The organic layer was washed with water and, brine, dried over anhydrous magnesium sulfate and concentrated under reduced pressure. This crude product was purified by column chromatography on silica gel, eluting with ethyl acetate:n-hexane=1:1. After removal of the solvent, 100 mg of the title compound was obtained as white foam. (yield: 80.6%)

$^1$H-NMR (300 MHz, CDCl$_3$) δ: 7.26 (d, 2H, J=8.7 Hz), 6.89 (m, 3H), 6.70 (d, 1H, J=2.6 Hz), 6.56 (dd, 1H, J=8.7, 2.6 Hz), 3.80 (s, 3H), 3.76 (s, 3H), 3.61 (d, 1H, J=11.7 Hz), 3.55 (m, 4H), 2.96 (d, 1H, J=11.7 Hz), 2.70 (bd, 1H), 2.00 (m, 6H), 1.38 (m, 2H), 1.15 (s, 3H), 1.21~1.06 (m, 14H)

Step 3) Synthesis of (3'RS,4'RS)-2-{8-[7-hydroxy-3-(4-hydroxyphenyl)-3-methylthiochroman-4-yl]octyl)-2-(4,4,5,5,5-pentafluoropentyl)propane-1,3-diol

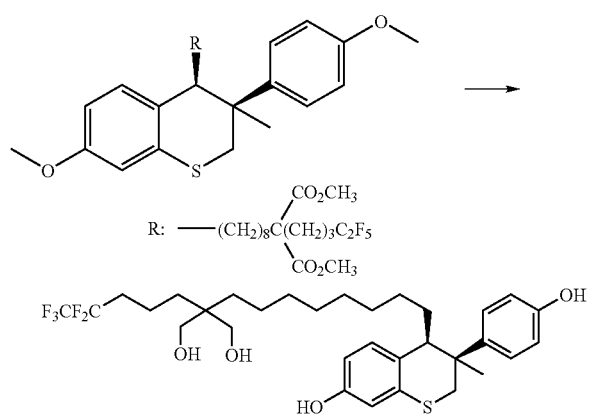

The solution of (3'RS,4RS)-2-{8-[7-methoxy-3-(4-methoxyphenyl)-3-methylthiochroman-4-yl]-octyl}-2-(4,4,5,5,5-pentafluoropentyl)propane-1,3-diol (100 mg, 0.155 mmol) in dry dichloromethane (5 ml) was cooled to 0° C. under argon atmosphere. To this solution was added dropwise boron tribromide (11.0 mol/l solution in dichloromethane, 0.93 ml, 0.928 mmol) and the resulting solution was warmed to 4° C. and stirred for overnight. After the reaction was completed, the mixture was poured in ice-water and extracted with dichloromethane The organic solvent was dried over anhydrous magnesium sulfate and concentrated under reduced pressure. This crude product was purified by preparative TLC on silica gel, eluting with ethyl acetate:n-hexane=1:1. After removal of the solvent, 75 mg of the title compound was obtained as white foam. (yield: 78.1%)

$^1$H-NMR (300 MHz, CDCl$_3$) δ: 7.21 (d, 2H, J=9.0 Hz), 6.82 (m, 3H), 6.65 (d, 1H. J=2.6 Hz), 6.48 (dd, 1H, J=8.7, 2.6 Hz), 5.88 (bs, 1H), 4.88 (bs, 1H), 3.62 (d, 1H, J=11.7 Hz), 3.60 (m, 4H), 2.93 (d, 1H, J=11.7 Hz), 2.67 (bd, 1H), 2.35 (bs, 2H), 2.00 (m, 2H), 1.30 (m, 6H), 1.15 (s, 3H), 1.21~1.06 (m, 14H)

Mass (ESI): 641 [M+Na], 619 [M+1]

EXAMPLE 26

Synthesis of (3RS,4RS)-7-hydroxy-3-(4-hydroxyphenyl)-3-methyl-4-(9-(2-aza-2-carbonyl-1-(4,4,5,5,5-pentafluoropentylamino)ethenyl)aminononyl)thiochroman Step 1) Synthesis of 1-cyano-3-(4,4,5,5,5-pentafluoropentyl)-2-methylisothiourea

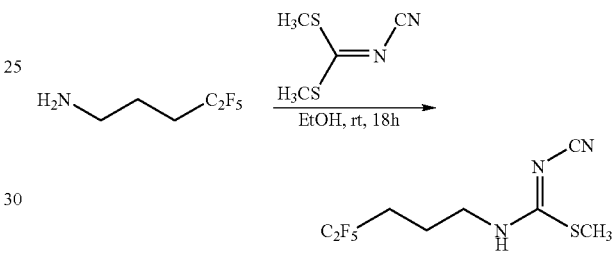

A solution of 4,4,5,5,5-pentafluoropentylamine (0.118M, 30 ml, 3.55 mmole) and of dimethyl N-cyanodithioiminocarbonate (700 mg, 4.26 mmole) in ethanol (30 ml) was heated under reflux for 18 hours. Concentration under reduced pressure, followed by crystallization from ethyl acetate and petroleum ether afforded 1-cyano-3-(4,4,5,5,5-pentafluoropentyl)-2-methylisothiourea (677 mg, 69%).

$^1$H-NMR (300 MHz, CDCl$_3$) δ: 3.5 (m, 2H), 2.5 (s, 3H), 2.0 (m, 4H)

Step 2) Synthesis of (3RS,4RS)-7-hydroxy-3-(4-hydroxyphenyl)-3-methyl-4-(9-(2-aza-2-carbonyl -1-(4,4,5,5,5-pentafluoropentylamino)ethenyl)aminononyl)thiochroman

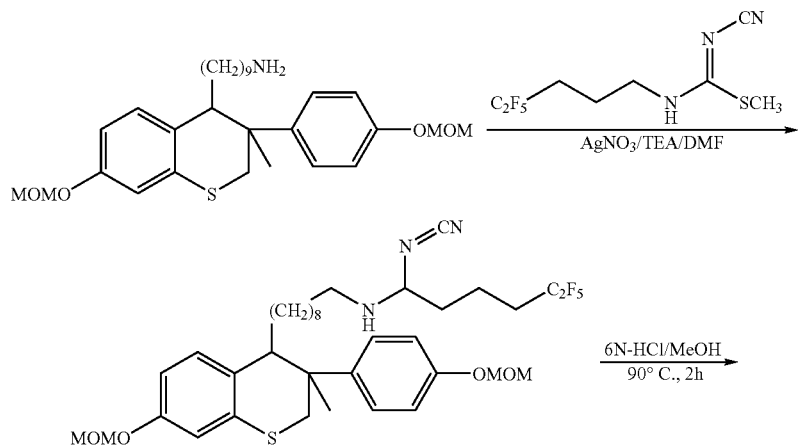

-continued

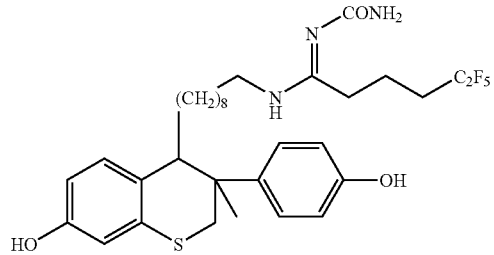

Silver nitrate (155 mg, 0.915 mmole) was added to a solution of 1-cyano-3-(4,4,5,5,5-pentafluoropentyl)-2-methylisothiourea (277 mg, 1.006 mmole) and (3RS,4RS)-7-methoxymethoxy-3-methyl-3-(4-methoxymethoxyphenyl)-4-(9-aminononyl)thiochroman (459 mg, 0.915 mmole) in 10 ml of a mixture of triethylamine/DMF (1/1). The reaction was stirred for 40 minutes at room temperature followed by filtration over celite. The filtrate was concentrated in vacuo and the residue was diluted with water and the resulting solution was extracted with ethyl acetate. Then, the organic layer was washed with water and saturated sodium chloride solution, dried over anhydrous magnesium sulfate, and concentrated under reduced pressure. The residue was dissolved in 6N hydrochloric acid (2 ml) and methanol (6 ml), which was stirred at 90° C. for 2 hours. This reaction solution was concentrated under reduced pressure which was subjected to flash chromatography on silica gel (dichloromethane:methanol=9:1) to give the title compound (94 mg) as white solid.

$^1$H-NMR (300 MHz, CD$_3$OD) δ: 7.14 (d, 2H, J=8.7 Hz, Ar—H), 6.75 (d, 1H, J=8.2 Hz, Ar—H), 6.68 (d, 2H, J=8.7 Hz), 6.47 (d, 1H, J=2.4 Hz), 6.35 (dd, 1H, J=8.2 Hz, J=2.4 Hz), 3.51 (d, 1H, J=11.6 Hz, C2-H), 3.2 (t, 2H, J=6.8 Hz), 3.07 (t, 2H, J=6.9 Hz), 2.85 (d, 1H, J=11.6 Hz, C2-H), 2.6 (m, 1H), 2.1 (m, 2H), 1.7 (m, 2H), 1.5 (m, 2H), 1.02 (s, 3H, C3-CH$_3$), 0.8–1.1 (m, 14H)

Mass (ESI) 659 (M+1)

EXAMPLE 27

Synthesis of (3RS,4RS)-7-hydroxy-3-(4-hydroxyphenyl)-3-methyl-4-(9-((1-((4,4,5,5,5-pentafuoropentyl)amino)-2-nitroethenyl)amino)nonyl)thiochroman Step 1) Synthesis of (3RS,4RS)-4-(azidononyl)-7-methoxymethyloxy-3-[4-(methoxymethyloxy)phenyl]-3-methylthiochroman

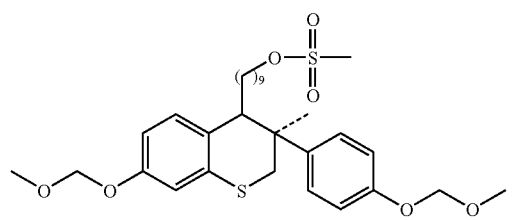

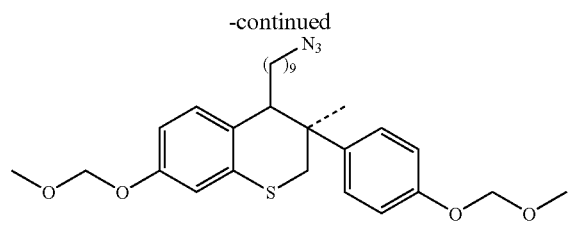

(3RS,4RS)-4-(9-Methanesulfonyloxynonyl)-7-methoxymethyloxy-3-[4-methoxymethyloxy)phenyl]-3-methylthiochroman (982 mg, 1.69 mmol) was dissolved in anhydrous N,N-dimethylformamide (25 ml). Sodium azide (441 mg, 6.76 mmol) and 18-crown-6 (45 mg, 0.169 mmol) was added. The mixture was stirred at 65° C. (for 19 h under nitrogen atmosphere. The mixture was filtered after cooling to room temperature. The filtrate was evaporated in vacuo. The residue was diluted with water and then extracted with ethyl acetate. The extracted organic layer was dried over anhydrous magnesium sulfate and then concentrated. The residue was subjected to column chromatography (n-hexane:ethyl acetate=8:1) to produce 873 mg (yield:98%) of the title compound as a pale yellow oil.

$^1$H-NMR (300 MHz, CDCl$_3$) δ 7.27 (d, 2H, J=9 Hz), 7.01 (d, 2H, J=9 Hz), 6.91 (d, 1H, J=9 Hz), 6.86 (d, 1H, J=2 Hz), 6.67 (dd, 1H, J=9 Hz, J=2 Hz), 5.17 (s, 2H), 5.12 (s, 2H), 3.61 (d, 1H, J=12 Hz), 3.48 (s, 3H), 3.47 (s, 3H), 3.20 (t, 2H, J=7 Hz), 2.98 (d, 1H, J=12 Hz), 2.72 (br, 1H), 1.50 (m, 2H), 1.27 (m, 4H), 1.15 (s, 3H), 0.90–1.12 (m, 10H)

Step 2) Synthesis of (3RS,4RS)-4-(azidononyl)-7-hydroxy-3-(4-hydroxyphenyl)-3-methylthiochroman

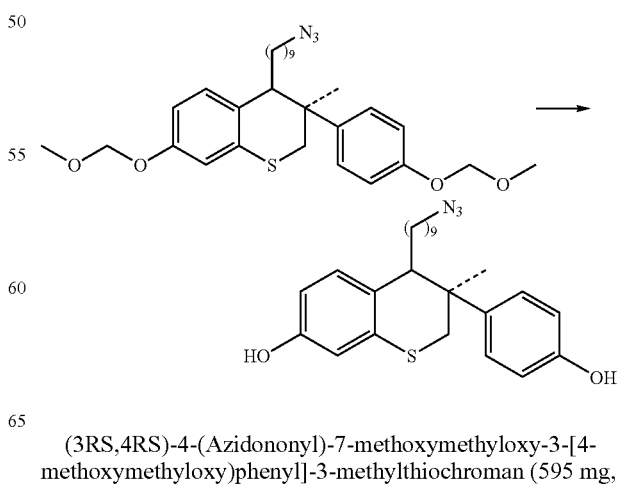

(3RS,4RS)-4-(Azidononyl)-7-methoxymethyloxy-3-[4-methoxymethyloxy)phenyl]-3-methylthiochroman (595 mg, 1.13 mmol) was dissolved in methanol (12 ml) and 6N HCl (0.2 ml). The mixture was stirred at 65° C. for 3 h under nitrogen atmosphere. When the reaction was completed, the mixture was evaporated. The residue was subjected to column chromatography (n-hexane:ethyl acetate=4:1) to give 480 mg (yield: 97%) of the title compound as a colorless oil.

$^{1}$H-NMR (300 MHz, CDCl$_{3}$) δ 7.22 (d, 2H, J=9 Hz), 6.86 (d, 1H, J=8 Hz), 6.81 (d, 2H, J=9 Hz), 6.65 (d, 1H, J=3 Hz), 6.48. (dd, 1H, J=8 Hz, J=3 Hz), 4.92 (s, 1H), 4.74 (s, 1H), 3.61 (d, 1H, J=12 Hz), 3.22 (t, 2H, J=2 Hz), 2.94 (d, 1H, J=12 Hz), 2.69 (br, 1H), 1.51 (m, 2H), 1.24 (m, 4H), 1.15 (s, 3H), 0.90–1.13 (m, 10H)

Step 3) Synthesis of (3RS,4RS)-4-(aminononyl)-7-hydroxy-3-(4-hydroxyphenyl)-3-methylthiochroman

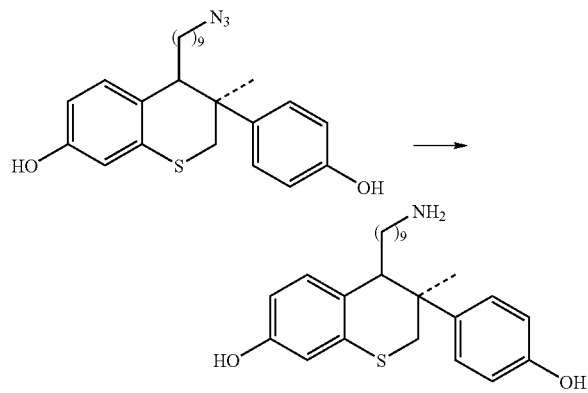

Methanol (70 ml) and 10% Pd/C (137 mg) were added to (3RS,4RS)-4-(azidononyl)-7-hydroxy-3-(4-hydroxyphenyl)-3-methylthiochroman (410 mg, 0.93 mmol) and the mixture was stirred for 2 h under hydrogen (normal pressure). When the reaction was completed, the mixture was filtered through celite pad, the filtrate was evaporated in vacuo to give 380 mg (yield: 98%) of the title compound as a pale yellow oil.

$^{1}$H-NMR (300 MHz, CDCl$_{3}$) δ 7.36 (d, 2H, J=10 Hz). 6.97 (d, 1H, J=8 Hz), 6.90 (d, 2H, J=9 Hz), 6.68 (d, 1H, J=2 Hz), 6.56 (dd, 1H, J=3 Hz, J=2 Hz), 3.73 (d, 1H, J=12 Hz), 3.07 (d, 1H, J=12 Hz), 2.86 (br, 1H), 2.72 (t, 2H, J=7 Hz), 1.53 (m, 2H), 1.33 (m, 4H), 1.24 (s, 3H) 0.9–1.21 (m, 10H)

Mass (ESI) 414 (M+1)

Step 4) Synthesis of (4,4,5,5,5-pentafluoropentyl)benzylamine

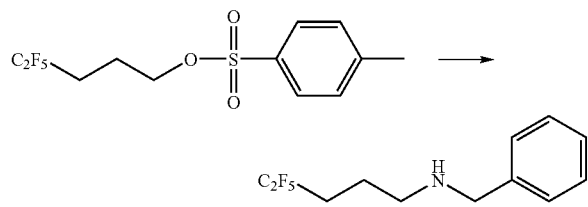

4,4,5,5,5-Pentafluoropentyloxytoluenesulfonate (1 g, 3 mmol) was dissolved in acetonitrile (10 ml). Benzylamine (646 mg, 6 mmol) and potassium carbonate (829 mg, 6 mmol) were added. The mixture was refluxed for 10 h under nitrogen atmosphere. When the reaction was completed, the mixture was cooled to room temperature. Water was added to reaction solution which was then extracted with ethyl acetate. The extracted organic layer was dried over anhydrous magnesium sulfate and then concentrated. The residue was subjected to column chromatography (dichloromethane: ethyl acetate=19:1) to give 590 mg (yield: 74%) of the title compound as a pale yellow liquid.

$^{1}$H-NMR (300 MHz, CDCl$_{3}$) δ 7.36 (m, 5H), 3.83 (s, 2H), 2.74 (t, 2H, J=7 Hz), 2.16 (m, 2H), 1.71 (m, 2H), 1.00 (s, 1H)

Step 5) Synthesis of (1-methylthio-2-nitrovinyl)(4,4,5,5,5-pentafluoropentyl)benzylamine

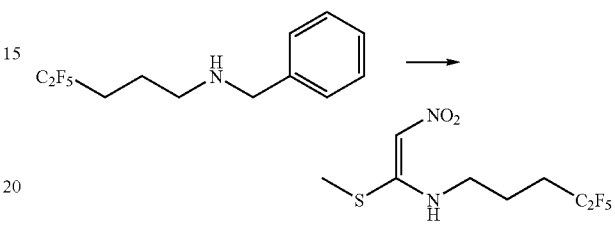

Ethanol (40 ml) and 20% Pd(OH)$_{2}$/C (400 mg) were added to (4,4,4,5,5,5-pentafluoropentyl)benzylamine (2.04 g, 7.64 mmol) and then stirred at room temperature for 10 h under hydrogen (normal pressure). The reaction mixture was filtered through celite pad. The filtrate (15.55 g, calculated 2.82 mmol) was added to dichloroethane (5 ml) and 1,1-bismethylthio-2-nitroethylene (112 mg, 0.68 mmol). The resulting mixture was stirred at room temperature for 10 minutes under nitrogen atmosphere. The mixture was heated at reflux for 16 h. When the reaction was completed, the mixture was cooled to room temperature. Water was added to reaction solution which was then extracted with dichlororpethane. The extracted organic layer was dried over anhydrous magnesium sulfate and then concentrated. The residue was subjected to column chromatography (100% dichloromethane) to give 532 mg (yield: 64%) of the title compound as a white solid.

$^{1}$H-NMR (300 MHz, CDCl$_{3}$) δ 6.53 (s, 11H), 3.51 (m, 2H), 2.42 (s, 3H), 2.07 (m, 2H), 1.22 (s, 2H)

Step 6) Synthesis of (3RS,4RS)-7-hydroxy-3-methyl-3-(4-hydroxyphenyl)-4-(9-(2-aza-2-carbamoyl-1-(4,4,5,5,5-pentafluoropentylamino)ethenyl)aminononyl)thiochroman

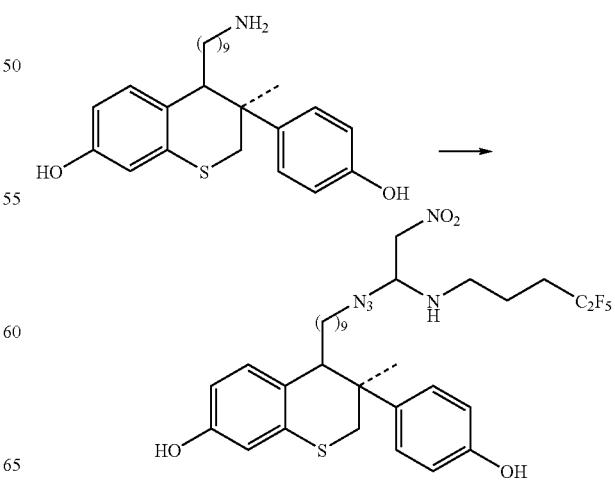

(3RS,4RS)-4-(aminononyl)-7-hydroxy-3-(4-hydroxyphenyl)-3-methylthiochroman (380 mg, 0.92 mmol) was added to acetonitrile (50 ml) and (1-methylthio-2-nitrovinyl)(4,4,5,5,5-pentafluoropentyl)amine (1.66 g, 5.61 mmol). The mixture was refluxed for 25 h under nitrogen atmosphere and then cooled to room temperature. The mixture was evaporated in vacuo. The residue was subjected to column chromatography (dichloromethane:methanol=97:3) to give 63 mg (yield: 10%) of the title compound as a yellow oil.

$^1$H-NMR (300 MHz, acetoned-6) δ 7.29 (d, 2H, J=9 Hz), 6.91 (d, 1H, J=8 Hz), 6.83 (d, 2H, J=9 Hz), 6.63 (d, 1H, J=2 Hz), 6.50 (dd, 1H, J=8 Hz, J=2 Hz), 5.59 (s, 1H), 3.62 (d, 1H, J=12 Hz), 3.41 (m, 2H), 3.29 (m, 2H), 3.00 (d 1H, J=12 Hz), 2.86 (br, 1H). 2.30 (m, 2H), 1.94 (m, 2H), 1.60 (m, 2H), 1.28 (m, 2H), 0.85–1.25 (m, 13H)

Mass (ESI) 660 (M+1)

EXAMPLE 28

Synthesis of (3RS,4RS),-7-hydroxy-3-(4-hydroxyphenyl)-methyl-4-[8-(4,4,5,5,5-pentafluoropentylsulfonylamino)octyl]chroman Step 1) Synthesis of (3RS,4RS)-4-(8-methanesulfonyloxyoctyl}7-methoxymethoxy-3-(4-methoxymethoxyphenyl)-3-methylchroman

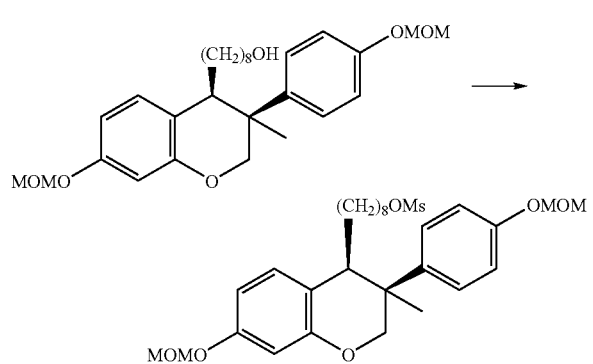

The title compound was prepared (yield: 95.6%) from (3RS,4RS)-4-(8-hydroxyoctyl)-7-methoxymethoxy-3-(4-methoxymethoxyphenyl)-3-methylchroman according to the same procedure as Step 5 of Example 7.

$^1$H-NMR (300 MHz, CDCl$_3$) δ: 7.10 (d, J=8.96 Hz, 2H), 7.01 (d, J=9.04 Hz, 2H), 6.92 (d, J=8.67 Hz, 1H), 6.56–6.53 (m, 2H), 5.15 (d, J=9.79 Hz, 4H), 4.50 (d, J=10.55 Hz, 1H), 4.24 (d, J=10.55 Hz, 1H), 4.16 (t, J=6.78 Hz, 2H), 3.47 (s, 6H), 2.63 (brd, J=8.29 Hz, 1H), 1.69–0.98 (m, 17H).

Step 2) Synthesis of (3RS,4RS)-4-(8-azidooctyl)-7-methoxymethoxy-3-(4-methoxymethoxyphenyl)-3-methylchroman

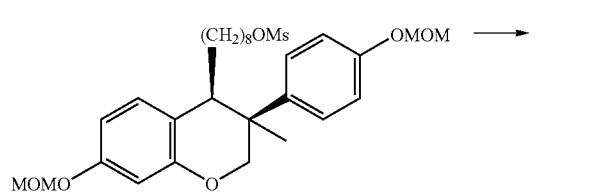

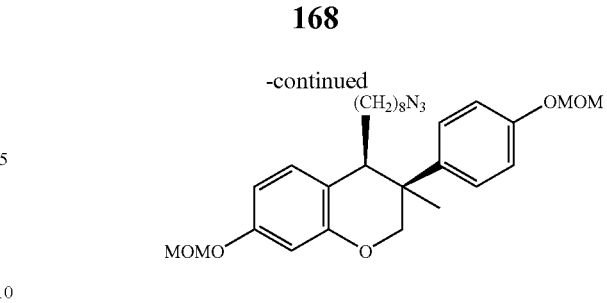

The title compound was prepared (yield: 73.2%) from (3RS,4RS)-4-(8-methanesulfonyloxyoctyl)-7-methoxymethoxy-3-(4-methoxymethoxyphenyl)-3-methylchroman according to the same procedure as Step 6 of Example 7.

$^1$H-NMR (300 MHz, CDCl$_3$) δ: 7.12 (d, J=9.04 Hz, 2H), 7.01 (d, J=8.67 Hz, 2H), 6.93 (d, J=9.04 Hz, 1H), 6.57–6.53 (m, 2H), 5.14 (d, J=9.80 Hz, 4H), 4.51 (d, J=10.55 Hz, 1H), 4.24 (dd, J=10.55 Hz, 1.88 Hz, 1H), 3.48 (d, J=1.50 Hz, 6H), 3.19 (t, J=7.16 Hz, 2H), 2.63 (brd, J=9.04 Hz, 1H), 1.55–0.98 (m, 17H).

Step 3) Synthesis of (3RS,4RS)-7-methoxymethoxy-3-(4-methoxymethoxyphenyl)-3-methyl-4-[8-(4,4,5,5,5-pentafluoropentylsulfonylamino)octyl]chroman

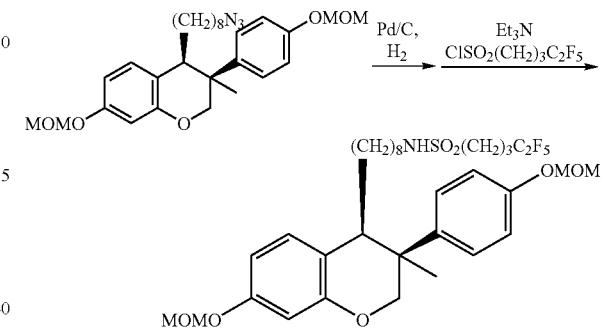

The title compound was prepared (yield: 74.6%) from (3RS,4RS)-4-(8-azidooctyl )-7-methoxymethoxy-3-(4-methoxymethoxyphenyl)-3-methylchroman according to the same procedure as Step 2 of Example 13.

$^1$H-NMR (300 MHz, CDCl$_3$) δ: 7.12 (d, J=8.67 Hz, 2H), 7.01 (d, J=9.04 Hz, 2H), 6.94–6.91 (m, 1H), 6.57–6.53 (m, 2H), 5.15 (d, J=10.93 Hz, 4H), 4.51 (d, J=10.55 Hz, 1H). 4.26–4.15 (m, 2H), 3.48 (d, J=2.26 Hz, 6H), 3.15–3.00 (m, 4H), 2.64–2.61 (brd, 1H), 12.30–2.05 (m, 4H), 1.51–0.90 (m, 17H).

Step 4) Synthesis of (3RS,4RS)-7-hydroxy-3-(4-hydroxyphenyl)-3-methyl-4-[8-(4,4,5,5,5-pentafluoropentylsulfonylamino)octyl]chroman

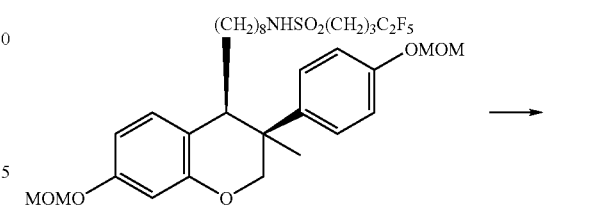

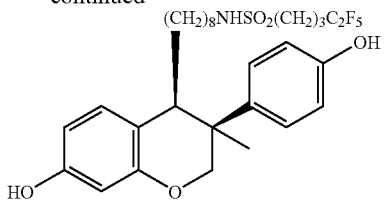

The title compound was prepared (yield: 63.3%) from (3RS,4RS)-7-methoxymethoxy-344-methoxymethoxyphenyl)-3-methyl-4-[8-(4,4,5,5,5-pentafluoropentylsulfonylamino)octyl]chroman according to the same procedure as Step 6 of Example 17.

¹H-NMR (300 MHz, CDCl₃) δ: 7.07 (d, J=8.66 Hz, 2H), 6.88 (d, J=7.53 Hz, 1H), 6.83 (d, J=8.66 Hz, 2H), 6.37–6.34 (m, 2H), 5.31 (s, 1H), 4.63 (s, 1H), 4.99 (d, J=10.17 Hz, 1H), 4.24–4.18 (m, 2H), 3.11–3.02 (m, 4H), 2.59–2.55 (m, 1H), 2.30–2.10 (m, 4H), 1.51–0.95 (m, 17H)

Mass (ESI): 608 (M+1)

EXAMPLE 29

Synthesis of (3RS,4RS)-7-hydroxy-3-(4-(hydroxyphenyl)-3-methyl-4-([4-(4-piperidylbutyloxy)phenyl]chroman Step 1) Synthesis of (3RS,4RS)-4-[4-(4-chlorobutyloxy)phenyl]-(7-(methoxymethoxy)-3-(4-(methoxymethoxy)phenyl)-3-methylchroman

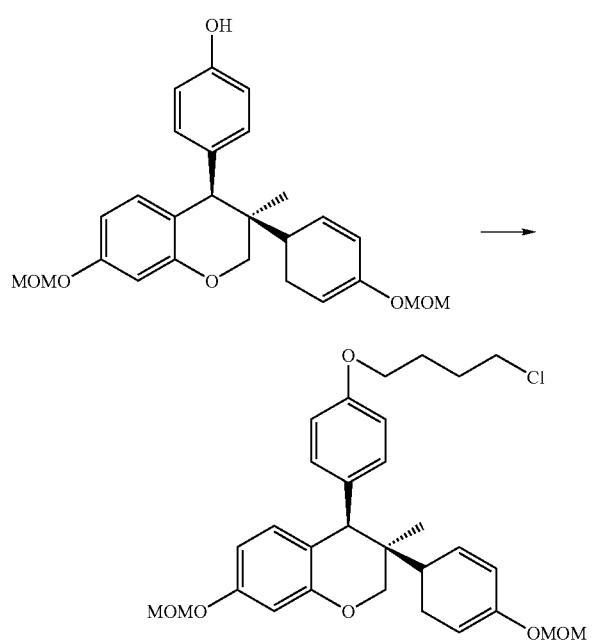

To (3RS,4RS)-4-[4-(4-hydroxyphenyl]-(7-(methoxymethoxy)-3-(4-(methoxymethoxy)phenyl)-3-methylchroman (413 mg, 0.9 mmol) and K₂CO₃ (261 mg, 1.9 mmol) in acetone (10 mL) was added 1-bromo-4-chlorobutane (436 mg, 3.6 mmol). The mixture was stirred at reflux for 5 h and then cooled to rt and poured into water. The aqueous layer was extracted with ethyl acetate. The extract was dried over MgSO₄ and filtered. The filtrate was evaporated under reduced pressure, and the concentrate thus obtained was subjected to silica gel column chromatography (n-hexane:ethyl acetate=8:1) to give 393 mg (yield. 78%) of a colorless oil ¹H-NMR (300 MHz, CDCl₃) δ: 7.17 (dd, J=8.67 Hz, 1H), 6.79 (d, 2H), 6.70 (dd, J=8.7 Hz, 2H), 6.09 (s, 1H), 6.59 (s, 1H), 6.45 (m, 2H), 6.15 (d, 1H) 5.98 (s, 1H), 5.04 (d, 4H), 4.53 (dd, J=10.5 Hz, 1H), 3.96 (dd, J=10.3, 1H), 3.84 (s, 1H), 3.79 (t, 2H), 3.55 (t, 2H), 3.45 (d, 6H), 1.95~1.82 (m, 4H), 1.43 (s, 3H)

Step 2) Synthesis of (3RS,4RS)-7-methoxymethoxy-3-(4-(methoxymethoxy)phenyl)-3-methyl-4-[4-(4-piperidylbutyloxy)phenyl]chroman

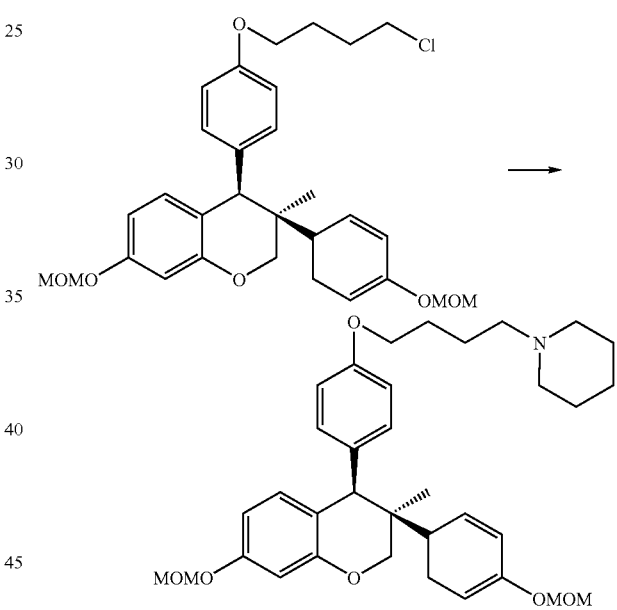

To (3RS,4RS)-4-[4-(4-chlorobutyloxy)phenyl]-(7-(methoxymethoxy)-3-(4-(methoxymethoxy)phenyl)-3-methylchroman (393 mg, 0.75 mmol) was added piperidine (738 mg, 7.5 mmol) and the mixture was refluxed for 12 h. After cooling, the mixture was extracted with ethyl acetate, dried over MgSO₄, and filtered. The filtrate was evaporated under reduced pressure, and the concentrate thus obtained was subjected to silica gel columnchromatography (CH₂Cl₂: methanol=20:1) to give 325 mg (yield: 75%) of a colorless oil.

¹H-NMR (300 MHz, MeOH-d) δ: 7.10 (dd, J=8.69 Hz, 1H), 6.78 (d, 2H), 6.71 (dd, J=8.7 Hz, 2H), 6.63 (s, 1H), 6.60 (s, 1H), 6.5 (m, 2H), 6.15 (d, 1H) 5.96 (s, 1H), 5.09 (d, 4H), 4.61 (dd, J=10.5 Hz, 1H), 3.97 (dd. J=10.6 Hz, 1H), 3.82 (s, 1H), 3.48 (t, 2H), 3.43 (t, 2H), 2.78 (t, 6H), 1.7 (m, 6H), 1.5 (m, 2H), 1.3 (s, 3H)

Step 3) Synthesis of (3RS,4RS)-7-hydroxy-3-(4-hydroxyphenyl)-3-methyl-4-[4-(4-piperidylbutyloxy)phenyl]chroman

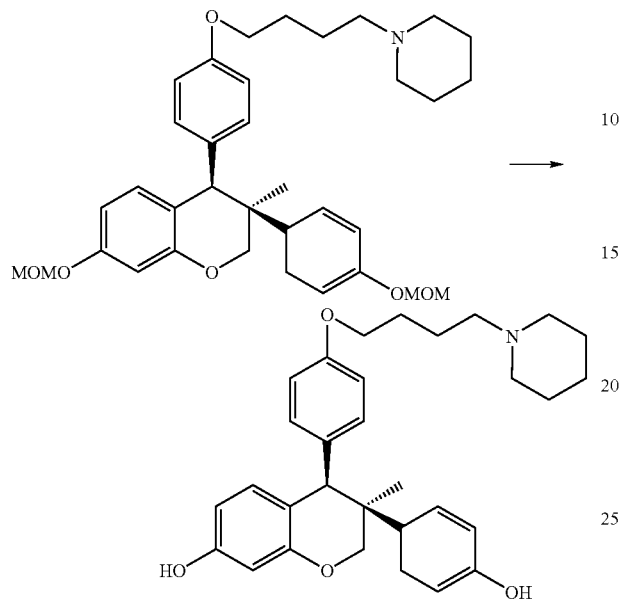

A mixture of (3RS,4RS)-7-methoxymethoxy-3-(4-(methoxymethoxy)phenyl)-3-methyl-4-[4-(4-piperidylbutyloxy) phenyl]chroman (325 mg, 0.56 mmol) p-toluenesulfonic acid (1.42 g, 5.6 mmol) and methanol was stirred at reflux for 12 h. After cooling, the mixture was extracted with ethyl acetate, dried over MgSO$_4$, and filtered. The filtrate was evaporated under reduced pressure, and the concentrate thus obtained was subjected to silica gel column chromatography (CH$_2$Cl$_2$:methanol=10:1) to give 160 mg (yield. 58%) of a white foamy solid.

$^1$H-NMR (300 MHz, MeOH-d) δ: 7.2 (dd, J=8.5 Hz, 2H), 6.7 (d, 1H), 6.48 (dd, J=8.7 Hz, 2H), 6.43 (m, 4H), 6.30 (s, 1H), 6.13 (d, 1H), 5.39 (s, 1H) 4.44 (dd, J=10.2 Hz, 1H), 3.87 (dd, J=t-0.5 Hz, 1H), 3.83 (s, 1H), 3.7 (t, 2H), 2.94 (m, 2H), 2.81 (m, 2H), 1.67 (m, 8H), 1.46 (2H), 1.3 (s, 3H).

EXAMPLE 30

Synthesis of (3RS,4RS)-7-hydroxy-3-methyl-3-(4-hydroxyphenyl)-4-(4-(3 (2-(4,4,5,5,5-pentafuoropentylsulfinyl)ethoxy)-(R)-2-hydroxypropyloxy)phenyl) chroman Step 1) Synthesis of 1-((2-oxiranyl)methoxy)-2-(4,4,5,5,5-pentafluoropentylthio)ethane

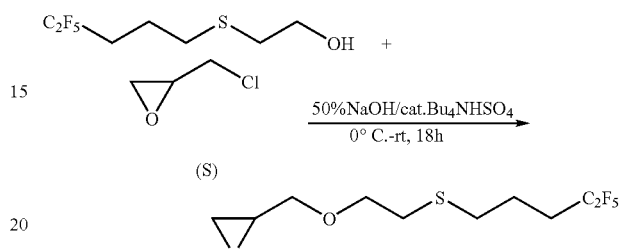

A mixture of 50% acqueous NaOH (1.85 ml), S-epichlorohydrin (1.142 g, 12.34 mmole) and t-butylammonium hydrogen sulfate (24 mg) was vigorously stirred at 0° C., for half an hour and allowed to reach room temperature. To this mixture was added 2-(4,4,5,5,5-pentafluoropentylthio) ethan-1-ol (735 mg, 3.08 mmole) at room temperature. The reaction mixture was stirred for 18 hours and quenched with water. The aqueous phase was extracted with ethyl acetate. Then, the organic layer was washed with water and saturated sodium chloride solution, dried over anhydrous magnesium sulfate, and concentrated under reduced pressure. The residue was subjected to flash chromatography on silica gel (n-hexane:ethyl acetate=7:1) to give the title compound (568 mg, yield 63%) as a colorless oil.

$^1$H-NMR (300 MHz, CDCl$_3$) δ: 3.73 (dd, 1H, J=11.3 Hz, J=2.5 Hz), 3.63 (m 2H), 3.32 (dd, 1H, J=11.3 Hz, J=5.5 Hz), 3.2 (m, 1H), 2.73 (m, 1H), 2.66 (t, 2H, J=6.3 Hz), 2.6 (t, 2H, J=7.1 Hz), 2.55 (dd, 1H, J=4.9 Hz, J=2.6 Hz), 2.16 (m, 1H), 1.88 (m 2H)

Mass (ESI): 295 (M+1), 327 (M+Na)

Step 2) Synthesis of (3RS,4RS)-7-methoxymethoxy-3-(4-methoxymethoxyphenyl)-3-methyl-4-(4-(3-(2-(4,4,5,5,5-pentafluoropentylthio)ethoxy)-(R)-2-hydroxypropyloxy) phenyl)chroman

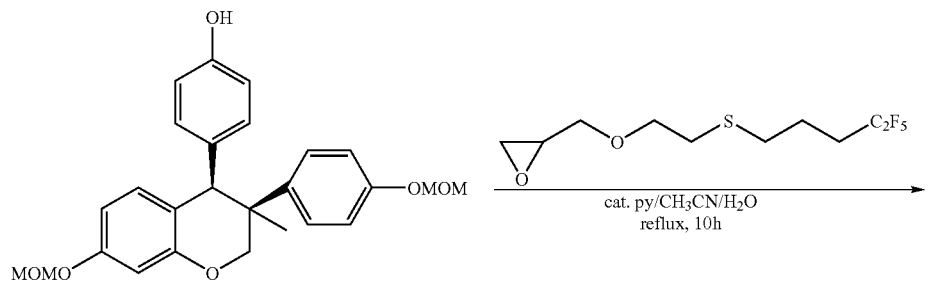

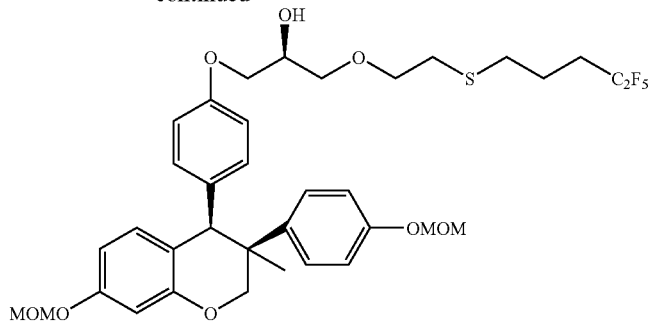

A mixture of (3RS,4RS)-7-methoxymethoxy-3-methyl-3-(4-methoxymethoxyphenyl)-4-(4-hydroxyphenyl)chroman (311 mg, 0.71 mmole), 1-((2-oxiranyl)methoxy)-2-(4,4,5,5,5-pentafluoropentylthio)ethane (568 mg, 1.93 mmole), acetonitrile (9 ml), water (3 ml) and pyridine (5 drops) was refluxed for 10 hours. After cooling, the reaction mixture was diluted with water and the aqueous phase was extracted with ethyl acetate. Then, the organic layer was washed with water and saturated sodium chloride solution, dried over anhydrous magnesium sulfate, and concentrated under reduced pressure. The residue was subjected to flash chromatography on silica gel (n-hexane:ethyl acetate=3:1) to give the title compound (448 mg, yield 86%) as a colorless oil.

$^1$H-NMR (300 MHz, CDCl$_3$) δ: 6.84 (d, 2H, J=9 Hz ), 6.78 (d, 2H, J=8.6 Hz ), 6.73 (d, 1H, J=8.6 Hz), 6.65 (d, 1H, J=3.78 Hz), 6.5 (m 5H), 5.14 (s, 2H). 5.08 (s. 2H), 4.55 (d, 1H, J=10.7 Hz, C2-H), 4.0 (m 2H), 3.9 (m, 3H), 3.6 (m, 4H), 3.48 (s, 3H), 3.43 (s, 3H), 2.69 (t, 2H, J=6.8 Hz), 2.61 (t, 2H, J=6.9 Hz), 2.5 (m, 1H), 2.15 (m 2H), 1.85 (m, 2H), 1.46 (s, 3H)

Mass (ESI): 731 (M+1)

Step 3) Synthesis of (3RS,4RS)-7-hydroxy-3-(4-hydroxyphenyl)-3-methyl-4-(4-(3-(2-(4,4,5,5,5-pentafluoropentylthio)ethoxy)-(R)-2-hydroxypropyloxy)phenyl)chroman

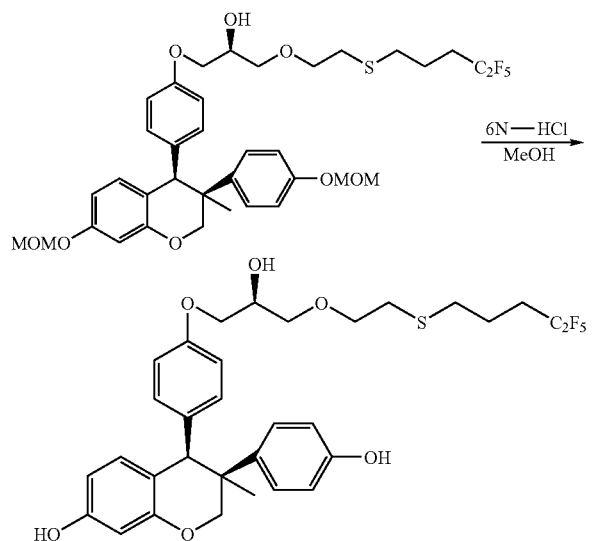

To a solution of 7-methoxymethoxy-3-(4-methoxymethoxyphenyl)-3-methyl-4-(4-(3-(2-(4,4,5,5,5-pentafluoropentylthio)ethoxy)-(R)-2-hydroxypropyloxy)phenyl)chroman (440 mg, 0.613 mmol) in methanol (9 ml) was added 6N HCl (3 ml) at room temperature, which was stirred for 40 minutes at 70° C. Water was added thereto, and the resulting solution was extracted with ethyl acetate. Then, the organic layer was washed with water and saturated sodium chloride solution, dried over anhydrous magnesium sulfate, and concentrated under reduced pressure. The residue was subjected to flash chromatography on silica gel (n-hexane:ethyl acetate=3:2) to give the title compound (269 mg, yield 68%) as a white solid.

$^1$H-NMR (300 MHz, CD$_3$OD) δ: 6.7 (d, 2H, J=6.9 Hz ), 6.46 (m 7H), 6.27 (d, 1H, J=2.4 Hz ), 6.18 (dd, 1H, J=2.4 Hz, 8.2 Hz), 4.44 (d, 1H, J=10.6 Hz, C2-H), 3.75 (m, 5H), 3.51 (t, 2H, J=6.5 Hz), 3.4 (m, 2H), 2.57 (t, 2H, J=6.5 Hz), 2.51 (t, 2H, J=7.0 Hz), 2.1 (m, 2H), 1.7 (m 2H), 1.31 (s, 3H)

Mass (ESI): 643 (M+1)

Step 4) Synthesis of (3RS,4RS)-7-hydroxy-3-(4-hydroxyphenyl)-3-methyl-4-(4-(3-(2-(4,4,5,5,5-pentafluoropentylsulfinyl)ethoxy)-R)-2-hydroxypropyloxy)phenyl)chroman

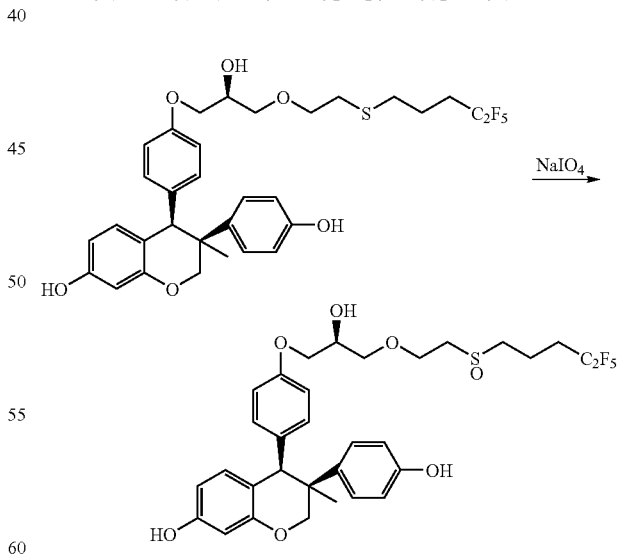

7-Hydroxy-3-(4-hydroxyphenyl)-3-methyl-4-(4-(3-(2-(4,4,5,5,5-pentafluoropentylthio)ethoxy)-(R)-2-hydroxypropyloxy)phenyl)chroman (118 mg, 0.18 mmol) was dissolved in MeOH (5 ml). Water (1 ml) and sodium periodate (59 mg, 0.28 mmol) were added thereto, and then the mixture was stirred at room temperature for 18 hours. The reaction solution was filtered, and the filtrate was concentrated. The residue was extracted with ethyl acetate, dried over anhydrous magnesium sulfate, and subjected to flash column chromatography (dichloromethane:methanol=19:1) to give the title compound (84 mg, yield 70%) as a yellow foamy solid.

$^1$H-NMR (300 MHz, CD$_3$OD) δ: 6.82 (d, 2H, J=8.6 Hz), 6.6 (m, 7H, Ar—H), 6.39 (d, 1H, J=2.3 Hz), 6.3 (dd, 1H, J=2.3 Hz, 8.3 Hz), 4.57 (d, 1H, J=10.6 Hz, C2-H), 3.8 (m 7H), 3.5 (m, 2H), 3.05 (m, 1H), 2.8 (m, 3H), 2.3 (m, 2H), 2.1 (m, 2H), 1.51 (s, 3H)

Mass (ESI): 659 (M+1)

EXAMPLE 31

Synthesis of (3RS,4RS)-7-hydroxy-3-(4-hydroxyphenyl)-3-methyl-4-{[4-(4,4,5,5,5-pentafluoropentylsulfinyl)butyloxy]butyl}chroman

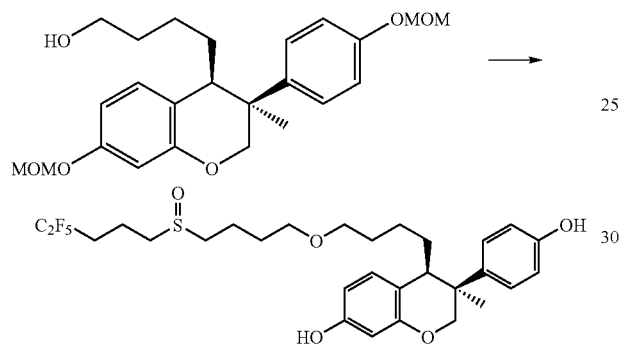

To a solution of (3RS,4RS)-4-(4-hydroxybutyl)-7-(methoxymethoxy)-3-[4-(methoxymethoxy)phenyl]-3-methyl-chroman (245 mg, 0.588 mmol) in dry THF (4 ml) were added 95% (w/w) sodium hydride (18 mg, 0.706 mmol) and 1-bromo-4-chlorobutane (0.67 ml, 5.88 mmol) at 0° C., and the mixture was stirred overnight under reflux. After the reaction was completed, the mixture was extracted with ethyl acetate: The organic layer was washed with brine, dried over anhydrous magnesium sulfate, and filtered. The organic solvent was removed under reduced pressure to give a crude intermediate (240 mg). To this crude intermediate and 4,4,5,5,5-pentafluoropentyl thioacetate (335 mg, 1.419 mmol) in methanol (4 ml)/water (2 ml) co-solvent were added sodium iodide (78 mg, 0.520 mmol) and sodium hydroxide (85 mg, 2.125 mmol), and the mixture was stirred for 18 hours under heating (50–60° C.). After the reaction was completed, the mixture was extracted with ethyl acetate. The organic layer was washed with brine, dried over anhydrous magnesium sulfate, and filtered. The organic solvent was removed under reduced pressure to obtain a crude intermediate. This crude intermediate was subjected to silica gel chromatography (n-hexane:ethyl acetate=4:1) to obtain pure intermediate (293 mg). To this intermediate in methanol (6 ml) was added c-HCl (0.6 ml), and the mixture was stirred for 3 hours under heating (50–55° C.). After the reaction was completed, the mixture was extracted with ethyl acetate. The organic layer was washed with brine, dried over anhydrous magnesium sulfate, and filtered. The organic solvent was removed under reduced pressure to obtain a crude intermediate (250 mg). To this intermediate in methanol (3 ml), water (1 ml), 1,4-dioxane (1 ml) co-solvent was added sodium periodate (105 mg, 0.490 mmol), and the mixture was stirred for 6 hours at room temperature. After the reaction was completed, the mixture was extracted with ethyl acetate. The organic layer was washed with brine, dried over anhydrous magnesium sulfate, and filtered. The organic solvent was removed under reduced pressure to obtain a crude product. This crude product was subjected to silica gel chromatography (n-hexane:ethyl acetate=1:1) to give the title product (184 mg) as solid (56%).

$^1$H-NMR (300 MHz, CDCl$_3$) δ: 7.14 (d, 2H), 6.88 (d, 1H), 6.83 (d, 2H), 6.49–6.33 (m, 2H), 4.49 (dd, 1H), 4.21 (dd, 1H), 3.26–3.09 (m, 4H), 2.87–2.72 (m, 3H), 2.68–2.54 (m, 2H), 2.33–2.08 (m, 4H), 1.83–1.02 (m, 10H), 1.26 (s, 3H)

Mass (ESI): 593 (M+1)

EXAMPLE 32

Synthesis of (3RS,4RS)-7-hydroxy-3-(4-hydroxyphenyl)-methyl-4-{5-(1N-methyl-N-[3-(4,4,5,5,5-pentafluoropentyl)sulfinyl]propyl}aminopentyl}chroman and (3RS,4RS)-7-hydroxy-3-(4-hydroxyphenyl)-methyl-4-{5-{N-methyl-N-oxo-N-[3-(4,4,5,5,5-pentafluoropentyl)sulfinyl]propyl}aminopentyl}chroman (3RS,4RS)-7-hydroxy-3-(4-hydroxyphenyl)-3-methyl ({5-{N-methyl-N-[3-(4,4,5,5,5-pentafluoropentylthio)propyl]aminopentyl}chroman (112 mg, 0.19 mmol) was dissolved in methanol (6 mL) and water (1.2 mL). Sodium periodate (50 mg, 0.23 mmol) was added thereto, and then the mixture was stirred for 13 hours at ambient temperature. Water was added and the reaction mixture was extracted with ethyl acetate. The combined organic layers were washed with brine and dried over anhydrous magnesium sulfate. The mixture was subjected to column chromatography (dichloromethane:methanol=10:1) to give the title compounds of 76.6 mg (66.6%) and 26.2 mg (22.8%) as an oil, respectively.

(3RS,4RS)-7-hydroxy-3-(4-hydroxyphenyl)-3-methyl-4-{5-{N-methyl-N-[3-(4,4,5,5,5-pentafluoropentyl)sulfiny]propyl}aminopentyl}chroman $^1$H-NMR (300 MHz, CD$_3$OD); δ 6.99 (d, J=8.67 Hz, 2H), 6.77 (d, J=8.23 Hz, 1H), 6.68 (d, J=8.68 Hz, 2H), 6.22 (dd, J=2.49 and 8.22 Hz, 1H), 6.15 (d, J=2.41 Hz, 1H), 4.40 (d, 10.50 Hz, 1H), 4.11 (dd, J=1.59 and 10.51 Hz, 1H), 2.71–2.79 (m, 4H), 2.54 (m, 1H), 2.40 (t, 2H), 2.17–2.22 (m, 4H), 2.12 (s, 3H), 2.01 (m, 2H), 1.83 (m, 2H), 1.00–1.21 (m, 11H)

Mass (ESI): M+1=606

(3RS,4RS)-7-hydroxy-3-(4-hydroxyphenyl)-3-methyl-4-{5-{N-methyl-N-oxo-N-[3-(4,4,5,5,5-pentafluoropentyl)sulfiny]propyl}aminopentyl}chroman $^1$H-NMR (300 MHz, CD$_3$OD); δ 7.01 (m, 2H), 6.81 (m, 1H), 6.66 (m, 2H), 6.13–6.25 (m, 2H), 4.42 (m, 1H), 2.63–3.08 (mi, 9H), 2.52 (m, 1H), 1.89–2.32 (m, 6H), 1.36–1.53 (m, 2H), 0.92–1.32 (m, 11H)

Mass (ESI): M+1=622

EXAMPLE 33

Synthesis of (3'RS,4'RS)-2-(4-(7-hydroxy)-3-(4-hydroxyphenyl)-3-methylchroman-4-yl)butyl-6-(4-(4,4,5,5,5-pentafluoropentyl)sulfinyl)hexanoic acid Step 1) Synthesis of 4-[4-(t-butyldimethylsilyloxy)-1-butynyl]-4-hydroxy-7-methoxymethoxy-3-(4-(methoxymethoxy)phenyl)-3-methylchroman

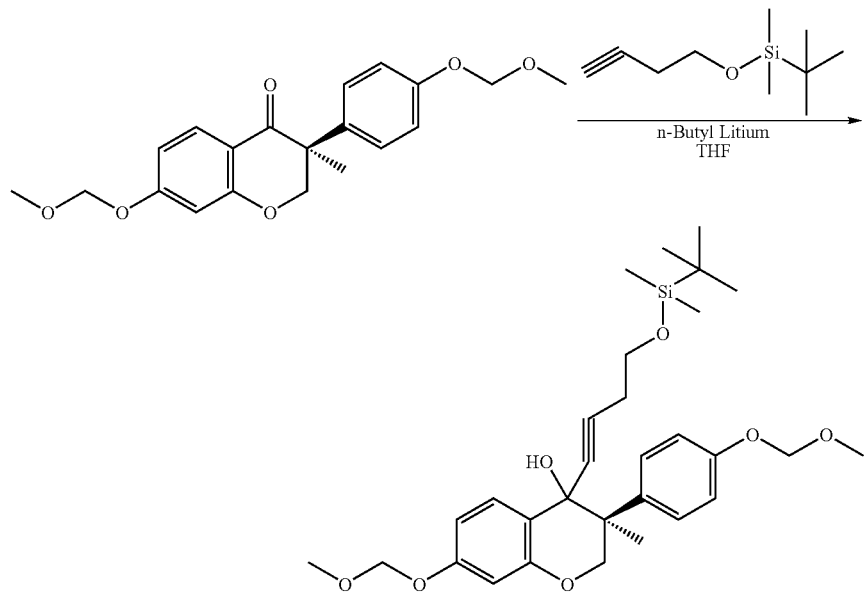

4-(t-Butyldimethylsilyloxy)-1-butyne (1.17 g, 6.4 mmol) was dissolved in dry tetrahydrofuran (20 ml) under argon atmosphere, which was then cooled down to −78° C. n-Butyllithium (2.29 ml, 5.72 mmol, 2.5M solution in tetrahydrofuran) was slowly added dropwise thereto, and the mixture was stirred at −78° C. for 30 minutes. To this mixture was added dropwise 7-methoxymethoxy-3-(4-methoxymethoxyphenyl)-3-methylchroman-4-one (1.14 g, 3.18 mmol) dissolved in dry tetrahydrofuran (10 ml) at −78° C., and the resulting reaction mixture was stirred at room temperature for 3 hours, and the reaction mixture was cooled to 0° C. The reaction was quenched with water, and the reaction solution was extracted with ethyl acetate. The organic layer was washed with water and saturated sodium chloride solution, dried over anhydrous magnesium sulfate, and concentrated. The residue was subjected to flash chromatography on silica gel (n-hexane:ethyl acetate=5:1) to give the title compound (1.6 g, yield 93%) as a colorless oil.

$^1$H-NMR (3000 MHz, CDCl$_3$) δ: 7.63 (d, 1H), 7.48 (d, 2H), 7.02 (d, 2H), 6.63 (dd, 1H), 6.53 (d, 1H), 5.15 (d, 4H), 4.9 (d, 1H), 4.15 (d, 1H), 3.75 (t, 2H), 3.5 (d, 6H), 2.49 (t, 2H), 2.1 (s, 1H), 1.5 (s, 3H), 0.9 (s, 9H), 0.08 (s, 6H)

Step 2) Synthesis of (3RS,4RS)-4-[4-(t-butyldimethylsilyloxy)-1-butyl]-7-methoxymethoxy-3-(4-(methoxymethoxy)phenyl)-3-methylchroman

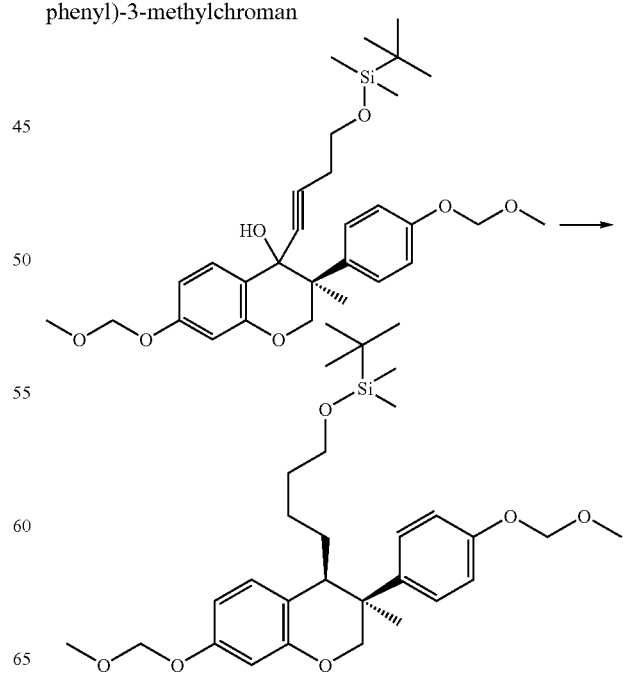

4-[4-(t-butyl dimethylsilyloxy)-1-butynyl]4-hydroxy-7-methoxymethoxy-3-(4-(methoxymethoxy)phenyl)-3-methylchroman (1.6 g, 2.95 mmol) was dissolved in ethyl acetate (30 ml), and then 10% Pd/C (0.6 g) was added thereto. The reaction suspension was stirred under hydrogen for 1 hour, filtered, and concentrated. The residue was subjected to silica gel column chromatography (n-hexane:ethyl acetate=20:1) to give the title compound (680 mg, yield 44%) as a colorless oil.

$^1$H-NMR (300 MHz, CDCl$_3$) δ: 7.25 (d, 2H), 7.05 (d, 2H), 6.98 (d, 1H), 6.6 (m, 2H), 5.2 (d, 4H), 4.55 (d, 1H), 4.3 (d, 1H), 3.53 (d, 6H), 3.45 (t, 2H), 2.7 (d, 1H), 1.4~1.08 (m, 9H), 0.9 (s, 9H), 0.07 (s, 6H)

Step 3) Synthesis of (3RS,4RS)-4-(4-hydroxybutyl)-7-methoxymethoxy-3-(4-methoxymethoxyphenyl)-3-methylchroman

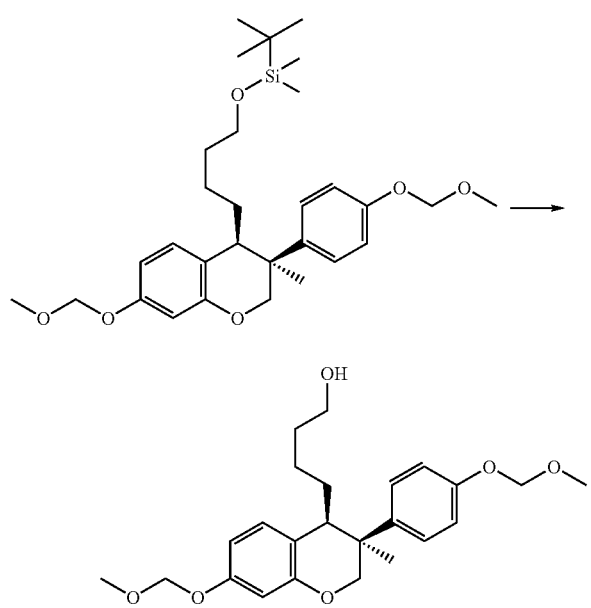

(3RS,4RS)-4-[4-(t-butyl dimethylsilyloxy)-1-butyl 3-(7-methoxymethoxy-3-(4-(methoxymethoxy)phenyl)-3-methylchroman (680 mg, 1.28 mmol) was dissolved in tetrahydrofuran (10 ml), and cooled to 0° C. To this solution was added tetrabutylammonium fluoride (2.6 ml, 2.56 mmol), and the reaction mixture was stirred at room temperature for 6 hours The solvent was removed by evaporation under vacuum, and the residue was dissolved in ethyl acetate, which was washed with water. The organic layer was separated, dried over anhydrous magnesium sulfate, and concentrated under reduced pressure. The product was purified by column chromatography on silica gel, eluting with 30% ethyl acetate in n-hexane to afford 487 mg of the title compound as a colorless oil. (yield: 92.4%)

$^1$H-NMR (300 MHz, CDCl$_3$) δ: 7.1 (d, 2H), 7.0 (d, 2H), 6.92 (d, 1H), 6.55 (m, 2H), 5.15 (d, 4H), 4.5 (d, 1H), 4.25 (d, 1H), 3.48 (d, 6H), 3.45 (d, 2H), 2.65 (d, 1H), 1.4~1.0 (m, 9H)

Step 4) synthesis of (3RS,4RS)-4-(4-methansulfonyloxybutyl)-7-methoxymethoxy-3-(4-methoxymethoxyphenyl)-3-methylchroman

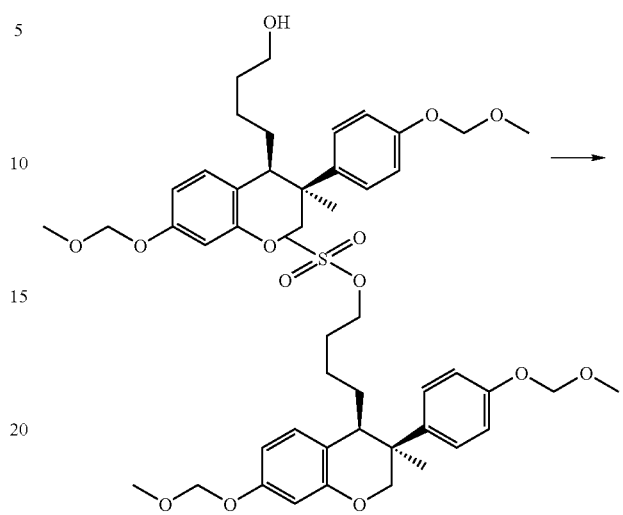

Hydroxy compound (487 mg, 1.17 mmol) was dissolved in dichloromethane (10 ml) and cooled to 0° C., to which were added triethylamine (0.41 ml, 2.9 mmol) and methanesulfonyl chloride (0.23 ml, 2.9 mmol). The reaction mixture was stirred at room temperature for 1.5 hour. After the reaction was completed, water was added to the reaction solution, and the resulting mixture was extracted with methylene chloride. The organic layer was washed with 1M HCl solution, water and saturated sodium chloride solution, dried over anhydrous magnesium sulfate, and concentrated. The product was purified by column chromatography on silica gel, eluting with 50% ethyl acetate in n-hexane to afford 578 mg of the title compound as a colorless oil. (yield: quant.)

$^1$H-NMR (300 MHz CDCl$_3$) δ 7.1 (d, 2H), 7.03 (d, 2H), 6.93 (d, 1H), 6.58 (m, 2H), 5.28 (d, 4H), 4.5 (d, 1H), 4.38 (d, 1H), 4.02 (t, 2H), 3.5 (d, 6H), 2.9 (s, 3H), 2.65 (d, 1H), 1.4~1.1 (m, 9H)

Step 5) Synthesis of (3RS,4RS)-4-(4-iodobutyl)-7-methoxymethoxy-3-(4-(methoxymethoxy)phenyl)-3-methylchroman

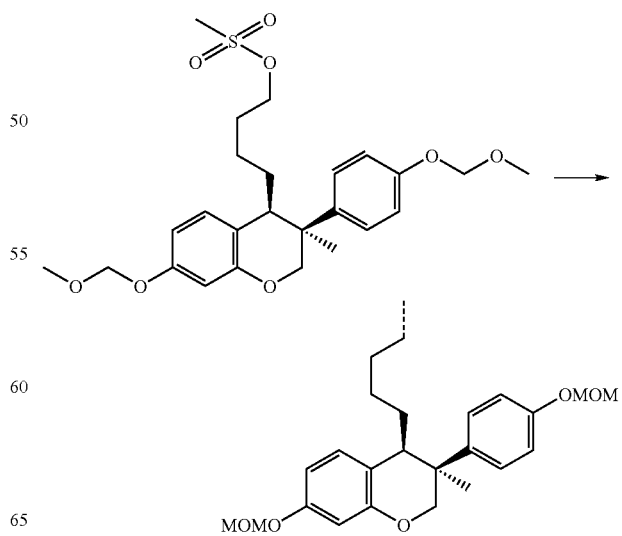

Mesylated compound (578 mg, 1.17 mmol) was dissolved in acetone (15 ml). To the reaction solution was added sodium iodide (0.87 g, 5.8 mmol). The reaction mixture was heated at reflux temperature, with stirring, for 3 hours and then allowed to cool to ambient temperature, then concentrated under reduced pressure in order to remove all of the acetone the residue was dissolved in ethyl acetate and filtrated. The organic solvent was removed by evaporation under vacuum. This product was purified by column chromatography on silica gel, eluting with 10% ethyl acetate in n-hexane to afford 539 mg of the title compound as a colorless oil. (yield: 87.5%)

$^1$H-NMR (300 MHz CDCl$_3$) δ: 7.12 (d, 2H), 7.0 (d, 2H), 6.9 (d, 1H), 6.53 (m, 2H), 5.15 (d, 4H), 4.5 (d, 1H), 4.28 (d, 1H), 3.5 (d, 6H), 3.0 (t, 2H), 2.65 (d, 1H), 1.4~1.1 (m, 9H)

Step 6) Synthesis of 4-(phenylmethoxy)butane-1-ol

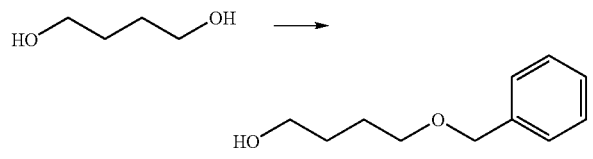

To a solution of diol compound (4.51 g, 50 mmol) in dry THF (50 ml) was added 60% NaH (1.6 g, 43 mmol) at 0° C. After stirring for 2 hours, benzyl bromide (5.7 g, 33 mmol) was added dropwise and stirred for 15 hours. After the reaction was completed, ice-water was added, and the mixture was extracted with ethyl acetate. The organic layer was washed with brine, dried over anhydrous sodium sulfate, and filtered. The organic solvent was removed under reduced pressure to give a crude product. This crude product thus obtained was subjected to silica gel column chromatography (n-hexane:ethyl acetate=10:1) to give the title compound (936 mg, yield: 16%).

$^1$H-NMR (300 MHz, CDCl$_3$) δ: 7.35 (m, 5H), 4.5 (s, 2H), 3.6 (t, 2H), 3.5 (t, 2H), 2.05 (bs, 1H), 1.7 (m, 4H)

Step 7) Synthesis of (methylsulfonyl)oxy(4-(phenylmethoxy)butane

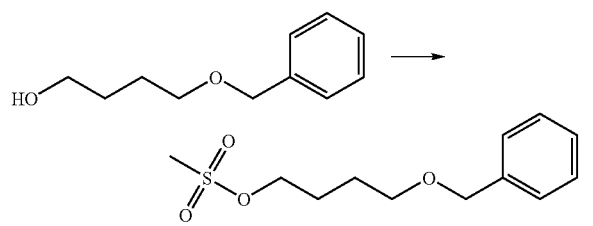

4-(Phenylmethoxy)butane-1-ol (936 mg, 5.2 mmol) was dissolved in dichloromethane (10 ml), to which were added triethylamine (1.8 ml, 13 mmol) and methanesulfonyl chloride (0.8 ml, 10.4 mmol). The reaction mixture was stirred at room temperature for 1 hour. After the reaction was completed, water was added to the reaction solution, and the resulting mixture was extracted with methylene chloride. The organic layer was washed with 1M HCl solution, water and saturated sodium chloride solution, dried over anhydrous magnesium sulfate, and concentrated. The product was purified by column chromatography on silica gel, eluting with 30% ethyl acetate in n-hexane to afford 1.34 g of the title compound as a colorless oil. (yield: quant)

Step 8) Synthesis of 4-iodo-1-(phenylmethoxy)butane

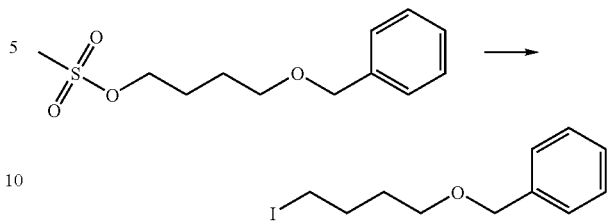

Mesylated compound (1.34 g, 5.2 mmol) was dissolved in acetone (30 ml). To the reaction solution was added sodium iodide (2.33 g, 15.5 mmol). The reaction mixture was stirred at reflux, for 14 hours and then allowed to cool to ambient temperature, then concentrated under reduced pressure. The residue was dissolved in ethyl acetate and filtrated. The organic solvent was removed by evporation under vacuum. This product was purified by column chromatography on silica gel, eluting with 5% ethyl acetate in n-hexane to afford 1.28 g of the title compound as a colorless oil. (yield: 85%)

$^1$H-NMR (300 MHz, CDCl$_3$) δ: 7.32 (m, 5H), 4.5 (s, 2H). 3.48 (t, 2H), 3.2 (t, 2H), 1.9 (m, 2H), 1.7 (m, 2H)

Step 9) Synthesis of diethyl 2-(4-(phenylmethoxy)butyl)propane-1,3-dioate

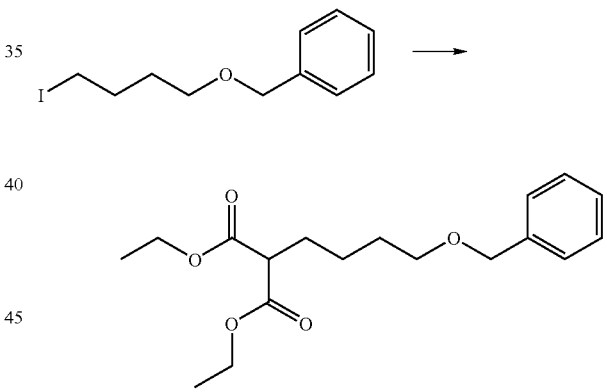

To a solution of diethyl malonate (0.4 g, 2.5 mmol) in dry THF (5 ml) was added 60% NaH (95 mg, 2.4 mmol) at room temperature. After stirring for 10 minutes, iodide compound (0.6 g, 2.07 mmol) was added and stirred at 50° C. for 2.5 hours. After the reaction was completed, the reaction mixture was cooled to room temperature ice-water was added, and the mixture was extracted with ethyl acetate. The organic layer was washed with brine, dried over anhydrous sodium sulfate, and filtered. The organic solvent was removed under reduced pressure to give a crude product. This crude product thus obtained was subjected to silica gel column chromatography (n-hexane:ethyl acetate=10:1) to give the title compound (621 mg, yield: 93%).

$^1$H-NMR (300 MHz, CDCl$_3$) δ: 7.32 (m, 5H), 4.5 (s, 2H), 4.2 (q, 4H), 3.97 (t, 2H), 3.8 (t, 1H), 1.9 (m, 2H), 1.6 (m, 2H), 1.4 (m, 2H), 1.25 (t, 6H)-

Step 10) Synthesis of (3RS,4RS)-diethyl2-(4-hydroxybutyl)-2-(4-[7-methoxymethoxy-3-(4-(methoxymethoxy)phenyl)-3-methylchroman-4-yl]butyl}-2-(4-phenoxybutyl)propan-1,3-dioate Step 11) Synthesis of (3RS,4RS)-diethyl2-(4-hydroxybutyl)-2-(4-(7-(methoxymethoxy)-3-(4-(methoxymethoxy)phenyl)-3-methylchroman-4-yl)butyl)propane-1,3-dioate

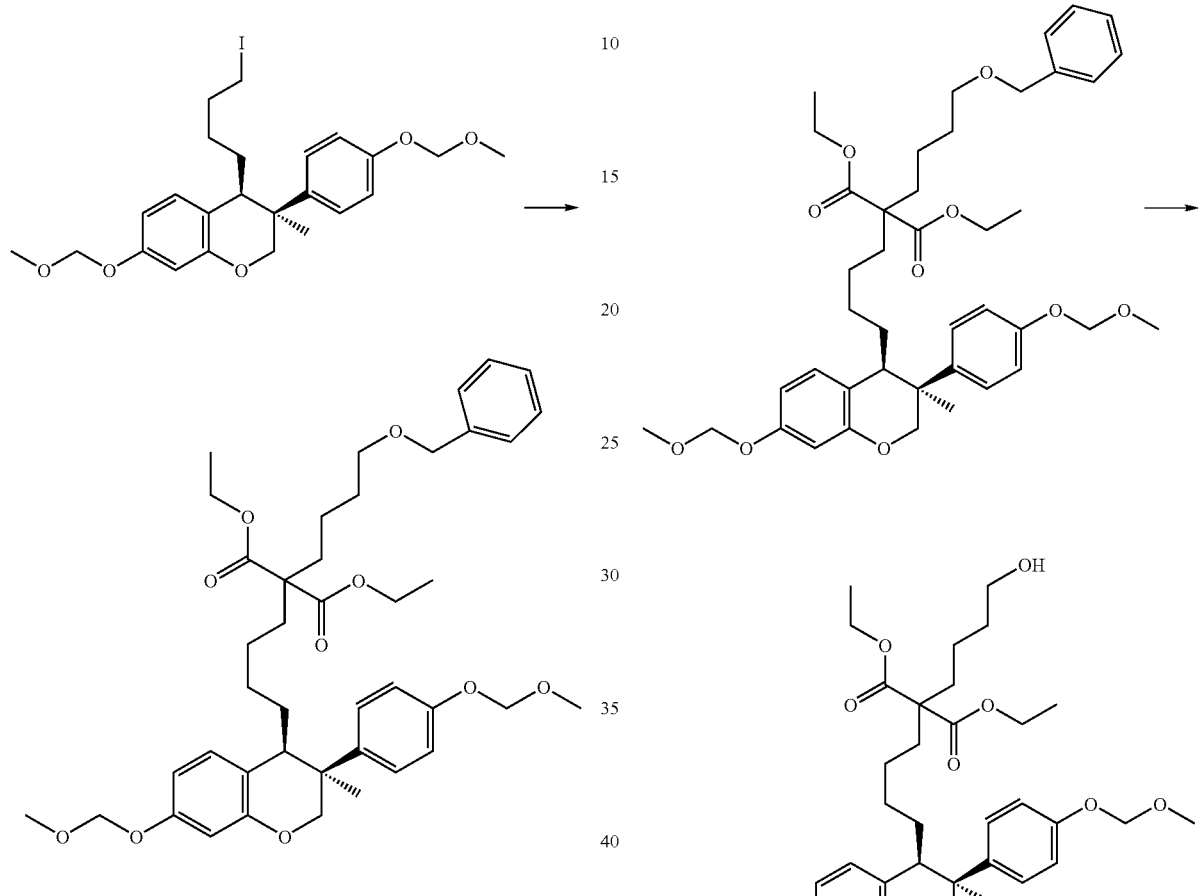

To a solution of the compound prepared in Step 5 (322 mg, 0.99 mmol) in dry THF (15 ml) was added 60% NaH (200 mg, 1.65 mmol) at room temperature. After stirring for 10 minutes, iodide compound (175 mg, 0.33 mmol) was added and the mixture was stirred for 20 hours at room temperature. After the reaction was completed, ice-water was added, and the mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane:ethyl acetate=5:1) to give the title compound (230 mg, yield: 97%).

$^1$H-NMR (300MHz, CDCl$_3$) δ: 7.3 (d, 5H), 7.1 (d, 2H), 7.0 (d, 2H), 6.9 (d, 1H), 6.53 (m, 2H), 5.1 (d, 4H), 4.5 (d, 1H), 4.43 (s, 2H), 4.2 (d, 1H), 4.1 (m, 4H), 3.47 (s, 6H), 3.4 (t, 2H), 2.6 (d, 1H), 1.8 (m, 2H), 1.7 (m, 2H), 1.55 (m, 2H) 1.3~1.15 (m, 17H)

(3RS,4RS)-diethyl2-(4-hydroxybutyl)-2-{4-[7-methoxymethoxy-3-(4-(methoxymethoxy)phenyl)-3-methylchroman-4-yl]butyl}-2-(4-phenoxybutyl)propan-1,3-dioate (442 mg, 0.613 mmol) was dissolved in abs. EtOH (15 ml), and then 10% Pd/C (0.25 g) was added thereto. The reaction suspension was stirred under hydrogen for 2 hours, filtered, and concentrated. The residue was subjected to silica gel column chromatography (n-hexane:ethyl acetate=3:1) to give the title compound (344 mg, yield: 89.0%) as a colorless oil.

$^1$H-NMR (300 MHz, CDCl$_3$) δ: 7.12 (d, 2H), 7.02 (d, 2H), 6.92 (d, 1H), 6.55 (m, 2H), 5.25 (d, 4H), 4:5 (d, 1H), 4.25 (d, 1H), 4.1 (m, 4H), 3.6 (t, 2H), 3.48 (s, 6H), 2.6 (d, 1H), 1.8 (m, 2H), 1.7 (m, 2H), 1.5 (m, 2H), 1.3~1.0(m, 17H)-

Step 12) Synthesis of diethyl (3RS,4RS)-2-(4-(7-(methoxymethoxy)-3-(4-(methoxymethoxy)phenyl)-3-methylchroman-4-yl)butyl)-2-(4-(methylsulfonyloxybutyl)propane-1,3-dioate Step 13) Synthesis of diethyl (3RS,4RS)-2-(4-(7-(methoxymethoxy)-3-(4-(methoxymethoxy)phenyl)-3-methylchroman-4-yl)butyl)-2-(4-(4,4,5,5,5-pentafluoropentylthio)butyl)propane-1,3-dioate

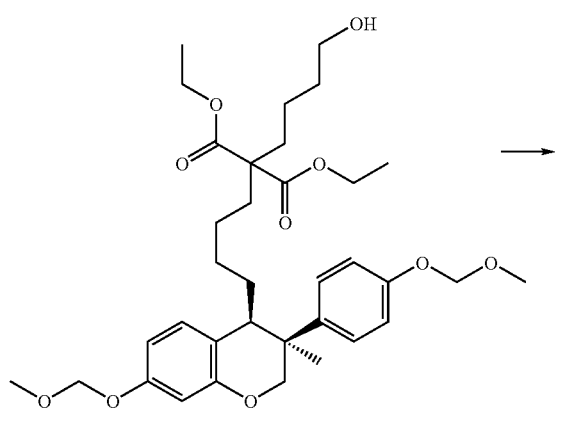

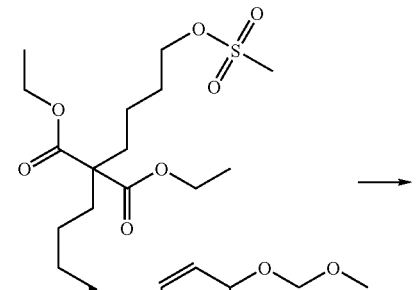

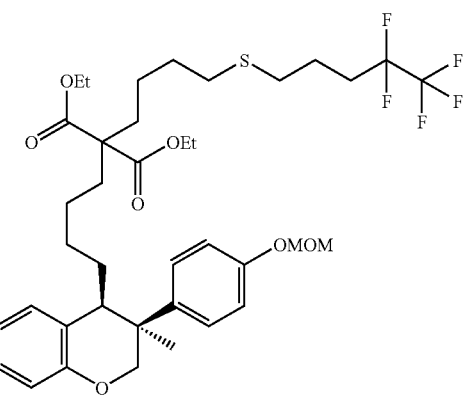

Hydroxy compound (344 mg, 0.545 mmol) was dissolved in dichloromethane (15 ml), to which were added triethylamine (0.19 ml, 1.36 mmol) and methanesulfonyl chloride (0.084 ml, 1.1 mmol). The reaction mixture was stirred at room temperature for 1 hour. After the reaction was completed, water was added to the reaction solution, and the resulting mixture was extracted with methylene chloride. The organic layer was washed with 1M HCl solution, water and saturated sodium chloride solution, dried over anhydrous magnesium sulfate, and concentrated. The product was purified by column chromatography on silica gel, eluting with 30% ethyl acetate in n-hexane to afford 374 mg of the title compound as a colorless oil. (yield: 97.0%)

$^1$H-NMR (300 MHz CDCl$_3$) δ: 7.15 (d, 2H), 7.0 (d, 2H), 6.92 (d, 1H), 6.58 (m, 2H), 5.18 (d, 4H), 4.52 (d, 1H), 4.25 (d, 1H), 4.2~4.15 (m, 6H), 3.48 (s, 6H), 2.98 (s, 3H), 2.62 (d, 1H), 1.85–1.48 (m, 6H), 1.3~1.0 (m, 17H)

1-(4,4,5,5,5-Pentafluoropentylthio)ethan-1-one (369 mg, 1.56 mmol) was dissolved in MeOH (1.3 ml). 2N-NaOH (0.8 ml) was added thereto, and the mixture was stirred at room temperature for 30 minutes. Mesylated compound (360 mg, 0.52 mmol) dissolved in MeOH (10.3 ml) was added thereto, which was then stirred at 60° C. for 1 hour. The reaction solution was cooled down to room temperature, water was added, and the resulting mixture was extracted with ethyl acetate. The organic extract was dried over anhydrous magnesium sulfate, and concentrated under reduced pressure. The residue was subjected to flash column chromatography (n-hexane:ethyl acetate=5:1) to give the title compound (390 mg, yield: 93%) as a colorless oil.

$^1$H-NMR (300 MHz, CDCl$_3$) δ: 7.15 (d, 2H), 7.0 (d, 2H), 6.9 (d, 1H), 6.55 (m, 2H), 5.15 (d, 4H), 4.5 (d, 1H), 4.25 (d, 1H), 4.1 (m, 4H), 3.5 (s, 6H), 2.65 (d, 1H), 2.55 (t, 2H), 2.45 (t, 2H), 2.2 (m, 2H), 1.9~1.6 (m, 6H), 1.5 (m, 2H), 1.3~1.0 (m, 17H)

Step 14) Synthesis of (3'RS,4'RS)-4-(7-(methoxymethoxy)-3-(4-(methoxymethoxy)phenyl)-3-methylchroman-4-yl)butyl)(4-(4,4,5,5,5-pentafluoropentylthio)butyl)methan-1,1-dicarboxylic acid

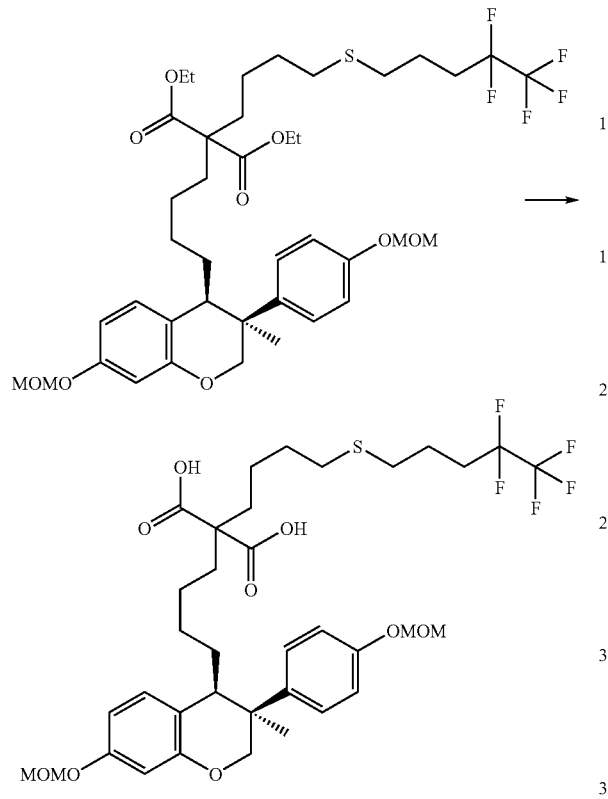

A soluton of dioate (386 mg, 0.48 mmol) and 85% KOH (1.26 g, 19.2 mmol) in ethanol (10 ml) and H₂O (5 ml) was held at reflux for 14 hours. After cooling, aqueous 1N HCl solution was added to adjust to pH 4~5. The reaction mixture was extracted with EA and concentrated under reduced pressure to give a crude title compound (345 mg, 96%) as a white foam.

¹H-NMR (300 MHz, CDCl₃) δ: 7.15 (d, 2H), 7.0 (d, 2H), 6.9 (d, 1H), 6.5 (m, 2H), 5.2 (m, 4H), 4.5 (d, 1H), 4.3 (d, 1H), 3.5 (m, 6H), 2.65 (d, 1H), 2.52 (m, 2H), 2.48 (m, 2H), 2.2 (m, 21, 1.85 (m, 4H), 1.7 (m, 2H), 1.5 (m, 2H), 1.3~1.0 (m, 11H)

Step 15) Synthesis of (3'RS,4'RS)-6-(7-hydroxy)-3-(4-hydroxyphenyl)-3-methylchroman-4-yl)-2-(4-(4,4,5,5,5-pentafluoropentylthio)butyl)hexanoic acid

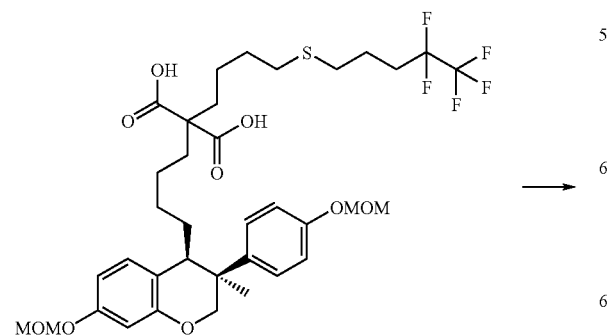

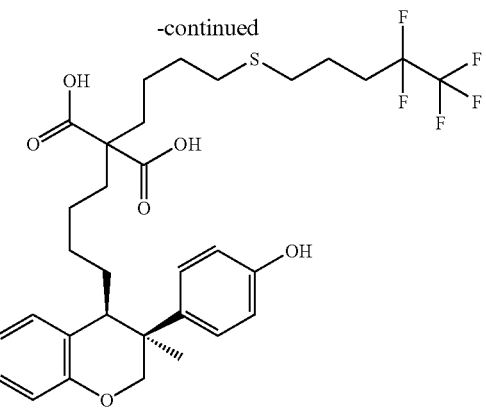

(3'RS,4'RS)-4-(7-(methoxymethoxy)-3-(4-(methoxymethoxy)phenyl)-3-methylchroman-4-yl)butyl)(4-(4,4,5,5,5-pentafluoropentylthio)butyl)methan-1,1-dicarboxylic acid (345 mg, 0.46 mmol) was dissolved in hydrochloric acid/methanol (10 ml), which was then stirred at 50° C. for 2 hours. The reaction solution was cooled down to room temperature, water was added, and the resulting mixture was extracted with ethyl acetate. The organic extract was dried over anhydrous magnesium sulfate, and concentrated under reduced pressure to give the title compound (310 mg, yield: quant) as a white foam ¹H-NMR (300 MHz, CDCl₃+CD₃OD) δ: 7.15 (d, 2H), 6.9 (d, 1H), 6.8 (d, 2H), 6.45 (m, 2H), 4.5 (d, 1H), 4.2 (d, 1H), 2.7~2.4 (m, 5H), 2.2 (m, 2H), 1.95~1.65 (m, 6H), 1.15 (m, 2H). 1.3~1.0 (m, 11H)

Step 16) Synthesis of 6-(7-(methoxymethoxy)-3-(4-(methoxymethoxy)phenyl)-3-methylchroman-4-yl)-2-(4-(4,4,5,5,5-pentafluoropentylthio)butyl)hexanoic acid

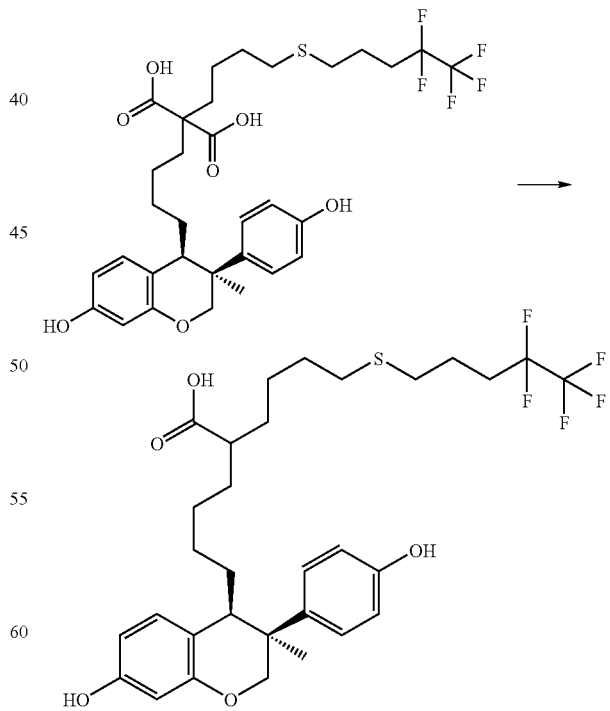

A solution of diacid (295 mg, 0.445 mmol) in toluene (50 ml) was held at reflux for 80 hours. After cooling, the organic solvent was removed under reduced pressure. The residue was subjected to column chromatography (EA: Hex=1:1) to give the target compound (271 mg, 95%) as a white foam.

$^1$H-NMR (300 MHz, CD$_3$OD) δ: 7.0 (d, 2H), 6.75 (d, 1H), 6.68 (d, 2H), 6.2 (m, 2H), 4.4 (d, 1H), 4.1 (d, 1H), 2.55 (m, 3H), 2.45 (m, 2H), 2.2 (m, 3H), 1.75 (m, 2H), 1.6~0.9 (m, 17H)

Mass (ESI): 619 (M+1)

Step 17) Synthesis of (3RS,4'RS)-2-(4-(7-hydroxy)-3-(4-hydroxyphenyl)-3-methylchroman-4-yl)butyl-6-(4-(4,4,5,5,5-pentafluoropentyl)sulfinyl)hexanoic acid

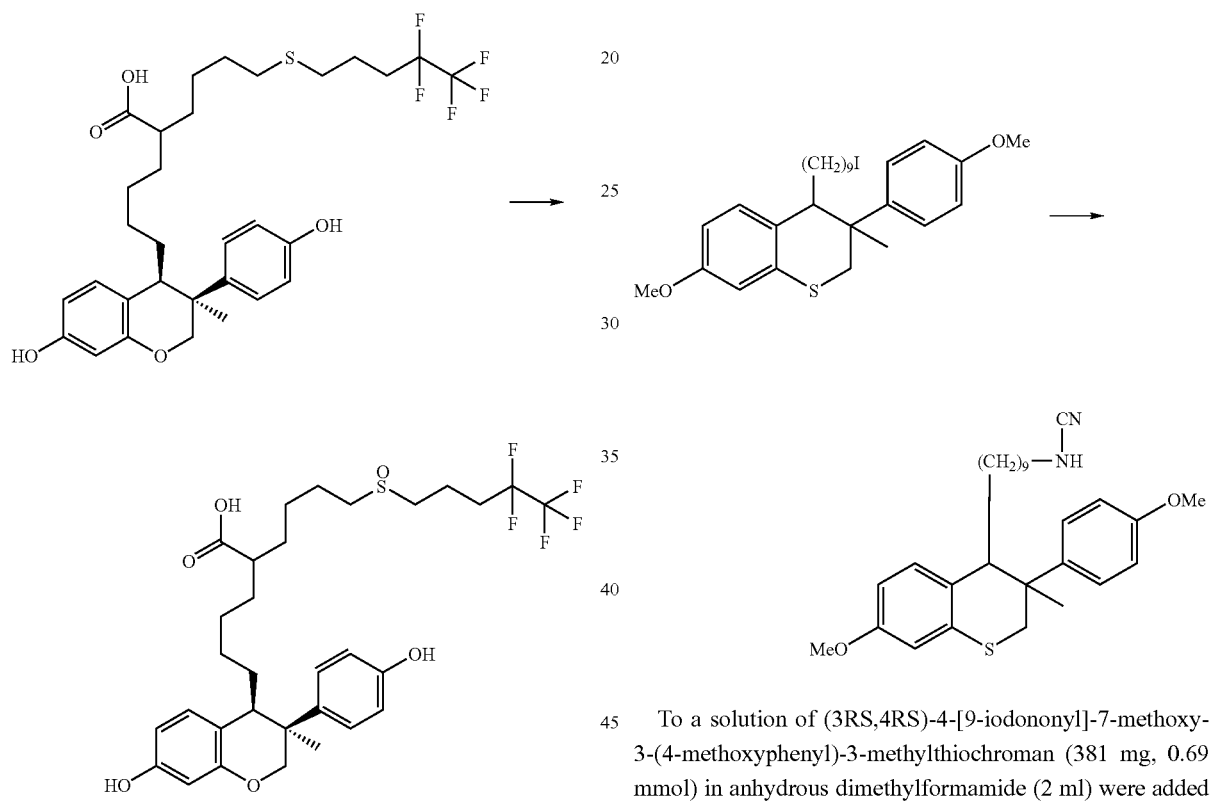

(3'RS,4'RS)-6-(7-(methoxymethoxy)-3-(4-(methoxymethoxy)phenyl)-3-methylchroman-4-yl)-2-(4-(4,4,5,5,5-pentafluoropentylthio)butyl)hexanoic acid (163 mg, 0.26 mmol) was dissolved in MeOH (1 ml) and 1,4-dioxane (1 ml). Water (0.25 ml) and sodium periodate (67 mg, 0.3 mmol) were added thereto, and then the mixture was stirred under the atmosphere of normal temperature for 4 hours. The reaction solution was filtered, and the filtrate was concentrated. The residue was extracted with ethyl acetate, dried over anhydrous magnesium sulfate, and subjected to flash column chromatography (methanol:ethyl acetate=1:40) to give the title compound (130 mg, yield: 78%) as a white foamy solid.

$^1$H-NMR (300 MHz, CD$_3$OD) δ: 7.0 (d, 2H), 6.75 (d, 1H), 6.6 (d, 2H), 6.2 (m, 2H), 4.4 (d, 1H), 4.1 (d, 1H), 2.75 (m, 4H), 2.5 (d, 1H), 2.3 (m, 2H), 2.0 (m, 3H), 1.65 (m, 2H), 1.5~0.9 (m, 12H)

Mass (ESI): 635(M+1)

EXAMPLE 34

Synthesis of (3RS,4RS)-7-hydroxy-3-(4-hydroxyphenyl)-3-methyl-4-[9-(N-cyano-N-pentylcarbonyl)aminononyl]thiochroman Step 1) synthesis of (3RS,4RS)-4-[9-(N-cyano)aminononyl]-7-methoxy-3-(4-methoxyphenyl)-3-methylthiochroman To a solution of (3RS,4RS)-4-[9-iodononyl]-7-methoxy-3-(4-methoxyphenyl)-3-methylthiochroman (381 mg, 0.69 mmol) in anhydrous dimethylformamide (2 ml) were added potassium carbonate (238 mg, 1.72 mmol) and cyanoamide (116 mg, 2.76 mmol), which was then stirred for 4 h at 50° C. Water was added thereto, and the resulting solution was extracted with ethyl acetate. Then, the organic layer was washed with water and saturated sodium chloride solution. The extract was dried over anhydrous magnesium sulfate and concentrated under reduced pressure. The residue was subjected to silica gel column chromatography (n-hexane: ethyl acetate=3:1) to give the title compound (238 mg, yield 74%) as a colourless oil.

$^1$H-NMR (300 MHz, CD$_3$OD) δ: 7.28 (m, 2H), 6.92–6.87 (m, 3H), 6.71 (m, 1H), 6.56 (m, 1H), 3.78 (s, 3H), 3.72 (s, 3H), 3.62 (m, 1H), 3.47 (m, 1H), 3.05–2.96 (m, 3H), 2.69 (bs, 1H), 1.52 (m, 2H), 1.28–0.92 (m, 17H)-

Step 2) Synthesis of (3RS,4RS)-7-methoxy-3-(4-methoxyphenyl)-3-methyl-4-[9-(N-cyano-N-pentylcarbonyl)aminononyl]thiochroman

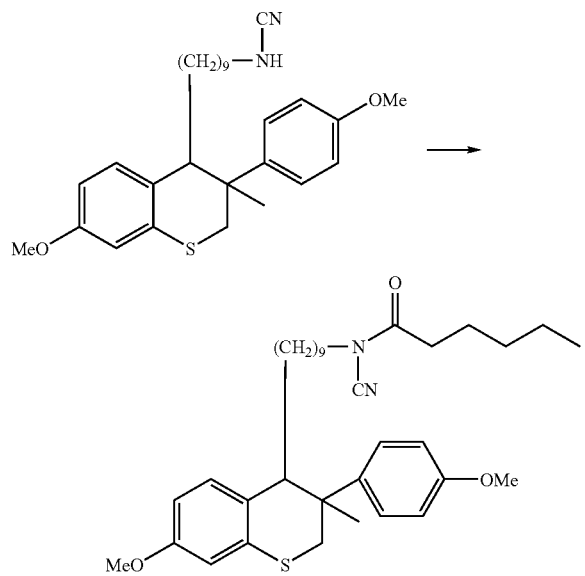

To a solution of (3RS,4RS)-4-[9-(N-cyano)aminononyl]-7-methoxy-3-(4-methoxyphenyl)-3-methylthiochroman (238 mg, 0.51 mmol) in anhydrous acetonitrile (2 ml)) were added diusopropylethylamine (0.186 ml, 1.07 mmol) and hexanoylchloride (0.086 ml, 0.61 mmol), which was then stirred for 10 min at 0° C. When the reaction was completed, water was added to the reaction mixture and extracted with ethyl acetate. Then, the organic layer was washed with water and 1N-HCl solution. The extract was dried over anhydrous magnesium sulfate and concentrated under reduced pressure. The residue was subjected to silica gel column chromatography (n-hexane:ethyl acetate=7:1) to give the title compound (288 mg, yield: 99%) as a colourless oil.

$^1$H-NMR (300 MHz, CDCl$_3$) δ: 7.27 (m. 2H), 6.93–6.88 (m, 3H), 6.72 (n, 1H), 6.55 (m, 1H), 3.78 (s, 3H), 3.71 (s, 3H), 3.62 (dd, 1H), 3.49 (t, 3H), 2.98 (dd, 1H), 2.70 (bs, 1H), 2.59 (t, 2H), 1.70–1.52 (m, 4H), 1.34–0.88 (m, 24H)

Mass (ESI): 587 (M$^+$+Na)

Step 3) Synthesis of (3RS,4RS)-7-hydroxy-3-(4-hydroxyphenyl)-3-methyl-4-[9-(N-cyano-N-pentylcarbonyl)aminononyl]thiochroman

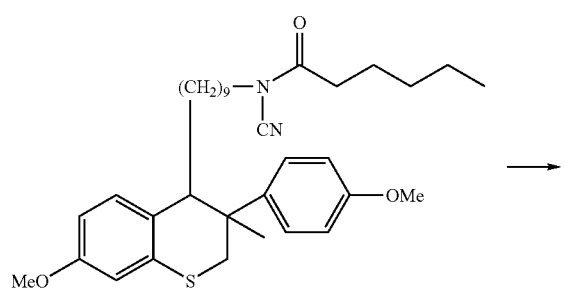

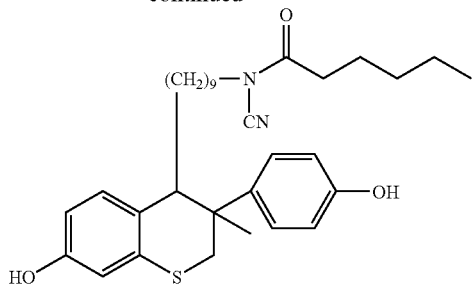

The title compound was prepared from (3RS,4RS)-7-methoxy-3-(4-methoxyphenyl)-3-methyl-4-[9-(N-cyano-N-pentylcarbonyl)aminononyl]thiochroman according to the same procedure as step 3 of Example 8.

$^1$H-NMR (300 MHz, CD$_3$OD) δ: 7.16 (m, 2H), 6.76 (m, 1H), 6.68 (m, 2H), 6.47 (m, 1H), 6.35 (m, 1H), 3.54–3.42 (m, 3H), 2.88 (m, 1H), 2.63 (m, 1H), 2.50 (t, 2H), 1.61–1.42 (m, 4H), 1.34–0.79 (m, 24H)

Mass (ESI): 537 (M$^+$+1)

EXAMPLE 35

Synthesis of (3RS,4RS)-7-hydroxy-3-(4-(hydroxyphenyl)-3-methyl-4-[5-oxa-9-(4,4,5,5,5-pentafluoropentylsulfonylamino)nonyl]chroman Step 1) Synthesis of (3RS,4RS)-4-(9-bromo-5-oxanonyl)-7-methoxymethoxy-3-(4-(methoxymethoxy)phenyl)-3-methylchroman

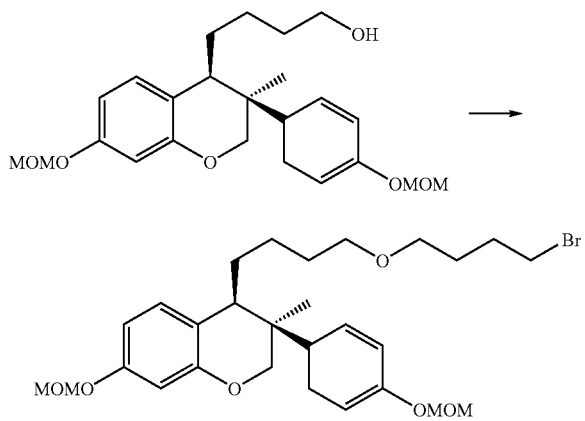

To a solution of alcohol compound (400 mg, 0.96 mmol) in dry tetrahydrofuran (5 mL) was added sodium hydride (27 mg, 1.1 mmol) at 0° C. After stirring for 30 minutes, 1,4-dibromobutane (2.07 g, 9.6 mmol) was added, and the resulting mixture was refluxed for 2 days. After the reaction was completed, water was added and the aqueous layer was extracted with ethyl acetate. The extract was dried over MgSO$_4$ and filtered. The filtrate was evaporated under reduced pressure, and the concentrate thus obtained was subjected to silica gel column chromatography (n-hexane:ethyl acetate=8:1) to give 276 mg (yield. 52%) of a colorless oil.

$^1$H-NMR (300 MHz, CDCl$_3$) δ: 7.04 (dd, J=8.6 Hz, 2H), 6.95 (m, 3H), 6.6 (d, 2H), 5.16 (d, 4H), 4.53 (dd, J=10.2 Hz, 1H), 4.26 (dd, J=10.5 Hz, 1H), 3.50 (d, 6H), 3.43 (t, 2H), 3.37 (t, 2H), 3.25 (t 2H), 2.63 (dd, 1H), 1.69 (m, 13H).

Step 2) Synthesis of (3RS,4RS)-4-(9-azido-5-oxanonyl)-7-methoxymethoxy-3-(4-(methoxymethoxy)phenyl)-3-methylchroman

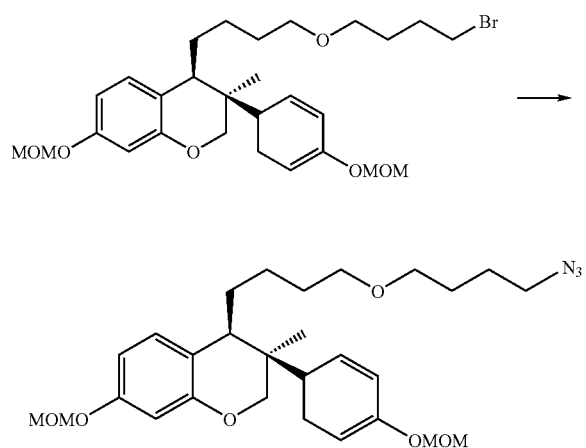

To (3RS,4RS)-4-(9-bromo-5-oxanonyl)-7-methoxymethoxy-3-(4-(methoxymethoxy)phenyl)-3-methylchroman (276 mg, 0.5 mmol) in. DMSO was added sodium azide (65.1 mg, 1 mmol). The mixture was stirred at 80° C. for 3 h. After cooling, the mixture was extracted with ethyl acetate, dried over MgSO$_4$, and filtered. The filtrate was evaporated under reduced pressure, and the concentrate thus obtained was subjected to silica gel column chromatography (n-hexane:ethyl acetate=10:1) to give 269 mg (yield. 100%) of a colorless oil.

$^1$H-NMR (300 MHz, CDCl$_3$) δ: 7.18 (dd, J=8.6 Hz, 2H). 6.9 (m, 3H), 6.5 (d, 2H), 5.13 (d, 4H), 4.53 (dd, J=10.3 Hz, 1H), 4.23 (dd, J=10.5 Hz, 1H), 3.60 (d, 6H), 3.43~3.2 (m, 4H), 2.7 (dd, 1H), 1.8 (m, 2H), 1.5~0.9 (m, 13H).

Step 3) Synthesis of (3RS,4RS)-4-(9-amino-5-oxanonyl)-7-methoxymethoxy-3-(4-(methoxymethoxy)phenyl)-3-methylchroman

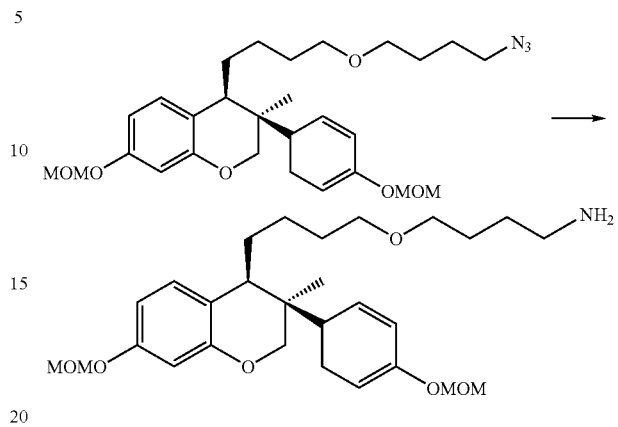

The (3RS,4RS)-4-(9-azido-5-oxanonyl)-7-methoxymethoxy-3-(4-(methoxymethoxy)phenyl)-3-methylchroman (250 mg, 0.19 mmol) was dissolved in methanoltetrahydofura (1.8/0.2 mL). Palladium charchol (75 mg, 0.05 mmol) was added, and resulting mixture was stirred at rt under hydrogen for 2 h. The mixture solution was concentrated and filtered through silica gel to give 170 mg of crude product as a colorless oil.

$^1$H-NMR (300 MHz, CDCl$_3$) δ: 7.08 (dd, J=8.63 Hz, 2H), 6.9 (m, 3H), 6.57 (d, 2H), 5.16 (d, 4H), 4.53 (dd, J=10.2 Hz, 1H), 4.26 (dd, J=10.5 Hz, 1H), 3.55 (d, 6H), 3.4~3.18 (m, 42H), 2.7 (m, 3H, C-4,), 1.8~0.9 (m, 13H).

Step 4) Synthesis of (3RS,4RS)-7-methoxymethoxy-3-(4-(methoxymethoxy)phenyl)-3-methyl-4-[5-oxa-9-(4,4,5,5,5-pentafluoropentylsulfonylwnino)nonyl]chroman

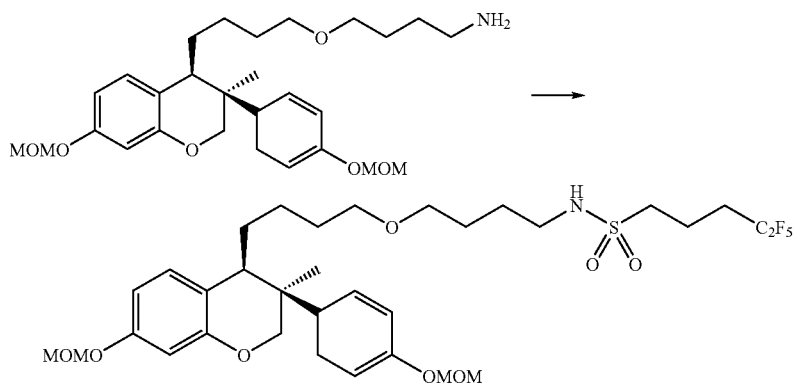

To (3RS,4RS)-4-(9-amino-5-oxanonyl)-7-methoxymethoxy-3-(4-(methoxymethoxy)phenyl)-3-methylchroman (109 mg, 0.2 mmol) in methylenchloride (3 mL) were added triethylamine (93.5 μL, 0.6 mmol) and 4,4,5,5,5-pentafluoropentylsulfonylchloride (145.6 mg, 0.5 mmol). The mixture was stirred at rt for 1 h. After cooling, the mixture was extracted with methylenchloride, dried over MgSO$_4$, and filtered. The filtrate was evaporated under reduced pressure, and the concentrate thus obtained was subjected to silica gel column chromatography (n-hexane: ethyl acetate=4:1) to give 125 mg (yield. 72%) of a colorless oil.

$^1$H-NMR (300 MHz, CDCl$_3$): 7.15 (dd, J=8.6 Hz, 2H), 6.7 (m, 3H), 6.61 (d, 2H), 5.17 (d, 4H), 4.52 (dd, J=10.2 Hz, 1H), 4.28 (dd, J=10.5 Hz, 1H), 3.48 (d, 6H), 3.39~3.28 (m, 5H), 3.1 (t, 2H), 2.65 (dd, 1H), 2.41~2.02 (m, 4H), 1.78~0.9 (m, 15H).

Step 5) Synthesis of (3RS,4RS)-7-hydroxy-3-(4-(hydroxyphenyl)-3-methyl-4-[5-oxa-9-(4,4,5,5,5-pentafluoropentylsulfonylamino)nonyl]chroman

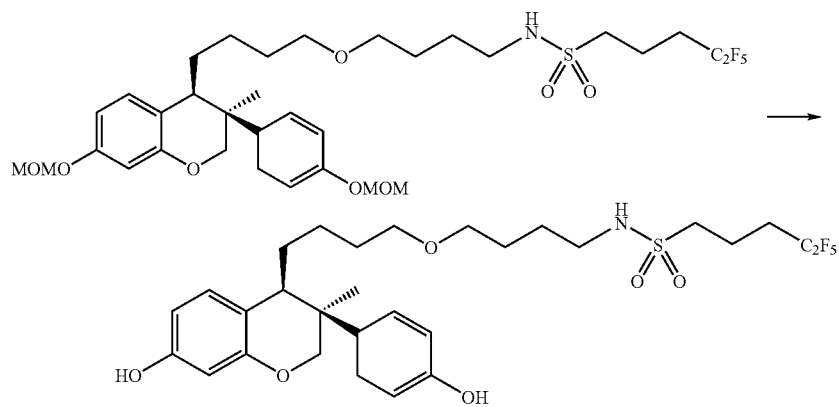

(3RS,4RS)-7-methoxymethoxy-3-(4-(methoxymethoxy)phenyl)-3-methyl-4-[5oxa-9-(4,4,5,5,5-pentafluoropentyl-sulfonylamino)nonyl]chroman (125 mg, 0.17 mmol) was treated with dry hydrochloric acid/methanol (2 mL), which was then stirred at rt for 2 h. Saturated aqueous sodium hydrogen carbonate was added to reaction solution and extracted with ethyl acetate, dried (MgSO$_4$), and filtered. The filtrate was evaporated under reduced pressure, and the concentrate thus obtained was subjected to silica gel column chromatography (n-hexane:ethyl acetate=2:1) to give 76.2 mg (yield. 72%) of a colorless oil.

$^1$H-NMR (300 MHz, CDCl$_3$) δ: 7.08 (dd, J=8.6 Hz, 2H), 6.80 (m, 3H), 6.32 (d, 2H), 6.0 (dd, J=8.2 Hz, 1H), 5.08 (t, 1H), 4.52 (dd, J=10.2 Hz, 1H), 4.25 (dd, J=10.6 Hz 1H), 3.30 (m, 4H), 3.09 (m, 4H), 2.63 (dd, J=8.9 Hz 1H), 2.38~1.92 (m, 4H). 1.52~0.61 (m, 15H).

EXAMPLE 36

Synthesis of (3'RS, 4'RS)-6,6,7,7,7-pentafuoro-2-(2-(4-(4-(7-hydroxy-3-(4-hydroxyphenyl)-3-methyl-chroman-4-yl)butyl)phenyloxy)ethyl)heptanoic acid Step 1) Synthesis of 3-methyl-7-methyloxymethyloxy)-3-(4-(methyloxymethyloxy)phenyl)-4-(4-(4-(t-butyldimethyl-silyloxy)phenyl)but-1-ynyl)chroman-4-ol

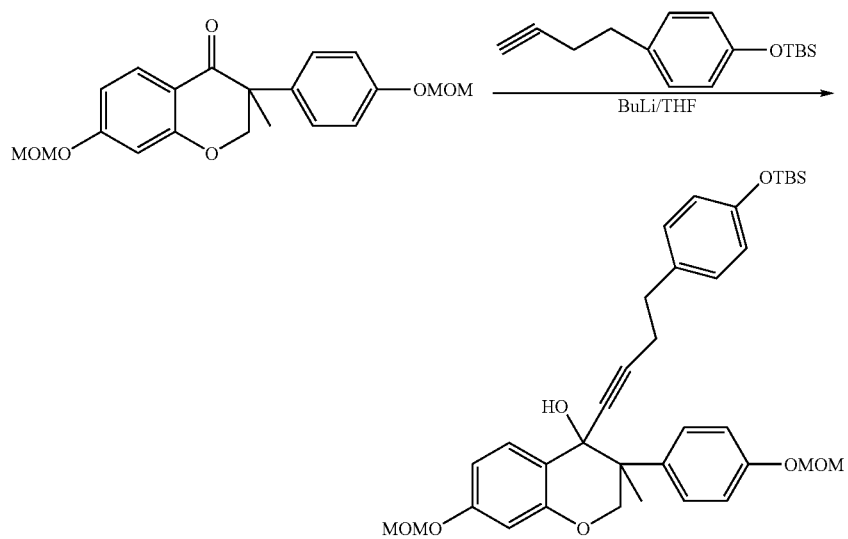

1-(4-but-3-ynylphenyloxy)-1,1,2,2-tetramethyl-1-silapropane (2.2 g, 8.4 mmol) was dissolved in dry tetrahydrofuran (15 ml) under argon atmosphere and then cooled to −78° C. 1.6M n-Butyllithium 5 ml, 8.0 mmol) was added dropwise thereto, and the mixture was warmed to −10° C. and stirred for 1 hour and then cooled to −78° C. 7-Methyloxymethyloxy-3-(4-methyloxymethyloxyphenyl)-3-methy-1 chroman-4-one (1.151 g, 4.2 mmol) was added portionwise and then warmed to room temperature and stirred for 1.5 hour. The reaction mixture was quenched by water. The reaction solvent was evaporated off, then the residue was dissolved in ethyl acetate, which was washed with water. The organic solvent was dried over anhydrous magnesium sulfate and removed by evaporation under vacuum This product was purified by column chromatography on silica gel, eluting with 10% ethyl acetate in n-hexane. After removal of the solvent, 1.87 g of the title compound was obtained as colorless oil. (yield: 72%)

$^1$H NMR (300 MHz, CDCl$_3$) δ: 7.53 (d, 1H, J=8.66 Hz), 7.36 (d, 2H, J=9.0 Hz), 6.99 (m, 4H), 6.71 (d, 2H, J=8.29 Hz), 6.61 (dd, 1H, J=2.26, 8.67 Hz), 6.5 (d, 1H, J=2.26 Hz), 5.14 (s, 2H), 5.11 (s, 2H), 4.83 (d, 1H, J=10.55 Hz), 3.99 (1H, J=10.55 Hz), 3.45 (s, 3H), 3.43 (s, 3H), 2.75 (m, 2H), 2.50 (m, 2H), 1.39 (s, 3H), 0.93 (s, 9H), 0.13 (s, 6H)

Step 2) Synthesis of (3RS,4RS)-4-(methyloxymethyloxy)-1-(3-methyl-7-methyloxymethyloxy)-4-(4-(t-butyldimethylsilyloxy)phenyl)butyl)chroman-3-yl)benzene

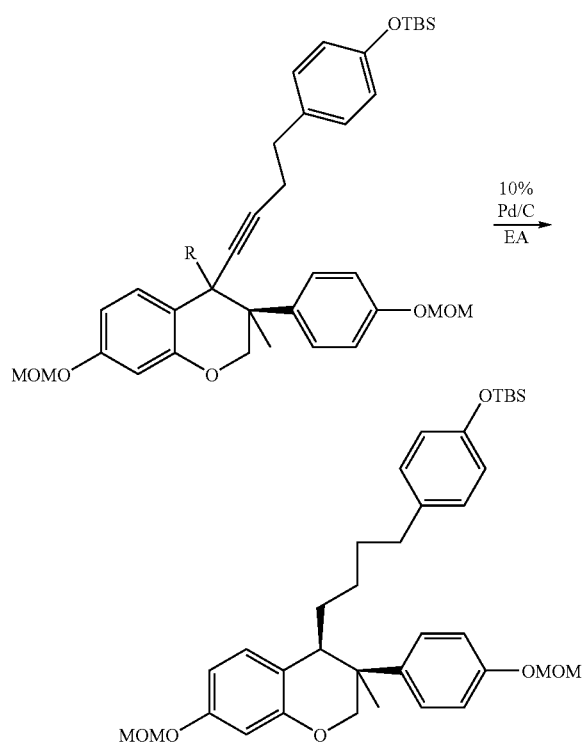

3-methyl -7-(methyloxymethyloxy)-3-(4-(methyloxymethyloxy)phenyl)-4(4-(4-(t-butyldimethylsilyloxy)phenyl)but-1-ynyl)chroman-4-ol (1.056 g, 1.7 mmol) was dissolved in ethylacetate (10 mL) and 10% palladium on carbon (352 mg) was added and stirred for 30 minutes under hydrogen (atmospheric pressure). The reaction mixture was filtered through cellite and concentrated under reduced pressure. The residue was purified by column chromatography on silica gel, eluting with ethyl acetate:n-hexane=1:19. After removal of the solvent, 772 mg of the title compound was obtained as colorless oil.

$^1$H NMR (300 MHz, CDCl$_3$. 3RS,4RS-compound) δ: 7.1 (d, 2H, J=8.7 Hz), 7.0 (d, 2H, J=9.0 Hz), 6.87 (m, 3H), 6.67 (d, 2H, J=8.3 Hz), 6.54 (m, 2H), 5.16 (s, 2H), 5.13 (s, 2H), 4.5 (d, 1H, J=10.55 Hz), 4.23 (d, 1H, J=10.55 Hz), 3.47 (s, 6H), 2.59 (m, 1H), 2.33 (t, 2H, J=7.5 Hz), 1.22 (s, 3H), 1.0–1.4 (m, 6H), 0.95 (s, 9H), 0.15 (s, 6H)

Step 3) Synthesis of (3RS,4RS)-4-(4-(3-methyl-7-(methyloxymethyloxy)-3-(4-(methyloxymethyloxy)phenyl)chroman-4-yl)butyl)benzen-1-ol

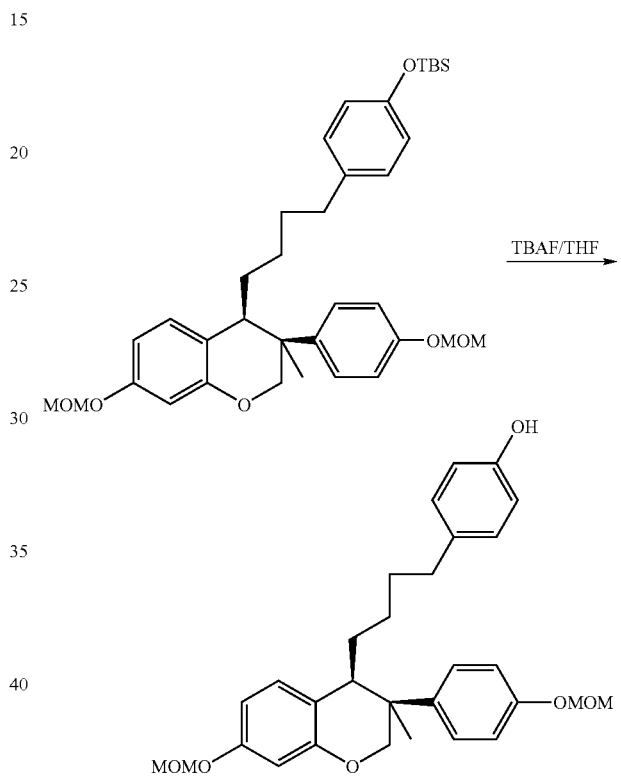

(3RS,4RS)-4-(methyloxymethyloxy)-1-(3-methyl-7-(methyloxymethyloxy)-4-(4-(t-butyldimethylsilyloxy)phenyl) butyl)chroman-3-yl)benzene (730 mg, 1.2 mmol) was dissolved in tetrahydrofuran (7 ml), and cooled to 0°. To this solution was added tetrabutylammonium fluoride (2.4 ml, 2.4 mmol), and the reaction mixture was stirred at room temperature for 2 hours. The solvent was removed by evaporation under reduced pressure and the residue was dissolved in ethyl acetate, which was washed with water. The organic layer was separated, dried over anhydrous magnesium sulfate, and concentrated under reduced pressure. The product was purified, by column chromatography on silica gel, eluting with 30% ethyl acetate in n-hexane to afford 572 mg of the title compound as a pale yellow oil. (yield: 96.0%)

$^1$H-NMR (300 MHz, CDCl$_3$, 3RS,4RS-compound) δ: 7.07 (d, 2H, J=9.0 Hz), 6.97 (d, 2H, J=8.67 Hz), 6.8 (m, 3H), 6.64 (d, 2H, J=8.66 Hz), 6.5 (m, 2H), 5.14 (s, 2H), 5.12 (s, 2H), 4.49 (d, 1H, J=10.55 Hz), 4.21 (d. 1H, J=10.55 Hz), 3.46 (s, 6H), 2.6 (m, 1H), 2.3 (m, 2H), 1.19 (s, 3H), 1.0–1.4 (m, 6H)

Step 4) Synthesis of diethyl 2-(2-bromoethyl)-2-(4,4,5,5,5-pentafluoropentyl)propane-1,3-dioate

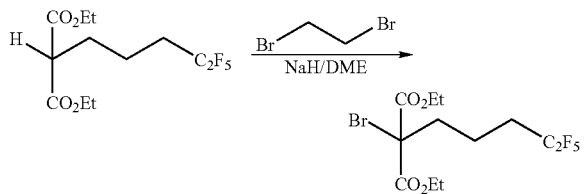

Diethyl 2-(4,4,5,5,5-pentafluoropentyl)propane-1,3-dioate (51 0 mg, 1.592 mmol) was dissolved in anhydrous dimethoxyethane (5 ml). Sodium hydride (60%. 88 mg, 2.2 mmol) was added to the solution and then stirred at room temperature for 1 h under nitrogen atmosphere. Dibromoethane (0.82 ml, 9.55 mmol) was added to the mixture and then stirred at 70° C. for 5 h under nitrogen atmosphere. When the reaction was completed, the mixture was cooled to room temperature. Water was added to reaction solution which was then extracted with ethyl acetate. The extracted organic layer was dried over anhydrous magnesium sulfate and then concentrated. The residue was subjected to column chromatography (n-hexane:dichloromethane=3:1) to obtain 489 mg (yield: 72° C.) of the title compound as a colorless oil.

$^1$H-NMR (300 MHz, CDCl$_3$) δ: 4.2 (q, 4H, J=7.1 Hz), 3.32 (m, 2H), 2.45 (m, 2H), 2.0 (m, 4H), 1.5 (m, 2H), 1.24 (t, 6H, J=7.1 Hz)

Step 5) Synthesis of (3'RS,4'RS)-(4,4,5,5,5-pentafluoropentyl)(2-(4-(4-(3-methyl-7-(methyloxymethyloxy)-3-(4-(methyloxymethyloxy)phenyl)chroman-4-yl)butyl)phenyloxy)ethyl)methane-1,1-dicarboxylic acid (3RS,4RS)-4-(4-(3-methyl-7-(methyloxymethyloxy)-3-(4-(methyloxymethyloxy)phenyl)chroman-4-yl)butyl)benzen-1-ol (335 mg, 0.68 mmol) was dissolved in anhydrous DMF (3 ml). Sodium hydride (60%, 35 mg, 0.884 mmol) was added to the solution and then stirred at room temperature for 1 h under nitrogen atmosphere. Diethyl 2-(2-bromoethyl)-2-(4,4,5,5,5-pentafluoropentyl)propane-1,3-dioate (726 mg, 1.7 mmol) was added to the mixture and then stirred at 70° C. for 3 h under nitrogen atmosphere. When the reaction was completed, the mixture was cooled to room temperature. Water was added to reaction solution which was then extracted with ethyl acetate. The extracted organic layer was dried over anhydrous magnesium sulfate and then concentrated. The residue was dissolved in ethyl alcohol (20 ml) and a solution of potassium hydroxide (1.85 g, 28 mmol) in water (10 ml) was added thereto. The resulting mixture was heated under reflux for overnight. The residue, left after removal of ethyl alcohol, was dissolved in water and adjusted to pH 3 with diluted HCl and extracted with ethyl acetate. The organic layer was washed with water and brine, dried over anhydrous magnesium sulfate, and removed by evaporation under vacuum to afford 549 mg of the title compound as a white foam.

$^1$H-NMR (300 MHz, CDCl$_3$, 3RS,4RS-compound) δ: 7.05 (d, 2H, J=8.9 Hz), 6.98 (d, 2H, J=8.9 Hz), 6.81 (d, 2H, J=8.7 Hz), 6.65 (d, 1H, J=8.3 Hz), 6.64 (d, 2H, J=8.7 Hz), 6.5 (d, 1H, J=2.4 Hz), 6.44 (dd, 1H, J=8.3 Hz, 2.4 Hz), 5.2 (m, 4H), 4.45 (d, 1H, J=10.5 Hz), 4.21 (d, 1H, J=10.5 Hz), 4.0 (m, 2H), 3.5 (s, 3H), 3.49 (s, 3H), 2.5 (m, 3H), 2.3 (m, 2H), 2.05 (m, 4H), 1.6 (m, 2H), 1.17 (s, 3H), 1.0–1.4 (m, 6H)

MS (ESI): 783 (M+1), 805 (M+Na)

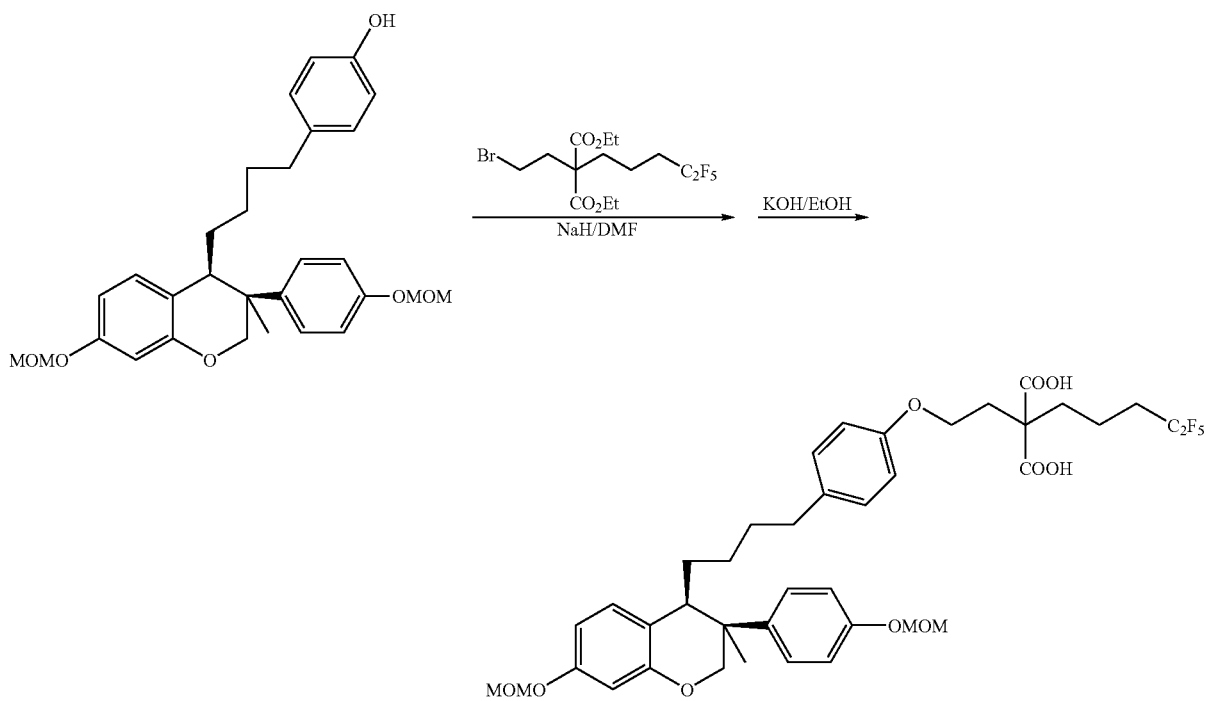

Step 6) Synthesis of (3'RS,4'RS)-(4,4,5,5,5-pentafluoropentyl)(2-(4-(4-(7-hydroxy-3-(4-hydroxyphenyl)-3-methylchroman-4-yl)butyl)phenyloxy)ethyl)methane-1,1-dicarboxylic acid

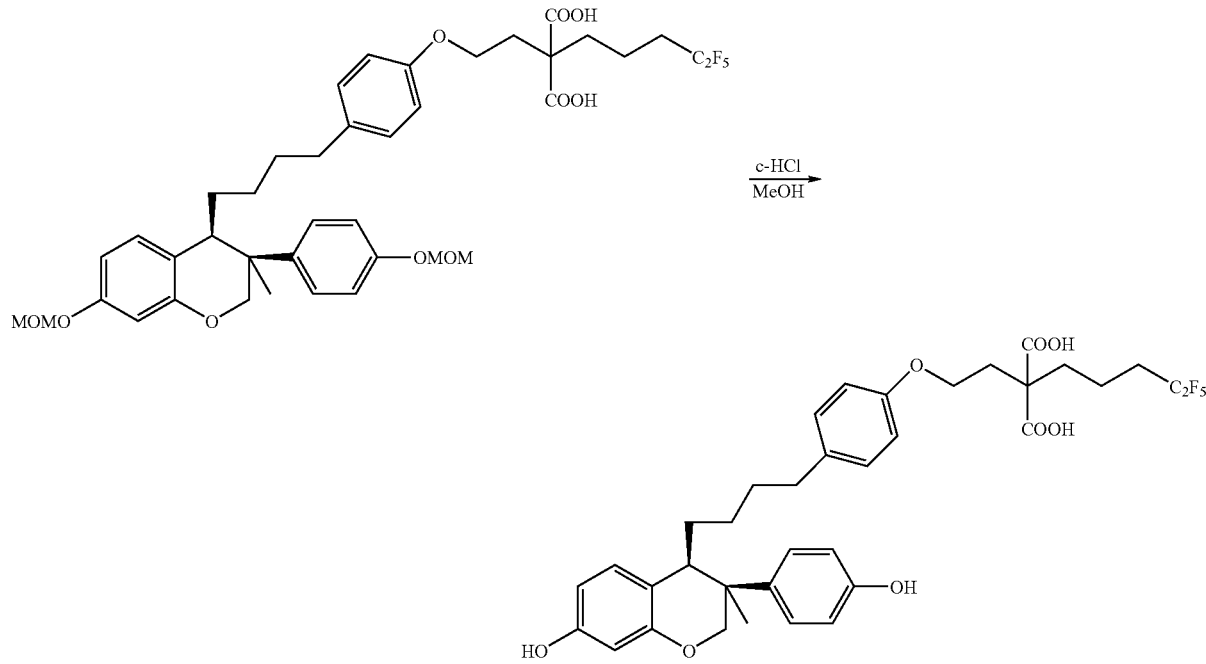

(3'RS,4'RS)(4,4,5,5,5-pentafluoropentyl)(2-(4-(4-(3-methyl-7-(methyloxymethyloxy)-3-(4-(methyloxymethyloxy)phenyl)chroman-4-yl)butyl)phenyloxy)ethyl)methane-1,1-dicarboxylic acid (549 mg, 0.679 mmol) was dissolved in hydrochloric acid/methanol (20 mg), which was then stirred at 50° C. for 2 hours. The reaction solution was cooled down to room temperature, water was added, and the resulting mixture was extracted with ethyl acetate. The organic extract was dried over anhydrous magnesium sulfate, and concentrated under reduced pressure to give the title compound (463 mg, yield: 98%) as a white foam $^1$H-NMR (300 MHz, CD$_3$OD) δ: 7.05 (d, 2H, J=8.6 Hz), 6.87 (d, 2H, J=8.6 Hz), 6.7 (m, 5H), 6.3 (m, 2H), 4.46 (d, 1H, J=10.5 Hz), 4.16 (d, 1H, J=10.5 Hz), 4.0 (m, 2H), 2.57 (m, 1H), 2.3 (m, 4H), 2.0 (m, 4H), 1.2 (s, 3H), 0.9–1.6 (m, 8H)

MS (ESI): 695 (M+1), 717 (M+Na)

Step 7) Synthesis of (3'RS,4'RS)-6,6,7,7,7-pentafluoro-2-(2-(4-(4-(7-hydroxy-3-(4-hydroxyphenyl)-3-methylchroman-4-yl)butyl)phenyloxy)ethyl)heptanoic acid

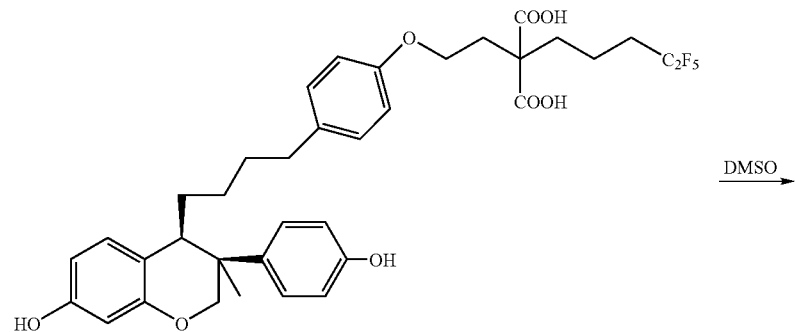

-continued

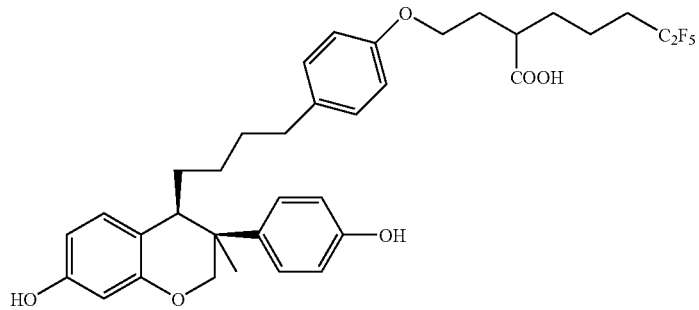

A solution of (3'RS,4'RS)-(4,4,5,5,5-pentafluoropentyl)(2-(4(4-(7-hydroxy-3-(4-hydroxyphenyl)-3-methylchroman-4-yl)butyl)phenyloxy)ethyl)methane-1,1-dicarboxylic acid (389 mg, 0.559 mmol) in dimethyl sulfoxide (3 ml) was heated to 130–140° C. for 3 hours. The reaction mixture was dissolved in ethyl acetate and washed with water and brine, dried over anhydrous magnesium sulfate. This product was purified by column chromatography on silica gel, eluting with ethyl acetate:n-hexane=1:2 2:1 to afford 268 mg of the title compound as a white foam. (yield: 74%)

$^1$H-NMR (300 MHz CD$_3$OD) δ: 7.1 (d, 2H, J=8.7 Hz), 6.9 (d, 2H, J=8.7 Hz), 6.75 (m, 5H), 6.3 (m, 2H), 4.5 (d, 1H, J=10.5 Hz), 4.2 (d, 1H, J=10.5 Hz), 4.0 (t, 2H, J=6.1 Hz), 2.63 (m, 2H), 2.35 (t, 2H, J=7.2 Hz), 2.1 (m, 4H), 1.67 (m, 4H), 1.2 (s, 3H), 0.9–1.3 (m, 6H)

MS (ESI): 651 (M+1), 673 (M+Na)

EXAMPLE 37

Synthesis of (3RS,4RS)-4-allyl-7-methoxy-3-(4-methoxyphenyl)-3-methylthiochroman Step 1) Synthesis of 4-hydroxy-7-methoxy-3-(4-methoxyphenyl)-3-methylthiochroman

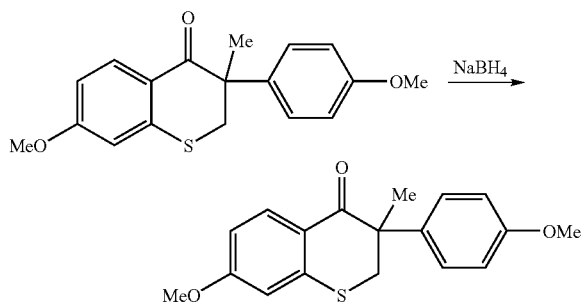

To a solution of 7-methoxy-3-(4-methoxyphenyl)-3-methylthiochroman-4-one (6.29 g, 20 mmol) in THF (20 ml) and EtOH (10 ml) was added NaBH$_4$ (1.51 g, 40 mmol), which was stirred overnight at room temperature. The reaction solution was added saturated aqueous NH$_4$Cl solution, extracted with CHCl$_3$, and washed with brine. The organic layer was dried over Na$_2$SO$_4$ and the solvent was removed under reduced pressure. The residue was purified by recrystallization with CHCl$_3$-hexane to give 5.33 g (84%) of 4-hydroxy-7-methoxy-3-(4-methoxyphenyl)-3-methylthiochroman.

$^1$H-NMR (270 MHz, CDCl$_3$) δ: 7.42 (d, 2H, J=8.8 Hz, Ar—H), 7.20 (d, 1H, J=8.2 Hz, Ar—H), 6.94 (d, 2H, J=8.8 Hz, Ar—H), 6.73 (d, 1H, J=2.8 Hz, Ar—H), 6.65 (dd, 1H, J=1.8, 8.5 Hz, Ar—H), 4.62 (brs, 1H, C4-H), 3.94 (d, 1H, J=12.1 Hz), 3.82 (s, 3H, OMe), 3.79 (s, 3H, OMe), 2.87 (d, 1H, J=12.1 Hz), 1.58 (d, 1H, J=3.0 Hz), 1.31 (s, 3H, C3-Me).

Step 2) Synthesis of (3RS,4RS)+allyl-7-methoxy-3-(4-methoxyphenyl)-3-methylthiochroman

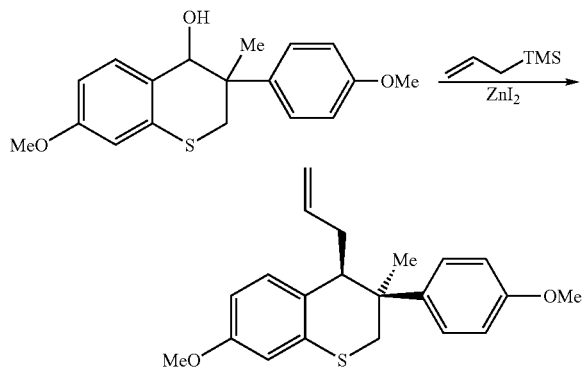

To a solution of 4-hydroxy-7-methoxy-3-(4-methoxyphenyl)-3-methylthiochroman (11.4 g, 36.3 mmol) in 1,2-dichloroethane (360 ml) was added zinc iodide (13.9 g, 43.5 mmol) and allyltrimethylsilane (11.5 ml, 72.5 mmol) which was stirred for 1 day at room temperature. The reaction solution was added saturated aqueous NHCl solution, extracted with CHCl$_3$, and washed with brine. The organic layer was dried over Na$_2$SO$_4$ and the solvent was removed under reduced pressure. The residue was purified by chromatography on silica-gel with 1% AcOEt in hexane to give 9.1$^9$g (74%) of (3RS,4RS)-4-allyl-7-methoxy-3-(4-methoxyphenyl)-3-methylthiochroman.

$^1$H-NMR (300 MHz CDCl$_3$) δ: 7.30 (d, 2H, J=9.1 Hz, Ar—H), 6.92 (d, 1H, J=8.9 Hz, Ar—H), 6.90 (d, 2H, J=8.5 Hz, Ar—H), 6.73 (d, 1H, J=2.8 Hz, Ar—H), 6.56 (dd, 1H, J=2.8, 8.5 Hz, Ar—H), 5.4–5.7 (m, 1H, allyl), 4.82 (d, 1H, J=9.9 Hz, allyl), 4.65 (d, 1H, J=7.0 Hz, allyl), 3.83 (s, 3H, OMe), 3.78 (s, 3H, OMe), 3.64 (d, 1H, J=11.8 Hz, C2-H), 2.87 (dd, 1H, J=1.7, 11.8 Hz, C2-H), 2.8–2.9 (m, 1H, C4-H), 1.8–2.0 (m, 2H), 1.23 (s, 3H, C3-Me).

EXAMPLE 38

Synthesis of (3RS,4RS)-7-hydroxy-3-(4-hydroxyphenyl)-3-methyl-4-{9-[2-(2,2,2-trifluoroethoxy)ethylsulfinyl]nonyl}thiochroman Step 1) Synthesis of t-butyl-2,2,2-trifluoroethoxyacetate

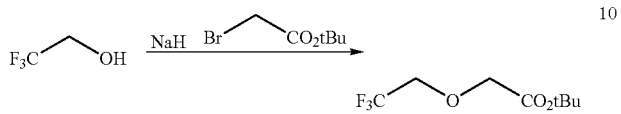

To a suspension of NaH (240 mg, 60–72%) in tetrahydrofuran (5 ml) was added 2,2,2-trifluoroethanol (500 mg, 5 mmol) at 0° C. After the mixture was stirred for 45 minutes at room temperature, t-butyl bromoacetate (0.9 ml, 6 mmol) was added and stirred at room temperature for 15 hours. The mixture was poured into ice-water and extracted with chloroform. The organic layer was dried over anhydrous magnesium sulfate and concentrated to give crude t-Butyl 2,2,2-trifluoroethoxyacetate (1.08 g, quant.).

$^1$H-NMR (270 MHz, CDCl$_3$) δ: 3.97 (2H, dd, J=9 and 18 Hz, —OCH$_2$CF$_3$), 4.11 (2H, s, —CH$_2$CO$_2$tBu), 1.48 (9H, s, tBu)

Step 2) Synthesis of 2-(2,2,2-trifluoroethoxy)ethyl p-toluenesulfonate

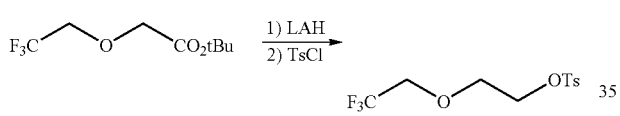

To a suspension of LAH (750 mg, 19.7 mmol) in ether (40 ml) was added crude t-butyl-2,2,2-trifluoroethoxyacetate (2.0 g, 9.3 mmol) in ether (10 ml) at 0° C. The mixture was stirred for 45 minutes at 0° C. Then, the mixture was poured into ice-water and extracted with ether. The organic layer was dried over anhydrous magnesium sulfate and concentrated to give crude 2-(2,2,2-trifluoroethoxy)ethanol (1.09 g, 81%). To a solution of crude 2-(2,2,2-trifluoroethoxy)ethanol (150 mg, 11.0 mmol) in dichloromethane (3 ml) was added triethylamine (110 mg, 1.1 mmol) and p-toluenesulfonylchloride (200 mg, 1.1 mmol). The mixture was stirred at room temperature for 2 days. The mixture was poured into water and extracted with chloroform. The organic layer was dried over anhydrous magnesium sulfate. After concentration, silica gel column chromatography (n-hexane/ethyl acetate=5/1) gave 2-(2,2,2-trifluoroethoxy)ethyl p-toluenesulfonate (188 mg, 63%)

$^1$H-NMR (270 MHz, CDCl$_3$) δ: 7.80 (2H, d, J=8 Hz, Ar—H), 7.35 (2H, d, J=8 Hz, Ar—H), 4.18 (2H, t, J=4 Hz, —CH$_2$OTs), 3.85~3.76 (4H, m, CF$_3$CH$_2$OCH$_2$—), 2.45 (3H, s, Ar—CH$_3$)

Step 3) Synthesis of 2-(2,2,2-Trifluoroethoxy)ethyl thioacetate

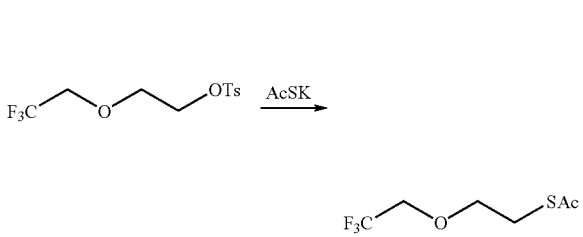

2-(2,2,2-trifluoroethoxy)ethyl p-toluenesulfonate (14.0 g, 47 mmol) and potassium thioacetate (10.0 g, 88 mmol) were dissolved in acetone (100 ml) and the mixture was stirred at room temperature for 2 days. The mixture was poured into water and extracted with ethyl acetate. The organic layer was dried over anhydrous magnesium sulfate. After concentration, silica gel column chromatography (n-hexane/ethyl acetate=10/1) gave 2-(2,2,2-Trifluoroethoxy)ethyl thioacetate (8.3 g, 87%)

$^1$H-NMR (270 MHz, CDCl$_3$) δ: 3.84 (2H, dd, J=9 and 17 Hz, CF$_3$CH$_2$O—), 3.73 (2H, t, J=6 Hz, CF$_3$CH$_2$OCH$_2$—), 3.10 (2H, t, J=6 Hz, —CH$_2$SAc), 2.35 (3H, s, —COCH$_3$)

Step 4) Synthesis of (3RS,4RS)-7-Methoxymethoxy-3-(4-methoxymethoxyphenyl)-3-methyl-4-{9-[2-(2,2,2-trifluoroethoxy)ethylthio]nonyl}thiochroman

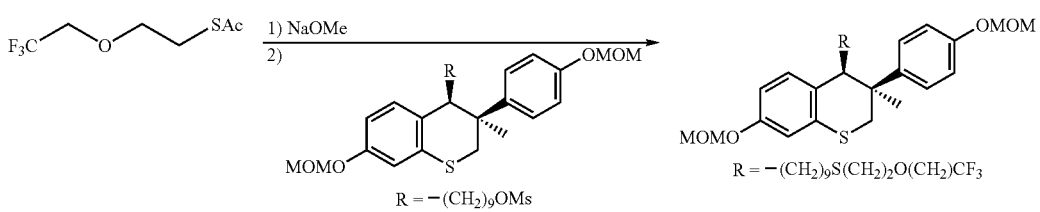

To a solution of 2-(2,2,2-Trifluoroethoxy)ethyl thioacetate (210 mg, 1.0 mmol) in methanol (3 ml) was added 1N sodium methoxide methanol solution (1.0 ml, 1.0 mmol) at room temperature. The mixture was stirred for 1 hour at room temperature. Then, 4-(9-mesyloxynonyl)-7-methoxymethoxy-3-(4-methoxymethoxyphenyl)-3-methylthiochroman (130 mg, 0.224 mmol) dissolved in tetrahydrofuran (3 ml) was added and stirred at room temperature for 1 day. After the reaction was completed, the mixture was concentrated, poured into ice-water and extracted with chloroform. The organic layer was dried over anhydrous magnesium sulfate. After concentration, silica gel column chromatography (n-hexane/ethyl acetate=20/1) gave (3RS,4RS)-7-Methoxymethoxy-3-(4-methoxymethoxyphenyl)-3-methyl-4-{9-[2-(2,2,2-trifluoroethoxy)ethylthio]nonyl}thiochroman (228 g, 95%)

¹H-NMR (270 MHz, CDCl₃) δ: 7.29 (2H, d, J=9 Hz, Ar—H), 7.03 (2H, d, J=9 Hz, Ar—H), 6.92 (1H, d, J=0.9 Hz, Ar—H), 6.88 (1H, d, J=2 Hz, Ar—H), 6.69 (1H, dd, J=8 and 2 Hz, Ar—H), 5.19 (2H, s, —OCH₂OCH₃), 5.14 (2H, s, —OCH₂OCH₃), 3.90~3.74 (4H, m, —CH₂OCH₂CF₃), 3.63 (1H, d, J=11 Hz, C2-H), 3.50 (3H, s, —OCH₃), 3.49 (3H, s, —OCH₃), 2.98 (1H, d, J=11 Hz, C2-H), 2.73~2.68 (3H, m, C4-H and —SCH₂—), 2.52 (2H, t, J=7 Hz, —SCH₂—), 1.56~1.07 (16H, m, alkyl-H), 1.17 (3H, s, C3-CH₃)

Step 5) Synthesis of (3RS,4RS)-7-hydroxy-3-(4-hydroxyphenyl)-3-methyl-4-{9-[2-(2,2,2-trifluoroethoxy)ethylthio]nonyl}thiochroman

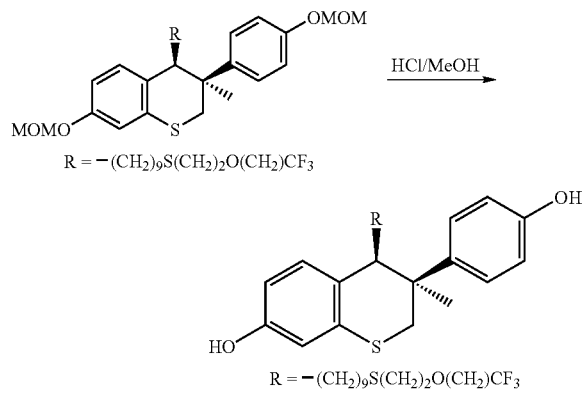

(3RS,4RS)-7-Methoxymethoxy-3-(4-methoxymethoxyphenyl)-3-methyl-4-{9-[2-(2,2,2-trifluoroethoxy)ethylthio]nonyl}thiochroman (136 mg, 0.211 mmol) was dissolved in 10% HCl/MeOH (20 ml) and the mixture was stirred at room temperature for 1 day. After the reaction was completed, the mixture was concentrated, and silica gel column chromatography (n-hexane/ethyl acetate=5/1) gave (3RS,4RS)-7-Hydroxy-3-(4-hydroxyphenyl)-3-methyl-4-{9-[2-(2,2,2-trifluoroethoxy)ethylthio}nonyl}thiochroman (100 mg, 85%)

¹H-NMR (270 MHz, CDCl₃) δ: 7.24 (2H, d, Ar—H), 6.89~6.82 (3H, m, Ar—H), 6.67 (1H, d, J=2 Hz, Ar—H), 6.50 (1H, dd, j=8 and 2 Hz, Ar—H), 3.91~3.76 (4H, m, —CH₂OCH₂CF—). 3.63 (1H, d, J=12 Hz, C2-H), 2.96 (1H, d, J=12 Hz, C2-H), 2.75~2.70 (3H, m, C4-H and —SCH₂—), 2.54 (2H, t, J=7 Hz, —SCH₂—), 1.58~1.06 (16H, m, alkyl-H), 1.17 (3H, s, C3-CH₃)

Step 6) Synthesis of (3RS,4RS)-7-hydroxy-3-(4-hydroxyphenyl)-3-methyl-4-{9-[2-(2,2,2-trifluoroethoxy)ethylsulfinyl]nonyl}thiochroman

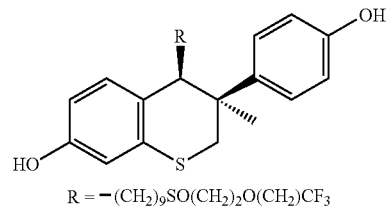

To a solution of (3RS,4RS)-7-hydroxy-344-hydroxyphenyl)-3-methyl-4-{9[2-(2,2,2-trifluoroethoxy)ethylthio]nonyl}thiochroman (100 mg, 0.180 mmol) in tetrahydrofuran (10 ml) was added Oxone® (monopersulfate compound; DuPont product) (56 mg, 0.090 mmol) at 0° C. Then, water (0.1 ml) was added to this mixture and stirred for 1 hour at 0° C. The mixture was dried over anhydrous magnesium sulfate, concentrated and silica gel column chromatography (n-hexane/ethyl acetate=1/3) gave (3RS,4RS)-7-hydroxy-3-(4-hydroxyphenyl)-3-methyl-4-{9-[2-(2,2,2-trifluoroethoxy)ethylsulfinyl]nonyl}thiochroman (74 mg, 72%)

¹H-NMR (270 MHz, CD₃OD) δ: 7.17 (2H, d, J=9 Hz, Ar—H), 6.79 (1H, d, J=8 Hz, Ar—H), 6.70 (2H, d, J=9 Hz, Ar—H), 6.48 (1H, d, J=2 Hz, Ar—H), 6.37 (1H, dd, J=8 and 2 Hz, Ar—H), 3.97~3.87 (4H, m, —CH₂OCH₂CF₃), 3.55 (1H, d, J=12 Hz, C2-H), 3.13~2.66 (6H, m, C2-H, C4-H and —CH₂SOCH₂—), 1.65 (2H, t, J=8 Hz, alkyl-H), 1.40~1.02 (14H, m, alkyl-H), 1.05 (3H, s, C3-CH₃)

EXAMPLE 39

Synthesis of (3'RS,4'RS)-8-[7-hydroxy-3-(4-hydroxyphenyl)-3-methylthiochroman-4-yl]octanoic acid Step 1) Synthesis of 6-(t-butyldimethylsilyloxy)-1-hexyne

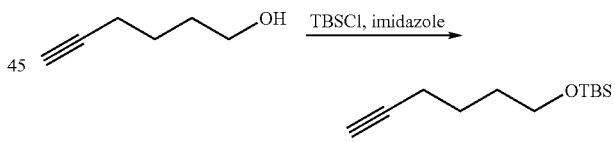

To a solution of 5-hexyne-1-ol (4.81 g, 49.0 mmol) in N,N-dimethylformamide (100 ml) were added imidazole (4.0 g, 59.0 mmol) and t-butyldimethylsilylchloride (8.12 g, 54.0 mmol) at 0° C., which was then stirred at the same temperature for 3 hour After the reaction was completed, water was added to the reaction solution, and the mixture was extracted with ethyl acetate. The extract was dried over anhydrous sodium sulfate and concentrated under reduced pressure. The residue was subjected to column chromatography (n-hexane:ethyl acetate=10:1) to give the title compound (10.0 g, yield: 99%) as a colorless oil.

¹H-NMR (270 MHz, CDCl₃) δ: 3.63 (t, J=6.6 Hz, 2H, —CH₂OTBS), 2.25–2.16 (m, 2H, propargyl-CH₂), 1.94 (t, J=2.6 Hz, 1H, acetylene-H), 1.62–1.43 (m, 4H, —CH₂CH₂—), 0.89 (s, 9H, -t-butyl-H), 0.05 (s, 6H, —SiMe2).-

Step 2) Synthesis of 4-[6 (t-butyldimethylsilyloxy)-1-hexynyl]-4-hydroxy-7-methoxy-3-(4-methoxyphenyl)-3-methylthiochroman

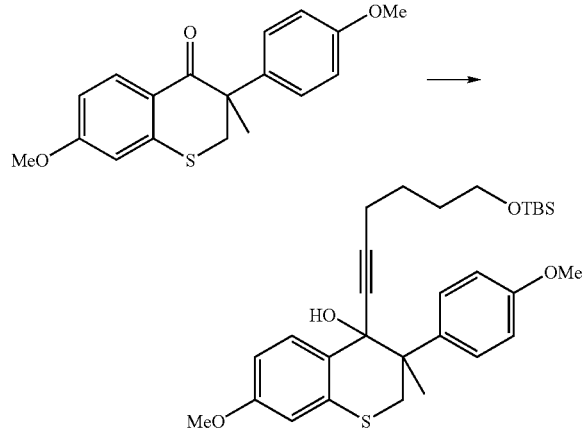

To a solution of 6-(t-butyldimethylsilyloxy)-1-hexyne (10.8 g, 50.9 mmol) in dry tetrahydrofuran (100 ml) was added dropwise n-butyl lithium (30.1 ml, 48.9 mmol, 1.63M in tetrahydrofuran) at −78° C., which was then stirred at −20° C. for 1 hour. To the reaction mixture, was then added 7-methoxy-3-(4-methoxyphenyl)-3-methylthiochroman-4-one (8.0 g, 25.5 mmol) dissolved in tetrahydrofuran at −78 C for 30 min, and the resulting mixture was stirred at −10° C. (for 24 hours. After the reaction was completed, saturated ammonium chloride solution was added to the reaction solution, and the mixture was extracted with ethyl acetate. The extract was dried over anhydrous sodium sulfate and concentrated under reduced pressure. The residue was subjected to column chromatography (n-hexane:ethyl acetate=4:1) to give the title compound (12.5 g, yield: 93%).

¹H-NMR (270 MHz, CDCl₃) δ: 7.85 (d, J=8.6 Hz, 1H, C5-H), 7.69 (d, J=8.9 Hz, 2H, Ar—H), 6.87 (d, J=8.9 Hz, 2H, Ar—H), 6.89–6.62 (m, 2H, C6-H and C8-H), 4.25 (d, J=12.5 Hz, 1H, C2-H), 3.81 (s, 3H, —OCH₃), 3.80 (s, 3H, —OCH₃), 3.60–3.55 (m, 2H, —CH₂OTBS), 2.70 (d, J=12.5 Hz, 1H, C2-H), 2.24–2.28 (m, 2H, propargyl-CH2), 2.17 (s, 1H, —OH), 1.59 (s, 3H, C3-CH₃), 1.58–1.45 (m, 4H, —CH₂CH₂—), 0.89 (s, 9H, -tbutyl-H), 0.05 (s, 6H, —SiMe2).

Step 3) Synthesis of 4-(6-hydroxyhexyl)-7-methoxy-3-(4-methoxyphenyl)-3-methylthiochroman

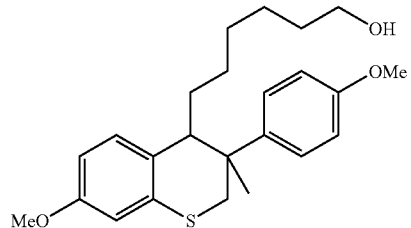

To a solution of 4-[6-(t-butyldimethylsilyloxy)-1-hexynyl])hydroxy-7-methoxy-3-(4-methoxyphenyl)-3-methylthiochroman (12.5 g, 23.8 mmol) in dichloromethane (200 ml) were added zinc iodide (15.2 g, 47.5 mmol) and sodium cyanoborohydride (12.0 g, 190.4 mmol), which was then stirred at room temperature for 12 hours. After the reaction was completed, water was added to the reaction mixture, and the resulting mixture was extracted with ethyl acetate. The extract was dried over anhydrous sodium sulfate, and concentrated under reduced pressure. The residue was used to next reaction without further purification.

The crude alkyne compound (12 g) was dissolved in ethyl acetate (100 ml), platinum oxide (3.0 g) was added, and the resulting mixture was stirred at room temperature under hydrogen for 20 hours. The reaction solution was concentrated and filtered through silica gel to give the crude compound.

The crude compound protected by TBS (12 g) was dissolved in tetrahydrofuran (100 ml), and tetranbutylammonium fluoride (TBAF, 30 ml, 1.0M solution in tetrahydrofuran) was added thereto at 0° C. The mixture was stirred at room temperature for, 1 hour, and stirred at 50° C., for further 2 hours. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane:ethyl acetate=1:1) to give the title compound (3.8 g, yield: 37%;(3RS,4RS):(3RS,4SR)=4:1).

¹H-NMR (270 MHz, CDCl₃) δ: 7.29 (d, J=8.9 Hz, 2H, Ar—H), 6.92 (d, J=8.2 Hz, 1H, C5-H), 6.90 (d, J=8.9 Hz, 2H, Ar—H), 6.73 (d, J=2.7 Hz, 1H, C8-H), 6.58 (dd, J=8.2 Hz and 2.7 Hz, 1H, C6-H), 3.82 (s, 3H, —OCH₃), 3.78 (s, 3H, —OCH₃), 3.68 (d, J=12.2 Hz, 1H, C2-H), 3.52 (t, J=6.6 Hz, 2H, —CH₂O—), 2.98 (d, J=12.2 Hz, 1H, C2-H), 2.74–2.71 (m, 1H, C4-H), 1.58–1.23 (m, 5H), 1.18 (s, 3H, C3-CH₃), 1.16–1.03 (m, 6H).

Step 4) Synthesis of 6-[7-methoxy-3-(4-methoxyphenyl)-3-methylthiochroman 4-yl]hexanal

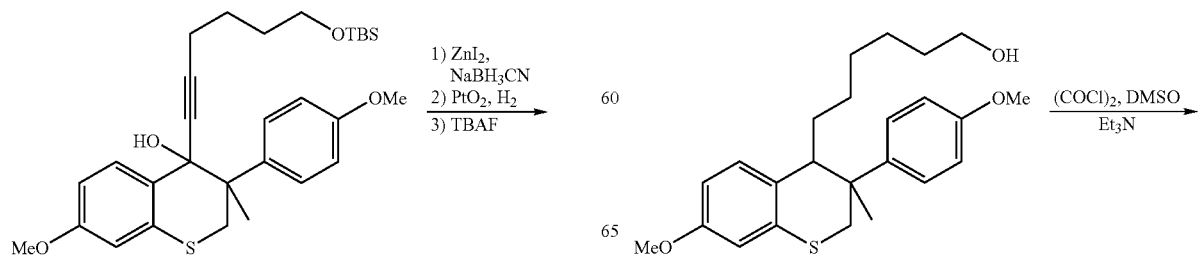

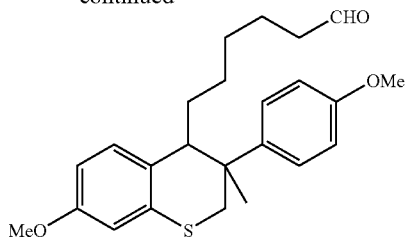

To a solution of oxalyl chloride (238 mg, 1.88 mmol) in dichloromethane (5 ml) was added dimethylsulfoxide (316 mg, 3.75 mmol) in dichloromethane (1 ml) at −70° C., which was then stirred at the same temperature for 10 minutes. Next, to the solution was added 4-(6-hydroxyhexyl)-7-methoxy-3-(4-methoxyphenyl)-3-methylthiochroman (500 mg, 1.25 mmol) in dichloromethane (5 ml) at −70° C., which was then stirred at the same temperature for 30 minutes. Then, to the reaction mixture was added triethylamine (1.0 ml, 7.5 mmol) at the same temperature and stirred for 30 minutes and warmed to room temperature. After the reaction was completed, water was added to the reaction mixture, and the resulting mixture was extracted with ethyl acetate. The extract was dried over anhydrous sodium sulfate, and concentrated under reduced pressure. The residue was used to next step without purification (470 mg, yield: 94%).

$^1$H-NMR (270 MHz, CDCl$_3$) δ: 9.66 (d, J=1.7 Hz, 1H, —CHO), 7.28 (d, J=8.9 Hz, 2H, Ar—H), 6.92 (d, J=8.6 Hz, 1H, C5-H), 6.90 (d, J=8.9 Hz, 2H, Ar—H), 6.73 (d, J=2.6 Hz, C8-H), 6.58 (dd, J=8.6 Hz and 2.6 Hz, 1H, C6-H), 3.82 (s, 3H, —OCH$_3$), 3.78 (s, 3H, —OCH$_3$), 3.68 (d, J=11.8 Hz, 1H, C2-H), 2.99 (d, J=11.8 Hz, 1H, C2-H), 2.73–2.71 (m, 1H, C4-H), 2.27 (dt, J=1.7 Hz and 7.2 Hz, 2H, —CH$_2$—CHO), 1.57–1.23 (m, 4H), 1.18 (s, 3H, C3-CH$_3$), 1.16–1.04 (m, 6H).

Step 5) Synthesis of methyl 8-[7-methoxy-3*4-methoxyphenyl)-3-methylthiochroman-4-yl]-2-octenate

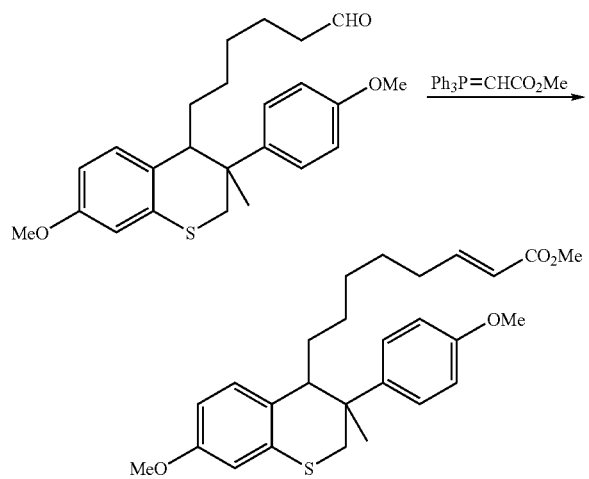

To a solution of 6-[7-methoxy-3-(4-methoxyphenyl)-3-methylthiochroman-4-yl]hexanal (180 mg, 0.45 mmol) in dichloromethane (1 ml) was added methyl(triphenylphosphoranylidene)acetate (227 mg, 0.68 mmol) at room temperature, which was then stirred at the same temperature for 2 days.

After the reaction was completed, the organic solvent was removed under reduced pressure to give a crude product. This crude product thus obtained was subjected to silica gel column chromatography (n-hexane:ethyl acetate=4:1) to give the title compound (160 mg, yield: 75%;(3RS,4RS): (3RS,4SR)=4:1).

$^1$H-NMR (270 MHz, CDCl$_3$) δ: 7.29 (d, J=9.2 Hz, 2H, Ar—H), 6.92 (d, J=8.5 Hz, 1H, C5-H), 6.90 (d, J=9.2 Hz, 2H, Ar—H), 6.85 (d, J=15.8 Hz, 1H, —CH═CHCO$_2$—), 6.73 (d, J=2.3 Hz, 1H, C8-H), 6.58 (dd, J=8.5 Hz and 2.3 Hz, 1H, C6-H), 5.73 (d, J=16.2 Hz, 1H, —CH═CHCO$_2$—), 3.82 (s, 3H, —OCH$_3$), 3.78 (s, 3H, —OCH$_3$), 3.71 (s, 3H, —CO$_2$CH$_3$), 3.69 (d, J=11.6 Hz, 1H, C2-H), 2.98 (d, J=11.6 Hz, 1H, C2-H), 2.73–2.70 (m, 1H, C4-H), 2.05–2.00 (m, 2H, —CH2CH═), 1.37–1.18 (m, 2H), 1.17 (s, 3H, C3-CH$_3$), 1.16–1.02 (m, 6H).

Step 6) Synthesis of Methyl 8-[7-methoxy-3-(4-methoxyphenyl)-3-methylthiochroman-4-yl]octanate

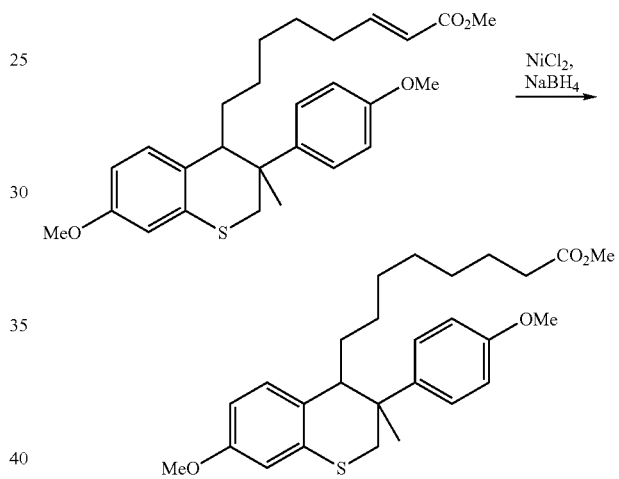

To a solution of methyl 8-[7-Methoxy-3-(4-methoxyphenyl)-3-methylthiochroman-4-yl]-2-octenate (160 mg, 0.34 mmol) in methanol (3 ml) and tetrahydrofuran (1 ml) were added sodium borohydride (129 mg, 3.40 mmol) and nickel (1 ml) chloride hexahydrate (16 mg, 0.068 mmol) at 0° C., which was then stirred at the same temperature for 2 hours. After the reaction was completed, water was added to the reaction mixture, and the resulting mixture was extracted with ethyl acetate. The extract was dried over anhydrous sodium sulfate, and concentrated under reduced pressure to give a crude product. This crude product thus obtained was subjected to silica gel column chromatography (n-hexane: ethyl acetate=4:1) to give the title compound (118 mg, yield: 73%; (3RS,4RS):(3RS,4SR)=4:1).

$^1$H-NMR (270 MHz, CDCl$_3$) d: 7.29 (d, J=8.9 Hz, 2H, Ar—H), 6.92 (d, J=8.3 Hz, 1H, C5-H). 6.90 (d, J=8.9 Hz, 2H, Ar—H), 6.74 (d, J=1.7 Hz, 1H, C8-H), 6.57 (dd, J=8.3 Hz and 1.7 Hz, 1H, C6-H), 3.82 (s, 3H, —OCH$_3$), 3.78 (s, 3H, —OCH$_3$), 3.64 (s, 3H, —CO$_2$CH$_3$), 3.63 (d, J=11.5 Hz, 1H, C2-H), 2.98 (d, J=11.5 Hz 1H, C2-H), 2.75–2.71 (m, 1H, C4-H), 2.22 (t, J=7.6 Hz, 2H, —CH$_2$CO$_2$—), 1.56–1.45 (m, 2U), 1.35–1.18 (m, 2H), 1.17 (s, 3H, C3-CH$_3$), 1.16–1.02 (m, 8H).

Step 7) Synthesis of methyl (3'RS,4'RS)-8-[7-hydroxy-3-(4-hydroxyphenyl)-3-methylthiochroman-4-yl]octanoate

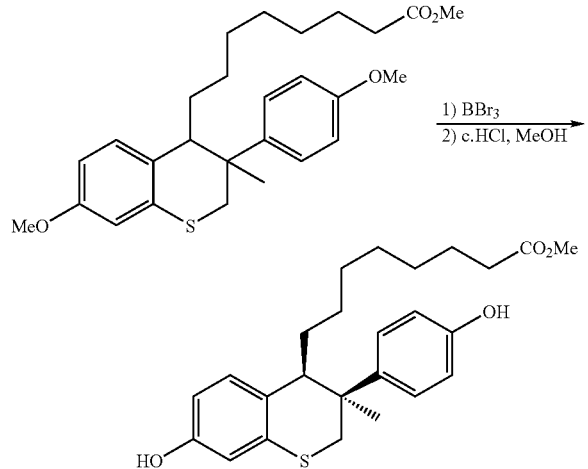

To a solution of methyl 8-[7-methoxy-3-(4-methoxyphenyl)-3-methylthiochroman-4-yl]octanoate (120 mg, 0.25 mmol) in dichloromethane (2 ml) was added boron tribromide (1.5 ml, 1.5 mmol, 1.0M solution in dichloromethane) at −78° C., which was then stirred at the same temperature for 1 hour and warmed up to room temperature and stirred for 5 hours. After the reaction was completed, water was added to the reaction mixture, and the resulting mixture was extracted with ethyl acetate. The extract was dried over anhydrous sodium sulfate, and concentrated under reduced pressure to give a crude product.

To a solution of this crude product in methanol (2 ml) was added concentrated hydrochloride (0.1 ml) at room temperature, which was then stirred at the same temperature for 24 hours. After the reaction was completed, water was added to the reaction mixture, and the resulting mixture was extracted with ethyl acetate. The extract was dried over anhydrous sodium sulfate, and concentrated under reduced pressure to give a crude product. This crude product thus obtained was subjected to preparative TLC (n-hexane:ethyl acetate=4:1) to give the title compound (77 mg, yield: 68%).

$^1$H-NMR (270 MHz, CDCl$_3$) δ: 7.24 (d, J=8.6 Hz, 2H, Ar—H), 6.86 (d, J=7.9 Hz, 1H, C5-H), 6.85 (d, J=8.6 Hz, 2H, Ar—H), 6.67 (d, J=2.7 Hz, 1H, C8-H), 6.49 (dd, J=7.9 Hz and 2.7 Hz, 1H, C6-H), 5.45 (brs, 1H, —OH), 4.72 (brs, 1H, —OH), 3.68 (s, 3H, —CO$_2$CH$_3$), 3.63 (d, J=11.9 Hz, 1H, C2-H), 2.93 (d, J=11.9 Hz, 1H, C2-H), 2.70–2.61 (m, 1H, C4-H), 2.24 (t, J=7.3 Hz, 2H, —CH$_2$CO$_2$—), 1.56–1.42 (m, 2H), 1.19 (s, 3H, C3-CH$_3$), 1.16–0.90 (m, 10H).

Step 8) Synthesis of (3'RS,4'RS)-8-[7-hydroxy-3-(4-hydroxyphenyl)-3-methylthiochroman-4-yl]octanoic acid

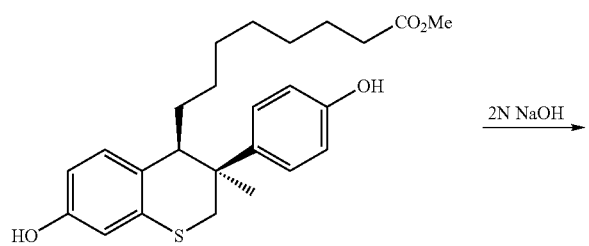

To a solution of (3'RS,4'RS)-methyl 8-[7-hydroxy-3-(4-hydroxyphenyl)-3-methylthiochroman-4-yl]octanoate (77 mg, 0.18 mmol) in methanol (0.5 ml) was added sodium hydroxide solution (0.5 ml, 2N solution in water) at room temperature, which was then stirred at the same temperature for 2 hours. After the reaction was completed, 2N hydrochloride solution (0.6 ml) and water was added to the reaction mixture, and the resulting mixture was extracted with ethyl acetate. The extract was dried over anhydrous sodium sulfate, and concentrated under reduced pressure to give a crude product. This crude product thus obtained was subjected to preparative TLC (n-hexane:ethyl acetate=1:2) to give the title compound (70 mg, yield: 94%).

$^1$H-NMR (270 MHz, CD$_3$OD) d: 7.24 (d, J=8.6 Hz, 0.2H, Ar—H), 6.85 (d, J=8.2 Hz, 1H, C5-H), 6.78 (d, J=8.6 Hz, 2H, Ar—H), 6.56 (d, J=2.3 Hz, 1H, C8-H), 6.44 (dd, J=8.2 Hz and 2.3 Hz, 1H, C6-H), 3.61 (d, J=11.5 Hz, 1H, C2-H), 2.95 (d, J=11.5 Hz, 1H, C2-H), 2.78–2.70 (m, 1H, C4H), 2.20 (t, J=7.6 Hz, 2H, —CH$_2$CO$_2$—), 1.48 (quin, J=6.9 Hz, 2H, —CH$_2$CH$_2$CO$_2$—), 1.27–1.03 (m, 13H).

EXAMPLE 40

Synthesis of (3'RS,4'RS)-6-[7-hydroxy-3-(4-hydroxyphenyl)-3-methylthiochroman-4-yl]hexanoic acid Step 1) Synthesis of (3'RS,4'RS)-6-[7-methoxy-3-(4-methoxyphenyl)-3-methylthiochroman-4-yl]hexanoic acid

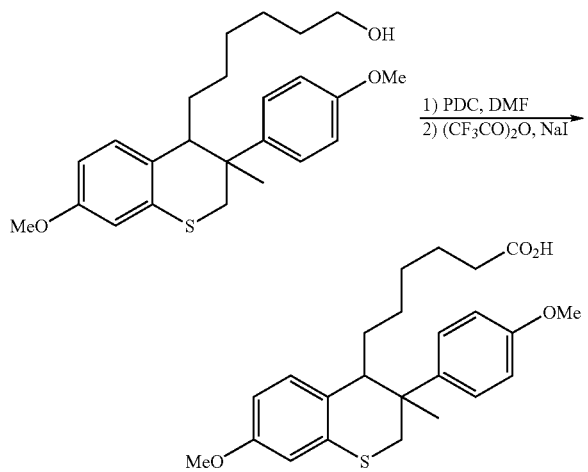

To a solution of (3'RS,4'RS)-4-(6-hydroxyhexyl)-7-methoxy-3-(4-methoxyphenyl)-3-methylthiochroman (100 mg, 0.25 mmol) in N,N-dimethylformamide (1 ml) was added pyridinium dichromate (188 mg, 0.50 mmol) at room temperature, which was then stirred at the same temperature for 15 hours. After the reaction was completed, the reaction mixture was filtered, and concentrated under reduced pressure to give a crude product. This crude product (34 mg) thus obtained was used to next step without purification.

To a solution of trifluoroacetic anhydride (66 mg, 0.32 mmol) in acetone (1 ml) was added dropwise a solution of the crude product (34 mg) and sodium iodide (36 mg, 0.24 mmol) in acetone (1 ml) at −60° C., which was then stirred at the same temperature for 10 minutes. After the reaction was completed, saturated sodium hydrogencarbonate solution was added to the reaction mixture, and then 5% sodium thiosulfate solution was also added. The resulting mixture was extracted with ethyl acetate. The extract was dried over anhydrous sodium sulfate, and concentrated under reduced pressure to give a crude product. This crude product thus obtained was subjected to preparative TLC (n-hexane:ethyl acetate=1:2) to give the title compound (31 mg, yield: 30%).

$^1$H-NMR (270 MHz CDCl$_3$). δ: 7.29 (d, J=8.9 Hz, 2H, Ar—H), 6.92 (d, J=8.3 Hz, 1H, C5-H), 6.90 (d, J=8.9 Hz, 2H, Ar—H), 6.74 (d, J=1.7 Hz, 1H, C8-H), 6.57 (dd, J=8.3 Hz and 1.7 Hz, 1H, C6-H), 3.82 (s, 3H, —OCH$_3$), 3.78 (s, 3H, —OCH$_3$), 3.64 (s, 3H, —CO$_2$CH$_3$), 3.63 (d, J=11.5 Hz, 1H, C2-H), 2.98 (d, J=11.5 Hz, 1H, C2-H), 2.75–2.71 (m, 1H, C4-H), 2.22 (t. J=7.6 Hz, 2H, —CH$_2$CO$_2$—), 1.56–1.45 (m, 2H), 1.35–1.18 (m, 2H), 1.17 (s, 3H, C3-CH$_3$), 1.16–1.02 (m, 9H).

Step 2) Synthesis of methyl (3'RS,4'RS)-6-[7-hydroxy-3-(4-hydroxyphenyl)-3-methylthiochroman-4-yl]hexanoate

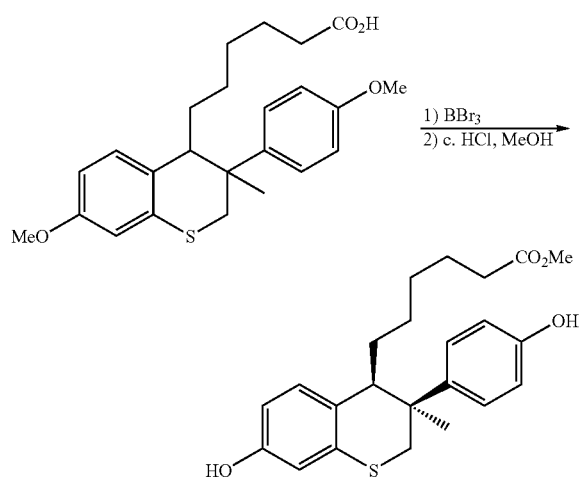

The title compound was prepared from (3'RS,4'RS)-6-[7-methoxy-3-(4-methoxyphenyl)-3-methylthiochroman-4-yl]hexanoic acid according to the same procedure as Step 7 of Example 39 (yield: 74%).

$^1$H-NMR (270 MHz, CDCl$_3$) δ: 7.23 (d, J=8.6 Hz, 2H, Ar—H), 6.85 (d, J=8.3 Hz, 1H, C5-H), 6.82 (d, J=8.6 Hz, 2H, Ar—H), 6.67 (d, J=2.5 Hz, 1H, C8-H), 6.49 (dd, J=8.3 Hz and 2.5 Hz, 1H, C6-H), 4.79 (brs, 1H, —OH), 4.65 (brs, 1H, —OH), 3.62 (s, 3H, —CO$_2$CH$_3$), 3.60 (d, J=11.6 Hz, 1H, C2-H), 2.95 (d, J=11.6 Hz, 1H, C2-H), 2.72–2.65 (m, 1H, C4-H), 2.16 (t, J=7.6 Hz, 2H, —CH$_2$CO$_2$—), 1.40 (quin, J=7.6 Hz, 2H, —CH$_2$CH$_2$CO$_2$—), 1.17 (s, 3H, C3-CH$_3$), 1.16–1.02 (m, 6H).

Step 3) Synthesis of (3'RS,4'RS)-6-[7-hydroxy-3-(4-hydroxyphenyl)-3-methylthiochroman-4-yl]hexanoic acid

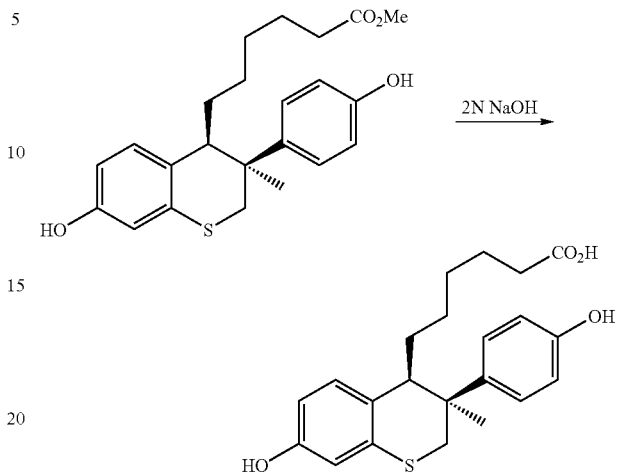

The title compound was prepared from methyl (3'RS, 4'RS)-6-[7-hydroxy-3-(4-hydroxyphenyl)-3-methylthiochroman-4-yl]hexanoate according to the same procedure as Step 8 of Example 39 (yield 78%).

$^1$H-NMR (270 MHz, CD$_3$OD) δ: 7.24 (d, J=8.3 Hz, 2H, Ar—H), 6.87 (d, J=8.3 Hz, 1H, C5-H), 6.78 (d, J=8.3 Hz, 2H, Ar—H), 6.56 (d, J=2.3 Hz, 1H, C8-H), 6.45 (dd, J=8.3 Hz and 2.3 Hz, 1H, C6-H), 3.61 (d, J=11.5 Hz, 1H, C2-H), 2.95 (d, J=11.5 Hz, 1H, C2-H), 2.80–2.72 (m, 1H, C4-H), 2.14 (t, J=7.3 Hz, 2H, —CH$_2$CO$_2$—), 1.42–1.30 (m 2H, —CH$_2$CH$_2$CO$_2$—), 1.22–1.01 (m, 9H).

EXAMPLE 41

Synthesis of (3'RS,4'RS)-7-[7-hydrox -3-(4-hydroxyphenyl)-3-methylthiochroman-4-yl]heptanoic acid Step 1) Synthesis of (3'RS,4'RS)-7-[7-methoxy-3-(4-methoxyphenyl)-3-methy-1-thiochroman-4-yl]heptanenitrile

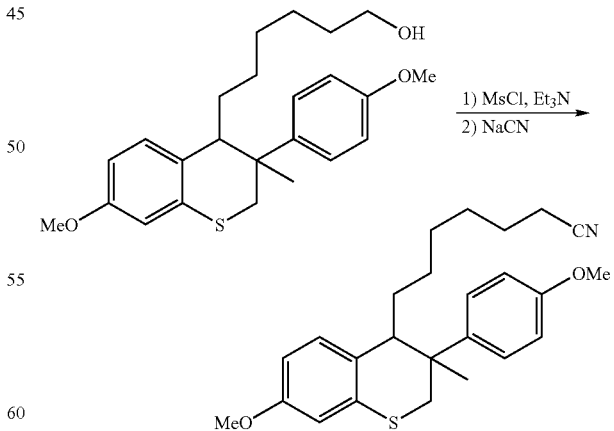

To a solution of (3'RS,4'RS)-4-(6-hydroxyhexyl)-7-methoxy-3-(4-methoxyphenyl)-3-methylthiochroman (200 mg, 0.50 mmol) in dichloromethane (5 ml) were added triethyamine (152 mg, 1.50 mmol) and methanesulfonyl chloride (86 mg, 0.75 mmol) at 0° C. which was then stirred at the same temperature for 10 minutes. After the reaction was completed, water was added to the reaction mixture. The resulting mixture was extracted with ethyl acetate. The extract was dried over anhydrous sodium sulfate, and concentrated under reduced pressure to give a crude product. This crude product thus obtained was used to next reaction without purification (235 mg).

To a solution of the crude product (235 mg, 0.49 mmol) in dimethylsulfoxide (1 ml) was added sodium cyanide (74 mg, 1.85 mmol) at room temperature, which was then stirred at 60° C. for 2 hours. After the reaction was completed, water was added to the reaction mixture. The resulting mixture was extracted with ethyl acetate. The extract was dried over anhydrous sodium sulfate, and concentrated under reduced pressure to give a crude product. This crude product thus obtained was subjected to preparative TLC (n-hexane:ethyl acetate=3:2) to give the title compound (178 mg, yield: 89%).

$^1$H-NMR (270 MHz, CDCl$_3$) δ: 7.28 (d, J=8.6 Hz, 2H, Ar—H), 6.90 (d, J=8.9 Hz, 1H, C5-H), 6.89 (d, J=8.6 Hz, 2H, Ar—H), 6.73 (d, J=2.7 Hz, 1H, C8-H), 6.58 (dd, J=8.9 Hz and 2.7 Hz, 1H, C6-H), 3.83 (s, 3H, —OCH$_3$), 3.78 (s, 3H, —OCH$_3$), 3.68 (d, J=11.9 Hz, 1H, C2-H), 2.98 (d, J=11.9 Hz, 1H, C2-H), 2.75–2.71 (m, 1H, C4-H), 2.21 (t, J=7.3 Hz, 2H, —CH$_2$CN), 1.60–1.45 (m, 2H), 1.18 (s, 3H, —CH$_3$), 1.22–1.02 (m, 8H).

Step 2) Synthesis of (3'RS,4'RS)-7-[7-methoxy-3-(4-methoxyphenyl)-3-methylthiochroman-4-yl]heptanoic acid

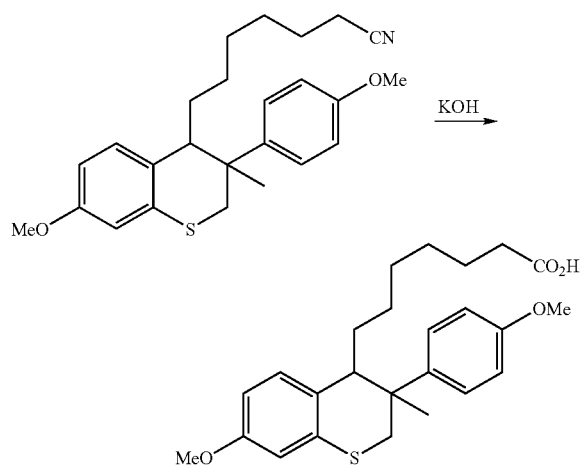

To a solution of (3'RS,4'RS)-7-[7-methoxy-3-(4-methoxyphenyl)-3-methylthiochroman-4-yl]heptanenitrile (111 mg, 0.27 mmol) in ethanol (2 ml) and water (2 ml) was added sodium hydroxide (300 mg, 5.4 mmol) at room temperature, which was then stirred at 80° C. for 15 hours. After the reaction was completed, 2N hydrochloride solution and water was added to the reaction mixture, and the resulting mixture was extracted with ethyl acetate. The extract was dried over anhydrous sodium sulfate, and concentrated under reduced pressure to give a crude product This crude product thus obtained was subjected to preparative TLC (n-hexane:ethyl acetate=1:2) to give the title compound (110 mg, yield: 95%).

$^1$H-NMR (270 MHz, CDCl$_3$) δ: 7.29 (d, J=8.6 Hz, 2H, Ar—H), 6.92 (d, J=8.2 Hz, 1H, C5-H), 6.89 (d, J=8.6 Hz, 2H, Ar—H), 6.73 (d, J=1.7 Hz, 1H, C8-H), 6.58 (dd, J=8.2 Hz and 1.7 Hz, 1H, C6-H), 3.82 (s, 3H, —OCH$_3$), 3.78 (s, 3H, —OCH$_3$), 3.68 (d, J=11.5 Hz, 1H, C2-H), 2.98 (d, J=11.5 Hz, 1H, C2-H), 2.75–2.71 (m, 1H, C4-H), 2.23 (t, J=7.2 Hz, 2H, —CH$_2$CO$_2$—), 1.56–1.02 (m, 11H), 1.17 (s, 3H, —CH$_3$).

Step 3) Synthesis of methyl (3'RS,4'RS)-methyl-[7-hydroxy-3-(4-hydroxyphenyl)-3-methylthiochroman-4-yl]heptanoic acid

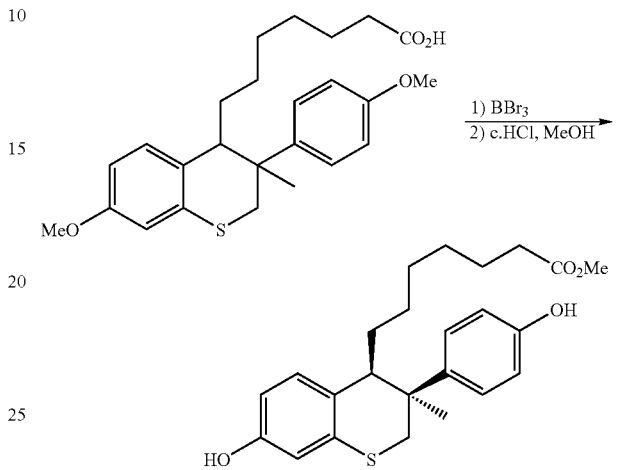

The title compound was prepared from (3'RS,4'RS)-7-[7-methoxy-3-(4-methoxyphenyl)-3-methylthiochroman-4-yl]heptanoic acid according to the same procedure as Step 7 of Example 39 (yield: 90%).

$^1$H-NMR (270 MHz, CDCl$_3$) δ: 7.23 (d, J=8.3 Hz, 2H, Ar—H), 6.87 (d, J=7.9 Hz, 1H, C5-H), 6.83 (d, J=8.3 Hz, 2 Hz, Ar—H), 6.67 (d, J=2.3 Hz, 1H, C8-H), 6.49 (dd, J=7.9 Hz and 2.3 Hz, 1H, C6-H), 5.03 (brs, 1H, —OH), 4.72 (brs, 1H, —OH), 3.65 (s, 3H, —CO$_2$CH$_3$), 3.63 (d, J=11.6 Hz, 1H, C2-H), 2.95 (d, J=11.6 Hz, 1H, C2-H), 2.72–2.65 (m, 1H, C4-H), 2.18 (t, J=7.9 Hz, 2H, —CH$_2$CO$_2$—), 1.55–1.40 (m, 2H), 1.18 (s, 3H, —CH$_3$), 1.17~1.02 (m, 8H).

Step 4) Synthesis of (3'RS,4'RS)-7-[7-hydroxy-3-(4-hydroxyphenyl)-3-methylthiochroman-4-yl]heptanoic acid

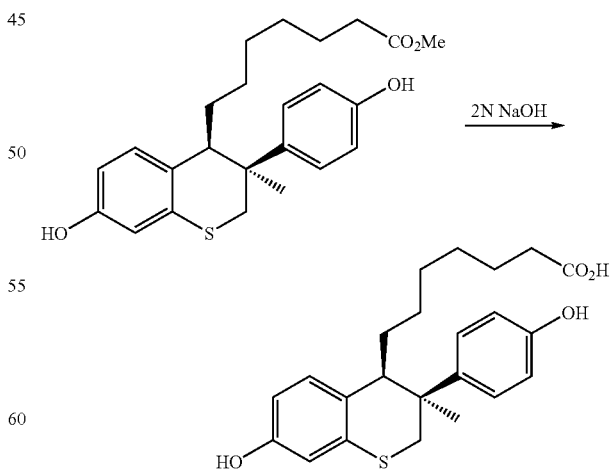

The title compound was prepared from methyl (3'RS,4'RS)-7-[7-hydroxy-3-(4-hydroxyphenyl)-3-methylthiochroman-4-yl]heptanoate according to the same procedure as Step 8 of Example 39 (yield: 84%).

$^1$H-NMR (270 MHz, CD$_3$OD) δ: 7.24 (d, J=8.9 Hz, 2H, Ar—H), 6.85 (d, J=8.2 Hz, 1H, C8-H), 6.78 (d, J=8.9 Hz, 2H, Ar—H), 6.56 (d, J=2.3 Hz, 1H, C5-H), 6.44 (dd, J=82 Hz and 2.3 Hz, 1H, C6-H), 3.62 (d, J=11.5 Hz, 1H, C2-H), 2.95 (d, J=11.5 Hz, 1H, C2-H), 2.80–2.72 (m, 1H, C4-H), 2.17 (t, J=7.3 Hz, 2H, —CH$_2$CO$_2$—), 1.48–1.40 (m 2H, CH$_2$CH$_2$CO$_2$—), 1.22–1.01 (m, 11H).

EXAMPLE 42

Synthesis of (3RS,4RS)-4-[4,7-dioxa-9-(4,4,5,5,5-pentafluoropentylsulfinyl)nonyl]-7-hydroxy-3-(4-hydroxyphenyl)-methylthiochroman Step 1) Synthesis of 5-(t-butyldimethylsilyloxy)-3-oxa-1-pentanol

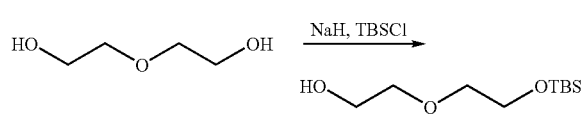

To a solution of di(ethyleneglycol) (2.0 g, 18.8 mmol) in dry tetrahydrofuran (80 ml) was added sodium hydride (754 mg, 60% in oil, 18.8 mmol) at 0° C., which then stirred at room temperature for 1 hour. Then, to the reaction mixture was added t-butyldimethylsilylchloride (2.84 g, 18.8 mmol) at 0° C., and the resulting mixture was stirred at the room temperature for 2 hours. After the reaction was completed, water was added to the reaction solution, and the mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane:ethyl acetate=4:1) to give the title compound (2.16 g, yield: 52%).

$^1$H-NMR (270 MHz, CDCl$_3$) δ: 3.78 (t, J=5.0 Hz, 2H, —CH$_2$), 3.72 (t, J=5.6 Hz, 2H, —CH$_2$), 3.62 (t, J=4.3 Hz, 2H, —CH$_2$), 3.60 (t, J=5.0 Hz, 2H, CH$_2$), 2.42 (t, 5.6 Hz, 1H, —OH), 0.91 (s, 9H, t-Bu), 0.08 (s, 6H, —SiMe2).

Step 2) Synthesis of 9-(t-butyldimethylsilyloxy)-4,7-dioxa-1-nonyne

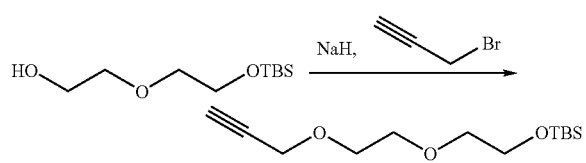

To a solution of 5-(t-butyldimethylsilyloxy)-3-oxa-1-pentanol (2.16 g, 9.8 mmol) in dry tetrahydrofuran (20 ml) was added sodium hydride (432 mg, 60% in oil, 10.8 mmol) at room temperature. The mixture was stirred for 30 minutes, and propalgyl bromide (2.9 g, 19.6 mmol) was added thereto. The mixture was stirred at room temperature for 12 hours. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane:ethyl acetate=8:1) to give the title compound (950 mg, yield: 38%).

$^1$H-NMR (270 MHz, CDCl$_3$) δ: 4.21 (d, J=2.3 Hz, 2H, C2-CH$_2$), 3.78 (t, J=5.3 Hz, 2H, —CH$_2$), 3.69 (s, 4H, —CH2×2), 3.57 (t, J=5.6 Hz, 2H, —CH$_2$), 2.42 (t, 2.3 Hz, 1H, C1-CH), 0.90 (s, 9H, -tbutyl-H), 0.07 (s, 6H, —SiMe$_2$).

Step 3) Synthesis of 4-[9-(t-butyldimethylsilyloxy)-4,7-dioxa-1-nonynyl]-4-hydroxy-7-methoxymethoxy-3-(4-methoxymethoxyphenyl)-3-methylthiochroman

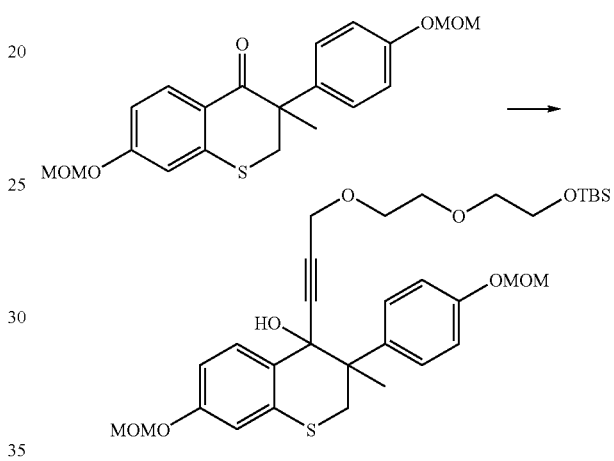

To a solution of 9-(t-butyldimethylsilyloxy)-4,7-dioxa-1-nonyne (1.03 g, 4.01 mmol) in dry tetrahydrofuran (10 ml) was added dropwise -n-butyl lithium (2.3 ml, 3.74 mmol, 1.63 mole/l in tetrahydrofuran) at −78° C., which was then stirred at −20° C. for 1 hour. Then, to this reaction mixture was added 7-methoxymethoxy-3-(4-methoxymethoxyphenyl)-3-methylthiochroman-4-one (1.0 g, 2.67 mmol) dissolved in tetrahydrofuran (10 ml) at the same temperature for 30 min, and the resulting mixture was stirred at −10° C. (for 24 hours. After the reaction was completed, saturated ammonium chloride solution was added to the reaction solution, and the mixture was extracted with ethyl acetate. The extract was dried over anhydrous sodium sulfate and concentrated under reduced pressure. The residue was subjected to column chromatography (n-hexane:ethyl acetate=4:1) to give the title compound (1.15 g, yield: 68%) as a colorless oil.

$^1$H-NMR (2.70 MHz, CDCl$_3$) δ: 7.82 (d, J=8.9 Hz, 1H, C5-H), 7.61 (d, J=8.9 Hz, 2H, Ar—H), 7.01 (d, J=8.9 Hz, 2H, Ar—H), 6.84 (d, J=2.3 Hz, 1H, C8-H), 6.75 (dd, J=8.9 Hz and 2.3 Hz, 1H, C6-H), 5.18 (s, 2H, —OCH$_2$OCH$_3$), 5.15 (s, 2H, —OCH$_2$OCH$_3$), 4.23 (d, J=12.1 Hz, 1H, C2-H), 4.22 (s, 2H, —CH$_2$O—), 3.77 (t, J=5.5 Hz, 2H, —CH$_2$O—), 3.65–3.45 (m, 6H), 3.49 (s, 3H, —OCH$_2$OCH$_3$), 3.47 (s, 3H, —OCH$_2$OCH$_3$), 2.70 (d, J=12.1 Hz, 1H, C2-H), 2.31 (s, 1H, —OH), 1.58 (s, 3H, C3-CH$_3$), 0.89 (s, 9H, -tbutyl-H), 0.06 (s, 6H, —SiMe$_2$).

Step 4) Synthesis of 4-(4,7-dioxa-9-hydroxynonyl)-7-methoxymethoxy-3-(4-methoxymethoxyphenyl)-3-methylthiochroman

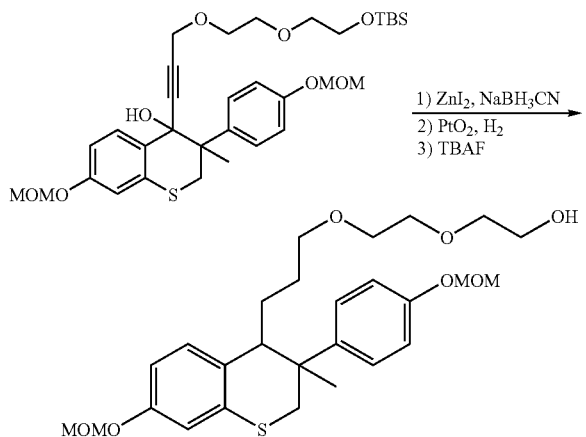

The title compound was prepared from 4-[9-(t-butyldimethylsilyloxy)-4,7-dioxa-1-nonynyl]4-hydroxy-7-methoxymethoxy-3-(4-methoxymethoxyphenyl)-3-methylthiochroman according to the same procedure as Step 3 of Example 39 (yield: 33%).

$^1$H-NMR (270 MHz, CDCl$_3$) δ: 7.28 (d, J=8.9 Hz, 2H, Ar—H), 7.02 (d, J=8.9 Hz, 2H, Ar—H), 6.95 (d, J=8.5 Hz, 1H, C5-H), 6.88 (d, J=2.3 Hz, 1H, C8-H), 6.68 (dd, J=8.5 Hz and 2.3 Hz, 1H, C6-H), 5.19 (s, 2H, —OCH$_2$OCH$_3$), 5.14 (s, 2H, —OCH$_2$OCH$_3$), 3.69–3.38 (m, 9H), 3.50 (s, 3H, —OCH$_2$OCH$_3$), 3.49 (s, 3H, —OCH$_2$OCH$_3$), 3.30–3.19 (m, 2H), 2.98 (d, J=11.6 Hz, 1H, C2-H), 2.81–2.75 (m, 1H, C4-H), 2.28 (brs, 1H, —OH), 1.53–1.20 (m, 4H), 1.17 (s, 3H, C3-CH$_3$).

Step 5) Synthesis of 4-[4,7-dioxa-9-(4,4,5,5,5-pentafluoropentylthio)nonyl]-7-methoxymethoxy-3-(4-methoxymethoxyphenyl)-3-methylthiochroman 4-(4,7-dioxa-9-hydroxynonyl)-7-methoxymethoxy-3-(4-methoxymethoxyphenyl)-3-methylthiochroman (290 mg, 0.57 mmol) was dissolved in dichloromethane (2 ml), and triethylamine (173 mg, 1.71 mmol) and methanesulfonylchloride (67 μl, 0.86 mmol) were sequentially added thereto at 0° C. The mixture was stirred at the same temperature for 10 minutes. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product This crude product thus obtained was used to next reaction without purification.

To a solution of thioesteracetate separately prepared (404 mg, 1.71 mmol) in methanol (2 ml) was added sodium methoxide (1.6 ml, 1.0M solution in methanol, 1.6 mmol) at room temperature. The mixture was stirred for 30 minutes, and a solution of crude mesylate in tetrahydrofuran (2 ml) was added thereto. The mixture was stirred at room temperature for 1 day. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane:ethyl acetate=3:1) to give the title compound (250 mg, yield: 64%, (3RS,4RS):(3RS,4SR)=4:1).

$^1$H-NMR (270 MHz, CDCl$_3$) δ: 7.28 (d, J=8.3 Hz, 2H, Ar—H), 7.02 (d, J=8.3 Hz, 2H, Ar—H), 6.94 (d, J=8.2 Hz, 1H, C5-H), 6.87 (d, J=2.3 Hz, 1H, C8-H), 6.68 (dd, J=8.2 Hz and 2.3 Hz 1H, C6H), 5.19 (s, 2H, —OCH$_2$OCH$_3$), 5.14 (s, 2H, —OCH$_2$OCH$_3$), 3.68–3.38 (m, 9H), 3.50 (s, 3H, —OCH$_2$OCH$_3$), 3.49 (s, 3H, —OCH$_2$OCH$_3$), 3.23–3.17 (m, 2H), 2.99 (d, J=11.5 Hz, 1H, C2-H), 2.81–2.75 (m, 1H, C4-H), 2.75–2.59 (m, 4H, —CH$_2$SCH$_2$—), 2.17–2.05 (m, 4H, —CH$_2$CH$_2$CF$_2$CF$_3$), 1.53–1.20 (m, 4H), 1.17 (s, 3H, C3-CH$_3$).

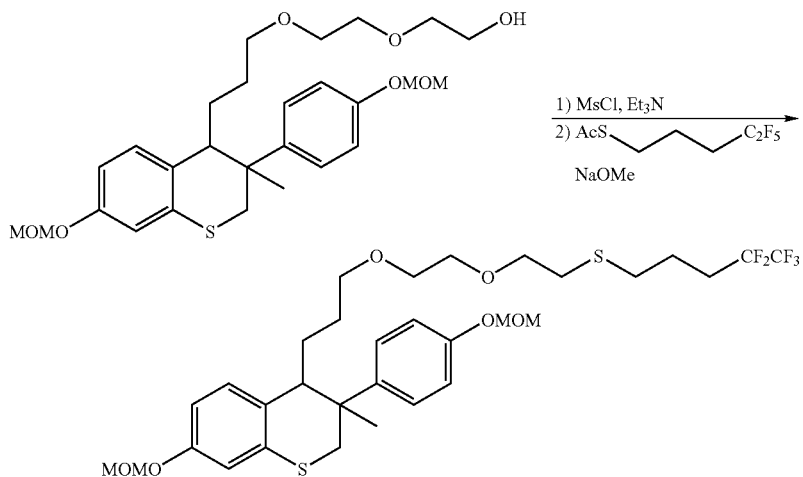

Step 6) Synthesis of (3RS,4RS)-4-[4,7-dioxa-9-(4,4,5,5,5-pentafluoropentylthio)nonyl]-7-hydroxy-3-(4-hydroxyphenyl)-3-methylthiochroman

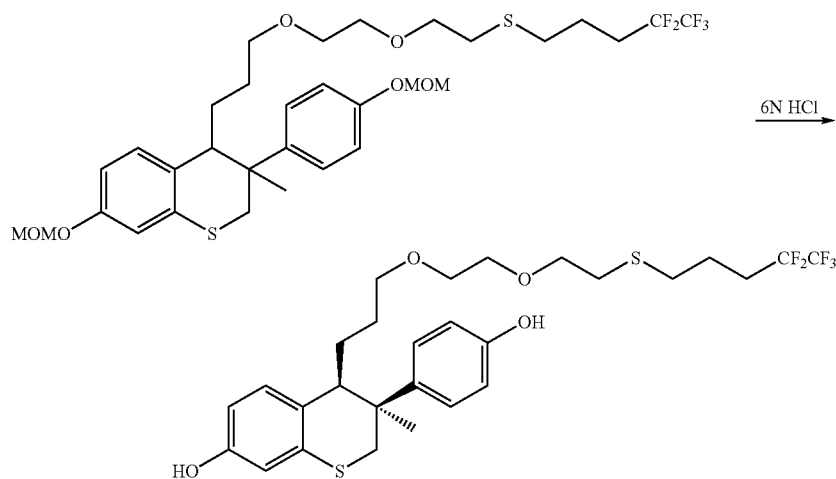

To a solution of 4-[4,7-dioxa-9-(4,4,5,5,5-pentafluoropentylthio)nonyl]-7-methoxymethoxy-3-(4-methoxymethoxyphenyl)-3-methylthiochroman (234 mg, 0.34 mmol) in tetrahydrofuran (1 ml) was added 6N hydrochloride solution (1 ml) at room temperature, which was then stirred for 26 hours. After the reaction was completed, saturated sodium hydrogencarbonate solution was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to preparative TLC (n-hexane:ethyl acetate=3:2) to give the title compound (45 mg, yield: 22%).

$^1$H-NMR (270 MHz, CDCl$_3$) δ: 7.23 (d, J=8.6 Hz, 2H, Ar—H), 6.88 (d, J=8.3 Hz, 1H, C5-H), 6.82 (d, J=8.6 Hz, 2H, Ar—H), 6.66 (d, J=2.4 Hz, 1H, C8-H), 6.47 (dd, J=8.3 Hz and 2.4 Hz, 1H, C6-H), 4.94 (brs, 1H, —OH), 4.82 (brs, 1H, —OH), 3.65–3.52 (m, 3H), 3.52–3.43 (m, 2H), 3.42–3.35 (m, 2H), 3.25–3.15 (m, 2H), 2.96 (d, J=11.5 Hz, 1H, C2-H), 2.78–2.70 (m, 1H, C4-H), 2.67 (t, J=6.6 Hz, 2H, —SCH$_2$—), 2.62 (t, J=7.2 Hz, 2H, —SCH$_2$—), 2.22–2.10 (m, 2H, —CH$_2$CH$_2$CF$_2$CF$_3$), 1.90–1.72 (m, 2H, —CH$_2$CH$_2$CF$_2$CF$_3$), 1.50–1.33 (m, 4H), 1.17 (s, 3H, C3-CH$_3$).

Step 7) Synthesis of (3RS,4RS)-4-[4,7-dioxa-9-(4,4,5,5,5-pentafluoropentylsulfinyl)nonyl]-7-hydroxy-3-(4-hydroxyphenyl)-3-methylthiochroman

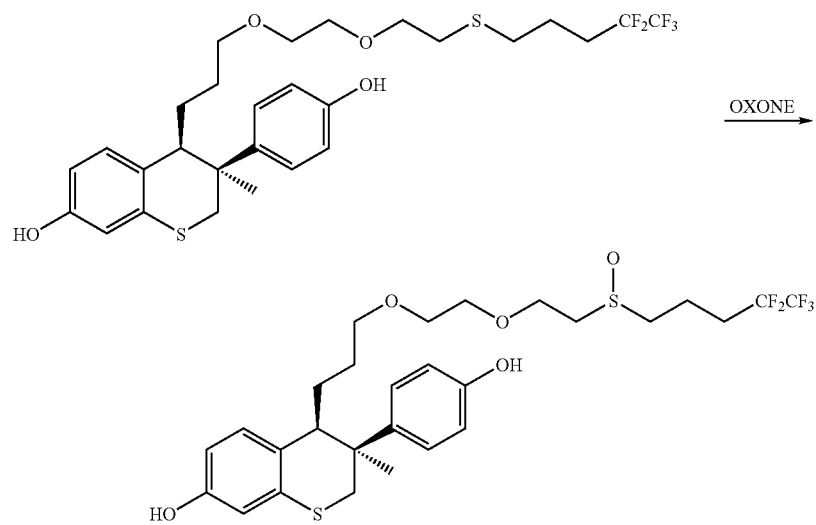

To a solution of thioether (43 mg, 0.072 mmol) in tetrahydrofuran (1 ml) was added Oxone® (monopersulfate compound; DuPont product) (22 mg, 0.036 mmol) at 0° C. Water (0.1 ml) was added thereto at the same temperature, which was then stirred for 2 hours. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to preparative TLC (n-hexane:ethyl acetate=1:10) to give the title compound (23 mg, yield: 52%).

$^1$H-NMR (270 MHz, CDCl$_3$) δ: 7.55 and 7.26 (s, total 1H, —OH), 7.22 (d, J=8.6 Hz, 2H, Ar—H), 6.86 (d, J=8.4 Hz, 1H, C5-H), 6.85 (d, J=8.6 Hz, 2H, Ar—H), 6.67 (d, J=2.3 Hz, 1H, C8-H), 6.49 (dd, J=8.4 Hz and 2.3 Hz, 1H, C6-H), 5.49 and 5.36 (s, total 1H, —OH), 3.84–3.51 (m, 4H), 3.48–3.05 (m, 6H), 3.00–2.60 (m, 5H), 2.35–2.10 (m, 4H, —C<u>H</u>$_2$C<u>H</u>$_2$CF$_2$CF$_3$), 1.42–1.22 (m, 4H), 1.21 and 1.19 (s, total 3H, C3-CH$_3$).

EI-MASS m/e=610 (M+).

EXAMPLE 43

Synthesis of (3RS,4RS)-7-hydroxy-3-(4-hydroxyphenyl)-3-methyl-4-[6-oxa-9-(4,4,5,5,5-pentafluoropentylsulfinyl)nonyl]thiochroman Step 1) Synthesis of 1-bromo-3-(t-butyldimethylsilyloxy) propane

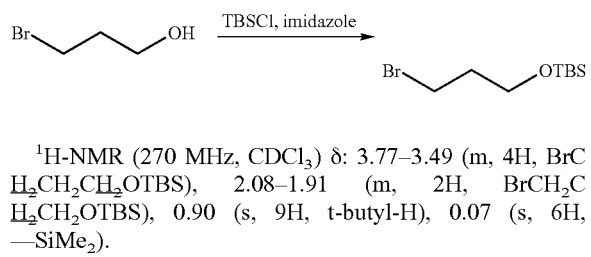

$^1$H-NMR (270 MHz, CDCl$_3$) δ: 3.77–3.49 (m, 4H, BrC<u>H</u>$_2$CH$_2$C<u>H</u>$_2$OTBS), 2.08–1.91 (m, 2H, BrCH$_2$C<u>H</u>$_2$CH$_2$OTBS), 0.90 (s, 9H, t-butyl-H), 0.07 (s, 6H, —SiMe$_2$).

Step 2) Synthesis of 9-(t-butyldimethylsilyloxy)-6-oxa-1-nonyne

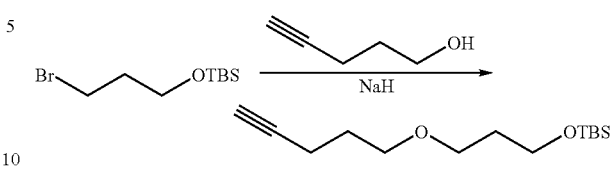

To a solution of 4-pentyn-1-ol (2.1 g, 26.1 mmol) in dry N,N-dimetylformamide (100 ml) was added sodium hydride (1.04 g, 60% in oil, 26.1 mmol) at room temperature. The mixture was stirred for 40 minutes, and 1-bromo-3-(t-butyldimethylsilyloxy) propane (4.4 g, 17.$^4$ mmol) was added thereto. The mixture was stirred at room temperature for 2 hours. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane:ethyl acetate=20:1) to give the title compound (920 mg, yield: 21%).

$^1$H-NMR (270 MHz, CDCl$_3$) δ: 3.69 (t, J=6.3 Hz, ZH, —CH$_2$OTBS), 3.50 (t, J=6.3 Hz, 4H, —C<u>H</u>$_2$OC<u>H</u>$_2$—), 2.28 (dt, J=2.6 Hz and 7.0 Hz, 2H, propargyl-CH$_2$), 1.94 (t, J=2.6 Hz, 1H, acetylene-CH), 1.83–1.70 (m, 4H, —CH$_2$×2), 0.89 (s, 9H, -tbutyl-H), 0.05 (s, 6H, —SiMe$_2$).

Step 3) Synthesis of 4-(9-hydroxy-6-oxanonyl)-7-methoxymethoxy-3-(4-methoxym ethoxyphenyl)-3-methylthiochroman

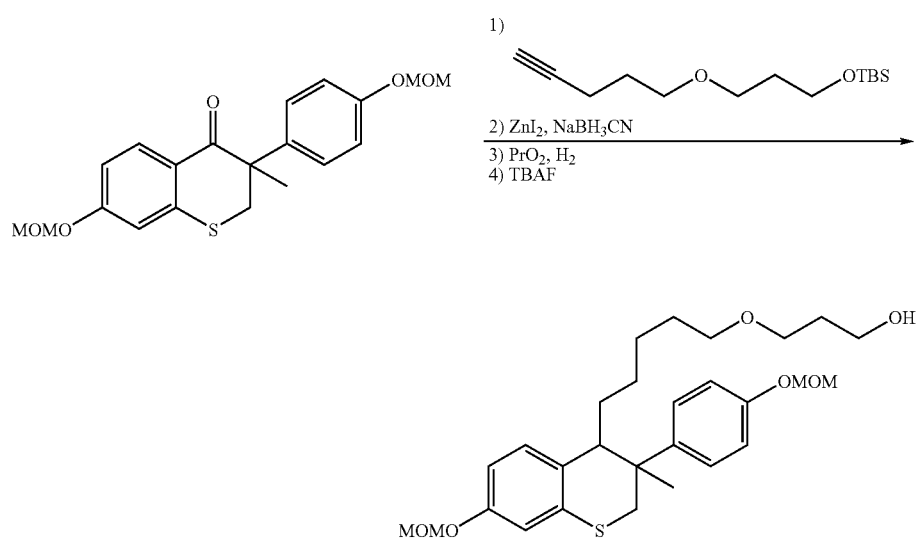

The title compound was prepared from 7-methoxymethoxy-3-(4-methoxymethoxyphenyl)-3-methylthiochroman-4-one according to the same procedure as Steps 2 to 3 of Example 39.

$^1$H-NMR (270 MHz, CDCl$_3$) δ: 7.28 (d, J=8.9 Hz, 2H, Ar—H), 7.02 (d, J=8.9 Hz, 2H, Ar—H), 6.92 (d, J=8.2 Hz, 1H, C5-H), 6.88 (d, J=2.6 Hz, 1H, C8-H), 6.69 (dd, J=8.2 Hz and 2.6 Hz, 1H, C6-H), 5.19 (s, 2H, —OCH$_2$OCH$_3$), 5.15 (s, 2H, —OCH$_2$OCH$_3$), 3.74–3.70 (m, 2H, —CH$_2$OH), 3.62 (d, J=11.6 Hz, 1H, C2-H), 3.55 (t, J=6.3 Hz, 2H, —OCH$_2$—), 3.51 (s, 3H, —OCH$_2$OCH$_3$), 3.49 (s, 3H, —OCH$_2$OCH$_3$), 3.28 (t, J=6.3 Hz, 2H, —OCH$_2$), 2.98 (d, J=11.6 Hz, 1H, C2-H), 2.74–2.70 (m, 1H, C4-H), 2.41 (brs, 1H, —OH), 1.84–1.74 (m, 2H), 1.42–1.25 (m, 2H), 1.17 (s, 3H, C3-CH$_3$), 1.17–1.00 (m, 6H).

Step 4) Synthesis of (3RS,4RS)-7-methoxymethoxy-3-(4-methoxymethoxyphenyl)-3-methyl-4-[6-oxa-9-(4,4,5,5,5-pentafluoropentylthio)nonyl]thiochroman The title compound was prepared from 4-(9-hydroxy-6-oxanonyl)-7-methoxymethoxy-3-(4-methoxymethoxyphenyl)-3-methylthiochroman according to the same procedure as Step 5 of Example 42 (yield: 74%)

$^1$H-NMR (270 MHz, CDCl$_3$) δ: 7.28 (d, J=8.6 Hz, 2H, Ar—H), 7.02 (d, J=86 Hz 2H, Ar—H), 6.92 (d, J=8.3 Hz, 1H, C5-H), 6.88 (d, J=2.7 Hz, 1C8-H), 6.68 (dd, J=8.3 Hz and 2.7 Hz, 1H, C6-H), 5.19 (s, 2H, —OCH$_2$OCH$_3$), 5.14 (s, 2H, —OCH$_2$OCH$_3$), 3.63 (d, J=11.6 Hz, 1H, C2-H), 3.51 (s, 3H, —OCH$_2$OCH$_3$), 3.49 (s, 3H, —OCH$_2$OCH$_3$), 3.41 (t, J=6.2 Hz, 2H, —OCH$_2$—), 3.26 (t, J=6.6 Hz, 2H, —OCH$_2$—), 2.98 (d, J=11.6 Hz, 1H, C2-H), 2.78–2.70 (m, 1H, C4-H), 2.57 (t, J=6.9 Hz, 2H, —CH$_2$SCH$_2$—), 2.55 (t, J=6.9 Hz, 2H, —CH$_2$SCH$_2$—), 2.25–2.05 (m, 2H, —CH$_2$CF$_2$CF$_3$), 1.92–1.74 (m, 4H, —CH$_2$CH$_2$CF$_2$CF$_3$ and —CH$_2$—), 1.38–1.32 (m, 2H), 1.17 (s, 3H, C3-CH$_3$), 1.17–1.01 (m, 6H).

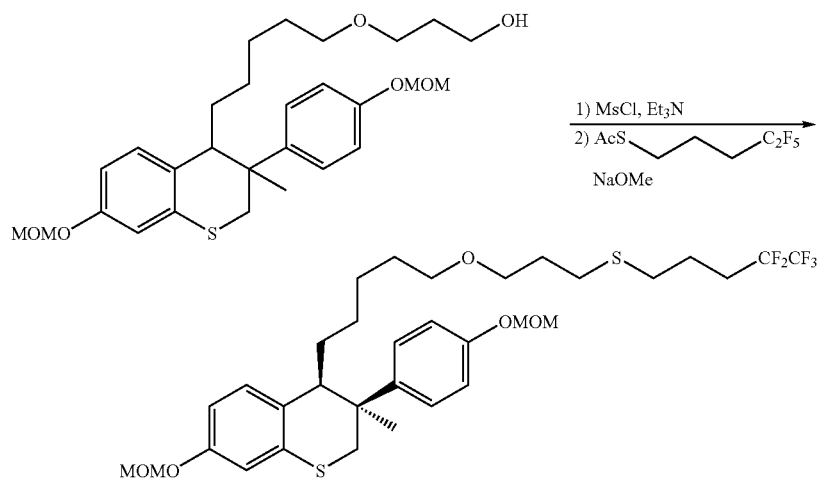

Step 5) Synthesis of (3RS,4RS)-7-hydroxy-3-(4-hydroxyphenyl)-3-methyl-4-[6-oxa-9-(4,4,5,5,5-pentafluoropentylthio)nonyl]thiochroman

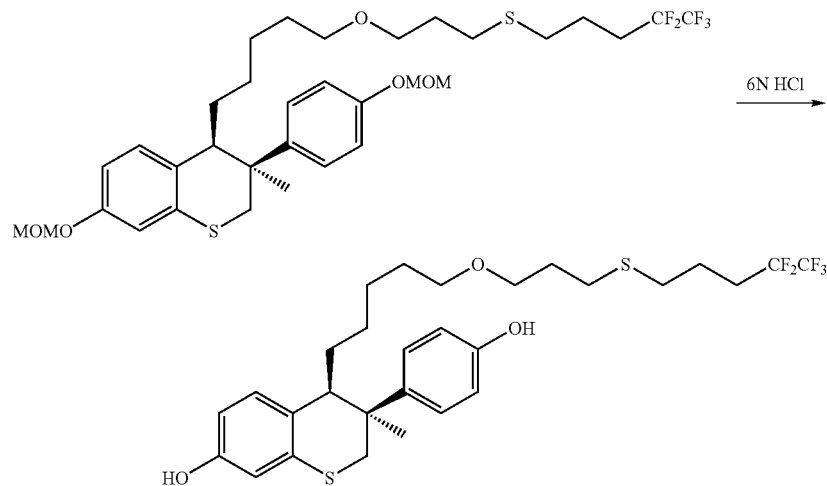

The title compound was prepared from (3RS,4RS)-7-methoxymethoxy-3-(4-methoxymethoxyphenyl)-3-methyl-4-[6-oxa-9-(4,4,5,5,5-pentafluoropentylthio)nonyl]thiochroman according to the same procedure as Step 6 of Example 42 (yield: 97%).

$^1$H-NMR (270 MHz, CDCl$_3$) δ: 7.24 (d, J=8.9 Hz, 2H, Ar—H), 6.86 (d, J=8.3 Hz, 1H, C5-H), 6.82 (d, J=8.9 Hz, 2H, Ar—H), 6.67 (d, J=2.3 Hz, 1H, C8-H), 6.49 (dd, J=8.3 Hz and 2.3 Hz, 1H, C6-H), 4.89 (brs, 1H, —OH), 4.74 (brs, 1H, —OH), 3.61 (d, J=11.5 Hz, 1H, C2-H), 3.41 (t, J=6.3 Hz, 2H, —OCH$_2$—), 3.26 (t, J=6.3 Hz, 2H, —OCH$_2$—), 2.95 (d, J=11.5 Hz, 1H, C2-H), 2.74–2.68 (m, 1H, C4-H), 2.58 (t, J=6.6 Hz, 2H, —SCH$_2$—), 2.55 (t, J=7.2 Hz, 2H, —SCH2—), 2.23–2.08 (m, 2H, —CH$_2$CF$_2$CF$_3$), 1.93–1.74 (m, 4H, —CH$_2$CH$_2$CF$_2$CF$_3$ and —CH$_2$—), 1.36–1.30 (m, 2H), 1.17 (s, 3H, C3-CH$_3$), 1.17–1.01 (m, 6H).

Step 6) Synthesis of (3RS,4RS)-7-hydroxy-3-(4-hydroxyphenyl)-3-methyl-4-[6-oxa-9-(4,4,5,5,5-pentafluoropentylsulfinyl)nonyl]thiochroman

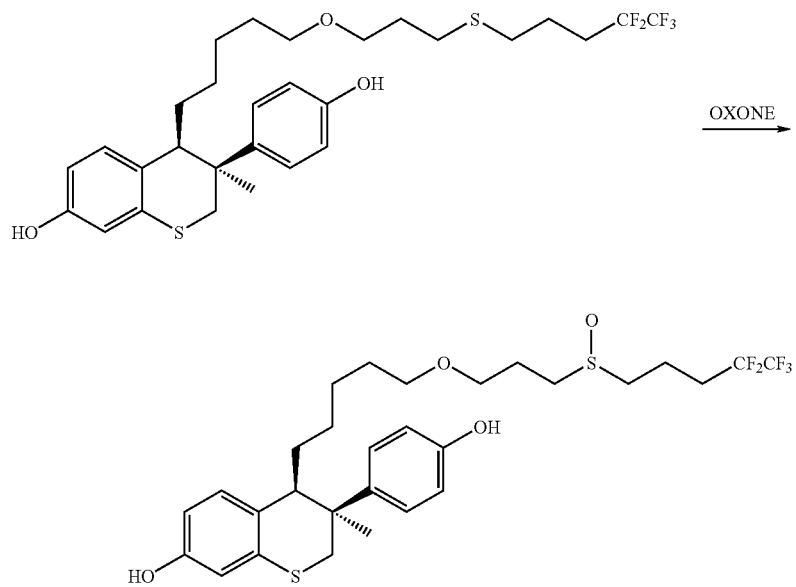

The title compound was prepared from (3RS,4RS)-7-hydroxy-3-(4-hydroxyphenyl)-3-methyl-4-[6-oxa-9-(4,4,5,5,5-pentafluoropentylsulfinyl)nonyl]thiochroman according to the same procedure as Step 7 of Example 42 (yield: 64%).

$^1$H-NMR (270 MHz, CDCl$_3$) δ: 7.61 and 7.31 (s, 1H, —OH), 7.22 (d, J=8.6 Hz, 2H, Ar—H), 6.87 (d, J=8.3 Hz, 1H, C5-H), 6.86 (d, J=8.6 Hz, 2H, Ar—H), 6.67 (d, J=2.4 Hz, 1H, C8-H), 6.49 (dd, J=8.3 Hz and 2.4 Hz, 1H, C6-H), 5.31 and 5.10 (s, total 1H, —OH), 3.63 (dd, J=11.2 Hz and 2.6 Hz, 1H, C2-H), 3.45–3.35 (m, 2H), 3.32–3.19 (m, 2H), 3.00–2.63 (m, 6H), 2.38–2.12 (m, 4H, —CH2CH2CF$_2$CF$_3$), 2.03–1.92 (m, 2H), 1.39–1.20 (m, 2H), 1.20 (s, 3H, C3-CH$_3$), 1.18–1.02 (m, 6H).

EXAMPLE 44

Synthesis of (3RS,4RS)-7-hydroxy-3-(4-hydroxyphenyl)-3-methyl-4-[7-oxa-9-(4,4,5,5,5-pentafluoropentylsulfinyl)nonyl]thiochroman Step 1) Synthesis of ethyl 3-oxa-8-nonynoate

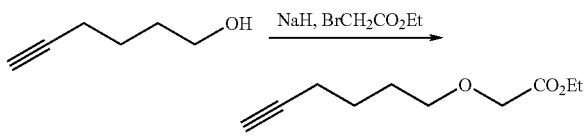

To a solution of 5-hexyn-1-ol (2.0 g, 20.4 mmol) in N,N-dimethylformamide (40 ml) was added sodium hydride (815 g, 60% in oil, 20.41 mmol) at 0° C. The mixture was stirred for 1 hour, and ethyl bromoacetate (3.4 ml, 30.5 mmol) was added thereto. The mixture was stirred at the same temperature for 1 hour. After the reaction was completed, water was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was subjected to silica gel column chromatography (n-hexane:ethyl acetate=4:1) to give the title compound (1.38 g, yield: 37%).

$^1$H-NMR (270 MHz, CDCl$_3$) δ: 4.28–4.13 (m, 2H, —CO$_2$CH$_2$CH$_3$), 4.07 (d, J=2.0 Hz, 1H, —OCH$_2$CO$_2$—), 3.56 (t, J=6.3 Hz, 2H, —CH$_2$O—), 2.24 (dt, J=2.7 Hz and 7.0 Hz, 2H, propargyl-CH$_2$), 1.97–1.94 (m, 1H, acetylene-H), 1.84–1.55 (m, 2H, —CH$_2$CH$_2$—), 1.33–1.23 (m, 3H, —CO$_2$CH$_2$CH$_3$).

Step 2) Synthesis of 9-(t-butyldimethylsilyloxy)-7-oxa-1-nonyne

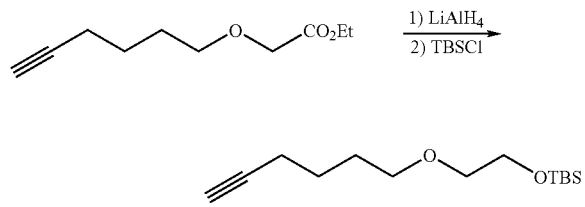

To a solution of ethyl 3-oxa-8-nonynoate (1.38 g, 7.5 mmol) in dry tetrahydrofuran (20 ml) was added lithium aluminium hydride (285 mg, 7.5 mmol) at 0° C., which was stirred at the same temperature for 30 minutes. After the reaction was completed, ethyl acetate was added thereto. The resulting mixture was extracted with ethyl acetate. The organic layer was washed with saturated saline solution, dried over anhydrous sodium sulfate, and filtered. The organic solvent was removed under reduced pressure to give a crude product. This crude product thus obtained was used to next reaction without purification (1.12 g).

To a solution of crude alcohol (1.12 g, 7.9 mmol) in N,N-dimethylformamide (10 ml) were added imidazole (591 mg, 8.7 mmol) and t-butyldimethylsilyl chloride (1.3 g, 8.7 mmol) at 0° C., which was then stirred at the same temperature for 30 minutes. After the reaction was completed, water was added to the reaction solution, and the mixture was extracted with ethyl acetate. The extract was dried over anhydrous sodium sulfate and concentrated under reduced pressure. The residue was subjected to column chromatography (n-hexane:ethyl acetate=10:1) to give the title compound (900 mg, yield: 47%) as a colorless oil.

$^1$H-NMR (270 MHz, CDCl$_3$) δ: 3.75 (t, J=5.3 Hz, 2H, —CH$_2$OTBS), 3.49 (t, J=6.9H, 4H, —CH$_2$OCH$_2$—), 2.22 (dt, J=2.6 Hz and 6.6 Hz, 2H, propargyl-CH2), 1.94 (t, J=2.6 Hz, 1H, acetylene-H), 1.72–1.55 (m, 4H, —CH$_2$CH$_2$—), 0.90 (s, 9H, t-butyl-H, 0.07 (s, 6H, —SiMe$_2$).

Step 3) Synthesis of (3RS,4RS)-4-(9-hydroxy-7-oxanonyl)-7-methoxymethoxy-3-(4-methoxymethoxyphenyl)-3-methylthiochroman

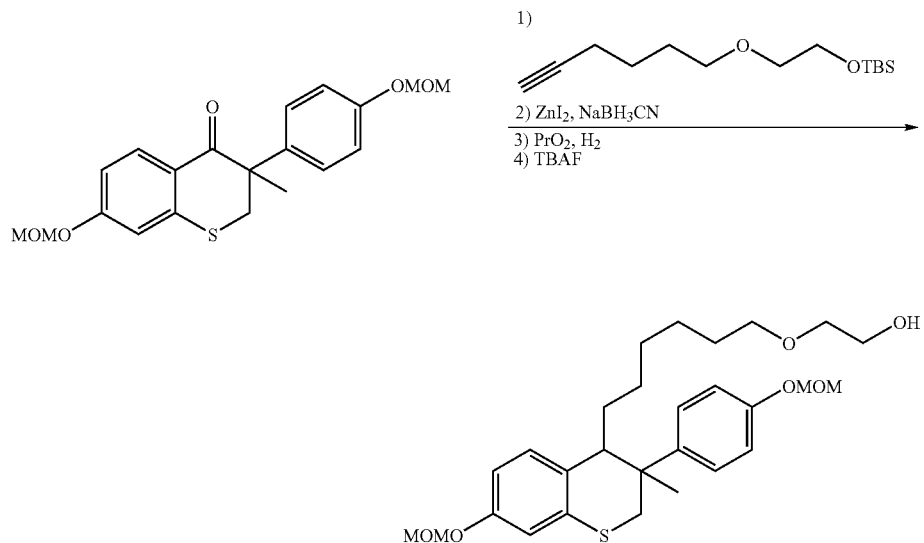

The title compound was prepared from 7-methoxymethoxy-3-(4-methoxymethoxyphenyl)-3-methylthiochroman-4-one according to the same procedure as Steps 2 to 3 of Example 39.

$^1$H-NMR (270 MHz, CDCl$_3$) δ: 7.28 (d, J=8.9 Hz, 2H, Ar—H), 7.02 (d, J=8.9 Hz, 2H, Ar—H), 6.92 (d, J=8.3 Hz, 1H, C5-H), 6.88 (d, J=2.7 Hz, 1H, C8-H), 6.69 (dd, J=8.3 Hz and 2.7 Hz, 1H, C6-H), 5.19 (s, 2H, —OCH$_2$OCH$_3$), 5.14 (s, 2H, —OCH$_2$OCH$_3$), 3.72–3.67 (m, 2H, —CH$_2$OH), 3.63 (d, J=11.5 Hz, 1H, C2-H), 3.51 (s, 3H, —OCH$_2$OCH$_3$), 3.49 (s, 3H, —OCH$_2$OCH$_3$), 3.48 (t, J=5.7 Hz, 2H, —OCH$_2$CH$_2$OH), 3.36 (t, J=6.6 Hz, 2H, —CH$_2$OCH$_2$CH$_2$OH), 2.98 (d, J=11.5 Hz, 1H, C2-H), 2.74–2.70 (m, 1H, C4-H), 1.95 (t, J=5.9 Hz, 1H, —OH), 1.54–1.17 (m, 4H), 1.17 (s, 3H, C3-CH$_3$), 1.16–1.01 (m, 6H).

Step 4) Synthesis of (3RS,4RS)-7-methoxymethoxy-3-(4-methoxymethoxyphenyl)-3-methyl-4-[7-oxa-9-(4,4,5,5,5-pentafluoropentylthio)nonyl]thiochroman The title compound was prepared from (3RS,4RS)-4-(9-hydroxy-7-oxanonyl)-7-methoxymethoxy-3-(4-methoxymethoxyphenyl)-3-methylthiochroman according to the same procedure as Step 5 of Example 42 (yield: 70%).

$^1$H-NMR (270 MHz, CDCl$_3$) δ: 7.28 (d, J=8.6 Hz, 2H, Ar—H), 7.02 (d, J=8.1 Hz, 2H, Ar—H), 6.92 (d, J=8.6 Hz, 1H, C5-H), 6.88 (d, =2.6 Hz, 1H, C8-H), 6.68 (dd, J=8.6 Hz and 2.6 Hz, 1H, C6-H), 5.19 (s, 2H, —OCH$_2$OCH$_3$), 5.14 (s, 2H, —OCH$_2$OCH$_3$), 3.62 (d, J=11.5 Hz, 1H, C2-H), 3.54 (t, J=6.6 Hz, 2H, —OCH$_2$CH$_2$S—), 3.50 (s, 3H, —OCH$_2$OCH$_3$), 3.49 (s, 3H, —OCH$_2$OCH$_3$), 3.33 (t, J=6.6 Hz, 2H, —CH$_2$OCH$_2$CH$_2$S—), 2.98 (d, J=11.5 Hz, 1H, C2-H), 2.75–2.70 (m, 1H, C4-H), 2.66 (t, J=6.9 Hz, 2H, —CH$_2$SCH$_2$—), 2.63 (t, J=6.9 Hz, 2H, —CH$_2$SCH$_2$—), 2.25–2.05 (m, 2H, —CH$_2$CF$_2$CF$_3$), 1.93–1.82 (m, 2H, —CH$_2$CH$_2$CF$_2$CF$_3$), 1.45–1.36 (m, 2H), 1.17 (s, 3H, C3-CH$_3$), 1.17–1.01 (m, 8H).

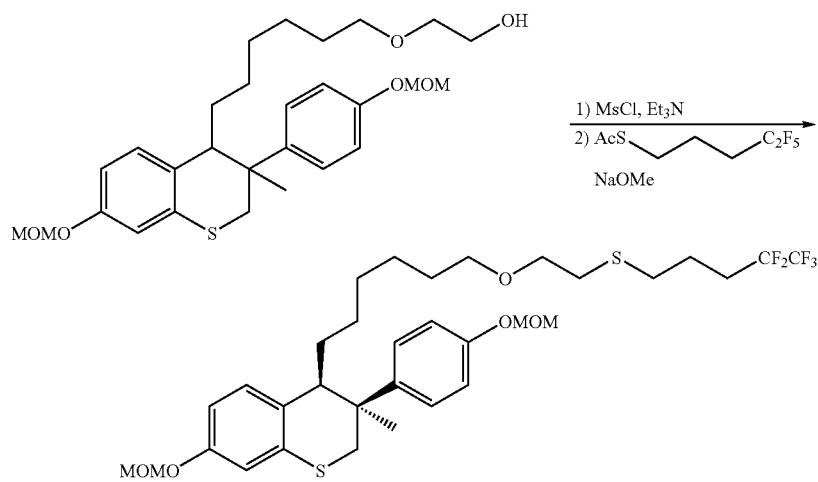

Step 5) Synthesis of (3RS,4RS)-7-hydroxy-3-(4-hydroxyphenyl)-3-methyl-4-[7-oxa-9-(4,4,5,5,5-pentafluoropentylthio)nonyl]thiochroman

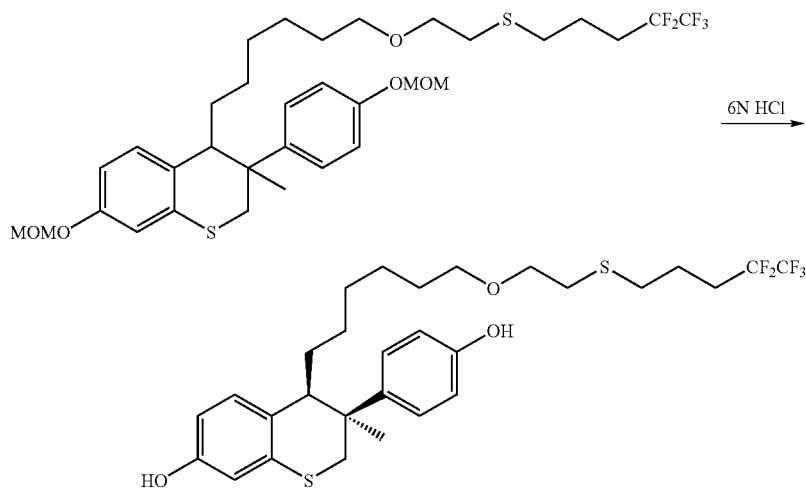

The title compound was prepared from (3RS,4RS)-7-methoxymethoxy-3-(4-methoxymethoxyphenyl)-3-methyl-4-[7-oxa-9-(4,4,5,5,5-pentafluoropentylthio)-nonyl]thiochroman according to the same procedure as Step 6 of Example 42 (yield: 92%).

¹H-NMR (270 MHz, CDCl₃) δ: 7.24 (d, J=8.9 Hz, 2H, Ar—H), 6.86 (d, J=8.6 Hz, 1H, C5-H), 6.82 (d, J=8.9 Hz, 2H, Ar—H), 6.67 (d, J=2.3 Hz, 1H, C8-H), 6.49 (dd, J=8.6 Hz and 2.3 Hz, 1H, C6-H), 4.92 (brs, 1H, —OH), 4.71 (brs, 2H, —OH), 3.62 (d, J=11.5 Hz, 1H, C2-H), 3.54 (t, J=6.6 Hz, 2H, —OCH₂CH₂S—), 3.32 (t, J=6.6 Hz, 2H, —CH₂OCH₂CH₂S—), 2.95 (d, J=11.5 Hz, 1H, C2-H), 2.70–2.65 (m, 1H, C4-H), 2.67 (t, J=6.6 Hz, 2H, —CH₂SCH₂—), 2.64 (t, J=6.9 Hz, 2H, —CH₂SCH₂—), 2.19–2.05 (m, 2H, —CH₂CF₂CF₃), 1.94–1.86 (m, 2H, —CH₂CH₂CF₂CF₃), 1.43–1.36 (m, 2H), 1.17 (s, 3H, C3-CH₃), 1.17–1.01 (m, 8H).

Step 6) Synthesis of (3RS,4RS)-7-hydroxy-3-(4-hydroxyphenyl)-3-methyl-4-[7-oxa-9-(4,4,5,5,5-pentafluoropentylsulfinyl)nonyl]thiochroman

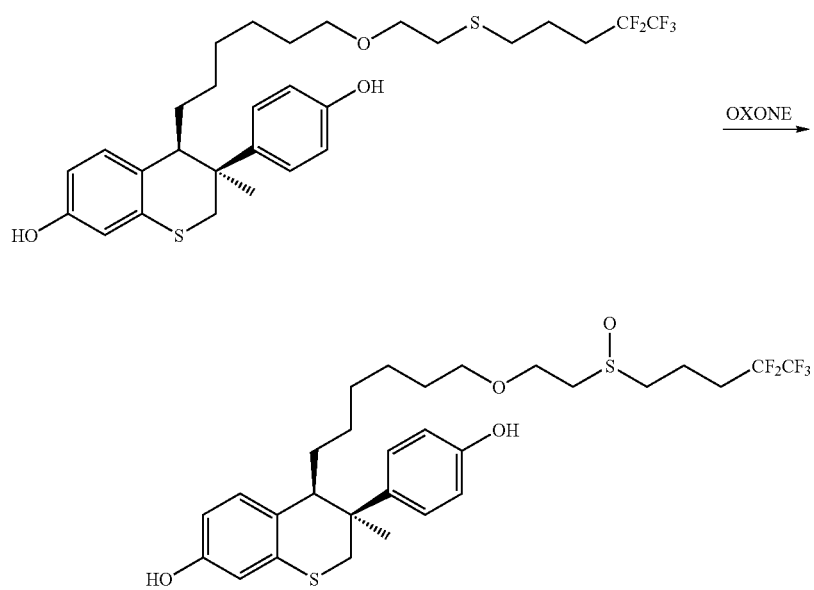

The title compound was prepared from (3RS,4RS)-7-hydroxy-3-(4-hydroxy-phenyl)-3-methyl-4-[7-oxa-9-(4,4,5,5,5-pentafluoropentylthio)nonyl]thiochroman according to the same procedure as Step 7 of Example 42 (yield: 62%).

¹H-NMR (270MHz CDCl₃) δ: 7.67 and 7.26 (s, total 1H, —OH), 7.23 (d, J=8.6 Hz, 2H, Ar—H), 6.86 (d, J=8.3 Hz, 1H, C5-H), 6.85 (d, J=8.6 Hz, 2H, Ar—H), 6.52 (d, J=3.0 Hz, 1H, C8-H), 6.48 (dd, J=8.3 Hz and 3.0 Hz, 1H, C6-H), 5.27 and 4.92 (s, total 1H, —OH), 3.82–3.76 (m, 2H), 70–3.60 (m, 1H), 3.38–3.21 (m, 2H), 3.20–3.09 (m, 1H), 3.00–2.80 (m, 5H), 2.70–2.60 (m, 1H), 2.38–2.18 (m, 4H, —CH₂CH₂CF₂CF₃), 2.03–1.92 (m, 2H), 1.38–126 (m, 2H), 1.21 (s, 3H, C3-CH₃), 1.20–0.80 (m, 6H).

EXAMPLE 45

Synthesis of (3RS,4RS)-7-hydroxy-3-(4-hydroxyphenyl)-3-methyl-4-[5-oxa-9-(4,4,5,5,5-pentafluoropentylsulfinyl)nonyl]thiochroman Step 1) Synthesis of 4-(t-butyldimethylsilyloxy)-1-butanol

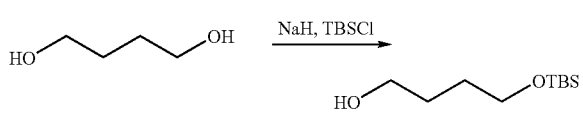

The title compound was prepared from 1,4-butanediol according to the same procedure as Step 1 of Example 42 (yield: 64%).

¹H-NMR (270 MHz, CDCl₃) δ: 3.67 (t, J=6.6 Hz, 2H, —CH₂OH), 3.65 (t, J=6.6 Hz, 2H, —CH₂OTBS), 2.51 (brs, 1H, —OH), 1.69–159 (m, 4H, —CH₂CH₂—), 0.91 (s, 9H, t-butyl-H), 0.07 (s, 6H, —SiMe₂—H).

Step 2) Synthesis of 4-(t-butyldimethylsilyloxy)butyl p-toluenesulfonate

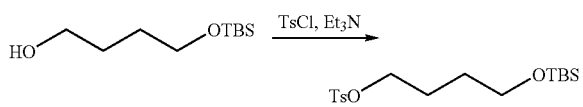

To a solution of 4-(t-butyldimethylsilyloxy)-1-butanol (2.8 g, 13.7 mmol) in dichloromethane (30 ml) were added triethyamine (3.83 ml, 27.4 mmol) and p-toluenesulfonyl chloride (2.88 g, 15.1 mmol) at 0° C., which was then stirred at the same temperature for 2 hours. After the reaction was completed, water was added to the reaction mixture. The resulting mixture was extracted with ethyl acetate. The extract was dried over anhydrous sodium sulfate, and concentrated under reduced pressure to give a crude product. This crude product thus obtained was subjected to silica gel column chromatography (n-hexane:ethyl acetate=5:1) to give the title compound (4.0 g, yield: 81%).

$^1$H-NMR (270 MHz, CDCl$_3$) δ: 7.79 (d, J=8.2 Hz, 2H, Ar—H), 7.34 (d, J=8.2 Hz, 2H, Ar—H), 4.06 (t, J=6.6 Hz, 2H, —CH$_2$OTs), 3.55 (t, J=6.2 Hz, 2H, —CH$_2$OTBS), 2.45 (s, 3H, —CH$_3$), 1.77–1.67 (m, 2H, —CH$_2$—), 1.56–1.47 (m, 2H, —CH$_2$—), 0.85 (s, 9H, t-butyl-H), 0.01 (s, 6H, —SiMe$_2$—H).

Step 3) Synthesis of 9-(t-butyldimethylsilyloxy)-5-oxa-1-nonyne

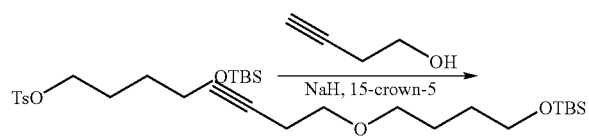

To a solution of 4-butyn-1-ol (587 mg, 8.38 mmol) in N,N-dimethylformamide (20 ml) were added sodium hydride (335 mg, 60% in oil, 8.38 mmol) and 15-crown-5 (369 mg, 1.12 mmol) at 0° C., which was then stirred at the same temperature for 1 hour. Then, to the reaction mixture was added 4-(t-butyldimethylsilyloxy)butyl p-toluenesulfonate (2.0 g, 5.58 mmol) in N,N-dimethylformamide (5 ml) at 0° C. which was then stiffed at the same temperature for 1 hour. After the reaction was completed, water was added to the reaction mixture. The resulting mixture was extracted with ethyl acetate. The extract was dried over anhydrous sodium sulfate, and concentrated under reduced pressure to give a crude product. This crude product thus obtained was subjected to silica gel column chromatography (n-hexane:ethyl acetate=5:1) to give the title compound (1.36 g, yield: 96%).

$^1$H-NMR (270 MHz, CDCl$_3$) δ: 3.63 (t, J=6.2 Hz, 2H, —OCH$_2$—), 3.65 (t, J=7.0 Hz, 2H, —OCH$_2$—), 3.48 (t, J=6.3 Hz, 2H, —OCH$_2$—), 2.46 (dt, J=2.6 Hz and 7.0 Hz, 1H, propargyl-CH$_2$), 1.97 (t, J=2.6 Hz, 1H, acetylene-CH), 1.66–1.51 (m, 4H, —CH$_2$CH$_2$—), 0.89 (s, 9H, t-butyl-H), 0.04 (s, 6H, —SiMe$_2$—H).

Step 4) Synthesis of (3RS,4RS)-4-(9-hydroxy-5-oxanonyl)-7-methoxymethoxy-3-(4-methoxymethoxyphenyl)-3-methylthiochroman

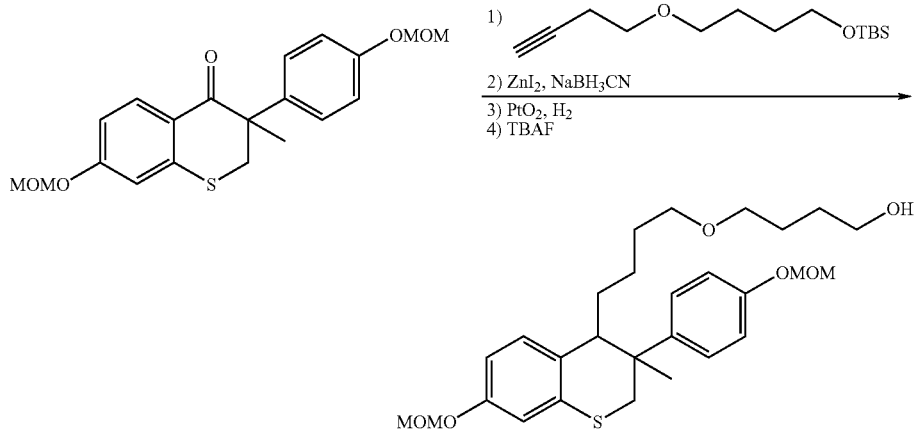

The title compound was prepared from 7-methoxymethoxy-3-(4-methoxymethoxyphenyl)-3-methylthiochroman-4-one according to the same procedure as Steps 2 to 3 of Example 39.

$^1$H-NMR (270 MHz, CDCl$_3$) δ: 7.28 (d, J=8.9 Hz, 2H, Ar—H), 7.02 (d, J=8.9 Hz, 2H, Ar—H), 6.93 (d, J=8.2 Hz, 1H, C5-H), 6.88 (d, J=2.3 Hz, 1H, C8-H), 6.69 (dd, J=8.2 Hz and 2.3 Hz, 1H, C6-H), 5.19 (s, 2H, —OCH$_2$OCH$_3$), 5.14 (s, 2H, —OCH$_2$OCH$_3$), 3.63 (d, J=11.8 Hz, 1H, C2-H), 3.62–3.60 (m, 2H, —CH$_2$OH), 3.50 (s, 3H, —OCH$_2$OCH$_3$), 3.49 (s, 3H, —OCH$_2$OCH$_3$), 3.33 (t, J=5.6 Hz, 2H, —OCH$_2$—), 3.22 (t, J=5.6 Hz, 2H, —OCH$_2$—), 2.98 (d, J=11.8 Hz, 1H, C2-H), 2.74–2.70 (m, 1H, C4-H), 2.41 (brs, 1H, —OH), 1.64–1.52 (m, 4H), 1.50–1.20 (m, 2H), 1.17 (s, 3H, C3-CH$_3$), 1.16–1.02 (m, 4H).

Step 5) Synthesis of (3RS,4RS)-7-methoxymethoxy-3-(4-methoxymethoxyphenyl)-3-methyl-4-[5-oxa-9-(4,4,5,5,5-pentafluoropentylthio)nonyl]thiochroman

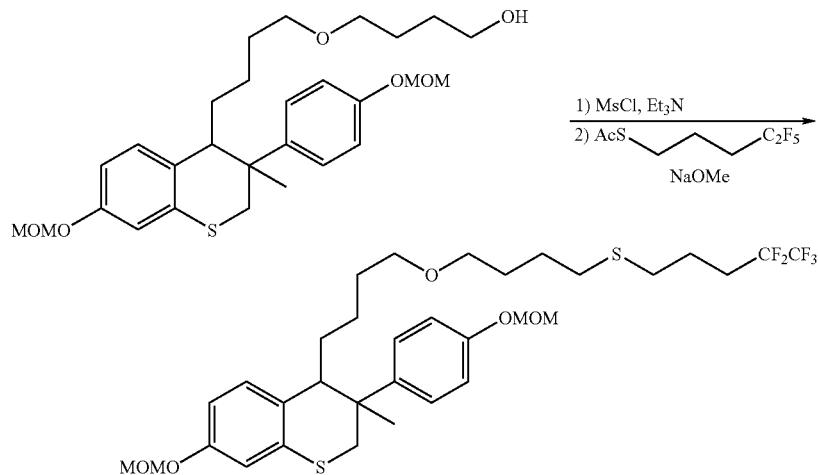

The title compound was prepared from (3RS,4RS)-4-(9-hydroxy-5-oxanonyl)-7-methoxymethoxy-3-(4-methoxymethoxyphenyl)-3-methylthiochroman according to the same procedure as Step 5 of Example 42 (yield: 83%).

$^1$H-NMR (270 MHz, CDCl$_3$) δ: 7.28 (d, J=8.6 Hz, 2H, Ar—H), 7.02 (d, J=8.9 Hz, 2H, Ar—H), 6.93 (d, J=8.2 Hz, 1H, C5-H), 6.88 (d, J=2.3 Hz, 1H, C8-H), 6.69 (dd, J=8.2 Hz and 2.3 Hz, 1H, C6-H), 5.19 (s, 2H, —OCH$_2$OCH$_3$), 5.14 (s, 2H, —OCH$_2$OCH$_3$), 3.63 (d, J=11.2 Hz, 1H, C2-H), 3.50 (s, 3H, —OCH$_2$OCH$_3$), 3.49 (s, 3H, —OCH$_2$OCH$_3$), 3.38–3.26 (m, 2H, —OCH$_2$—), 3.25–3.14 (m, 2H, —OCH$_2$—), 2.98 (d, J=11.2 Hz, 1H, C2-H), 2.76–2.71 (m, 1H, C4-H), 2.58 (t, J=6.9 Hz, 2H, —CH$_2$SCH$_2$—), 2.52–2.45 (m, 2H, —CH$_2$SCH$_2$—), 2.20–2.05 (m, 2H, —CH$_2$CF$_2$CF$_3$), 1.93–1 82 (m, 2H, —CH$_2$CH$_2$CF$_2$CF$_3$), 1.61–1.40 (m, 4H), 1.40–1.25 (m, 2H), 1.17 (s, 3H, C3-CH$_3$), 1.17–1.03 (m, 4H).

Step 6) Synthesis of (3RS,4RS)-7-hydroxy-3-(4-hydroxyphenyl)-3-methyl-4-[5-oxa-9-(4,4,5,5,5-pentafluoropentylthio)nonyl]thiochroman

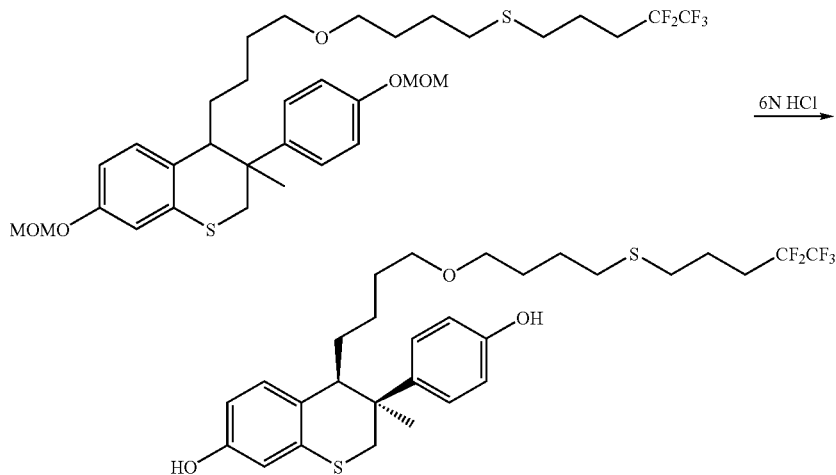

The title compound was prepared from (3RS,4RS)-7-methoxymethoxy-3-(4-methoxymethoxyphenyl)-3-methyl-4-[5-oxa-9-(4,4,5,5,5-pentafluoropentylthio)nonyl]-thiochroman according to the same procedure as Step 6 of Example 42 (yield: 78%).

$^1$H-NMR (270 MHz, CDCl$_3$) δ: 7.24 (d, J=8.9 Hz, 2H, Ar—H), 6.87 (d, J=8.3 Hz, 1H, C5-H), 6.82 (d, J=8.9 Hz, 2H, Ar—H), 6.67 (d, J=2.6 Hz, 1H, C8-H), 6.49 (dd, J=8.3 Hz and 2.6 Hz, 1H, C6-H), 4.93 (brs, 1H, —OH), 4.80 (brs, 2H, —OH), 3.62 (d, J=11.6 Hz, 1H, C2-H), 3.30–3.23 (m, 2H, —OCH$_2$—), 3.19 (t, J=6.3 Hz, 2H, —OCH$_2$—), 2.95 (d, J=11.6 Hz, 1H, C2-H), 2.74–2.68 (m, 1H, C4-H), 2.59 (t, J=7.0 Hz, 2H, —CH$_2$SCH$_2$—), 2.55–2.46 (m, 2H, —C H₂SCH₂—), 2.23–2.05 (m, 2H, —CH₂CF₂CF₃), 1.94–1.86 (m, 2H, —CH₂CH₂CF₂CF₃), 1.5–1.50 (m, 2H), 1.42–1.30 (m, 2H), 1.17 (s, 3H, C3-CH₃), 1.17–1.01 (m, 6H).

Step 7) Synthesis of (3RS,4RS)-7-hydroxy-3-(4-hydroxyphenyl)-3-methyl-4-[5-oxa-9-(4,4,5,5,5-pentafluoropentylsulfinyl)nonyl]thiochroman

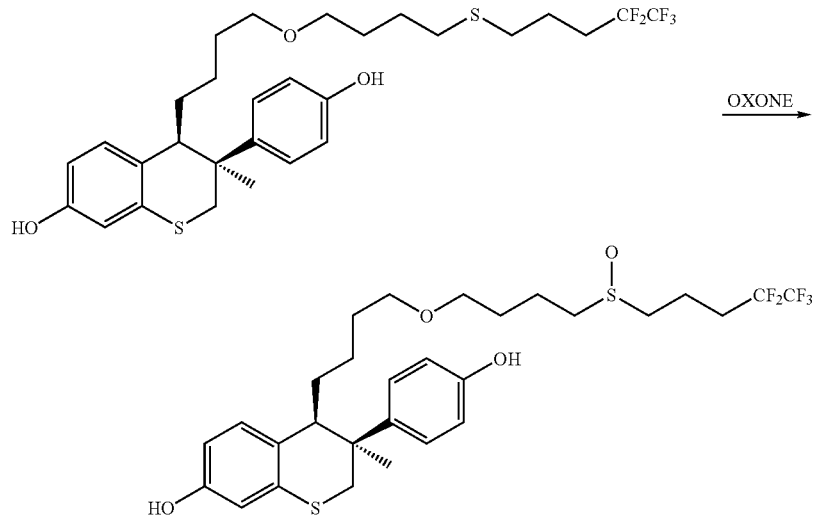

The title compound was prepared from (3RS,4RS)-7-hydroxy-3-(4-hydroxyphenyl)-3-methyl-4-[5-oxa-9-(4,4,5,5,5-pentafluoropentylthio)nonyl]thiochroman according to the same procedure as Step 7 of Example 42 (yield: 64%).

¹H-NMR (270 MHz, CDCl₃) δ: 7.22 (d, J=8.9 Hz, 2H, Ar—H), 7.03 and 6.64 (s, total 1H, —OH), 6.87 (d, J=8.2 Hz, 1H, C5-H), 6.86 (d, J=8.9 Hz, 2H, Ar—H), 6.67 (d, J=2.6 Hz, 1H, C8-H), 6.52 (dt, J=8.2 Hz and 2.6 Hz, 1H, C6-H), 6.04 and 5.71 (s, total 1H, —OH), 3.68–3.62 (m, 1H), 3.25–3.09 (m, 4H), 3.00–2.58 (m, 7H), 2.38–2.18 (m, 4H, —CH₂CH₂CF₂CF₃), 1.82–1.60 (m, 4H), 1.38–1.05 (m, 6H), 1.21 and 1.20 (s, total 3H, C3-CH₃).

EXAMPLE 46

Synthesis of (3'RS,4'RS)-[7-hydroxy-3-(4-hydroxyphenyl)-3-methylthiochroman-4-yl]nonanoic acid Step 1) Synthesis of (3'RS,4'RS)-6-[7-methoxy-3-(4-methoxyphenyl)-3-methylthiochroman-4-yl]-3-nonenoic acid

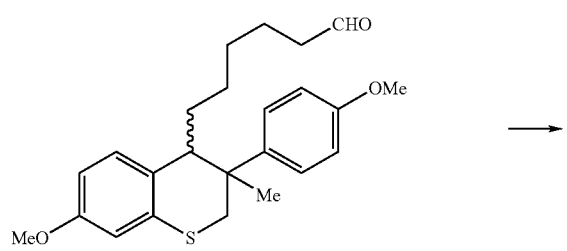

To a solution of Ph₃P(CH₂)₂CO₂H Cl salt (1.162 g, 3.14 mmol) in DMSO (1 ml) was added freshly prepared 2 M NaCH₂SOCH₃ in DMSO solution (0.5 ml) and the mixture was stirred for 0.5 h at room temperature. The DMSO solution (1.5 ml) of 6-[7-methoxy-3-(4-methoxyphenyl)-3-methylthiochroman-4-yl]hexanal (250 mg, 0.63 mmol) was added to the above solution at room temperature and the resulting mixture was stirred at 60° C. for 16 h. The reaction was quenched with 6N HCl, which was extracted with ethyl acetate. The organic layer obtained was washed with water and saturated saline solution and then, dried over MgSO₄. The solvent was evaporated off and the residue was subjected to flash chromatography on silica gel (hexane:ethyl acetate=2:1) to give the title compound (283 mg, yield: 100%).

¹H-NMR (270 MHz, CDCl₃) δ: 7.28 (d, J=9 Hz, 2H, Ar—H), 6.94 (d, J=8 Hz, 1H, Ar—H), 6.90 (d, J=9 Hz, 2H, Ar—H), 6.75 (d, J=2 Hz, 1H, Ar—H), 6.58 (dd, J=8, 2 Hz, 1H, Ar—H), 5.80–5.40 (m, 2H, olefin-H), 3.82 (s, 3H, OCH₃), 3.77 (s, 3H, OCH₃), 3.62 (d, J=11 Hz, 1H, C2-H), 2.97 (d, J=11 Hz, 1H, C2-H). 2.75 (brs, 1H, C4-H), 2.10 (m, 2H, CH₂CO₂H), 1.20–0.90 (m, 13H, alkyl-H and CH₂CH=CH).

Step 2) Synthesis of 6-[7-methoxy-3-(4-methoxyphenyl)-3-methylthiochroman-4-yl]-nonanoic acid

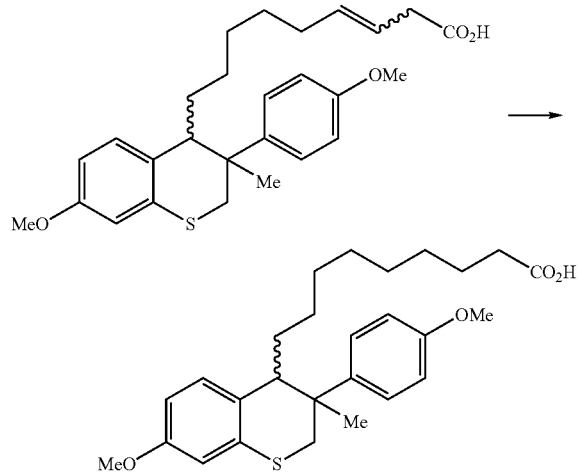

To a solution of 6-[7-hydroxy-3-(4-methoxyphenyl)-3-methylthiochroman-4-yl]-3-nonenoic acid (254 mg, 0.56 mmol) in ethyl acetate (5 ml) was added platinum(IV) oxide hydrate (130 mg, 0.56 mmol) and the mixture was stirred for 16 h at room temperature under hydrogen atmosphere. The catalyst was filtered off and washed with methanol. The filtrate was concentrated and the residue was subjected to flash chromatography on silica gel (ethyl acetate) to give the title compound (222 mg, yield: 87%).

$^{1}$H-NMR (270 MHz, CDCl$_{3}$) δ: 7.30 (d, J=9 Hz, 2H, Ar—H), 6.94 (d, J=8 Hz, 1H, Ar—H), 6.90 (d, J=9 Hz, 2H, Ar—H), 6.72 (d, J=2 Hz, 1H, Ar—H), 6.57 (dd, J=8, 2 Hz, 1H, Ar—H), 3.82 (s, 3H, OCH$_{3}$), 3.78 (s, 3H, OCH$_{3}$), 3.62 (d, J=11 Hz, 1H, C2-H), 2.97 (d, J=11 Hz, 1H, C2-H), 2.75 (brs, 1H, C4-H), 2.29 (t, J=7 Hz, 2H, CH$_{2}$CO$_{2}$H), 1.65–1.45 (q, J=7 Hz, CH$_{2}$CH$_{2}$CO$_{2}$H), 1.30–0.90 (m, 15H, alkyl-H).

Step 3) Synthesis of methyl (3'RS,4'RS) and (3SR,4RS)-6-[7-hydroxy-3-(4-hydroxyphenyl)-3-methylthiochroman-4-yl]nonanoate

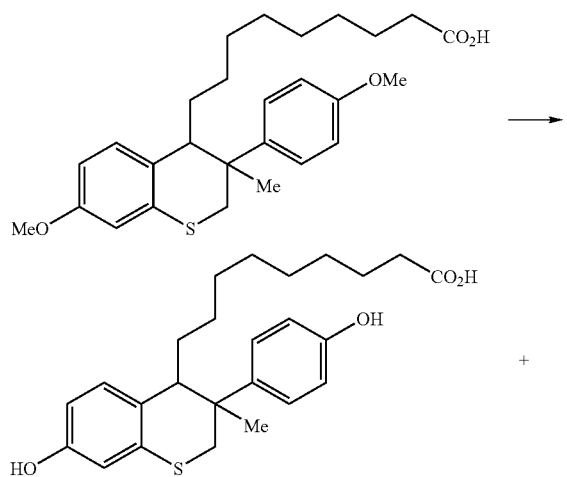

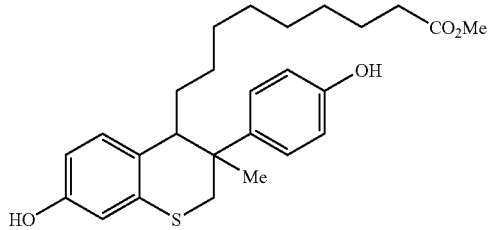

To a solution of 6-[7-methoxy-3-(4-methoxyphenyl)-3-methylthiochroman-4-yl]nonanoic acid (222 mg, 0 49 mmol) in methylene chloride (6 ml) was added BBr$_{3}$ (1.0 M, 3.0 ml, 3 mmol) at −78° C., which was then slowly warmed over 3 h. After the reaction was completed, saturated aqueous NaHCO$_{3}$ was added at 0° C. The resulting mixture was then extracted with methylene chloride and the organic layer obtained was washed with saturated saline solution. The organic layer was dried over MgSO$_{4}$ and the solvent was evaporated off. The residue (210 mg) was used for the next step without further purification. The residue was dissolved with methanol (5 ml) and one drop of concentrated H$_{2}$SO$_{4}$ was added to the solution at room temperature. The reaction mixture was stirred for 3 h and then, saturated aqueous NaHCO$_{3}$ was added. The mixture was extracted with ethyl acetate and the organic layer obtained was washed with saturated saline solution and dried over MgSO$_{4}$ and then, the solvent was evaporated off. The residue was subjected to preparative thin layer chromatography on silica gel (n-hexane:ethyl acetate=4:1) to give the less polar (3RS,4RS) and the more polar (3SR, 4RS) title compounds (140 mg, yield: 53% for (3RS,4RS), 19 mg, yield: 7% for (3SR, 4RS)).

$^{1}$H-NMR (270 MHz, CDCl$_{3}$) δ: 7.29 (d, J=9 Hz, 2H, Ar—H), 6.91 (d, J=8 Hz, 1H, Ar—H), 6.98 (d, J=9 Hz, 2H, Ar—H), 6.72 (d, J=2 Hz, 1H, Ar—H), 6.54 (dd, J=8, 2 Hz, 1H, Ar), 6.05 (brs, 1H, ArOH), 5.28 (brs, 1H, ArOH), 3.74 (s, 3H, CO$_{2}$CH$_{3}$), 3.67 (d, J=11 Hz, 1H, C2-H), 2.97 (d, J=11 Hz, 1H, C2-H), 2.75 (brs, 1H, C4-H), 2.32 (t, J=7 Hz, 2H, CH$_{2}$CO$_{2}$CH$_{3}$), 1.65–1.45 (q, J=7 Hz, CH$_{2}$CH$_{2}$CO$_{2}$CH$_{3}$), 1.30–0.90 (m, 15H, alkyl-H). : 7.25 (d, J=9 Hz, 2H, Ar—H), 6.70 (d, J=8 Hz, 1H, Ar—H), 6.43 (d, J=9 Hz, 2H, Ar—H), 6.48 (d, J=2 Hz, 1H, Ar—H), 6.33 (dd, J=8, 2 Hz, 1H, Ar—H), 5.20 (brs, 2H, ArOH), 3.67 (s, 3H, CO$_{2}$CH$_{3}$), 3.21 (AB q, J=11 Hz, 2H, C2-H), 2.85 (brd, 1H, C4-H), 2.32 (t, J=7 Hz, 2H, CH$_{2}$CO$_{2}$CH$_{3}$), 1.65–1.45 (q, J=7 Hz, CH$_{2}$CH$_{2}$CO$_{2}$CH$_{3}$), 1.30–0.90 (m, 15H, alkyl-H).

Step 4) Synthesis of (3'RS,4RS)-6-[7-hydroxy-3-(4-hydroxyphenyl)-3-methylthiochroman-4-yl]nonanoic acid

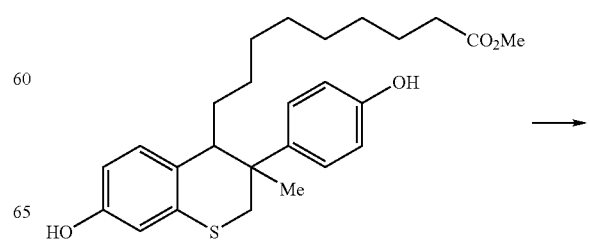

-continued

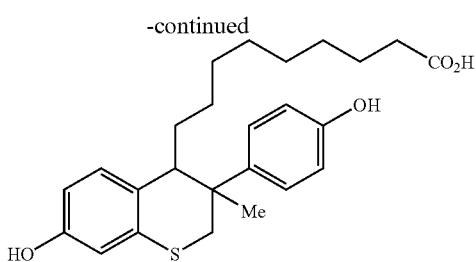

To a solution of methyl (3'RS,4'RS)-6-[7-hydroxy-3-(4-hydroxyphenyl)-3-methylthiochroman-4-yl]nonanoate (70 mg, 0.16 mmol) in methanol (1 ml) was added 2N NaOH (0.5 ml) at room temperature and the reaction mixture was stirred for 3 h. After 6N HCl was added, the mixture was extracted with diethyl ether. The organic layer obtained was washed with saturated saline solution, which was dried over MgSO$_4$ and the solvent was evaporated off. The residue was subjected to preparative thin layer chromatography on silica gel (ethyl acetate) to give the title compound (60 mg, yield: 88%).

$^1$H-NMR (270MHz, CD$_3$OD) δ: 7.23 (d, J=9 Hz, 2H, Ar—H), 6.86 (d, J=8 Hz, 1H, Ar—H), 6.78 (d, J=9 Hz, 2H, Ar—H), 6.57 (d, J=2 Hz, 1H, Ar—H), 6.45 (dd, J=8, 2 Hz, 1H, Ar—H), 3.60 (d, J=11 Hz, 1H, C2-H), 2.94 (d, J=11 Hz, 1H, C2-H), 2.75 (brs, 1H, C4-H), 2.22 (t, J=7 Hz, 2H, CH$_2$CO$_2$H), 1.60–1.40 (q, J=7 Hz, CH$_2$CH$_2$CO$_2$H), 1.30–0.90 (m, 15H, alkyl-H).

EXAMPLE 47

Synthesis of (3'RS,4'RS)-10-[7-hydroxy-3-(4-hydroxyphenyl)-3-methylthiochroman-4-yl]decanoic acid Step 1) Synthesis of 6-[7-methoxy-3-(4-methoxyphenyl)-3-methylthiochroman-4-yl]4-decenoic acid

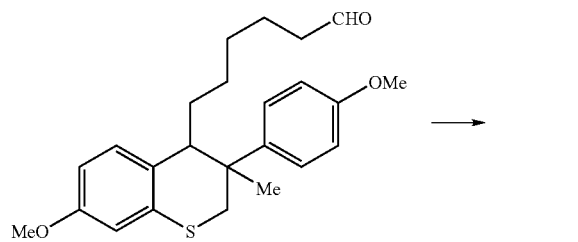

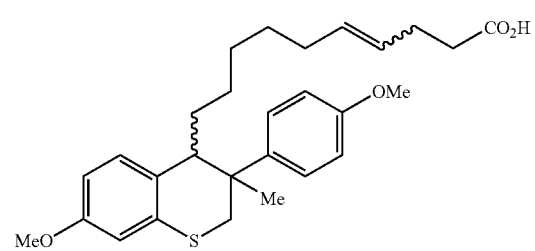

To a solution of Ph$_3$P(CH$_2$)3CO$_2$H Cl salt (1.87 g, 4.87 mmol) in DMSO (3 ml) was added freshly prepared 2 M NaCH$_2$SOCH$_3$ in DMSO solution (4.87 ml) and the mixture was stirred for 0.5 h at room temperature. The DMSO solution (4.0 ml) of 6-[7-methoxy-3-(4-methoxyphenyl)-3-methylthiochroman-4-yl]hexanal (388 mg, 0.97 mmol) was added to the above solution at room temperature and the resulting mixture was stirred at 60° C. for 16 h. The reaction was quenched with 6N-HCl, which was extracted with ethyl acetate. The organic layer obtained was washed with water and saturated saline solution and then, dried over MgSO$_4$. The solvent was evaporated off and the residue was subjected to flash chromatography on silica gel (hexane:ethyl acetate=2:1) to give the title compound (445 mg, yield: 98%).

$^1$H-NMR (270 MHz, CDCl$_3$) δ: 7.28 (d, J=9 Hz, 2H, Ar—H), 6.94 (d, J=8 Hz, 1H, Ar—H), 6.90 (d, J=9 Hz, 2H, Ar—H), 6.72 (d, J=2 Hz, 1H, Ar—H), 6.57 (dd, J=8, 2 Hz, 1H, Ar—H), 6.40–6.20 (m, 2H, olefin-H), 3.82 (s, 3H, OCH$_3$), 3.77 (s, 3H, OCH$_3$), 3.62 (d, J=11 Hz, 1H, C2-H), 2.97 (d, J=11 Hz, 1H, C2-H), 2.75 (brs, 1H, C4-H), 2.45–2.20 (m, 4H, CH$_2$CH$_2$CO$_2$H), 1.90–1.80 (m, 2H, CH$_2$CH—CH), 1.20–0.90 (m, 11H, alkyl-H).

Step 2) Synthesis of 6-[7-methoxy-3-(4-methoxyphenyl)-3-methylthiochroman-4-yl]decanoic acid

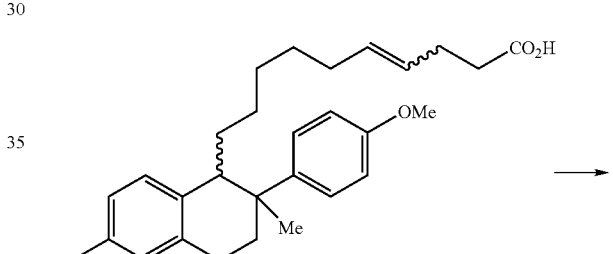

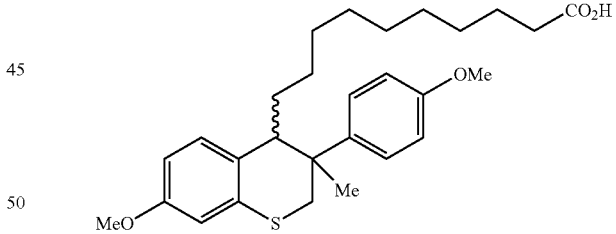

The title compound was prepared from 6-[7-methoxy-(4-methoxyphenyl)-3-methylthiochroman-4-yl]-4-decenoic acid (445 mg, 0.95 mmol) according to the same procedure for the synthesis of 6-[7-methoxy-3(4-methoxyphenyl)-3-methylthiochroman-4-yl]nonanoic acid (400 mg, yield: 90%).

$^1$H-NMR (270, CDCl$_3$) δ: 7.30 (d, J=9 Hz, 2H, Ar—H), 6.94 (d, J=8 Hz, 1H, Ar—H), 6.90 (d, J=9 Hz, 2H, Ar—H), 6.72 (d, J=2 Hz, 1H, Ar—H), 6.57 (dd, J=8, 2 Hz, 1H, Ar—H), 3.82 (s, 3H, OCH$_3$), 3.78 (s, 3H, OCH$_3$), 3.62 (d, J=11 Hz, 1H, C2-H), 2.97 (d, J=11 Hz, 1H, C2-H), 2.75 (brs, 1H, C4-H), 2.29 (t, J=7 Hz, 2H, CH$_2$CO$_2$H), 1.65–1.45 (q, J=7 Hz, CH$_2$CH$_2$CO$_2$H), 1.30–0.90 (m, 17H, alkyl-H).

Step 3) Synthesis of methyl (3'RS,4'RS)-6-[7-hydroxy-3-(4-hydroxyphenyl)-3-methylthiochroman-4-yl]decanoate

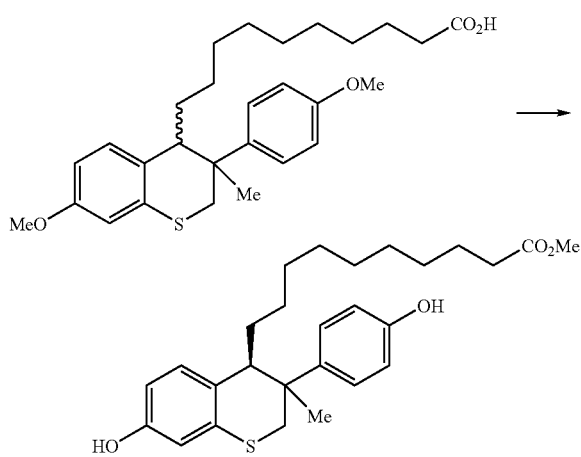

The title compound was prepared from 6-[7-methoxy-3-(4-methoxyphenyl)-3-methylthiochroman-4-yl]decanoic acid (400 mg, 0.85 mmol) according to the same procedure for the synthesis of methyl (3'RS,4'RS)-6-[7-hydroxy-3-(4-hydroxyphenyl)-3-methylthiochroman-4-yl]nonanoate (219 mg, yield: 56%).

$^1$H-NMR (270 MHz, CDCl$_3$) δ: 7.22 (d, J=9 Hz, 2H, Ar—H), 6.87 (d, J=8 Hz, 1-H, Ar—H), 6.83 (d, J=9 Hz, 2H, Ar—H), 6.67 (d. J=2 Hz, 1H, Ar—H), 6.50 (dd, J=8, 2 Hz, 1H, Ar—H), 5.88 (brs, 1H, ArOH), 5.20 (brs, 1H, ArOH), 3.70 (s, 3H, CO—CH$_3$), 3.63 (d, J=11 Hz, 1H, C2-H), 2.95 (d, J=11 Hz, 1H, C2-H), 2.68 (brs, 1H, C4-H), 2.31 (t, J=7 Hz, 2H, CH$_2$CO$_2$CH$_3$), 1.65–1.45 (q, J=7 Hz, CH$_2$CH$_2$CO$_2$CH$_3$), 1.30–0.90 (m, 17H, alkyl-H).

Step 4) Synthesis of (3'RS,4'RS)-6-[7-hydroxy-3-(4-hydroxyphenyl)-3-methylthiochroman-4-yl]decanoic acid

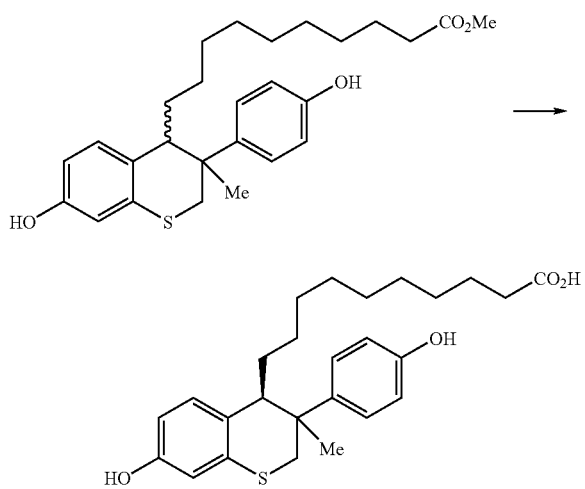

The title compound was prepared from methyl (3'RS, 4'RS)-6-[7-hydroxy-3-(4-hydroxyphenyl)-3-methylthiochroman-4-yl]decanoate (35 mg, 0.076 mmol) according to the same procedure for the synthesis of (3'RS,4'RS)-6-[7-hydroxy-3-(4-hydroxyphenyl)-3-methylthiochroman-4-yl] nonanoic acid.

$^1$H-NMR (270 MHz, CD$_3$OD) δ: 7.24 (d, J=9 Hz, 2H, Ar—H), 6.86 (d, J=8 Hz, 1H, Ar—H), 6.78 (d, J=9 Hz, 2H, Ar—H), 6.57 (d, J=2 Hz, 1H, Ar—H), 6.45 (dd, J=8, 2 Hz, 1H, Ar—H), 3.61 (d, J=11 Hz, 1H, C2-H), 2.94 (d, J=11 Hz, 1H, C2-H), 2.75 (brs, 1H, C4-H), 2.25 (t, J=7 Hz, 2H, CH$_2$CO$_2$H), 1.60–1.40 (q, J=7 Hz, CH$_2$CH$_2$CO$_2$H), 130–0.90 (m, 17H, alkyl-H).

EXAMPLE 48

Synthesis of (E)-3-[7-hydroxy-3-(4-hydoxyphenyl)-2H-chromen-4-yl]phenylacrylic acid Step 1) Synthesis of 4-[3-(1,3-dioxolan-2-yl)-phenyl]-7-methoxy-3-(4-methoxyphenyl)thiochroman-4-ol

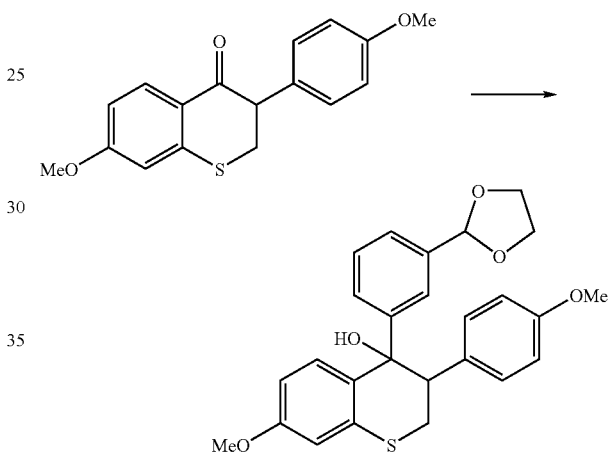

To a solution of 2-(3-bromophenyl)-1,3-dioxolane (3.04 g, 13.28 mmol) in dry tetrahydrofuran (35 ml) was added n-butyl lithium (8.37 ml, 13.316 mmol, 1.59 mol/l tetrahydrofuran solution) dropwise as −78° C. over 10 minutes and stirred for 50 minutes at the same temperature. Then to the reaction mixture was added 7-methoxy-3-(4-methoxyphenyl)thiochroman-4-one (2 g, 6.658 mmol) dissolved in tetrahydrofiuran at the same temperature over 10 minutes. The reaction mixture was stirred for 6 h at −78° C. and followed at −10C for 2 h. When the reaction was completed, water was added to the reaction solution which was then extracted with ethyl acetate. The extract was dried over anhydrous magnesium sulfate and concentrated under reduced pressure. The residue was purified with column chromatography (n-hexane:ethyl acetate=8:1 to 7:3) to give 1.50 g (yield: 50%) of the title compound as a colorless oil. In this reaction, 0.77 g (38%) of the unreacted starting compound was recovered.

$^1$H-NMR (270 MHz, CDCl$_3$) δ: 7.30–7.06 (m, 5H, Ar—H), 6.85 (m, 2H, Ar—H), 6.72 (d, J=2.3 Hz, 1H, C8-H), 6.65 (d, J=8.6 Hz, 2H, C5-H), 6.50 (dd, J=8.6 and 2.7 Hz, 1H, C6-H), 5.71 (s, 1H, dioxolan C2-H), 3.98 (m. 4H, 2×OCH2), 3.78 (s, 3H, OCH3), 3.74 (m, 1H, C3-H), 3.71 (s, 3H, OCH3), 3.30 (dd, J=10.8 and 2.3 Hz, 1H, C2-H), 2.87 (dd, J=12.5 and 2.7 Hz, 1H, C2-H), 2.17 (s, 1H, OH)

Step 2) Synthesis of 3-[7-methoxy-3-(4-methoxyphenyl)-2H-chromen-4-yl]benzaldehyde

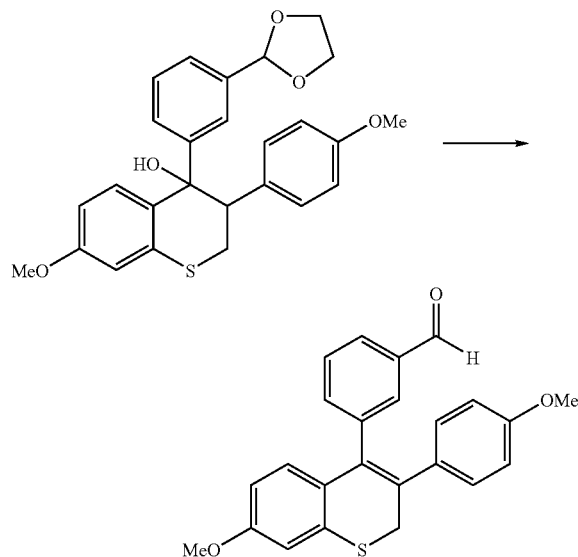

The solution of 4-[3-(1,3-dioxolan-2-yl)-phenyl]-7-methoxy-3-(4-methoxyphenyl)-thiochroman-4-ol (1.4 g, 3.107 mmol) in 5N hydrochloric acid solution (65 ml) was heated at 100° C. for 4.5 h. When the reaction was completed, water was added to the reaction mixture and extracted with ethyl acetate. The extract was washed with saturated sodium hydrogen carbonate solution and sodium chloride solution, dried over anhydrous magnesium sulfate and concentrated under reduced pressure. The residue was flash chromatographied on silica gel (n-hexane:ethyl acetate=8:2) to give 0.963 g (yield: 80%) of the title compound as a colorless oil.

$^1$H-NMR (270 MHz, CDCl$_3$) δ: 9.88 (s, 1H, CHO), 7.71 (d, J=7.5 Hz, 1H, Ar—H), 7.51 (s, 1H, Ar—H), 7.53 (m, 2H, Ar—H), 6.93 (m, 3H, Ar—H), 6.53 (dd, J=8.5 and 2.7 Hz, 1H, thiochroman C6-H), 3.80 (s, 3H, OCH$_3$), 3.79 (m, 2H, thiochroman C2-H), 3.71 (s, 3H, OCH$_3$)

Step 3) Synthesis of (E)-3-[7-methoxy-3-(4-methoxyphenyl)-2H-chromen-4-yl]-phenylacrylic acid

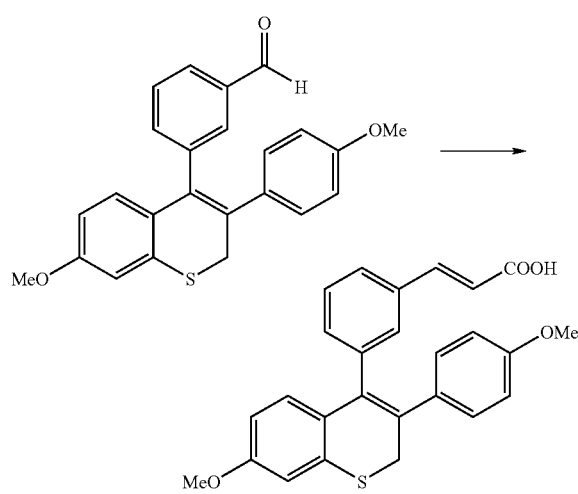

The mixture of 3-[7-methoxy-3-(4-methoxyphenyl)-2H-chromen-4-yl]benzaldehyde (0.963 g, 2.479 mmol) and malonic acid (0.774 g, 7.44 mmol) in piperidine (0.24 ml) and pyridine (2.4 ml) was stirred at 65° C. for 2 h. When the reaction was completed, water and ethyl acetate were added to the reaction mixture, which was acidified with 1N hydrochloric acid solution. Then the mixture was extracted with ethyl acetate, washed with water and saturated sodium chloride solution and dried over anhydrous magnesium sulfate. The organic solution was filtrated and evaporated to give 1.00 g (yield:93%) of the title compound as a white solid.

$^1$H-NMR (270 MHz, CDCl$_3$) δ: 7.60 (d, J=15.8 Hz, 1H, C3-H), 7.31 (d, J=7.3 Hz, 1H, Ar—H), 7.14 (m, 3H, Ar—H), 7.01 (d, J=7.6 Hz, 1H, Ar—H), 6.90 (m, 2H, Ar—H), 6.62 (m, 3H, Ar—H)), 6.48 (dd, J=8.5 and 2.3 Hz, 1H, thiochroman C6-H), 6.23 (d, J=15.8 Hz, 1H, C2-H), 3.75 (s, 3H, OCH$_3$), 3.68 (m, 2H, thiochroman C2-H), 3.67 (s, 3H, OCH$_3$)

Step 4) Synthesis of (E)-3-[7-hydroxy-3-(4-hydoxyphenyl)-2H-chromen-4-yl]-phenylacrylic acid

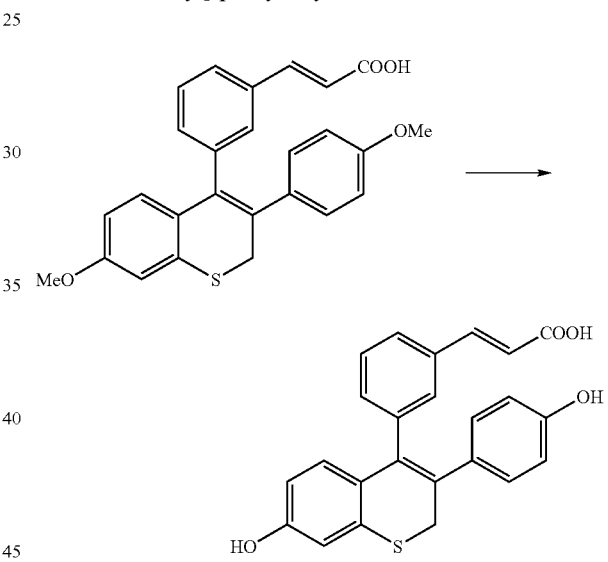

To a solution of (E)-3-[7-methoxy-3-(4-methoxyphenyl)-2H-chromen-4-yl]phenylacrylic acid (505 mg, 1.173 mmol) in methylene chloride (30 ml) was added borontribromide (1.0M in methylene chloride, 7.03 ml) at −78° C. and stirred at 0° C. for 3.5 h. After the reaction was completed, the reaction was quenched with sodium thiosulfate solution and water, which was then extracted with ethyl acetate. The extract was dried over anhydrous magnesium sulfate and concentrated under reduced pressure. The residue was flash chromatographied on silica gel (n-hexane:ethyl acetate=10:4) to give 60 mg of the title compound (unstable on air) as a pink oil.

$^1$H-NMR (270 MHz, CDCl$_3$) δ: 7.63 (d, J=15.8 Hz, 1H, C3-H), 7.35 (d, J=6.9 Hz, 1H, Ar—H), 7.23 (m, 3H, Ar—H), 7.07 (d, J=7.9 Hz, 1H, Ar—H), 6.89 (m, 2H, Ar—H), 6.65 (dd, J=8.6 and 2.6 Hz, 1H, Ar—H), 6.58 (d, J=8.6 Hz, 2H, Ar—H), 6.46 (dd, J=8.6 and 2.6 Hz, 1H, thiochroman C6-H), 6.28 (d, J=15.8 Hz, 1H, C2-H), 3.74 (m, 2H, thiochroman C2-H)

EXAMPLE 49

Synthesis of (3'RS,4'RS)-(E)-3-[-7-hydroxy-3-(4-hydoxyphenyl)thiochroman-4-yl]phenylacrylic acid Step 1) Synthesis of 4-[3-(t-butyldimethylsilyloxymethyl)phenyl]-7-methoxy-3-(4-methoxyphenyl)thiochroman-4-ol

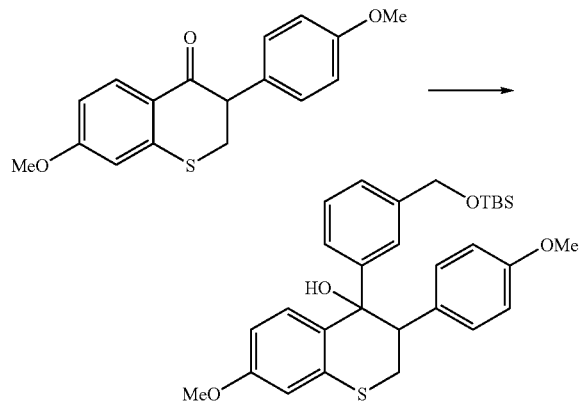

To a solution of (3-bromobenzyloxy)-t-butyldimethylsilane (2.207 g, 7.326 mmol) in dry tetrahydrofuran (20 ml) was added n-butyl lithium (4.18 ml, 6.66 mmol, 1.59M tetrahydrofuran solution) at −78° C. over 25 minutes and stirred for 50 minutes. Then to the reaction mixture was added 7-methoxy-3-(4-methoxyphenyl)thiochroman-4-one (1 g, 3.33 mmol) dissolved in tetrahydrofuran at the same temperature over 10 minutes. The reaction mixture was stirred for 20 minutes at −78° C., followed at −15° C. for 12 h and at 0° C. for 8 h. When the reaction was completed, water was added to the reaction solution which was then extracted with ethyl acetate. The extract was dried over anhydrous magnesium sulfate and concentrated under reduced pressure. The residue was purified with column chromatography (n-hexane:ethyl acetate=8:2) to give 0.49 g (yield: 28%) of the title compound as a colorless oil. In this reaction 0.55 g (55%) of the unreacted starting compound was recovered.

$^1$H-NMR (270 MHz, CDCl$_3$) δ: 7.1 0 (m, 5H, Ar—H), 6.88 (dd, J=8.9 Hz, 2H, Ar—H), 6.72 (d, J=2.6 Hz, 1H, C5—H), 6.65 (d, J=8.6 Hz, 2H, Ar—H), 6.51 (dd, J=8.9 and 2.6 Hz, 1H, C6-H), 4.63 (s, 2H, OCH$_2$TBS), 3.78 (s, 3H, OCH$_3$), 3.72 (s, 3H, OCH$_3$), 3.70 (m, 1H, C3-H), 3.55 (dd, J=11.6 and 2.3 Hz, 1H, C2-H), 2.89 (dd, J=11.2 and 2.3 Hz, 1H, C2-H), 2.12 (s, 1H, OH), 0.88 (s, 9H, t-butyl H), 0.02 (s, 6H, 2×CH$_3$)

Step 2) Synthesis of 4-[-3-(t-butyldimethylsilyloxymethyl)phenyl]-7-methoxy-3-(4-methoxyphenyl)thiochroman

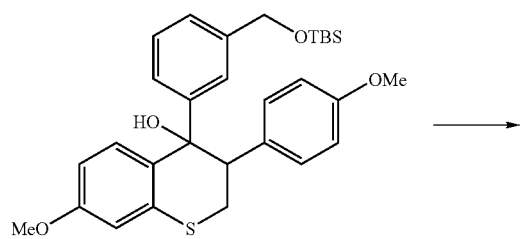

-continued

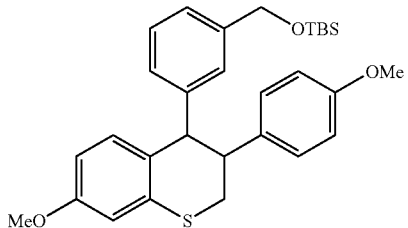

To a solution of 4-[3-(t-butyldimethylsilyloxymethyl)phenyl]-7-methoxy-3 (4-methoxyphenyl)thiochroman-4-ol (619 mg, 1.184 mmol) in 1,2-dichloroethane (70 ml) were added zinc iodide (567 mg, 1.776 mmol) and sodium cyanoborohydride (558 mg, 8.88 mmol) and stirred at 68° C. for 2.5 hours. When the reaction was completed, water was added to the reaction mixture and extracted with ethyl acetate: The extract was dried over anhydrous magnesium sulfate and concentrated under reduced pressure. The residue was flash chromatographed on silica gel (n-hexane:ethyl acetate=8:2) to give 365 mg (yield: 61%, 3RS,4RS/3RS, 4SR=6:1) of the title compound as a white solid. In this reaction, 260 mg (42%) of the unreacted starting compound was recovered.

$^1$H-NMR (270 MHz, CDCl$_3$) δ: 7.02 (m, 3H, Ar—H), 6.85 (d, J=8.6 Hz, 1H, Ar—H), 6.71 (m, 4H, Ar—H), 6.54 (m, 2H, Ar—H), 6.45 (d, J=7.3 Hz, 1H, Ar—H), 4.56 (s, 2H, O—CH$_2$TBS), 4.18 (d, J=3.3 Hz, 1H, C4-H), 3.78 (s, 3H, OCH$_3$), 3.77 (s, 3H, OCH$_3$), 3.55 (ddd, J=12.6, 3.3 and 2.6 Hz, 1H, C3-H), 3.40 (dd, J=12.6 and 12.3 Hz, 1H, C2-H), 2.78 (dd, J=12.3 Hz, and not resolved, 1H, C2-H), 0.88 (s, 9H, t-butyl H), 0.02 (s, 6H, 2×CH$_3$)

Step 3) Synthesis of 3-[7-methoxy-3-(4-methoxyphenyl)thiochroman-4-yl]benzyl-alcohol

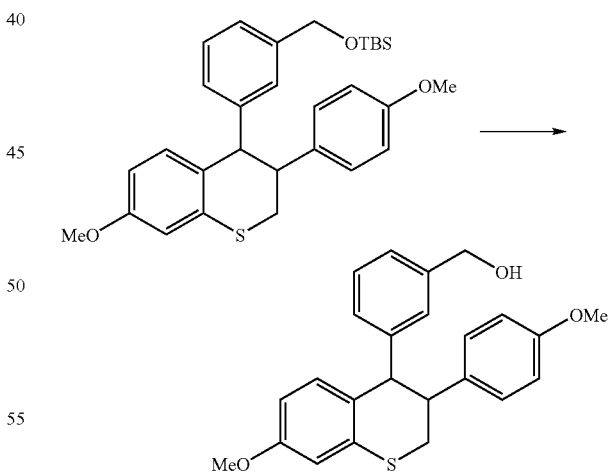

4-[3-(t-butyldimethylsilyloxymethyl)phenyl]-7-methoxy-3-(4-methoxyphenyl)thiochroman (480 mg, 0.947 mmol) was dissolved in tetrahydrofuran (40 ml), and added 3N hydrochloric acid solution (2.7 ml) thereto. The reaction mixture was stirred at room temperature for 4 h. When the reaction was completed, water was added to the reaction solution which was then extracted with ethyl acetate. The extract was washed with sodium hydrogen carbonate solution, dried over anhydrous magnesium sulfate and concentrated under reduced pressure. The residue was flash chromatographied on silica gel (n-hexane:ethyl acetate=1:1) to obtain 358 mg (yield: 96%) of the title compound as a white solid.

$^1$H-NMR (270 MHz, CDCl$_3$) δ: 7.14 (m, 2K Ar—H), 7.07–6.49 (m, 9H, Ar—H), 4.47 (s, 2H, OCH$_2$TBS), 4.20 (d, J=3.3 Hz, 1H, thiochroman C4-H), 3.79 (s, 3H, OCH$_3$), 3.78 (s, 3H, OCH$_3$), 3.58 (ddd, J=12.6, 3.3 and 2.6 Hz, 1H, thiochroman. C3-H), 3.38 (dd, J=12.6 and 12.2 Hz, 1H, thiochroman C2-H), 2.79 (dd, J=12.2 Hz, and not resolved, 1H, thiochroman C2-H)

Step 4) Synthesis of 3-[7-methoxy-3-(4-methoxyphenyl)thiochroman-4-yl]benzaldehyde

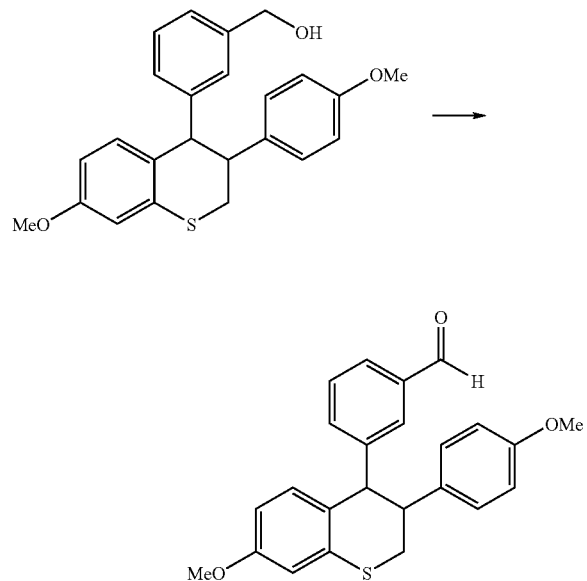

The mixture of 3-[7-methoxy-3-(4-methoxyphenyl)thiochroman-4-yl]benzyl alcohol (358 mg, 0.912 mmol) and manganese(IV) oxide (634 mg, 7.296 mmol) in methylene chloride (80 ml) was stirred at 40° C. for 3 h. When the reaction was completed, methylene chloride was added to the reaction mixture, which was then filtrated over silica gel and washed with several times with methylene chloride. The organic layer was concentrated under reduced pressure to give 360 mg (quant.) of the title compound as a white crystal.

$^1$H-NMR (270 MHz, CDCl$_3$) δ: 9.79 (s, 1H, CHO), 7.67 (d, J=13.6 Hz, 1H, Ar—H), 7.05–6.63 (m, 9H, Ar—H), 6.56 (dd, J=8.6 and 2.7 Hz, 1H, thiochroman C6-H), 4.29 (d, J=4.0 Hz, 1H, thiochroman C4-H), 3.80 (s, 3H, OCH$_3$), 3.77 (s, 3H, OCH$_3$), 3.63 (ddd, J=12.8, 3.3 and 3.0 Hz, 1H, thiochroman C3-H), 3.30 (dd, J=12.9 and 12.5 Hz, 1H, thiochroman C2-H), 2.83 (dd, J=12.5 Hz, and not resolved, 1H, thiochroman C2-H)

Step 5) Synthesis of (E)-3-[7-methoxy-3-(4-methoxyphenyl)thiochroman-4-yl]phenylacrylic acid

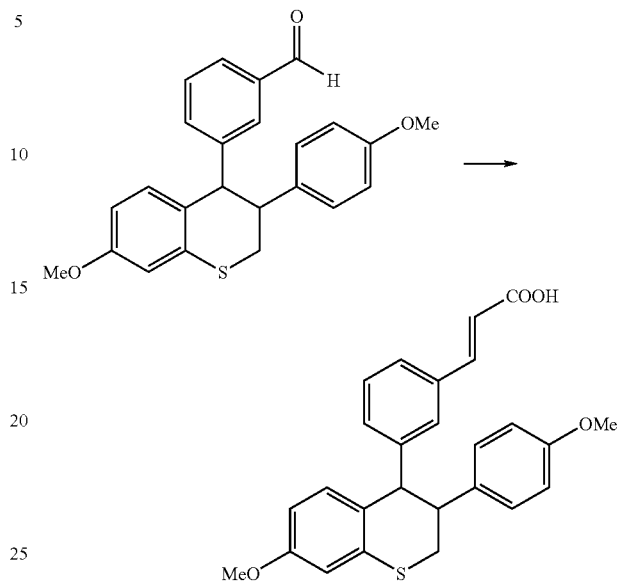

The title compound was prepared from 3-[7-methoxy-3-(4-methoxyphenyl)-thiochroman-4-yl]benzaldehyde and malonic acid according to the same method for the synthesis of (E)-3-[7-methoxy-3-(4-methoxyphenyl)-2H-chromen-4-yl]phenylacrylic acid.

$^1$H-NMR (270 MHz CDCl$_3$) δ: 7.59 (d, J=16.2 Hz, 1H, C3-H), 7.31–6.33 (m, 1H, Ar—H), 6.13 (d, J=16.2 Hz, C2-H), 4.21 (d, J=3.3 Hz, 1H, thiochroman C4-H), 3.80 (s, 3H, OCH$_3$), 3.79 (s, 3H, OCH$_3$), 3.62 (ddd, J=13.2, 3.6 and 3.0 Hz, 1H, thiochroman C3-H), 3.30 (dd, J=13.2 and 12.2 Hz, H, thiochroman C2-H), 2.82 (dd, J=12.2 Hz, and not resolved, 1H, thiochroman C2-H)

Step 6) Synthesis of (3'RS,4'RS)-(E)-3-[-7-hydroxy-3-(4-hydoxyphenyl)-thiochroman-4-yl]phenylacrylic acid

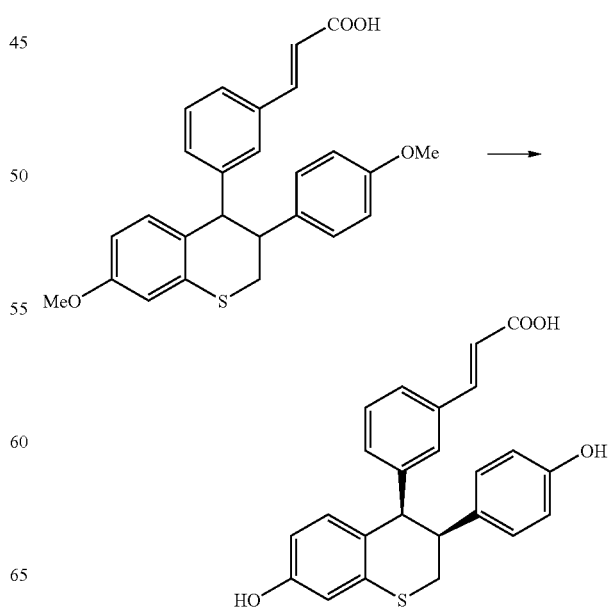

To a solution of (E)-3-[7-methoxy-3-(4-methoxyphenyl)thiochroman-4-yl]phenylacrylic acid (478 mg, 1.106 mmol) in methylene chloride (60 ml) was added borontribromide (6.64 ml, 11.0 mol/A in methylene chloride) at −78° C. and stirred at 0° C. for 3 h. After the reaction was completed, the reaction was quenched with sodium thiosulfate solution and water, which was then extracted with ethyl acetate. The extract was dried over anhydrous magnesium sulfate and concentrated under reduced pressure to give the crude product (430 mg). Then the crude product was dissolved in methanol (40 ml) and added conc. sulfuric acid 8 drops. After the reaction mixture was stirred at 40° C. for 6 h, the solvent was evaporated. The residue was subjected to flash chromatography on silica gel (n-hexane:ethyl acetate=7:3) to give 390 mg of the 3RS,4RS/3RS,4SR mixture (10:1.5). The purification using the preparative TLC (n-hexane:ethyl acetate:methanol=9:1:0.5) afforded the 3RS,4RS isomer in 115 mg. Then to the solution of the 3RS,4RS ester (115 mg, 0.274 mmol) in methanol (3 ml) was added 2N sodium hydroxide solution (1 ml) and stirred for 1 hour. After the hydrolysis was completed, the reaction mixture was acidified with 1N hydrochloric acid solution, extracted with ethyl acetate and washed with water and sodium chloride solution. The organic layer was dried over magnesium sulfate, concentrated under reduced pressure and purified with preparative TLC (n-hexane:ethyl acetate=2:1) to give 65.4 mg (59% from ester) of the title compound as a white solid.

$^1$H-NMR (270 MHz, CD$_3$OD) δ: 7.36 (d, J=15.9 Hz, 1H, C3-H), 7.23 (d, 17.3 Hz, 1H, Ar—H), 7.04 (dd, J=7.9 and 7.2 Hz, 1H, Ar—H), 6.68 (d, J=8.5 MHz, 1H, Ar—H), 6.56 (m, 7H, Ar—H), 6.34 (dd, I=8.2 and 2.3 Hz, 1H, thiochroman C6-H), 6.06 (d, J=15.9 Hz, C2-H), 4.13 (d, J=3.3 Hz, 1H, thiochroman C4-H), 3.42 (ddd, J=13.2, 3.6 and 3.3 Hz, 1H, thiochroman C3-H), 3.20 (dd, J=not resolved, 1H, thiochroman C2-H), 2.82 (dd, J=not resolved, 1H, thiochroman C2-H)

EXAMPLE 50

Synthesis of (3RS,4RS)-4-[9-(4-cyanobutylsulfinyl)nonyl]-7-hydroxy-3-(4-hydroxyphenyl)-3-methylthiochroman Step 1) Synthesis of (3RS,4RS)-4-[9-(4-cyanobutylthio)nonyl]-7-methoxy-3-(4-methoxyphenyl)-3-methylthiochroman

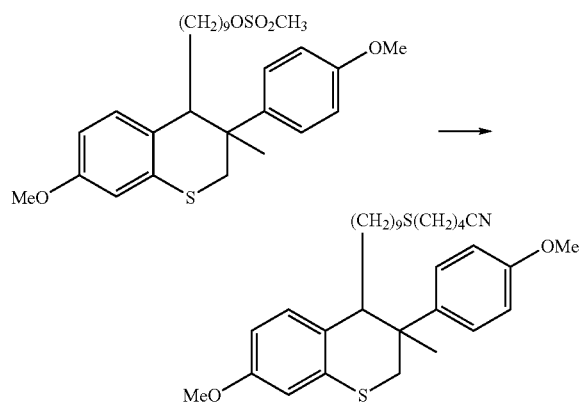

To a solution of 4-cyanobutyl thioacetate (613 mg, 3.90 mmol) in methanol (10 ml) and was added 1M sodium methoxide (3.06 ml) and stirred at room temperature for 1 h. Then (3RS,4RS)-4-(9-methansulfonyloxynonyl)-7-methoxy-3-(4-methoxyphenyl)-3-methylthiochroman (290 mg, 0.557 mmol) dissolved in dry tetrahydrofuran (5 ml) was added dropwise thereto at room temperature and stirred overnight. When the reaction was completed, water was added to the reaction solution which was then extracted with ethyl acetate. The organic layer was washed with water and saturated sodium chloride solution and dried over anhydrous magnesium sulfate. The residue was concentrated under reduced pressure and flash chromatographed on silica gel (n-hexane:ethyl acetate=8:2) to give 495 mg (165%, contains the 4-cyanobutan-1-thiol) of the title compound as a colorless oil.

$^1$H-NMR (270 MHz, CDCl$_3$) δ: 7.24 (d, J=8.6 Hz, 2H, Ar—H), 6.86 (m, 3H, Ar—H), 6.67 (d, J=2.3 Hz, 1H, C8-H), 6.52 (dd, J=8.2 and 2.3 Hz, 1H, C6-H), 3.76 (s, 3H, OCH$_3$), 3.72 (s, 3H, OCH$_3$), 3.62 (d, J=12.2 Hz, 1H, C2-H), 2.93 (d, J=12.2 Hz, 1H, C2-H), 2.72 (brt, 1H, C4-H), 2.53–2.30 (m, 6H, 2×SCH$_2$ and CH$_2$CN), 1.74–1.65 (m, 6H, alkyl-H), 1.46–1.02 (m, 17H, C3-CH$_3$ and alkyl-H)

Step 2) Synthesis of (3RS,4RS)-4-[9-(4-cyanobutylthio)nonyl]-7-hydroxy-3-(4-hydroxyphenyl)-3-methylthiochroman

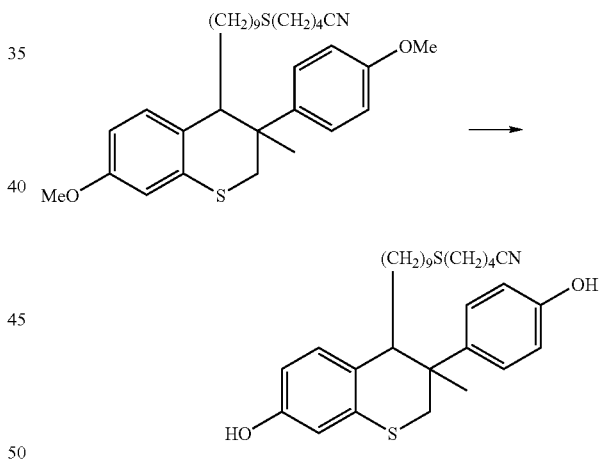

The title compound was prepared from 4-[9-(4-cyanobutylthio)nonyl]-7-methoxy-3-(4-methoxyphenyl)-3-methylthiochroman according to the same method for the synthesis of (3RS,4RS)-7-hydroxy-3-(4-hydroxyphenyl)-3-methyl-4-[9-(4,4,5,5,5-pentafluoropentylthio)nonyl]thiochroman described in International Patent Appln. No. PCT/KR97/00265.

$^1$H-NMR (270 MHz, CDCl$_3$) δ: 7.24 (d, J=8.6 Hz, 2H, Ar—H), 6.85 (m, 3H, Ar—H), 6.66 (d, J=2.3 Hz, 1H, C8-H), 6.50 (dd, J=8.3 and 2.3 Hz, 1H, C6-H), 5.20 (s, 1H, OH), 4.96 (s, 1H, OH), 3.62 (d, J=11.5 Hz, 1H, C2-H), 2.95 (d, J=11.5 Hz, 1H, C2-H), 2.69 (brt, 1H, C4-H), 2.57–2.36 (m, 6H, 2×SCH$_2$ and CH$_2$CN), 1.78–1.65 (m, 6H, alkyl-H), 1.52–1.05 (m, 17H, C3-CH$_3$ and alkyl-H)

Step 3) Synthesis of (3RS,4RS)-4-[9-(4-cyanobutylsulfinyl) nonyl]-7-hydroxy-3-(4-hydroxyphenyl)-3-methylthiochroman

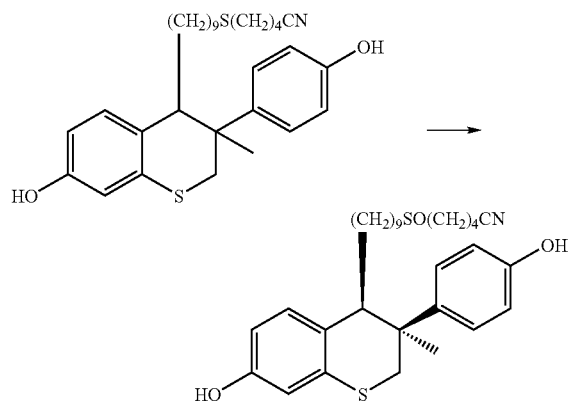

The title compound was prepared from 4-[9-(4-yanobutylthio)nonyl]-7-hydroxy-3-(4-hydroxyphenyl)-3-methylthiochroman according to the same method for the synthesis of (3RS,4RS)-7-hydroxy-3-(4-hydroxyphenyl)-3-methyl-4-[9-(4,4,5,5,5-pentafluoropentylsulfinyl)nonyl]thiochroman described in International Patent Appln. No. PCT/KR97/00265.

$^1$H-NMR (270MHz, CD$_3$OD) δ: 7.17 (m, 2H, Ar—H), 6.74 (m, 3H, Ar—H), 6.48 (brd, 1H, C8-H), 6.35 (brdd, 1H, C6-H), 3.53 (d, J=11.2 Hz, 1H, C2-H), 2.88 (d, J=11.2 Hz, 1H, C2-H), 2.75 (m, 5H, C4-H and 2×S(O)CH$_2$), 2.45 (t, J=6.6 Hz, 2H, CH$_2$CN), 1.75–1.61 (m, 4H, alkyl-H), 1.31–1.05 (m, 19H, C3-CH, and alkyl-H)

EXAMPLE 51

Synthesis of (3'RS,4'RS)-4-{7-hydroxy-3-methyl-4-[9-(4,4,5,5,5-pentafluoropentylsulfinyl)nonyl]chroman-3-yl}benzoic acid Step 1) Synthesis of 3-(4-hydroxyphenyl)-7-methoxymethyloxy-3-methylchroman-4-one

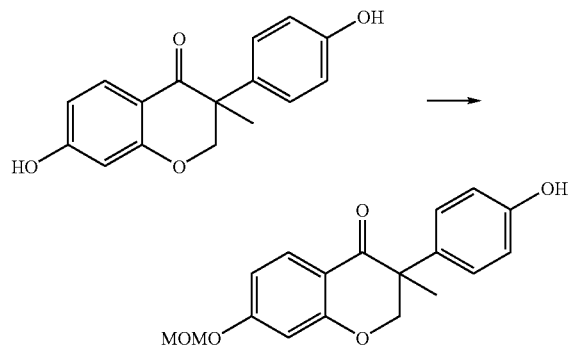

To a solution of 7-hydroxyl-3-(4-hydroxyphenyl)-3-methylchroman-4-one (4.65 g, 17.20 mmol) in dry dimethylformamide (120 ml) was added sodium hydride (454 mg, 18.92 mmol) at room tempetarure and stirred for 30 minutes. To the reaction mixture was then added methoxymethyl chloride (1.523 g, 18.92 mmol) at the same temperature and stirred for 2 h. When the reaction was completed, water was added to the reaction solution which was then extracted with ethyl acetate. The extract was dried over anhydrous magnesium sulfate and concentrated under reduced pressure. The residue was purified with column chromatography (n-hexane:ethyl acetate=8:2 to 7:3) to give 3.55 g (yield: 66%) of the title compound as a white solid.

$^1$H-NMR (270 MHz, CDCl$_3$) δ: 7.87 (d, J=8.9 Hz, 1H, C5-H), 7.24 (d, J=8.9 Hz, 2H, Ar—H), 6.74 (d, J=8.5 Hz, 2H, Ar—H), 6.65 (dd, J=8.2 and 2.3 Hz, 1H, C6-H), 6.53 (d, J=2.3 Hz, 1H, C8-H), 5.84 (s, 1H, OH), 5.16 (s, 2H, OCH$_2$OCH$_3$), 4.78 (d, J=11.8 Hz, C2-H), 4.30 (d, J=11.8 Hz, C2-H), 3.45 (s, 3H, OCH$_2$OCH$_3$), 1.44 (s, 3H, C3-CH$_3$)

Step 2) Synthesis of 3-(4-benzyloxyphenyl)-7-methoxymethyloxy-3-methylchroman-4-one

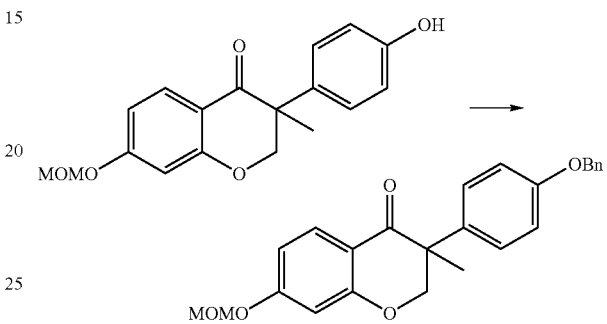

To a mixture of 3-(4-hydroxyphenyl)-7-methoxymethyloxy-3-methylchroman-4-one (3.55 g, 11.293 mmol) and potassium carbonate (9.35 g, 67.76 mmol) in acetone (130 ml) was added benzyl bromide (5.795 g, 33.879 mmol) at room temperature and stirred overnight. When the reaction was completed, water was added to the reaction solution which was then extracted with ethyl acetate. The extract was dried over anhydrous magnesium sulfate and concentrated under reduced pressure. The residue was purified by column chromatography (n-hexane:ethyl acetate=9:1 to 7:3) to give 4.59 g (yield: quant.) of the title compound as a colorless oil.

$^1$H-NMR (270 MHz CDCl$_3$) δ: 7.87 (d, J=8.9 Hz, 1H, C5-H), 7.37 (m, 7H, Ar—H), 6.92 (d, J=8.2 Hz, 2H, Ar—H), 6.65 (dd, J=8.2 and 2.3 Hz, 1H, C6-H), 6.53 (d, J=2.3 Hz, 1H, C8-H), 5.16 (s, 2H, OCH$_2$OCH$_3$), 5.01 (s, 2H, CH$_2$-Ph), 4.81 (d, J=11.9 Hz, C2-H), 4.32 (d, J=11.9 Hz, C2-H), 3.45 (s, 3H, OCH$_2$OCH$_3$), 1.44 (s, 3H, C3-CH$_3$)

Step 3) Synthesis of 3-(4-benzyloxyphenyl-4-[9-(t-butyldimethylsilyloxy)-1-nonynyl]-7-methoxymethyloxy-3-methylchroman

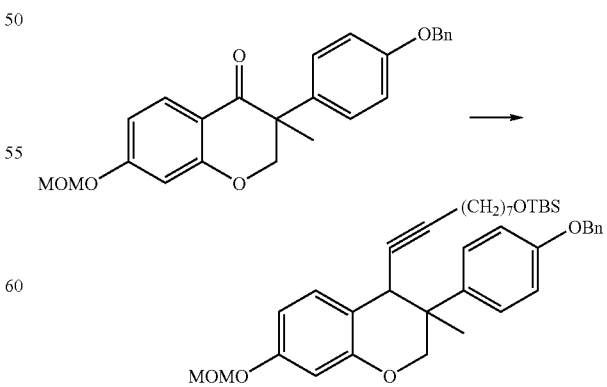

The title compound was prepared from 3-(4-benzyloxyphenyl)-7-methoxymethyloxy-3-methylchroman-4-one according to the same method for the synthesis of 4-[9-(t-Butyldimethylsilyloxy)-1-nonynyl]-7-methoxymethyloxy-3-(4-methoxymethyloxy-phenyl)-3-methylchroman described in International Patent Appln. No. PCT/KR97/00265.

¹H-NMR (270 MHz, CDCl₃) δ: 7.36–7.19 (m, 8H, Ar—H), 6.85 (d, J=8.5 Hz, 2H, Ar—H), 6.57 (dd, J=8.3 and 2.3 Hz, 1H, C6-H), 6.48 (d, J=2.0 Hz, 1H, C8-H), 5.09 (s, 2H, OC_H_₂OCH₃), 4.98 (s, 2H, CH₂-Ph), 4.46 (d, J=10.6 Hz, 1H, C2-H), 4.13 (d, J=10.6 Hz,1H, C2-H), 3.78 (brs, 1H, C4-H), 3.55 (t, J=6.6 Hz, 2H, CH₂OTBS), 3.43 (s, 3H, OC_H_₂OCH₃), 1.97 (m, 2H, propargyl-CH2), 1.53–1.15 (m, 13H, C3-CH₃ and alkyl-H), 0.85 (s, 9H, t-butyl-H), 0.00 (s, 6H, 2×CH₃)

step 4) Synthesis of 4-[9-(t-butyldimethylsilyloxy)nonyl]-3-(4-hydoxyphenyl)-7-methoxymethyloxy-3-methylchroman

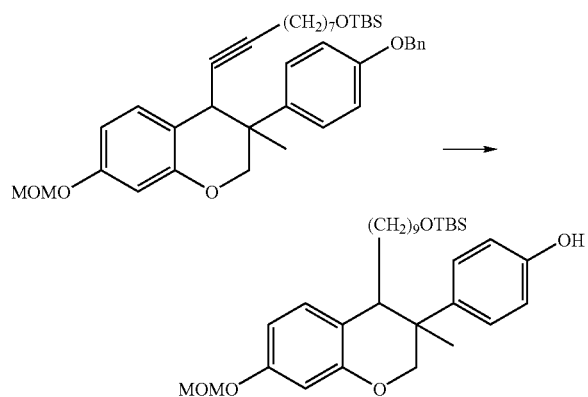

The title compound was prepared from 3-(4-benzyloxy]phenyl)-4-[9-(t-butyldimethylsilyloxy)-1-nonynyl]-7-methoxymethyloxy-3-methylchroman according to the same method for the synthesis of 4-[9-(t-butyldimethylsilyloxy)-1-nonyl]-7-methoxymethyloxy-3-(4-methoxymethyloxyphenyl)-3-methylchroman described in International Patent Appln. No. PCT/KR97/00265.

¹H-NMR (270 MHz, CDCl₃) δ: 7.07 (d, J=8.6 Hz, 2H, Ar—H), 6.95 (d, 8.9 Hz, 1H, Ar—H), 6.81 (m, 2H, Ar—H), 6.55 (m, 2H, Ar—H), 5.14 (s, 2H, OC_H_₂OCH₃), 4.50 (d, J=10.3 Hz, C2-H), 4.24 (d, J=10.6 Hz, C2-H), 3.68 (dd, J=6.6 and 6.3 Hz, 2H, C_H_₂OH), 3.49 (s, 3H, OCH₂OC_H_₃), 2.59 (brt, 1H, C4-H), 1.53–1.04 (m, 19H, C3-CH₃ and alkyl-H), 0.89 (s, 9H, t-butyl-H), 0.05 (s, 6H, 2×CH₃)

Step 5) Synthesis of 4-[9-(t-butyldimethylsilyloxy)nonyl]-7-methoxymethyloxy-3-methyl-3-(4-trifluoromethanesulfonyloxyphenyl)chroman

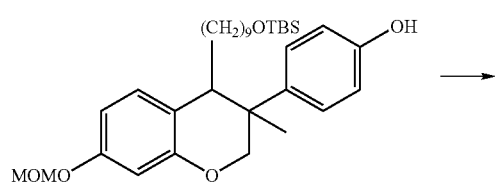

-continued

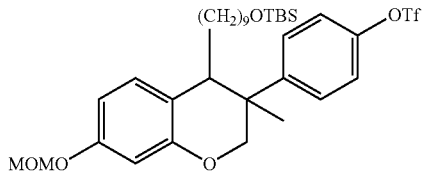

To a solution of 4-[9-(t-butyidimethylsilyloxy)nonyl]-3-(4-hydoxyphenyl)-7-methoxymethyloxy-3-(4-hydoxyphenyl)-3-methylchroman (3.38 g, 6.07 mmol) in dry tetrahydrofuran (30 ml) was added sodium hydride (233 mg, 9.712 mmol) at 0° C. and stirred at room temperature for 30 min. After the reaction mixture was cooled to 0° C., N-phenyltrifluoromethansulfonimide (3.469 g, 9.712 mmol) was added potionwise thereto and stirred at 50° C. for 30 min. When the reaction was completed, water was added to the reaction solution which was then extracted with ethyl acetate. The extract was dried over anhydrous magnesium sulfate and concentrated under reduced pressure. The residue was purified with column chromatography (n-hexane: ethyl acetate=8:2) to give 4.50 g (yield:>100%, contains small amount of by-products) of the title compound as a pale yellow oil.

¹H-NMR— (270 MHz, CDCl₃) δ: 7.24 (m, 4H, Ar—H), 6.92 (m, 1H, Ar—H), 6.55 (m, 2H, Ar—H), 5.11 (s, 2H, OC_H_₂OCH₃), 4.49 (d, J=10.3 Hz, 1H, C2-H), 4.22 (d, J=10.6 Hz, 1H, C2-H), 3.54 (dd, J=6.9 and 6.3 Hz, 2H, C_H_₂OTBS), 3.53 (s, 3H, OCH₂OC_H_₃), 2.68 (brt, 1H, C4-H), 1.39–1.03 (m, 19H, C3-CH₃ and alkyl-H), 0.85 (s, 9H, t-butyl-H), 0.00 (s, 6H, 2×CH₃)

Step 6) Synthesis of (3'RS,4'RS)-4-{4-[9-(t-butyldimethylsilyloxy)nonyl]-7-methoxymethyloxy-3-methylchroman-3-yl}benzoic acid methyl ester

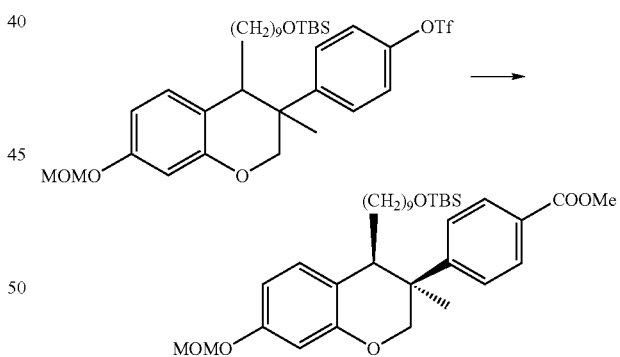

A mixture of 4-[9-(t-butyldimethylsilyloxy)nonyl]7-methoxymethyloxy-3-methyl-3-(4-trifluoromethanesulfonyloxyphenyl)-3-methylchroman (2.80 g, 4.064 mmol), triethylamine (1.13 ml, 8.128 mmol), palladium acetate (320 mg, 1.425 mmol), 1,1-bis(diphenylphosphinoferrocene (850 mg, 1.533 mmol) and methanol (2.7 ml) in dimethyl formamide (8 ml) was purged with carbon monoxide for 5 minutes and stirred under a carbon monoxide ballon at 70° C. for 2.5 h. Ethyl acetate and water were added and the ethyl acetate layer was washed with water, dried over anhydrous magnesium sulfate and concentrated under reduced pressure. The residue was purified with column chromatography (n-hexane:ethyl acetate=95:5) to give 1.61 g (yield: 66%, 3RS,4RS-isomer) of the title compound as a colorless oil.

$^1$H-NMR (270 MHz, CDCl$_3$) δ: 8.03 (d, J=8.3 Hz, 2H, Ar—H), 7.28 (d, J=8.5 Hz, 2H, Ar—H), 6.95 (m, 1H, Ar—H), 6.57 (m, 2H, Ar—H), 5.15 (s, 2H, OC$\underline{H}_2$OCH$_3$), 4.57 (d, J=10.2 Hz, 1H, C2-H), 4.31 (d, J=10.2 Hz, 1H, C2-H), 3.92 (s, 3H, COOC$\underline{H}_3$), 3.56 (t, J=6.6 Hz, 2H, C$\underline{H}_2$OTBS), 3.49 (s, 3H, OCH$_2$OC$\underline{H}_3$), 2.72 (brt, 1H, C4-H), 1.56–1.07 (m, 19H, C3-CH$_3$ and alkyl-H), 0.88 (s, 9H, t-butyl-H), 0.03 (s, 6H, 2×CH$_3$)

Step 7) Synthesis of (3'RS,4'RS)-4-[4-(9-hydroxynonyl)-7-methoxymethyloxy-3-methylchroman-3-yl]benzoic acid methyl ester

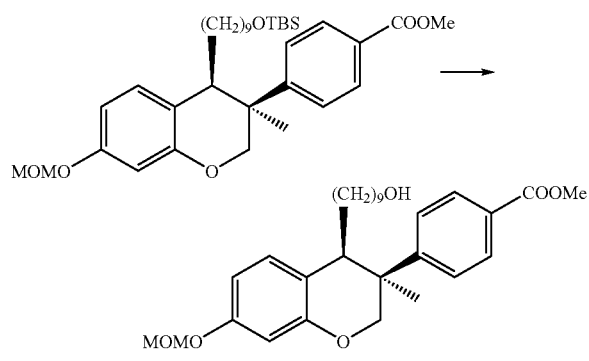

The title compound was prepared from (3RS,4RS)-{4-[9-(t-butyl-dimethylsilyloxy)nonyl]-7-methoxymethyloxy-3-methylchroman-3-yl}benzoic acid methyl ester according to the same method for the synthesis of 4-(9-hydroxynonyl)-7-methoxymethyloxy-3-(4-methoxymethyloxyphenyl)-3-methylchroman described in International Patent Appln. No. PCT/KR97/00265.

$^1$H-NMR (270 MHz CDCl$_3$) δ: 8.03 (d, J=8.3 Hz, 2H, Ar—H), 7.29 (d, J=8.6 Hz, 2H, Ar—H), 6.96 (m, 1H, Ar—H), 6.57 (m, 2H, Ar—H), 5.15 (s, 2H, OC$\underline{H}_2$OCH$_3$), 4.57 (d, J=10.2 Hz, 1H, C2-H), 4.31 (d, J=10.2 Hz, 1H, C2-H), 3.92 (s, 3H, COOCH$_3$), 3.60 (t, J=6.6 Hz, 2H, C$\underline{H}_2$OH), 3.49 (s, 3H, OCH$_2$OC$\underline{H}_3$), 2.71 (brt, 1H, C4-H), 1.50–1.06 (m, 19H, C3-CH$_3$ and alkyl-H)

Step 8) Synthesis of (3'RS,4'RS)-4-[4-(9-methanesulfonyloxynonyl)-7-methoxymethyloxy-3-methylchroman-3-yl]benzoic acid methyl ester

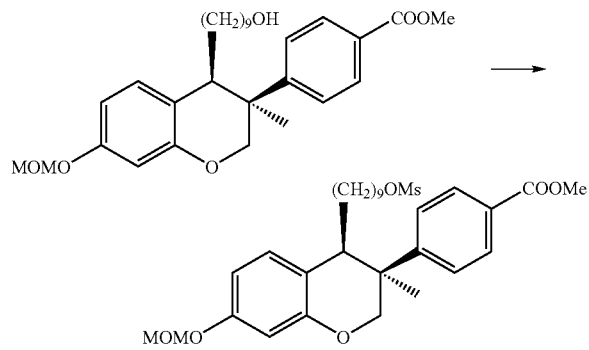

The title compound was prepared from (3'RS,4RS)-4-[4-(9-hydroxynonyl)-7-methoxymethyloxy-3-methylchroman-3-yl]benzoic acid methyl ester according to the same method for the synthesis of. 4-(9-methanesulfonyloxynonyl)-7-methoxymethyloxy-3-(4-methoxymethyloxyphenyl)-3-methylchroman described in International Patent Appln. No. PCT/KR97/00265.

$^1$H-NMR (270 MHz, CDCl$_3$) δ: 8.03 (d, J=8.3 Hz, 2H, Ar—H), 7.29 (d, J=8:3 Hz, 2H, Ar—H), 6.95 (m, 1H, Ar—H), 6.57 (m, 2H, Ar—H), 5.15 (s, 2H, OC$\underline{H}_2$OCH$_3$), 4.57 (d, J=10.2 Hz, 1H, C2-H), 4.31 (d, J=10.2 Hz, 1H, C2-H), 4.19 (t, J=6.6 Hz, 2H, C$\underline{H}_2$OH), 3.92 (s, 3H, COOCH$_3$), 3.49 (s, 3H, OCH$_2$OC$\underline{H}_3$), 2.98 (s, 3H, OSO$_2$CH$_3$), 2.98 (brt, 1H, C4-H), 1.72–1.08 (m, 19H, C3-CH$_3$ and alkyl-H)

Step 9) Synthesis of (3'RS,4'RS)-4-{7-Methoxymethyloxy-3-methyl-4-[9-(4,4,5,5,5-pentafluoropentylthio)nonyl]chroman-3-yl}benzoic acid methyl ester

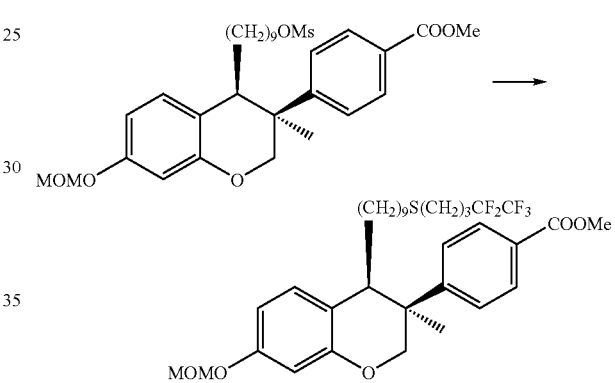

4,4,5,5,5-Pentafluoropentyl thioacetate (872 mg, 3.892 mmol) was dissolved in absolute methanol (20 ml) and 1M sodium methoxide (3.9 ml) was added thereto. The reaction solution was stirred for 1 h at room temperature and (3RS,4RS)-4-[4-(9-methanesulfonyloxynonyl)-7-methoxymethyloxy-3-methylchroman-3-yl]benzoic acid methyl ester (1.46 g, 2.594 mmol) dissolved in dry tetrahydrofuran (15 ml) was added dropwise thereto at room temperature. The reaction mixture was stirred overnight. When the reaction was completed, water was added to the reaction solution which was then extracted with ethyl acetate. The extract was dried over anhydrous magnesium sulfate and concentrated under reduced pressure. The residue was purified with column chromatography (n-hexane:ethyl acetate=9:1) to give 1.539 g (yield: 66%) of the title compound as a pale yellow oil.

$^1$H-NMR (270 MHz, CDCl$_3$) δ: 8.03 (d, J=8.3 Hz, 2H, Ar—H), 7.29 (d, J=8.3 Hz, 2H, Ar—H), 6.95 (m, 1H, Ar—H), 6.57 (m, 2H, Ar—H), 5.15 (s, 2H, OC$\underline{H}$hd 2OCH$_3$), 4.56 (d, 10.3 Hz, 1H, C2-H), 4.32 (d, J=10.3 Hz, 1H, C2-H), 3.92 (s, 3H, COOCH$_3$), 3.49 (s, 3H, OCH$_2$OC$\underline{H}_3$), 2.76 (brt, 1H, C4-H), 2.57 (dd, J=7.3 and 6.6 Hz, 2H, SCH$_2$), 2.47 (dd, J=7.3 and 6.6 Hz, 2H, SCH$_2$), 2.19–1.08 (m, 4H, alkyl-H), 1.60–1.07 (m, 19H, C3-CH$_3$ and alkyl-H)

Step 10) Synthesis of (3'RS,4'RS)-4-{7-hydroxy-3-methyl-4-[9-(4,4,5,5,5-pentafluoropentylthio)nonyl]chroman-3-yl}benzoic acid methyl ester

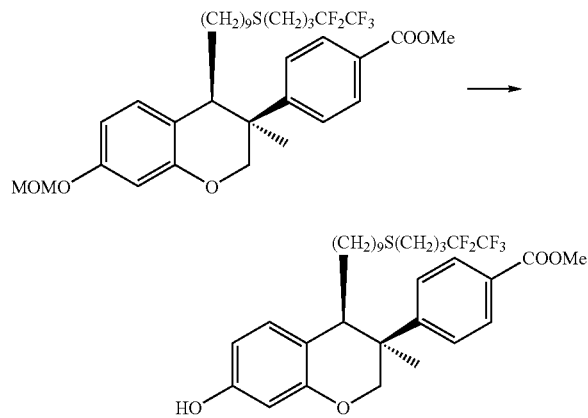

To a solution of (3'RS,4'RS)-4-{7-methoxymethyloxy-3-methyl-4-[9(4,4,5,5,5-pentafluoropentylthio)nonyl]chroman-3-yl)benzoic acid methyl ester (1.539 g, 2.329 mmol) in isopropanol (200 ml) and tetrahydrofuran (40 ml) was added 5N hydrochloric acid solution (75 ml) at room temperature and stirred for 1 hour. After adding water, the solution was extracted with ethyl acetate. The organic layer was then washed with water and saturated sodium chloride, dried over anhydrous magnesium sulfate and concentrated under reduced pressure. The residue was purified with column chromatography (n-hexane:ethyl acetate=9:1 to 1:1) to give 1.36 g (yield: 95%) of the title compound as a colorless oil.

$^1$H-NMR (270 MHz, CDCl$_3$) δ: 8.03 (d, J=8.3 Hz, 2H, Ar—H), 7.29 (d, J=8.3 Hz, 2H, Ar—H), 6.91 (m, 1H, Ar—H), 6.39 (m, 2H, Ar—H), 5.07 (s, 1H, OH), 4.56 (d, J=10.2 Hz, 1H, C2-H), 4.29 (d, J=10.2 Hz, 1H, C2-H), 3.92 (s, 3H, COOCH$_3$), 2.76 (brt, 1H, C4-H), 2.57 (dd, J=6.6 and 6.3 Hz, 2H, SCH$_2$), 2.47 (dd, J=6.6 and 6.3 Hz, 2H, SCH$_2$), 2.20–1.89 (m, 4H, alkyl-H), 1.60–1.07 (m, 19H, C3-CH$_3$ and alkyl-H)

Step 11) Synthesis of (3'RS,4'RS)-4-{7-hydroxy-3-methyl-4-[9-(4,4,5,5,5-pentafluoropentylthio)nonyl]chroman-3-yl}benzoic acid

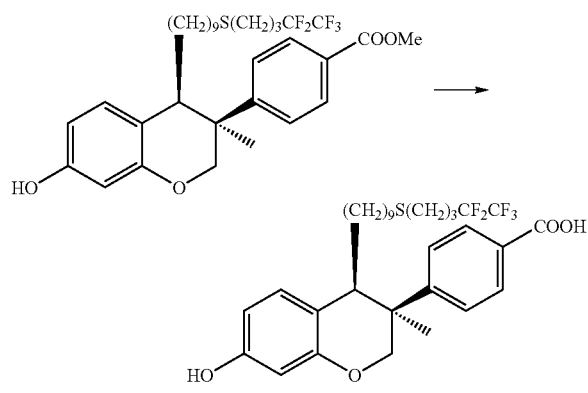

The mixture of (3'RS,4'RS)-4-{7-hydroxy-3-methyl-4-[9-(4,4,5,5,5pentafluoropentylthio)nonyl]chroman-3-yl}benzoic acid methyl ester (360 mg, 0.583 mmol) and 2N sodium hydroxide (2.25 ml) in methanol (9 ml) and tetrahydrofuran (0.9 ml) was stirred at room temperature for 1 hour. When the reaction was completed, water and diethyl ether were added to the reaction solution which was then extracted with diethyl ether. The water layer was acidified with 5N hydrochloric acid solution, extracted with ethyl acetate, washed with water, dried over magnesium sulfate and concentrated under reduced pressure. The concentrate was purified with preparative TLC (n-hexane:ethyl acetate=1:1) to give 346 mg (yield: 98%) of the title compound as a white solid.

$^1$H-NMR (270 MHz, CDCl$_3$) δ: 8.11 (d, J=8.5 Hz, 2H, Ar—H), 7.34 (d, J=8.6 Hz, 2H, Ar—H), 6.91 (m, 1H, Ar—H), 6.41 (m, 2H, Ar—H), 4.58 (d, J=10.3 Hz, 1H, C2-H), 4.31 (d, J=10.3 Hz, 1H, C2-H), 2.76 (brt, 1H, C4-H), 2.56 (dd, J=7.3 and 6.9 Hz, 2H, SCH$_2$), 2.47 (dd, J=7.3 and 6.9 Hz, 2H, SCH$_2$), 2.24–1.86 (m, 4H, alkyl-H), 1.61–1.08 (m, 19H, C3-CH$_3$ and alkyl-H)

Step 12) Synthesis of (3'RS,4'RS)-4-{7-hydroxy-3-methyl-4-[9-(4,4,5,5,5-pentafluoropentylsulfinyl)nonyl]chroman-3-yl)benzoic acid

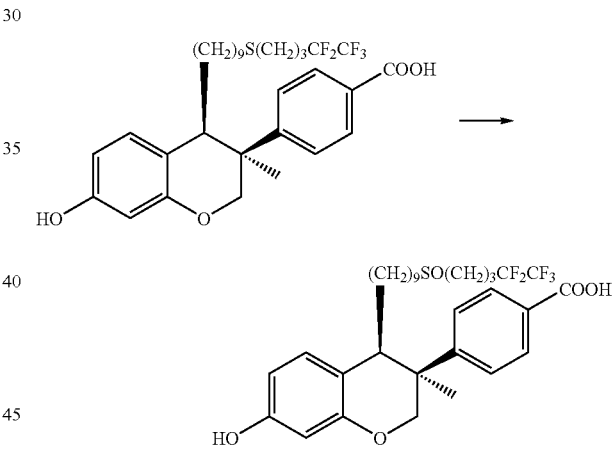

To a mixture of (3'RS,4'RS)-4-{7-hydroxy-3-methyl-4-[9-(4,4,5,5,5-pentafluoropentylthio)-nonyl]chroman-3-yl}benzoic acid (346 mg, 0.574 mmol) in tetrahydrofuran (20 ml) and Oxone® (monopersulfate compound; DuPont product) (247 mg, 0.401 mmol) was added water at the room temperature and stirred for 30 minutes. After adding water, the reaction solution was extracted with ethyl acetate. The extract was concentrated under reduced pressure and purified with preparative TLC with (n-hexane:ethyl acetate=1:1) to give 239 mg (yield: 67%) of the title compound as a white solid.

$^1$H-NMR (270 MHz, CDCl$_3$) δ: 8.07 (d, J=8.6 Hz, 2H, Ar—H), 7.31 (d, J=8.3 Hz, 2H, Ar—H), 6.89 (d, J=7.9 Hz, 1H, Ar—H), 6.62 (brs, 1H, COOH), 6.42 (m, 2H, Ar—H), 4.55 (d, J=10.3 Hz, 1H, C2-H), 4.28 (d, J=10.3 Hz, 1H, C2-H),: 2.92–2.59 (m, 5H, C4-H, and 2×S(O)CH$_2$), 2.18 (m, 4H, alkyl-H), 1.72 (m, 2H, alkyl-H), 1.30–0.98 (m, 17H, C3-CH$_3$ and alkyl-H)

EXAMPLE 52

Synthesis of (3'RS,4'RS)-4-{7-hydroxy-3-methyl-4-[9-(4,4,5,5-pentafuoropentylsulfinyl)nonyl]chroman-3-yl}benzyl alcohol Step 1) Synthesis of (3'RS,4'RS)-4-(7-hydroxy-3-methyl-4-[9-(4,4,5,5-pentafluoropentylthio)nonyl]chroman-3-yl}benzyl alcohol

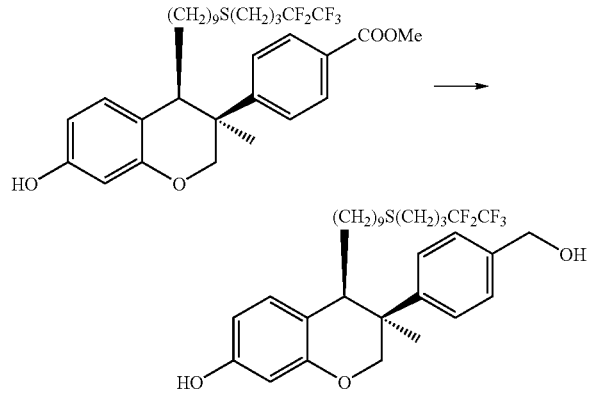

To a solution of (3'RS,4'RS)-4-{7-hydroxy-3-methyl-4-[9-(4,4,5,5-pentafluoropentylthio)nonyl]chroman-3-yl}benzoic acid methyl ester (58 mg, 0.094 mmol) in dry tetrahydrofuran (3 ml) was added lithium aluminum hydride (10.7 mg, 0.282 mmol) at room temperature and stirred for 3 h. When the reaction was completed, ammonium chloride solution was added to the reaction solution which was then extracted with ethyl acetate. The extract was washed with water, dried over anhydrous magnesium sulfate and concentrated under reduced pressure. The residue was purified with column chromatography (n-hexane:ethyl acetate=1:1) to give 52 mg (yield: 94%) of the title compound as a colorless oil.

$^1$H-NMR (270 MHz, CDCl$_3$) δ: 7.42 (d, J=8.0 Hz, 2H, Ar—H), 7.30 (d, J=9.2 Hz, 2H, Ar—H), 6.97 (d, J=7.9 Hz, 1H, Ar—H), 6.43 (m, 2H, Ar—H), 5.25 (s, 1H, OH), 4.76 (s, 2H, Ph-CHhd 2OH), 4.61 (d, J=10.6 Hz, 1H, C2-H), 4.34 (d, J=10.6 Hz, 1H, C2-H), 2.77, (brt, 1H, C4-H), 2.63 (dd, J=7.3 and 6.9 Hz, 2H, SCH$_2$), 2.53 (dd, J=7.3 and 6.9 Hz, 2H, SCH$_2$), 2.18 (m, 2H, alkyl-H), 1.93 (m, 2H, alkyl-H), 1.56 (m, 2H, alkyl-H), 1.40–0.91 (m, 17H, C3-CH$_3$ and alkyl-H)

Step 2) Synthesis of (3'RS,4'RS)-{7-hydroxy-3-methyl-4-[9-(4,4,5,5-pentafluoropentylsulfinyl)nonyl]chroman-3-yl}benzyl alcohol

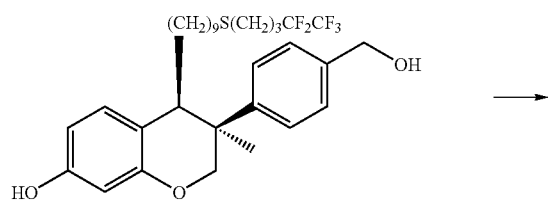

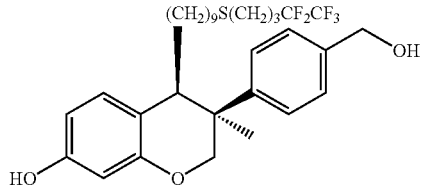

The title compound was prepared from (3'RS,4'RS)-4-{7-hydroxy-3-methyl-4-[9-(4,4,5,5-pentafluoropentylthio)nonyl]chroman-3-yl}benzyl alcohol according to the same method for the synthesis of (3'RS,4'RS)-1f-7-hydroxy-3-methyl-4-[9-(4,4,5,5-pentafluoropentylsulfinyl)-nonyl]chroman-3-yl}benzoic acid $^1$H-NMR (270 MHz, CDCl$_3$) δ 7.35 (d, J=8.2 Hz, 2H, Ar—H), 7.19 (d, J=8.3 Hz, 2H, Ar—H), 6.95 (m, 1H, Ar—H), 6.86 (d, J=8.9 Hz, 1H, Ar—H), 6.38 (m, 2H, Ar—H), 4.68 (s, 2H, Ph-CH$_2$OH), 4.54 (d, J=10.6 Hz, 1H, C2-H), 4.26 (d, J=10.6 Hz, 1H, C2-H), 2.81–2.55 (m, 5H, C4-H, and 2×S(O)CH$_2$), 2.16 (m, 4H, alkyl-H), 1.70 (m, 2H, alkyl-H), 1.36–1.07 (m, 17H, C3-CH$_3$ and alkyl-H)

EXAMPLE 53

Synthesis of (A) (3RS,4RS)-7-hydroxy-3-(4-hydroxyphenyl)-3-methyl-4-{3-[4-(4,4,5,5,5-pentatfluoropentylsulfinyl)propylphenoxy]-1-propyl}chroman and (B) (3RS,4RS)-7-hydroxy-3-(4-hydroxyphenyl)-3-methyl-4-{3-[4-(4,4,5,5,5-pentafluoropentylsulfonyl)propylphenoxy]-1-propyl}chroman Step 1) Synthesis of 4-{3-[4-(3-t-butyldimethylsilyloxypropyl)phenoxy]-1-propynyl}-7-methoxymethyloxy-3-(4-methoxymethyloxyphenyl)-3-methylchroman-4-ol

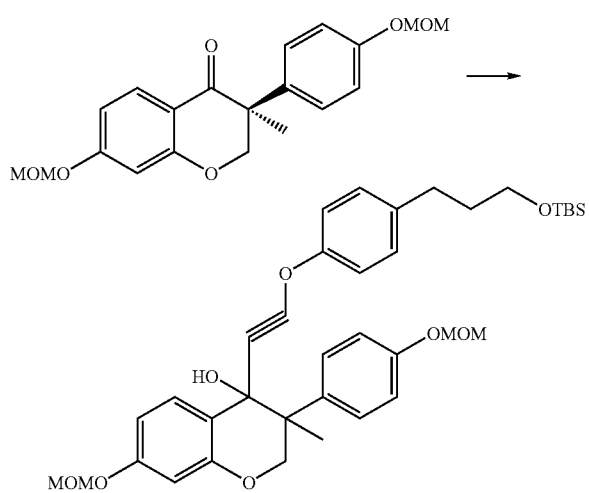

The title compound was prepared from 7-methoxymethyloxy-3-(4-methoxymethyloxyphenyl)-3-methylchroman-4-one and 3-[4-(3-t-butyldimethylsilyloxypropyl)phenoxy]-1-propyn according to the same method for the synthesis of 4-[9-(t-butyldimethylsilyloxy)1-nonynyl]-7-methoxy-3-(4-methoxyphenyl)-3-methylthiochroman.

$^1$H-NMR (270 MHz, CDCl$_3$): d 7.55 (d, J=8.6 Hz, 1H, C5-H), 7.31 (d, J=8.9 Hz, 2H, Ar—H), 7.14 (d, J=8.6 Hz,

2H, Ar—H), 6.92 (2×d, J=8.6 and 8.5 Hz, 4H, Ar—H), 6.63 (dd, J=8.6 and 2.3 Hz, 1H, C6-H), 6.57 (d, J=2.3 Hz, 1H, C8-H), 5.16 (s, 2H, OC$\underline{H}_2$OCH$_3$), 5.15 (s, 2H, OC$\underline{H}_2$OCH$_3$), 4.85 (d, J=10.2 Hz, 1H, C2-H), 4.77 (s, 2H, C3-CH$_2$), 4.02 (d, J=10.2 Hz, 1H, C2-H), 3.62 (t, J=6.3 Hz, 2H, CH$_2$—OTBS), 3.49 (s, 3H, OCH$_2$O$\underline{CH}_3$), 3.47 (s, 3H, OCH$_2$O$\underline{CH}_3$), 2.64 (dd, J=8.0 and 7.5 Hz, PhC$\underline{H}_2$CH$_2$CH$_2$—OTBS), 2.13 (s, 1H, OH), 1.81 (m, 2H, Ph-CH$_2$C$\underline{H}_2$CH$_2$—OTBS), 1.43 (s, 3H1, C3-CH$_3$), 0.90 (s, 9H, t-butyl-H), 0.04 (s, 6H, 2×CH$_3$)

Step 2) Synthesis of 4-{3-[4-(3-t-butyldimethylsilyloxypropyl)phenoxy]-1-propynyl}-7-methoxymethyloxy-3-(4-methoxymethyloxyphenyl)-3-methylchroman

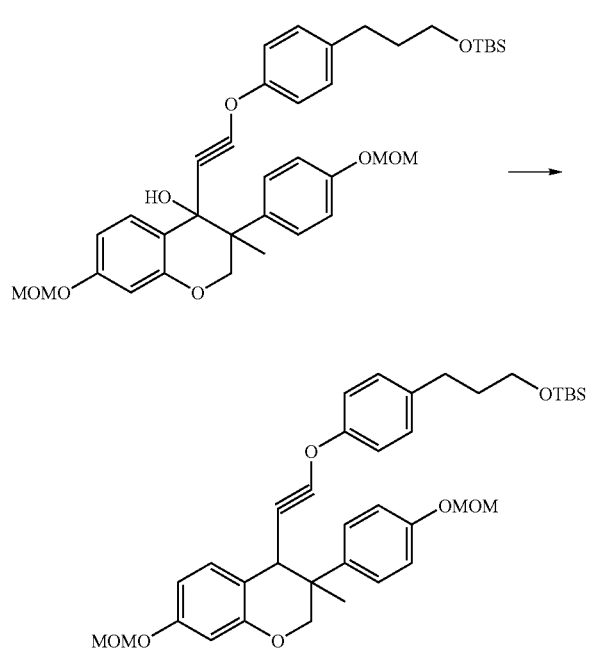

The title compound was prepared from 4-{3-[4-(3-t-butyldimethylsilyloxypropyl)phenoxy]-1-propynyl}-7-methoxymethyloxy-3-(4-methoxymethyloxyphenyl)-3-methylchroman-4-ol according to the same method for the synthesis of 4-[9-(t-butyldimethylsilyloxy)-1-nonynyl]-7-methoxy-3-(4-methoxyphenyl)-3-methylthiochroman described in International Patent Appln. No. PCT/KR 97/00265.

$^1$H-NMR (270 MHz, CDCl$_3$) δ: 7.28 (m, 3H, Ar—H), 7.04 (d, J=8.2 Hz, 2H, Ar—H), 6.90 (d, J=8.7 Hz, 2H, Ar—H), 6.72 (d, J=8.6 Hz, 2H, Ar—H), 6.60 (dd, J=8 6 and 2.3 Hz, 1H, C6-H), 6.52 (d, J=2.3 Hz, 1H, C8-H), 5.14 (s, 2H, OC$\underline{H}_2$OCH$_3$), 5.13 (s, 2H, OC$\underline{H}_2$OCH$_3$), 4.52 (s, 2H, C3-CH$_2$), 4.44 (d, J=10.2 Hz, 1H, C2-H), 4.14 (d, J=10.2 Hz, 1H, C2-H), 3.88 (s, 1H, C4H), 3.63 (t, J=6.3 Hz, 2H, CH$_3$—OTBS), 3.47 (s, 6H, 2×OCH$_2$OC$\underline{H}_3$), 2.61 (dd, J=7.9 and 7.3 Hz, PhC$\underline{H}_2$CH$_2$—OTBS), 1.80 (m, 2H, PhCH$_2$C$\underline{H}_2$CH$_2$—OTBs), 1.36 (s, 3H, C3-CH$_3$), 0.91 (s, 9H, t-butyl-H), 0.06 (s, 6H, 2×CH$_3$)

Step 3) Synthesis of (3RS,4RS)4-{3-[4-(3-t-butyldimethylsilyloxypropyl)phenoxy]-1-propyl}-7-methoxymethyloxy-3-(4-methoxymethyloxyphenyl)-3-methylchroman

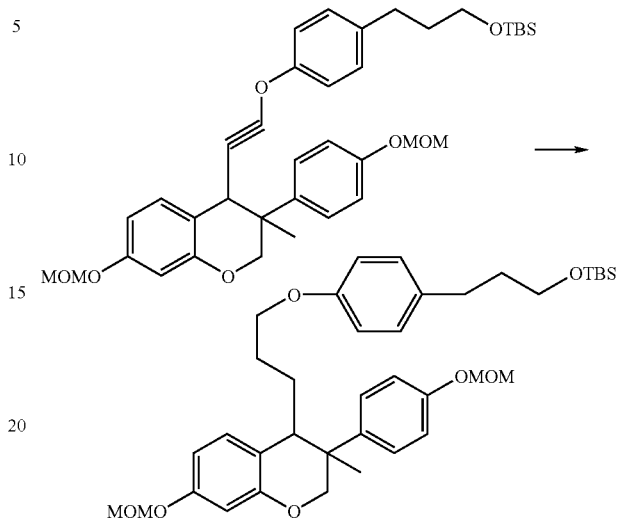

The title compound was prepared from 4-{3-[4-(3-t-butyldimethylsilyloxypropyl)phenoxy]-1-propynyl}-7-methoxymethyloxy-3-(4-methoxymethyloxyphenyl)-3-methylchroman according to the same method for the synthesis of 4-[9-(t-butyldimethylsilyloxy)-1-nonyl]-7-methoxy-3-(4-methoxyphenyl)-3-methylthiochroman described in International Patent Appln. No. PCT/KR97/00265.

$^1$H-NMR (270 MHz, CDCl$_3$) δ: 7.28–6.94 (m, 7H, Ar—H), 6.68 (d, J=8.2 Hz, 2H, Ar—H), 6.55 (m, 2H, Ar—H), 5.18 (s, 2H, OC$\underline{H}_2$OCH$_3$), 5.15 (s, 2H, OC$\underline{H}_2$OCH$_3$), 4.55 (d, J=10.4 Hz, 1H, C2-H), 4.28 (d, J=10.2 Hz, 1H, C2-H), 3.71 (dd, J=6.9 and 6.3 Hz, 2H, C3-CH$_2$), 3.60 (t, J=6.3 Hz, 2H, CH$_2$—OTBS), 3.49 (s, 6H, 2×OCH$_2$OC$\underline{H}_3$), 2.78 (brt, 1H, C4-H), 2.58 (dd, J=8.5 and 7.3 Hz, PhC$\underline{H}_2$CH$_2$CH$_2$—OTBS), 1.76 (m, 2H, C2-CH$_2$ and PhCH$_2$C$\underline{H}_2$CH$_2$—OTBS), 1.44 (m, 2H, C$_1$-CH$_2$), 1.27 (s, 3H, C3-CH$_3$), 0.91 (s, 9H, t-butyl-H), 0.06 (s, 6H, 2×CH$_3$)

Step 4) Synthesis of 4-{3-[4-(3-hydroxypropyl)phenoxy]-1-propyl}-7-methoxymethyloxy-3-(4-methoxymethyloxyphenyl)-3-methylchroman

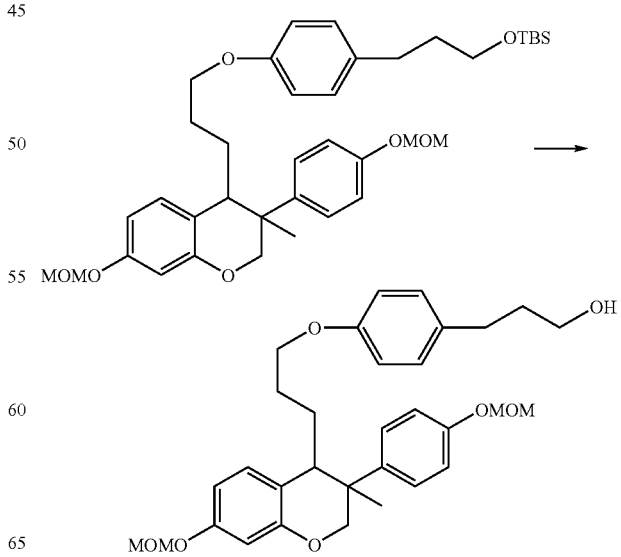

The title compound was prepared from (3RS,4RS)-4-{3-[4-(3-t-butyl-dimethylsilyloxypropyl)phenoxy]-1-propyl}-7-methoxymethyloxy-3-(4-methoxymethyloxyphenyl)-3-methylchroman according to the same method for the synthesis of 4-[9-hydroxy-1-nonyl]-7-methoxymethyloxy-3-(4-methoxymethyloxyphenyl)-3-methylchroman described in International Patent Appln. No. PCT/KR97/00265.

$^1$H-NMR (270MHz CDCl$_3$) δ: 7.04 (m, 5H, Ar—H), 6.74 (d, J=8.6 Hz, 2H, Ar—H), 6.67 (d, J=8.6 Hz, 2H, Ar—H), 6.54 (m, 2H, Ar—H), 5.18 (s, 2H, 2×OCH$_2$OCH$_3$), 5.15 (s, 2H, OCH$_2$OCH$_3$), 4.54 (d, J=10.5 Hz, 1H, C2-H), 4.28 (d, J=10.5 Hz, 1H, C2-H), 3.69 (m, 4H, C3-CH$_2$ and CH$_2$OH), 3.49 (s, 6H, OCH$_2$OCH$_3$), 2.72 (brt, 1H, C4-H), 2.62 (m, 2H, PhCH$_2$CH$_2$CH$_2$—OTBS), 1.80 (m, 6H, alkyl-H), 1.26 (s, 3H, C3-CH$_3$)

Step 5) Synthesis of (3RS,4RS)-4-{3-[4-(3-methanesulfonyloxypropyl)phenoxy]-1-propyl}-7-methoxymethyloxy-3-(4-methoxymethyloxyphenyl)-3-methylchroman

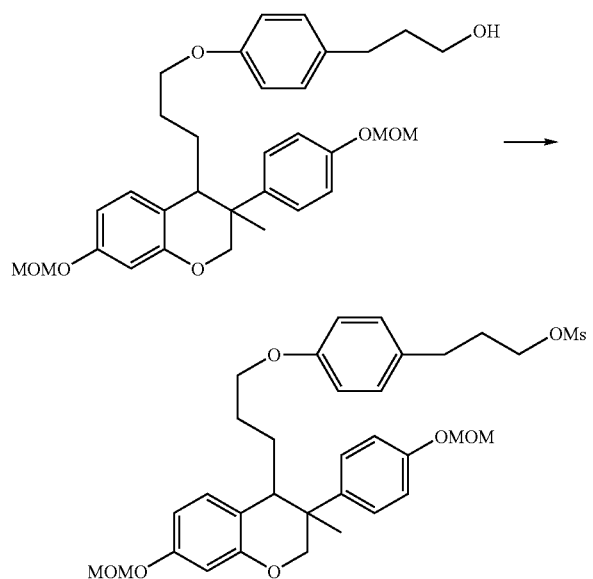

The title compound was prepared from (3RS,4RS8)-4-{3-[4-(3-hydroxypropyl)phenoxy]-1-propyl}-7-methoxymethyloxy-3-(4-methoxymethyloxyphenyl)-3-methylchroman according to the same method for the synthesis of 4-(9-methanesulfonyloxynonyl)-7-methoxymethyloxy-3-(4-methoxymethyloxyphenyl)-3-methylchroman described in International Patent Appln. No. PCT/KR97/00265.

$^1$H-NMR (270 MHz, CDCl$_3$) δ: 7.28–6.93 (m, 7H, Ar—H), 6.68 (d, J=8.6 Hz, 2H, Ar—H), 6.55 (m, 2H, Ar—H), 5.17 (s, 2H, OCH$_2$OCH$_3$), 5.15 (s, 2H, OCH$_2$OCH$_3$), 4.54 (d, J=10.5 Hz, 1H, C2-H), 4.28 (d, J=10.5 Hz, 1H, C2-H), 4.19 (m, 2H, CH$_2$OSO$_2$CH$_3$), 3.70 (dd, J=6.9 and 6.3 Hz, 2H, C3-CH$_2$), 3.49 (s, 6H, 2×OCH$_2$OCH$_3$), 2.98 (s, 3H, OSO$_2$CH$_3$), 2.71 (brt, 1H, C4-H), 2.66 (dd, J=7.6 and 6.9 Hz, PhCH$_2$CH$_2$CH$_2$O), 1.99 (m, 4H, PhCH$_2$CH$_2$CH$_2$O and C2-CH$_2$), 1.73 (m, 2H, C1-CH$_2$), 1.26 (s, 3H, C3-CH$_3$)

Step 6) Synthesis of (3RS,4RS)-7-methoxymethyloxy-3-(4-methoxymethyl oxyphenyl)-3-methyl-4-{3-[4-(4,4,5,5,5-pentafluoropentylthio)propylphenoxy]-1-propyl}chroman

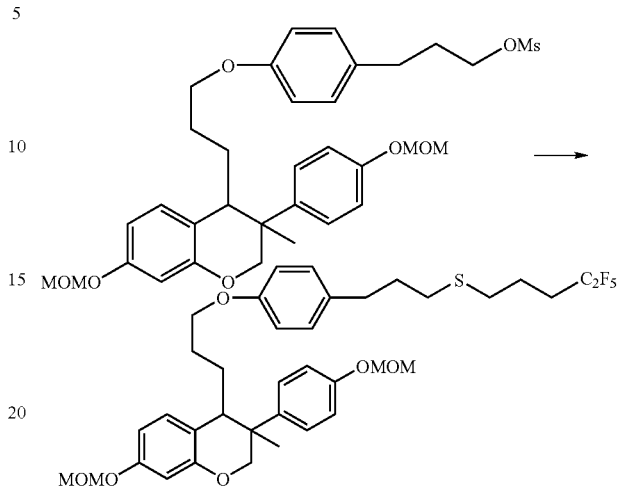

The title compound was prepared from (3RS,4RS)-4-{3-[4-(3-methanesulfonyloxypropyl)phenoxy]-1-propyl}-7-methoxymethyloxy-3-(4-methoxymethyloxyphenyl)-3-methylchroman according to the same method for the synthesis of (3RS,4RS)-7-methoxy-3-(4-methoxyphenyl)-3-methyl-4-[9-(4,4,5,5,5-pentafluoropentylthio)nonyl]thiochroman described in International Patent Appln. No. PCT/KR97/00265.

$^1$H-NMR (270 MHz, CDCl$_3$) δ: 7.28–6.94 (m, 71H, Ar—H), 6.68 (d, J=8.6 Hz, 2H, Ar—H), 6.54 (m, 2H, Ar—H), 5.18 (s, 2H, OCH$_2$OCH$_3$), 5.15 (s, 2H, OCH$_2$OCH$_3$), 4.54 (d, J=10.6 Hz, 1H, C2-H), 4.28 (d, J=10.6 Hz, 1H, C2-H), 3.72 (d, J=7.3 and 6.6 Hz, 2H, C3-CH$_2$), 3.49 (s, 6H, 2×OCH$_2$OCH$_3$), 2.72 (brt, 1H, C4-H), 2.55 (m, 6H, PhCH$_2$CH$_2$CH$_2$S and 2×S—CH$_2$), 2.18 (m, 2H, alkyl-H), 1.85 (m, 6H, PhCH$_2$CH$_2$CH$_2$S, C2-CH$_2$, and alkyl-1H), 1.27 (m, 5H, C3-CH and alkyl-H) step 7) Synthesis of (3RS,4RS)-7-hydroxy-3-(4-hydroxyphenyl)-3-methyl-4-{3-[4-(4,4,5,5,5-pentafluoropentylthio)propylphenoxy]-1-propyl}chroman

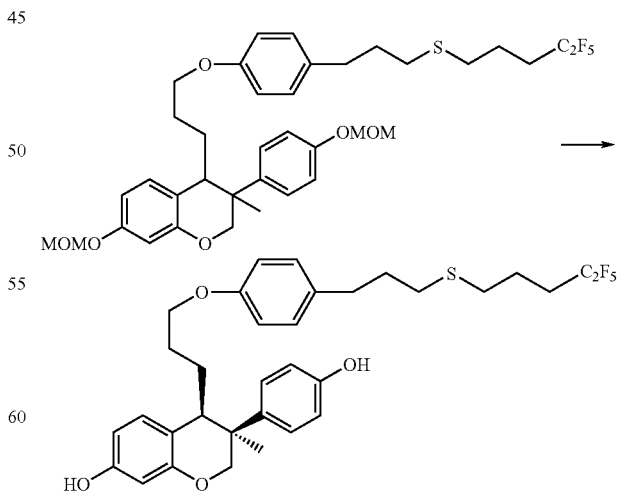

The title compound was prepared from (3RS,4RS)-7-methoxymethyloxy-3-(4-methoxymethyloxyphenyl)-3-methyl-4-{3-[4-(4,4,5,5,5-pentafluoropentylthio)propylphenoxy]-1-propyl}chroman according to the same method for the synthesis of (3'RS,4'RS)-4-{7-hydroxy-3-methyl-4-[9-(4,4,5,5,5-pentafluoropentylthio)nonyl]chroman-3-yl}benzoic acid methyl ester.

$^1$H-NMR (270 MHz, CDCl$_3$) δ: 7.05 (m, 4H, Ar—H), 6.93 (d, J=8.9 Hz, 1H, C5-H), 6.80 (d, J=8.5 Hz, 2H, Ar—H), 6.67 (d, J=8.5 Hz, 2H, Ar—H), 6.37 (m, 2H, Ar—H), 4.79 (s, 1H, OH), 4.73 (s, 1H, OH), 4.52 (d, J=10.3 Hz, 1H, C2-H), 4.25 (d, J=10.3 Hz, 1H, C2-H), 3.71 (d, J=6.6 and 6.3 Hz, 2H, C3-CH$_2$), 2.69 (brt, 1H, C4-H), 2.54 (m, 6H, PhCH$_2$CH$_2$CH$_2$S and 2×S—CH$_2$), 2.30 (m, 2H, alkyl-H), 1.90–1.55 (m, 6H, PhCH$_2$CH$_2$CH$_2$—OTBS, C2-CH$_2$, and alkyl-H), 1.39–1.07 (m, 5H, C3-CH$_3$ and alkyl-H)

Step 8) Synthesis of (A) (3RS,4RS)-7-hydroxy-3-(4-hydroxyphenyl)-3-methyl-4-{3-[4-(4,4,5,5,5-pentafluoropentylsulfinyl)propylphenoxy]-1-propyl}chroman and (B) (3RS,4RS)-7-hydroxy-3-(4-hydroxyphenyl)-3-methyl-4-{3-[4-(4,4,5,5,5-pentafluoropentylsulfonyl)propylphenoxy]-1-propyl}chroman

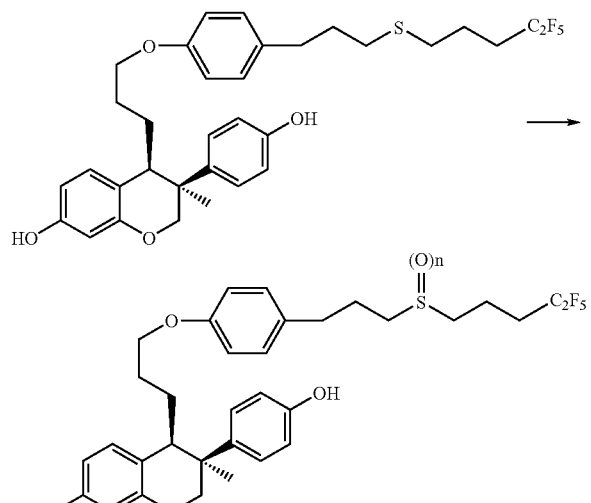

A) n = 1, B) n = 2

To a mixture of (3RS,4RS)-7-hydroxy-3-(4-hydroxyphenyl)-3-methyl-4-{3-[4-(4,4,5,5,5-pentafluoropentylthio)propylphenoxy-[-1-propyl}chroman (256 mg, 0.41 mmol) in tetrahydrofuran (20 ml) and Oxone® (monopersulfate compound; DuPont product) (251 mg, 0.41 mmol) was added water (1 ml) at room temperature and stirred for 30 minutes. After adding water, the reaction solution was extracted with ethyl acetate. The extract was concentrated under reduced pressure and purified with preparative TLC (n-hexane:ethyl acetate=1:1) to give 167 mg (yield: 63.6%) of the title compound (A) and 92 mg (yield: 34%) of the title compound (B).

$^1$H-NMR (270 MHz, CDCl$_3$ A) δ: 7.02 (d, J=8.3 Hz, 4H, Ar—H), 6.87 (d, J=8.6 Hz, 1H, C5-H), 6.73 (d, J=8.6 Hz, 2H, Ar—H), 6.64 (d, J=8.4 Hz, 2H, Ar—H), 6.37 (m, 2H, Ar—H), 5.66 (s, 1H, OH), 5.63 (s, 1H, OH), 4.50 (d, J=10.6 Hz, 1H, C2-H), 4.23 (d, J=10.6 Hz, 1H, C2-H), 3.79 (m, C3-CH$_2$), 2.69 (m, 7H, C4-H, PhCH$_2$CH$_2$S(O) and 2×S(O)CH$_2$), 2.09 (m, 4H, alkyl-H), 1.62 (m, 2H, alkyl-H), 1.26 (m, 7H, C3-CH$_3$ and alkyl-H)

$^1$H-NMR (270 MHz, CDCl$_3$ B) δ: 7.04 (m, 4H, Ar—H), 6.91 (d, J=8.9 Hz, 1H, C5-H), 6.77 (d, J=8.5 Hz, 2H, Ar—H), 6.67 (d, J=8.3 Hz, 2H, Ar—H), 6.36 (m, 2H, Ar—H), 5.12 (s, 1H, OH), 4.94 (s, 1H, OH), 4.52 (d, J=10.5 Hz, 1H, C2-H), 4.25 (d, J=10.5 Hz, 1H, C2-H), 3.31 (m, C3-CH$_2$), 2.97 (m, 2×SO$_2$CH$_2$), 2.70 (m. 3H, C4-H and Ph CH$_2$CH$_2$CH$_2$SO$_2$), 2.28–2.08 (m, 4H, alkyl-H), 1.69 (m, 2H, alkyl-H), 1.28–1.16 (7H, C3-CH$_3$ and alkyl-H)

EXAMPLE 54

Synthesis of (A) (3RS,4RS)-7-hydroxy-3-(4-hydroxyphenyl)-3-methyl-4-{4-[4-(4,4,5,5-pentafluoropentylsulfonylethyloxy)phenyl]-1-butyl}chroman and (B) (3RS,4RS)-7-hydroxy-3-(4-hydroxyphenyl)-3-methyl-4-{4-[4-(4,4,5,5,5-pentafluoropentylsulfonylethyloxy)phenyl]-1-butyl}chroman Step 1) Synthesis of 4-{4-[4-(t-butoxycarbonylmethyloxy)phenyl]-1-butyl}-7-methoxymethyloxy-3-(4-methoxymethyloxyphenyl)-3-methylchroman

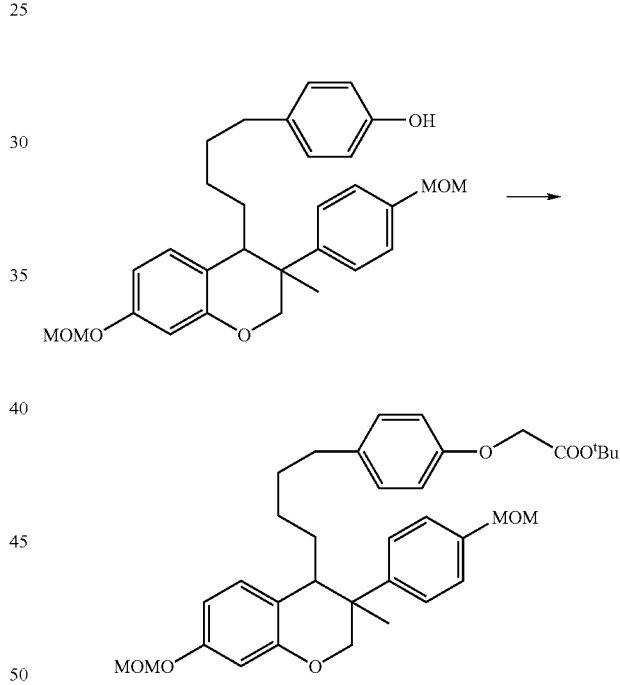

To a solution of 4-[4-(4-hydroxyphenyl)-1-butyl]-7-methoxymethyloxy-3-(4-methoxymethyloxyphenyl)-3-methylchroman (481 mg, 0.976 mmol) in dry tetrahydrofuran (8 ml) was added sodium hydride (22.7 mg, 1.418 mmol) at room temperature and stirred for 20 minutes. Bromoacetic acid tert-butylester (276.7 mg, 1.418 mmol) was added thereto at the same temperature and stirred for 20 minutes. After the reaction was completed, water was added to the reaction solution, and the resulting solution was extracted with ethyl acetate. The organic layer was washed with water and saturated sodium chloride solution, dried over anhydrous magnesium sulfate, and concentrated under reduced pressure to give 589 mg (yield: quant.) of the title compound as a colorless oil. The resulting compound was used in the next reaction without purification.

$^1$H-NMR (270 MHz, CDCl$_3$) δ: 7.24 (d, J=8.3 Hz, 2H, Ar—H), 7.00 (m, 5H, Ar—H), 6.75 (d, J=8.3 Hz, 2H, Ar—H), 6.56 (m, 2H, Ar—H), 5.18 (s, 2H, OCH$_2$OCH$_3$), 5.15 (s, 2H, OCH$_2$OCH$_3$), 4.56 (d, J=10.5 Hz, 1H, C2-H), 4.42 (s, 2H, Ph-OCH$_2$CO), 4.25 (d, J=10.5 Hz, 1H, C2-H), 3.48 (s, 6H, 2×OCH$_2$OCH$_3$), 2.65 (brt, 1H, C4-H), 2:35 (brt, J=not resolved, 2H, C4-CH$_2$), 1.48–1.08 (16H, C3-CH$_3$ alkyl-H and t-butyl-H)

Step 2) Synthesis of 4-{4-[4-(hydroxyethyloxy)phenyl]-1-butyl}-7-methoxymethyloxy-3-(4-methoxymethyloxyphenyl)-3-methylchroman

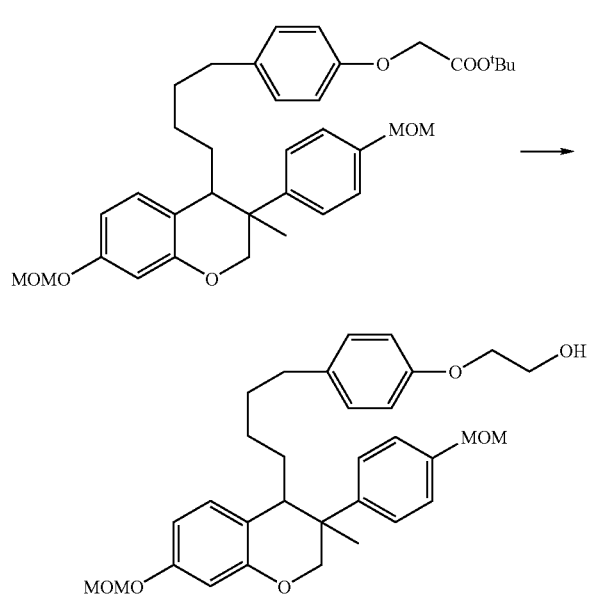

To a solution of 4-{4-[4-(t-butoxycarbonylmethyloxy)phenyl]-1-butyl}-7-methoxymethyloxy-3-(4-methoxymethyloxyphenyl)-3-methylchroman (744 mg, 1.226 mmol) in dry tetrahydrofuran (10 mi) was added lithium aluminum hydride (71.8 mg, 1.89 mmol) at 0° C. and stirred for 4 h at the room temperature. When the reaction was completed, 17% sodium hydroxide solution was added to the reaction solution until the white precipitate appeared, and then added ethyl acetate to the reaction mixture. The resulting mixture was filtered over celite and washed several times with ethyl acetate. The filtrate was concentrated under reduced pressure to give the title compound (658 mg, yield: quant.) as a colorless oil. The resulting compound was used in the next reaction without purification.

$^1$H-NMR (270 MHz, CDCl$_3$) δ: 7.12 (d, J=8.5 Hz, 2H, Ar—H), 6.94 (m, 5H, Ar—H), 6.79 (d, J=8.5 Hz, 2H, Ar—H), 6.52 (m, 2H, Ar—H), 5.18 (s, 2H, OCH$_2$OCH$_3$), 5.15 (s, 2H, OCH$_2$OCH$_3$), 4.52 (d, J=10.2 Hz, 1H, C2-H), 4.24 (d, J=10.5 Hz, 1H, C2-H), 4.05 (m, 2H, Ph-OCH$_2$CH$_2$OH), 3.92 (m, 2H, Ph-OCH$_2$CH$_2$OH), 3.49 (s, 6H, 2×OCH$_2$OCH$_3$), 2.63 (brt, 1H, C4-H), 2.36 (brt, J=not resolved, 2H, C4-CH$_2$), 1.58–1.07 (m, 9H, C3-CH— and alkyl-H)

Step 3) Synthesis of 4-{4-[4-(methanesulfonyloxyethyloxy)phenyl]-1-butyl}-7-methoxymethyloxy-3-(4-methoxymethyloxyphenyl)-3-methylchroman

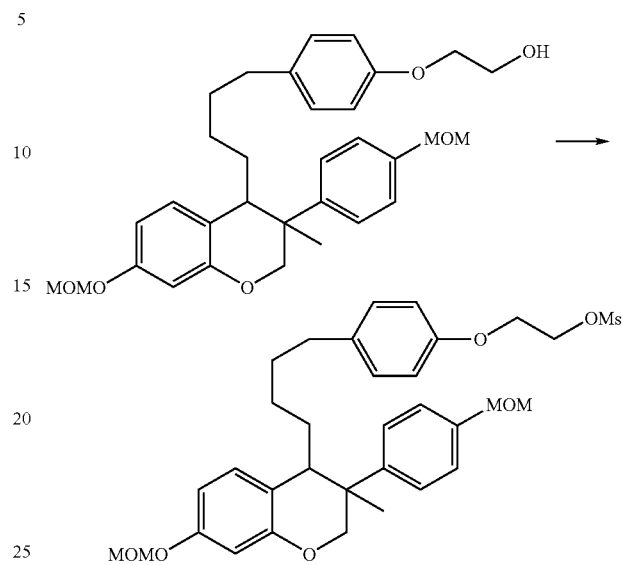

The title compound was prepared from 4-{4-[4-(hydroxyethyloxy)phenyl]-1-butyl}-7-methoxymethyloxy-3-(4-methoxymethyloxyphenyl)-3-methylchroman according to the same method for the synthesis of 4-(9-methanesulfonyloxynonyl)-7-methoxymethyloxy-3-(4-methoxymethyloxyphenyl)-3-methylchroman described in International Patent Appln. No. PCT/KR97/00265.

$^1$H-NMR (270 MHz, CDCl$_3$) δ: 7.13 (d, J=8.9 Hz, 2H, Ar—H), 6.95 (m, 5H, Ar—H), 6.77 (d, J=8.6 Hz, 2H, Ar—H), 6.52 (m, 2H, Ar—H), 5.18 (s, 2H, OCH$_2$OCH$_3$), 5.15 (s, 2H, OCH$_2$OCH$_3$), 4.53 (m, 3H, C2-H and Ph-OCH$_2$CH$_2$OSO$_2$CH$_3$), 4.22 (m, 3H, C2-H and Ph-OCH$_2$CH$_2$OSO$_2$CH$_3$), 3.48 (s, 6H, 2×OCH$_2$OCH$_3$), 3.08 (s, 3H, OSO$_2$CH$_3$), 2.69 (brt, 1H, C4-H), 2.36 (brt, J=not resolved, 2H, C4CH$_2$), 1.51–1.08 (m, 9H, C3-CH$_3$ and alkyl-H)

Step 4) Synthesis of 7-methoxymethyloxy-3-(4-methoxymethyloxyphenyl)-3-methyl-4-{4-[4-(4,4,5,5,5-pentafluoropentylthioethyloxy)phenyl]-1-butyl}chroman

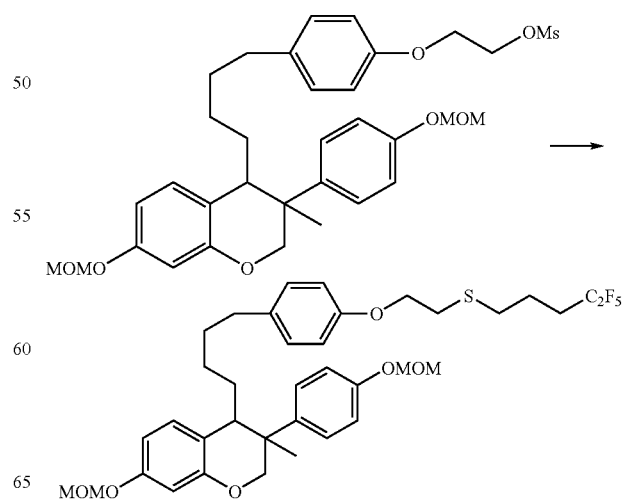

The title compound was prepared from 4-{4-[4-(methanesulfonytoxyethyloxy)-phenyl]-1-butyl}-7-methoxymethyloxy-3-(4-methoxymethyloxyphenyl)-3-methylchroman according to the same method for the synthesis of 7-methoxy-3-(4-methoxyphenyl)-3-methyl-4-[9-(4,4,5,5,5-pentafluoropentylthio)nonyl]thiochroman described in International Patent Appln. No. PCT/KR97/00265.

¹H-NMR (270 MHz, CDCl₃) d. 7.13 (d, J=8.6 Hz, 2H, Ar—H), 6.95 (m, 5H, Ar—H), 6.76 (d, J=8.6 Hz, 2H, Ar—H), 6.53 (m, 2H, Ar—H), 5.18 (s, 2H, OC<u>H</u>₂OCH₃), 5.15 (s, 2H, OC<u>H</u>₂OCH₃), 4.52 (d, J=10.6 Hz, 1H, C2-H), 4.25 (d, J=10.6 Hz, 1H, C2-H), 4.11 (dd, J=6.6 and 6.2 Hz, 2H, Ph-OC<u>H</u>₂CH₂S), 3.49 (s, 6H, 2×OCH₂OC<u>H</u>₃), 2.98 (dd, J=6.9 and 6.2 Hz, 2H, SCH₂), 2.71 (dd, J=6.9 and 6.0 Hz, 2H, SCH₂), 2.66 (brt, 1H, C4-H), 2.35 (dd, J=6.9 and 6.3 Hz, 2H, C4-CH₂), 2.15 (m, 2H, alkyl-H), 1.95 (m, 2H, alkyl-H), 1.56–1.09 (m, 9H, C3-CH₃ and alkyl-H), Step 5) Synthesis of (3RS,4RS)-7-hydroxy-3-(4-hydroxyphenyl)-3-methyl-4-{[4-[4-(4,4,5,5,5-pentafluoropentylthioethyloxy)phenyl]-1-butyl}chroman

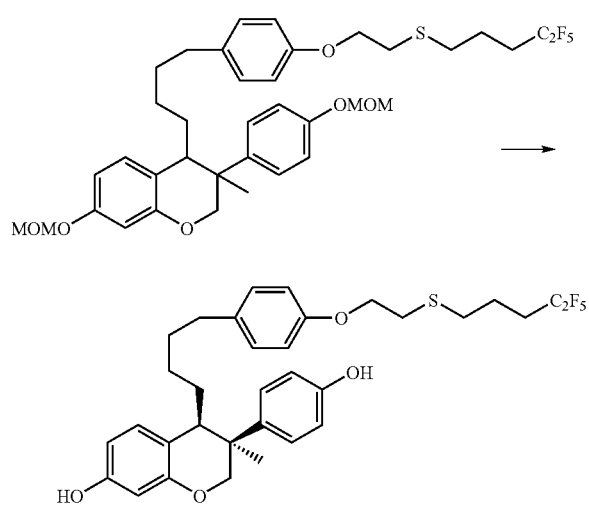

The title compound was prepared from 7-methoxymethyloxy-3-(4-methoxymethyloxyphenyl)-3-methyl-4-{4-[4-(4,4,5,5,5-pentafluoropentylthioethyloxy)phenyl]-1-butyl)chroman according to the same method for the synthesis of 7-hydoxy-3-(4-hydoxyphenyl)-3-methyl-4-[9-(4,4,5,5,5-pentafluoropentylthio)nonyl]-thiochroman described in International Patent Appln. No. PCT/KR97/00265.

¹H-NMR (270 MHz, CDCl₃) δ: 7.05 (d, J=8.6 Hz, 2H, Ar—H), 6.94 (d, J=8.5 Hz, 2H, Ar—H), 6.78 (m, 5H, Ar—H), 6.33 (m, 2H, Ar—H), 4.86 (s; 1H, OH), 4.83 (s, 1H, OH), 4.50 (d, J=10.2 Hz, 1H, C2-H), 4.22 (d, J=10.2 Hz, 1H, C2-H), 4.15 (m, 2H, Ph-OC<u>H</u>₂CH₂S), 2.89 (t, J=6.6 Hz, 2H, SCH₂), 2.72 (t, J=6.9 Hz, 2H, SCH₂), 2.61 (brt, 1H, C4-H), 2.36 (m, C4-CH₂), 2.14 (m, 2H, alkyl-H), 1.94 (m, 2H, alkyl-H), 1.54–1.07 (m, 9H, C3-CH3 and alkyl-H)

Step 6) Synthesis of (A) (3RS,4RS)-7-hydroxy-3-(4-hydroxyphenyl)-3-methyl-4-{4-[4-(4,4,5,5,5-pentafluoropentylsulfinylethyloxy)phenyl]-1-butyl}chroman and (B) (3RS,4RS)-7-hydroxy-3-(4-hydroxyphenyl)-3-methyl-4-(4-[4-(4,4,5,5,5-pentafluoropentylsulfonylethyloxy)phenyl]-1-butyl}chroman

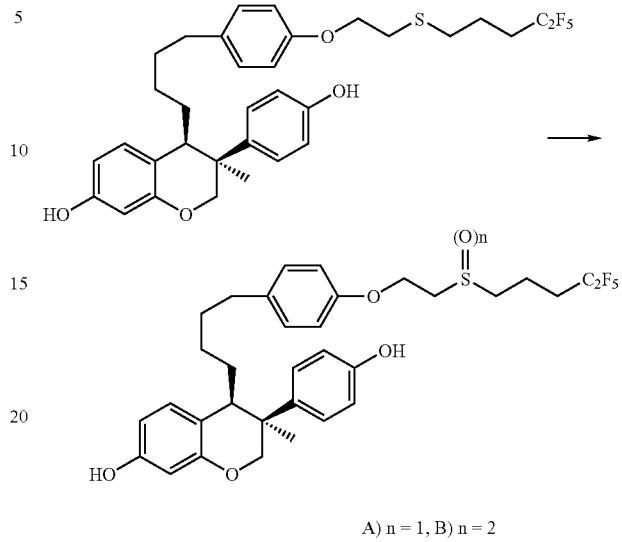

A) n = 1, B) n = 2

The title compounds were prepared from (3RS,4RS) 7-hydroxy-3-(4-hydroxyphenyl)-3-methyl-4-{4-[4-(4,4,5,5,5-pentafluoropentylthioethyloxy)phenyl]-1-butyl)chroman according to the same methods for the synthesis of (A) (3RS,4RS)-7-hydroxy-3-(4-hydroxyphenyl)-3-methyl-1 {3-[4-(4,4,5,5,5-pentafluoropentylsulfinyl)propylphenoxy]-1-propyl}chroman and (B) (3RS,4RS)-7-hydroxy-3-(4-hydroxyphenyl)-3-methyl-4-{3-[4-(4,4,5,5,5-pentafluoropentylsulfonyl)propylphenoxy]-1-propyl}chroman.

¹H-NMR (270 MHz, CD₃OD, A) δ: 6.69 (d, J=8.2 Hz, 2H, Ar—H), 6.85 (d, J=8.3 Hz, 2H, Ar—H), 6.69 (m, 5H, Ar—H), 6.14 (m, 2H, Ar—H), 4.42 (d, J=10.5 Hz, 1H, C2-H), 4.28 (m, 2H, Ph-OC<u>H</u>₂CH₂S), 4.11 (d, J=10.5 Hz, 1H, C2-H), 3.23 (m, 2H, S(O)CH₂), 2.91 (m, 2H, S(O)CH₂), 2.51 (brt, 1H, C4-H), 2.26 (m, 4H, alkyl-H), 2.05 (m, 2H, alkyl-H), 1.23–0.92 (m, 9H, C3-CH₃ and alkyl-H)

¹H-NMR (270 MHz, CDCl₃, B) δ: 7.03 (d, J=8.6 Hz, 2H, Ar—H), 6.96 (d, J=8.6 Hz, 2H, Ar—H), 6.77 (m, 4H, Ar—H), 6.63 (d, J=8.3 Hz, 1H, C5-H), 6.34 (d, J=2.3 Hz, 1H, C8-H), 6.23 (dd, J=7.7 and 2.3 Hz, 1H, C6-H), 5.36 (s, 1H, OH), 5.21 (s, 1H, OH), 4.49 (d, J=10.6 Hz, 1H, C2-H), 4.41 (dd, J=5.3 and 4.9 Hz, 2H, Ph-OC<u>H</u>₂CH₂S), 4.21 (d, J=10.6 Hz, 1H, C2-H), 3.45 (dd, J=5.3 and 4.9 Hz, 2H, SO₂CH₂), 3.26 (t, J=7.2 Hz, 2H, SO₂CH₂), 2.59 (brt, 1H, C4-H), 2.43–2.20 (m, 6H, alkyl-H), 1.42–1.09 (m, 9H, C3-CH₃ and alkyl-H)

EXAMPLE 55

Synthesis of (3'RS,4'RS)-1-[7-hydroxy-4-(4-hydroxyphenyl)-3-methylchroman-4-yl]-14,14,15,15,15-pentafluoropentadecan-10-ol Step 1) Synthesis of 13,13,14,14,14-pentafluorotetradec-1-en-9-one

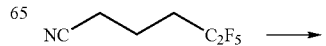

-continued

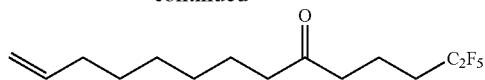

To a mixture of magnesium turnings (613.5 mg, 25.25 mmol) in dry diethyl ether (30 ml) was added 8-bromo-1-octene (4.236 ml, 25.25 mmol) and stirred at room temperature for 1 h until magnesium was dissolved. Then to the Grignard solution was added dry benzene (15 ml) and followed 5,5,6,6,6-pentafluorohaxanenitrile (1.89 g, 10.10 mmol) dissolved in dry diethyl ether (15 ml) was added dropwise at room temperature. After the reaction mixture was stirred for 1 h, 1N hydrochloric acid solution (27 ml) was added and stirred for 1 hour additionally. Then to the reaction solution was added water, which was extracted with ethyl acetate. The organic layer was washed with water and saturated sodium chloride solution, dried over anhydrous magnesium sulfate and concentrated under reduced pressure. The residue was purified with column chromatography (n-hexane:ethyl acetate=9:1) to give 1.892 g (yield: 62%) of the title compound as a colorless oil.

$^1$H-NMR (270 MHz, CDCl$_3$) δ: 5.83–5.71 (m, 1H, CH$_2$=CH), 4.96 (d, J=17 Hz, 1H, CH$_2$=CH), 4.92 (d, J=11 Hz, 1H, CH$_2$=CH), 2.51 (t, J=7 Hz, 2H, COCH$_2$), 2.39 (t, J=7 Hz, 2H, COCH$_2$), 2.03–1.83 (m, 6H, CH$_2$=CHCH$_2$ and CF$_2$CH$_2$CH$_2$), 1.56 (m, 2H, COCH$_2$CH$_2$), 1.29 (m, 6H, CH$_2$CH$_2$CH$_2$).

Step 2) Synthesis of (3'RS,4'RS)-1-[7-methoxymethyloxy-4-(4-methoxymethyloxyphenyl)-3-methylchroman-4-yl]-14,14,15,15,15-pentafluoropentadec-2-en-10-one

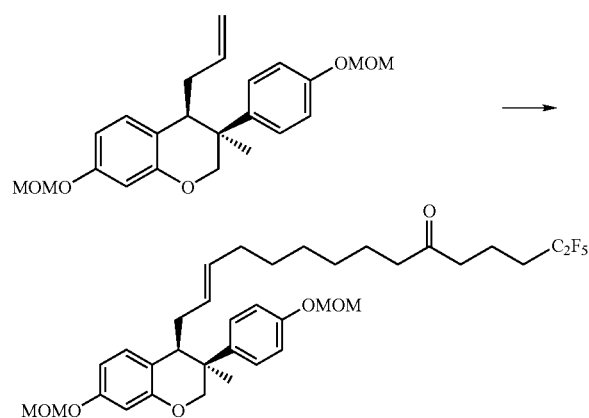

To a solution of (3RS,4RS)-4-allyl-7-methoxymethyloxy-3-(4-methoxymethyloxyphenyl)-3-methylchroman (300 mg, 0.780 mmol) and 13,13,14,14,14-pentafluorotetradec-1-en-9-one (512 mg, 1.706 mmol) in dry methylene chloride (4 ml) was added benzylidenebis(tricyclohexylphosphine)dichlororuthenium (32 mg, 0.039 mmol) dissolved in dry methylene chloride (2.5 ml) and stirred at 45° C for 135 minutes. When the reaction was completed, the reaction solution was concentrated under reduced pressure and the residue was purified with column chromatography (n-hexane:ethyl acetate=9:1) to give 402 mg (yield: 78%) of the title compound as a colorless oil.

$^1$H-NMR (270 MHz, CDCl$_3$) δ: 7.15 (d, J=9 Hz, 2H, Ar—H), 7.03 (d, J=9 Hz, 2H, Ar—H), 6.93 (d, J=8 Hz, 1H, Ar—H), 6.55 (m, 2H, Ar—H), 5.25–5.00 (m, 2H, CH=CH), 5.18 (s, 3H, OCH$_2$OCH$_3$), 5.15 (s, 3H, OCH$_2$OCH$_3$), 4.51 (d, J=11 Hz, 1H, C2-H), 4.25 (d, J=11 Hz, 1H, C2-H), 3.50 (s, 3H, OCH$_2$OCH$_3$), 3.49 (s, 3H, OCH$_2$OCH$_3$), 2.72 (brt, 1H, C4-H), 2.51 (t, J=7 Hz, COCH$_2$), 2.39 (t, J=7 Hz, COCH$_2$), 2.15–1.68 (m, 6H, CH$_2$CH=CH$_2$ and CF$_2$CH$_2$CH$_2$), 1.60–1.10 (m, 13H, alkyl-H).

Step 3) Synthesis of (3'RS,4'RS)-1-[7-methoxymethyloxy-4-(4-methoxymethyloxyphenyl)-3-methylchroman-4-yl]-14,14,15,15,15-pentafluoropentadecan-10-one

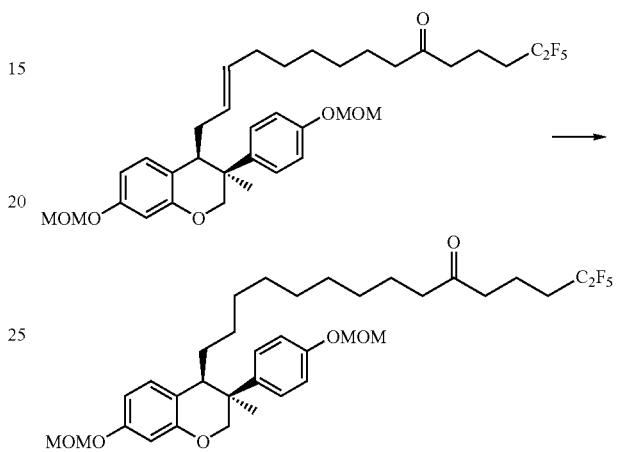

To a solution of (3'RS,4'RS)-1-[7-methoxymethyloxy-4-(4-methoxymethyloxyphenyl)-3-methylchroman-4-yl]-14,14,15,15,15-pentafluoropentadec-2-en-10-one (402 mg, 0.612 mmol) in ethyl acetate (20 ml) and tetrahydrofuran (1 ml) was added 10% Pd—C (30 mg) and stirred at room temperature overnignt under hydrogen gas (normal pressure). Ethyl acetate was added to the reaction solution which was then filtered over celite and washed several times with ethyl acetate. The organic solution was concentrated under reduced pressure to give the title compound (405 mg, yield:>100%) as colorless oil. The resulting compound was used in the next reaction without purification.

$^1$H-NMR (270 MHz, CDCl$_3$) δ: 7.13 (d, J=8 Hz, 2H, Ar—H), 7.02 (d, J=8 Hz, 2H, Ar—H), 6.94 (d, J=9 Hz, 1H, Ar—H), 6.56 (m, 2H, Ar—H), 5.18 (s, 3H, OCH$_2$OCH$_3$), 5.15 (s, 3H, OCH$_2$OCH$_3$), 4.52 (d, J=10 Hz, 1H, C2-H), 4.25 (d, J=10 Hz, 1H, C2-H), 3.50 (s, 3H, OCH$_2$OCH$_3$), 3.49 (s, 3H, OCH$_2$OCH$_3$), 2.64 (m, 1H, C4-H), 2.50 (t, J=7 Hz, COCH$_2$), 2.37 (t, J=7 Hz, COCH$_2$), 2.12–1.80 (m, 4H, CF$_2$CH$_2$CH$_2$), 1.60–0.95 (m, 19H, alkyl-H).

Step 4) Synthesis of (3'RS,4'RS)-1-[7-hydroxy-4-(4-hydroxyphenyl)-3-methylchroman-4-yl]-14,14,15,15,15-pentafluoropentadecan-10-one

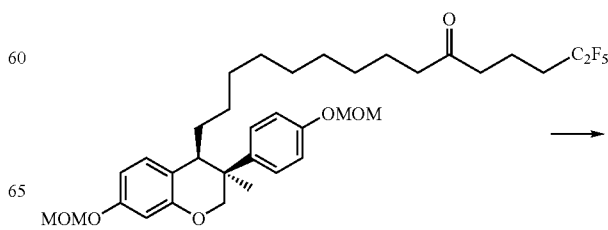

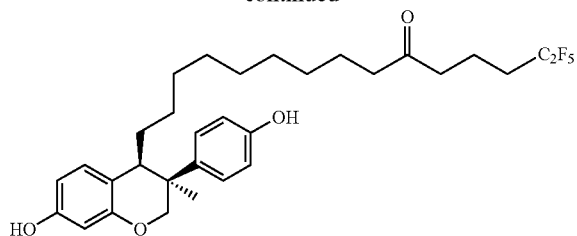

To a solution of (3'RS,4'RS)-1-[7-methoxymethyloxy-4-(4-methoxymethyloxyphenyl)-3-methylchroman-4-yl]-14,14,15,15,15-pentafluoropentadecan-10-one (405 mg, 0.615 mmol) in methanol (14 ml) and tetrahydrofuran (5 ml) was added saturated hydrochloric acid in methanol (14 ml) at room temperature and stirred for 2 h. After adding water, the solution was extracted with ethyl acetate. The organic layer was then washed with water and saturated sodium chloride solution, dried over magnesium sulfate and concentrated under reduced pressure. The residue was flash chromatographed on silica gel (n-hexane:ethyl acetate=7:3) to give 345 mg (yield: 98.8%) of the title compound as a colorless oil.

$^1$H-NMR (270 MHz, CDCl$_3$) δ: 7.07 (d, J=8 Hz, 2H, Ar—H), 6.90 (d, J=8 Hz, 2H, Ar—H), 6.84 (d, J=8 Hz, 1H, Ar—H), 6.38 (m, 2H, Ar—H), 5.80 (s, 1H, Ar—OH), 5.06 (s, 1H, Ar—OH), 4.50 (d, J=11 Hz, 1H, C2-H), 4.23 (d, J=11 Hz, 1H, C2-H), 2.60 (m, 1H, C4-H), 2.55 (t, J=7 Hz, COCH$_2$), 2.42 (t, J=7 Hz, COCH$_2$), 2.12–1.80 (m, 4H, CF$_2$CH$_2$CH$_2$), 1.50 (q, J=7 Hz, 2H, alkyl-H), 1.30–0.95 (m, 17H, alkyl-H)

Step 5) Synthesis of (3'RS,4'RS)-1-[7-hydroxy-4-(4-hydroxyphenyl)-3-methylchroman-4-yl]-14,14,15,15,15-pentafluoropentadecan-10-ol

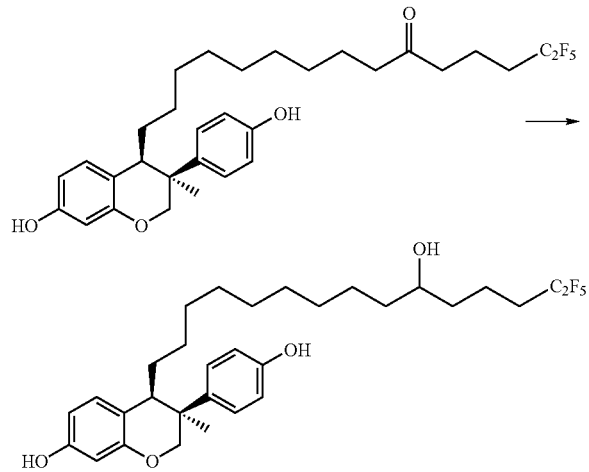

To a solution of (3'RS,4'RS)-1-[7-hydroxy-4-(4-hydroxyphenyl)-3-methylchroman-4-yl]-14,14,15,15,15-pentafluoropentadecan-10-one (1 90 mg, 0.333 mmol) in dry tetrahydrofuran (10 ml) was added lithium aluminum hydride (12.6 mg, 0.333 mmol) at 0° C. and stirred for 1 h at the same temperature. When the reaction was completed, 17% sodium hydroxide solution was added to the reaction solution until the white precipitate as formed, and then added ethyl acetate to the reaction mixture. The resulting solution was filtered over celite and washed several times with ethyl acetate. The organic solution was concentrated under reduced pressure and purified with preparative TLC to give the title compound (180 mg, 94%) as a white solid.

$^1$H-NMR (270 MHz, CDCl$_3$) δ: 7.08 (d, J=8 Hz, 2H, Ar—H), 6.90 (d, J=8 Hz, 2H, Ar—H), 6.82 (d, J=8 Hz, 1H, Ar—H), 6.39 (m, 2H, Ar—H), 5.80 and 5.68 (each s, total 1H, Ar—OH), 5.10 (s, 1H, Ar—OH), 4.50 (d, J=11 Hz, 1H, C2-H), 4.23 (d, J=11 Hz, 1H, C2-H), 3.68 (m, 1H, CHOH), 2.60 (m, 1H, C4H), 2.18–1.90 (m, 4H, CF$_2$CH$_2$CH$_2$), 1.81–1.00 (m, 23H, alkyl-H)

EXAMPLE 56

Synthesis of (3RS,4RS)-7-hydroxy-3-methyl-4 19-(4,4,5,5 pentafluoropentylsulfinyl)nonyl]-3-(3-pyridyl)chroman Step 1) Synthesis of 2-hydroxy-4-methoxy-2-(3-pyridyl)acetophenone

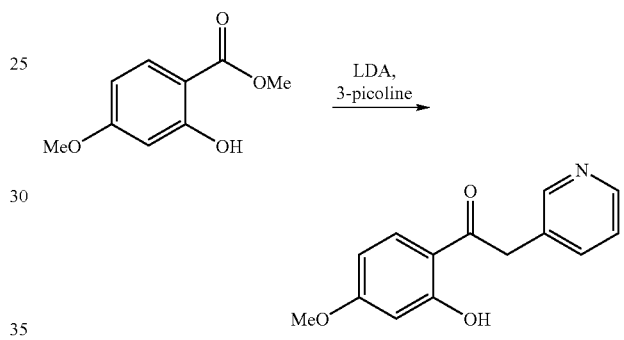

The title compound was prepared from 3-picoline and methyl 4-methoxysalicylate according to the similar procedure described in Example 12, Step 1.

$^1$H-NMR (270 MHz, CDCl$_3$) δ: 12.5 (s, 1H, ArOH), 8.5–8.6 (m, 2H, pyridyl), 7.74 (d, 1H, J=8.9 Hz, Ar—H), 7.5–7.7 (m, 1H), 7.2–7.4 (m, 1H, pyridyl), 6.3–6.6 (m, 2H, Ar—H), 4.23 (s, 2H, C(O)CH2), 3.84 (s, 3H, OMe).

Step 2) Synthesis of 7-methoxy-3-(3-pyridyl)chroman-4-one

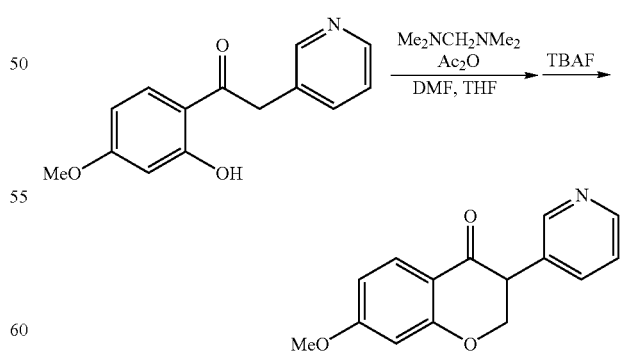

The title compound was prepared from 2-hydroxy-4-methoxy-2-(3-pyridyl)acetophenone according to the similar procedure described in Example 12, Step 2.

$^1$H-NMR (300 MHz, CDCl$_3$) δ: 8.5–8.7 (m, 2H, pyridyl), 7.89 (d, 1H, J=8.8 Hz, Ar—H), 7.5–7.7 (m, 1H, pyridyl), 7.2–7.3 (m, 1H, pyridyl), 6.5–6.7 (m, 1H, Ar—H), 6.46 (d, 1H, J=2.5 Hz, Ar—H), 4.5–4.8 (m, 2H, C2-H), 3.96 (dd, 1H, J=5.2, 8.5 Hz), 3.86 (s, 3H, OMe).

Step 3) Synthesis of 7-methoxy-3-methyl-3-(3-pyridyl)chroman-4-one

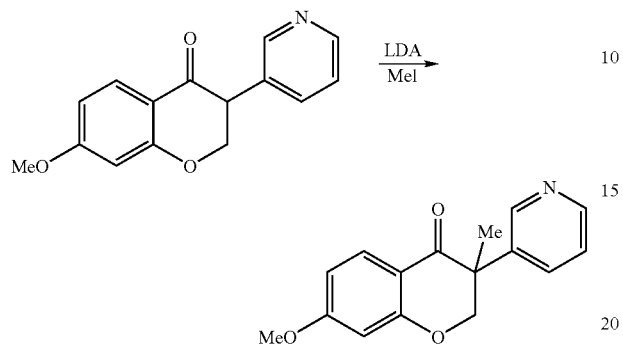

The title compound was prepared from 7-methoxy-3-(3-pyridyl)chroman-4-one according to the similar procedure described in Example 12, Step 3.

$^1$H-NMR (300 MHz, CDCl) δ: 8.71 (d, 1H, J=2.5 Hz, pyridyl), 8.49 (dd, 1H, J=1.7, 4.9 Hz, pyridyl), 7.86 (d, 1H, J=8.8 Hz, Ar—H), 7.6–7.8 (m, 1H, pyridyl), 7.24 (dd, 1H, J=0.8, 4.9 Hz, pyridyl), 6.57 (dd, 1H, J=2.5, 8.8 Hz, Ar—H), 6.35 (d, 1H, J=2.5 Hz, Ar—H), 4.85 (d, 1H, J=12.1 Hz, C2-H), 4.37 (d, 1H, J=12.1 Hz, C2-H), 3.79 (s, 3H, OMe), 1.51 (s, 3H, C3-Me).

Step 4) Synthesis of 4-[9-(t-butyldimethylsilyloxy)nonyl]4-hydroxy-7-methoxy-3-methyl-3-(3-pyridyl)chroman

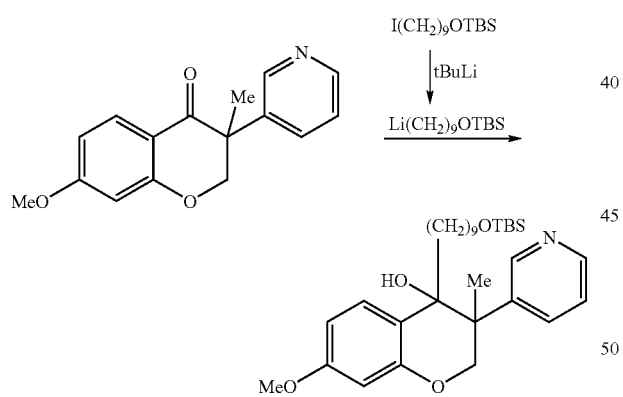

To a solution of 9-(t-butyldimethylsilyloxy)nonyl iodide (1.05 g, 2.7 mmol) in pentane (10 ml) and diethylether (7 ml) was added at −78° C. t-BuLi (1.64M in pentane, 3.62 ml, 5.94 mmol), which was stirred for 10 minutes and then stirred for 1 h at room temperature. The mixture was cooled to −78° C. again, and a solution of 7-methoxy-3-methyl-3-(3-pyridyl)chroman-4-one (436 mg, 1.62 mmol) dissolved in THF (5 ml) was added thereto. The resulting solution was stirred at −78° C. for 30 minutes, and then stirred for 1 h at room temperature. The reaction solution was neutralized under ice-cooling using saturated aqueous NH$_4$Cl solution, extracted with AcOEt, and washed with brine. The organic layer was dried over Na$_2$SO$_4$ and the solvent was removed under reduced pressure. The recidue was purified by chromatography on silica-gel with 70% AcOEt/hexane to give 642 mg (75%) of 4-[9-(t-butyldimethylsilyloxy)nonyl]-4-hydroxy-7-methoxy-3-methyl-3-(3-pyridyl)chroman.

$^1$H-NMR (300 MHz, CDCl$_3$) δ: 8.72 (d, 1H, J=1.9 Hz, pyridyl), 8.0–8.1 (m, 1H, pyridyl), 7.7–7.9 (m, 1H, pyridyl), 7.12 (d, 1H, J=-9.3 Hz, Ar—H), 7.02 (dd, 1H, J=4.7, 8.0 Hz, pyridyl), 6.3–6.5 (m, 2H, Ar—H), 4.58 (d, 1H, J=12.1 Hz, C2-H), 4.36 (d, 1H, J=12.1 Hz, C2-H), 3.76 (s, 3H, OMe), 3.58 (t, 2H, J=6.6 Hz, CH$_2$O), 2.34 (brs, 1H, OH), 1.9–2.1 (m, 1H), 1.6–1.8 (m, 1H), 1.44 (s, 3H, C3-Me), 0.9–1.8 (m, 14H), 0.89 (s, 9H SiBu-t), 0.04 (s, 6H, SiMe$_2$).

Step 5) Synthesis of (3RS,4RS)-4-[9-(t-butyldimethylsilyloxy)nonyl]-7-methoxy-3-methyl-3-(3-pyridyl)chroman

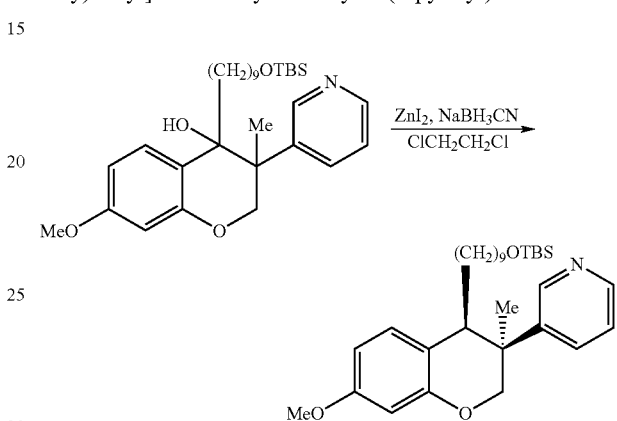

The title compound was prepared from 4-[9-(t-butyldimethylsilyloxy)-1-nonyl]4-hydroxy-7-methoxy-3-methyl-3-(3-pyridyl)chroman according to the general procedure described in this patent.

$^1$H-NMR (300 MHz, CDCl$_3$) δ: 8.4–8.6 (m, 2H, pyridyl), 7.5–7.6 (m, 1H, pyridyl), 7.2–7.4 (m, 1H, pyridyl), 6.96 (d, 1H, J=8.2 Hz, Ar—H), 6.48 (dd, 1H, J=2.8, 8.5 Hz, Ar—H), 6.43 (d, 1H, J=2.5 Hz, Ar—H), 4.57 (d, 1H, J=10.4 Hz, C2-H), 4.31 (dd, 1H, J=1.9, 10.4 Hz, C2-H), 3:78 (s, 3H, OMe), 3.57 (t, 2H, J=6.9 Hz, CH$_2$O), 2.6–2.8 (m, 1H, C4-H), 1.4–1 6 (m, 2H), 1.32 (s, 3H, C3-Me), 1.0–1.4 (m, 14H), 0.88 (s, 9H, SiBu-t), 0.04 (s, 6H, SiMe-2).

Step 6) Synthesis of (3RS,4RS)-4-(9-hydroxynonyl)-7-methoxy-3-methyl-3-(3-pyridyl)chroman

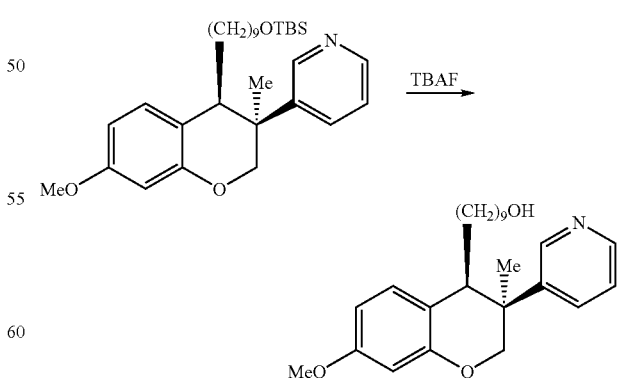

The title compound was prepared from (3RS,4RS)-4-[9-(t-butyl-dimethyl-silyloxy)-nonyl]-7-methoxy-3-methyl-3-(3-pyridyl)chroman according to the general procedure described in this patent.

¹H-NMR (300 MHz, CDCl₃) δ: 8.4–8.6 (m, 2H, pyridyl), 7.5–7.6 (m, 1H, pyridyl), 7.2–7.4 (m, 1H, pyridyl), 6.96 (d, 1H, l=8.2 Hz, Ar—H), 6.4–6.6 (m, 2H, Ar—H), 4.57 (d, 1H, J=10.2 Hz, C2-H), 4.30 (d, 1H, J=10.2 Hz, C2-H), 53.79 (s, 3H, OMe), 3.62 (t, 2H, J=6.0 Hz, C$\underline{H_2}$O), 2.6–2.8 (m, 1H, C4-H), 2.00 (brs, 1H, OH), 1.4–1.6 (m, 2H), 1.32 (s, 3H, C3-Me), 1.0–1.4 (m, 14H).

Step 7) Synthesis of (3RS,4RS)-7-methoxy-3-methyl-4-[9-(4,4,5,5,5-pentafluoropentylthio)nonyl]-3-(3-pyridyl)chroman

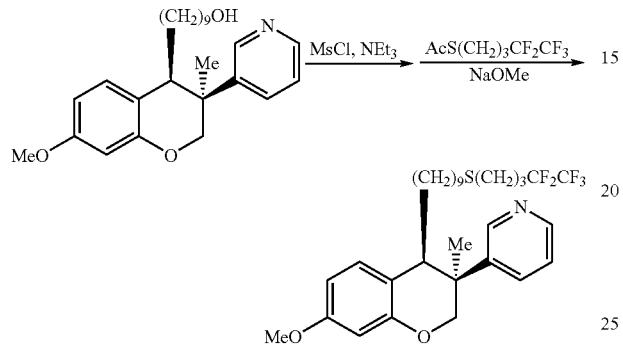

The title compound was prepared from (3RS,4RS)-4-(9-hydroxynonyl)-7-methoxy-3-methyl-3-(3-pyridyl)chroman according to the general procedure described in this patent.

¹H-NMR (300 MHz, CDCl₃) δ: 8.4–8.6 (m, 2H, pyridyl), 7.4–7.6 (m, 1H, pyridyl), 7.2–7.4 (m, 1H, pyridyl), 6.97 (d, 1H, J=8.3 Hz, Ar—H), 6.4–6.6 (m, 2H, Ar—H), 4.57 (d, 1H, J=10.2 Hz, C2-H), 4.30 (d, 1H, J=10.2 Hz, C2-H), 3.78 (s, 3H, OMe), 2.6–2.8 (m, 1H, C4-H), 2.58 (t, 2H, J=6.9 Hz), 2.48 (t, 2H, J=6.9 Hz), 2.0–2.3 (m, 2H), 1.8–2.0 (m, 2H), 1.4–1.6 (m, 2H), 1.32 (s, 3H, C3-Me), 1.0–1.4 (m, 14H).

Step 8) Synthesis of (3RS,4RS)-7-hydroxy-3-methyl-4-[9-(4,4,5,5,5-pentafluoropentylsulfinyl)nonyl]-3-(3-pyridyl)chroman

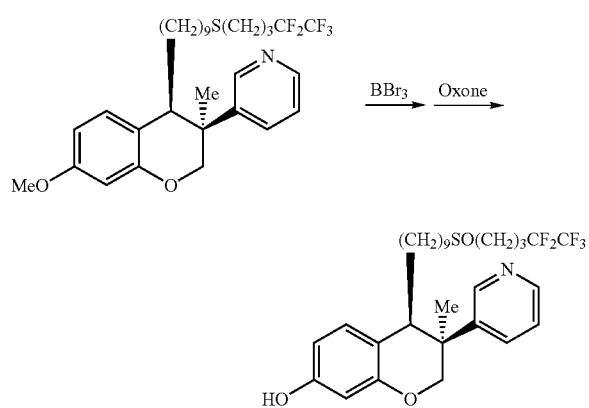

The title compound was prepared from (3RS,4RS3-(7-methoxy-3-methyl-4-[9-(4,4,5,5,5-pentafluoropentylthio)nonyl]-3-(3-pyridyl)chroman according to the general procedure described in this patent.

¹H-NMR (300 MHz, MeOH-d-4) δ: 8.48 (d, 1H, J=2.2 Hz, pyridyl), 8.41 (dd, 1H, J=1.4, 5.0 Hz, pyridyl), 7.7–7.9 (m, 1H, pyridyl), 7.43 (dd, 1H, J=4.7, 8.0 Hz, pyridyl), 6.89 (d, 1H, J=8.2 Hz, Ar—H), 6.33 (dd, 1H, J=2.5, 8.5 Hz), 6.26 (d, 1H, J=2.5 Hz), 4.54 (d, 1H, J=10.7 Hz, C2-H), 4.29 (d, 1H, J=10.7 Hz, C2-H). 2.7–2.9 (m, 5H), 2.2–2.5 (m, 2H), 2.0–2.2 (m, 2H), 1.6–1.8 (m, 2H), 1.29 (s, 3H, C3-Me), 1.0–1.5 (m, 14H).

EXAMPLE 57

Synthesis of (3RS,4RS)-7-hydroxy-3-(4-hydroxyphenyl)-4-[9-(4,4,5,5,5-pentafluoropentylsulfinyl)nonyl]chroman Step 1) (3RS,4RS)-4-(9-benzyloxynonyl)-7-methoxymethoxy-3-(4-methoxymethoxyphenyl)chroman-2-one

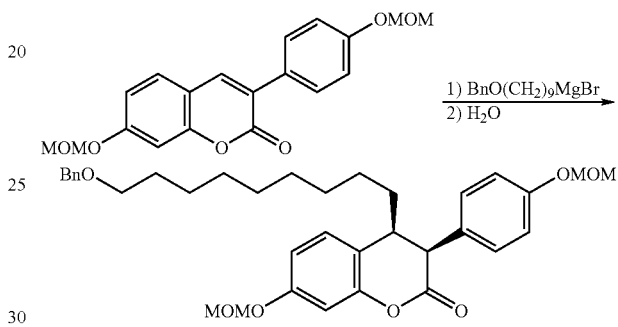

To a suspension of 7-methoxymethoxy-3-methoxymethoxyphenylchromen-2-one (182 mg, 0.532 mmol) in THF (1.5 ml) between −30 and −20° C. under nitrogen was added dropwise 9-benzyloxynonyl magnesium bromide (0.509M in THF, 3.0 ml, 1.53 mmol). The resulting suspension was stirred between −20 and −10° C. for 2.5 h. An additional 9-benzyloxynonyl magnesium bromide (0.509M in THF, 0.5 ml, 0.25 mmol) was added, and the reaction mixture was stirred between −20 and −10° C. for 2 hr. The reaction was quenched by addition of saturated aqueous NH₄Cl (0.6 ml), and the layers were separated. The organic layer was washed with saturated aqueous NaCl, dried (Na₂SO₄), filtered, concentrated, and purified by column chromatography (silica gel, 20% AcOEt/hexane) to afford (3RS,4RS)-4-(9-benzyloxynonyl)-7-methoxymethoxy-3-(4-methoxy-methoxyphenyl)chroman-2-one (219 mg, 71%).

¹H-NMR (270 MHz, CDCl₃) δ: 7.38–7.22 (7H, m, Ar—H), 7.18–6.98 (3H, m, Ar—H), 6.84–6.78 (2H, m, Ar—H), 5.18 (4H, s, —OC$\underline{H_2}$OCH₃×2), 4.49 (2H, s, —OC$\underline{H_2}$Ph), 4.11 (1H, s, C3-H), 3.50 (3H, s, —OCH₃), 3.48 (3H, s, —OCH₃), 3.44 (2H, t, J=7.5 Hz, —C$\underline{H_2}$OBn), 3.98–3.88 (1H, mn, C4-H), 1.65–1.02 (16H, m, alkyl-H)

Step 2) (3RS,4RS)-2-(1-benzyloxynonyl-3-hydoxy-2-methoxymethoxyphenyl)propyl-5-methoxymethoxy-phenol

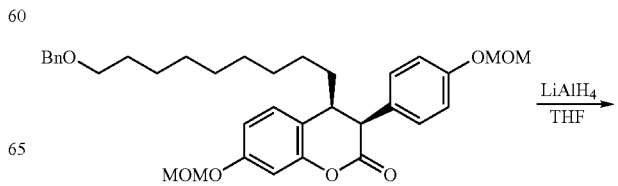

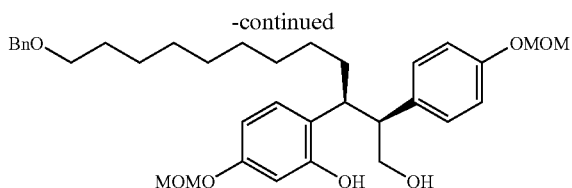

To a solution of (3RS,4RS)-4-(9-benzyloxynonyl)-7-methoxymethoxy-3-(4-methoxymethoxyphenyl)-chroman-2-one (206 mg, 0.357 mmol) in THF (4 ml) at 0° C. was added LiAlH4 (14 mg, 0.369 mmol). The resulting suspension was stirred at 0° C. for 1 hr. The reaction was quenched by addition of saturated aqueous $Na_2SO_4$ (0.5 ml) and the mixture was stirred at 0° C. for 1 hour, which was extracted with ethyl acetate, dried over dry $Na_2SO_4$, and filtered. The filtrate was concentrated and purified by column chromatography (silica gel, 33% AcOEt/hexane) to afford (3RS,4RS)-2-(1-benzyloxynonyl-3-hydoxy-2-methoxymethoxyphenyl)propyl-5-methoxymethoxyphenol (146 mg, 70%).

$^1$H-NMR (270 MHz, CDCl$_3$) δ: 7.47 (1H, brs, —OH), 7.37–7.27 (5H, m, Ar—H), 6.87 (2H, d, J=8.6 Hz, Ar—H), 6.72 (2H, d, J=8.6 Hz, Ar—H), 6.58 (1H, d, J=2.3 Hz, Ar—H), 6.42 (1H, dd, J=8.6 and 2.3 Hz, Ar—H), 6.32 (1H, d, J=8.6 Hz, Ar—H), 5.15 (2H, s, —OCH$_2$OCH$_3$), 5.14 (2H, s, —OCH$_2$OCH$_3$), 4.50 (2H, s, —CH$_2$Ph), 3.70–3.60 (2H, m, —CH$_2$OH), 3.49 (3H, s, —OCH$_3$), 3.48 (3H, s, —OCH$_3$), 3.46 (2H, t, J=6.6 Hz, —CH$_2$OBn), 3.20–3.10 (1H, m, —CHCH$_2$OH), 3.83–3.75 (1H, m, C2-CH), 1.70–1.02 (16H, m, alkyl-H)

Step 3) (3RS,4RS)-4-(9-benzyloxynonyl)-7-methoxymethoxy-3-(4-methoxymethoxyphenyl)chroman

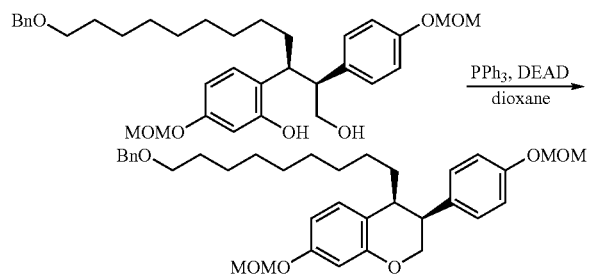

To a mixture of (3RS,4RS)-2-(1-benzyloxynonyl-3-hydoxy-2-methoxymethoxyphenyl)propyl-5-methoxymethoxyphenol (160 mg, 0.276 mmol) and triphenylphosphine (217 mg, 0.827 mmol) in dioxane (3 ml) at room temperature under nitrogen was added diethyl azodicarboxylate (0.13 ml, 0.826 mmol). The resulting solution was stirred at room temperature for 1 hr, and then poured into H$_2$O. The mixture was extracted with AcOEt. The organic layer was washed with saturated aqueous NaCl, dried over Na$_2$SO$_4$, filtered, concentrated, and purified by column chromatography (silica gel, 20% AcOEt/hexane) to afford (3RS,4RS)-4-(9-benzyloxynonyl)-7-methoxymethoxy-3-(4-methoxymethoxyphenyl)chroman (136 mg, 88%).

$^1$H-NMR (270 MHz, CDCl$_3$) δ: 7.36–7.26 (5H, m, Ar—H), 7.08–7.95 (5H, m, Ar—H), 6.62–6.55 (2H, m, Ar—H), 5.16 (2H, s, —OCH$_2$OCH$_3$), 5.15 (2H, s, —OCH$_2$OCH$_3$), 4.49 (2H, s, —CH$_2$Ph), 4.43 (1H, d, J=10 Hz, C2-H), 4.37 (1H, dd, J=10 and 4.3 Hz, C2-H), 3.48 (3H, s, —OCH$_3$), 3.47 (3H, s, —OCH$_3$), 3.44 (2H, t, J=6.6 Hz, —CH$_2$OBn), 3.40–3.30 (1H, m, C3-H), 2.94–2.82 (1H, m, C4-H), 1.70–1.02 (16H, m, alkyl-H)

Step 4) (3RS,4RS)-4-(9-hydroxynonyl)-7-methoxymethoxy-3-(4-methoxymethoxyphenyl)chroman

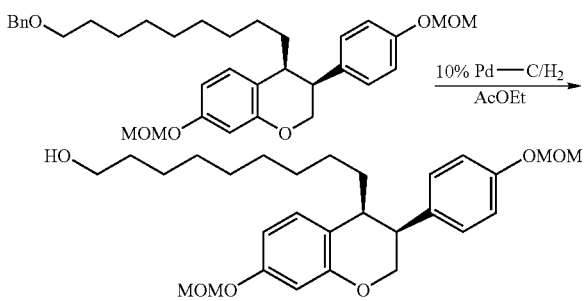

To a solution of (3RS,4RS)-4-(9-benzyloxynonyl)-7-methoxymethoxy-3-(4-methoxymethoxyphenyl)chroman (262 mg, 0.466 mmol) in AcOEt/EtOH (1:1, 10 ml) was added 10% Pd on carbon (25 mg, 0.023 mmol). The reaction flask was flushed with nitrogen, and hydrogen gas was introduced. The black slurry was stirred at room temperature under 1 atm of H$_2$ for 2 hr. The reaction mixture was filtered through a small pad of celite, and the filtrate was concentrated. The residue was purified by column chromatography (silica gel, 33% AcOEt/hexane) to afford (3RS,4RS)-4-(9-hydroxynonyl)-7-methoxy-methoxy-3-(4-methoxymethoxyphenyl)chroman (222 mg, quant.)

$^1$H-NMR (270 MHz, CDCl$_3$) δ: 7.05 (2H, d, J=8.6 Hz, Ar—H), 7.00 (1H, d, J=7.3 Hz, Ar—H), 6.99 (2H, d, J=8.6 Hz, Ar—H), 6.58 (1H, dd, J=7.3 and 2.6 Hz, Ar—H), 6.57 (1H, d, J=2.6 Hz, Ar—H), 5.17 (2H, s, —OCH$_2$OCH$_3$), 5.15 (2H, s, —OCH$_2$OCH$_3$), 4.43 (1H, d, J=9.6 Hz, C2-H), 4.38 (1H, dd, J=9.6 and 4.0 Hz, C2-H), 4.67–4.57 (2H, m, —CH$_2$OH), 3.49 (6H, S, —OCH$_3$×2), 3.40–3.30 (1H, m, C3-H), 2.94–2.82 (1H, m, C4-H), 1.60–1.02 (16H, m, alkyl-H)

Step 5) (3RS,4RS)-4-(9-methanesulfonyloxynonyl)-7-methoxymethoxy-3-(4-methoxymethoxyphenyl)chroman

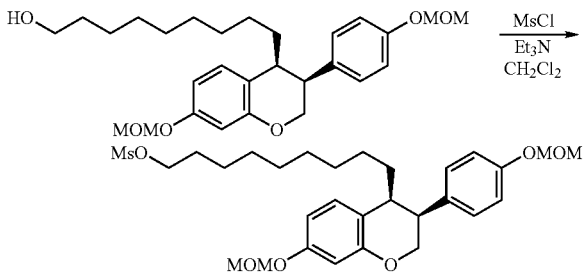

To a solution of (3RS,4RS)-4-(9-hydroxynonyl)-7-methoxymethoxy-3-(4-methoxymethoxyphenyl)chroman (222 mg, 0.470 mmol) and triethylamine (0.135 ml, 0.961 mmol) in CH$_2$Cl$_2$ (5 ml) at 0° C. under nitrogen was added methanesulfonyl chloride (0.055 ml, 0.71 mmol). The resulting solution was stirred at 0° C. for 45 min, and then poured into H$_2$O. The mixture was extracted with CH$_2$Cl$_2$. The organic layer was washed with saturated aqueous NaCl, dried over Na$_2$SO$_4$, filtered, and concentrated to afford (3RS,4RS)-4-(9-methanesulfonyloxynonyl)-7-methoxymethoxy-3-(4-methoxymethoxyphenyl)chroman (255 mg, 99%).

$^1$H-NMR (270 MHz, CDCl$_3$) δ: 7.08–6.96 (5H, m, Ar—H), 6.61–6.55 (2H, m, Ar—H), 5.17 (2H, s, —OC$\underline{H}_2$OCH$_3$), 5.15 (2H, s, —OC$\underline{H}_2$OCH$_3$), 4.43 (1H, d, J=10 Hz, C2-H), 4.38 (1H, dd, J=10 and 4.0 Hz, C2-H), 4.20 (2H, t, J=6.6 Hz, —C$\underline{H}_2$OMs), 3.49 (6H, s, —OCH$_3$×2), 3.40–3.30 (1H, m, C3-H), 2.99 (3H, s, —SO$_2$C$\underline{H}_3$), 2.94–2.82 (1H, m, C4-H), 1.80–1.02 (16H, m, alkyl-H)

Step 6) (3RS,4RS)-7-methoxymethoxy-3-(4-methoxymethoxyphenyl)-4-[9-(4,4,5,5,5-pentafluoropentylthio)nonyl]chroman 7-methoxymethoxy-3-(4-methoxymethoxyphenyl)-4-[9-(4,4,5,5,5-pentafluoropentylthio)nonyl]chroman (203 mg, 68%).

$^1$H-NMR (270 MHz, CDCl$_3$) δ: 7.09–6.96 (5H, m, Ar—H), 6.61–6.53 (2H, m, Ar—H), 5.17 (2H, s, —OC$\underline{H}_2$OCH$_3$), 5.15 (2H, s, —OC$\underline{H}_2$OCH$_3$), 4.44 (1H, d, J=10 Hz, C2-H), 4.38 (1H, dd, J=10 and 4.0 Hz, C2-H), 3.49 (6H, s, —OCH$_3$×2), 3.40–3.30 (1H, m, C3-H), 2.94–2.82 (1H, m, C4-H), 2.58 (2H, t, J=6.9 Hz, —SC$\underline{H}_2$—), 2.49 (2H, t, J=6.9 Hz, —SC$\underline{H}_2$—), 2.30–1.80 (4H, m, alkyl-H), 1.60–1.02 (16H, m, alkyl-H)

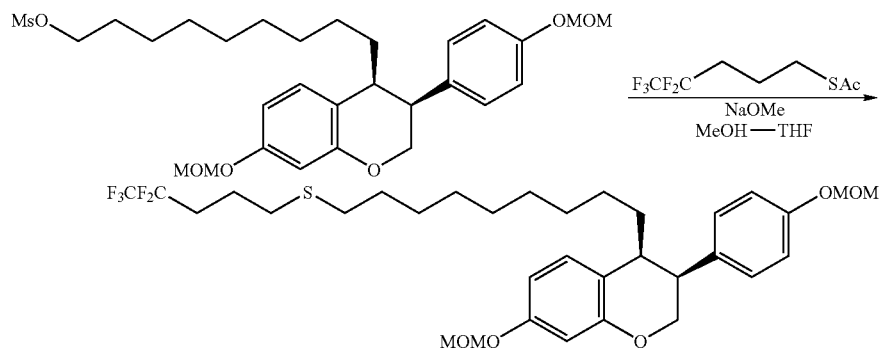

Step 7) (3RS,4RS)-7-hydroxy-3-(4-hydroxyphenyl)-4-[9-(4,4,5,5,5-pentafluoropentylthio)nonyl]chroman

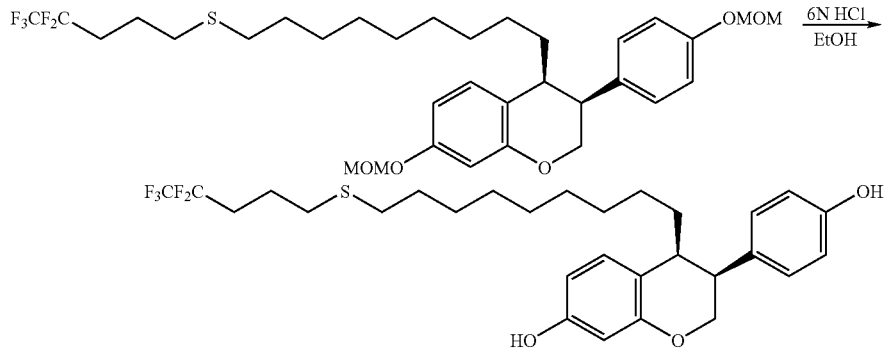

To a solution of 4,4,5,5,5-pentafluoropentyl tihoacetate (186 mg, 0.787 mmol) in MeOH (2 ml) at room temperature under nitrogen was added sodium methoxide (1.0M in MeOH, 0.7 ml, 0.7 mmol). The resulting solution was stirred at room temperature for 30 min, and then (3RS,4RS)-4-(9-methanesulfonyloxynonyl)-7-methoxymethoxy-3-(4-methoxymethoxyphenyl)chroman (255 mg, 0.463 mmol) in THF (2 ml) was added. The reaction mixture was stirred at room temperature for 19 hr, and then poured into H$_2$O. The mixture was extracted with AcOEt. The organic layer was washed with saturated aqueous NaCl, dried over Na$_2$SO$_4$, filtered, concentrated, and purified by column chromatography (silica gel, 33% AcOEt/hexane) to afford (3RS,4RS)-

To a solution of (3RS,4RS)-7-methoxymethoxy-3-(4-methoxymethoxyphenyl)-4-[9-(4,4,5,5,5-pentafluoropentylthio)nonyl]chroman (204 mg, 0.314 mmol) in EtOH (2 ml) was added 6N HCl (0.2 ml, 1.2 mmol). The resulting solution was stirred between 40 and 45° C. for 17 hr, and then poured into H$_2$O. The mixture was extracted with AcOEt. The organic layer was washed with saturated aqueous NaCl, dried over Na$_2$SO$_4$, filtered, concentrated, and purified by column chromatography (silica gel, 33% AcOEt/hexane) to afford (3RS,4RS)-7-hydroxy-3-(4-hydroxyphenyl)-4-[9-(4,4,5,5,5-pentafluoropentylthio)nonyl]chroman (140 mg, 80%).

$^1$H-NMR (270 MHz, CDCl$_3$) δ: 7.00 (2H, d, J=8.6 Hz, Ar—H), 6.96 (1H, d, J=8.6 Hz, Ar—H), 6.78 (2H, d, J=8.6 Hz, Ar—H), 6.43–6.32 (2H, m, Ar—H), 4.83 (1H, s, OH), 4.68 (1H, s, OH), 6.43–6.32 (2H, m, C2-H), 3.37–3.27 (1H, m, C3-H), 2.92–2.81 (1H, m, C4-H), 2.59 (2H, t, J=6.9 Hz, —S$\underline{CH_2}$—), 2.49 (2H, t, J=6.9 Hz, —S$\underline{CH_2}$—), 2.23–2.02 (2H, m, alkyl-H), 1.98–1.80 (2H, m, alkyl-H), 1.61–1.02 (16H, m, alkyl-H)

Step 8) (3RS,4RS)-7-hydroxy-3-(4-hydroxyphenyl)-4-[9-(4,4,5,5,5-pentafluoropentylsulfinyl)nonyl]chroman

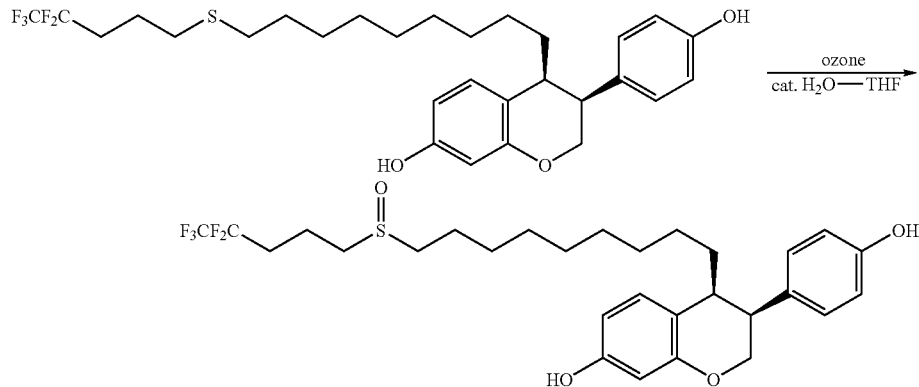

To a solution of (3RS,4RS)-7-hydroxy-3-(4-hydroxyphenyl)-4-[9-(4,4,5,5,5-pentafluoropentylthio)nonyl]chroman (140 mg, 0.250 mmol) and H$_2$O (0.05 ml) in THF (1.2 ml) at 0° C. was added Oxone® (monopersulfate compound; DuPont product) (77 mg, 0.125 mmol). The resulting solution was stirred at 0° C. for 3.5 hr, and then poured into H$_2$O. The mixture was extracted with AcOEt. The organic layer was washed with saturated aqueous NaCl, dried over Na$_2$SO$_4$, filtered, concentrated, and purified by column chromatography (silica gel, 60% AcOEt/hexane) to afford (3RS,4RS)-7-hydroxy-3-(4-hydroxyphenyl)-4-[9-(4,4,5,5,5-pentafluoropentylsulfinyl)nonyl]chroman (105 mg, 73%).

$^1$H-NMR (270 MHz, CDCl$_3$) δ: 7.65 and 7.54 (total 1H, s, OH), 7.02–6.92 (3H, m, Ar—H), 6.80 (2H, d, J=8.2 Hz, Ar—H), 6.40 (1H, dd, J=8.3 and 2.3 Hz, Ar—H), 6.36 (1H, d, J=2.3 Hz, Ar—H), 5.59 and 5.52 (total 1H, s, OH), 4.43–4.32 (2H, m, C2-H), 3.38–3.24 (1H, m, C3-H), 2.95–2.58 (5H, m), 2.38–2.10 (4H, m), 1.82–1.61 (2H, m), 1.44–0.90 (14H, m)

EXAMPLE 58

Synthesis of (3RS,4RS)-7-hydroxy-3-(4-hydroxyphenyl)-4-(9-oxo-14,14,15,15,15-pentafluoro)pentadecyl-3-methylchroman Step 1) Synthesis of 3-oxo-2-(4,4,5,5,5-pentafluoropentyl)-dec-9-enoic acid ethyl ester

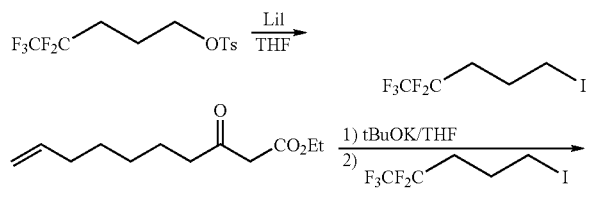

-continued

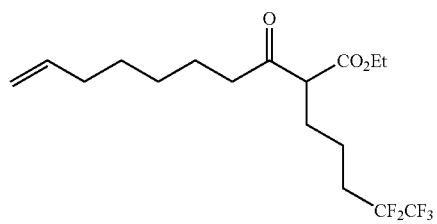

To a solution of 4,4,5;5,5-pentafluoropentyl p-toluenesulfonate (11.5 g, 34.6 mmol) in THF (60 ml) was added lithium iodide (9.26 g, 69.2 mmol). This resulting mixture was refluxed under nitrogen for 2 hr and then cooled.

On the other hand, to a solution of 3-oxo-dec-9-enoic acid ethyl ester (4.32 g, 20.3 mmol) in THF (15 ml) at 0° C. was added potassium tert-butoxide (2.73 g, 24.3 mmol) This resulting mixture was stirred at room temperature under nitrogen for 30 min. The mixture of 4,4,5,5,5-pentafluoroiodopentane was added and mixture was refluxed under nitrogen for 2 days, and then poured into H$_2$O. The mixture was extracted with hexane. The organic layer was washed with saturated aqueous NaCl, dried over Na$_2$SO$_4$, filtered, concentrated, and purified by column chromatography (silica gel, 60% CHCl$_3$/hexane) to afford 3-oxo-2-(4,4,5,5,5-pentafluoropentyl)-dec-9-enoic acid ethyl ester (4.46 g, 59%).

$^1$H-NMR (270 MHz, CDCl$_3$) δ: 5.87–5.71 (1H, m, —$\underline{CH}$=CH$_2$), 5.15–4.90 (2H, m, —CH=$\underline{CH_2}$), 4.20 (2H, q, J=7.3 Hz, —O$\underline{CH_2}$CH$_3$), 3.44 (1H, t, J=7.3 Hz, —CO-CHCO—), 3.66–3.40 (2H, m, Alkyl-H), 2.18–1.82 (6H, m, Alkyl-H), 1.70–1.44 (4H, m, Alkyl-H), 1.43–1.21 (4H, m, Alkyl-H), 1.27 (3H, t, J=7.3 Hz, —OCH$_2$$\underline{CH_3}$)

Step 2) (3RS,4RS)-4-(10-ethoxycarbonyl-9-oxo-14,14,15,15,15-pentafluoro)pentadecyl-7-methoxymethoxy-3-(4-methoxymethoxyphenyl)-3-methylchroman

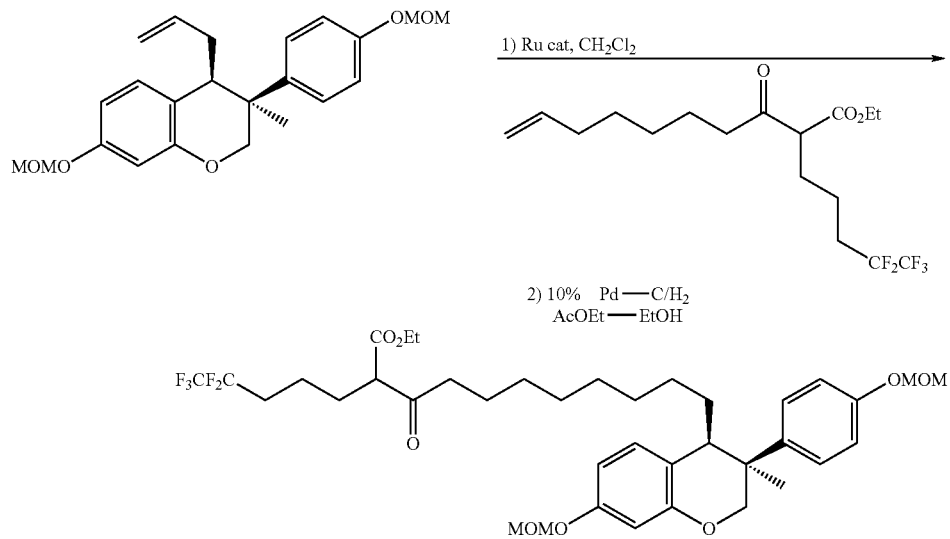

1) The mixture of (3RS,4RS)-4-allyl-7-methoxymethoxy-3-(4-methoxymethoxyphenyl)-3-methyl-chroman (500 mg, 1.30 mmol), 3-oxo-2-(4,4,5,5,5-pentafluoropentyl)-dec-9-enoic acid ethyl ester (968 mg, 2.60 mmol), benzylidene bis(tricyclohexylphosphine)-dichlororuthenium (53 mg, 0.064 mmol) and CH2Cl2 (10 ml) was refluxed under nitrogen for 4 hr. This resulting mixture was concentrated, and then this crude mixture was purified by column chromatography (silica gel, 17% AcOEt/hexane) to afford (3RS, 4RS)-4-[(10-ethoxycarbonyl-9-oxo-14,14,15,15,15-pentafluoro)pentadec-2-enyl]-7-methoxymethoxy-3-(4-methoxymethoxyphenyl)-3-methylchroman (638 mg) as a E/Z mixture.

2) To a solution of (3RS,4RS)-4-[(10-ethoxycarbonyl-9-oxo-14,14,15,15,15-pentafluoro)pentadec-2-enyl]-7-methoxymethoxy-3-(4-methoxymethoxyphenyl)-3-methylchroman (638 mg) in AcOEt/EtOH (1:1, 10 ml) was added 10% Pd on C (53 mg, 0.050 mmol). The reaction flask was flushed with nitrogen, and hydrogen gas was introduced. The black slurry was stirred at room temperature under 1 atm of H$_2$ for 2 days. The reaction mixture was filtered through a small pad of Celite, and the filtrate was concentrated. The residue was purified by column chromatography (silica gel, 18% AcOEt/hexane) to afford (3RS,4RS)-4-(10-ethoxycarbonyl-9-oxo-14,14,15,15,15-pentafluoro)pentadecyl-7-methoxy-methoxy-3-(4-methoxymethoxyphenyl)-3-methylchroman (590 mg, 62%).

$^1$H-NMR (270 MHz, CDCl$_3$) δ: 7.13 (2H, d, J=8.6 Hz, Ar—H), 7.02 (2H, d, J=8.6 Hz, Ar—H), 6.94 (1H, d, J=9.2 Hz, Ar—H), 6.59–6.53 (2H, m, Ar—H), 5.18 (2H, s, —OCH$_2$OCH$_3$), 5.15 (2H, s, —OCH$_2$OCH$_3$), 4.52 (1H, d, J=10.2 Hz, C2-H), 4.26 (1H, d, J=10.2 Hz, C2-H), 4.19 (2H, q, J=7.3 Hz, —OCH$_2$CH$_3$), 3.49 (3H, s, —OCH$_3$), 3.49 (3H, s, —OCH$_3$), 3.42 (1H, t, J=7.3 Hz, —COCHCO—), 2.68–2.61 (1H, m, C4-H), 2.60–2.36 (2H, m, Alkyl-H), 2.17–1.83 (4H, m, Alkyl-H), 1.63–1.45 (4H, m, Alkyl-H), 1.37–0.97 (12H, m, Alkyl-H), 1.26 (3H, t, J=7.3 Hz, —OCH$_2$CH$_3$), 1.24 (3H, s, C3-CH$_3$)

Step 3) (3RS,4RS)-4-(10-ethoxycarbonyl-9-oxo-14,14,15,15,15-pentafluoro)pentadecyl-7-hydroxy-3-(4-hydroxyphenyl)-3-methylchroman

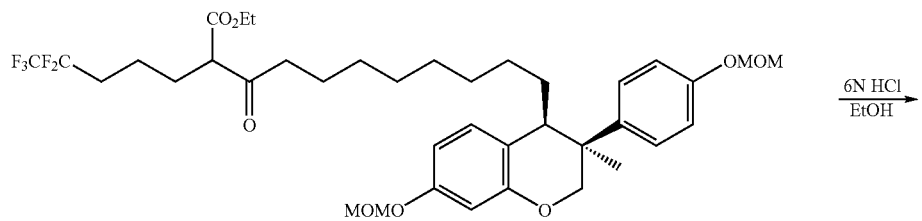

-continued

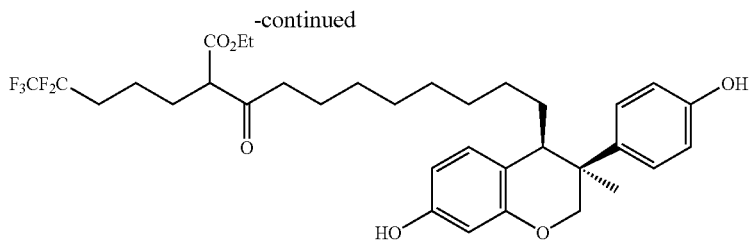

To the solution of (3RS,4RS)-4-(10-ethoxycarbonyl-9-oxo-14,14,15,15,15-pentafluoro)pentadecyl -7-methoxymethoxy-3-(4-methoxymethoxyphenyl)-3-methylchroman (618 mg, 0.846 mmol) in EtOH (4 ml) was added 6N HCl (0.7 ml, 4.2 mmol). The resulting solution was stirred at room temperature for 1 day and between 40 and 45° C. for 2 hr, and then poured into H₂O. The mixture was extracted with AcOEt. The organic layer was washed with saturated aqueous NaCl, dried (Na₂SO₄), filtered, concentrated, and purified by column chromatography (silica gel, 33% AcOEt/hexane) to afford (3RS,4RS)-4-(10-ethoxycarbonyl-9-oxo-14,14,15,15,15-pentafluoro)pentadecyl-7-hydroxy-3-(4-hydroxyphenyl)-3-methylchroman (421 mg, 77%).

¹H-NMR (270 MHz, CDCl₃) δ: 7.08 (2H, d, J=8.6 Hz, Ar—H), 6.89 (1H, d, J=8.6 Hz, Ar—H), 6.84 (2H, d, J=8.6 Hz, Ar—H), 6.42–6.32 (2H, m, Ar—H), 5.61 (1H, s, OH), 4.94–4.91 (1H, m, OH), 4.50 (1H, d, J=6.9 Hz, C2-H), 4.29–4.15 (3H, m, C2-H and —OC$\underline{H}_2$CH₃), 3.46 (1H, t, J=6.9 Hz, —COC$\underline{H}$CO—), 2.63–2.35 (3H, m, C4-H and alkyl-H), 2.16–1.85 (4H, m, alkyl-H), 1.70–1.40 (4H, m, alkyl-H), 1.34–0.95 (12H, m, alkyl-H), 1.28 (3H, t, J=6.9 Hz, —OCH₂C$\underline{H}_3$), 1.25 (3H, s, C3-C$\underline{H}_3$)

Step 4) (3RS,4RS)-7-hydroxy-3-(4-hydroxyphenyl)-4-(9-oxo-14,14,15,15,15-pentafluoro)pentadecyl-3-methylchroman To a solution of (3RS,4RS)-4-(10-ethoxycarbonyl-9-oxo-14,14,15,15,15-pentafluoro)pentadecyl-7-hydroxy-3-(4-hydroxyphenyl)-3-methylchroman (115 mg, 0.179 mmol) in THF (3 ml) at 0° C. was added aqueous 1N NaOH (3.0 ml, 3.0 mmol). The resulting solution was stirred at 0° C. for 15 min and at room temperature for 19 hr, and then poured into H₂O. The mixture was extracted with AcOEt. The organic layer was washed with saturated aqueous NaCl, dried over Na₂SO₄, filtered, concentrated, and purified by column chromatography (silica gel, 33% AcOEt/hexane) to afford (3RS,4RS)-7-hydroxy-3-(4-hydroxyphenyl)-4-(9-oxo-14,14,15,15,15-pentafluoro)pentadecyl-3-methylchroman (88.9 mg, 87%).

¹H-NMR (270 MHz, CDCl₃) δ: 7.08 (2H, d, J=8.6 Hz, Ar—H), 6.92–6.83 (3H, m, Ar—H), 6.40–6.34 (2H, m, Ar—H), 5.78 (1H, s, OH), 4.80 (1H, s, OH), 4.50 (1H, d, J=10.6 Hz, C2-H), 4.29–4.21 (1H, m, C2-H), 2.62–2.53 (1H, m, C4-H), 2.48 (2H, t, J=6.6 Hz, —COC$\underline{H}_2$—), 2.39 (2H, t, J=7.6 Hz, —COC$\underline{H}_2$—), 2.15–1.93 (2H, m, alklyl-H), 1.74–1.42 (6H, m, allyl-H), 1.33–0.98 (12H, m, alkyl-H), 1.26 (3H, s, C3-C$\underline{H}_3$)

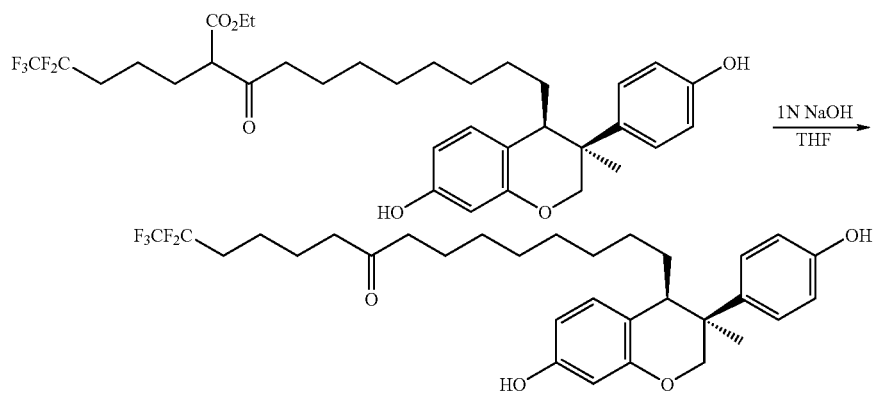

EXAMPLE 59

Synthesis of (3RS,4RS)-7-hydroxy-3-(4-hydroxyphenyl)-4-(9-hydroxy-10-hydroxycarbonyl-14,14,15,15,15-pentafluoro)pentadecyl-3-methylchroman

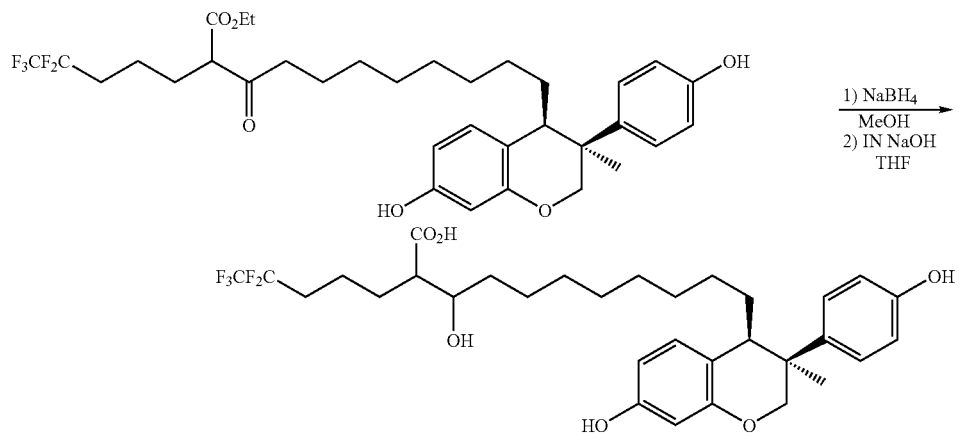

1) To a solution of (3RS,4RS)-7-hydroxy-3-(4-hydroxyphenyl)-4-(9-oxo-14,14,15,15,15-pentafluoro)pentadecyl-3-methylchroman (120 mg, 0.187 mmol) in MeOH (2 ml) at 0° C. was added sodium borohydride (9 mg, 0.238 mmol). The resulting mixture was stirred at 0° C. for 30 minutes, and then quenched with H₂O. This mixture was extracted with AcOEt. The organic layer was washed with, saturated aqueous NaCl, dried (Na₂SO₄), filtered, concentrated, and purified by column chromatography (silica gel, 40% AcOEt/hexane) to afford (3RS,4RS)-4-(10-ethoxycarbonyl-9-hydroxy-14,14,15,15,15-pentafluoro)pentadecyl-7-hydroxy-3-(4-hydroxyphenyl)-3-methylchroman (109 mg).

2) To the solution of (3RS,4RS)-4-(10-ethoxycarbonyl-9-hydroxy-14,14,15,15,15-pentafluoro)-pentadecyl-7-hydroxy-3-(4-hydroxyphenyl)-3-methylchroman (100 mg) in THF (3 ml) at 0° C. was added aqueous 1N NaOH (3 ml). The resulting solution was stirred at room temperature for 19 hr, and then acidified with 2N HCl (pH 1). The mixture was extracted with AcOEt. The organic layer was washed with saturated aqueous NaCl, dried (Na₂SO₄), filtered, concentrated, and purified by column chromatography (silica gel, 10% MeOH/CHCl₃) to afford (3RS,4RS)-7-hydroxy-3-(4-hydroxyphenyl)-4-(9-hydroxy-10-hydroxycarbonyl-14,14,15,15,15-pentafluoro)pentadecyl-3-methylchroman (85.7 mg, 74%).

$^1$H-NMR (270 MHz, DMSO-d-6) δ: 9.18 (1H, brs, —CO₂H), 7.06 (2H, d, J=8.3 Hz, Ar—H), 6.81 (1H, d, J=8.2 Hz, Ar—H), 6.73 (2H, d, J=8.3 Hz, Ar—H), 6.27 (1H, dd, J=8.2 and 2.0 Hz, Ar—H), 6.19 (1H, d, J=2.0 Hz, Ar—H), 4.40 (1H, d, J=10.6 Hz, C2-H), 4.16 (1H, d, J=10.6 Hz, C2-H), 4.58–4.40 (1H, m, —CHOH), 2.62–2.52 (1H, m, C4-H), 2.32–2.03 (4H, m, alkyl-H), 1.64–0.81 (19H, m, alkyl-H), 1.12 (3H, s, C3-CH₃)

EXAMPLE 60

Synthesis of (3RS,4RS)-7-hydroxy-4-[(10 ethoxycarbonyl-14,14,15,15,15-pentafluoro)pentadec-9-enyl]-(4-hydroxyphenyl)-3-methylchroman Step 1) (3RS,4RS)-4-(10-ethoxycarbonyl-9-methanesulfonyloxy-14,14,15,15,15-pentafluoro)pentadecyl-7-methoxymethoxy-3-(4-methoxymethoxyphenyl)-3-methylchroman

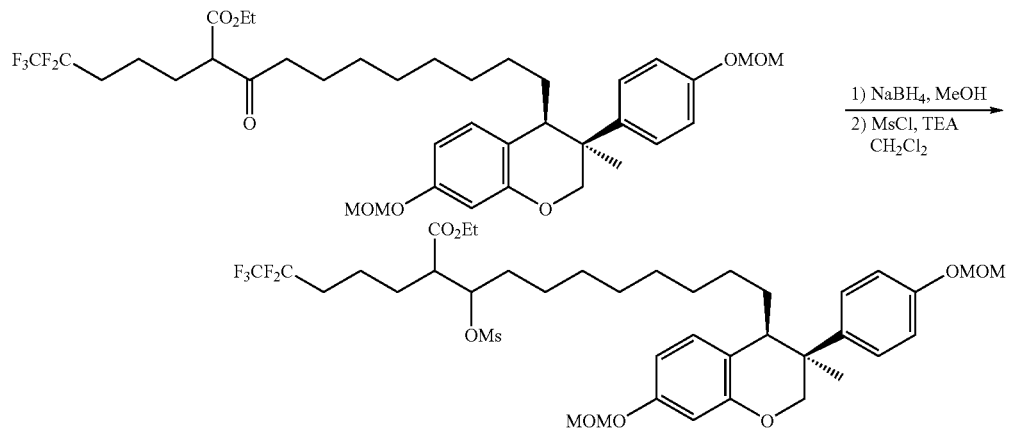

1) To the solution of (3RS,4RS)-4-(10-ethoxycarbonyl-9-oxo-14,14,15,15,15-pentafluoro)pentadecyl-7-methoxymethoxy-3-(4-methoxymethoxyphenyl)-3-methylchroman (250 mg, 0.342 mmol) in MeOH (4 ml) at 0° C. was added sodium borohydride (17 mg, 0.449 mmol). The resulting mixture was stirred at 0° C. for 1 hr, and then quenched with H$_2$O. This mixture was extracted with AcOEt. The organic layer was washed with saturated aqueous NaCl, dried over Na$_2$SO$_4$, filtered, concentrated.

2) To this crude mixture was added triethylamine (0.144 ml, 1.02 mmol) and CH$_2$Cl$_2$ (4 ml), and then methanesulfonyl chloride (0.04 ml, 0.517 mmol) was added at 0° C. This resulting mixture was stirred at 0° C. for 1 hr, and then quenched with H$_2$O. The mixture was extracted with CH$_2$Cl$_2$. The organic layer was washed with saturated aqueous NaCl, dried over Na$_2$SO$_4$, filtered, concentrated, and purified by column chromatography (silica gel, 25% AcOEt/hexane) to afford (3RS,4RS)-4-(10-ethoxycarbonyl-9-methanesulfonyloxy-14,14,15,15,15-pentafluoro)pentadecyl-7-methoxymethoxy-3-(4-methoxymethoxyphenyl)-3-methylchroman (254 mg, 92%).

$^1$H-NMR (270 MHz, CDCl$_3$) δ: 7.13 (2H, d, J=8.9 Hz, Ar—H), 7.02 (2H, d, J=8.9 Hz, Ar—H), 6.94 (1H, d, J=9.2 Hz, Ar—H), 6.59–6.54 (2H, m, Ar—H), 5.18 (2H, s, —OC$\underline{H}_2$OCH$_3$), 5.15 (2H, s, —OC$\underline{H}_2$OCH$_3$), 4.95–4.84 (1H, m, —C$\underline{H}$OMs), 4.52 (1H, d, J=10.6 Hz, C2-H), 4.26 (1H, d, J=10.6 Hz, C2-H), 4.18 (2H, q, J=6.9 Hz, —OC$\underline{H}_2$CH$_3$), 3.50 (3H, s, —OCH$_2$OC$\underline{H}_3$), 3.49 (3H, s, —OCH$_2$OC$\underline{H}_3$), 3.02 and 2.99 (total 3H, s, —OSO$_2$C$\underline{H}_3$), 2.87–2.77 (1H, m, —C$\underline{H}$CO$_2$Et), 2.65–2.60 (1H, m, C4-H), 2.18–1.93 (2H, m, alkyl-H), 1.83–1.50 (6H, m, alkyl-H), 1.41–0.98 (14H, m, alkyl-H), 1.27 (3H, t, J=6.9 Hz, —OCH$_2$CH$_3$) 1.24 (3H, s, C3-CH$_3$)

Step 2) (3RS,4RS)-4-[(10-ethoxycarbonyl-14,14,15,15,15-pentafluoro)pentadec-9-enyl]-7-methoxymethoxy-3-(4-methoxymethoxyphenyl)-3-methylchroman To a solution of (3RS,4RS)-4-(10-ethoxycarbonyl-9-methanesulfonyloxy-14,14,15,15,15-pentafluoro)pentadecyl-7-methoxymethoxy-3-(4-methoxy-methoxyphenyl)-3-methylchroman (236 mg, 0.291 mmol) in CH$_2$Cl$_2$ (3 ml) at 0° C. under nitrogen was added 1,8-diazabicyclo[5,4,0]undec-7-ene (0.32 ml, 2.14 mmol). This resulting mixture was stirred at room temperature for 5 hr, and then poured into H$_2$O. The mixture was extracted with CH$_2$Cl$_2$. The organic layer was washed with saturated aqueous NaCl, dried (Na$_2$SO$_4$), filtered, concentrated, and purified by column chromatography (silica gel, 25% AcOEt/hexane) to afford (3RS,4RS)-4-[(10-ethoxycarbonyl-14,14,15,15,15-pentafluoro)pentadec-9-enyl]-7-methoxymethoxy-3-(4-methoxymethoxyphenyl)-3-methylchroman (184 mg, 88%) as a E/Z mixture.

$^1$H-NMR (270 MHz, CDCl$_3$) δ: 7.13 (2H, d, J=8.9 Hz, Ar—H), 7.02 (2H, d, J=8.9 Hz, Ar—H), 6.94 (1H, d, J=9.2 Hz, Ar—H), 6.80 (0.65H, t, J=7.3 Hz, —C$\underline{H}$=CCO$_2$Et- of E isomer), 6.60–6.52 (2H, m, Ar—H), 5.88 (0.35H, t, J=6.6 Hz, —C$\underline{H}$=CCO$_2$Et- of Z isomer), 5.18 (2H, S, —OC$\underline{H}_2$OCH$_3$), 5.15 (2H, s, —OC$\underline{H}_2$OCH$_3$), 4.52 (1H, d, J=10.2 Hz, C2-H), 4.26 (1H, d, J=10.6 Hz, C2-H), 4.20 (2H, q, J=7.3 Hz, —OC$\underline{H}_2$CH$_3$), 3.49 (6H, s, —OCH$_2$OC$\underline{H}_3$×2), 2.69–2.60 (1H, m, C4-H), 2.43–2.27 (2H, m, alkyl-H), 2.19–1.89 (4H, m, alkyl-H), 1.80–1.63 (2H, m, alkyl-H), 1.65–0.98 (14H, m, alkyl-H), 1.29 (3H, t, J=7.3 Hz, —OCH$_2$C$\underline{H}_3$), 1.25 (3H, s, C3-CH$_3$)

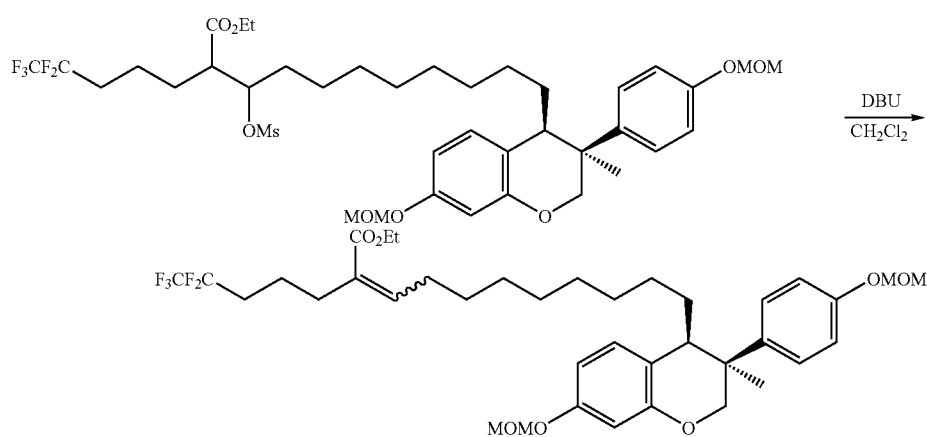

Step 3) (3RS,4RS)-7-hydroxy-4-[(10-ethoxycarbonyl-14,14,15,15,15-pentafluoro)pentadec-9-enyl]-3-(4-hydroxyphenyl)-3-methylchroman

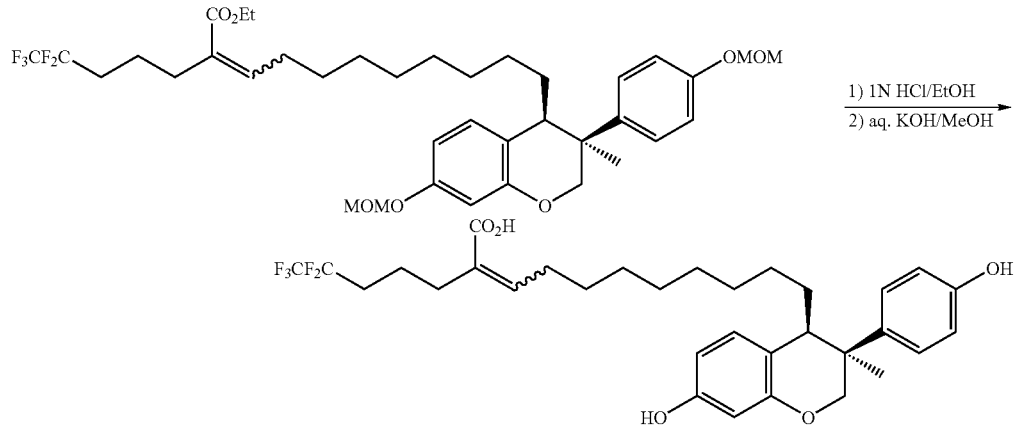

1) To a solution of (3RS,4RS)-4-[(10-ethoxycarbonyl-14,14,15,15,15-pentafluoro)pentadec-9-enyl]-7-methoxymethoxy-3-(4-methoxymethoxyphenyl)-3-methylchroman (E/Z=c.a. ½, 173 mg, 0.242 mmol) in EtOH (3 ml) was added 6N HCl (0.3 ml, 1.8 mmol). The resulting solution was stirred at room temperature for 2.5 days and at 35° C. for 4 hr, and then poured into $H_2O$. The mixture was extracted with AcOEt. The organic layer was washed with saturated aqueous NaCl, dried ($Na_2SO_4$), filtered, concentrated, and purified by column chromatography (silica gel, 25% AcOEt/hexane) to afford (3RS,4RS)-7-hydroxy-4-[(10-ethoxycarbonyl-14,14,15,15,15-pentafluoro)pentadec-9-enyl]-3-(4-hydroxyphenyl)-3-methylchroman (134 mg).

2) To the solution of (3RS,4RS)-7-hydroxy-4-[(10-ethoxycarbonyl-14,14,15,15,15-pentafluoro)-pentadec-9-enyl]-3-(4-hydroxyphenyl)-3-methylchroman (123 mg) in MeOH (3 ml) at 0° C. was added the solution of KOH (85%, 150 mg, 2.27 mmol) in $H_2O$ (3 ml). The resulting solution was stirred at room temperature for 4 hr, and then acidified with 2N HCl (pH 1). The mixture was extracted with AcOEt The organic layer was washed with saturated aqueous NaCl, dried over $Na_2SO_4$, filtered, concentrated, and purified by column chromatography (silica gel, 66% AcOEt/hexane) to afford (3RS,4RS)-7-hydroxy-4-[(10-hydroxycarbonyl-14,14,15,15,15-pentafluoro)-pentadec-9-enyl]-3-(4-hydroxyphenyl)-3-methylchroman (52.1 mg, 36%) as E/Z mixtures.

$^1$H-NMR (270 MHz, CDCl$_3$) δ: 7.08 (2H, d, J=8.9 Hz, Ar—H), 6.98 (0.85H, t, J=7.6 Hz, —CH=CCO$_2$Et- of E isomer), 7.90 (1H, d, J=8.9 Hz, Ar—H), 6.83 (2H, d, J=8.9 Hz, Ar—H), 6.42–6.33 (2H, m, Ar—H), 6.09 (0.15H, t, J=7.3 Hz, —CH=CCO$_2$Et- of Z isomer), 4.51 (1H, d, J=10.6 Hz, C2-H), 4.24 (1H, d, J=10.6 Hz, C2-H), 2.65–2.56 (1H, m, C4-H), 2.43–2.29 (2H, m, alkyl-H), 2.23–1.91 (4H, m, alkyl-H), 1.85–1.62 (2H, m, alkyl-H), 1.48–0.93 (14H, m, alkyl-H), 1.24 (3H, s, C3-CH3)

EXAMPLE 61

Synthesis of 1,1,1,2,2-pentafluoro-14-[(3RS,4RS)-7-hydroxy-3-(4-hydroxyphenyl)-3-methylchroman-4-yl]-5-tetradecanone Step 1) Synthesis of 4,4,5,5,5-pentafluoropentanoic acid.

To a stirred solution of Jones reagent (20 ml, 160 mmol) in acetone (20 ml), cooled in an ice bath, a solution of 4,4,5,5,5-pentafluoro-1-pentanol (7.12 g, 40 mmol) in acetone (30 ml) was added dropwise. After remaining ice bath, the mixture was stirred continuously at room temperature for 1 h. The mixture was poured into ice/water and extracted with diethyl ether. Crude ether washed was extracted with aqueous 2 N sodium hydroxide. On the inorganic layer was acidified with aqueous 6 N hydrochloric acid and the organic layer was extracted with diethyl ether. The final extract was washed with brine, dried over anhydrous sodium sulfate and concentrated in vacuo to give crude 4,4,5,5,5-pentafluoropentanoic acid as colorless liquid (6.31 g, 82%), which was used in the next step without further purification.

$^1$H NMR (300 MHz, CDCl$_3$) δ: 11.5–9.5 (1H, br.s, CO2H), 2.70 (2H, t, J=7.8 Hz, C2-H), 2.53–2.33 (2H, m, C3-H).

Step 2) Synthesis of 4,4,5,5,5-pentafluoropentanoyl chloride.

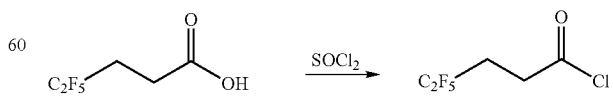

A mixture of 4,4,5,5,5-pentafluoropentanoic acid (7:44 g, 38.7 mmol) and thionyl chloride (23.0 g, 194 mmol) was stirred at reflux for 2 h. Excess thionyl chloride was removed by heating at normal pressure and the residue was distilled in vacuum using effective Vigreux column to give 4,4,5,5,5-pentafluoropentanoyl chloride as colorless liquid (62° C./103 mmHg, 4.41 g, 54%).

$^1$H NMR (300 MHz, CDCl$_3$) δ: 3,23 (2H, t, J=7.6 Hz, C2-H), 2.58–2.38 (2H, m, C3-H).

Step 3) Synthesis of ethyl 6,6,7,7,7-pentafluoro-3-oxoheptanoate.

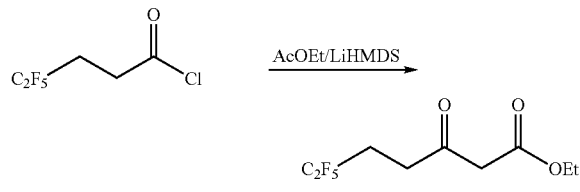

To a stirred solution of ethyl acetate enolate, prepared from ethyl acetate (4.4 g, 50 mmol) and sodium hexamethyldisilazide (50 mmol) in THF at −70° C., was added neat 4,4,5,5,5-pentafluoropentanoyl chloride (2.1 g, 10 mmol) at −70° C. Cooling bath was removed and the reaction mixture was allowed to warm to room temperature. The mixture was diluted with diethyl ether and quenched with water. The organic layer was separated, washed with aqueous 2 N hydrochloric acid, saturated sodium bicarbonate solution, brine, dried over anhydrous sodium sulfate and concentrated in vacuum. The crude product was purified by flash chromatography on-silica gel (hexane ethyl acetate 5:1) to give ethyl 6,6,7,7,7-pentafluoro-3-oxoheptanoate as colorless oil yield: 1.46 g (56%).

$^1$H NMR (300 MHz, CDCl$_3$) δ: 4.22 (2H, q, J=7.1 Hz, OCH$_2$Me), 3.50 (2H, s, C2-H), 2.89 (2H, m, C4-H), 2.50–2.30 (2H, m, C5-H), 1.29 (3H, t, J=7.1 Hz, MeCH$_2$O).

Step 4) Synthesis of 8-iodo-1-octene.

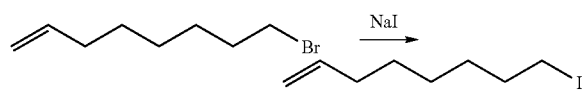

A mixture of 8-bromo-1-octene (1.34 g, 7 mmol) and sodium iodide (5.25 g, 35 mmol) in 2-butanone (15 ml) was stirred under reflux for 1 h. The mixture was concentrated in vacuo to a half of its original volume and hexane and water was added. Organic layer was washed with 5% aqueous sodium thiosulfate, saturated sodium bicarbonate and brine, dried over anhydrous sodium sulfate and concentrated in vacuum. Purification by flash chromatography on silica gel (hexane) gave 8-iodo-1-octene as colorless oil. yield: 1.54 g (92%).

$^1$H NMR (300 MHz, CDCl$_3$) δ: 5.88–5.73 (1H, m, C2-H), 5.0–54.91 (2H, m, C1-H), 3.19 (2H, t, J=7.0 Hz, C8-H), 2.05 (2H, m, C3-H), 1.81 (2H, m, C7-H), 1.47–1.24 (6H, m, alkyl-H).

Step 5) Synthesis of ethyl 2-(4,4,5,5,5-pentafluoro-1-oxopentyl)-9-decenoate.

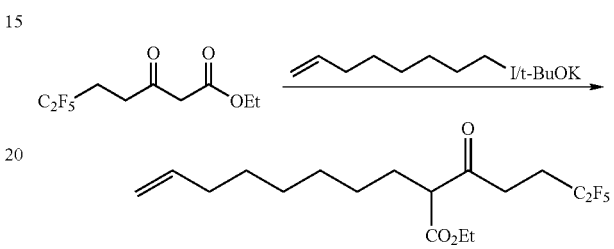

To a stirred solution of ethyl 6,6,7,7,7-pentafluoro-3-oxoheptanoate (262 mg, 1 mmol) in anhydrous THF (4 ml), potassium tret-butoxide (112 mg, 1 mmol) was added as a solid and the mixture was stirred at room temperature for 30 min. Then to a solution of 8-iodo-1-octene (357 mg, 1.5 mmol) in anhydrous THF (1 ml) was added and the mixture was stirred at room temperature continued for 3 days. The mixture was concentrated, diluted with diethyl ether, washed with water, brine, dried over anhydrous sodium sulfate and concentrated in vacuum. Crude product was purified by flash chromatography on silica gel (hexane:ethyl acetate 10:1) to give ethyl 2-(4,4,5,5,5-pentafluoro-1-oxopentyl)-9-decenoate as a colorless oil. yield: 200 mg (54%).

$^1$H NMR (300 MHz, CDCl$_3$) δ: 5.88–5.71 (1H, m, C9-H), 5.03–4.88 (2H, m, C10-H), 4.20 (2H, q, J=7.1 Hz, OCH$_2$Me), 3.46 (1H, t, J=7.4 Hz, C2-H), 2.97–2.69 (2H, m, C2'-H), 2.48–2.28 (2H, m, C3'-H), 2.03 (2H, m), 1.86 (2H, m), 1.42–1.23 (6H, m), 1.27 (3H, t, J=7.1 Hz, MeCH$_2$O).

Step 6) Synthesis of ethyl (E,Z)-2-(4,4,5,5,5-pentafluoro-1-oxopentyl)-11-[(3RS,4RS)-7-methoxymethoxy-3-(4-methoxymethoxyphenyl)-3-methylchroman-4-yl]-9-undecenoate.

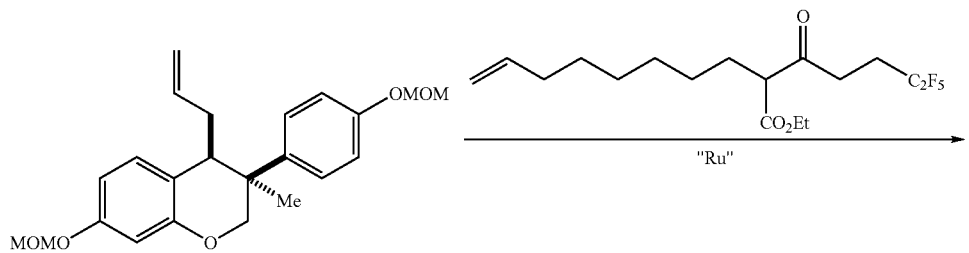

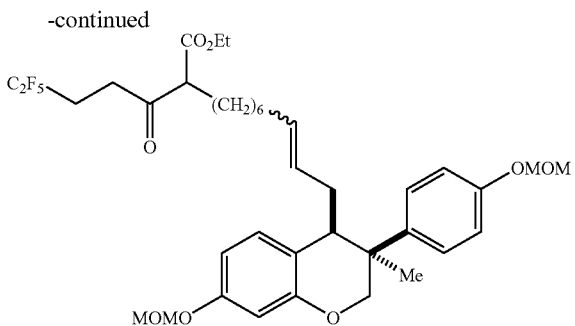

A solution of (3RS,4RS)-4-allyl-7-methoxymethoxy-3-(4-methoxymethoxyphenyl)-3-methylchroman (346 mg, 0.9 mmol), ethyl 2-(4,4,5,5,5-pentafluoro-1-oxopentyl)-9-decenoate (667 mg, 1.8 mmol) and benzylidene bis(tricyclohexylphosphine)-dichlororuthenium (41 mg, 0.05 mmol) in methylene chloride (10 ml) was stirred under reflux for 2 h. The mixture was concentrated and crude product was purified directly by flash chromatography on silica gel (hexane: ethyl acetate 5:1) to give ethyl (E,Z)-2-(4,4,5,5,5-pentafluoro-1-oxopentyl)-11-[(3RS,4RS)-7-methoxymethoxy-3-(4-methoxymethoxyphenyl)-3-methylchroman-4-yl]-9-undecenoate as a colorless oil. yield: 483 mg (74%).

$^1$H NMR (300 MHz, CDCl$_3$) δ: 7.20–6.90 (5H, m, Ar—H), 6.60–6.50 (2H, m, Ar—H), 5.27–4.97 (6H, mn, OC$\underline{H}_2$OMe and C9-H, C10-H), 4.59–4.47 (1H, m, C2"-H), 4.30–4.15 (3H, n, C2"-H and OC$\underline{H}_2$Me), 3.51–3.41 (7H, m, C2-H and $\underline{Me}$OCH$_2$O), 2.97–2.69 (3H, m, C4"-H and C2'-H), 2.48–2.28 (2H, m, C3'-H), 1.94–1.46 (6H, m), 1.36–1.16 (14H, m, alkyl-H).

Step 7) Synthesis of ethyl 2-(4,4,5,5,5-pentafluoro-1-oxopentyl)-11-[(3RS,4RS)-7-methoxymethoxy-3-(4-methoxymethoxyphenyl)-3-methylchroman-4-yl]undecanoate.

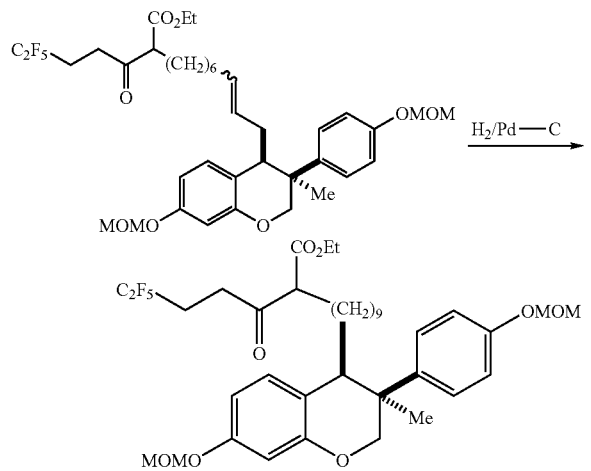

To a solution of ethyl (E,Z)-2-(4,4,5,5,5-pentafluoro-1-oxopentyl)-11-[(3RS,4RS)-7-methoxymethoxy-3-(4-methoxymethoxyphenyl)-3-methylchroman-4-yl]-9-undecenoate (483 mg, 0.66 mmol) in ethyl acetate (30 ml), 10% Pd/C (120 mg) was added and the reaction mixture was stirred under H$_2$ at normal pressure at room temperature for 1 h. Catalyst was filtered out and filtrate was concentrated in vacuum to give ethyl 2-(4,4,5,5,5-pentafluoro-1-oxopentyl)-11-[(3RS,4RS)-7-methoxymethoxy-3-(4-methoxymethoxyphenyl)-3-methylchroman-4-yl]undecanoate as a colorless oil, which was used in the next step without further purification. yield: 483 mg (quant.).

$^1$H NMR (300 MHz, CDCl$_3$) δ: 7.17–6.92 (5H, m, Ar—H), 6.60–6.53 (2H, m, Ar—H), 5.18 and 5.15 (2H each, s, OC$\underline{H}_2$OMe), 4.52 (1H, d, JAB=10.1 Hz, C2"-H), 4.26 (1H, dd, JAB=10.1 Hz, J=1.7 Hz, C2"-H), 4.19 (2H, q, J=7.1 Hz, OC$\underline{H}_2$Me), 3.50 and 3.49 (3H each, s, $\underline{Me}$OCH$_2$O), 3.44 (1H, t, J=7.4 Hz, C2-H), 2.96–2.69 (2H, m, C2'-H), 2.64 (1H, m, C4"-H), 2.48–2.27 (2H, m, C3'-H), 1.92–1.75 (2H, m), 1.31–1.02 (22H, m, alkyl-H).

Step 8) Synthesis of ethyl 2-(4,4,5,5,5-pentafluoro-1-oxopentyl)-11-[(3RS,4RS)-7-hydroxy-3-(4-hydroxyphenyl)-3-methylchroman-4-yl]undecanoate.

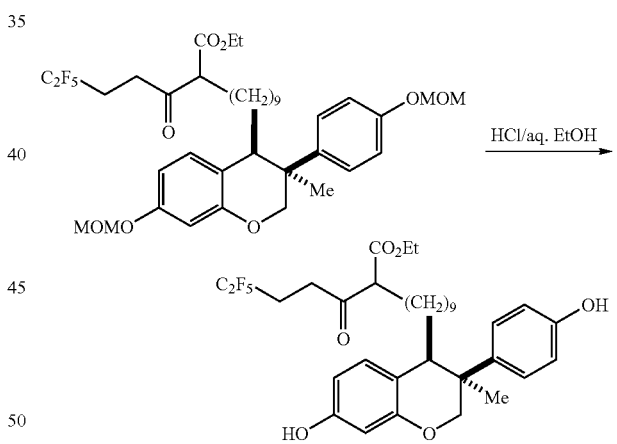

To a stirred solution of ethyl 2-(4,4,5,5,5-pentafluoro-1-oxopentyl)-11-[(3RS,4RS)-7-methoxymethoxy-3-(4-methoxymethoxyphenyl)-3-methylchroman-4-yl]undecanoate (128 mg, 0.17 mmol) in ethyl alcohol (5 ml), was added concentrated aqueous hydrochloric acid (10 drops) at room temperature under N$_2$ atmosphere. The mixture was stirred at room temperature continued for 2.5 days and diluted with ethyl acetate. The organic layer was washed with saturated aqueous sodium bicarbonate and brine, dried over anhydrous sodium sulfate and concentrated in vacuum. Crude product was purified by flash chromatography on silica gel (hexane:ethyl acetate=3:2) to give ethyl 2-(4,4,5,5,5-pentafluoro-1-oxopentyl)-11-[(3RS,4RS)-7-hydroxy-3-(4-hydroxyphenyl)-3-methylchroman-4-yl]undecanoate as a colorless glassy oil. yield: 102 mg (94%).

$^1$H NMR (300 MHz, CDCl$_3$) δ: 7.13–6.80 (5H, m, Ar—H), 6.41–6.34 (2H, m, Ar—H), 5.45 and 4.95 (1H each, s, OH), 4.51 (1H, d, JAB=10.4 Hz, C2"-H), 4.28–4.17 (3H, m, C2"-H and OC$\underline{H}_2$Me), 3.49 (1H, t, J=7.4 Hz, C2-H), 2.99–2.69 (2H, m, C2'-H), 2.60 (1H, m, C4"-H), 2.51–2.29 (2H, m, C3'-H); 1.95–1.76 (2H, m), 1.28 (3H, t, J=7.1 Hz, MeCH$_2$O), 1.27–0.98 (22H, m, alkyl-H).

Step 9) Synthesis of 1,1,1,2,2-pentafluoro-14-[(3RS,4RS)-7-hydroxy-3-(4-hydroxyphenyl)-3-methylchroman-4-yl]-5-tetradecanone.

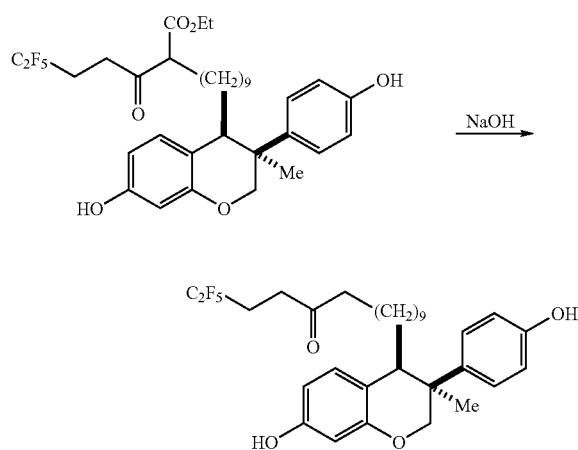

To a solution of ethyl 2-(4,4,5,5,5-pentafluoro-1-oxopentyl)-11-[(3RS,4RS)-7-hydroxy-3-(4-hydroxyphenyl)-3-methylchroman-4-yl]undecanoate (102 mg, 0.16 mmol) in THF (2.5 ml), 1 N aqueous sodium hydroxide solution (2.5 ml) was added at room temperature under N$_2$ atmosphere. The solution was stirred at room temperature for 16 h and at 50° C. for 2 h. The mixture was cooled to room temperature, diluted with water and extracted with methylene chloride. Organic extracts were dried over anhydrous potassium sulfate and concentrated in vacuum. Crude product was purified by flash chromatography on silica gel (hexane:ethyl acetate=2:1) to give 1,1,1,2,2-pentafluoro-14-[(3RS,4RS)-7-hydroxy-3-(4-hydroxyphenyl)-3-methylchroman-4-yl]-5-tetradecanone as colorless oil. yield: 96 mg (quant.).

$^1$H NMR (300 MHz, CDCl$_3$) δ: 7.12–6.80 (5H, m, Ar—H), 6.42–6.34 (2H, m, Ar—H), 5.48 and 4.99 (1H each, s, OH), 4.51 (1H, d, JAB=10.2 Hz, C2'-H), 4.24 (1H, dd, JAB=10.2 Hz, J=1.9 Hz, C2'-H), 2.74 (2H, m, C4-H), 2.61 (1H, m, C4'-H), 2.48 (2H, t, J=7.4 Hz, C6-H), 2.47–2.27 (2H, m, C3-H), 1.65–1.50 (2H, m), 1.30–0.98 (19H, m, alkyl-H).

$^{13}$C NMR (75 MHz, CDCl$_3$) δ: 208.3, 154.9, 153.8, 153.0, 137.4, 131.2, 126.3, 118.2, 115.27, 107.14, 102.7, 69.4, 45.4, 43.0, 38.3, 34.5, 33.5, 29.3, 29.2, 29.1, 29.0, 27.6, 26.7, 23.8.

EXAMPLE 62

Synthesis of (E)-6,6,7,7,7-pentafluoro-2-{9-[(3RS,4RS)-7-hydroxy-3-(4-hydroxyphenyl)-3-methylchroman-4-yl]nonyl}-2-heptenoic acid Steps 1)~7) see above in Example 61.

Step 8) Synthesis of ethyl 2-(4,4,5,5,5-pentafluoro-1-hydroxypentyl)-11-[(3RS,4RS)-7-methoxymethoxy-3-(4-methoxymethoxyphenyl)-3-methylchroman-4-yl]undecanoate.

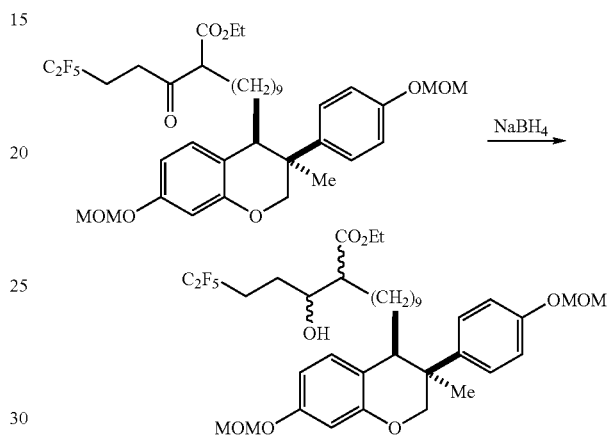

To a stirred solution of ethyl 2-(4,4,5,5,5-pentafluoro-1-oxopentyl)-11-[(3RS,4RS)-7-methoxymethoxy-3-(4-methoxymethoxyphenyls-3-methylchroman-4-yl]undecanoate (300 mg, 0.41 mmol) in methyl alcohol, (15 ml), cooled to 0–5° C. on ice bath, sodium tetrahydroborate (62 mg, 1.64 mmol) was added as a solid under N$_2$ atmosphere and stirring at 0–5° C. continued for 1.5 h. The mixture was partitioned between ethyl acetate and water, organic layer was separated, washed with water and brine, dried over anhydrous sodium sulfate and concentrated in vacuum. Crude product was purified by flash chromatography on silica gel (hexane:ethyl acetate=5:2) to give ethyl 2-(4,4,5,5,5-pentafluoro-1-hydroxypentyl)-11-[(3RS,4RS)-7-methoxymethoxy-3-(4-methoxymethoxyphenyl)-3-methylchroman-4-yl]undecanoate as a colorless oil (mixture of anti and syn isomers at C2/C1') yield: 279 mg (93%)

Syn Isomer (Major):

$^1$H NMR (300 MHz, CDCl$_3$) δ: 7.17–6.91 (5H, m, Ar—H), 6.60–6.53 (2H, m, Ar—H), 5.18 and 5.15 (2H each, s, OC$\underline{H}_2$OMe), 4.53 (1H, d, J$_{AB}$=10.4 Hz, C2"-H), 4.26 (1H, dd, J$_{AB}$=10.4 Hz, J=1.9 Hz, C2"-H), 4.19 (2H, q, J=7.1 Hz, OC$\underline{H}_2$Me), 3.67 (1H, m, C1'-H), 3.50 and 3.49 (3H each, s, MeOC$\underline{H}_2$O), 2.82 (1H, d, J=8.5 Hz, C2-H), 2.65 (1H, m, C4"-H), 2.47–1.97 (4H, m), 1.84–1.55 (4H, m), 1.28 (3H, t, J=7.1 Hz, MeCH$_2$O), 1.27–1.02 (17H, m, alkyl-H).

Anti Isomer (Minor):

$^1$H NMR (300 MHz, CDCl$_3$) δ: 7.17–6.91 (5H, m, Ar—H), 6.60–6.53 (2H, m, Ar—H), 5.18 and 5.15 (2H each, s, OC$\underline{H}_2$OMe), 4.53 (1H, d, JAB=10.4 Hz, C2"-H), 4.26 (1H, dd, J$_{AB}$=10.4 Hz, J=1.9 Hz, C2"-H), 4.18 (2H, q, J=7.1 Hz, OC$\underline{H}_2$Me), 3.80 (1H, m, C1'-H), 3.50 and 3.49 (3H each, s, MeOC$\underline{H}_2$O), 2.69–2.59 (2H, m), 2.49–1.93 (4H, m), 1.77–1.61 (2H, m), 1.28 (3H, t, J=7.1 Hz, MeH$_2$O), 1.32–1.02 (17H, m, alkyl-H).

Step 9) Synthesis of ethyl (E,Z)-6,6,7,7,7-pentafluoro-2-{9-[(3RS,4RS)-7-methoxymethoxy-3-(4-methoxymethoxyphenyl)-3-methylchroman-4-yl]nonyl}-2-heptenoate.

Step 10) Synthesis of (E)-6,6,7,7,7-pentafluoro-2-{9-[(3RS,4RS)-7-methoxymethoxy-3-(4-methoxymethoxyphenyl)-3-methylchroman-4-yl]nonyl}-2-heptenoic acid.

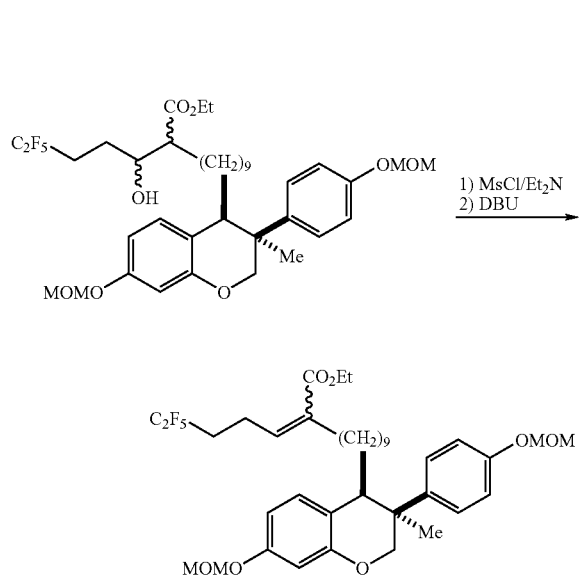

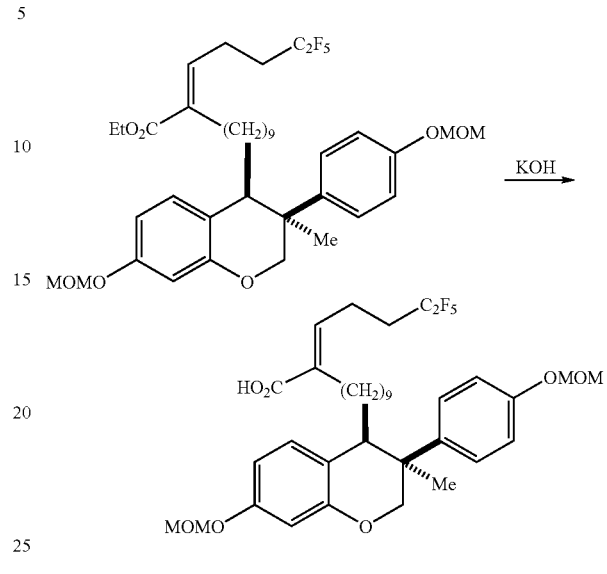

To a stirred solution of ethyl 2-(4,4,5,5,5-pentafluoro-1-hydroxypentyl)-11-[(3RS,4RS)-7-methoxymethoxy-3-(4-methoxymethoxyphenyl)-3-methylchroman-4-yl]undecanoate (279 mg, 0.38 mmol) and triethylamine (61 mg, 0.6 mmol) in methylene chloride (2 ml), methane sulfonyl chloride (52 mg, 0.45 mmol) was added at room temperature and the reaction mixture was stirred at room temperature for 3 h. After 1,8-diazabicyclo[5.4.0]undec-7-ene (0.2 ml) was added. The mixture was stirred continued at room temperature for 16 h The mixture was diluted with diethyl ether and washed with 2 N aqueous hydrochloric acid, saturated sodium hydrogen carbonate and brine, dried over anhydrous sodium sulfate and concentrated in vacuum. Crude product was purified by flash chromatography on silica gel (hexane: ethyl acetate=4:1) to give ethyl (E,Z)-6,6,7,7,7-pentafluoro-2-{9-[(3RS,4RS)-7-methoxymethoxy-3-(4-methoxymethoxyphenyl)-3-methylchroman-4-yl]nonyl}-2-heptenoate as a colorless oil. yield: 235 mg (86%).

E Isomer (Major):

$^1$H NMR (300 MHz, CDCl$_3$) δ: 7.17–6.92 (5H, m, Ar—H), 6.63 (1H, t, J=7.4 Hz, C3-H), 6.60–6.53 (2H, m, Ar—H), 5.18 and 5.15 (2H each, s, OC$\underline{H}_2$OMe), 4.52 (1H, d, J$_{AB}$=10.2 Hz, C2"-H), 4.26 (1H, dd, J$_{AB}$=10.2 Hz, J=1.6 Hz, C2"-H), 4.19 (2H, q, J=7.2 Hz, OC$\underline{H}_2$Me), 3.50 and 3.49 (3H each, s, MeOCH$_2$O), 2.64 (1H, m, C4"-H), 2.50–2.40 (2H, m), 2.34–2.04 (4H, m), 1.27 (3H, t, J=7.1 Hz, $\underline{Me}$CH$_2$O), 1.32–0.98 (19H, m, alkyl-H).

Z-isomer (Minor):

$^1$H NMR (300 MHz, CDCl$_3$) δ: 7.17–6.92 (5H, m, Ar—H), 6.60–6.53 (2H, m, Ar—H), 5.80 (1H, t, J=7.4 Hz, C3-H), 5.18 and 5.15 (2H each, s, OC$\underline{H}_2$OMe), 4.52 (1H, d, J$_{AB}$=10.2 Hz, C2"-H), 4.26 (1H, dd, JAB=10.2 Hz, J=1.6 Hz, C2"-H), 4.20 (2H, q, J=7.2 Hz, OC$\underline{H}_2$Me), 3.50 and 3.49 (3H each, s, $\underline{Me}$OCH$_2$O), 2.70–2.59 (3H, m), 2.20–2.02 (4H, m), 1.30 (3H, t, J=7.2 Hz, $\underline{Me}$CH$_2$O), 1.32–0.98 (19H, m, alkyl-H).

To a stirred solution of ethyl (E)-6,6,7,7,7-pentafluoro-2-{9-[(3RS,4RS)-7-methoxymethoxy-3-(4-methoxymethoxyphenyl)-3-methylchroman-4-yl]nonyl}-2-h eptenoate (116 mg, 0.16 mmol) in ethyl alcohol (5 ml), 5 N aqueous potassium hydroxide solution was added and the mixture was stirred under N$_2$ atmosphere at 70° C. for 5 h. After cooling to room temperature the reaction mixture was acidified by 6 N aqueous hydrochloric acid and extracted with methylene chloride. Extracts were dried over anhydrous sodium sulfate and concentrated in vacuum to give crude (E)-6,6,7,7,7-pentafluoro-2-{9-[(3RS,4RS)-7-methoxymethoxy-3-(4-methoxymethoxyphenyl)-3-methylchroman-4-yl]nonyl}-2-heptenoic acid as a colorless oil. yield: 111 mg (quant.). The sample was used in the following step without further purification.

$^1$H NMR (300 MHz, CDCl$_3$) δ: 7.17–6.92 (5H, m, Ar—H), 6.79 (1H, t, J=7.3 Hz, C3-H), 6.60–6.53 (2H, m, Ar—H), 5.18 and 5.15 (2H each, s, OC$\underline{H}_2$OMe), 4.53 (1H, d, JAB=10.7 Hz, C2"-H), 4.26 (1H, dd, JAB=10.7 Hz, J=1.9 Hz, C2"-H), 3.49 (6H, s, $\underline{Me}$OCH$_2$O), 2.65 (1H, m, C4"-H), 2.55–2.44 (2H, m), 2.34–2.07 (4H, m), 1.44–0.98 (19H, m, alkyl-H).

Step 11) Synthesis of (E)-6,6,7,7,7-pentafluoro-2-{9-[(3RS,4RS)-7-hydroxy-3-(4-hydroxyphenyl)-3-methylchroman-4-yl]nonyl}-2-heptenoic acid.

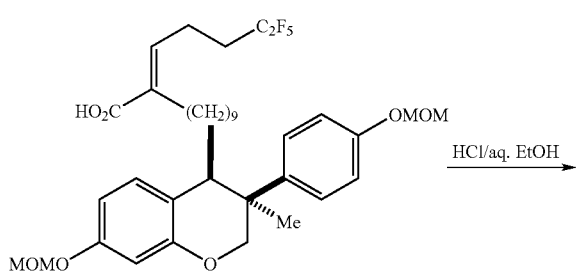

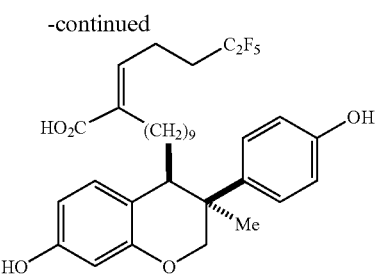

To a stirred solution of (E)-6,6,7,7,7-pentafluoro-2-{9-[(3RS,4RS)-7-methoxymethoxy-3-(4-methoxymethoxyphenyl)-3-methylchroman-4-yl]nonyl}-2-heptenoic acid (111 mg, 0.16 mmol) in ethyl alcohol (5 ml), was added 6 N aqueous solution of hydrochloric acid (30 drops) and the reaction mixture was stirred at 40° C. for 6 h. The reaction mixture was diluted with water and extracted with methylene chloride. Organic extracts were dried over anhydrous sodium sulfate and concentrated in vacuum. Crude product was purified by flash chromatography on silica gel (hexane:ethyl acetate:methyl alcohol=10:10:1), and then additionally by preparative thin-layer chromatography on Merck Silicagel 60 plates (hexane:ethyl acetate:methyl alcohol=5:5:1) to give (E)-6,6,7,7,7-pentafluoro-2-{9-[(3RS,4RS)-7-hydroxy-3-(4-hydroxyphenyl)-3-methychroman-4-yl]nonyl}-2-heptenoic acid as a colorless amorphous solid. yield: 47.4 mg (49%)

$^1$H NMR (300 MHz, CDCl$_3$) δ: 7.12–6.80 (6H, m, Ar—H and C3-H), 6.41–6.35 (2H, m, Ar—H), 4.51 (1H, d, $J_{AB}$=10.4 Hz, C2"-H), 4.24 (1H, dd, $J_{AB}$=10.4 Hz, J=1.6 Hz, C2"-H), 2.61 (1H, m, C4"-H), 2.56–2.44 (2H, m), 2.35–2.07 (4H, m), 1.44–0.99 (19H, m, alkyl-H).

EXAMPLE 63

Synthesis of (3RS,4RS)-7-hydroxy-3-(4-hydroxyphenyl)-3-methyl-4-[9-(4,4,5,5,5-pentafluoropentylsulfonylamino)nonyl]chroman Step 1) Synthesis of (3RS,4RS)-7-methoxymethoxy-3-(4-methoxymethoxyphenyl)-3-methyl-4-[9-(4,4,5,5,5-pentafluoropentylamino)nonyl]chroman

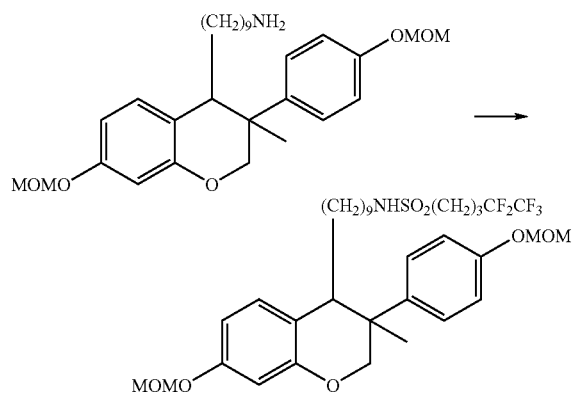

4-(9-aminononyl)-7-methoxymethoxy-3-(4-methoxymethoxyphenyl)-3-methylchroman (82.3 mg, 0.17 mmol) was dissolved in 5 ml of methylenechloride under argon atmosphere, which was then cooled down to 0° C. 4,4,5,5,5-pentafluoropentylsulfonyl chloride (110.4 mg, 0.42 mmol) in 1 ml of methylene chloride and triethylamine (0.07 ml, 0.5 mmol) was added thereto, and the mixture was stirred at the same temperature for 30 minutes. The reaction was quenched with water, and extracted with chloroform. The organic layer was dried over anhydrous magnesium sulfate, and concentrated. The residue was subject to flash chromatography in silica gel (n-hexane:ethyl acetate=5:1) to give the title compound (81 mg, yield: 67%) as a colorless oil.

$^1$H-NMR (270 MHz, CDCl$_3$) δ: 7.13 (d, J=8.9 Hz, 2H, Ar—H), 7.03 (d, J=8.9 Hz, 2H, Ar—H), 6.95 (d, J=9.2 Hz, 1H, C5-H), 6.58–6.54 (m, 2H, Ar—H), 5.18 (s, 2H, OCH$_2$CH$_3$), 5.15 (s, 2H, OCH$_2$CH$_3$), 4.53 (d, J=10.2 Hz, 1H, C2-H), 4.26 (d, J=10.6 Hz, 1H, C2-H), 4.25 (brs, 1H, NH), 3.06–3.13 (m, 4H, CH$_2$—NH and SO$_2$CH$_2$), 3.50 (s, 3H, OCH$_2$CH$_3$), 3.49 (s, 3H, OCH$_2$CH$_3$), 2.6–2.7 (m, 1H, C4-H), 2.38–2.05 (m, 4H, CH$_2$CH$_2$CF$_2$CF$_3$) 1.58–0.94 (m, 19H, C3-CH$_3$ and alkyl-H)

Step 2) Synthesis of (3RS,4RS)-7-hydroxy-3-(4-hydroxyphenyl)-3-methyl-4-[9-(4,4,5,5,5-pentafluoropentylsulfonylamino)nonyl]-chroman

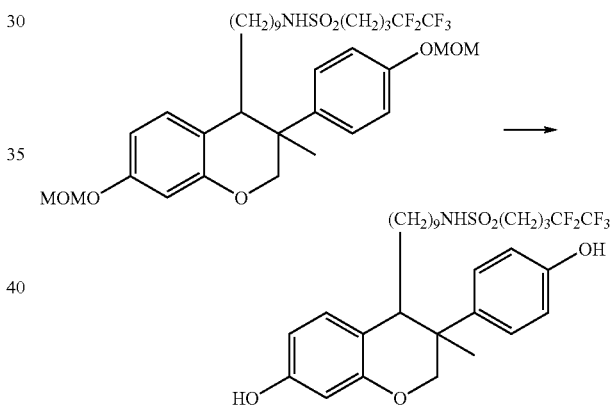

A mixture of (3RS,4RS)-7-hydroxy-3-(4-hydroxyphenyl)-3-methyl-4-[9-(4,4,5,5,5-pentafluoropentylsulfonylamino)nonyl]chroman (81 mg, 0.011 mmol) and 9~10% HCl/MeOH (0.5 ml) was stirred at room temperature for 1 h. To the mixture was added 9~10% HCl/MeOH (0.5 ml) and stirred at room temperature for 24 h. The reaction was quenched with saturated sodium hydrogen carbonate solution and the resulting mixture was extracted with chloroform. The organic layer was dried over anhydrous magnesium sulfate and concentrated. The residue was separated by preparetive TLC (chloroform:MeOH=9:1) to give the title compound (82 mg, yield: 82%) as a colorless oil.

$^1$H-NMR (270 MHz, CDCl$_3$) δ: 7.08 (d, J=8.6 Hz, 2H, Ar—H), 6.90 (d, J=7.9 Hz, 1H, C5-H), 6.84 (d, J=8.6 Hz, 2H, Ar—H), 6.40–6.37 (m, 2H, Ar—H), 5.56 (brs., 1H, Ar—OH), 5.10 (brs., 1H, Ar—OH), 4.53~4.42 (m, 2H, C2-H and NH), 4.23 (d, J=10.6 Hz, 1H, C2-H), 3.14–3.07 (m, 4H, CH$_2$—NH and SO$_2$CH$_2$), 2.65–2.56 (m, 1H, C4-H), 2.38–2.05 (m, 4H, CH$_2$CH$_2$CF$_2$CF$_3$) 1.58–0.95 (m, 19H, C3-CH$_3$ and alkyl-H)

EXAMPLE 64

Synthesis of (3'RS,4'RS)-(E)-3-{4-[7-hydroxy-3-(4-hydroxyphenyl)thiochromen-4-yl]phenyl}propeneoic acid Step 1) Synthesis of 4-(Bromophenyl)-(1,3)-dioxolane.

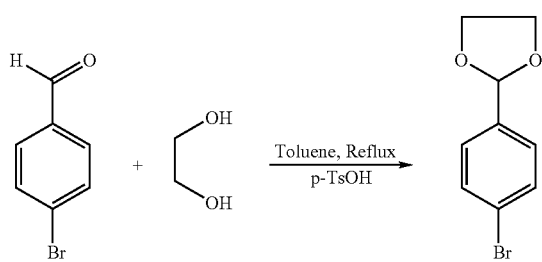

In a round-bottomed flask equipped with a Dean Stark trap and a condenser, was added a solution of p-Bromobenzaldehyde (5 g, 27 mmol) in toluene (25 mL). To this mixture were then added p-toluenesulfonic acid (50 mg, 0.26 mmol) and etylene glycol (1.84 g, 29.7 mmol). The mixture was heated to reflux under nitrogen atmosphere for 8 h. The progress of the reaction was monitored by TLC. When the reaction was complete, the mixture was cooled down, the solvent was removed under reduced pressure, the residue material was distilled to give an oil (5.49 g, 89%).

$^1$H-NMR (300 MHz, CDCl$_3$) δ: 7.50 (2H, d, J=8.3 Hz, Ar—H), 7.34 (2H, d, J=8.3 Hz, Ar—H), 5.77 (s, 1H, Ar—CH), 4.03 (m, 4H, O—CH$_2$)

Step 2) Synthesis of (3'RS,4'RS)-4-{[4-(1,3-dioxolane)-2-ylphenyl]-7-methoxy-3-(4-methoxyphenyl)thiochroman-4-ol

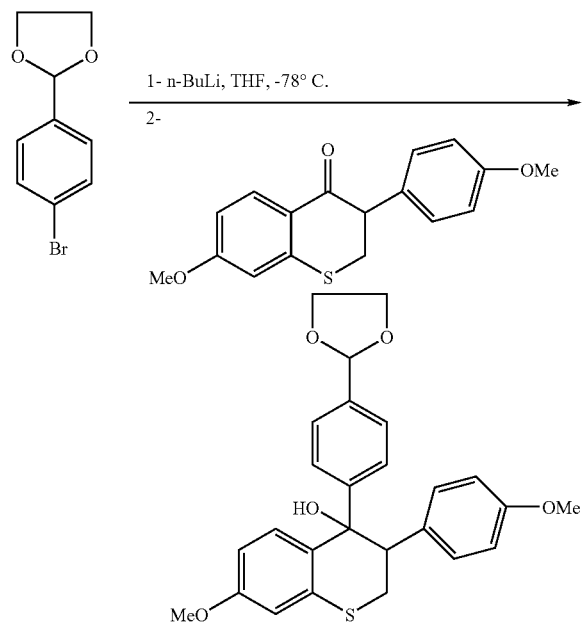

To a solution of 2-[4-(bromophenyl)]-1,3-dioxolane (687 mg, 3 mmol) in THF (15 mL) at 78° C. under nitrogen was added n-Butyllithium (1.61 M solution in hexane, 3.3 mmol, 2.04 mL) dropwise. The reaction mixture was stirred at that temperature for 45 minutes. Chromanone derivative (840 mg, 2.8 mmol) in THF (10 mL) was then added. The reaction mixture was gradually warmed up to room temperature and stirred overnight. Water was added and the organic layer was extracted by ethyl acetate, washed with brine, dried, concentrated under reduced pressure to give 1.51 g of crude mixture. Column chromatography of the mixture (hexane/ethyl acetate: 3/1) gave 995 mg of the title compound (73%).

$^1$H-NMR (300 MHz, CDCl$_3$) δ: 7.3 (2H, d, J=9 Hz, Ar—H), 7.2 (2H, d, J=9 Hz, Ar—H), 6.8~6.4 (7H, m, Ar—H), 5.7 (1H, s, Ar—CH—O), 4.1 (4H, m, oxalane), 3.8 (3H, s, Ar—OMe), 3.7 (4H, m, C2H, Ar—OMe), 3.51 (1H, d, J=10.8 Hz, C3H), 2.86 (1H, dd, J=13,2.3 Hz, C2H), 2.1 (1H, s, OH)

Step 3) Synthesis of (3'RS,4'RS)-{4-[7-methoxy-3-(4-methoxyphenyl)thiochroman-4-yl]phenyl}benzaldehyde

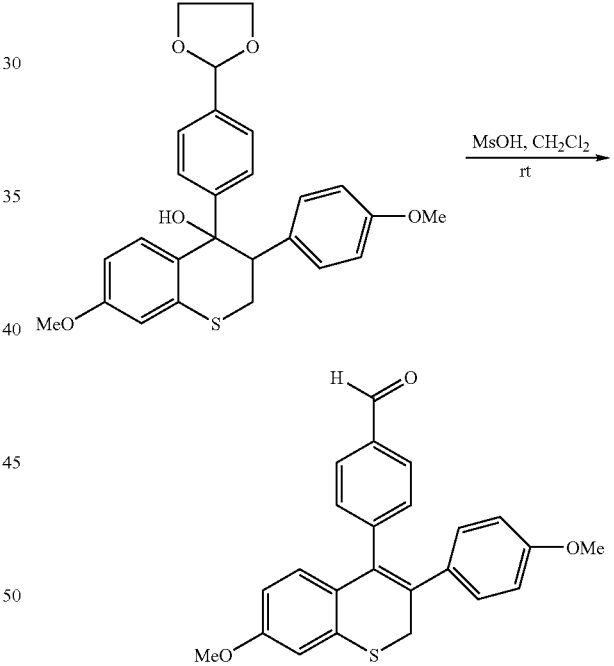

To a solution of chromanol derivative (1 g, 2.2 mmol) in methylene chloride (10 mL) at room temperature was slowly added methaesulfonic acid. The reaction mixture turned red. After about 15 minutes TLC showed the completion of the reaction. Water was added and the aqueous layer was extracted by ethyl acetate. The organic layer was washed with saturated sodium bicarbonate, saturate sodium chloride, dried, concentrated to give 1.31 g of the crude product. Flash chromatography of the crude mixture (Hexane/ethyl acetate: 5/1) formed 0.83 g (97%) of the pure title compound. Spectroscopic analysis of the product showed that both dehydration and deprotection had taken place.

¹H-NMR (300 MHz, CDCl₃) δ: 9.95 (1H, s, aldehyde), 7.72 (2H, d, J=8.3 Hz, Ar—H), 7.2 (2H, d, J=7.9 Hz, Ar—H); 6.9 (3H, m, Ar—H), 6.64 (3h, d, J=8.6 Hz, Ar—H), 6.54 (1H, m, Ar—H), 3.8 (3H, s, Ar—OMe), 3.76 (2H, s, C2H), 3.73 (3H, s, Ar—OMe).

Step 4) Synthesis of (3'RS,4'RS)-(E)-3-{4-[7-methoxy-3-(4-methoxyphenyl)thiochromene-4-yl]phenyl}propeneoic acid

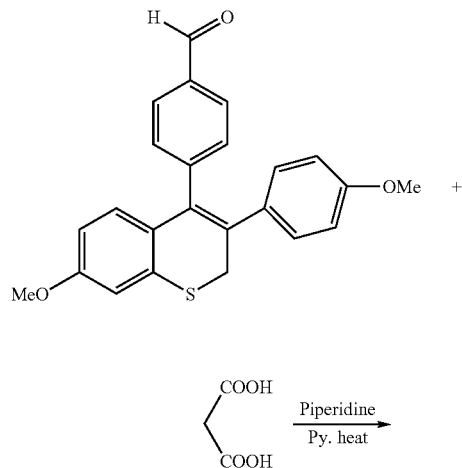

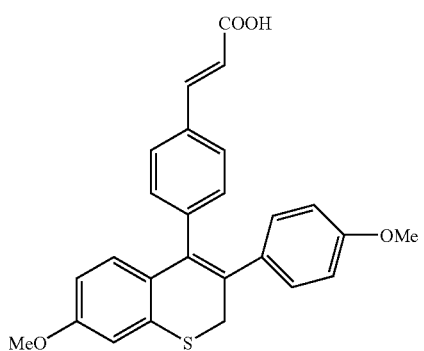

To a solution of thiochromene aldehyde derivative (0.39 g, 1.02 mmol) in pyridine (8 mL), was added malonic acid (321 mg, 3.07 mmol) and piperidine (87.1 mg, 1.02 mmol). The mixture was heated up and stirred at 60° C. for 1 h and at 100° C. for 1.5 h after which TLC showed completion. Ice water was added and the mixture was acidified by 2N HCl to pH 2~3. The reaction mixture was extracted three times by ethyl acetate and the organic layer was washed with brine, dried, concentrated under reduced pressure to give 0.55 g of crude product which was purified by flash chromatography (ethyl acetate) to form 0.43 g (97%) of the desired compound.

¹H-NMR (300 MHz, CDCl₃) δ: 7.25 (1H, d, J=16 Hz, vinyl), 7.4 (2H, d, J=8.2 Hz, Ar—H), 7.06 (2H, d, J=8.2, Ar—H), 6.94 (3H, m, Ar—H), 6.68 ((3H, m, Ar—H), 6.54 (1H, m, Ar—H), 6.4 ((1H, d, i=16 Hz, vinyl), 3.83 (3H, s, Ar—OMe), 3.75 (2H, s, C2H), 3.73 (3H, s, Ar—OMe).

Step 5) Synthesis of (3'RS,4'RS)-(E)-3-{4-[7-hydroxy-3-(4-hydroxyphenyl)thiochromene-4-yl]phenyl}propenoic acid

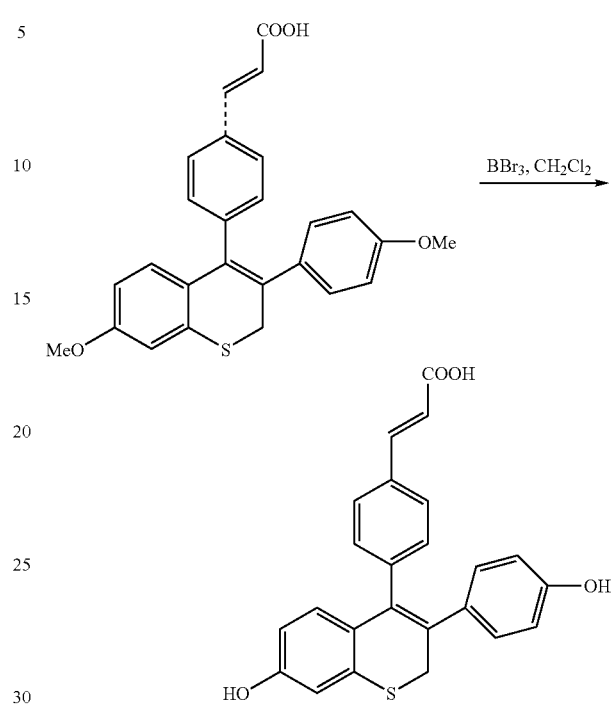

To a solution of thiochromene acid derivative (200 mg, 0.46 mmol) in methylene chloride (5 mL) at 10° C. under nitrogen was added a solution of boron tribromide in methylene chloride (1 M, 1.86 mL). The reaction mixture was stirred at 0° C. for 3 h. When TLC analysis showed the completion of the reaction, water was added and the mixture was acidified to pH 3 with 0.5 N HCl, extracted by ethyl acetate and dried, concentrated to give 0.23 g of the crude mixture. Purification by flash chromatography (MeOH/CH₂Cl₂:1/10) produced 136.5 mg (73%) of the title compound.

¹H-NMR (300 MHz, CDCl₃) δ: 7.63 (1H, d, J=16 Hz, vinyl), 7.54 (2H, d, J=8.0 Hz, Ar—H), 7.06 (2H, d, J=8.0 Hz), 6.9 (3H, m, Ar—H), 6.87 (1H, s, Ar—H), 6.6~6.4 (6H, Ar—H, Ar—OH, vinyl), 3.7 (2H, s, C2H).

EXAMPLE 65

Synthesis of (3'RS,4'RS)-(E)-3-{4-[7-hydroxy-3-(4-hydroxyphenyl)thiochroman-4-yl]phenyl}propeneoic acid Step 1) Synthesis of (4-bromo-benzyloxy)-tert-butyl-dimethyl-silane

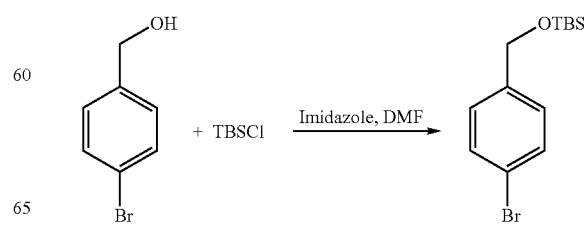

To a solution of p-bromobenzyl alcohol (5.0 g, 26.7 mmol) in DMF (10 mL) was added imidazole (4.54 g, 66.7 mmol) followed by addition of tert-butyldimethylsilyl chloride (6.01 g, 40 mmol). The progress of the reaction was monitored by TLC. When the reaction was complete (about 2 h), methanol was added and diluted by 20% ethyl acetate in hexane. The organic layer was washed several times with water and then with brine, dried, concentrated under reduced pressure to give 7.5 g of the crude product which was passed through a short column chromatography to give 7.3 g (91%) of the desired compound.

$^1$H-NMR (300 MHz, CDCl$_3$) δ: 7.44 (2H, d, J=8.5 Hz, Ar—H), 7.19 (2H, d, J=8.5 Hz, Ar—H), 4.68 (2H, s, benzyl), 0.94 (9H, s, t-Bu), 0.09 (6H, s, Me).

Step 2) Synthesis of (3'RS,4'RS)-4-{[7-methoxy-3-(4-methoxyphenyl)-thiochroman-4-yl]phenyl}methanol

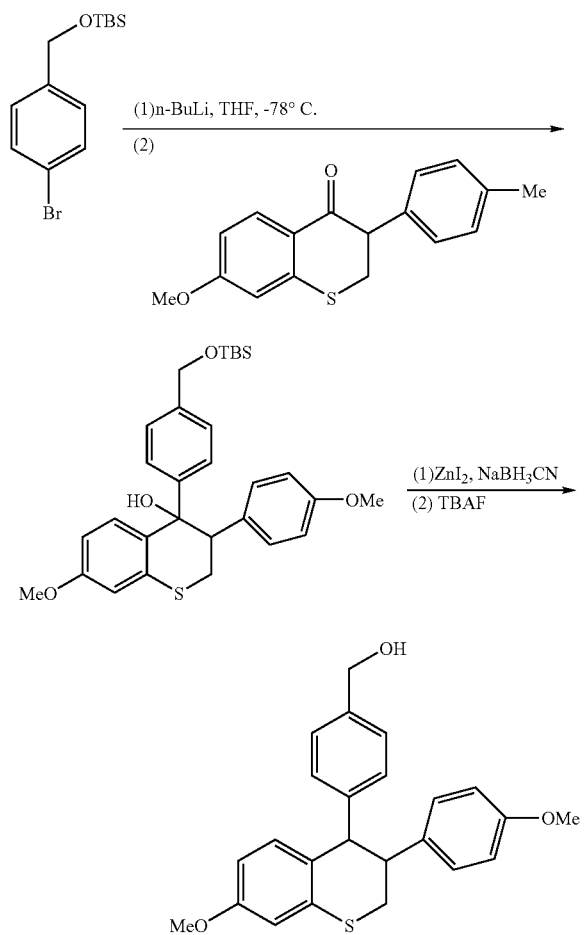

To a solution of (4-bromobenzyloxy)tert-butyldimethylsilane (0.99 g, 3.32 mmol) in THF (15 mL) at 78° C. under nitrogen was added n-butyllithium (1.61 M solution in hexane, 3.32 mmol, 2.06 mL) dropwise. The reaction mixture was stirred at that temperature for 45 minutes. Thiochromanone derivative (0.5 g, 1.66 mmol) in THF (10 mL) was then added. The reaction mixture was gradually warmed up to room temperature and stirred overnight. Water was added and the organic layer was extracted by ethyl acetate washed with brine, dried, and concentrated under reduced pressure to give 1.41 g of crude mixture. After passing through a short column, the mixture which contained the desired product, starting material and some deoxygenated chromenone, was treated with zinc iodide (794 mg, 2.49 mmol) and sodium cyanoborohydride (617 mg, 9.9 mmol) in 1,2-dichloroethane (10 mL). After completion of the reaction, saturated ammonium chloride was added and extracted by 50% ethyl acetate in hexane. Since the desired product and the small impurities were not separated, the mixture was dissolved in THF (10 mL) and treated with a solution of tetrabutylammonium fluoride (1M in THF). When the reaction was complete, the desired product was separated from the by-products by flash chromatography (methylene chloride/ethyl acetate: 25/1) to give 378 mg (55%) of the title compound.

$^1$H-NMR (300 MHz, CDCl$_3$) δ: 7.08 (2H, d, J=8 Hz, Ar—H), 6.9~6.7 (2H, m, Ar—H), 6.6~6.45 (7H, m, Ar—H), 4.6 (2H, s, benzyl-O), 4.2 (1H, d, J=4.5 Hz, C4H), 3.78 (6H, s, Ar—OMe), 3.75~3.54 (2H, m, C2H), 2.8 (1H, d, J=12, C3H).

Step 3) Synthesis of (3'RS,4'RS)-4-[7-methoxy-3-(4-methoxyphenyl)-thiochroman-4-yl]benzaldehyde

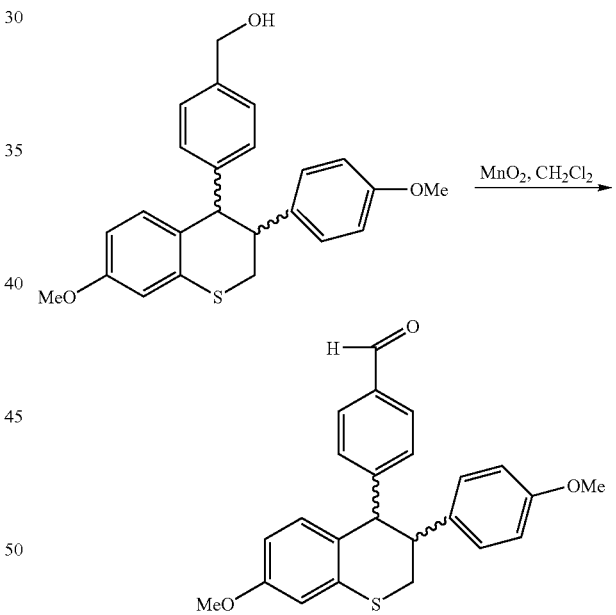

To a solution of thiochroman derivative (320 mg, 0.82 mmol) in methylene chloride (8 mL) was added manganese (IV) oxide (568 mg, 6.5 mmol). The reaction mixture was stirred at room temperature for 5 h. When the reaction was complete, the mixture was diluted with methylene chloride and filtered through a short path of celite. The solvent was removed under reduced pressure to give 312 mg (97%) of the desired compound.

$^1$H-NMR (300 MHz, CDCl$_3$) δ: 9.9 (1H, s, aldehyde), 7.6 (2H, d, J=8.24 Hz, Ar—H), 6.8~6.4 (9H, m, Ar—H), 4.25 (1H, d, J=4.3 Hz, C4H), 3.79 (6H, s, Ar—OMe), 3.60~3.30 (2H, m, C2H), 2.85 (1H, d, J=12.0 Hz, C3H).

Step 4) Synthesis of (3'RS,4'RS)-(E)-3-{4-[7-methoxy-(4-methoxyphenyl)thiochroman-4-yl]phenyl}propeneoic acid

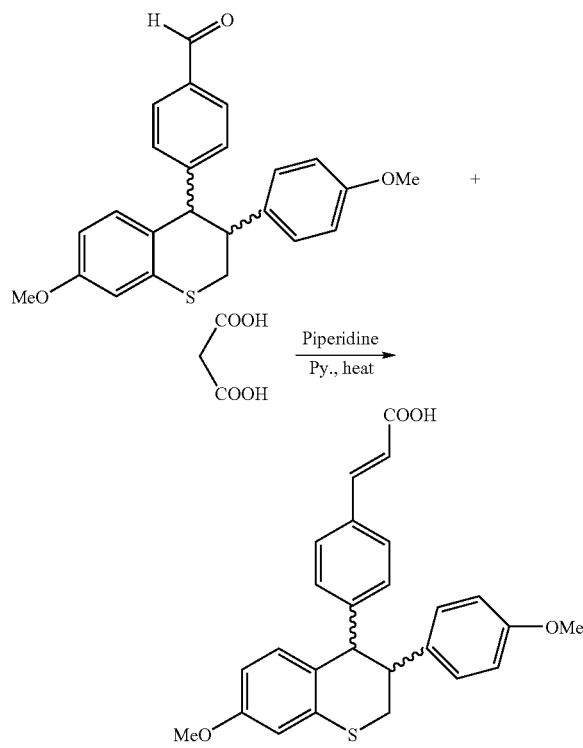

To a solution of thiochroman aldehyde derivative (312 mg, 0.8 mmol) in pyriding (7 mL), was added malonic acid (356 mg, 2.44 mmol) and piperidine (69.0 mg, 0.81 mmol). The mixture was heated up and stirred at 60° C. for 1 h and at 100° C. for 2 h after which TLC showed completion. Ice-water was added and the mixture was acidified by 2 N HCl to pH 2~3. The reaction mixture was extracted three times by ethyl acetate and the organic layer was washed with brine, dried, concentrated under reduced pressure to give 0.55 g of crude product which was purified by flash chromatography (ethyl acetate) to form 0.384 g (82%) of the desired compound.

$^1$H-NMR (300 MHz, CDCl) δ: 7.68 (1H, d, J=16H, vinyl), 6.8~6.5 (11H, m, Ar—H), 6.3 (1H, d, J=16, vinyl), 4.22 (1H, d, J=3.6, C4H), 3.79 (6H, s, Ar—OMe), 3.55 (1H, m, C2H), 3.4 (1H, t, J=12 Hz, C2H ), 2.82 (1H, d, J=12 Hz, C3H).

Step 5) Synthesis of (3'RS,4'RS)-(E)-3-{4-[7-hydroxy-3-(4-hydroxyphenyl)thiochroman-4-yl]phenyl}propeneoic acid

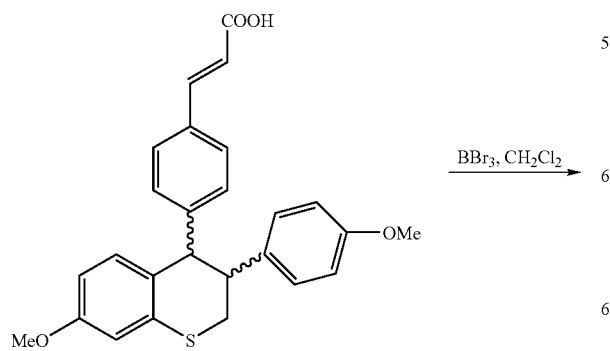

To a solution of thiochroman acid derivative (250 mg, 0.58 mmol) in methylene chloride (7.5 mL) at 10° C. under nitrogen was added a solution of boron tribromide in methylene chloride (1 M, 2.32 mL). The reaction mixture was stirred at 0° C. for 3 h. When TLC analysis showe the completion of the reaction, water was added and the mixture was acidified to pH 3 by 0.5 N HCl, extracted by ethyl acetate, dried, and concentrated to give 0.23 g of the crude mixture. Purification by flash chromatography (MeOH/CH$_2$Cl$_2$:1/10) produced 220 mg (94%) of the final product.

$^1$H-NMR (300 MHz, CDCl$_3$) δ: 7.68 (1H, d, J=16 Hz, vinyl),), 7.6~7.4 (3H, m, Ar—H), 7.15~6.6 (10H, m, Ar—H, Ar—OH) 6.3 (1H, d, J=16 Hz, vinyl), 4.32 (1H, d, J=3.6, C4H), ), 3.55 (1H, m, C2H), 3.4 (1H, t, J=12 Hz, C2H ), 2.85 (1H, d, J=12 Hz, C4H).

EXAMPLE 66

Synthesis of (3'RS,4'RS)-(E)-3-{4-[7-hydroxy-3-(4-hydroxyphenyl)-3-methylthiochroman-4-yl]phenyl}propeneoic acid Step 1) Synthesis of (3'RS,4'RS)-4-{[(tert-butyl-dimethyl-silanyloxy)methylphenyl]-7-methoxy-3-(4-methoxyphenyl)}-3- methylthiochroman

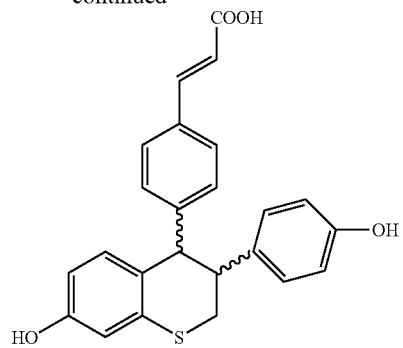

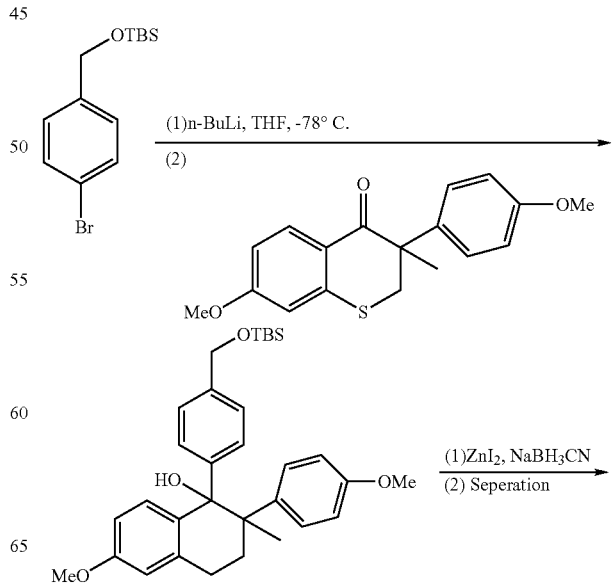

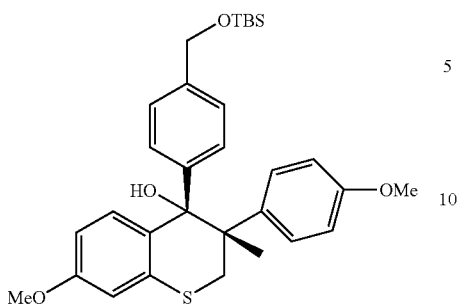

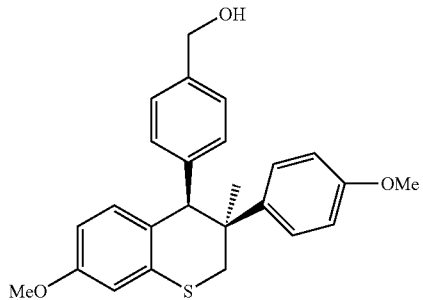

To a solution of (4-bromobenzyloxy)(tert-butyl)(dimethyl) silane (1.8 g, 6.0 mmol) in THF (30 mL) at 78° C. under nitrogen was added n-butyllithium (1.61 M solution in hexane, 6.0 mmol, 3.72 mL) dropwise. The reaction mixture was stirred at that temperature for 45 minutes. Thiochromanone derivative (0.94 g, 3.0 mmol) in THF (30 mL) was then added. The reaction mixture was gradually warm up to room temperature and stirred overnight. Water was added and the organic layer was extracted by ethyl acetate, washed with brine, dried, and concentrated under reduced pressure to give 2.53 g of the crude mixture. The crude mixture was purified by column chromatography (25% ethyl acetate-hexane) to remove the starting material and by-products and obtain 1.45 g (79%) of the desired compound. A portion of this compound (0.8 g, 1.5 mmol) was treated with zinc iodide (620 mg, 1.94 mmol) and sodium cyanoborohydride (612 mg, 9.7 mmol) in 1,2-dichloro ethane (25 mL). After completion of the reaction, saturated ammonium chloride was added and extracted by 50% ethyl acetate-hexane to form 0.82 g of the crude product which was a mixture of cis and trans compounds. Separation of the mixture by flash chromatography (hexane:ethyl acetate 10;1) gave 390 mg of the major (trans) and 180 mg of the minor (cis) compound (desired).

$^1$H-NMR (cis) (300 MHz, CDCl$_3$) δ: 7.35 (2H, d, J=9.0 Hz, Ar—H), 7.17 (2H, d, J=7.7 Hz, Ar—H), 7.12 (2H, d, J=8.2 Hz, Ar—H), 6.85 (2H, d, J=8.8 Hz), 6.79~6.69 (3H, m, Ar—H), 4.71 (1H, s, C4H), 3.75 (3H, s, Ar—OMe), 3.68 (3H, s, Ar—OMe), 3.21 (1H, d, J=12 Hz, C2H), 3.08 (1H, d, J=12 Hz, C2H), 1.17 (3H, s, C3Me), 0.94 (9H, s, t-Bu), 0.09 (6H, s, Si(Me)2).

Step 2) synthesis of (3'RS,4'RS)-4-{[7-methoxy-3-(4-methoxyphenyl)-3-methylthiochroman-4-yl]phenyl}methanol

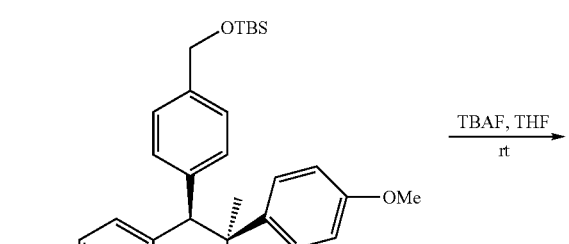

The minor (cis) compound obtained in the previous experiment (180 mg, 0.3 mmol) was dissolved in THF (5 mL) and treated with a 1 mL of a solution of tetrabutylammonium fluoride (1 M in THF). When the reaction was complete, the desired product was separated from the by-products by flash chromatography (hexane/ethyl acetate: 3/2) to give 93 mg (76%) of the desired compound $^1$H-NMR (300 MHz, CDCl$_3$) δ: 7.02 (2H, d, J=9.1 Hz, Ar—H), 6.94 (2H, d, J=8.2 Hz, Ar—H), 6.85 (2H, d, J=8.5 Hz, Ar—H), 6.79–6.73 (3H, m, Ar—H), 4.49 (2H, s, benzyl-O), 3.76 (6H, s, Ar—OMe), 3.69 (11H, d, J=12.3 Hz, C2H), 2.71 (1H, d, J=12.3 Hz, C2H), 1.61 (3H, s, C3Me).

Step 3) Synthesis of (3'RS,4'RS)-4-[7-methoxy-3-(4-methoxyphenyl)-3-methylthiochroman-4-yl]benzaldehyde

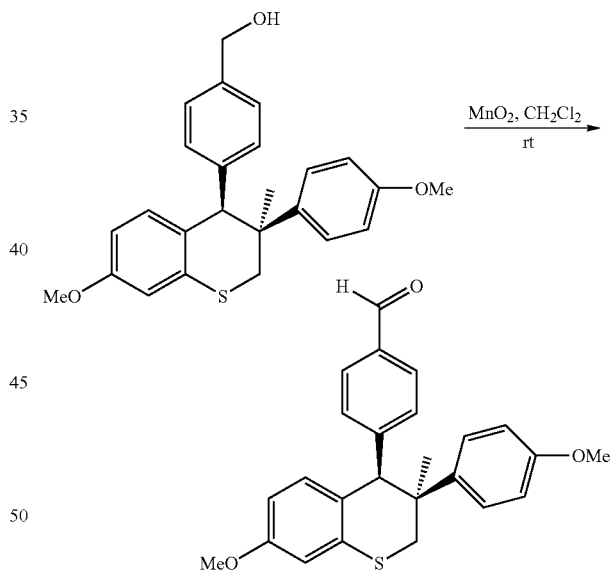

To a solution of alcohol thiochroman derivative (930 mg, 0.23 mmol) in methylene chloride (2 mL) was added manganese(IV) oxide (160 mg, 1.84 mmol). The reaction mixture was stirred at room temperature for 5 h. When the reaction was complete, the mixture was diluted with methylene chloride and filtered through a short path of celite. The solvent was removed under reduced pressure to give 88 mg (96%) of the desired compound.

$^1$H-NMR (300 MHz, CDCl$_3$) δ: 9.83 (1H, s, aldehyde), 7.47 (2H, d, J=8.3 Hz, Ar—H), 7.01 (2H, d, J=9.1 Hz, Ar—H), 6.85~6.72 (6H, m, Ar—H), 6.53 (1H, d, J=8.51 Hz, Ar—H), 4.07 (1H, s, C4H), 3.79 (3H, s, Ar—OMe), 3.77 (3H, s, Ar—OMe), 3.67 (1H, d, J=14.0 Hz, C2H), 2.74 (1H, d, J=14.0 Hz, C2H), 1.58 (3H, s, C3Me).

Step 4) Synthesis of (3'RS,4'RS)-(E)-3-{4-[7-methoxy-3-(4-methoxyphenyl)-3-methylthiochroman-4-yl]phenyl}propeneoic acid

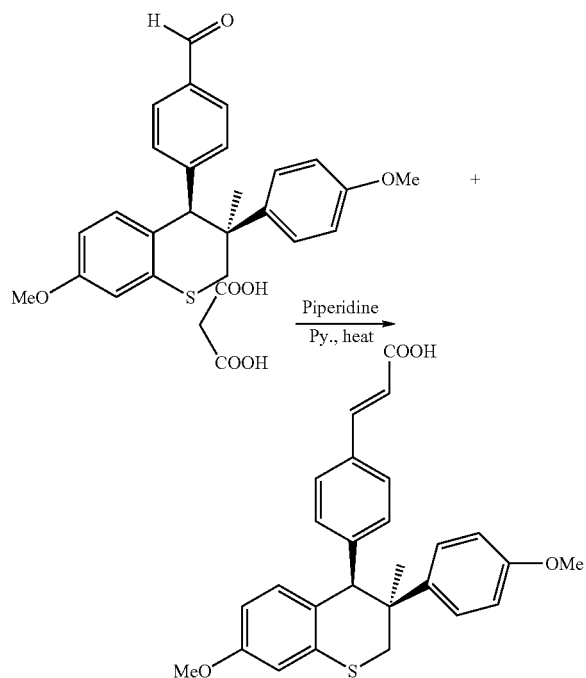

To a solution of thiochroman aldehyde derivative (88 mg, 0.23 mmol) in pyridine (2 mL), were added malonic acid (256 mg, 2.44 mmol) and piperidine (68.0 mg, 0.6 mmol). The mixture was heated up and stirred at 60° C. for 1 h and at 100° C. for 2 h after which TLC showed completion. Ice-water was added and the mixture was acidified by 2N HCl to pH 2~3. The reaction mixture was extracted three times with ethyl acetate and the organic layer was washed with brine, dried, and concentrated under reduced pressure to give 91 mg of crude product which was purified by flash chromatography (ethyl acetate) to provide 91 mg (94%) of the desired compound.

$^1$H-NMR (300 MHz, CDCl$_3$) δ: 7.59 (1H, d, J=16 Hz, vinyl), 7.14 (2H, d, J=9.0 Hz, Ar—H), 7.03 (2H, d, J=9.1 Hz, Ar—H), 6.86~6.74 (4H, m, Ar—H), 6.60~6.54 (3H, m, Ar—H), 6.27 (1H, d, J=16 Hz, vinyl), 4.01 (1H, s, C4H), 3.78 (6H, s, Ar—OMe), 3.69 (1H, d, J=12.2 Hz, C2H), 2.74 (1H, d, J=12.2 Hz, C2H), 1.58 (3H, s, C3-Me).

Step 5) Synthesis of (3'RS,4'RS)-(E)-3-{4-[7-hydroxy-3-(4-hydroxyphenyl)-3-methylthiochroman-4-yl]phenyl}propeneoic acid

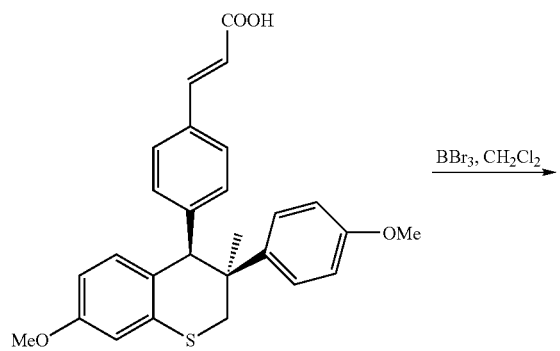

To a solution of thiochronian acid derivative (90 mg, 0.2 mmol) in methylene chloride (2.5 mL) at 10° C. under nitrogen was added a solution of boron tribromide in methylene chloride (1 M, 0.8 mL). The reaction mixture was stirred at 0° C. for 3 h. When TLC analysis showed the completion of the reaction, water was added and the mixture was acidified to pH 3 with 0.5 N HCl, extracted by ethyl acetate, dried, and concentrated to give 88.0 mg of the crude mixture. Purification by flash chromatography (MeOH/CH$_2$Cl$_2$:1/10) produced 71 mg (85%) of the final product.

$^1$H-NMR (300 MHz, CDCl$_3$) δ: 8.15 (1H, s, Ar—OH), 7.69~7.60 (3H, m, Ar—H, vinyl), 7.43~7.34 (4H, m, Ar—H), 6.83 (1H, d, J=8.24 Hz, Ar—H), 6.69 (2H, d, 15 Hz, Ar—H), 6.50 (2H, m, Viny, Ar—OH), 6.37 (1H, dd, J=6.9, 3 Hz, Ar—H), 4.68 (1H, s, C4H), 3.22 (2H, m, C2H), 1.16 (3H, s, C3Me).

EXAMPLE 67

Synthesis of (3'RS,4'RS)-N-[2-(4,4,5,5,5-pentafluoropentylsulfinyl)]ethyl-4-{4-[7-hydroxy-3-(4-hydryoxyphenyl)3-methylchroman-4-yl]butyl}phenyl-N-methylamine Step 1) Synthesis of 2-[(4-bromophenyl)methylamino]ethanol

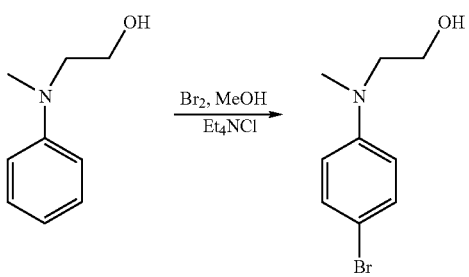

To a solution of 2-(N-methylanilino)ethanol (0.76 g, 5 mmol) in methylene chloride (5 mL) were added tetraethylammonium chloride (83.0 mg, 0.5 mmol) and 0.1 mL of methanol. While stirring, a solution of bromine (0.8 g, 5 mmol) in methylene chloride (5 mL) was added slowly in a period of 5 minutes. When the color of the bromine persisted, triethylamine (0.75 mL) was added dropwise. The reaction mixture was diluted by ethyl acetate, washed with saturated sodium bicarbonate and brine, dried, and concentrated under reduced pressure to give 1.31 g of crude product which contained some 2,6-dibromo derivative. Flash chromatography of the crude mixture (35% ethyl acetate/hexane) gave 0.87 g (75%) of the desired product.

$^1$H-NMR (300 MHz, CDCl$_3$) δ: 7.28 (2H, d, 9 Hz, Ar—H), 6.65 (2H, d, J=9 Hz, Ar—H), 3.79 (2H, t, J=5.5 Hz, N—CH$_2$), 3.45 (2H, t, J=5.5 Hz, O—CH$_2$), 2.94 (3H, s, N-Me), 1.64 (1H, br s, OH).

Step 2) Synthesis of (4-bromophenyl)methyl[(tert-bytyldimethylsilanyloxy)ethyl]amine

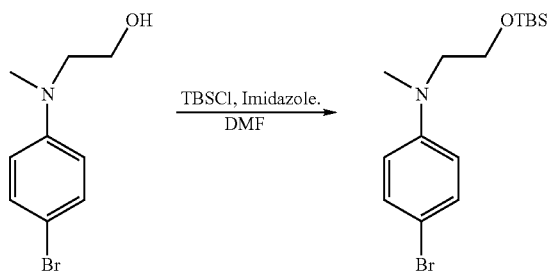

To a solution of 2-(N-methyl-4-bromoamino)ethanol (0.62 g, 2.7 mmol) in DMF (1.5 mL) was added imidazole (0.46 g, 6.7 mmol) followed by addition of tert-butyldimethylsilyl chloride (0.48 g, 3.2 mmol). The reaction mixture was stirred at room temperature and the progress of the reaction was monitored by TLC. When the reaction was complete (about 2 h), methanol was added and diluted by 20% ethyl acetate-hexane. The organic layer was washed with water several times and brine, dried, and concentrated under reduced pressure to give 0.99 g of the crude product which was purified by flash chromatography (5% ethyl acetate in hexane) to give 0.88 g (95%) of the desired compound.

$^1$H-NMR (300 MHz, CDCl$_3$) δ: 7.27 (2H, d, 9 Hz, Ar—H), 6.57 (2H, d, J=9 Hz, ArH), 3.79 (2H, t, J=6.0 Hz, N—CH$_2$), 3.45 (2H, t, J=6.0 Hz, O— CH$_2$), 2.95 (3H, s, N-Me), 0.87 (9H, s, t-BuSi), 0.01 (6H, s, Me-Si).

Step 3) Synthesis of [4-allylphenyl-N-(tert-butyldimethylsilanyloxy)ethyl-N-methyl]amine

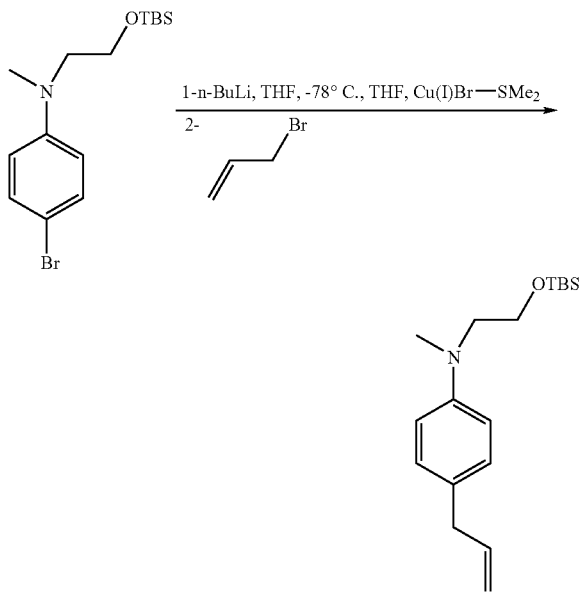

To a solution of bromoaniline derivative (344 mg, 1 mmol) in THF (10 mL) at −78° C. under mitrogen, was added n-butyllithium (1.54 M solution in hexane, 0.71 mL, 1.1 mmol) and stirred at that temperature for 45 minutes. Solid copper(II) bromide-dimehylsulfide complex (205.6 mg, lmmol) was added and the reaction mixture was stirred at 78° C., for 2 h. Allyl bromide (241 mg, 2 mmol) in THF (2 mL) was added dropwise and when the addition was complete, the reaction mixture was warmed up to room temperature and saturated ammonium chloride was added and was extracted by 50% ethyl acetate in hexane. The, organic layer was washed with brine and dried over magnesium sulfate and concentrated under reduced pressure to give 390 mg of a crude mixture. Flash chromatography of (5% ethyl acetate in hexane) produced 256 mg (84%) of the desired compound.

$^1$H-NMR (300 MHz, CDCl$_3$) δ: 7.05 (2H, d, 9.0 Hz, Ar—H), 6.66 (2H, d, J=9.0 Hz, Ar—H), 5.95 (1H, allyl), 5.03 (2H, allyl), 3.76 (2H, t, J=6.3 Hz, N—CH$_2$), 3.44 (2H, t, J=6.3 Hz, O—CH$_2$), 3.35 (d, J=6.6 Hz, Ar—CH$_2$), 2.96 (3H, s, N-Me), 0.89 (9H, s, t-BuSi), 0.02 (6H, s, Me-Si).

Step 4) Synthesis of N-[2-(tert-butyldimethylsilanyloxy)] ethyl-N-methyl-4-{(3'RS,4'RS)-4-[7-methoxymethoxy-3-(4-methoxymethoxyphenyl)-3-methylchroman-4-yl] butyl}phenylamine

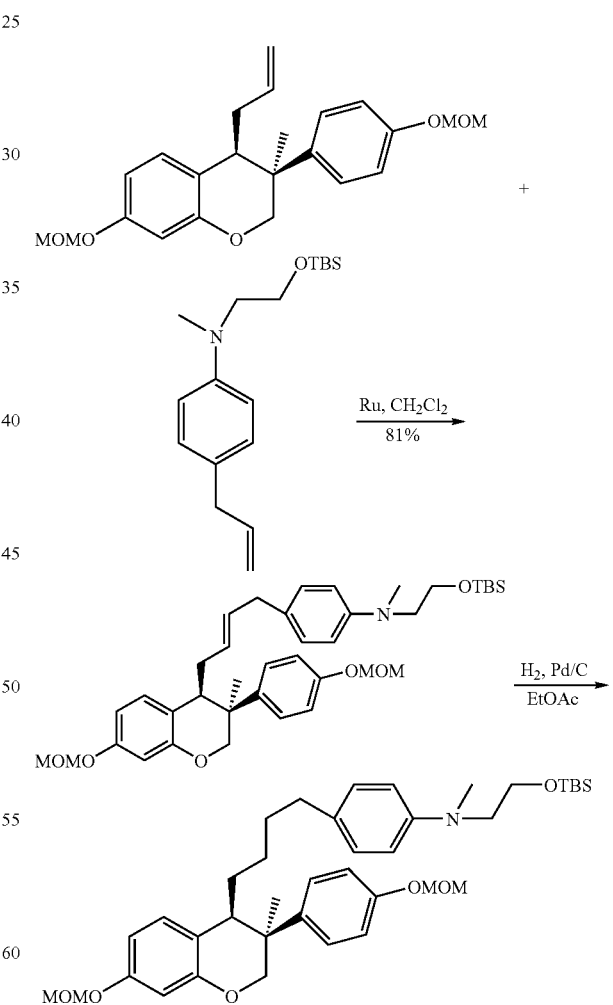

A solution of allyl chroman derivative (154 mg, 0.4 mmol), ally aniline (247 mg, 0.8 mmol) and benzylidine-bis(tricyclohexylphosphine)-dichlororuthenium (15 mg, 10 mol %) in methylene chloride (5 mL) was refluxed under nitrogen. When the starting material disappeared, the solvent was removed. Flash chromatography of the crude mixture gave 355 mg (83%) of the desired compound as the main product. To this compound in ethyl acetate (2 mL) was added 10% palladium on charcoal (180 mg, 50% w/w). The reaction mixture was stirred at room temperature for 2 h. When the reaction was complete, it was diluted by ethyl acetate and filtered through celite. The solvent was removed under reduced pressure to give 346 mg (81% overall) of the desired product.

$^1$H-NMR (300 MHz, CDCl$_3$) δ: 7.12 (2H, d, J=9.0 Hz, Ar—H), 7.023 (2H, d, J=9.0 Hz, Ar—H), 6.9 (3H, m, Ar—H), 6.6~6.4 (4H, m, Ar—H), 5.18 (2H, s, Ar—OCH$_2$), 5.15 (2H, s, Ar—OCH$_2$), 4.53 (1H, d, J=10.4 Hz —OCH$_2$), 4.24 (1H, d, J=10.4 Hz, -C2H), 3.72 (2H, t, J=6.6, 6.6 Hz, N—CH$_2$), 3.51 (6H, s, OMe), 3.41 (2H, t, J=6.6 Hz, 6.6 Hz, —SiOCH$_2$), 2.95 (3H, s, N-Me), 2.64 (1H, brs, C4H), 2.31 (2H, brm, N—Ar—CH$_2$—), 1.28 (6H, m, (CH$_2$)$_2$, 0.89 (9H, s, t-BuSi), 0.02 (6H, s, Me-Si).

Step 5) Synthesis of 4-{(3'RS,4'RS)-4-[7-methoxymethoxy-3-(4-methoxymethoxyphenyl)-3-methylchroman-4-yl]butyl}phenyl-N-methylamino ethanol

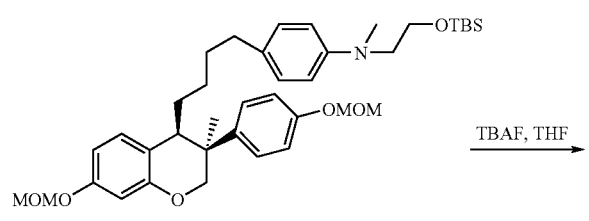

TBAF, THF

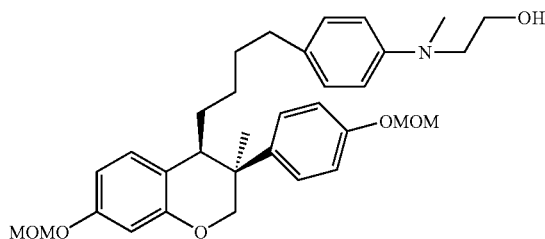

A solution of the chroman derivative (550 mg, 0.83 mmol) was dissolved in THF (5 mL) and treated with a 1.7 mL of a solution of tetrabutylammonium fluoride (1 M in THF). When the reaction was complete, the reaction mixture was diluted with ethyl acetate. A column chromatography gave 390 mg (86%) of the desired compound.

$^1$H-NMR (300 MHz CDCl$_3$) δ: 7.19 (2H, d, J=9.0 Hz, Ar—H), 7.03 (2H, d, J=9.0 Hz, Ar—H), 6.9 (3H, m, Ar—H), 6.72 (2H, d, J=9 Hz, Ar—H), 6.55 (2H, m, Ar—CH), 5.18 (2H, s, Ar—OCH$_2$), 5.15 (2H, s, Ar—OCH$_2$), 4.53 (1H, d, J=10.4 Hz, —C2H), 4.24 (1H, d, J=10.4 Hz, -C2H), 3.75 (2H, t, J=6.6 Hz, N—CH$_2$), 3.50 (6H, s, OMe), 3.41 (2H, t, J=6.6 Hz, OCH$_2$), 2.95 (3H, s, NMe), 2.62 (1H, brs, C4H), 2.39 (2H, brm, N—Ar—CH2-), 1.28 (6H, m, (CH2)2.

Step 6) Synthesis of 4-{(3'RS,4RS)-4-[7-methoxymethoxy-3-(4-methoxymethoxyphenyl)-3-methylchroman-4-yl]butyl}phenyl-N-methylaminoethylsulfonate

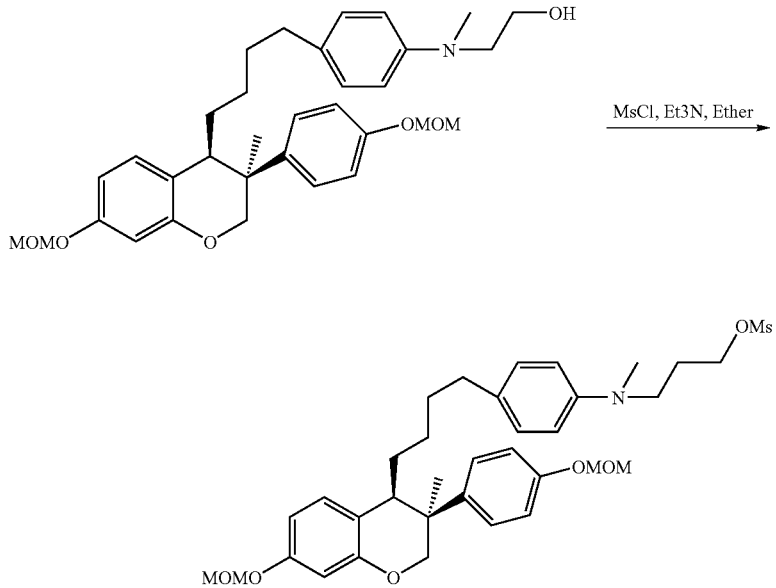

To a solution of chroman alcohol derivative (390 mg, 0.71 mmol) in ether (3.5 mL) at 0° C. was added triethylamine (135 μl, 0.97 mmol) followed by addition of methanesulfonyl chloride (64 μl, 0.83 mmol). After 30 minutes the reaction was complete. The reaction was quenched with water and extracted with ether, washed with 1N HCl, saturated sodium bicarbonate, and brine. The organic layer was dried over magnesium sulfate and concentrated under reduced pressure to give 412 mg of the crude product which was passed through a short column (50% ethyl acetate in hexane) to give 401 mg (92%) of the mesylated compound.

$^1$H-NMR (300 MHz, CDCl$_3$) δ: 7.12 (2H, d, J=8.8 Hz, Ar—H), 7.03 (2H, d, J=9.0 Hz, Ar—H), 5.18 (2H, s, Ar—OCH$_2$), 5.15 (2H, s, Ar—OCH$_2$), 4.53 (1H, d, J=10.4 Hz, -C2H), 4.35 (2H, t, J=6.0 Hz, Ar—N—CH$_2$), 4.25 (1H, d, J=10.4 Hz, -C2H), 3.5 (2H, t, J=6.0 Hz, MsOCH$_2$), 3,49 (6H, s, OMe), 2.96 (3H, s, Nme), 2.96 (sH, s, CH$_3$-methane), 2.63 (1H, brd, C4H) 2.32 (2H, Bankrupt, J=6.9 Hz, N—Ar—CH$_2$—), 1.26 (6H, m, (CH$_2$)$_2$).

Step 7) Synthesis of N-[2-(4,4,5,5,5-pentafluoropentylsulfano)ethyl-4-{4-[(3'RS,4'RS)-7-methoxymethoxy-3-(4-methoxymethoxyphenyl)-3-methylchroman-4-yl]butyl}phenyl-N-methylamine To a solution of thioacetate (0.87 g, 3.66 mmol) in methanol (2 mL) at room temperature under nitrogen was added a 1 M solution of sodium methoxide (1.28 mL) and the mixture was stirred for 30 minutes. A solution of previously prepared mesylate (0.401 g, 0.64 mmol) in THF (2 mL) was added to the above solution dropwise in a period of 10 minutes. The reaction mixture was stirred overnight. Wen the reaction was complete, the mixture was diluted with ethyl acetate and was adjusted to pH 6 using 50% aqueous aetic acid. The reaction mixture was then poured into ice-water and extracted with ethyl acetate. The organic layer was washed with brine, dried, and concentrated under reduced pressure to give 430 g of the crude product. Flash chromatography (25% ethyl acetate in hexane) resulted in 0.38 g (81%) of the pure product.

$^1$H-NMR (300 MHz, CDCl$_3$) δ: 7.19 (2H, d, J=8.2 Hz, Ar—H), 7.03 (2H, d, J=8.9 Hz, Ar—H), 6.91 (3H, m, Ar—H), 6.57 (4H, m, Ar—H), 5.18 (2H, s, Ar—OCH$_2$), 5.15 (2H, s, Ar—OCH$_2$), 4.53 (1H, d, J=9.9 Hz, -C2H), 4.31 (1H, d, J=9.9 Hz, -C2H), 3.52~3.46 (8H, m), 2.93 (3H, s, N-Me), 2.71~2.61 (6H, m), 2.4~1.8 (9H, m), 1.25 (4H, m).

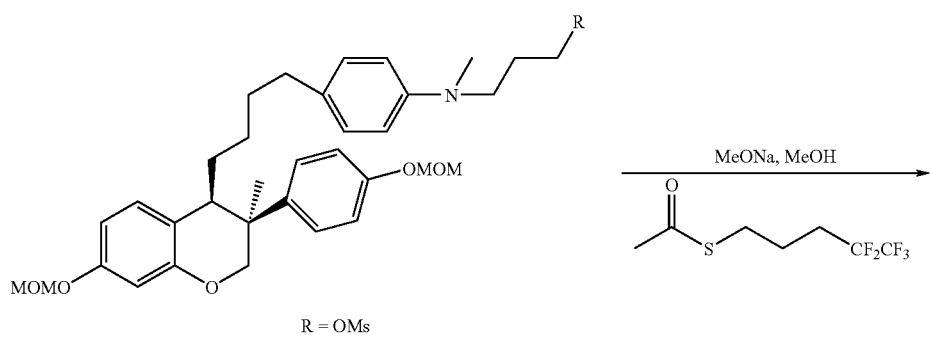

R = OMs

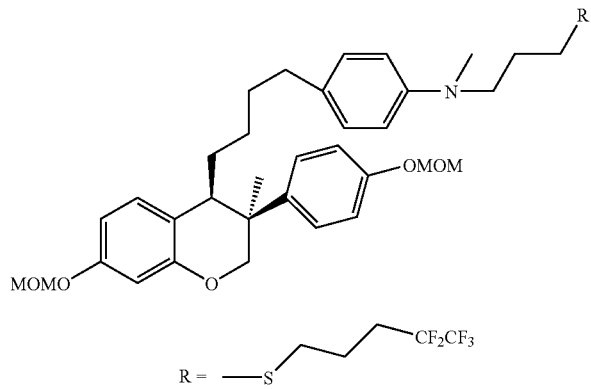

R = —S~~~CF$_2$CF$_3$

Step 8) Synthesis of N-[2-(4,4,5,5,5-pentafluoro-pentyl-sulfenyl)]ethyl-4-(3'RS,4'RS)-4-[7-hydroxy-3-(4-hydryoxyphenyl)-3-methylchroman-4-yl]butyl}phenyl-N-methylamine

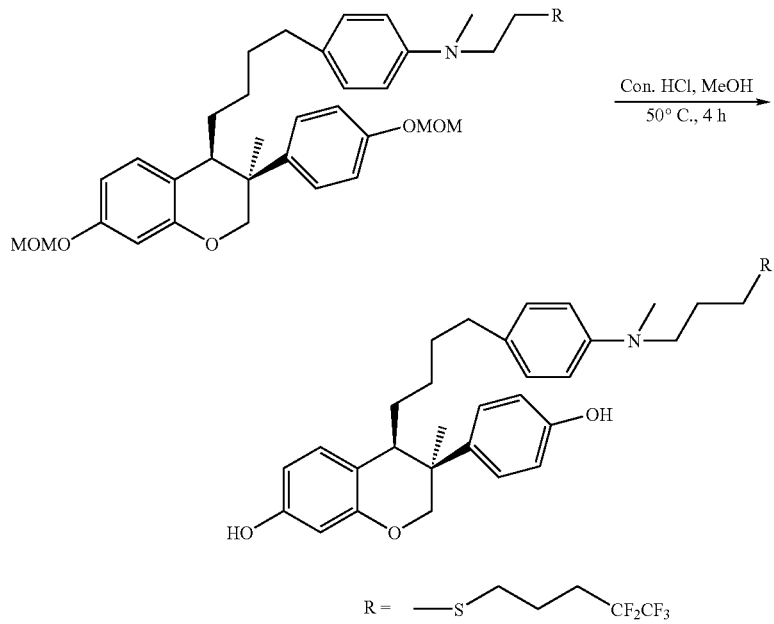

To a solution of the sulfide (302 mg, 0.42 mmol) in methanol (4 mL) was added concentrated hydrochloric acid (138 μl, 1.66 mmol) and the reaction mixture was warmed up gradually to 50° C. After 5 h the reaction was quenched by adding water. The organic layer extracted with ethyl acetate was washed with brine, dried and concentrate to afford 370 mg of a crude mixture. Flash chromatography (30% ethyl acetate in hexane) resulted in 261 mg (98%) of the pure product.

$^1$H-NMR (300 MHz, CDCl$_3$) δ: 7.05 (2H, d, J=8.8 Hz, Ar—H), 6.90 (2H, d, J=8.5 Hz, Ar—H), 6.82 (3H, m, Ar—H), 6.60 (2H, d, J=8.8 Hz, Ar—H), ), 6.34 (2H, m, Ar—H), 4.80 (1H, brs, OH, Ar—OH), 4.75 (1H, brs, Ar—OH), 4.50 (1H, d, J=10.4 Hz, -C2H), 4.22 (1H, d, J=10.4 Hz, —C2H), 3.49 (2H, m), 2.93 (3H, s, N-Me), 2.63 (5H, m), 2.40~1.8 (6H, m), 1.4~1.1 (6H, m, alkyl, C3Me)

Step 9) Synthesis of N-[2-(4,4,5,5,5-pentafluoropentylsulfinyl)]ethyl-4-{(3'RS,4'RS)-4-[7-hydroxy-3-(4-hydryoxyphenyl)-3-methylchroman-4-yl]butyl}phenyl-N-methylamine

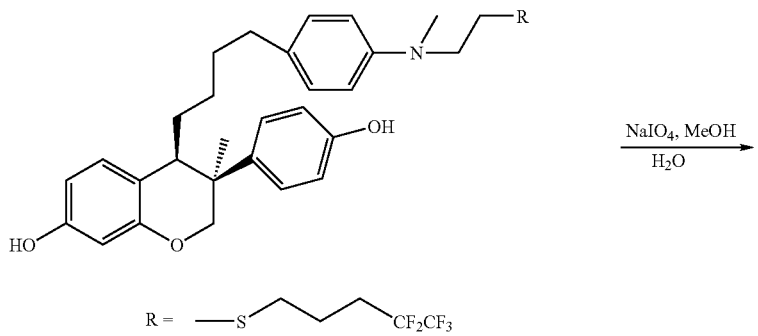

-continued

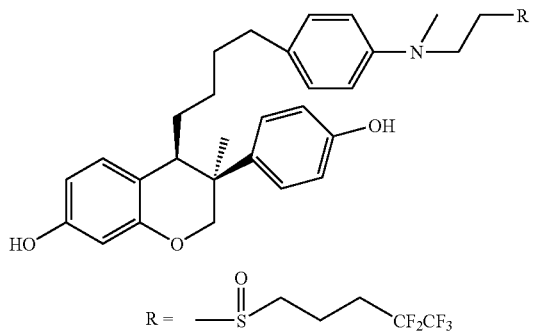

R = —S(=O)—CH2CH2CH2—CF2CF3

To a solution of sulfide (189 mg, 0.3 mmol) in methanol (3 mL) and water (0.6 mL) was added solid sodium periodate (127 mg, 0.6 mmol) and the reaction was stirred for 1.5 hour at room temperature. When the starting material disappeared, the solvent was removed under reduced pressure. Saturated ammonium chloride was added and the reaction mixture was extracted by ethyl acetate. The organic layer was dried over magnesium sulfate and concentrated under reduced pressure to give 192 mg of a crude product, which was purified by flash chromatography to give 180 mg (95%) of the final product.

$^1$H-NMR (300 MHz, CDCl$_3$) δ: 7.04 (2H, d, J=8.2 Hz, Ar—H), 6.85 (2H, d, J=8.8 Hz, Ar—H), 6.83~6.63 (7H, m, Ar—H+Ar—OH), 6.44~6.28 (3H, m, Ar—H+Ar—OH), 6.07 (1/2 H, brs, Ar—OH), 5.67 (1/2 H, brs, Ar—OH), 4.54 (1H, d, J=10.5 Hz, C2H), 4.24 (1H, d, J=10.5 Hz, C2H), 3.80 (2H, m, CH$_2$CF$_2$), 3.01~2.2 (14H, m, N-Me, alkyl, CH$_2$—SO), 1.4~1.1 (9H, m, alkyl, C3-Me).

EXAMPLE 68

Synthesis of 6-{4-[(3RS,4RS)-7-hydroxy-3-(4-hydroxyphenyl)3-methylchroman-4-yl]phenoxy)-2-(4,4,5,5,5-pentafluoropentyl)hexanoic acid Step 1) Synthesis of (4,4,5,5,5-pentafluoropentyl)malonic acid diethyl ester C$_2$F$_5$—CH$_2$CH$_2$CH$_2$—I → C$_2$F$_5$—CH$_2$CH$_2$CH$_2$—CH(CO$_2$Et)$_2$ To a solution of 1-iodo-(4,4,5,5,5-pentafluoropentane (18.0 g, 0.06 mol) in tetrahydrofuran (180 ml) was added sodium hydride (3.5 g, 0.08 mol), which was then stirred for 30 minutes at room temperature. Diethylmalonate (15.0 g, 0.09 mol) was added to this reaction mixture and the reaction mixture was stirred overnight at room temperature. When the reaction was completed, water was added to the reaction mixture and extracted with ethyl acetate. Then, the organic layer was washed with water and saturated sodium chloride solution. The extract was dried over anhydrous magnesium sulfate and concentrated under reduced pressure. The residue was subjected to silica gel column chromatography (n-hexane:ethyl acetate=15:1) to give the title compound (16.3 g, yield: 82%) as a colorless liquid.

$^1$H-NMR (270 MHz, CDCl$_3$) δ: 3.94 (q, J=7.0 Hz, 4H), 3.07 (t, J=7.2 Hz, 1H), 1.88–1.66 (m, 4H), 1.43–1.32 (m, 2H), 1.06–0.95 (t, J=7.0 Hz, 6H)

Step 2) Synthesis of (4-chlorobutyl)-(4,4,5,5,5-pentafluoropentyl)-malonic acid diethyl ester

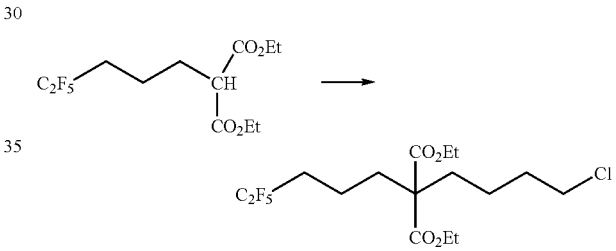

The title compound was prepared from 1-bromo-4-chlorobutane according to the same procedure as step 1 of Example 71.

$^1$H-NMR (270 MHz, CDCl$_3$) δ: 4.18 (q, J=7.0 Hz, 4H), 3.51 (t, J=6.6 Hz, 2H), 2.12–1.83 (m, 6H), 1.82–1.72 (m, 2H), 1.57–1.25 (m, 4H), 1.23 (t, J=7.0 Hz, 6H)

step 3) Synthesis of 4-iodobutyl-(4,4,5,5,5-pentafluoropentyl)malonic acid diethyl ester

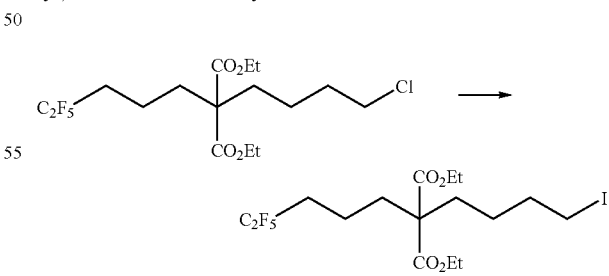

The title compound was prepared from 4-chlorobutyl-(4,4,5,5,5-pentafluoropentyl)malonic acid diethyl ester according to the same procedure as step 2 of Example 71.

$^1$H-NMR (270 MHz, CDCl$_3$) δ: 4.18 (q, J=7.2 Hz, 4H), 3.17 (t, J=6.6 Hz, 2H), 2.13–1.76 (m, 8H), 1.54–1.42 (m, 2H), 1.36–1.21 (m, 8H)

Step 4) Synthesis of (3RS,4RS)-4-[4-(t-butyldimethylsilyloxy)phenyl]-7-(methoxymethoxy)-3-[4-(methoxymethoxy)phenyl]-3-methylchroman

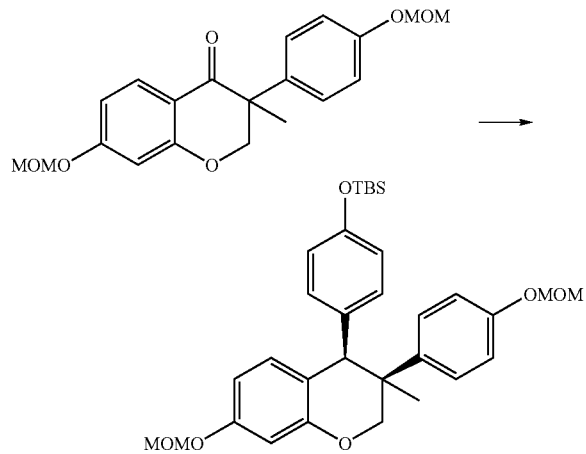

The title compound was prepared from 7-(methoxymethoxy)-3-(4-methoxymethoxyphenyl)-3-methylchroman-4-one according to the same procedure as Step 4 of Example 3.

$^1$H-NMR (270 MHz, CDCl$_3$) δ: 6.8 (m, 5H, Ar—H), 6.6 (d, J=2.3 Hz, 1H, Ar—H), 6.53 (m, 1H, Ar—H), 6.44 (m, 4H, Ar—H), 5.16 (s, 2H, OC$\underline{H}_2$OCH$_3$), 5.1 (s, 2H, OC$\underline{H}_2$OCH$_3$), 4.56 (d, 1H, C2-H), 3.99 (d, 1H, C2-H), 3.88 (s, 1H, C4-H), 3.50 (s, 3H, OCH$_2$OC$\underline{H}_3$), 3.44 (s, 3H, OCH$_2$OC$\underline{H}_3$), 1.55 (s, 3H, C3-CH$_3$), 0.91 (s, 9H, t-butyl-H), 0.08 (s, 6H, 2×CH$_3$)

Step 5) Synthesis of diethyl 2-(4,4,5,5,5-pentafluoropentyl)-2-(4-((3RS,4RS)-4-(3-methyl-7-(methyloxymethyloxy)-3-(4-(methyloxymethyloxy)phenyl)chroman-4-yl)phenyloxy) butyl)propane-1,3-dioate

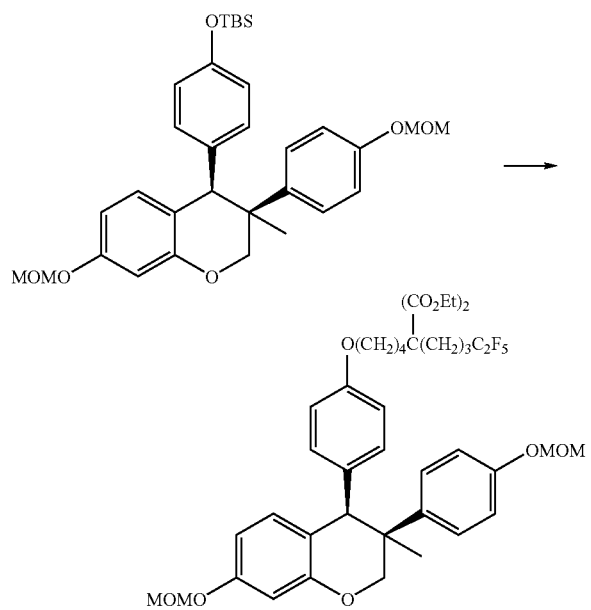

To a solution of (3RS,4RS)-4-[4-(t-butyldimethylsilyloxy)phenyl]-7-(methoxymethoxy)-3-[4-(methoxymethoxy) phenyl]-3-methylchroman (1.1 g, 1.99 mmol) in tetrahydrofuran (10 ml) was added 1N-tetrabutylainmoniumfluoride (3.99 ml, 3.99 mmol) in tetrahydrofuran and stirred at room temperature for 1 hour. After the reaction was completed, the reaction mixture was treated with water and extracted with ethyl acetate. The extract was dried over, anhydrous magnesium sulfate and concentrated under reduced pressure. The residue was subjected to chromatography on silica gel (n-hexane:ethyl acetate=2:1) to give (3RS,4RS)-4-(4-hydroxyphenyl)-7-(methoxymethoxy)-3-[4-(methoxymethoxy)pheny]-3-methylchroman (0.84 g, 96.4%) as a foamy oil. To a solution of (3RS,4RS)-4-(4-hydroxyphenyl)-7-(methoxymethoxy)phenyl-]-3-methylchroman (0.31 g, 0.71 mmol) in dimethylformamide (6 ml) was added potassium carbonate (0.39 g, 2.84 mmol) and 5,5-di-(ethoxycarbonyl)-1-iodo-5(4,4,5,5,5-pentafluoropentyl)butane (0.54 g, 1.07 mmol) and stirred at 80° C. for 3 hours. After the reaction was completed, the reaction mixture was treated with water and extracted with ethyl acetate. The extract was dried over anhydrous magnesium sulfate and concentrated under reduced pressure. The residue was subjected to chromatography on silica gel (n-hexane:ethyl acetate=4:1) to give the title compound (0.552 g, 96%) as a foamy oil.

$^1$H-NMR (270 MHz, CDCl$_3$) δ: 6.93~6.71 (m, 5H, Ar—H), 6.66 (d, 1H, Ar—H), 6.58~6.42 (m, 5H, Ar—H), 5.16 (s, 2H, OC$\underline{H}_2$OCH$_3$), 5.11 (s, 2H, OC$\underline{H}_2$OCH$_3$), 4.58 (d, 1H, C2-H), 4.25~4.09 (q, 4H, 2×C$\underline{H}_2$CH$_3$), 4.03 (d, 1H, C2-H), 3.91 (s, 1H, C4-H), 3.81 (m, 2H, OC$\underline{H}_2$-alkyl), 3.5 (s, 3H, OC$\underline{H}_3$OCH$_3$), 3.45 (s, 3H, OCH$_2$OC$\underline{H}_3$), 2.15~1.84 (m, 6H, alkyl-H), 1.81~1.64 (m, 2H, alkyl-H), 1.54~1.41 (m, 5H, C3-CH$_3$ and alkyl-H), 1.39~1.15 (m, 8H, 2×CH$_2$ C$\underline{H}_3$ and alkyl-H)

Step 6) Synthesis of (4,4,5,5,5-pentafluoropentyl)(4-(4-((3RS,4RS)-3-methyl-7-(methyloxymethyloxy)-3-(4-methyloxymethyloxy)phenyl)chroman-4-yl)phenyloxy)butyl) methane-1,1-dicarboxylic acid

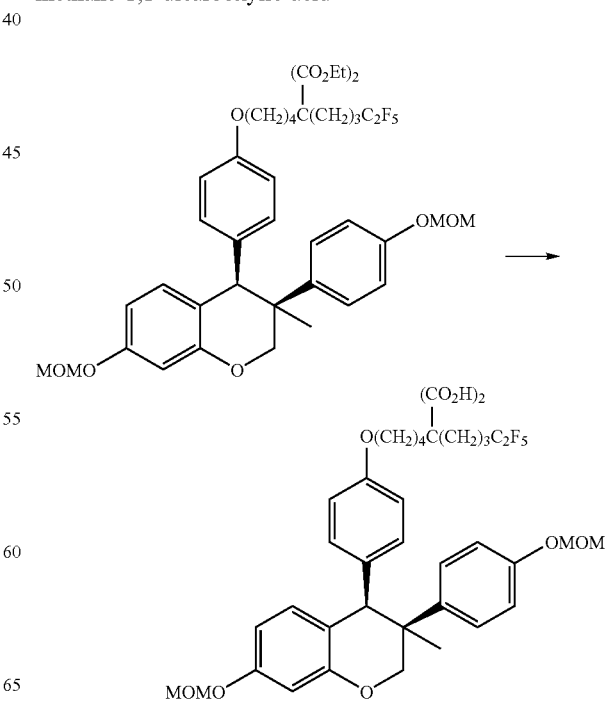

To a solution of diethyl 2-(4,4,5,5,5-pentafluoropentyl)-2-(4-((3RS,4RS)-4-(3-methyl-7-(methyloxymethyloxy)-3-(4-(methyloxymethyloxy)phenyl)chroman-4-yl)phenyloxy)butyl)propane-1,3-dioate (0.552 g, 0.68 mmol) in ethanol (10 ml) was added the solution of potassium hydroxide (1.53 g, 27.23 mmol) in water (5 ml) and the mixture was stirred at refluxed overnight. After the reaction was completed, the reaction mixture was treated with 2N-HCl solution (pH=4) and extracted with ethyl acetate. The extract was dried over anhydrous magnesium sulfate and concentrated under reduced pressure to give the title compound (0.513 g, quantitative) as a foamy oil.

$^1$H-NMR (270 MHz, CDCl$_3$) δ: 6.87~6.7 (m, 5H, Ar—H), 6.65 (d, 1H, Ar—H), 6.5 (dd, 1H, Ar—H), 6.43 (s, 4H, Ar—H), 5.23~5.04 (m, 4H, 2×OC$\underline{H}_2$OCH$_3$), 4.55 (d, 1H, C2-H), 3.97 (d, 1H, C2-H), 3.91~3.73 (m, 3H, C4-H and OC$\underline{H}_2$-alkyl), 3.48 (d, 6H, 2×OCH$_2$OC$\underline{H}_3$), 2.13~1.84 (brs, 6H, alkyl-H), 1.81~1.14 (brs, 9H, C3-CH$_3$ and alkyl-H)

Step 7) Synthesis of (4,4,5,5,5-pentafluoropentyl)(4-((3RS,4RS)-4-(7-hydroxy-3-(4-hydroxyphenyl)-3-methylchroman-4-yl)phenyloxy)butyl)methane-1,1-dicarboxylic acid

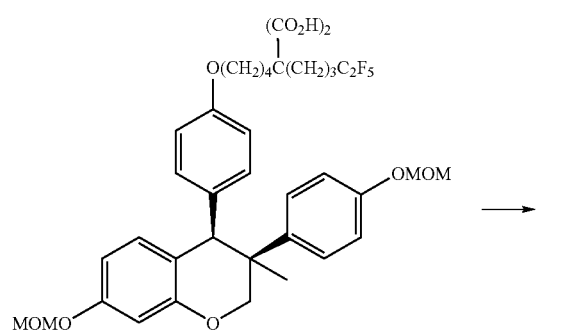

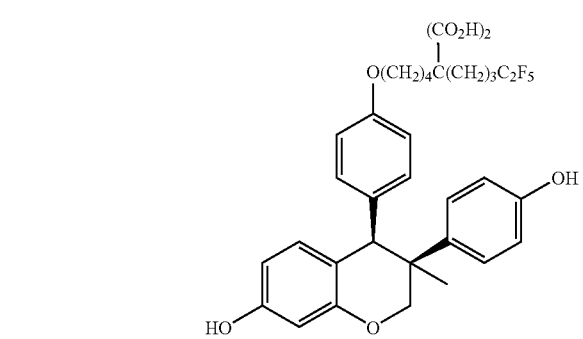

The title compound was prepared from (4,4,5,5,5-pentafluoropentyl)(4-(4-((3RS,4RS)-3-methyl-7-(methyloxymethyloxy)-3-(4-(methyloxymethyloxy)phenyl)chroman-4-yl)phenyloxy)butyl)methane-1,1-dicarboxylic acid according to the same procedure as Step 10 of Example 9

$^1$H-NMR (270 MHz, CD$_3$OD) δ: 6.8~6.15 (brs, 1H, Ar—H), 4.57~4.42 (m, 1H, C2-H), 4.1~3.7 (m, 4H, C2-H and C4-H, OC$\underline{H}_2$-alkyl), 2.2–1.8 (brs, 6H alkyl-H), 1.75~1.1 (brs, C3-H and alkyl-H)

Step 8) Synthesis of 6-{4-[(3RS,4RS)-7-hydroxy-3-(4-hydroxyphenyl)-3-methylchroman-4-yl]phenoxy}-2-(4,4,5,5,5-pentafluoropentyl)hexanoic acid

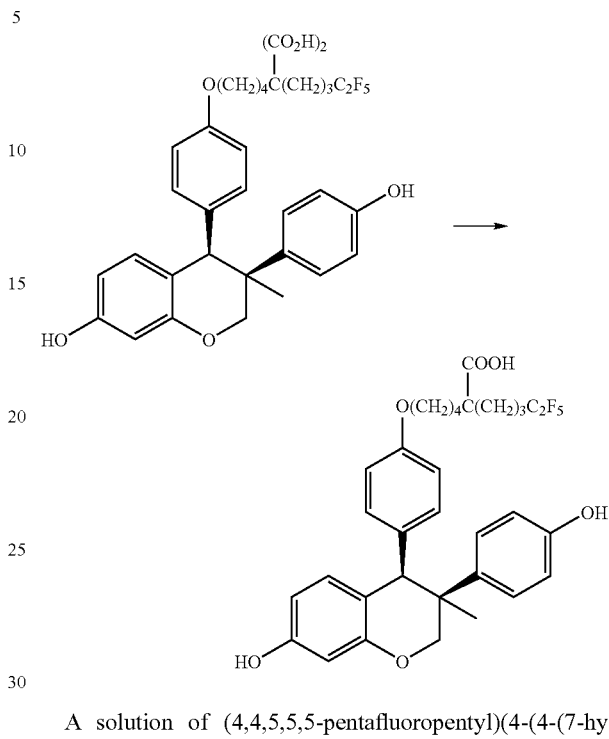

A solution of (4,4,5,5,5-pentafluoropentyl)(4-(4-(7-hydroxy-3-(4-hydroxyphenyl)-3-methylchroman-4-yl)phenyloxy)butyl)methane-1,1-dicarboxylic acid (0.19 g, 0.285 mmol) in dimethylsulfoxide (7.6 ml) was stirred at 125° C. for 3 hours. After the reaction was completed, the reaction mixture was treated with saturated NaCl solution and extracted with ethyl acetate:hexane=1:1. The extract was dried over anhydrous magnesium sulfate and concentrated under reduced pressure. The residue was subjected to chromatography on silica gel (n-hexane:ethyl acetate=2:1) to give the title compound (0.12 g, 67.6%) as a white foamy solid.

$^1$H-NMR (270 MHz, CDCl$_3$) δ: 6.78 (m, 3H, Ar—H), 6.61 (d, J=8.91, 2H, Ar—H), 6.49 (d, J=1.98, 4H, Ar—H), 6.46 (d, 1H, Ar—H), 6.35 (dd, 1H, Ar—H), 4.59 (d, 1H, C2-H), 4.02 (d, 1H, C2-H), 3.86 (m, 3H, C4-H and OC$\underline{H}_2$-alkyl), 2.43 (m, 1H), C$\underline{H}$—COOH), 2.18~1.90 (m, 2H, alkyl-H), 1.87~1.38 (brs, 13H, C3-H, and alkyl-H)

EXAMPLE 69

Synthesis of 7-{4-[(3RS,4RS)-7-hydroxy-3-(4-hydroxyphenyl-3-methylchroman-4-yl]phenoxy}-2-(4,4,5,5,5-pentafluoropentyl)heptanoic acid Step 1) Synthesis of 7-(t-butyldimethylsilyloxy)heptyl bromide

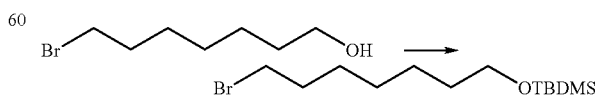

To a solution of 7-bromoheptanol (50 g, 25.6 mmole) and imidazole (4.2 g, 61.5 mmole) in dry tetrahydrofuran (80 ml) was added t-butyldimethylsilyl chloride (4.6 g, 30.8 mmole)

dropwise during 1 hour at room temperature. Then the reaction mixture was stirred overnight at room temperature. When the reaction was completed, water was added to the reaction solution which was then extracted with ethyl acetate. The extract was dried over anhydrous magnesium sulfate and concentrated under reduced pressure. The residue was purified with column chromatography (n-hexane:ethyl acetate=20:1) to give 5.7 g (yield: 72%) of the title compound as a colorless oil.

$^1$H-NMR (270 MHz, CDCl$_3$) δ: 3.61 (t, 2H, OCH$_2$), 3.41 (t, 2H, BrCH$_2$), 1.85 (q, 2H, CH$_2$), 1.61–1.30 (m, 8H, alkyl-H), 0.90 (s, 9H, t-butyl), 0.10 (s, 6H, dimethyl)

Step 2) Synthesis of ethyl [2-(ethoxycarbonyl)-2-(4,4,5,5,5-pentafluoropentyl)-9-(t-butyldimethylsilyloxy)]nonanoate

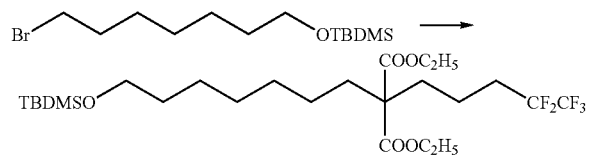

To a solution of ethyl , [2-(ethoxycarbonyl)-5-(1,1,2,2,2-pentafluoroethyl)]pentanoate (1.0 g, 3.1 mmole) in dry tetrahydrofuran (5.0 ml) was added 60% sodium hydride in oil (136 mg, 3.41 mmole) under nitrogen stream at room temperature. After 30 minutes, to reaction mixture was added 7-(t-butyldimethylsilyloxy)heptyl bromide at room temperature. Then the reaction mixture was stirred overnight at room temperature. When the reaction was completed, water was added to the reaction solution which was then extracted with ethyl acetate. The extract was dried over anhydrous magnesium sulfate and concentrated under reduced pressure. The residue was purified with column chromatography (n-hexane:ethyl acetate=30:1) to give 910 mg (yield: 54%) of the title compound as a colorless oil.

$^1$H-NMR (270 MHz, CDCl$_3$) δ: 4.20 (q, 4H, COOCH$_2$× 2), 3.60 (t, 2H, OCH$_2$), 2.15–1.04 (m, 24H, alkyl-H, CH$_3$× 2), 0.94 (s, 9H, t-butyl), 0.10 (s, 6H, dimethyl)

Step 3) Synthesis of diethyl 2-(4,4,5,5,5-pentafluoropentyl)-2-(7-hydroxyheptyl)propane-1,3-dioate

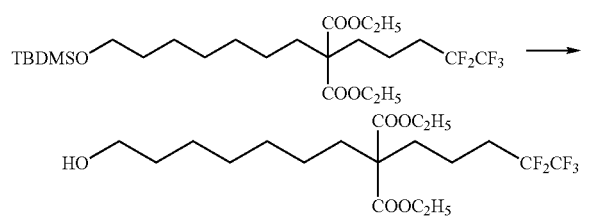

To a solution of ethyl [2-(ethoxycarbonyl)-2-(4,4,5,5,5-pentafluoropentyl)-9-(t-butyldimethylsilyloxy)]nonanoate (900 mg, 1.64 mmole) and dry tetrahydrofuran (20 ml) was added 1.0M tetra-butylammonium fluoride in THF at room temperature. Then the reaction mixture was stirred for 4 hours at room temperature. When the reaction was completed, water was added to the reaction solution which was then extracted with ethyl acetate. And the organic layer was washed with sat. sodium bicarbonate soln. and sat. sodium chloride soln. The extract was dried over anhydrous magnesium sulfate and concentrated under reduced pressure. The residue was purified with column chromatography (n-hexane:ethyl acetate=4:1) to give 700 mg (yield: 98%) of the title compound as a colorless oil.

$^1$H-NMR (270 MHz, CDCl$_3$) δ: 4.20 (q, 4H, COOCH$_2$× 2), 3.64 (t, 2H, OCH$_2$), 2.18–1.06 (m, 24H, alkyl-H, CH$_3$×2)

step 4) Synthesis of diethyl 2-(4,4,5,5,5-pentafluoropentyl)-2-(6-methylsulfinyloxy)hexyl)propane-1,3-dioate

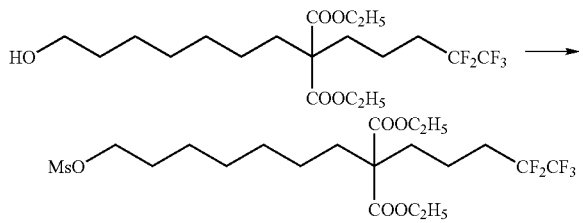

To a solution of diethyl 2-(4,4,5,5,5-pentafluoropentyl)-2-(7-hydroxyheptyl)propane-1,3-dioate (710 mg, 1.63 mmole) in methylene chloride (10 ml) was added triethylamine (0.68 ml, 4.90 mmole) at room temperature. After 10 minute, to reaction mixture was added methanesulfonyl chloride at room temperature. Then the reaction mixture was stirred for 1 hour at room temperature. When the reaction was completed, water was added to the reaction solution which was then extracted with ethyl acetate. The extract was dried over anhydrous magnesium sulfate and concentrated under reduced pressure. The residue was purified with column chromatography (n-hexane:ethyl acetate=4:1) to give 840 mg (yield: 99%) of the title compound as a colorless oil.

$^1$H-NMR (270 MHz, CDCl$_3$) δ: 4.23–4.08 (m, 6H, OCH$_2$, COOCH$_2$×2), 3.02 (s, 3H, SO$_2$CH$_3$), 2.18–1.05 (m, 24H, alkyl-H, CH3×$_2$)

Step 5) Synthesis of 7-iodoheptyl-(4,4,5,5,5-pentafluoropentyl)malonic acid diethyl ester

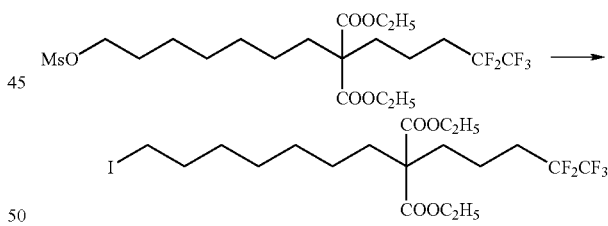

To a solution of diethyl 2-(4,4,5,5,5-pentafluoropentyl)-2-(6-methylsulfinyloxy)hexyl)propane-1,3-dioate (830 mg, 1.62 mmole) in dry acetone (20 ml) was added sodium iodide (3.6 g, 24.30 mmole) at room temperature. Then the reaction mixture was refluxed for 3.5 hours. When the reaction was completed, water was added to the reaction solution, which was then extracted with ethyl acetate. And the organic layer was washed with 2N hydrochloride soln. and sat. sodium chloride soln. The extract was dried over anhydrous magnesium sulfate and concentrated under reduced pressure. The residue was purified with column chromatography (n-hexane:ethyl acetate=40:1) to give 780 mg (yield: 89%) of the title compound as a colorless oil.

$^1$H-NMR (270 MHz, CDCl$_3$) δ: 4.20 (q, 4H, COOCH$_2$× 2), 3.18 (t, 2H, ICH$_2$), 2.17–1.07 (m, 24H, alkyl-H, CH$_3$×2)

Step 6) Synthesis of 7-{4-[(3RS,4RS)-7-hydroxy-3-(4-hydroxyphenyl)-3-methylchroman-4-yl]phenoxy}-2-(4,4,5,5,5-pentafluoropentyl)heptanoic acid

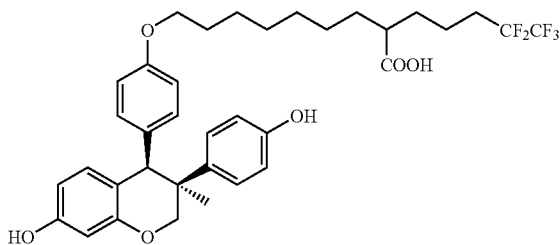

The title compound was prepared according to the same procedure as synthesis of Example 68 from (3RS,4RS)-(4-hydroxyphenyl)-7-(methoxymethoxy)-3-[4-(methoxymethoxy)phenyl]-3-methylchroman.
$^1$H-NMR (270 MHz, CDCl$_3$) δ: 6.81 (d, 2H, Ar—H), 6.72 (d, 1H, Ar—H), 6.62 (d, 2H, Ar—H), 6.59–6.43 (m, 5H, Ar—H), 6.35 (dd, 1H, Ar—H), 4.56 (d, 1H, C2-H), 4.00 (dd, 1H, C2-H), 3.86 (s, 1H, C4H), 3.84 (t, 2H, OCH2), 2.40 (m, 1H, CHCOO), 2.03 (m, 2H, CH2CF2), 1.85–1.21 (m, 19H, C3-CH3, alkyl-H)

EXAMPLE 70

Synthesis of 8-{4-[(3RS,4RS)-7-hydroxy-3-(4-hydroxyphenyl)-3-methylchroman-4-yl]phenoxy}-2-(4,4,5,5,5-pentafluoropentyl)octanoic acid Step 1) Synthesis of 5-chloropentyl-(4,4,5,5,5-pentafluoropentyl)malonic acid diethyl ester

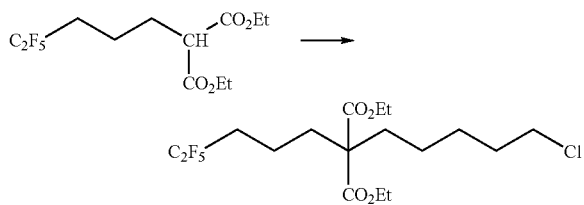

The title compound was prepared from 1-bromo-5-chloropentane according to the same procedure as step 1 of Example 71.
$^1$H-NMR (270 MHz CDCl$_3$) δ: 4.17 (q, J=7.3 Hz, 4H), 3.49 (t, J=6.6 Hz, 2H), 2.12–1.82 (m, 6H), 1.81–1–72 (m, 2H), 1.58–1.38 (m, 4H), 1.26–1.13 (m, 8H)

Step 2) Synthesis of 5-iodopentyl-(4,4,5,5,5-pentafluoropentyl)malonic acid diethyl ester

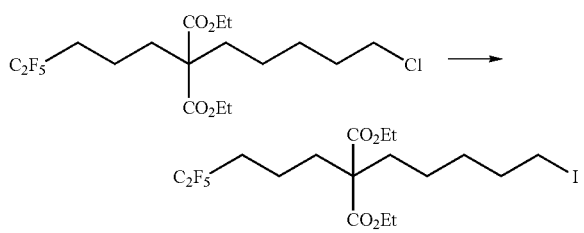

The title compound was prepared from 5-chloropentyl-(4,4,5,5,5-pentafluoropentyl)malonic acid diethyl ester according to the same procedure as step 2 of Example 71.
$^1$H-NMR (270 MHz, CDCl$_3$) δ: 4.17 (q, J=7.2 Hz, 4H), 3.16 (t, J=6.6 Hz, 2H), 2.13–1.77 (m, 8H), 1.57–1.38 (m, 4H), 1.25–1.12 (m, 8H)

Step 3) Synthesis of 8-{4-[(3RS,4RS)-7-hydroxy-3-(4-hydroxyphenyl)-3-methylchroman-4-yl]phenoxy}-2-(4,4,5,5,5-pentafluoropentyl)octanoic acid

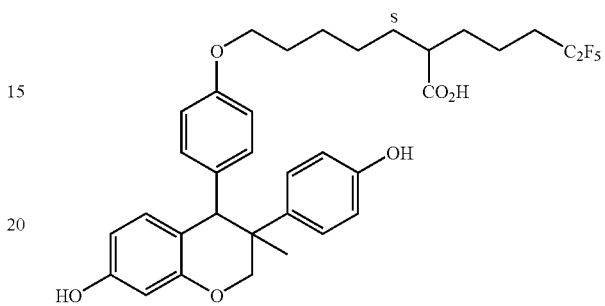

The title compound was prepared according to the same procedure as synthesis of Example 68 from (3RS,4RS)-4-(4-hydroxyphenyl)-7-(methoxymethoxy)-3-[4-(methoxymethoxy)phenyl]-3-methylchroman.
$^1$H-NMR (270 MHz, CD$_3$OD) δ: 6.80–6.67 (m, 3H), 6.57 (d, J=8.6 Hz, 2H), 6.48–6.42 (m, 5H), 6.32 (m, 1H), 4.54 (m, 1H), 3.96 (m, 1H), 3.86–3.78 (m, 3H), 2.42–2.35 (m, 1H), 2.11–1.91 (m, 2H), 1.77–1.23 (m, 15H)

EXAMPLE 71

Synthesis of 9-{4-[(3RS,4RS)-7-hydroxy-3-(4-hydroxyphenyl)-3-methylchroman-4-yl]phenoxy}-2-(4,4,5,5,5-pentafluoropentyl)nonanoic acid step 1) Synthesis of 6-chlorohexyl-(4,4,5,5,5-pentafluoropentyl)malonic acid diethyl ester

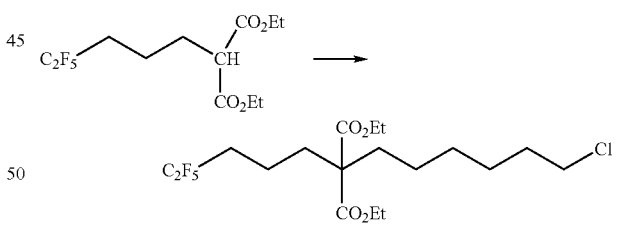

To a solution of (4,4,5,5,5-pentafluoropentyl)malonic acid diethyl ester (1 g, 3.12 mmol) in tetrahydrofuran (15 ml) was added sodium hydride (175 mg, 4.37 mmol), which was then stirred for 30 min at rt. 1-Bromo-6-chlorohexane (0.7 ml, 4.68 mmol) was added to this reaction mixture and the reaction mixture was refluxed overnight. When the reaction was completed, water was added to the reaction mixture and extracted with ethyl acetate. Then, the organic layer was washed with water and saturated sodium chloride solution. The extract was dried over anhydrous magnesium sulfate and concentrated under reduced pressure. The residue was subjected to silica gel column chromatography (n-hexane:ethyl acetate=30:1) to give the title compound (760 mg, yield: 56%) as a colorless liquid.

¹H-NMR (270 MHz, CDCl₃) δ: 4.17 (q, J=7.2 Hz, 4H), 3.50 (t, J=6.6 Hz, 2H), 2.12–1.82 (m, 6H), 1.81–1.72 (m, 2H), 1.57–1.12 (m, 14H)

Step 2) Synthesis of 6-iodohexyl-(4,4,5,5,5-pentafluoropentyl)malonic acid diethyl ester

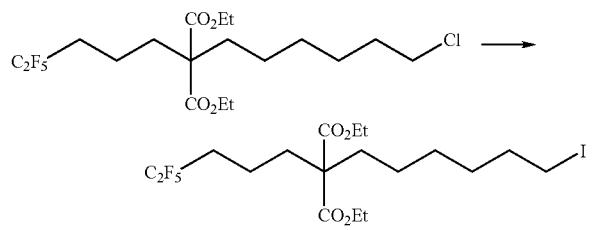

To a solution of 6-chlorohexyl-(4,4,5,5,5-pentafluoropentyl)malonic acid diethyl ester (743 mg, 1.69 mmol) in acetone (5 ml) was added sodium iodide (761 mg, 5.08 mmol), which was then refluxed for 4 h. When the reaction was completed, water was added to the reaction mixture and extracted with ethyl acetate. Then, the organic layer was washed with wafer and saturated sodium chloride solution. The extract was dried over anhydrous magnesium sulfate and concentrated under reduced pressure. The residue was subjected to silica gel column chromatography (n-hexane:ethyl acetate=15:1) to give the title compound (801 mg, yield: 89%) as a colorless liquid.

¹H-NMR (270 MHz, CDCl₃) δ: 4.17 (q, J=7.0 Hz, 4H), 3.15 (t, J=7.0 Hz, 2H), 2.13–1.72 (m, 8H), 1.58–1.12 (m, 14H)

Step 3) Synthesis of 9-{4-[(3RS,4RS)-7-hydroxy-3-(4-hydroxyphenyl)-3-methylchroman-4-yl]phenoxy}-2-(4,4,5,5,5-pentafluoropentyl)nonanoic acid

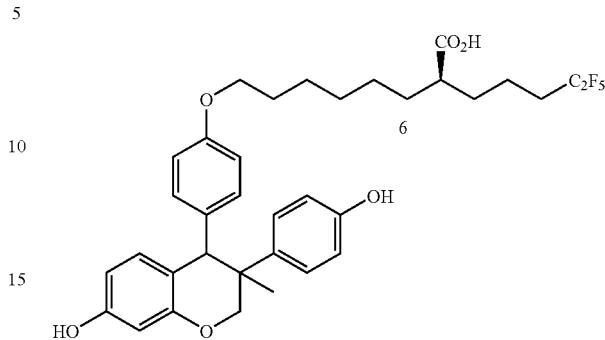

The title compound was prepared according to the same procedure as synthesis of Example 68 from (3RS,4RS)-4-(4-hydroxyphenyl)-7-(methoxymethoxy)-3-[4-(methoxymethoxy)phenyl]-3-methylchroman.

¹H-NMR (270 MHz, CD₃OD) δ: 6.77 (d, J=8.5 Hz, 2H), 6.69 (d, J=8.2 Hz, 1H), 6.57 (d, J=8.5 Hz, 2H), 6.47–6.43 (m, 5H), 6.33 (m, 1H), 4.54 (m, 1H), 3.96 (m, 1H), 3.87–3.78 (m, 3H), 2.42–2.34 (m, 1H), 2.11–1.92 (m, 2H), 1.76–1.22 (m, 17H)

The following compounds of Examples 72 to 205 were prepared according to the similar procedures as Examples 1 to 71. These compounds are represented in the following Table 1

TABLE 1

| COM. NO. | NAME | STRUCTURE | PHYSICAL DATA |
|---|---|---|---|
| 72 | (3RS,4RS)-7-hydroxy-3-(4-hydroxyphenyl)-4-{9-{[(4,4,5,5,5-pentafluoropentyl)amino]-iminomethyl}amino]nonyl}-3-methylchroman | 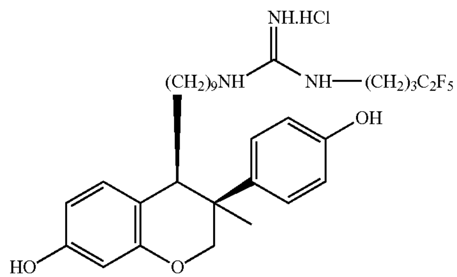 | ¹H-NMR(300 MHz, DMSO-d₆) δ: 0.8–1.3(m, 16H), 1.11(s, 3H), 1.45(m, 2H), 1.73(m, 2H), 1.73(m, 2H), 2.26(m, 2H), 2.58(d, 1H),3.08(m, 2H), 3.2(m, 2H), 4.15(d, 1H), 4.4(d, 1H), 6.2(d, 1H), 6.28(dd, 1H), 6.7(d, 2H), 6.8(d, 1H), 7.05(d, 2H), 7.4(brs, 1H), 7.63(brs, 1H), 7.56(brs, 1H), 9.15(brs, 1H), 9.3(brs, 1H) Mass(ESI): 600(M + 1) |
| 73 | N-n-butyl-11-[(3RS,4RS)-7-hydroxy-3-(4-hydroxyphenyl)-3-methylchroman-4-yl]-N-methylundecaneamide | 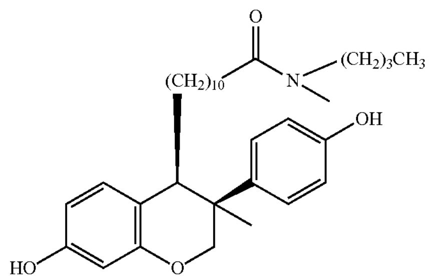 | ¹H-NMR(300 MHz, CDCl₃) δ: 0.95–1.70(brs, 26H), 2.36(m, 2H), 2.60(m, 1H), 2.99(s, 1.5H), 3.03(s, 1.5H), 3.31(t, 1H), 3.43(t, 1H), 4.27(d, 1H), 4.55(d, 1H), 6.14(s, 1H), 6.93(m, 3H),7.09(d, 2H), 8.07(s, 1H) |
| 74 | (3RS,4RS)-7-hydroxy-3-(4-hydroxyphenyl)-4-{9-[(4,4,5,5,5-pentafluoropentyl)carbamoylamino]nonyl}-3-methylchroman | 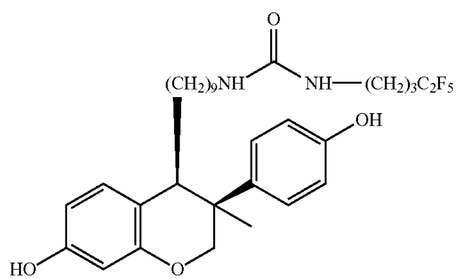 | ¹H-NMR(300 MHz, CDCl₃) δ: 0.9–1.2(m, 18H), 1.3(s, 2H), 1.65(m, 2H), 1.9–2.1(m, 2H), 3.0(m, 2H), 3.15(m, 2H), 4.1(d, 1H), 4.35(d, 1H), 5.15(s, 1H), 5.35(s, 1H), 6.25(t, 2H), 6.7(t, 3H), 6.9(d, 2H), 8.2(s, 1H), 8.6(s, 1H) Mass(ESI): 601(M + 1) |

TABLE 1-continued

| COM. NO. | NAME | STRUCTURE | PHYSICAL DATA |
|---|---|---|---|
| 75 | (3RS,4RS)-7-hydroxy-3-(4-hydroxyphenyl)-3-methyl-4-[2-(5-(4-(4,4,5,5,5-pentafluoropentylsulfinyl)butyl)fur-2-yl)ethyl]chroman | 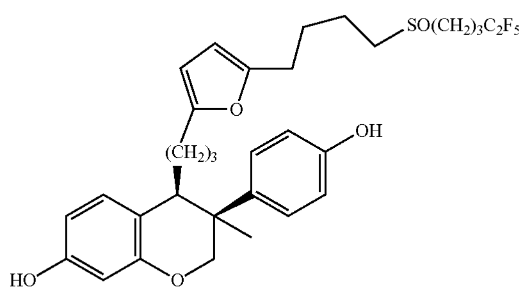 | $^1$H-NMR(300 MHz, CDCl$_3$) δ: 7.55(d, J=22.99 Hz, 1H), 7.00–6.78(m, 5H), 6.39–6.35(m, 2H), 5.84–5.81(m, 2H), 5.32(d, J=15.45 Hz, 1H),4.50(d, J=10.18 Hz, 1H), 4.25(d, J=10.55 Hz, 1H), 2.88–2.10(m, 12H), 1.90–1.60(m, 5H), 1.34–1.13(m, 4H) Mass(ESI): 615(M + 1) |
| 76 | (3RS,4RS)-7-hydroxy-3-(4-hydroxyphenyl)-3-methyl-4-[5-((3-(4,4,5,5,5-pentafluoropentylsulfinyl)propyl)-methoxyamino)pentyl]chroman | 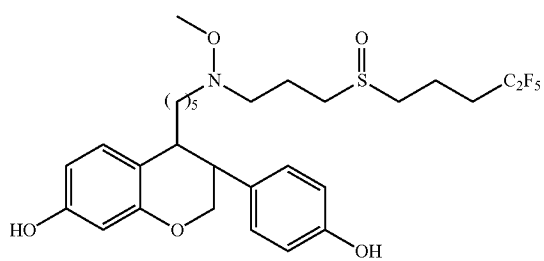 | $^1$H-NMR(300 MHz, CDCl$_3$) δ: 7.40(br, 1H), 7.04(d, 2H, J=9 Hz), 6.86(d, 1H, J=8 Hz), 6.82(d, 2H, J=9 Hz), 6.37(m, 2H), 6.03(br, 1H),4.47(d, 1H, J=11 Hz), 4.20(m, 1H, J=11 Hz), 3.43(s, 3H), 2.84(m, 4H), 2.65(m, 2H), 2.55(br, 1H), 2.45(m, 2H), 2.26(m, 2H), 2.18(m, 2H), 1.98(m, 2H), 0.98–1.29(m, 11H) Mass(ESI): 622(M + 1) |

TABLE 1-continued

| COM. NO. | NAME | STRUCTURE | PHYSICAL DATA |
|---|---|---|---|
| 77 | (3RS,4RS)-7-hydroxy-3-(4-hydroxyphenyl)-3-methyl-4-(9-(4,4,5,5-pentafluoropentyl)-2,2-dioxo-2,1,3-thiadizolidinyl)nonylchroman | 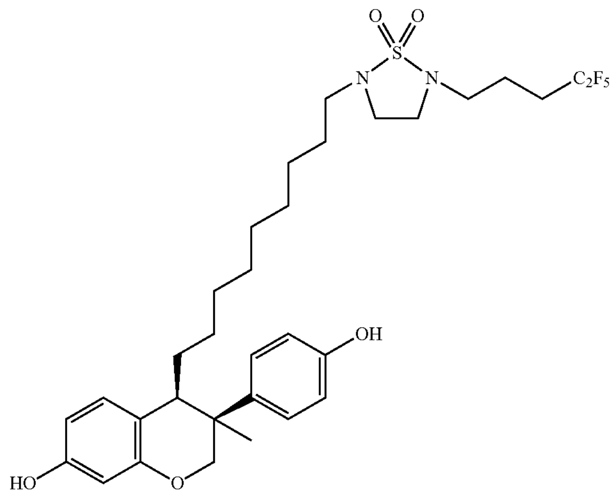 | ¹H-NMR(300 MHz, CDCl3) δ: 7.05(d, 2H, J=8.66 Hz), 6.87(d, 1H, J=7.91 Hz), 6.82(d, 2H, J=9.04 Hz), 6.34(m, 2H), 4.48(d, 1H, J=10.55 Hz),4.21(dd, 1H, J=10.55 Hz), 3.31(s, 4H), 3.13(t, 2H, J=6.78 Hz), 3.01(t, 2H, J=7.16 Hz), 2.57(d, 1H, J=7.46 Hz), 2.25–2.09(m, 2H), 1.99–1.90(m, 2H), 1.60–1.54(m, 2H), 1.32–0.98(m, 17H) Mass(ESI): 663(M + 1) |
| 78 | (3RS,4RS)-7-hydroxy-3-methyl-3-(4-hydroxyphenyl)-4-(9-((((4,4,5,5-pentafluoropentyl)amino)-N-carbamoyliminо)methyl)amino)nonyl)-chroman | 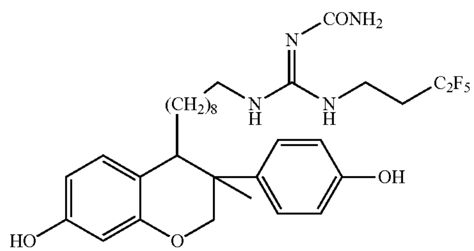 | ¹H-NMR(300 MHz, CD3OD) δ: 6.98(d, 2H, J=8.7 Hz, Ar—H), 6.75(d, 2H, J=8.24 Hz, Ar—H),6.68(d, 2H, J=8.7 Hz), 6.21(dd, 1H, J=2.5 Hz, J=8.24 Hz), 6.14(d, 1H, J=2.6 Hz), 4.39(d, 1H, J=10.5 Hz, C2–H), 4.1(d, 1H, J=10.5 Hz, C2–H), 3.06(t, 2H, J=6.9 Hz), 2.51(m, 1H), 2.1(m, 2H), 1.7(m, 2H), 1.5(m, 2H), 1.09(s, 3H, C3–CH3), 0.9–1.2(m, 14H) |
| 79 | (3RS,4RS)-7-hydroxy-3-methyl-3-(4-hydroxyphenyl)-4-(9-((((4,4,5,5-pentafluoropentyl)amino)-N-cyanoimino)methyl)amino)nonyl)-thiochroman | 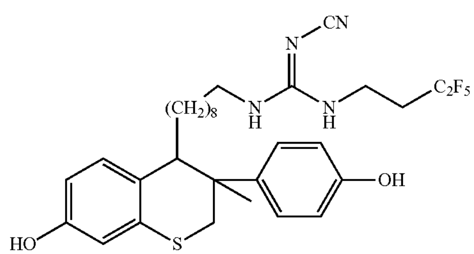 | ¹H-NMR(300 MHz, CD3OD) δ: 7.23(d, 2H, J=8.7 Hz, Ar—H), 6.85(d, 1H, J=8.2 Hz, Ar—H),6.77(d, 2H, J=8.7 Hz), 6.55(d, 1H, J=2.47 Hz), 6.43(dd, 1H, J=8.2 Hz, J=2.47 Hz), 3.6(d, 1H, J=11.6 Hz, C2–H), 3.3(t, 2H), 3.15(t, 2H, J=7.1 Hz), 2.94(d, 1H, J=11.6 Hz, C2–H), 2.73(m, 1H), 2.1(m, 2H), 1.8(m, 2H), 1.5(m, 2H), 1.1(s, 3H, C3–CH3), 0.9–1.3(m, 14H) |

TABLE 1-continued

| COM. NO. | NAME | STRUCTURE | PHYSICAL DATA |
|---|---|---|---|
| 80 | (3RS,4RS)-7-hydroxy-3-methyl-3-(4-hydroxyphenyl)-4-(3-(4-(3-(4,4,5,5,5-pentafluoropentyl)sulfinyl)-propyl)piperazinyl)-propyl)chroman | 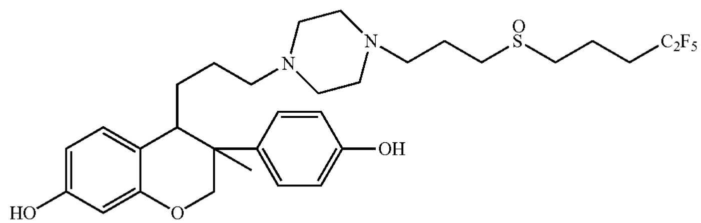 | $^1$H-NMR(300 MHz, CD$_3$OD) δ: 7.0(d, 2H, J=8.7 Hz, Ar—H), 6.79(d, 2H, J=8.3 Hz, Ar—H), 6.68(d, 2H, J=8.7 Hz), 6.21(dd, 1H, J=2.4 Hz, J=8.3 Hz), 6.14(d, 1H, J=2.4 Hz), 4.4(d, 1H, J=10.6 Hz, C2-H), 4.11(d, 1H, J=10.6 Hz, C2-H), 2.75(m, 4H), 2.6(m, 1H), 2.3(m, 12H), 2.0(m, 4H), 1.75(m, 2H), 1.1(s, 3H, C3-CH$_3$), 0.9–1.2(m, 4H) Mass(ESI): 633(M + 1) |
| 81 | (3RS,4RS)-7-hydroxy-3-(4-hydroxyphenyl)-3-methyl-4-[9-((2-piperidinoethyl)-sulfinyl)nonyl]chroman | 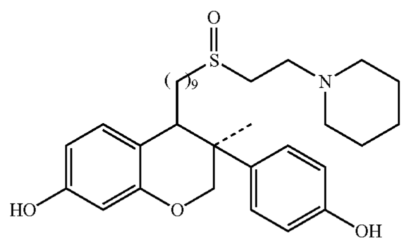 | $^1$H-NMR(300 MHz, CDCl$_3$) δ: 6.97(d, 2H, J=9 Hz), 6.76(d, 1H, J=8 Hz), 6.68(d, 2H, J=9 Hz), 6.22(dd, 1H, J=8 Hz, J=3 Hz), 6.15(d, 1H, J=2 Hz), 4.39(d, 1H, J=10 Hz), 4.12(d, 1H, J=7 Hz), 2.68(m, 4H), 2.52(br, 1H), 2.40(m, 4H), 1.63(t, 2H, J=7 Hz), 1.50(m, 4H), 1.33(m, 4H), 0.85–1.22(m, 17H) Mass(ESI): 542(M + 1) |
| 82 | (3RS,4RS)-4-[9-(2-(3-cyanophenyl)ethyl)sulfinyl)nonyl]-7-hydroxy-3-(4-hydroxyphenyl)-3-methylthiochroman | 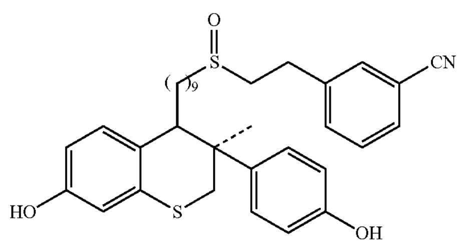 | $^1$H-NMR(300 MHz, CDCl$_3$) δ: 7.40–7.58(m, 4H), 7.21(d, 2H, J=9 Hz), 6.84(m, 3H), 6.65(d, 2 Hz), 6.48(dd, 1H, J=8 Hz, J=2 Hz), 5.71(s, 1H), 5.58(s, 1H), 3.61(dd, 1H, J=10 Hz, J=3 Hz), 3.17(t, 2H, J=8 Hz), 3.04(m, 1H), 2.71–2.96(m, 3H), 2.62(m, 2H), 1.71(m, 2H), 1.27(m, 4H), 0.85–1.21(m, 13H) Mass(ESI): 576(M + 1) |

TABLE 1-continued

| COM. NO. | NAME | STRUCTURE | PHYSICAL DATA |
|---|---|---|---|
| 83 | (3RS,4RS)-7-hydroxy-3-(4-hydroxyphenyl)-3-methyl-4-[4-(3-(2-(4,4,5,5,5-pentafluoropentylsulfinyl)ethoxy)propoxy)phenyl]chroman | 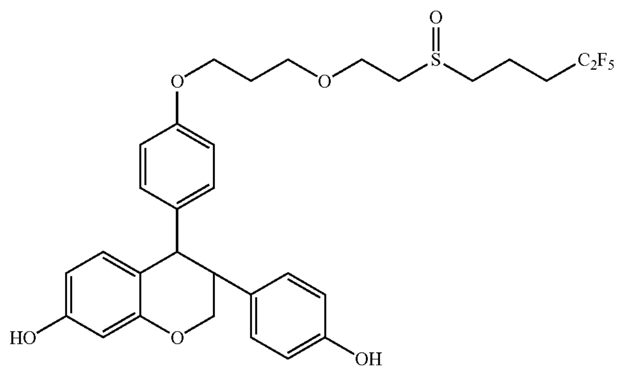 | $^1$H-NMR(300 MHz, CDCl$_3$) δ: 7.06(s, 1H), 6.75(m, 3H), 6.62(d, 2H, J=9 Hz), 6.53(m, 5H), 6.37(dd, 1H, J=8 Hz, J=2 Hz), 5.97(s, 1H),4.58(d, 1H, J=11 Hz), 3.96(m, 3H), 3.85(m, 3H), 3.62(t, 2H, J=6 Hz), 2.99(m, 2H), 2.86(m, 2H, J=7 Hz), 2.17(m, 4H), 1.97(t, 2H, J=6 Hz), 1.52(s, 3H) Mass(ESI) 643(M + 1) |
| 84 | (3RS,4RS)-7-hydroxy-3-(4-hydroxyphenyl)-3-methyl-4-[5-((3-(4,4,5,5,5-pentafluoropentylsulfinyl)propyl)-phenylmethoxyamino)pentyl]-chroman | 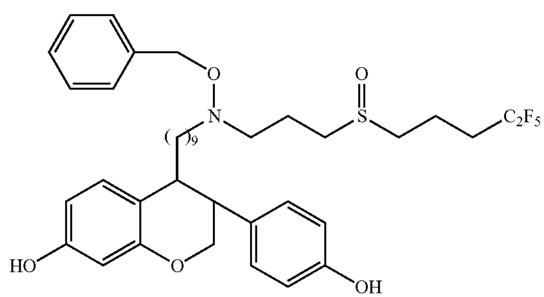 | $^1$H-NMR(300 MHz, CDCl$_3$) δ: 7.46(br, 1H), 7.28(m, 5H), 7.03(d, 2H, J=8 Hz), 6.87(d, 1H, J=8 Hz),6.82(d, 2H, J=8 Hz), 6.38(d, 1H, J=3 Hz), 6.35(s, 1H), 5.94(br, 1H), 4.57(s, 2H), 4.48(d, 1H, J=11 Hz), 4.20(m, 1H), 2.68(m, 5H), 2.55(m, 4H), 2.27(m, 2H), 2.14(m, 2H), 1.88(m, 2H), 0.95–1.33(m, 11 Hz) Mass(ESI) 698(M + 1) |

TABLE 1-continued

| COM. NO. | NAME | STRUCTURE | PHYSICAL DATA |
|---|---|---|---|
| 85 | (3RS,4RS)-7-hydroxy-3-(4-hydroxyphenyl)-3-methyl-4-[4-(2-((3-(4,4,5,5-pentafluoropentyl)sulfinyl)propyl)methyl]amino)ethoxy)phenyl]-chroman | 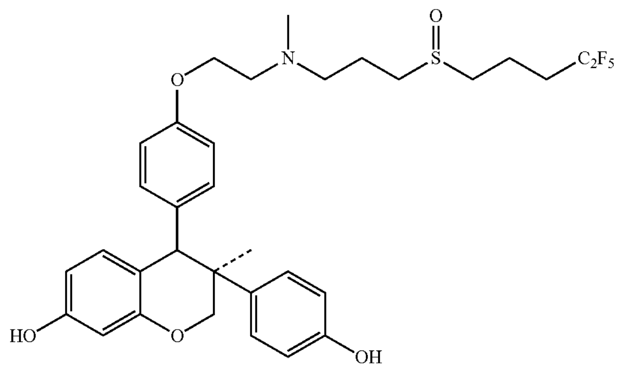 | $^1$H-NMR(300 MHz, CDCl$_3$) δ: 6.69(m, 3H), 6.58(d, 1H, J=2 Hz), 6.55(d, 1H, J=2 Hz), 6.45(s, 4H),6.43(d, 1H, J=3 Hz), 6.32(m, 1H), 4.53(dd, 1H, J=11 Hz, J=3 Hz), 3.96(m, 3H), 3.80(s, 1H), 2.78(m, 4H), 2.70(m, 2H), 2.56(m, 2H), 2.30(s, 3H), 2.14(m, 4H), 1.90(m, 2H), 1.48(d, 3H, J=3 Hz) Mass(ESI) 656(M + 1) |
| 86 | (3RS,4RS)-7-hydroxy-3-(4-hydroxyphenyl)-3-methyl-4-[6-aza-6-(4,4,5,5-pentafluoropentylsulfinyl)-ethoxy-5-hexenyl]chroman | 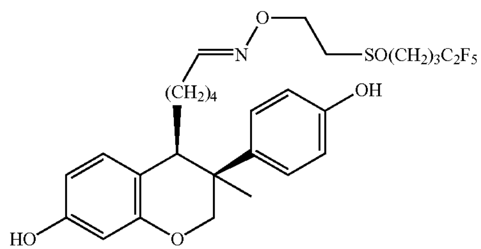 | $^1$H-NMR(300 Hz, CDCl$_3$) δ: 7.25(m, 0.5H), 7.17(d, J=8.64 Hz, 2H), 6.98(m, 3H), 6.65(t, 0.5H), 6.46(m, 2H), 4.62–4.23(m, 4H),3.25–3.00(m, 2H), 3.00–2.75(m, 2H), 2.73(brs, 1H), 2.37–1.94(m, 6H), 1.47–0.90(m, 9H) Mass(ESI): 592(M + 1) |
| 87 | (3RS,4RS)-7-hydroxy-3-(4-hydroxyphenyl)-3-methyl-4-[9-carboxy-9-(4,4,5,5-pentafluoropentylthio)-nonyl]chroman | 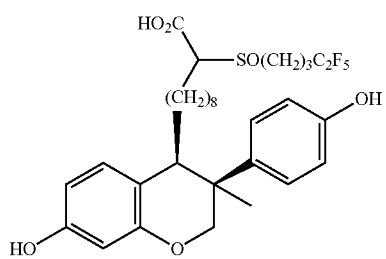 | $^1$H-NMR(300 MHz, CDCl$_3$) δ: 7.10(d, 2H), 6.95–6.75(m, 3H), 6.40–6.28(m, 2H), 4.45(d, J=10.57 Hz, 1H), 4.12(d, J=10.41 Hz, 1H), 4.22(t, J=6.47 Hz, 1H),2.80–2.54(m, 3H), 2.30–2.02(m, 2H), 2.00–0.90(m, 2H) Mass(ESI): 619(M + 1) |

TABLE 1-continued

| COM. NO. | NAME | STRUCTURE | PHYSICAL DATA |
|---|---|---|---|
| 88 | (3RS,4RS)-7-hydroxy-3-(4-hydroxyphenyl)-3-methyl-4-[9-carboxy-9-(4,4,5,5,5-pentafluoropentyl)-sulfinyl)nonyl]chroman | 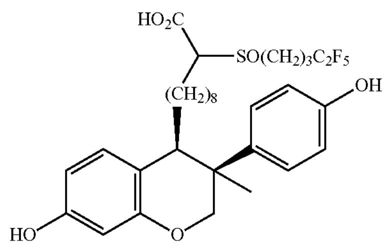 | $^1$H-NMR(300 MHz, MeOH-d$_4$) δ: 6.98(d, J=8.71 Hz, 2H), 6.81–6.69(m, 3H), 6.25–6.08(m, 2H) 4.34(d, J=10.39 Hz, 1H), 4.08(d, J=10.42 Hz, 1H),3.40–3.10(m, 1H), 3.00–2.65(m, 3H), 2.49(d, J=7.83 Hz, 1H), 2.33–2.10(m, 2H), 2.10–0.81(m, 21H) Mass(ESI): 657(M + Na) |
| 89 | (3RS,4RS)-7-hydroxyphenyl-3-(4-hydroxyphenyl)-4-[4-methyloxycarbonyl-propyloxy)phenyl]-3-methyl-chroman | 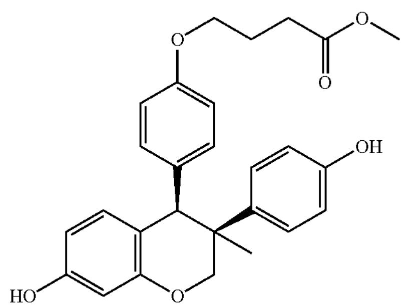 | $^1$H-NMR(300 MHz, CDCl$_3$) δ: 6.74(d, 2H), 6.67(d, 1H), 6.55(d, 2H), 6.48–6.40(m, 5H), 6.28(dd, 1H), 4.51(d, 1H, J=10.6 Hz), 3.96(d, 1H, J=10.6 Hz),3.84(t, 2H), 3.82(s, 1H), 3.65(s, 3H), 2.42(t, 2H, J=7.3 Hz), 2.02–1.93(m, 2H), 1.46(s, 3H). Mass(ESI): 449(M + 1), 471(M + Na) |
| 90 | (3RS,4RS)-4-{4-[7-hydroxy-3-(4-hydroxyphenyl)-3-methylchroman-4-yl]-phenoxy}butanoic acid | 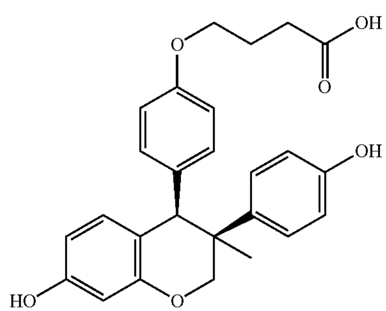 | $^1$H-NMR(300 MHz, MeOH-d$_4$) δ: 6.71(d, 2H), 6.50(d, 1H), 6.43(d, 2H), 6.41–6.36(m, 4H), 6.29–6.14(m, 2H), 4.46(d, 1H, J=10.6 Hz), 3.86(d, 1H, J=10.6 Hz), 3.81–3.75(m, 3H),2.30(t, 2H, J=7.3 Hz), 1.93–1.85(m, 2H), 1.334(s, 3H) Mass(ESI): 435(M + 1), 457(M + Na) |

TABLE 1-continued

| COM. NO. | NAME | STRUCTURE | PHYSICAL DATA |
|---|---|---|---|
| 91 | (3RS,4RS)-ethyl-1-{4-[7-hydroxy-phenyl)-3-(4-hydroxy-phenyl)-3-methylchroman-4-yl]-phenoxy}butyl]piperidine-2-carboxylate | 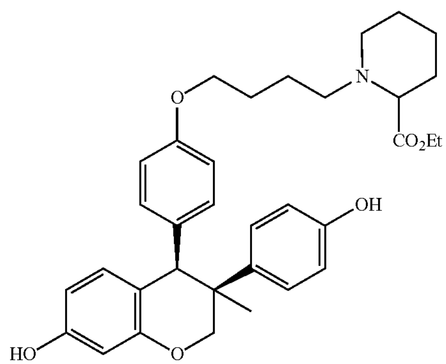 | $^1$H-NMR(300 MHz, CDCl$_3$ + MeOH-d$_4$) δ: 6.73(d, 2H), 6.62(d, 1H), 6.55(d, 2H), 6.44–6.37(m, 5H), 6.29(dd, 1H), 4.50(d, 1H, J=10.6), 4.12(q, 2H, J=6.8 Hz), 3.93(d, 1H, J=10.6 Hz), 3.82(s, 1H), 3.76(t, 2H), 3.02–2.96(m, 2H), 2.55–2.48(m, 1H), 2.30–2.24(m, 1H), 2.12–2.08(m, 1H), 1.78–1.53(m, 10H), 1.42(s, 3H), 1.19(t, 3H, J=6.8 Hz) Mass(ESI): 560(M + 1) |
| 92 | (3RS,4RS)-1-{4-[7-hydroxy-3-(4-hydroxyphenyl)-3-methylchroman-4-yl]-phenoxy}butyl]piperidine-2-carboxylic acid | 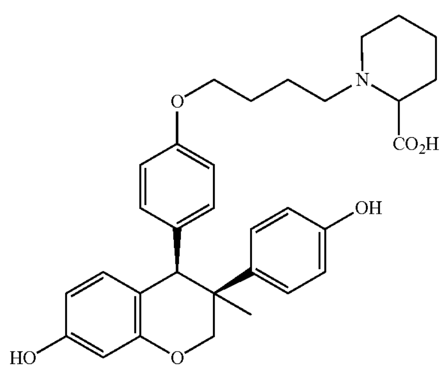 | $^1$H-NMR(300 MHz, MeOH-d$_4$) δ: 6.96(d, 2H), 6.78(d, 1H), 6.71(d, 2H), 6.68(m, 4H), 6.50(d, 1H), 6.43(dd, 1H), 4.71(d, 1H, J=10.6 Hz), 4.12(d, 1H, J=10.6 Hz), 4.06(s, 1H), 4.04(t, 2H), 3.77–3.68(m, 1H), 3.61–3.55(m, 1H), 3.47–3.40(m, 1H), 3.26–3.00(m, 2H), 2.39–2.30(m, 1H), 2.08–1.88(m, 9H), 1.68(s, 3H) Mass(ESI): 532(M + 1), 554(M + Na) |

TABLE 1-continued

| COM. NO. | NAME | STRUCTURE | PHYSICAL DATA |
|---|---|---|---|
| 93 | (3RS,4RS)-7-hydroxy-3-(4-hydroxyphenyl)-3-methyl-4-{4-{methyl[3-(4,4,5,5,5-pentafluoropentylthio)propyl]amino}butoxy}phenyl}chroman | 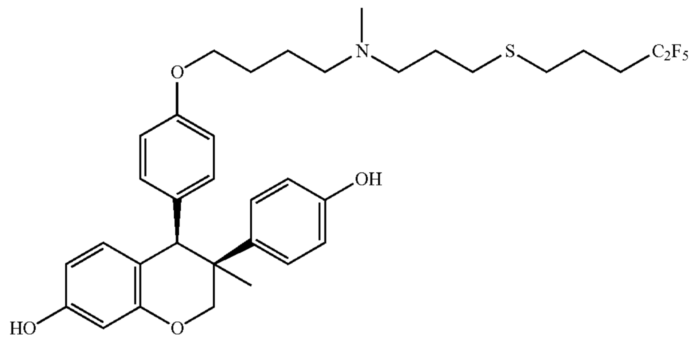 | ¹H-NMR(300 MHz, MeOH-d₄) δ: 6.87(d, 2H), 6.68(d, 1H), 6.58(d, 2H),6.56(m, 4H), 6.42(d, 1H), 6.34(dd, 1H), 4.63(d, 1H, J=10.6 Hz), 4.01(d, 1H, J=10.6 Hz), 3.96(s, 1H), 3.90(t, 2H), 2.70–2.48(m, 8H), 2.39–2.22(m, 2H), 2.32(s, 3H), 1.96–1.64(m, 8H), 1.52(s, 3H) Mass(ESI): 669(M + 2) |
| 94 | (3RS,4RS)-7-hydroxy-3-(4-hydroxyphenyl)-3-methyl-4-{[7-(4,4,5,5,5-pentafluoropentylsulfinyl)heptyloxy]methyl}chroman | 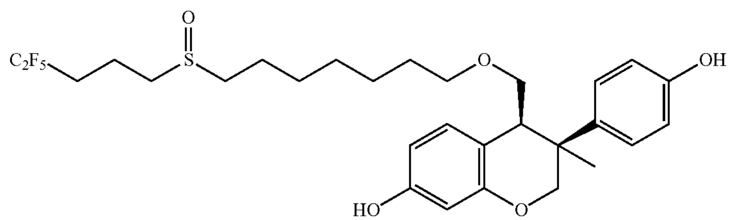 | ¹H-NMR(300 MHz, CDCl₃) δ: 7.08(d, 2H), 6.99(d, 1H), 6.80(d, 2H), 6.43–6.36(m, 2H), 4.66(dd, 1H), 4.13(d, 1H), 3.23–3.08(m, 2H), 3.08–2.92(m, 2H),2.87–2.72(m, 4H), 2.68–2.57(m, 1H), 1.78–1.06(m, 10H), 1.30(s, 3H) Mass(ESI): 593(M + 1), 615(M + Na) |
| 95 | (3RS,4RS)-7-hydroxy-3-(4-hydroxyphenyl)-3-methyl-4-{[6-(4,4,5,5,5-pentafluoropentylsulfinyl)hexyloxy]ethyl}chroman | 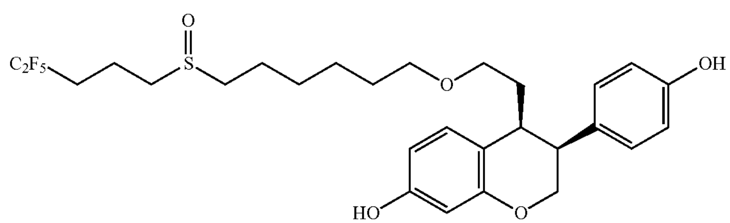 | ¹H-NMR(300 MHz, CDCl₃) δ: 7.08(d, 2H), 6.91(d, 1H), 6.83(d, 2H), 6.39–6.36(m, 2H), 4.47(d, 1H), 4.26(dd, 1H), 3.37–3.10(m, 4H),2.88–2.58(m, 5H), 2.36–2.14(m, 4H), 1.88–1.77(m, 2H), 1.55–1.18(m, 8H), 1.26(s, 3H) Mass(ESI): 593(M + 1) |

TABLE 1-continued

| COM. NO. | NAME | STRUCTURE | PHYSICAL DATA |
|---|---|---|---|
| 96 | (3RS,4RS)-2-{{5-[7-hydroxy-3-(4-hydroxyphenyl)-3-methyl-chroman-4-yl]pentyl}-{3-[(4,4,5,5,5-pentafluoropentyl)-sulfinyl]propyl}amino}-acetic acid | 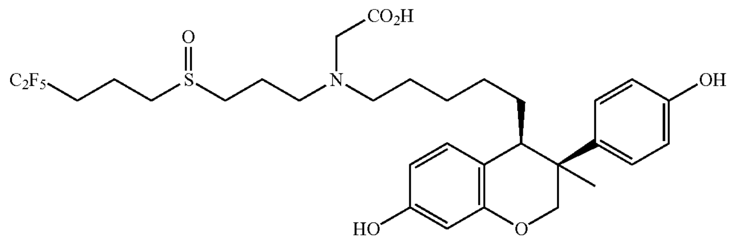 | ¹H-NMR(300 MHz, MeOH-d₄) δ: 7.10(d, 2H), 6.88(d, 1H), 6.79(d, 2H), 6.33(d, 1H), 6.25(s, 1H), 4.52(d, 1H), 4.21(d, 1H), 3.57(s, 2H), 3.23(t, 1H), 3.02–2.85(m, 6H), 2.69–2.63(m, 1H), 2.47–2.28(m, 2H), 2.22–2.06(m, 4H), 1.58–1.07(m, 8H), 1.21(s, 3H) Mass(ESI): 650(M + 1) |
| 97 | (3RS,4RS)-3-(4-hydroxy-phenyl)-3-methyl-4-{5-[4-[(4,4,5,5,5-pentafluoropentyl)sulfinyl]methyl]piperidyl]-pentyl}chroman-7-ol | 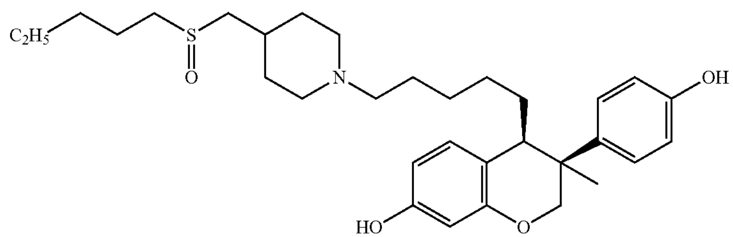 | ¹H-NMR(300 MHz, MeOH-d₄) δ: 6.95(d, 2H), 6.70(d, 1H), 6.61(d, 2H), 6.15(d, 1H), 6.10(d, 1H), 4.38(d, 1H), 4.09(d, 1H), 3.05–2.51(m, 6H), 2.33–1.64(m, 10H), 1.41–0.97(m, 11H), 1.05(s, 3H) Mass(ESI): 632(M + 1) |
| 98 | 7-hydroxy-3-[4-hydroxy-2-(methyloxymethyl)phenyl]-4-(4,4,5,5,5-pentafluoropentyl-sulfinyloctyloxy)-2H-chromene | 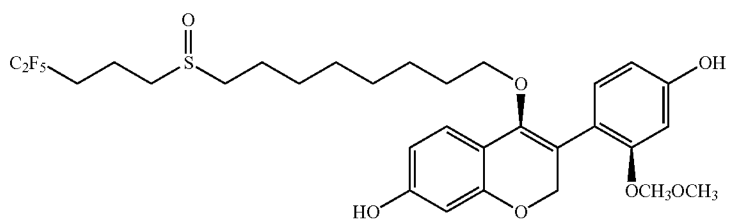 | ¹H-NMR(300 MHz, CDCl₃); δ 7.85(d, J=8.67 Hz, 1H), 7.28(dd, J=7.92 Hz, 1H), 6.68(s, 1H), 6.58(dd, J=2.26 and 8.67 Hz, 1H), 6.43(dd, J=2.26and 4.14 Hz, 1H), 6.35(dd, J=2.26 and 8.29 Hz, 1H), 6.21(d, J=2.26 Hz, 1H), 4.75(d, J=10.92 Hz, 1H), 4.45(d, J=10.92 Hz, 1H), 3.94(d, J=9.8 Hz, 1H), 3.82(d, J=9.79 Hz, 1H), 3.64(t, 2H), 3.47(s, 3H), 2.70–2.84(m, 4H), 2.20–2.26(m, 4H), 1.76–1.79(m, 4H), 0.94–1.42(m, 8H) Mass(ESI): 637(M + 1) |

TABLE 1-continued

| COM. NO. | NAME | STRUCTURE | PHYSICAL DATA |
|---|---|---|---|
| 99 | (3RS,4RS)-7-hydroxy-3-(4-hydroxyphenyl)-4-(4-(N-methyl-N-4-(4,4,5,5,5-pentafluoropentyl)sulfinyl)butyl-amino)butyl)-3-methylchroman | 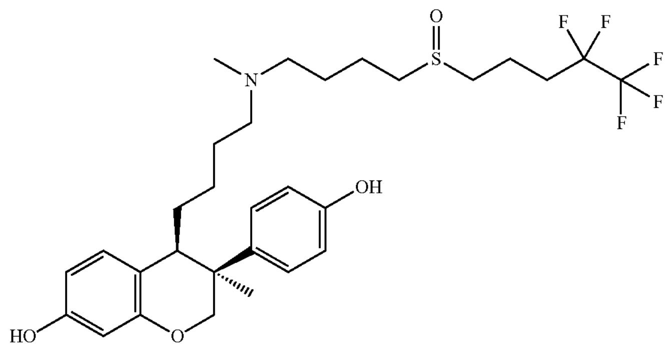 | $^1$H-NMR(300 MHz, MeOH-d$_4$) δ: 7.13(d, 2H, J=8.7 Hz), 6.90(d, 1H, J=8.25 Hz), 6.81(d, 2H, J=8.77 Hz), 6.34(dd, 1H,J=8.2 Hz), 6.28(d, 1H, J=2.44 Hz), 4.53(d, 1H, J=10.64 Hz), 4.23(d, 1H, J=10.59 Hz), 2.93–2.83(m, 4H), 2.68(d, 1H, J=7.46 Hz), 2.58(t, 2H), 2.44–2.29(m, 7H), 2.11(m, 2H), 1.81–1.63(m, 4H), 1.40–1.09(m, 9H) Mass(ESI): 606(M + 1) |
| 100 | (3RS,4RS)-7-hydroxy-3-(4-hydroxyphenyl)-4-(4-(N-methyl-N-4-(4,4,5,5,5-pentafluoropentyl)sulfonyl)butyl-amino)butyl)-3-methylchroman | 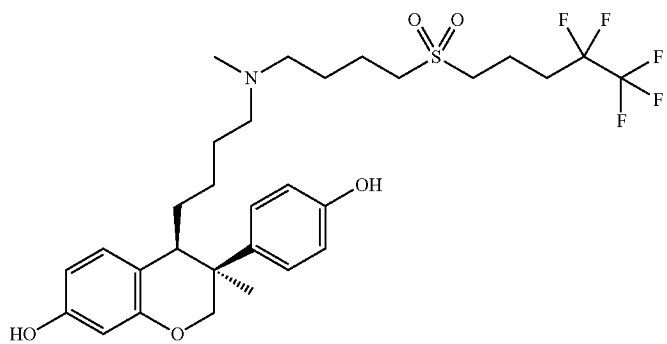 | $^1$H-NMR(300 MHz, MeOH-d$_4$) δ: 7.01(d, 2H, J=8.76 Hz), 6.77(d, 1H, J=8.25 Hz), 6.69(d, 2H, J=8.76 Hz), 6.22(dd, 1H, J=8.15 Hz), 6.15(d,1H, J=2.45 Hz), 4.40(d, 1H, J=10.64 Hz), 4.13(d, 1H, J=10.59 Hz), 3.10(t, 2H, J=7.53 Hz), 3.03(t, 2H, J=7.48 Hz), 2.68(d, 1H, J=7.46 Hz), 2.56(t, 2H, J=7.86 Hz), 2.40(t, 2H), 2.34–2.19(m, 7H), 2.06–2.00(m, 2H), 1.76–1.65(m, 2H), 1.60–1.49(m, 2H), 1.27–0.96(m, 9H) Mass(ESI): 622(M + 1) |

TABLE 1-continued

| COM. NO. | NAME | STRUCTURE | PHYSICAL DATA |
|---|---|---|---|
| 101 | (3RS,4RS)-7-hydroxy-3-(4-hydroxyphenyl)-4-(5-(N-methyl-N-3-(4,4,5,5,5-pentafluoropentylsulfonyl)propylamino)pentyl)-3-methylchroman | 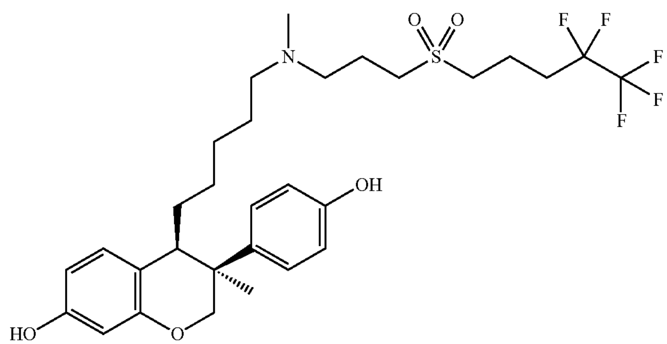 | ¹H-NMR(300 MHz, MeOH-d4) δ: 7.08(d, 2H, J=9.05 Hz), 6.84(d, 1H, J=8.29 Hz), 6.75(d, 2H, J=9.04 Hz), 6.29(dd, 1H, J=8.28 Hz), 6.23(d, 1H,J=2.26 Hz), 4.47(d, 1H, J=10.92 Hz), 4.17(dd, 1H, J=10.55 Hz), 3.18(t, 2H, J=7.54 Hz), 3.08(t, 2H, J=7.54 Hz), 2.62(d, 1H, J=8.29 Hz), 2.45(t, 2H, J=7.92 Hz), 2.35(m, 7H), 2.24(t, 2H, J=7.91 Hz), 2.17(s, 3H), 2.13–2.05(m, 2H), 1.96–1.88(m, 2H), 1.29–0.98(m, 11H) Mass(ESI): 622(M + 1) |
| 102 | (3RS,4RS)-7-hydroxy-3-(4-hydroxyphenyl)-4-(3-(N-methyl-N-5-(4,4,5,5,5-pentafluoropentylsulfinyl)-pentylamino)propyl)-3-methylchroman | 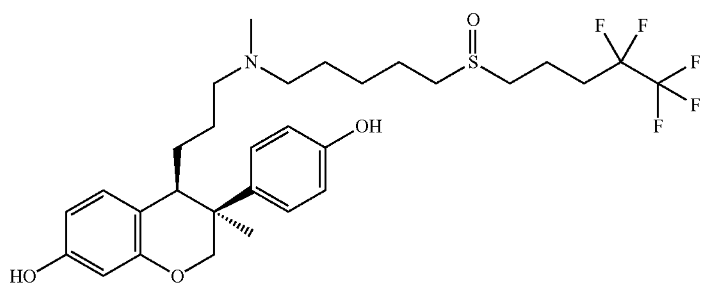 | ¹H-NMR(300 MHz, MeOH-d4) δ: 7.07(d, 2H, J=8.67 Hz), 6.86(d, 1H, J=8.29 Hz), 6.75(d, 2H, J=8.67 Hz), 6.29(dd, 1H,J=7.91, 2.63 Hz), 6.22(d, 1H, J=2.63 Hz), 4.47(d, 1H, J=10.55 Hz), 4.17(d, 1H, J=10.55 Hz), 2.89–2.73(m, 4H), 2.64(d, 1H, J=7.53 Hz), 2.40–2.23(m, 4H), 2.14–2.02(m, 7H), 1.71(m, 2H), 1.47–0.98(m, 11H) Mass(ESI): 605(M + 1) |
| 103 | (3RS,4RS)-4-[4-(4-cyanopropyloxy)phenyl]-7-hydroxy-3-(4-hydroxyphenyl)-3-methylchroman | 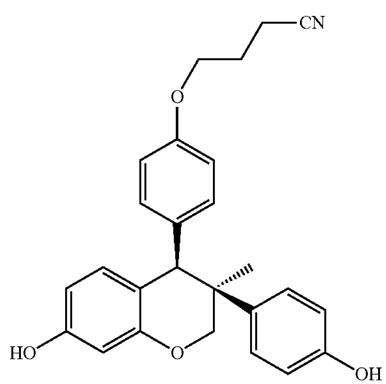 | ¹H-NMR(300 MHz, MeOH-d4) δ: 7.2(dd, 2H), 6.9–6.7(d, 7H), 6.4(t, 1H), 6.3(d, 1H), 4.45(dd, 1H, J=10.3 Hz, 1H), 4.12(dd, 1H, J=10.4 Hz, 1H), 4.02(s, 1H), 3.9(t, 2H), 2.64(t, 2H),2.15(m, 2H), 1.18(s, 3H) Mass(ESI): 416(M + 1) |

TABLE 1-continued

| COM. NO. | NAME | STRUCTURE | PHYSICAL DATA |
|---|---|---|---|
| 104 | (3RS,4RS)-7-hydroxy-3-(4-hydroxyphenyl)-4-[4-(4-piperidylbutyloxy)phenyl]-chroman | 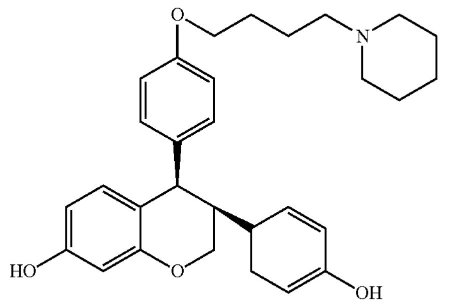 | ¹H-NMR(300 MHz MeOH-d4) δ: 6.59(dd, 2H), 6.54(m, 7H), 6.2(t, 2H), 4.0(m, 1H), 3.85(t, 2H), 3.36(m, 1H), 3.1~2.82(m, 7H), 1.7(m, 8H), 1.55(s, 3H) |
| 105 | (3RS,4RS)-7-hydroxy-3-(4-hydroxyphenyl)-3-methyl-4-[4-(5-N-oxypiperidylpentyloxy)phenyl]-chroman | 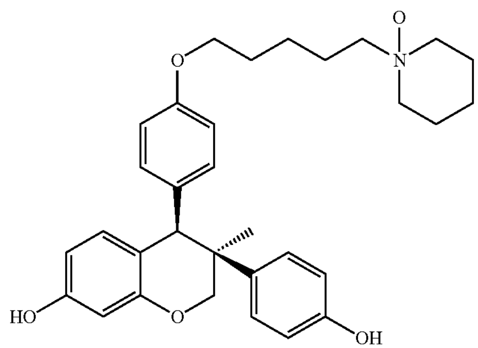 | ¹H-NMR(300 MHz, MeOH-d4) δ: 7.07(dd, 2H), 6.68(d, 1H), 6.46(dd, 2H), 6.4(m, 4H), 6.28(s, 1H), 6.1(d, 1H), 4.28(dd, J=10.2 Hz, 1H),4.1(dd, J=10.5 Hz, 1H), 3.75(m, 2H), 3.7(s, 1H), 3.1(m, 6H), 2.0(m, 2H), 1.88~1.26(m, 10H), 0.95(s, 3H) Mass(ESI): 518(M + 1) |
| 106 | (3RS,4RS)-7-hydroxy-3-(4-hydroxyphenyl)-4-[11-(4,4,5,5,5-pentyfluoropentyl)sulfonylamino-11-iminoundecyl]chroman | 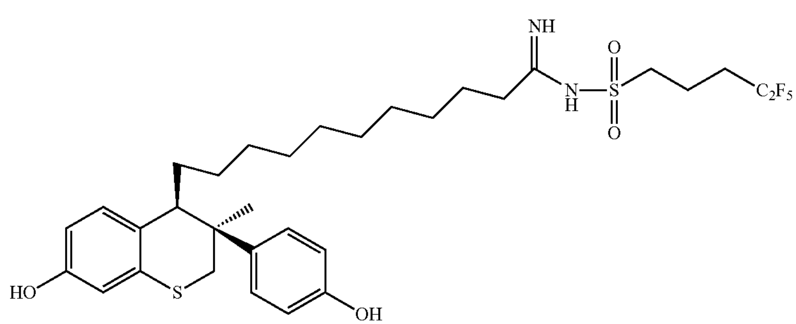 | ¹H-NMR(300 MHz, MeOH-d4) δ: 7.23(dd, 2H), 6.85(d, 1H), 6.79(dd, 2H), 6.58(s, 1H), 6.45(d, 1H), 3.6(dd, J=11.6 Hz, 1H), 3.2(broad, 1H, NH),3.15(t, 2H), 2.93(dd, J=11.5 Hz, 1H), 2.75(m, 1H), 2.45~2.23(m, 4H), 2.07(m, 2H), 1.65(m, 2H), 1.39~0.9(m, 19H) Mass(ESI): 679(M + 1) |

TABLE 1-continued

| COM. NO. | NAME | STRUCTURE | PHYSICAL DATA |
|---|---|---|---|
| 107 | (3RS,4RS)-7-hydroxy-3-(4-(hydroxyphenyl)-4-[5-N-methyl-N-8,8,9,9,9-pentafluoro-4-carboxyl-nonylamino]-chroman | 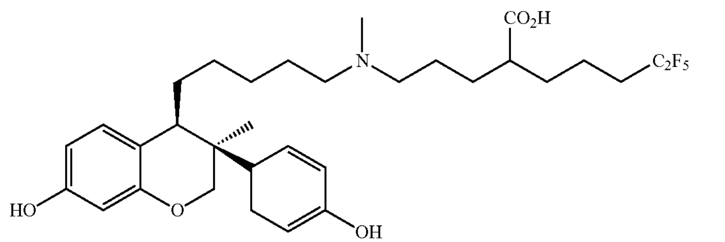 | $^1$H-NMR(300 MHz, MeOH-d4) δ: 7.0(dd, J=8.7 Hz, 2H), 6.78(d, 1H), 6.66(dd, J=8.7 Hz, 2H), 6.2(d, 1H), 6.12(s, 1H),4.4(dd, J=10.5 Hz, 1H), 4.08(dd, J=10.6 Hz, 1H), 2.87(m, 2H), 2.75(m, 2H), 2.55(m, 4H), 2.25~1.85(m, 3H), 1.7~0.89(m, 18H) Mass(ESI): 616(M + 1) |
| 108 | (3RS,4RS)-7-hydroxy-3-(4-(hydroxyphenyl)-3-methyl-4-[5-oxa-9-(4,4,5,5,5-pentafluoropentylsulfonyl-amino)nonyl]chroman | 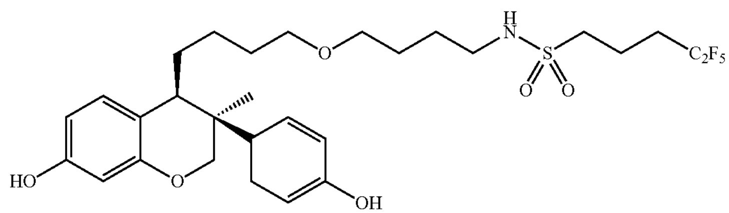 | $^1$H-NMR(300 MHz, CDCl$_3$) δ: 7.08(dd, J=8.6 Hz, 2H), 6.80(m, 3H), 6.32(d, 2H), 6.0(dd, J=8.2 Hz, 1H), 5.08(t, 1H),4.52(dd, J=10.2 Hz, 1H), 4.25(dd, J=10.6 Hz, 1H), 3.30(m, 4H),3.09(m, 4H), 2.63(dd, J=8.9 Hz, 1H), 2.38~1.92(m, 4H), 1.52~0.61(m, 15H) |
| 109 | (5-(7-hydroxy-3-(4-hydroxyphenyl)-3-methyl)chroman-4-yl)pentyl)-(methylsulfonyl)(3-(4,4,5,5,5-pentafluoropentylsulfinyl)-propyl)amine | 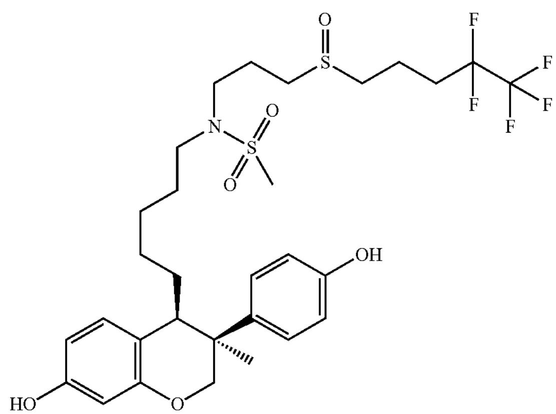 | $^1$H-NMR(300 MHz, CD$_3$OD) δ: 7.0(d, 2H), 6.84(d, 1H), 6.7(d, 2H), 6.2(m, 2H), 4.4(d, 1H), 4.1(d, 1H),3.1(m, 2H), 2.9(m, 2H), 2.75(m, 7H), 2.55(d, 1H), 2.25(m, 2H), 1.9(m, 4H), 1.3~1.1(m, 11H) Mass(ESI): 670(M + 1) |

TABLE 1-continued

| COM. NO. | NAME | STRUCTURE | PHYSICAL DATA |
|---|---|---|---|
| 110 | 8-(3-methyl-8-methyloxy-3-(4-methyloxyphenyl)-5-thiabicyclo[4,4,0]deca-1(6),7,9-trien-2yl)-2-(4,4,5,5,5-pentafluoropentyl)octanoic acid | 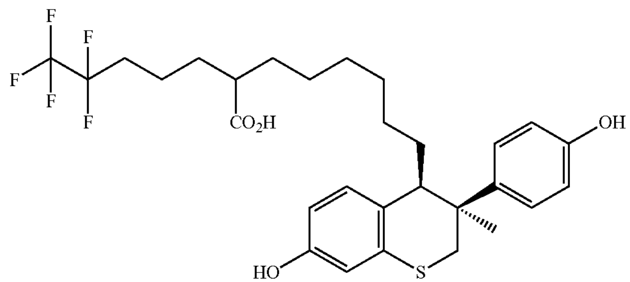 | ¹H-NMR(300 MHz, CD₃OD) δ: 7.1(d, 2H), 6.7(d, 1H), 6.6(d, 2H), 6.45(d, 1H), 6.35(dd, 1H), 3.5(d, 1H), 2.9(d, 1H),2.65(bs, 1H), 2.1(m, 3H), 1.5(m, 4H), 1.3–1.0(m, 15H) Mass(ESI): 575(M + 1) |
| 111 | (3RS,4RS)-10-[7-hydroxy-3-(4-hydroxyphenyl)-3-methylchroman-4-yl]-2-(4,4,5,5,5-pentafluoropentyl)-decanoic acid | 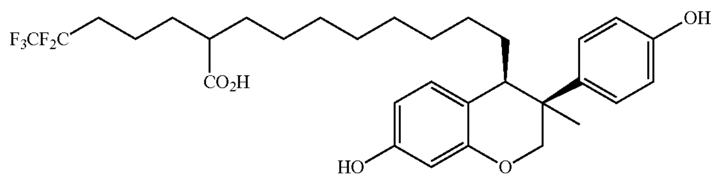 | ¹H-NMR(300 MHz, CDCl₃) δ: 7.00(d, 2H), 6.82(d, 1H, J=6.7 Hz), 6.76(d, 2H, J=8.5 Hz), 6.30(m, 2H), 4.43(d, 1H,J=10.4 Hz), 4.16(d, 1H, J=10.4 Hz), 2.53(bd, 1H), 2.33(m, 1H), 1.96(m, 2H), 1.55(s, 6H), 1.19(s, 3H), 1.21–1.06(m, 14H) Mass(ESI): 587(M + 1) |
| 112 | (3RS,4RS)-7-hydroxy-3-(4-hydroxyphenyl)-3-methyl-4-{5-[N-methyl-N-[1-hydroxycarbonyl)-3-(4,4,5,5,5-pentafluoropentyl)-sulfinyl]propyl]-amino-pentyl}chroman | 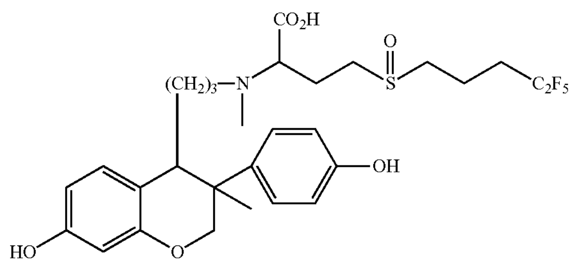 | ¹H-NMR(300 MHz, CD₃OD) δ: 7.56(m, 2H),7.00(m, 1H), 6.73(m, 2H), 6.21(m, 1H), 6.15(m, 1H), 4.40(m, 1H), 4.10(m, 1H), 3.23(m, 1H), 2.92–2.82(m, 2H), 2.65(s, 3H), 2.53(m, 1H), 2.28–1.96(m, 6H), 1.43–1.05(m, 11H) Mass(ESI): 650(M⁺ + 1) |
| 113 | (3RS,4RS)-7-hydroxy-3-(4-hydroxyphenyl)-3-methyl-4-{5-[N-methyl-N-[3-(4,4,5,5,5-pentafluoropentyl)-sulfinyl]propionyl]-amino-pentyl}chroman | 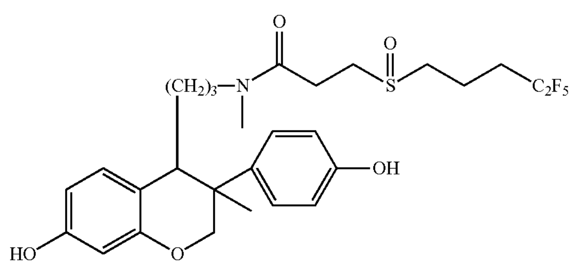 | ¹H-NMR(300 MHz, CDCl₃) δ: 7.75–7.09(m, 1H), 6.96(m, 2H), 6.86(m, 3H), 6.37(m, 2H),5.98–5.76(m, 1H), 4.47(m, 1H), 4.12(m, 1H), 3.48–2.45(m, 10H), 2.34–2.05(m, 4H), 1.34–0.88(m, 13H) Mass(ESI): 620(M⁺ + 1) |

TABLE 1-continued

| COM. NO. | NAME | STRUCTURE | PHYSICAL DATA |
|---|---|---|---|
| 114 | (3RS,4RS)-4-[9-(N-cyano)-aminononyl]-7-hydroxy-3-(4-hydroxyphenyl)-3-methyl-thiochroman | 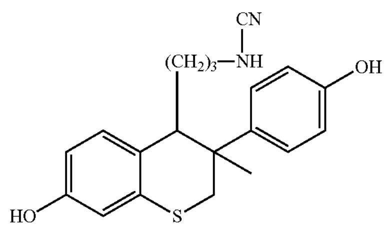 | $^1$H-NMR(300 MHz, CD$_3$OD) δ: 7.15(m, 2H), 6.77–6.67(m, 3H), 6.47(m, 1H), 6.35(m, 1H), 3.51(m, 1H), 2.86(m, 3H), 2.64(m, 1H),1.46–1.38(m, 2H), 1.18–0.99(m, 17H) Mass(ESI): 439(M$^+$ + 1) |
| 115 | (3RS,4RS)-7-hydroxy-3-(4-hydroxyphenyl)-3-methyl-4-{5-[N-methyl-N-oxo-N-[3-(4,4,5,5,5-pentafluoropentyl]sulfinyl]pentyl]}aminopentyl]chroman | 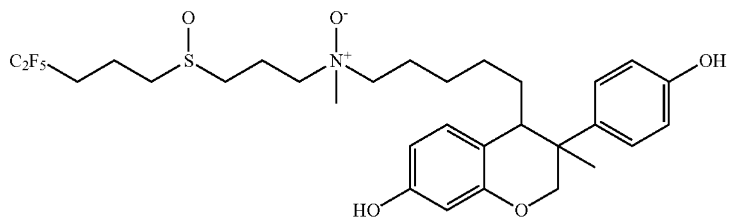 | $^1$H-NMR(300 MHz, CD$_3$OD) δ: 7.01(m, 2H), 6.81(m, 1H), 6.66(m, 2H),6.25–6.13(m, 2H), 4.42(m, 1H), 4.11(m, 1H), 3.08–2.63(m, 9H), 2.52(m, 1H), 2.32–1.89(m, 6H), 1.53–1.36(m, 2H), 1.32–0.92(m, 11H) Mass(ESI): 622(M$^+$ + 1) |
| 116 | (3RS,4RS)-7-hydroxy-3-(4-hydroxyphenyl)-3-methyl-4-{10-{N-[(5-hydroxycarbonyl)pentyl]-N-cyano}aminodecyl]}thiochroman | 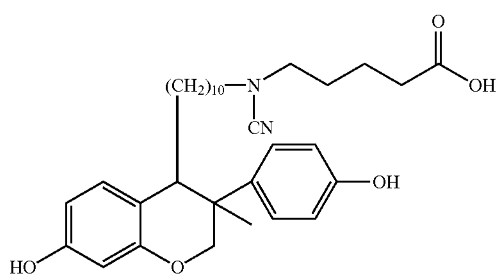 | $^1$H-NMR(300 MHz, CD$_3$OD) δ: 7.13(m, 2H), 6.78–6.66(m, 3H), 6.47(m, 1H), 6.32(m, 1H), 3.47(m, 1H),3.01–2.83(m, 5H), 2.62(m, 1H), 2.22(m, 2H), 1.62–1.43(m, 6H), 1.28–0.92(m, 19H) Mass(ESI): 553(M$^+$ + 1) |
| 117 | (3RS,4RS)-7-hydroxy-3-(4-hydroxyphenyl)-4-{2-{2-[4-(4,4,5,5,5-pentafluoropentyl)sulfinyl]-n-butyl]oxazolinyl}ethyl]-3-methylchroman | 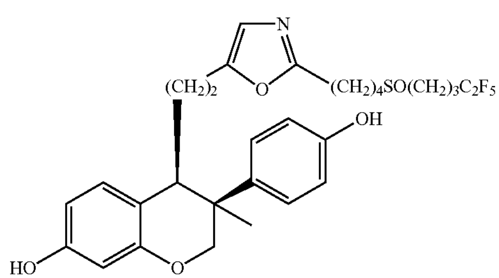 | $^1$H-NMR(300 MHz, CD$_3$OD) δ: 6.95(d, 2H), 6.75(d, 1H), 6.68(d, 2H),6.45(s, 1H), 6.24(dd, 1H), 6.17(d, 1H), 4.43(d, 1H), 4.14(d, 1H), 2.8–2.5(m, 7H), 2.39(t, 2H), 2.3–2.1(m, 2H), 1.98(m, 2H), 1.73(m, 4H), 1.5(m, 1H), 1.25(m, 1H), 1.1(s, 3H) Mass(ESI): 616(M + 1) |

TABLE 1-continued

| COM. NO. | NAME | STRUCTURE | PHYSICAL DATA |
|---|---|---|---|
| 118 | (3RS,4RS)-7-hydroxy-3-(4-hydroxyphenyl)-4-{5-[4-(4,4,5,5,5-pentafluoropentylsulfinyl)piperidinyl]-pentyl}-3-methylchroman | [structure with SO(CH$_2$)$_3$C$_2$F$_5$ piperidinyl chain on chroman] | $^1$H-NMR(300 MHz, CDCl$_3$) δ: 7.01(d, 2H), 6.76(d, 1H), 6.68(d, 2H), 6.22(dd, 1H), 6.15(d, 2H), 4.4(d, 1H),4.09(d, 1H), 2.9~2.5(m, 6H), 2.3~2.09(m, 4H), 2.05~1.91(m, 5H), 1.8~1.5(m, 3H), 1.2~0.8(m, 11H). Mass(ESI): 618(M + 1) |
| 119 | (3RS,4RS)-7-hydroxy-3-(4-hydroxyphenyl)-4-{9-[N-hydroxy-N-(4,4,5,5,5-pentafluoropentyl)carbamoyl-amino]nonyl}-3-methylthiochroman | [structure with OH H NCON(CH$_2$)$_3$C$_2$F$_5$ chain on thiochroman] | $^1$H-NMR(300 MHz, CDCl$_3$) δ: 7.05(t, 3H), 6.67(m, 3H), 6.48(d, 1H), 6.31(dd, 1H), 5.92(s, 1H), 5.78(s, 1H), 5.1(s, 1H), 3.5~3.15(m, 6H), 2.75(d, 1H), 2.5(d, 1H), 1.89(m, 2H), 1.67(m, 2H), 1.01~0.76(m, 16H). Mass(ESI): 634(M + 1) |
| 120 | (3RS,4RS)-7-hydroxy-4-{9-[(carbamoyl-amino)nonyl]-7-hydroxy-3-(4-hydroxyphenyl)-3-methylchroman | [structure with (CH$_2$)$_9$NHCONH$_2$ chain on chroman] | $^1$H-NMR(300 MHz, CDCl$_3$) δ: 7.11(d, 2H), 6.87(d, 1H), 6.8(d, 2H), 6.33(dd, 1H), 6.27(d, 1H), 4.51(d, 1H), 4.24(d, 1H), 3.08(t, 2H), 2.65(d, 1H),1.44(m, 2H), 1.31~1.11(m, 17H). Mass(ESI): 441(M + 1) |
| 121 | (3RS,4RS)-7-hydroxy-3-(4-hydroxyphenyl)-4-{9-{[[4-(4,4,5,5,5-pentafluoropentyl]sulfonyl]carbamoyl-amino}nonyl}-3-methylthiochroman | [structure with (CH$_2$)$_9$NHCONHSO$_2$(CH$_2$)$_3$C$_2$F$_5$ chain on thiochroman] | $^1$H-NMR(300 MHz, CDCl$_3$) δ: 7.14(d, 2H), 6.76(d, 1H), 6.68(d, 2H), 6.42(d, 1H), 6.34(dd, 1H),3.52(d, 1H), 3.4(t, 2H), 3.03(t, 2H), 2.87(d, 1H), 2.65(d, 1H), 2.2(m, 2H), 1.96(m, 2H), 1.35(m, 2H), 1.19~0.97(m, 17H). Mass(ESI): 703(M + 23) |

TABLE 1-continued

| COM. NO. | NAME | STRUCTURE | PHYSICAL DATA |
|---|---|---|---|
| 122 | (3RS,4RS)-7-hydroxy-3-(4-hydroxyphenyl)-4-{2-[2-[4-(4,4,5,5,5-pentafluoropentyl)sulfinyl]-n-butyl]-oxazolinyl]ethyl}-3-methylthiochroman | 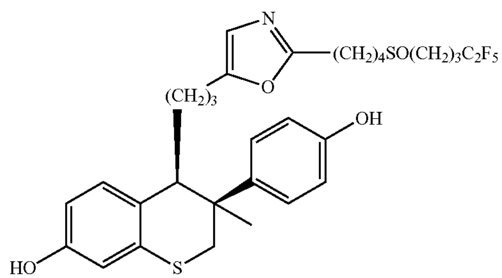 | 1H-NMR(300 MHz, CDCl3) δ: 7.16(d, 2H), 6.8(d, 1H), 6.64(d, 2H),6.48(d, 2H), 6.38(dd, 1H), 3.54(d, 1H), 2.89(d, 1H), 2.8–2.55(m, 7H), 2.35–2.1(m, 4H), 1.99(m, 2H), 1.71(m, 4H), 1.35(d, 2H), 1.01(s, 3H). Mass(ESI): 632(M + 1) |
| 123 | (3RS,4RS)-7-hydroxy-3-(4-hydroxyphenyl)-4-{7-[(4,4,5,5,5-pentafluoropentyl)sulfonylamino]-heptyl}-3-methylchroman | 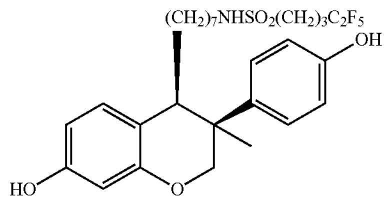 | 1H-NMR(300 MHz, CDCl3) δ: 6.99(d, 2H), 6.76(d, 1H), 6.68(d, 2H), 6.22(dd, 1H), 6.15(d, 1H), 4.39(d, 1H),4.1(d, 1H), 3.02(d, 2H), 2.87(t, 2H), 2.52(d, 1H), 2.21(m, 2H), 1.94(m, 2H), 1.33(m, 2H), 1.16–0.9(m, 13H). Mass(ESI): 594(M + 1) |
| 124 | (3RS,4RS)-7-hydroxy-3-(4-hydroxyphenyl)-4-{5-[N-methyl-N-[2-(4,4,5,5,5-pentafluoropentylsulfinyl)ethyl]-sulfonylamino]pentyl}-3-methylchroman | 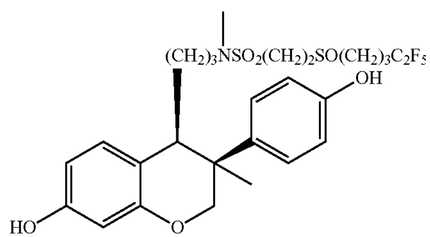 | 1H-NMR(300 MHz, CDCl3) δ: 7.01(d, 2H), 6.78(d, 1H),6.68(d, 2H), 6.22(dd, 1H), 6.14(d, 1H), 4.4(d, 1H), 4.12(d, 1H), 3.29–3.1(m, 3H), 3.02–2.9(m, 3H), 2.85–2.8(m, 2H), 2.69(s, 3H), 2.55(d, 1H), 2.3–2.1(m, 2H), 2.05–1.95(m, 2H), 1.3–0.9(m, 1H). Mass(ESI): 656(M + 1) |
| 125 | (3RS,4RS)-7-hydroxy-3-(4-hydroxyphenyl)-4-{[11-carboxyl-11-(4,4,5,5,5-pentafluoropentyl)]undecyl}-3-methylthiochroman | 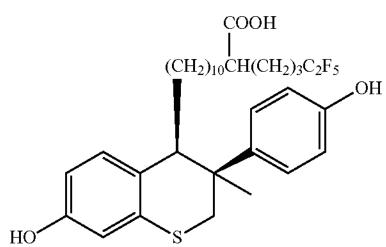 | 1H-NMR(300 MHz, CD3OD) δ: 7.13(d, 2H), 6.71(d, 1H), 6.68(d, 2H), 6.47(d, 1H), 6.35(dd, 1H),3.52(d, 1H), 2.86(d, 1H), 2.6(m, 1H), 2.23(m, 1H), 2.05(m, 2H), 1.56–1.03(m, 27H). Mass(ESI): 631(M + 1) |

TABLE 1-continued

| COM. NO. | NAME | STRUCTURE | PHYSICAL DATA |
|---|---|---|---|
| 126 | (3RS,4RS)-7-hydroxy-3-(4-hydroxyphenyl)-4-{[11-carbamoyl-11-(4,4,5,5,5-pentafluoropentyl)]undecyl]-3-methylthiochroman | CONH$_2$—(CH$_2$)$_{10}$CH(CH$_2$)$_3$C$_2$F$_5$ on 3-methylthiochroman with 4-hydroxyphenyl and 7-OH | $^1$H-NMR(300 MHz, CD$_3$OD) δ: 7.15(d, 2H), 6.76(d, 1H), 6.68(d, 2H), 6.42(d, 1H), 6.35(dd, 1H),3.51(d, 1H), 2.85(d, 1H), 2.63(m, 1H), 2.2–1.9(m, 3H), 1.52–1.02(m, 27H). Mass(ESI): 630(M + 1) |
| 127 | (3RS,4RS)-7-hydroxy-3-(4-hydroxyphenyl)-3-methyl-4-[9-(4,4,5,5,5-pentafluoropentyl)-9-(hydroxycarbonyl)-nonyl]chroman | COOH—(CH$_2$)$_9$CH(CH$_2$)$_3$CF$_2$CF$_3$ on chroman with 4-hydroxyphenyl and 7-OH | $^1$H-NMR(300 MHz, CD$_3$OD) δ: 7.12(d, 2H, Ar—H), 6.90(d, 1H, Ar—H), 6.82(d, 2H, Ar—H),6.34(dd, 1H, Ar—H), 6.28(d, 1H, Ar—H), 4.53(d, 1H, C2-H), 4.22(dd, 1H, C2-H), 2.65(brs, 1H, C4-H), 2.37(m, 1H, CHCOO), 2.15(m, 2H, CH$_2$CF$_2$), 1.75–0.98(m, 25H, C3-CH$_3$, alkyl-H) |
| 128 | (3RS,4RS)-7-hydroxy-3-(4-hydroxyphenyl)-3-methyl-4-[9-(4,4,5,5,5-pentafluoropentyl)-9-(hydroxycarbonyl)-nonyl]thiochroman | COOH—(CH$_2$)$_9$CH(CH$_2$)$_3$CF$_2$CF$_3$ on thiochroman with 4-hydroxyphenyl and 7-OH | $^1$H-NMR(300 MHz, CD$_3$OD) δ: 7.34(d, 2H, Ar—H), 6.96(d, 1H, Ar—H), 6.88(d, 2H, Ar—H),6.67(d, 1H, Ar—H), 6.55(dd, 1H, Ar—H), 3.70(d, 1H, C2-H), 3.05(d, 1H, C2-H), 2.85(brs, 1H, C4-H), 2.42(m, 1H, CHCOO), 2.20(m, 2H, CH$_2$CF$_2$), 1.83–1.07(m, 25H, C3-CH$_3$, alkyl-H) |
| 129 | (3RS,4RS)-7-hydroxy-3-(4-hydroxyphenyl)-3-methyl-4-{9-[4,4,5,5,5-pentafluoropentanesulfonyl)-(N-hydroxycarbonylmethyl)-amino]-nonyl}thiochroman | CH$_2$COOH—(CH$_2$)$_9$NSO$_2$(CH$_2$)$_3$CF$_2$CF$_3$ on thiochroman with 4-hydroxyphenyl and 7-OH | $^1$H-NMR(300 MHz, CD$_3$OD) δ: 7.34(d, 2H, Ar—H),6.98(d, 1H, Ar—H), 6.88(d, 2H, Ar—H), 6.67(d, 1H, Ar—H), 6.55(dd, 1H, Ar—H), 4.10(s, 2H, CH$_2$COO), 3.72(d, 1H, C2-H), 3.38(t, 2H, NCH$_2$), 3.06(d, 1H, C2-H), 2.85(brs, 1H, C4-H), 2.43(m, 2H, CH$_2$SO$_2$), 2.21(m, 2H, CH$_2$CF$_2$), 1.75–0.90(m, 21H, C3-CH$_3$, alkyl-H) |

TABLE 1-continued

| COM. NO. | NAME | STRUCTURE | PHYSICAL DATA |
|---|---|---|---|
| 130 | (3RS,4RS)-7-hydroxy-3-(4-hydroxyphenyl)-3-methyl-4-[8-(4,4,5,5,5-pentafluoropentyl)sulfonyl)octyl]chroman | 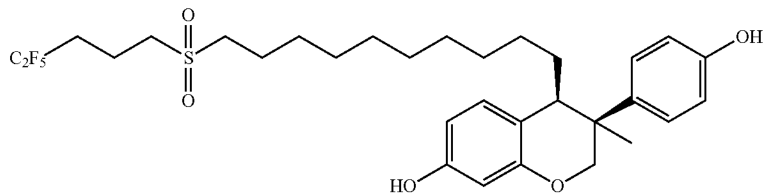 | $^1$H-NMR(CDCl$_3$, 270 MHz); δ 7.08(d, J=8.58 Hz, 1H), 6.90(d, J=7.92 Hz, 1H), 6.83(d, J=8.58 Hz, 2H), 6.38(m, 2H),5.43–5.35(br, 1H), 4.93(br, 1H), 4.51(d, J=10.23 Hz, 1H), 4.24(d, J=10.55 Hz, 1H), 3.10–2.97(m, 4H), 2.60(m, 1H), 2.35–2.18(m, 4H), 1.83(m, 2H), 1.60(m, 2H), 1.43–0.98(m, 17H) |
| 131 | (3RS,4RS)-7-hydroxy-3-(4-hydroxyphenyl)-3-methyl-4-{6-[N-methyl-N-2-(4,4,5,5,5-pentafluoropentylthio)ethylamino]hexyl}chroman. HCl salt | 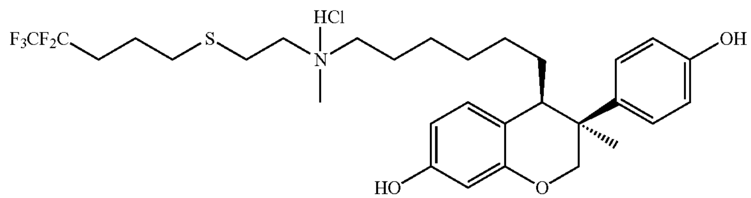 | $^1$H-NMR(CD$_3$OD, 270 MHz); δ 7.06(d, 2H), 6.84(d, 1H), 6.75(d, 2H), 6.28(dd, 1H), 6.23(d, 1H),4.446(d, 1H), 4.17(d, 1H), 3.16–2.73(m, 7H), 2.73–2.49(m, 3H), 2.36–2.07(m, 2H), 1.97–1.73(br, 2H), 1.66–1.43(br, 2H), 1.37–0.89(m, 13H) |
| 132 | (3RS,4RS)-7-hydroxy-3-(4-hydroxyphenyl)-3-methyl-4-{6-[N-methyl-N-2-(4,4,5,5,5-pentafluoropentylsulfinyl)ethylamino]hexyl}chroman | 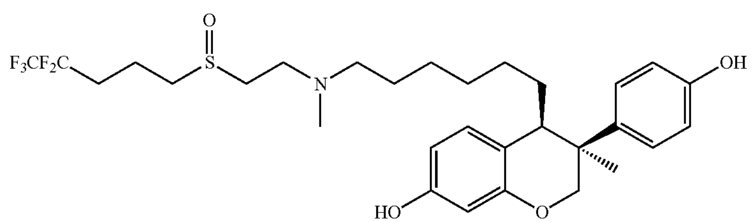 | $^1$H-NMR(CD$_3$OD, 270 MHz); δ 7.06(d, 2H), 6.89(d, 1H), 6.66(d, 2H), 6.35(dd, 1H), 6.14(d, 1H), 4.47(d, 1H), 4.17(d, 1H),3.09–2.53(m, 7H), 2.46–2.11(m, 7H), 2.04(m, 2H), 1.44–0.85(m, 13H) |

TABLE 1-continued

| COM. NO. | NAME | STRUCTURE | PHYSICAL DATA |
|---|---|---|---|
| 133 | (3RS,4RS)-3-(4,4,5,5,5-penta-fluoropentyl)-12-(7-hydroxy-3-(4-hydroxyphenyl)-3-methylchroman-4-yl)-dodecanoic acid | 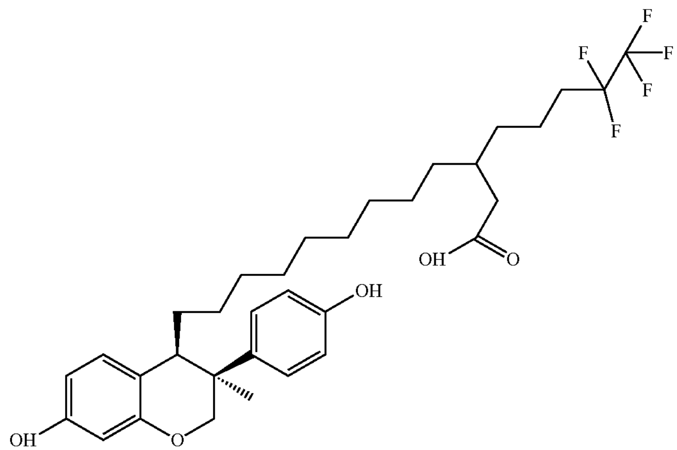 | ¹H-NMR(300 MHz, CD₃OD) δ: 6.98(d, 2H, J=8.75 Hz), 6.75(d, 1H, J=8.26 Hz), 6.67(d, 2H, J=8.76 Hz), 6.2(dd, 1H, J=2.55 Hz, 8.23 Hz),6.13(d, 1H, J=2.55 Hz), 4.39(d, 1H, J=10.3 Hz), 4.1(d, 1H, J=10.3 Hz), 2.53(bd, 1H, 2.0(m, 4H), 1.21–1.06(m, 26H) Mass(ESI): 615(M + 1) |
| 134 | (3RS,4RS)-4-allyl-7-methoxymethoxy-3-(4-methoxymethoxyphenyl)-3-methylchroman | 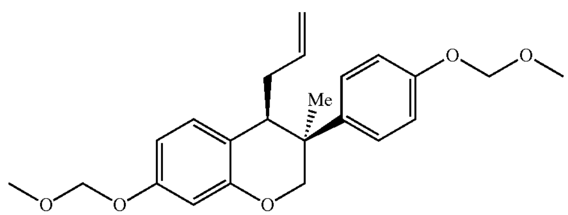 | ¹H-NMR(270 MHz, CDCl₃) δ: 7.15(d, 2H, J=8.9 Hz, Ar—H), 7.03(d, 2H, J=8.9 Hz, Ar—H), 6.96(d, 1H, J=7.9 Hz, Ar—H), 6.57(s, 1H, Ar—H),6.5–6.6(m, 1H, Ar—H), 5.5–5.7(m, 1H, vinyl-H), 5.18(s, 2H, OCH₂OMe), 5.15(s, 2H, CH₂OMe), 4.86(d, 1H, J=9.9 Hz, vinyl-H), 4.71(dd, 1H, J=17.2 Hz, 1.7 Hz, vinyl-H), 4.52(d, 1H, J=10.7 Hz, C2-H), 4.25(dd, 1H, J=10.6, 1.7 Hz, C2-H), 3.50(s, 3H, OCH₃), 3.49(s, 3H, OCH₃),2.7–2.9(m, 1H, C4-H), 2.0–2.1(m, 1H, allylic-H), 1.8–1.9(m, 1H, allylic-H), 1.29(s, 3H, C3-Me) |
| 135 | (3RS,4RS)-7-hydroxy-3-(4-hydroxyphenyl)-3-methyl-4-{9-[3-(methoxy)-propylsulfinyl]nonyl}-thiochroman | 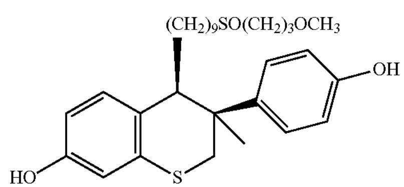 | ¹H-NMR(270 MHz, CD₃OD) δ: 7.18(d 2H, J=9 Hz, Ar—H), 6.79(d, 1H, J=8 Hz, Ar—H), 6.71(d, 2H, J=9 Hz Ar—H), 6.49(d, 1H, J=2 Hz, Ar—H),6.37(dd, 1H, J=8 and 2 Hz, Ar—H), 3.55(d, 1H, J=12 Hz, C2-H), 3.45(t, 2H, J=5 Hz, —CH₂OCH₃), 3.27(s, 3H, —CH₂OCH₃), 2.91–2.65(m, 6H, C2-H, C4-H and —CH₂SOCH₂—), 1.98–1.88(m, 2H, alkyl-H), 1.66–1.58(m, 2H, alkyl-H), 1.30–0.90(m, 14H, alkyl-H),1.05(s, 3H, C3-CH₃) |

TABLE 1-continued

| COM. NO. | NAME | STRUCTURE | PHYSICAL DATA |
|---|---|---|---|
| 136 | (3RS,4RS)-7-hydroxy-3-(4-hydroxyphenyl)-3-methyl-4-{6-[3-(4,4,5,5,5-pentafluoropentylsulfinyl)-propylsulfinyl]hexyl}-thiochroman | (CH$_2$)$_6$SO(CH$_2$)$_3$SO(CH$_2$)$_3$CF$_2$CF$_3$ on thiochroman with 4-hydroxyphenyl and methyl; HO on thiochroman | $^1$H-NMR(270 MHz, CD$_3$OD) δ: 7.18(d, 2H, J=9 Hz, Ar—H), 6.80(d, 1H, J=8 Hz, Ar—H), 6.71(d, 2H, J=9 Hz, Ar—H), 6.49(d, 1H, J=2 Hz, Ar—H), 6.37(dd, 1H, J=8 and 2 Hz, Ar—H), 3.55(d, 1H, J=12 Hz, C2-H), 2.98–2.58(m, 10H, C2-H, C4-H and —CH$_2$SOCH$_2$CH$_2$SOCH$_2$—), 2.38–1.96(m, 6H, CF$_3$CF$_2$CH$_2$CH$_2$CH$_2$SOCH$_2$CH$_2$—), 1.53(m, 2H, alkyl-H),1.30–0.90(m, 8H, alkyl-H), 1.06(s, 3H, C3-CH$_3$) |
| 137 | (3RS,4RS)-7-hydroxy-3-(4-hydroxyphenyl)-3-methyl-4-{6-[2-(4,4,5,5,5-pentafluoropentylsulfinyl)-ethylsulfinyl]hexyl}-thiochroman | (CH$_2$)$_6$SO(CH$_2$)$_2$SO(CH$_2$)$_3$CF$_2$CF$_3$ on thiochroman with 4-hydroxyphenyl and methyl; HO on thiochroman | $^1$H-NMR(270 MHz, CD$_3$OD) δ: 7.18(d, 2H, J=9 Hz, Ar—H), 6.80(d, 1H, J=8 Hz, Ar—H), 6.71(d, 2H, J=9 Hz, Ar—H), 6.49(d, 1H, J=3 Hz, Ar—H), 6.37(dd, 1H, J=8 and 3 Hz, Ar—H), 3.56(d, 1H, J=12 Hz, C2-H), 3.23–2.65(m, 10H, C2-H, C4-H and —CH$_2$SOCH$_2$CH$_2$SOCH$_2$—), 2.39–2.20(m, 2H, CF$_3$CF$_2$CH$_2$—), 2.08–1.99(m, 2H, CF$_3$CF$_2$CH$_2$CH$_2$—),1.55(br, 2H, alkyl-H), 1.30–1.00(m, 8H, alkyl-H), 1.06(s, 3H, C3-CH$_3$) |
| 138 | 2-{4-[(3RS,4RS)-7-hydroxy-3-(4-hydroxyphenyl)-3-methylchroman-4-yl]butoxy}-5-(4,4,5,5,5-pentafluoropentyl-sulfinyl)pentanoic acid | (CH$_2$)$_4$OCH(CO$_2$H)(CH$_2$)$_3$SO(CH$_2$)$_3$CF$_2$CF$_3$ on chroman with 4-hydroxyphenyl and methyl; HO on chroman | $^1$H-NMR(270 MHz, CD$_3$OD) δ: 7.03(d, 2H, J=9 Hz, Ar—H), 6.82–6.80(m, 1H, Ar—H), 6.71(d, 2H, J=9 Hz, Ar—H), 6.27–6.17(m, 2H, Ar—H), 4.44(d, 1H, J=11 Hz, C2-H), 4.14(d, 1H, J=11 Hz, C2-H), 3.66(br, 1H, CH(CO$_2$H)-), 3.40(br, 1H, CH$_2$O—), 3.08(br, 1H, CH$_2$O—), 2.80–2.58(m, 5H, C4-H and —CH$_2$SOCH$_2$—), 2.37–2.18m, (2H, CF$_3$CF$_2$CH$_2$—),2.06–1.98(m, 2H, CF$_3$CF$_2$CH$_2$CH$_2$—),1.75(br, 4H, alkyl-H), 1.30–0.97(m, 6H, alkyl-H), 1.13(s, 3H, C3-CH$_3$) |
| 139 | | (CH$_2$)$_6$SO(CH$_2$)$_3$CF$_2$CF$_3$ on chroman with 4-(COOMe)phenyl and methyl; HO on chroman | $^1$H-NMR(270 MHz, CDCl$_3$) δ: 8.01(d, J=8.6 Hz, 2H, Ar—H), 7.29(d, J=8.6 Hz, 2H, Ar—H), 6.87(d, J=7.9 Hz, 1H, Ar—H), 6.79(brs, 1H, OH), 6.71(brs, 1H, OH), 6.42(m, 2H, Ar—H), 4.56(d, J=10.5 Hz, 1H, C2-H), 4.28(d, J=10.5 Hz, 1H, C2-H), 3.91(s, 3H, COOCH$_3$), 2.76–2.58(m, 5H, C4-H and 2xS(O)CH$_2$), 2.18(m, 4H, alkyl-H), 1.72(m, 2H, alkyl-H), 1.27–0.98(m, 17H, C3-CH$_3$ and alkyl-H) |

TABLE 1-continued

| COM. NO. | NAME | STRUCTURE | PHYSICAL DATA |
|---|---|---|---|
| 140 | | 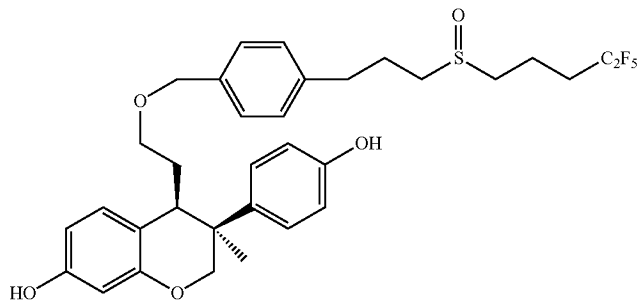 | ¹H-NMR(270 MHz, CD₃OD): δ: 7.21(d, J=8.5 Hz, 2H, Ar—H), 7.06(brd, J=not resolved, 2H, Ar—H), 6.95(d, J=8.6 Hz, 2H, Ar—H), 6.75(m, 3H, Ar—H), 6.23(m, 2H, Ar—H), 4.6–4.05(m, 6H, PhCH₂CH₂S(O), C4-H and 2xC2-H), 3.39–2.93(m, 6H, 2xS(O)CH₂ and C2-CH₂),2.84(brt, 1H, C4-H), 2.35(m, 2H, alkyl-H), 2.10(m, 2H, alkyl-H), 1.23(m, 5H, C3-CH₃ and alkyl-H) |
| 141 | methyl(3RS,4RS)-6-[7-hydroxy-3-(4-hydroxyphenyl)-3-methyl-thiochroman-4-yl]octanoate | 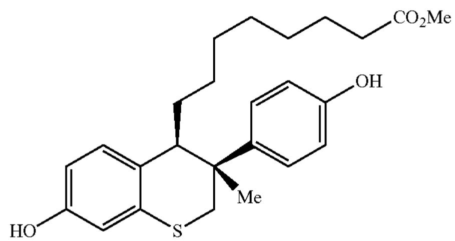 | ¹H-NMR(270 MHz, CDCl₃) δ: 7.24(d, J=9 Hz, 2H, Ar—H), 6.85(d, J=8 Hz, 1H, Ar—H), 6.83(d, J=9 Hz, 2H, Ar—H), 6.67(d, J=2 Hz, 1H, Ar—H), 6.50(dd, J=8, 2 Hz, 1H, Ar—H), 5.58(brs, 1H, ArOH),4.88(brs, 1H, ArOH), 3.69(s, 3H, CO₂CH₃), 3.64(d, J=11 Hz, 1H, C2-H), 2.92(d, J=11 Hz, 1H, C2-H), 2.67(brs, 1H, C4-H), 2.23(t, J=7 Hz, 2H, CH₂CO₂CH₃), 1.65–1.45(q, J=7 Hz, CH₂CH₂CO₂CH₃), 1.30–0.90(m, 13H, alkyl-H). |
| 142 | (3RS,4RS)-7-hydroxy-4-[4-hydroxy-9-(4,4,5,5,5-pentafluoropentylsulfinyl)non-1-yl]-3-hydroxyphenyl-3-methyl-chroman | 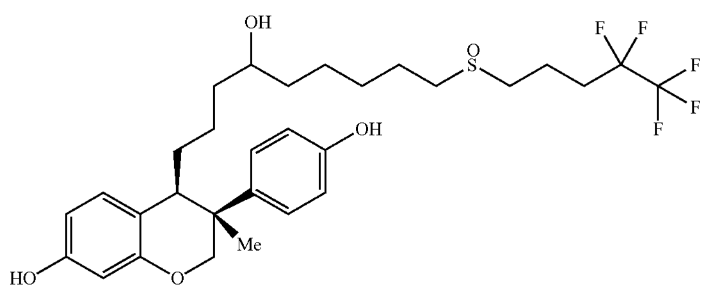 | ¹H-NMR(270 MHz, CD₃OD) δ: 7.08(d, J=9 Hz, 2H, Ar—H), 6.88(d, J=8 Hz, 1H, Ar—H), 6.77(d, J=9 Hz, 2H, Ar—H), 6.31(dd, J=8, 2 Hz, 1H, Ar—H),6.24(d, J=2 Hz, 1H, Ar—H), 4.50(d, J=11 Hz, 1H, C2-H), 4.20(d, J=11 Hz, 1H, C2-H), 3.30(brs, 1H, CHOH), 2.95–2.70(m, 4H, CH₂SOCH₂), 2.65(m, 1H, C4-H), 2.45–2.20(m, 2H, CH₂CF₂), 2.15–2.00(m, 2H, CH₂CH₂CF₂), 1.85–1.65(m, 2H, CH₂CH₂SO), 1.50–1.00(m, 15H, alkyl-H) |

TABLE 1-continued

| COM. NO. | NAME | STRUCTURE | PHYSICAL DATA |
|---|---|---|---|
| 143 | (3RS,4RS)-7-hydroxy-3-hydroxyphenyl-4-[4-oxo-9-(4,4,5,5,5-pentafluoropentyl-sulfinyl)non-1-yl]-3-methylchroman | 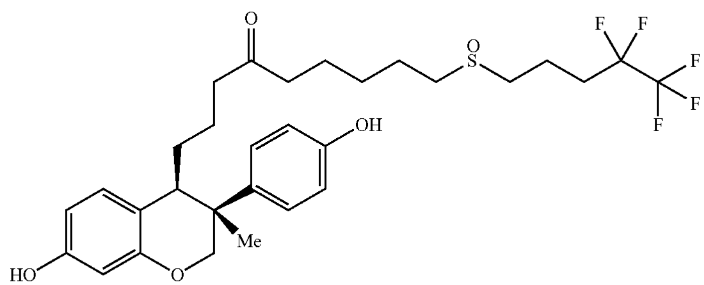 | $^1$H-NMR(270 MHz, CDCl$_3$) δ: 7.64, 7.52(each s, total 1H, ArOH), 7.05(d, J=9 Hz, 2H, Ar—H), 6.88(d, J=8 Hz, 1H, Ar—H), 6.84(d, J=9 Hz, 2H, Ar—H),6.39–6.33(m, 2H, Ar—H), 5.45, 5.38(each s, tatal 1H, Ar—OH), 4.48(d, J=11 Hz, 1H, C2-H), 4.22(d, J=11 Hz, 1H, C2-H), 2.95–2.70(m, 4H, CH$_2$SOCH$_2$), 2.59(m, 1H, C4-H), 2.35–2.05(m, 8H, CH$_2$COCH$_2$, and CH$_2$CH$_2$CF$_2$), 2.15–2.00(m, 2H, CH$_2$CH$_2$CF$_2$), 1.85–1.70(m, 2H,CH$_2$CH$_2$SO), 1.50–1.00(m, 11H, alkyl-H) |
| 144 | (3RS,4RS)-4-[7,7-difluoro-5-oxa-9-(4,4,5,5,5-pentafluoropentylsulfinyl)non-1-yl]-7-hydroxy-3-hydroxyphenyl-3-methylchroman | 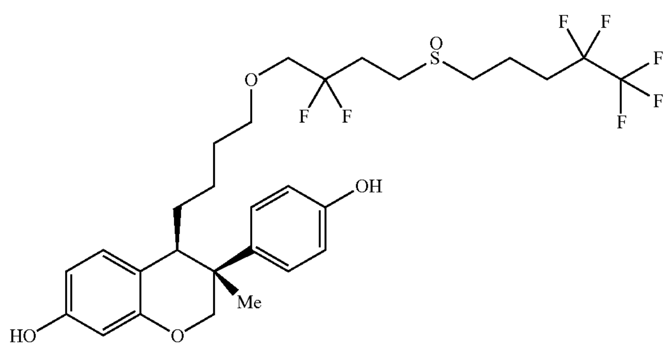 | $^1$H-NMR(270 MHz, CD$_3$OD) δ: 7.14(d, J=9 Hz, 2H, Ar—H), 6.91(d, J=8 Hz, 1H, Ar—H), 6.82(d, J=9 Hz, 2H, Ar—H), 6.35(dd, J=8, 2 Hz, 1H, Ar—H),6.28(d, J=2 Hz, 1H, Ar—H), 4.52(d, J=11 Hz, 1H, C2-H), 4.26(d, J=11 Hz, 1H, C2-H), 3.61(t, J=12 Hz, 2H, OCH$_2$CF$_2$), 3.40(t, J=6 Hz, CH$_2$CH$_2$O), 3.13–2.85(m, 4H, CH$_2$SOCH$_2$), 2.70(m, 1H, C4-H), 2.50–2.25(m, 4H, CH$_2$CF$_2$X$_2$), 2.15–2.00(m, 2H, CH$_2$CH$_2$CF$_2$),2.15–2.08(m, 2H, CH$_2$CH$_2$CF$_2$CF$_3$), 1.50–1.05(m, 9H, alkyl-H) |
| 145 | (3RS,4RS)-1-[9-(7-hydroxy-3-(4-hydroxyphenyl-3-methyl-chroman-4-yl]nonylcyclo-hexanecarboxylic acid | 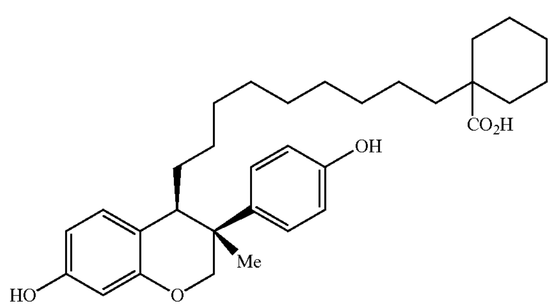 | $^1$H-NMR(270 MHz, CDCl$_3$) δ: 7.07(d, J=9 Hz, 2H, Ar—H), 6.90(d, J=8 Hz, 1H, Ar—H), 6.83(d, J=9 Hz, 2H, Ar—H), 6.40–6.30(m, 2H, Ar—H), 4.51(d, J=11 Hz, 1H, C2-H), 4.23(d, J=11 Hz, 1H, C2-H), 2.60(m, 1H, C4-H), 2.13–2.03(m, 2H, CH$_2$CCO$_2$H), 1.65–0.95(m, 29H, alkyl-H) |

TABLE 1-continued

| COM. NO. | NAME | STRUCTURE | PHYSICAL DATA |
|---|---|---|---|
| 146 | (3RS,4RS)-4-[6,6-dimethyl-5-oxa-9-(4,4,5,5-pentafluoropentylsulfinyl)nonyl]-7-hydroxy-3-(4-hydroxyphenyl)-3-methyl]chroman | 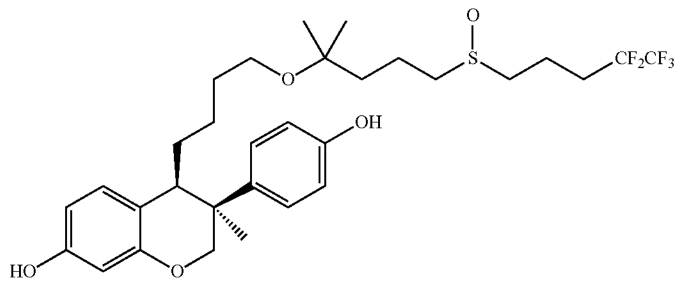 | ¹H-NMR(270 MHz, CDCl₃) δ: 7.19(s, 1H, —OH), 7.07(d, J=8.3 Hz, 2H, Ar—H), 6.91(d, J=4.0 Hz, 1H, Ar—H), 6.85(d, J=8.3 Hz, 2H, Ar—H),6.41–6.36(m, 2H, Ar—H), 5.76 and 5.48(s, total 1H, —OH), 4.53–4.49(m, 1H, C2-H), 4.25–4.16(m, 1H, C2-H), 3.05–3.00(m, 2H), 2.92–2.68(m, 3H), 2.63–2.50(m, 2H), 2.38–2.18(m, 4H, —CH₂CH₂CF₂CF₃), 1.82–1.63(m, 2H), 1.60–1.39(m, 2H), 1.30–1.21(m, 6H), 1.07(s, 3H, —CH₃),1.04(s, 3H, —CH₃), 1.02 and 1.01(s, total 3H, C3-CH₃) |
| 147 | (3RS,4RS)-7-hydroxy-3-(4-hydroxyphenyl)-3-methyl-4-[N-methyl-6-aza-9-(4,4,5,5-pentafluoropentylsulfonyl)-amino)nonyl]chroman | 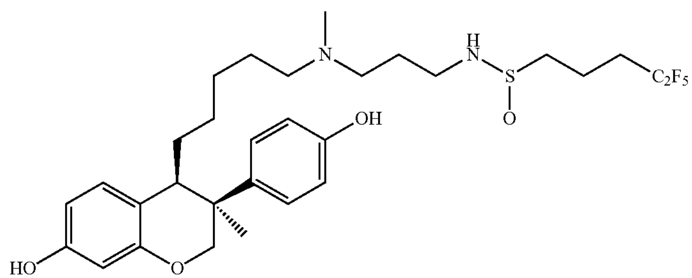 | ¹H-NMR(270 MHz, CDCl₃) δ: 7.07(d, J=8.6 Hz, 2H, Ar—H), 6.88(d, J=7.9 Hz, 1H, Ar—H), 6.82(d, J=8.6 Hz, 2H, Ar—H), 6.38–6.34(m, 2H, Ar—H),4.48(d, J=10.6 Hz, 1H, C2-H), 4.23(d, J=10.6 Hz, 1H, C2-H), 3.78–3.70(m, 2H, —CH₂N—), 3.54(t, J=7.3 Hz, 3H, —SO₂CH₂— and NH), 2.62–2.58(m, 1H, C4-H), 2.38–2.15(m, 8H, —CH₂NCH₂— and —CH₂CH₂CF₂CF₃), 2.13(s, 3H, —NCH₃), 1.91–1.82(m, 2H),1.25(s, 3H, C3-CH3), 1.25–1.18(m, 4H), 1.17–1.00(m, 4H) |
| 148 | (3RS,4RS)-7-hydroxy-3-(4-hydroxyphenyl)-3-methyl-4-[4-methyl-5-oxa-9-(4,4,5,5-pentafluoropentylsulfinyl)-nonyl]chroman | 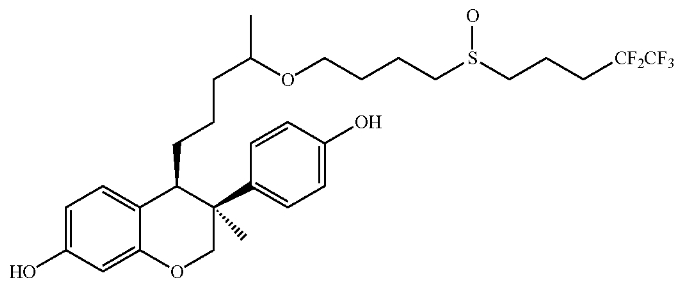 | ¹H-NMR(270 MHz, CD₃OD) δ: 7.18(d, J=8.3 Hz, 2H, Ar—H), 6.87(dd, J=8.2 Hz and 1.6 Hz, 1H, Ar—H), 6.78(d, J=8.3 Hz, 2H, Ar—H), 6.31(dd, J=8.2 Hz and 2.0 Hz, 1H, Ar—H), 6.24(d, J=2.0 Hz, 1H, Ar—H), 4.50(d, J=10.5 Hz, 1H, C2-H), 4.20(d, J=10.5 Hz, 1H, C2-H), 3.45–3.42(m, 1H, —CH₂CHO—CH₂—), 3.27–3.18(m, 2H, —CH₂CHO—CH₂—), 2.90–2.78(m, 4H, —CH₂SCH₂—), 2.70–2.60(m, 1H, C4-H), 2.45–2.22(m, 2H, —CH₂CH₂CF₂CF₃), 2.18–2.02(m, 2H, —CH₂CH₂CF₂CF₃), 1.89–1.54(m, 4H), 1.41–1.01(m, 6H), 1.20(s, 3H, —CHCH₃), 1.01 and 0.98(s, total 3H, C3-CH₃) |

TABLE 1-continued

| COM. NO. | NAME | STRUCTURE | PHYSICAL DATA |
|---|---|---|---|
| 149 | (3RS,4RS)-7-hydroxy-3-(4-hydroxyphenyl)-3-methyl-4-[4-(3-(4,4,5,5-pentafluoropentylsulfinyl)propyloxy)phenylpropyl]chroman | 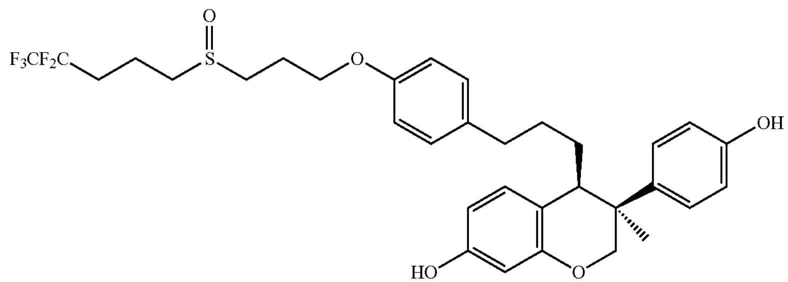 | $^1$H-NMR(270 MHz, CDCl$_3$) δ: 7.24 and 7.22(s, total 1H, OH), 6.96–6.65(m, 9H, Ar—H), 6.40–6.33(m, 2H, Ar—H), 5.19(s, 1H, OH),4.45(1H, d, J=10.6 Hz, C2-H), 4.25–4.09(m, 3H, —OCH$_2$— and C2-H), 3.13–2.74(m, 5H), 2.57–2.14(m, 9H), 1.74–1.59(m, 1H), 1.43–1.11(m, 1H), 1.21(s, 3H, C3-CH$_3$), 1.06–0.85(m, 1H) |
| 150 | (Z)-6,6,7,7,7-pentafluoro-2-{9-[(3RS,4RS)-7-hydroxy-3-(4-hydroxyphenyl)-3-methyl-chroman-4-yl]nonyl}-2-heptenoic acid | 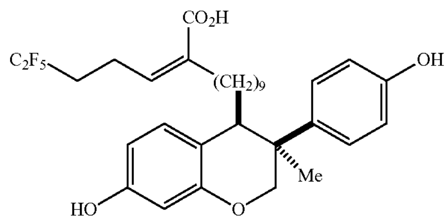 | $^1$H-NMR(300 MHz, CDCl$_3$) δ: 7.12–6.80(m, 5H, Ar—H), 6.41–6.34(m, 2H, Ar—H), 5.99(t, 1H, J=7.7 Hz, C3-H), 4.51(d, 1H, J$_{AB}$=10.2 Hz, C2"-H),4.24(dd, 1H, J$_{AB}$=10.2 Hz, J=1.9 Hz, C2"-H), 2.84–2.72(m, 2H), 2.61(m, 1H, C4"-H), 2.31–2.07(m, 4H), 1.46–0.98(m, 19H, alkyl-H) |
| 151 | 2-(4,4,5,5-pentafluoro-1-hydroxypentyl)-11-[(3RS,4RS)-7-hydroxy-3-(4-hydroxyphenyl)-3-methylchroman-4-yl]-undecanoic acid | 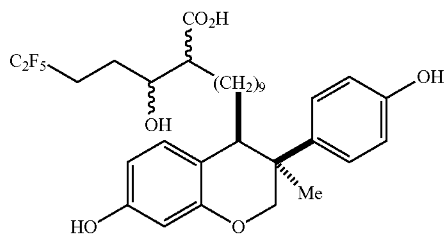 | $^1$H-NMR(300 MHz, CDCl$_3$) δ: 7.12–6.78(m, 5H, Ar—H), 6.41–6.33(m, 2H, Ar—H),4.51(d, 1H, J$_{AB}$=10.2 Hz, C2"-H), 4.24(dd, 1H, J$_{AB}$=10.2 Hz, J=1.6 Hz, C2"-H), 3.89 and 3.78(m, 0.33H and 0.67H, C-1'-H, anti and syn), 2.60(m, 1H, C4"-H), 2.58–1.53(m, 9H), 1.41–0.94(m, 17H, alkyl-H) |

TABLE 1-continued

| COM. NO. | NAME | STRUCTURE | PHYSICAL DATA |
|---|---|---|---|
| 152 | (E)-3-{4-[4-[(3RS,4RS)-7-hydroxy-3-(4-hydroxyphenyl)-3-methylthiochroman-4-yl]-benzyl]}propeneoic acid | 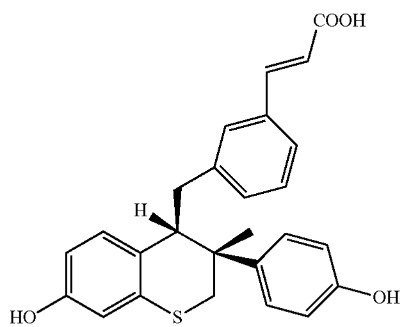 | ¹H-NMR(300 MHz, CDCl₃) δ: 7.65(d, 1H, J=16 Hz, vinyl), 7.40~7.2(m, 6H, Ar—H, Ar—OH), 6.80~6.61(m, 5H, Ar—H, Ar—OH),6.25(d, 1H, J=16 Hz, Vinyl), 6.22(m, 1H, Ar—H), 6.08(d, 1H, J=8.2 Hz, Ar—H), 3.76(d, 1H, J=12 Hz, C2-H), 3.05(s, 1H, 12 Hz, C2-H), 2.95(d, 1H, J=10.5 Hz, benzyl(CH₂)), 2.49(d, 1H, J=10.5 Hz, benzyl(CH₂)), 2.29(dd, 1H, J=10.9, 1.3 Hz, C4-H), 1.26(s, 3H, C3-Me) |
| 153 | 2-{2-[(3RS,4RS)-7-hydroxy-3-(4-hydroxyphenyl)-3-methyl]chroman-4-yl]ethyl}-5-{[(4-(4,4,5,5,5-pentafluoropentyl)sulfinyl]butyl]}oxazole | 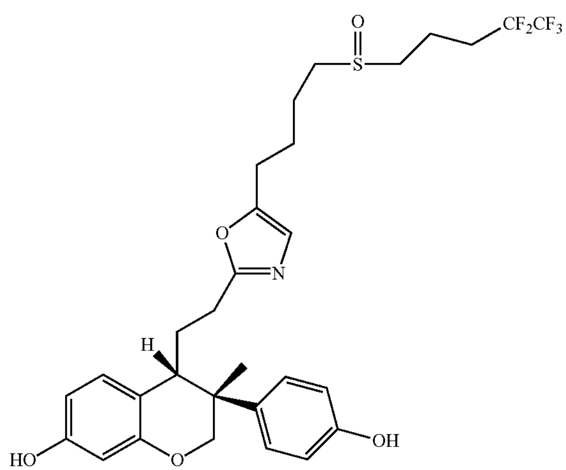 | ¹H-NMR(300 MHz, Acetone-d6) δ: 8.02(s, 1H, oxazole), 7.06(m, 4H, Ar—H), 6.84(m, 2H, Ar—H),6.64(brs, 1H, Ar—OH), 6.42~6.32(m, 2H, Ar—H, Ar—OH), 6.54(d, 1H, J=11 Hz, C2-H), 4.27(d, 1H, J=10.5 Hz, C2-H), 2.8~2.1(m, 14H, CH₂, CF₂, Alkyl, CH₂SO), 1.8~1.6(m, 5H, —(CH₂)ₙ,), 1.20(s, 3H, C3-Me) |

TABLE 1-continued

| COM. NO. | NAME | STRUCTURE | PHYSICAL DATA |
|---|---|---|---|
| 154 | (3RS,4RS)-6-[7-hydroxy-3-(4-hydroxyphenyl)-3-methylthiochroman-4-yl]nonanoic acid | 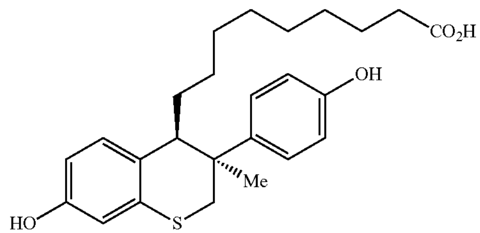 | $^1$H-NMR(270 MHz, CD$_3$OD) δ: 7.22(d, J=9 Hz, 2H, Ar—H), 6.65(d, J=8 Hz, 1H, Ar—H), 6.50(d, J=9 Hz, 2H, Ar—H), 6.37(d, J=2 Hz, 1H, Ar—H),6.25(dd, J=8, 2 Hz, 1H, Ar—H), 3.22(AB q, J=11 Hz, 2H, C2-H), 2.91(brd, 1H, C4-H), 2.26(t, J=7 Hz, 2H, CH$_2$CO$_2$H), 1.60–1.40(q, J=7 Hz, CH$_2$CH$_2$—CO$_2$H), 1.30–0.90(m, 15H, alkyl-H) |
| 155 | (3RS,4RS)-7-hydroxy-3-(4-hydroxyphenyl)-3-methyl-4-[10-(4,4,5,5,5-pentafluoropentylsulfonyl)-aminodecyl]chroman | 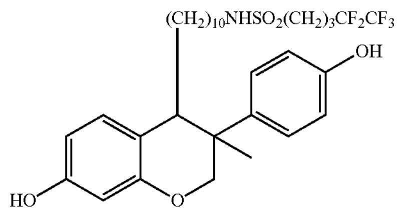 | $^1$H-NMR(270 MHz, CDCl$_3$) δ: 7.07(d, J=8.6 Hz, 2H, Ar—H), 6.90(d, J=8.3 Hz, 1H, C5-H), 6.83(d, J=8.6 Hz, 2H, Ar—H),6.39–6.37(m, 2H, Ar—H), 5.51(brs, 1H, Ar—OH), 5.30(brs, 1H, Ar—OH), 4.62~4.36(m, 2H, C2-H and NH), 4.23(d, J=10.6 Hz, 1H, C2-H), 3.14–3.07(m, 4H, CH$_2$—NH and SO$_2$CH$_2$), 2.65–2.56(m, 1H, C4-H), 2.38–2.05(m, 4H, CH$_2$CH$_2$CF$_2$CF$_3$), 1.58–0.95(m, 21H, C3-CH$_3$ and alkyl-H) |
| 156 | 9-{4-[(3RS,4RS)-7-hydroxy-3-(4-hydroxyphenyl)-3-methylthiochroman-4-yl]-phenoxy}-2-(4,4,5,5,5-pentafluoropentyl)nonanoic acid | 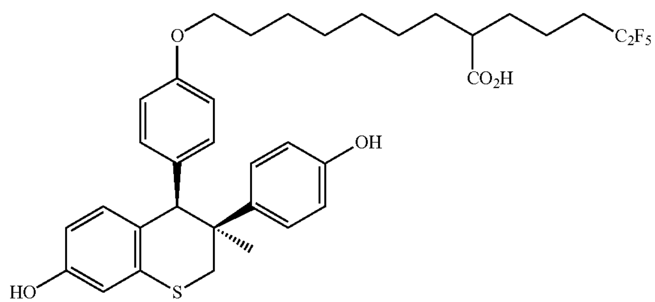 | |

TABLE 1-continued

| COM. NO. | NAME | STRUCTURE | PHYSICAL DATA |
|---|---|---|---|
| 157 | 8-{4-[(3RS,4RS)-7-hydroxy-3-(4-hydroxyphenyl)-3-methylthiochroman-4-yl]-phenoxy}-2-(4,4,5,5,5-pentafluoropentyl)octanoic acid | 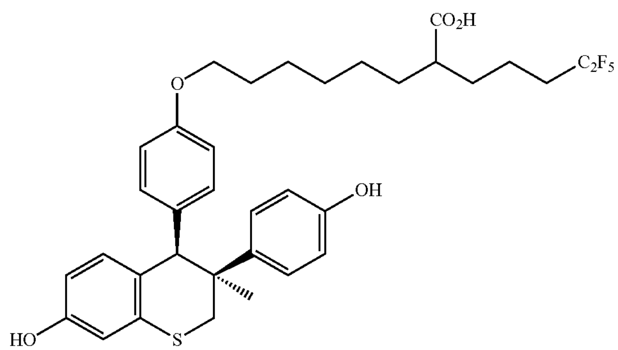 | |
| 158 | 7-{4-[(3RS,4RS)-7-hydroxy-3-(4-hydroxyphenyl)-3-methylthiochroman-4-yl]-phenoxy}-2-(4,4,5,5,5-pentafluoropentyl)heptanoic acid | 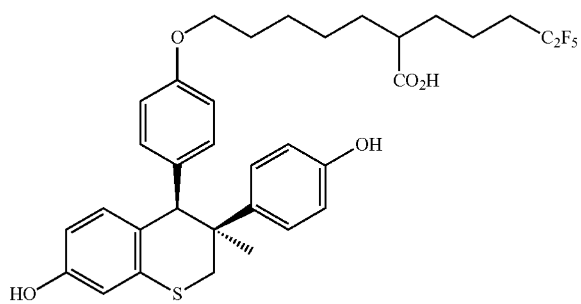 | |
| 159 | 6-{4-[(3RS,4RS)-7-hydroxy-3-(4-hydroxyphenyl)-3-methylthiochroman-4-yl]-phenoxy}-2-(4,4,5,5,5-pentafluoropentyl)hexanoic acid | 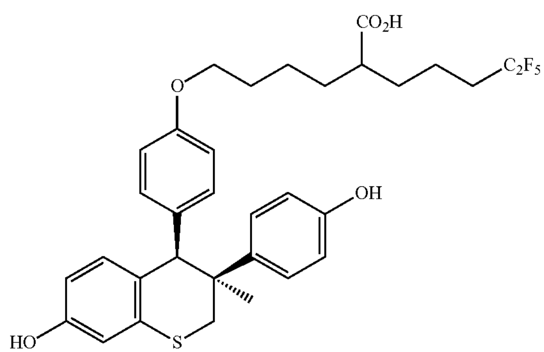 | |

TABLE 1-continued

| COM. NO. | NAME | STRUCTURE | PHYSICAL DATA |
|---|---|---|---|
| 160 | 5-{4-[(3RS,4RS)-7-hydroxy-3-(4-hydroxyphenyl)-3-methylchroman-4-yl]-phenoxy}-2-(4,4,5,5,5-pentafluoropentyl)pentanoic acid | 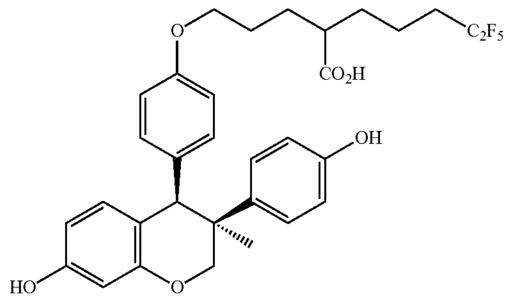 | |
| 161 | 5-{4-[(3'RS,4RS)-7-hydroxy-3-(4-hydroxyphenyl)-3-methylthiochroman-4-yl]-phenoxy}-2-(4,4,5,5,5-pentafluoropentyl)pentanoic acid | 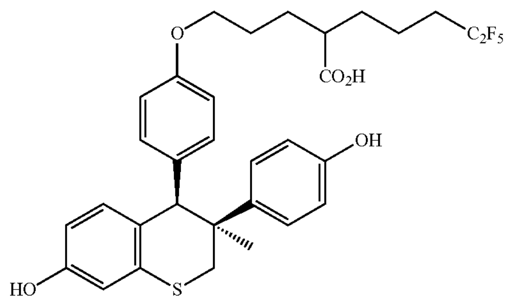 | |
| 162 | (3'RS,4RS)-11-[7-hydroxy-3-(4-hydroxyphenyl)-3-methylthiochroman-4-yl]-2-(4,4,5,5,5-pentafluoropentyl)undecanoic acid | 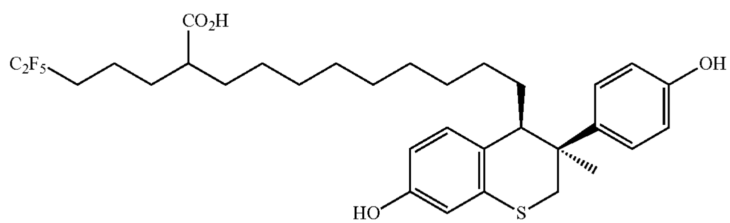 | |

TABLE 1-continued

| COM. NO. | NAME | STRUCTURE | PHYSICAL DATA |
|---|---|---|---|
| 163 | (3'RS,4RS)-11-[7-hydroxy-3-(4-hydroxyphenyl)-3-methylchroman-4-yl]-2-(4,4,5,5,5-pentafluoropentyl)undecanoic acid | 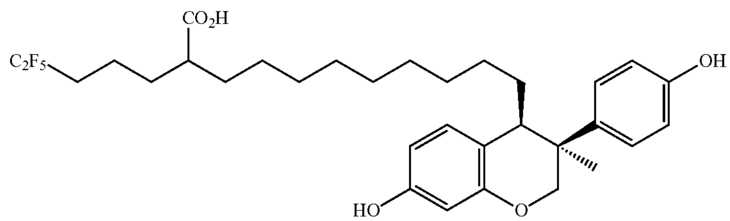 | |
| 164 | (3'RS,4RS)-12-[7-hydroxy-3-(4-hydroxyphenyl)-3-methylthiochroman-4-yl]-2-(4,4,5,5,5-pentafluoropentyl)dodecanoic acid | 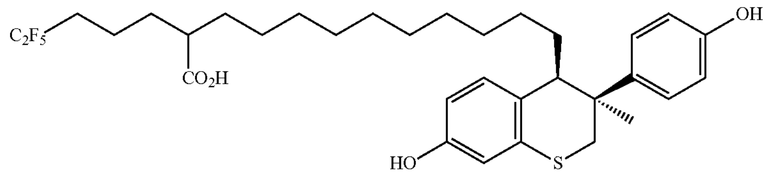 | |
| 165 | (3'RS,4RS)-12-[7-hydroxy-3-(4-hydroxyphenyl)-3-methylthiochroman-4-yl]-2-(4,4,5,5,5-pentafluoropentyl)dodecanoic acid | 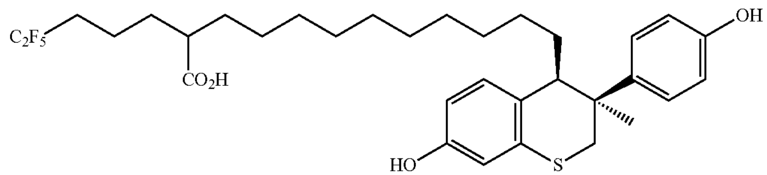 | |
| 166 | (3'RS,4RS)-9-[7-hydroxy-3-(4-hydroxyphenyl)-3-methylthiochroman-4-yl]-2-(4,4,5,5,5-pentafluoropentyl)nonanoic acid | 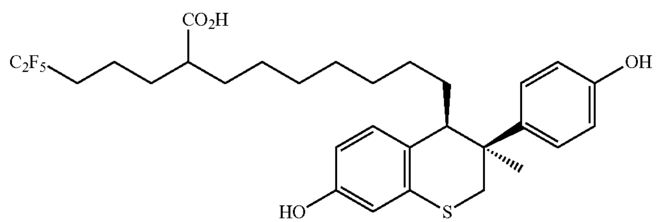 | |

TABLE 1-continued

| COM. NO. | NAME | STRUCTURE | PHYSICAL DATA |
|---|---|---|---|
| 167 | (3'RS,4RS)-9-[7-hydroxy-3-(4-hydroxyphenyl)-3-methylchroman-4-yl]-2-(4,4,5,5,5-pentafluoropentyl)-nonanoic acid | 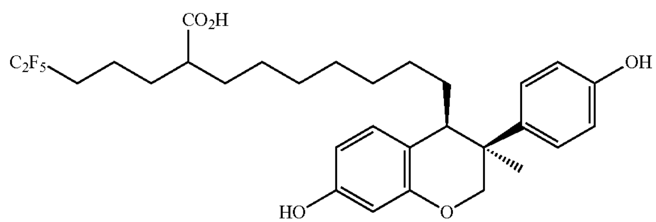 | |
| 168 | (3'RS,4RS)-10-[7-hydroxy-3-(4-hydroxyphenyl)-3-methylchroman-4-yl]-2-(4,4,5,5,5-pentafluoropentyl)-decanoic acid | 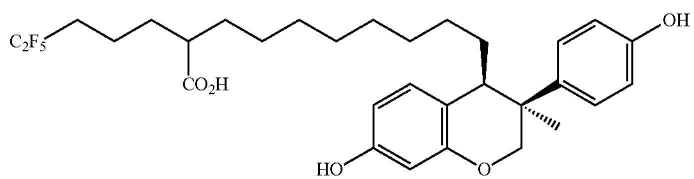 | |
| 169 | (3'RS,4RS)-10-[7-hydroxy-3-(4-hydroxyphenyl)-3-methylthiochroman-4-yl]-2-(4,4,5,5,5-pentafluoropentyl)-decanoic acid | 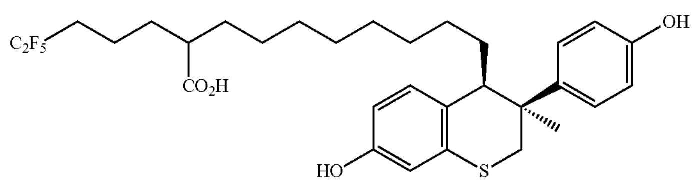 | |
| 170 | (3'RS,4RS)-10-[7-hydroxy-3-(4-hydroxyphenyl)-3-methylchroman-4-yl]-2-(4,4,5,5,5-pentafluorobutyl)-decanoic acid | 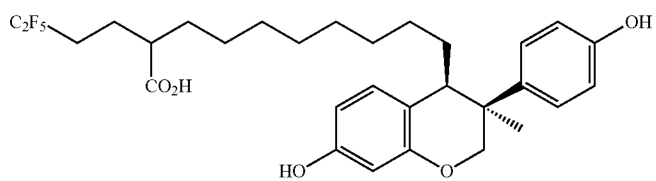 | |
| 171 | (3'RS,4RS)-10-[7-hydroxy-3-(4-hydroxyphenyl)-3-methylthiochroman-4-yl]-2-(3,3,4,4,4-pentafluorobutyl)-decanoic acid | 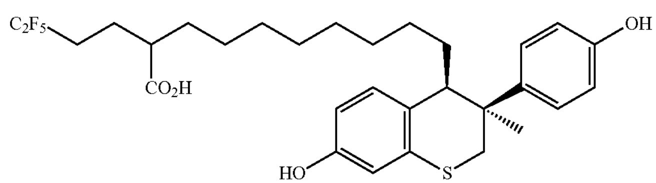 | |

TABLE 1-continued

| COM. NO. | NAME | STRUCTURE | PHYSICAL DATA |
|---|---|---|---|
| 172 | (3'RS,4RS)-10-[7-hydroxy-3-(4-hydroxyphenyl)-3-methylchroman-4-yl]-2-(5,5,6,6,6-pentafluorohexyl)-decanoic acid | 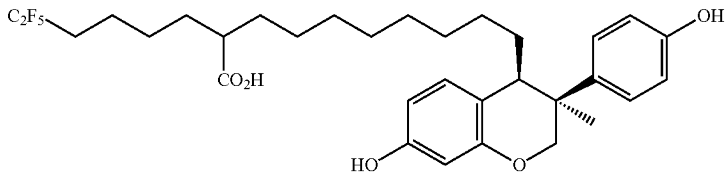 | |
| 173 | (3'RS,4RS)-10-[7-hydroxy-3-(4-hydroxyphenyl)-3-methylthiochroman-4-yl]-2-(5,5,6,6,6-pentafluorohexyl)-decanoic acid | 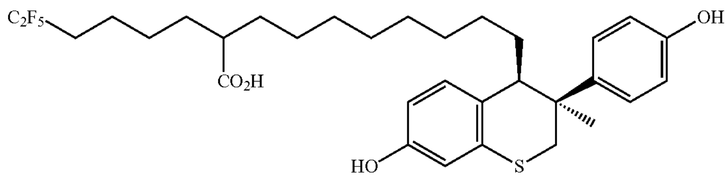 | |
| 174 | (3'RS,4RS)-10-[7-hydroxy-3-(4-hydroxyphenyl)-3-methylchroman-4-yl]-2-(6,6,7,7,7-pentafluoroheptyl)-decanoic acid | 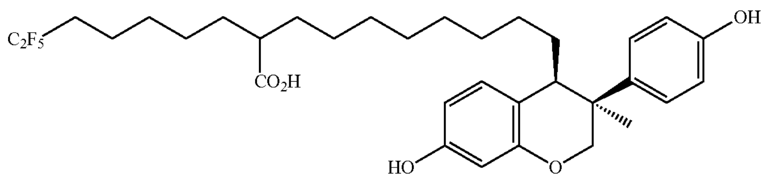 | |
| 175 | (3'RS,4RS)-10-[7-hydroxy-3-(4-hydroxyphenyl)-3-methylthiochroman-4-yl]-2-(6,6,7,7,7-pentafluoroheptyl)-decanoic acid | 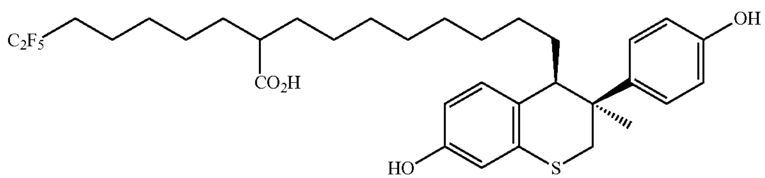 | |
| 176 | (3'RS,4RS)-10-[7-hydroxy-3-(4-hydroxyphenyl)-3-methylchroman-4-yl]-2-(3,3,4,4,4-pentafluorobutyl)-undecanoic acid | 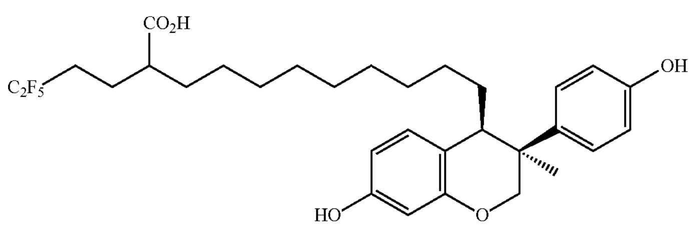 | |

TABLE 1-continued

| COM. NO. | NAME | STRUCTURE | PHYSICAL DATA |
|---|---|---|---|
| 177 | (3'RS,4RS)-11-[7-hydroxy-3-(4-hydroxyphenyl)-3-methylthiochroman-4-yl]-2-(3,3,4,4,4-pentafluorobutyl)-undecanoic acid | 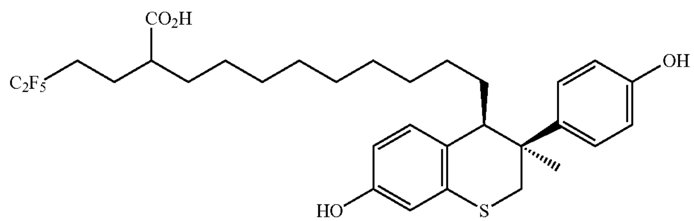 | |
| 178 | (3'RS,4RS)-11-[7-hydroxy-3-(4-hydroxyphenyl)-3-methylchroman-4-yl]-2-(5,5,6,6,6-pentafluorohexyl)-undecanoic acid | 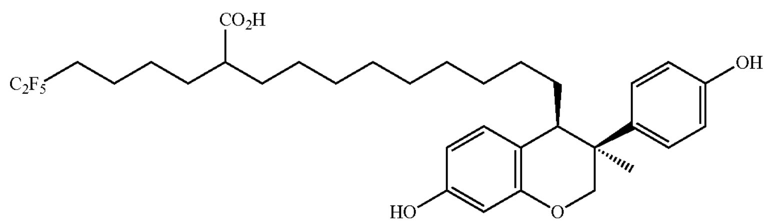 | |
| 179 | (3'RS,4RS)-11-[7-hydroxy-3-(4-hydroxyphenyl)-3-methylthiochroman-4-yl]-2-(5,5,6,6,6-pentafluorohexyl)-undecanoic acid | 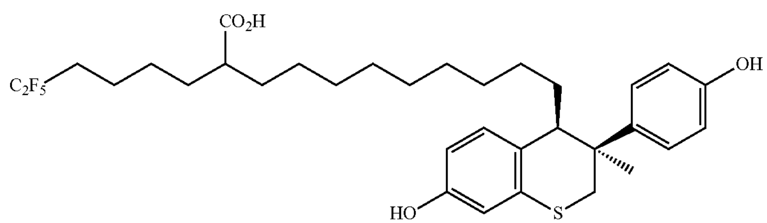 | |
| 180 | (3'RS,4RS)-11-[7-hydroxy-3-(4-hydroxyphenyl)-3-methylchroman-4-yl]-2-(6,6,7,7,7-pentafluoroheptyl)-undecanoic acid | 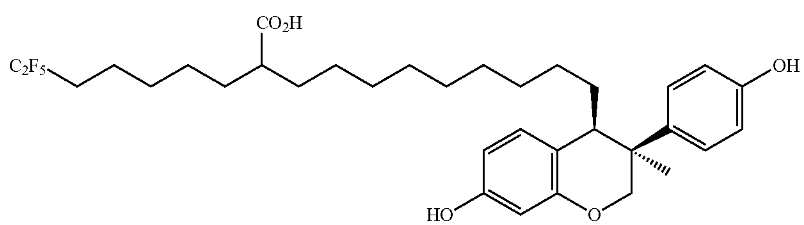 | |

TABLE 1-continued

| COM. NO. | NAME | STRUCTURE | PHYSICAL DATA |
|---|---|---|---|
| 181 | (3′RS,4RS)-11-[7-hydroxy-3-(4-hydroxyphenyl)-3-methylthiochroman-4-yl]-2-(6,6,7,7,7-pentafluoroheptyl)-undecanoic acid | 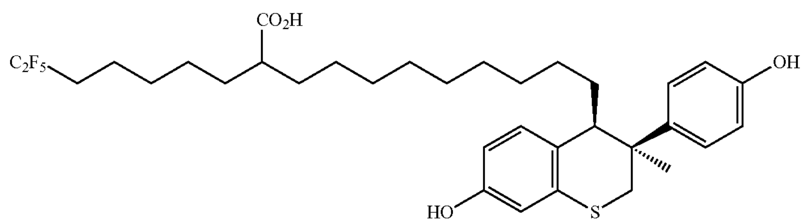 | |
| 182 | (3′RS,4RS)-11-[7-hydroxy-3-(4-hydroxyphenyl)-3-methylthiochroman-4-yl]-2-methyl-2-(4,4,5,5,5-penta-fluoropentyl)undecanoic acid | 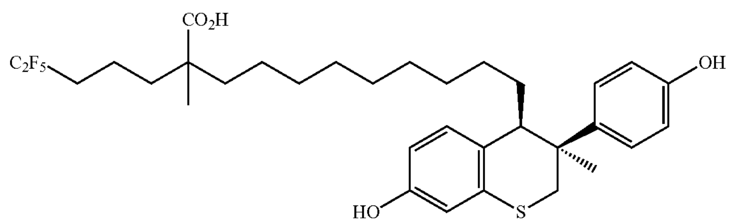 | |
| 183 | (3′RS,4RS)-11-[7-hydroxy-3-(4-hydroxyphenyl)-3-methylchroman-4-yl]-2-methyl-2-(4,4,5,5,5-penta-fluoropentyl)undecanoic acid | 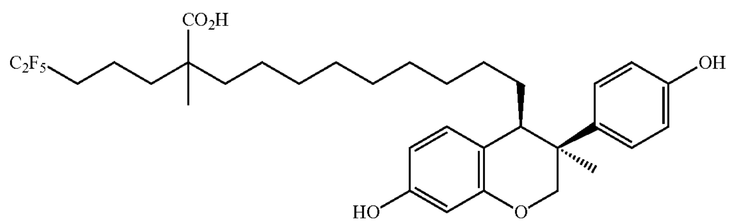 | |
| 184 | (3′RS,4RS)-10-[7-hydroxy-3-(4-hydroxyphenyl)-3-methylthiochroman-4-yl]-2-methyl-2-(4,4,5,5,5-penta-fluoropentyl)decanoic acid | 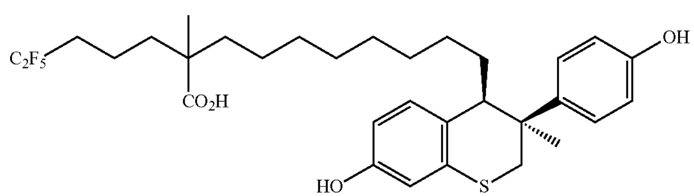 | |

TABLE 1-continued

| COM. NO. | NAME | STRUCTURE | PHYSICAL DATA |
|---|---|---|---|
| 185 | (3'RS,4RS)-10-[7-hydroxy-3-(4-hydroxyphenyl)-3-methyl]chroman-4-yl]-2-methyl-2-(4,4,5,5,5-pentafluoropentyl)decanoic acid | 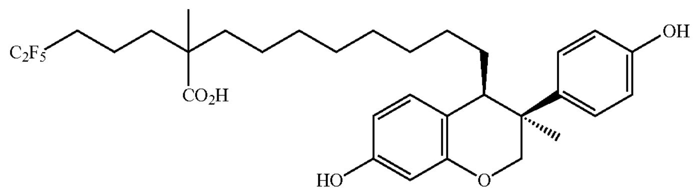 | |
| 186 | (3'RS,4RS)-11-[7-hydroxy-3-(4-hydroxyphenyl)-3-methyl]thiochroman-4-yl]-2-ethyl-2-(4,4,5,5,5-pentafluoropentyl)undecanoic acid | 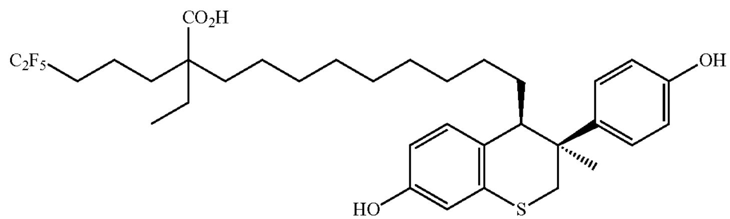 | |
| 187 | (3'RS,4RS)-11-[7-hydroxy-3-(4-hydroxyphenyl)-3-methyl]chroman-4-yl]-2-ethyl-2-(4,4,5,5,5-pentafluoropentyl)undecanoic acid | 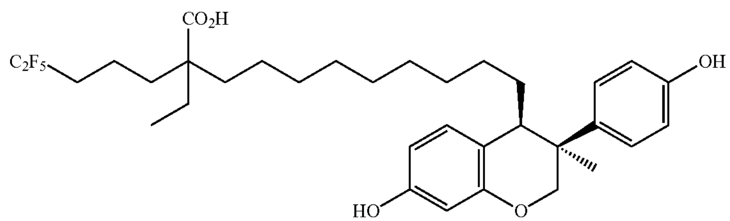 | |
| 188 | (3'RS,4RS)-10-[7-hydroxy-3-(4-hydroxyphenyl)-3-methyl]thiochroman-4-yl]-2-ethyl-2-(4,4,5,5,5-pentafluoropentyl)pentyl)decanoic acid | 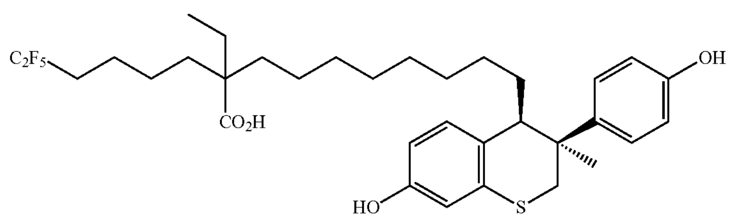 | |

TABLE 1-continued

| COM. NO. | NAME | STRUCTURE | PHYSICAL DATA |
|---|---|---|---|
| 189 | (3'RS,4RS)-10-[7-hydroxy-3-(4-hydroxyphenyl)-3-methylchroman-4-yl]-2-ethyl-2-(4,4,5,5,5-pentafluoropentyl)decanoic acid | 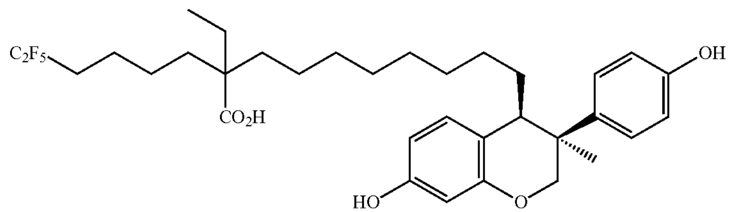 | |
| 190 | (3'RS,4RS)-11-[7-hydroxy-3-(4-hydroxyphenyl)-3-methylchroman-4-yl]-2-methyl-2-(5,5,6,6,6-pentafluorohexyl)undecanoic acid | 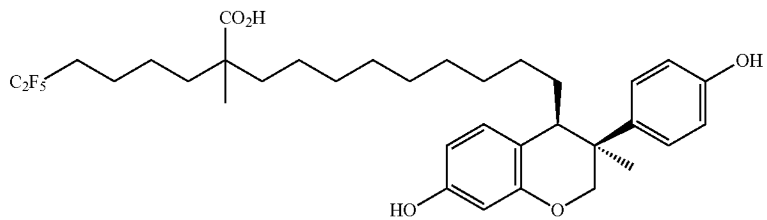 | |
| 191 | (3'RS,4RS)-11-[7-hydroxy-3-(4-hydroxyphenyl)-3-methylthiochroman-4-yl]-2-methyl-2-(5,5,6,6,6-pentafluorohexyl)undecanoic acid | 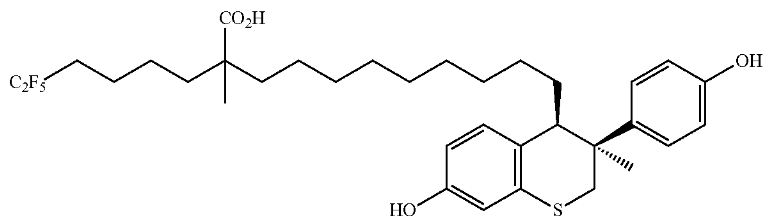 | |
| 192 | (3'RS,4RS)-11-[7-hydroxy-3-(4-hydroxyphenyl)-3-methylchroman-4-yl]-2-methyl-2-(6,6,7,7,7-pentafluoroheptyl)undecanoic acid | 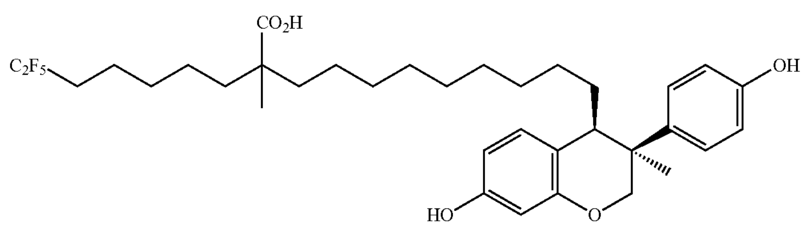 | |

TABLE 1-continued

| COM. NO. | NAME | STRUCTURE | PHYSICAL DATA |
|---|---|---|---|
| 193 | (3'RS,4RS)-11-[7-hydroxy-3-(4-hydroxyphenyl)-3-methylthiochroman-4-yl]-2-methyl-2-(6,6,7,7,7-penta-fluoroheptyl)undecanoic acid | 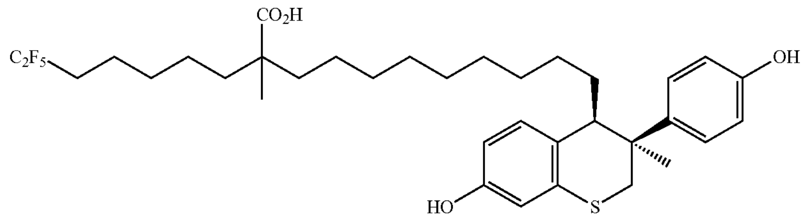 | |
| 194 | (3'RS,4RS)-11-[7-hydroxy-3-(4-hydroxyphenyl)-3-methylchroman-4-yl]-2-ethyl-2-(5,5,6,6,6-penta-fluorohexyl)undecanoic acid | 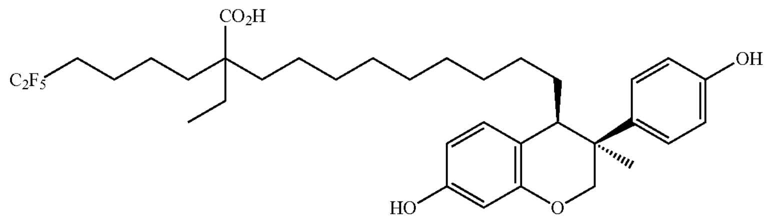 | |
| 195 | (3'RS,4RS)-11-[7-hydroxy-3-(4-hydroxyphenyl)-3-methylthiochroman-4-yl]-2-ethyl-2-(5,5,6,6,6-penta-fluorohexyl)undecanoic acid | 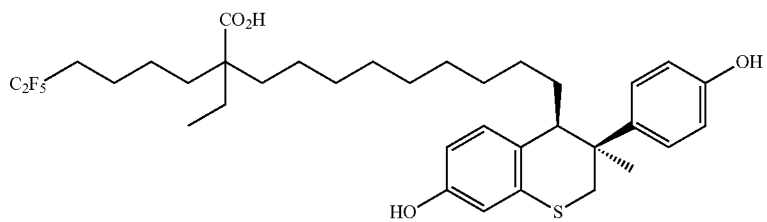 | |
| 196 | (3'RS,4RS)-11-[7-hydroxy-3-(4-hydroxyphenyl)-3-methylchroman-4-yl]-2-ethyl-2-(6,6,7,7,7-penta-fluoroheptyl)undecanoic acid | 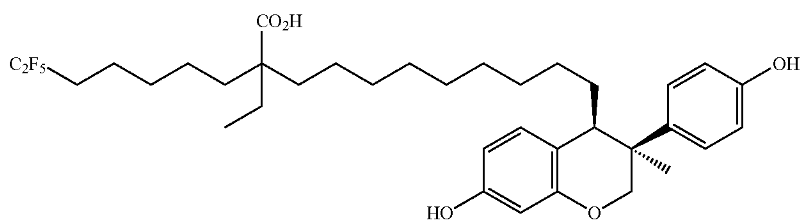 | |

TABLE 1-continued

| COM. NO. | NAME | STRUCTURE | PHYSICAL DATA |
|---|---|---|---|
| 197 | (3'RS,4RS)-11-[7-hydroxy-3-(4-hydroxyphenyl)-3-methylthiochroman-4-yl]-2-ethyl-2-(6,6,7,7,7-pentafluoroheptyl)undecanoic acid | 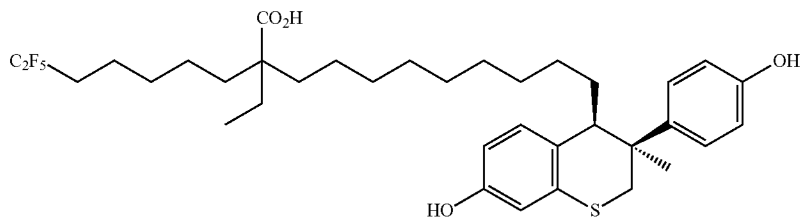 | |
| 198 | (3'RS,4RS)-10-[7-hydroxy-3-(4-hydroxyphenyl)-3-methylchroman-4-yl]-2-methyl-2-(5,5,6,6,6-pentafluorohexyl)decanoic acid | 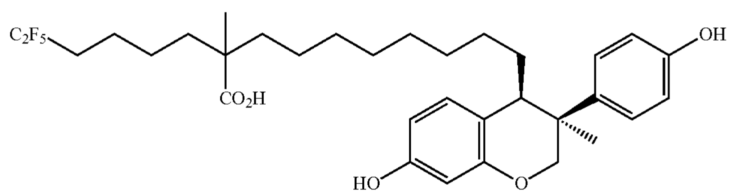 | |
| 199 | (3'RS,4RS)-10-[7-hydroxy-3-(4-hydroxyphenyl)-3-methylthiochroman-4-yl]-2-methyl-2-(5,5,6,6,6-pentafluorohexyl)decanoic acid | 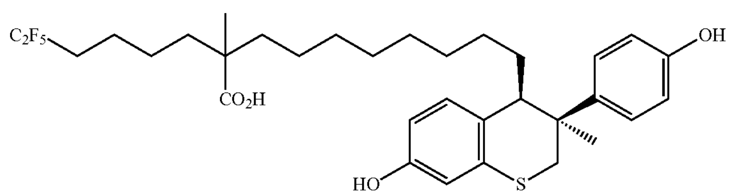 | |
| 200 | (3'RS,4RS)-10-[7-hydroxy-3-(4-hydroxyphenyl)-3-methylchroman-4-yl]-2-methyl-2-(6,6,7,7,7-pentafluoroheptyl)decanoic acid | 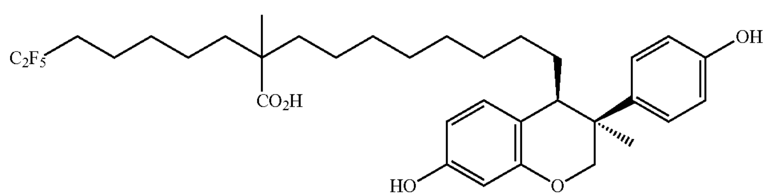 | |
| 201 | (3'RS,4RS)-10-[7-hydroxy-3-(4-hydroxyphenyl)-3-methylthiochroman-4-yl]-2-methyl-2-(6,6,7,7,7-pentafluoroheptyl)decanoic acid | 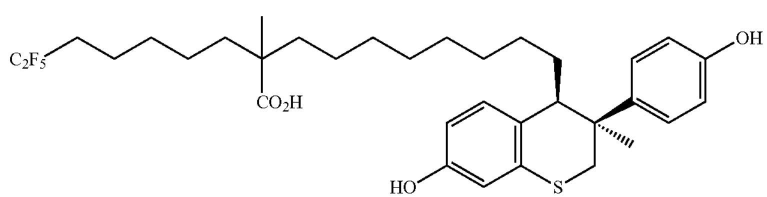 | |

TABLE 1-continued

| COM. NO. | NAME | STRUCTURE | PHYSICAL DATA |
|---|---|---|---|
| 202 | (3'RS,4RS)-10-[7-hydroxy-3-(4-hydroxyphenyl)-3-methylchroman-4-yl]-2-ethyl-2-(5,5,6,6,6-pentafluorohexyl)decanoic acid | 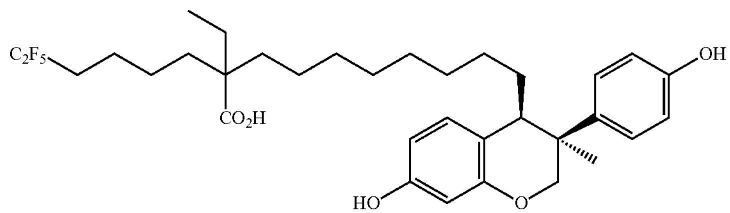 | |
| 203 | (3'RS,4RS)-10-[7-hydroxy-3-(4-hydroxyphenyl)-3-methylthiochroman-4-yl]-2-ethyl-2-(5,5,6,6,6-pentafluorohexyl)decanoic acid | 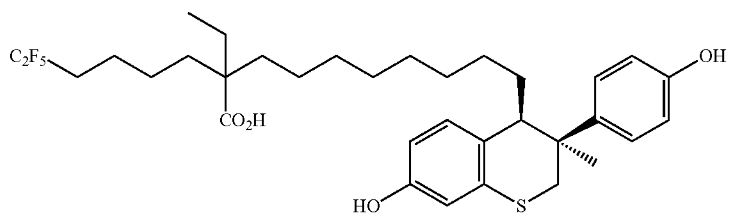 | |
| 204 | (3'RS,4RS)-10-[7-hydroxy-3-(4-hydroxyphenyl)-3-methylchroman-4-yl]-2-ethyl-2-(6,6,7,7,7-pentafluoroheptyl)decanoic acid | 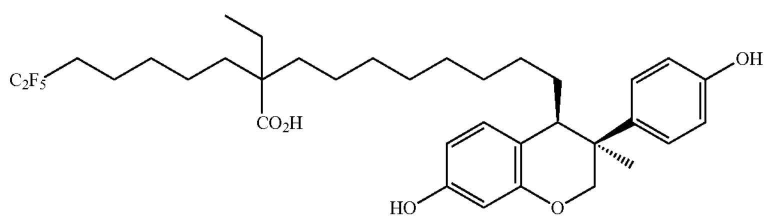 | |
| 205 | (3'RS,4RS)-10-[7-hydroxy-3-(4-hydroxyphenyl)-3-methylthiochroman-4-yl]-2-ethyl-2-(6,6,7,7,7-pentafluoroheptyl)decanoic acid | 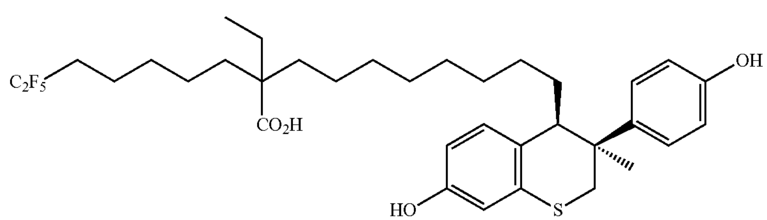 | |

Experiment 1

Cell Growth Inhibiting Activity

In this experiment, the cell growth inhibiting activity was determined by using the compounds of Examples 1, 2, 3, 5, 22, 127 and 128 as the test compound and the known anti-estrogenic compound ZMI89154 having the following structure (see, EP0124369 B1) as the control compound, according to the method described hereinafter.

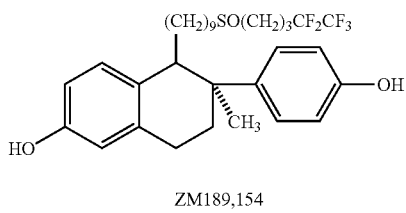

ZM189,154

MCF-7 cell lines (ATCC) were incubated in MEM (minimum essential medium) which is supplemented by 3% DCC (dextran coated charcoal)-treated 5% FBS (fetal bovine serum) but does not contain phenol red, for one week. One day before drug administration, incubated MCF-7 cells were plated in 96-well plate in the concentration of $5 \times 10^3$ cells per well. After the 96-well plate was incubated for one day, 0.1 nM of estradiol and the test compound in the given concentration were added to each well. The plate was incubated for 7 days at 37° C. and then MTT solution (Sigma) was added to each well in the amount of 15 µl and allowed to react for 2 hours at 37° C. After the reaction was completed, the solubilizing/stopping solution (constitution: SDS, acetic acid, N,N-dimethylformamide) was added to each well in the amount of 100 µl. Then, the absorption for each well at 570 nm was measured by means of a plate reader. $IC_{50}$ value for inhibiting cell growth of 50% was calculated from the results as measured and described in the following Table 2.

TABLE 2

| | | $IC_{50}$ value of the test compounds(nM) | | | | | | |
|---|---|---|---|---|---|---|---|---|
| Test com. | Ex. 1 | Com. I of Ex. 2 | Com. II of Ex. 2 | Ex. 3 | Ex. 5 | Ex. 22 | Ex. 127 | Ex. 128 | Zm189154 |
| $IC_{50}$ (nM) | 60.4 | 67.5 | 1000 | 54.5 | 387.4 | 850.5 | 3313 | 4993 | 77(trans) 9.2(cis) |

Experiment 2

Anti-Estrogenic Activity (Subcutaneous Administration)

Anti-estrogenic activity of the test compound by subcutaneous administration was determined according to the method described hereinafter. In this experiment, the compounds of Examples 1, 2, 3, 4, 5, 22, 127 and 128 were used as the test compound and the known anti-estrogenic compound ZM189154 was used as the control compound as in Experiment 1.

The anti-estrogenic activity was determined by subcutaneously injecting 17β-estradiol-benzoate (Sigma) to mice (ICR, weight 30±2 g), which were ovariectomized two weeks before, in an amount of 0.1 µg/day, per mouse for 3 days and then measuring the degree that the test compound inhibits the increase of uterine weight by stimulus with estradiol. In this experiment, the test compound or the control compound was dissolved in peanut oil (Sigma) and injected subcutaneously for 3 days, once a day. After 24 hours from the last injection, the test animal was sacrificed and uterus was removed and weighed. The results as measured are described in the following Table 3.

TABLE 3

Anti-estrogenic activity of the test compound in ovariectomized mice which were administered with 17 β-estradiol

| Test compound/dosage (s.c., 3 days) | | Inhibition (%) |
|---|---|---|
| Compound of Example 1 | 30 µg/mouse | 27.5 |
| Compound I of Example 2 | 30 µg/mouse | 30.8 |
| Compound II of Example 2 | 30 µg/mouse | −9.3 |
| Compound of Example 3 | 30 µg/mouse | 11.7 |
| Compound of Example 4 | 30 µg/mouse | 26.4 |
| Compound of Example 5 | 30 µg/mouse | 9.8 |
| Compound of Example 22 | 30 µg/mouse | 51.0 |
| Compound of Example 127 | 30 µg/mouse | 40.0 |
| Compound of Example 128 | 30 µg/mouse | 54.3 |
| Control compound ZM189154 | 30 µg/mouse | 73.8 |

From the results described in the above Table 3, it could be seen that the compounds of Examples 1, 2, 4, 22, 127 and 128 according to the present invention substantially inhibit the increase of uterine weight by estradiol.

Experiment 3

Anti-estr Genic Activity (Oral Administration)

Oral anti-estrogenic activity in vivo of the test compound was determined according to the method described hereinafter. In this experiment, the compound of Example 3, 22, 127 and 128 were used as the test compound and the known anti-estrogenic compound ZM189154 was used as the control compound as in Experiment 2.

Anti-estrogenic activity was determined by oral administration of 17β-estradiol-benzoate (Sigma) to mice (ICR, weight 30±2 g), which were ovariectomized 2 weeks before, in the amount of 0.1 µg/day, per mouse for 3 days and then measuring the degree that the test compound inhibits the increase in uterus weight by stimulus with estradiol. In this experiment, the test compound or the control compound was suspended in 5% arabic gum solution and orally administered for 3 days, once a day. After 24 hours from the last administration, the test animal was sacrificed and uterus was removed and weighed. The results as measured are described in the following Table 4.

TABLE 4

Anti-estrogenic activity of the test compound in ovariectomized mice which were administered with 17 β-estradiol (oral administration, 3 days)

| Test compound/dosage (p.o., 3 days) | | Inhibition (%) |
|---|---|---|
| Compound of Example 3 | 10 mg/kg | 0.6 |
| Compound of Example 22 | 10 mg/kg | 81.3 |
| Compound of Example 127 | 10 mg/kg | 44.5 |
| Compound of Example 128 | 10 mg/kg | 70.0 |
| ZM189154 | 10 mg/kg | 41.7 |

From the results described in the above Table 4, it could be seen that the compound according to the present invention administered via oral route substantially inhibits the increase of uterine weight by estradiol.

What is claimed is:

1. A thiobenzopyran derivative represented by the following formula (1):

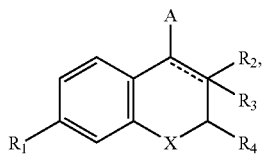

(1)

pharmaceutically acceptable salt or stereoisomer thereof, in which

X represents S, $R_1$ represents hydrogen, hydroxy, or —$OR_6$ (wherein $R_6$ represents acyl or alkyl), $R_2$ represents phenyl which is optionally substituted by one or more substituents selected from a group consisting of hydroxy, lower alkyl, halogen, nitro, hydroxymethyl, carboxy, alkoxycarbonyl, —$OR_6$ (wherein $R_6$ represents acyl or alkyl) and amino which is optionally substituted by one or two lower alkyl; or represents 5- or 6-membered unsaturated heterocycle containing nitrogen, oxygen or sulfur as the hetero atom, $R_3$ represents hydrogen or lower alkyl, provided that $R_3$, does not exist when ----- is a double bond (wherein ----- represents a single bond or a double bond), $R_4$ represents hydrogen or lower alkyl, A represents hydrogen; hydroxyalkyl; carboxyalkyl; carboxyvinylphenyl; pyrrole substituted by carboxyvinylbenzyl; or represents a group selected from the following formulae (a) to (l);

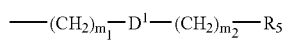  (a)

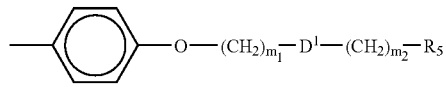  (b)

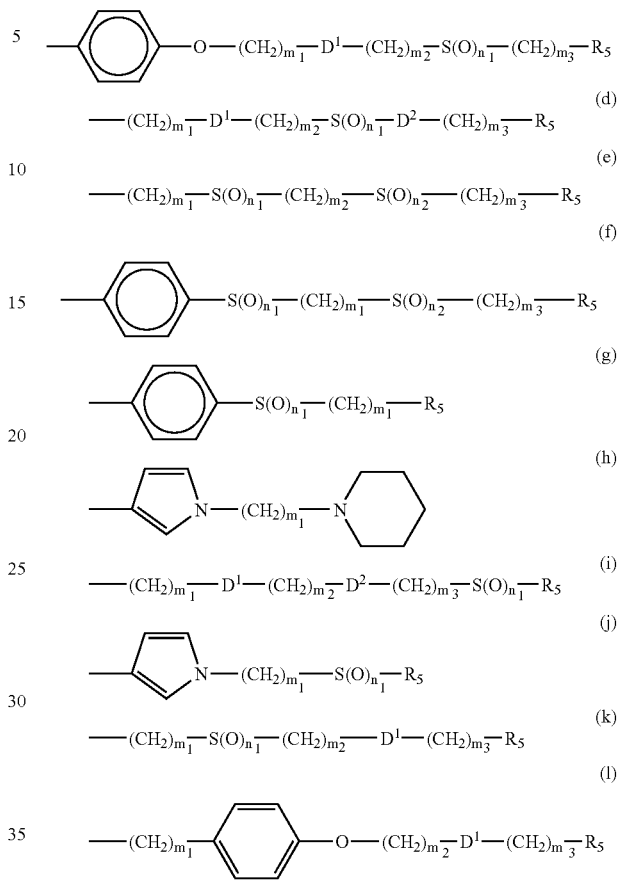

in the above formulae (a) to (l)

$m_1$, to $m_3$ independently of one another represent an integer of 0 to 15, $n_1$, to $n_2$ independently of one another represent an integer of 0, 1 or 2, $R_5$ represents cyano; alkyl; halogenoalkyl; alkoxy; hydroxy; carboxy; alkoxycarbonyl; carbamoyl; monoalkylamino; phenyl which is optionally substituted by one or more substituents selected from a group consisting of straight-chain or branched alkyl, carboxy and cyano; piperidinyl which is optionally substituted by one or more substituents selected from a group consisting of carboxy, alkyl and alkoxycarbonyl; cyclohexyl which is optionally substituted by carboxy; imidazolyl; dialkylamino; or piperidinyl oxide, $D^1$ and $D^2$ independently of one another represent a direct bond, or a group selected from the following:

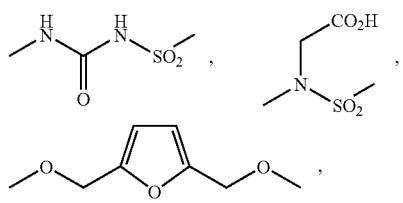

-continued
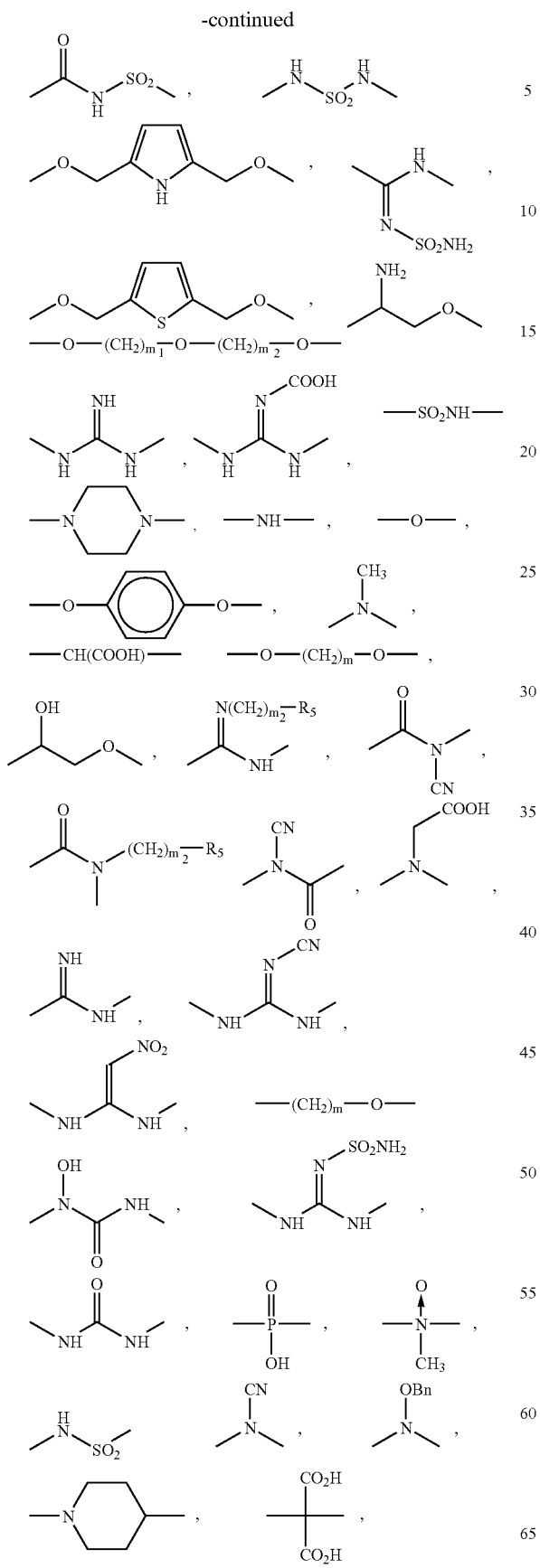
-continued
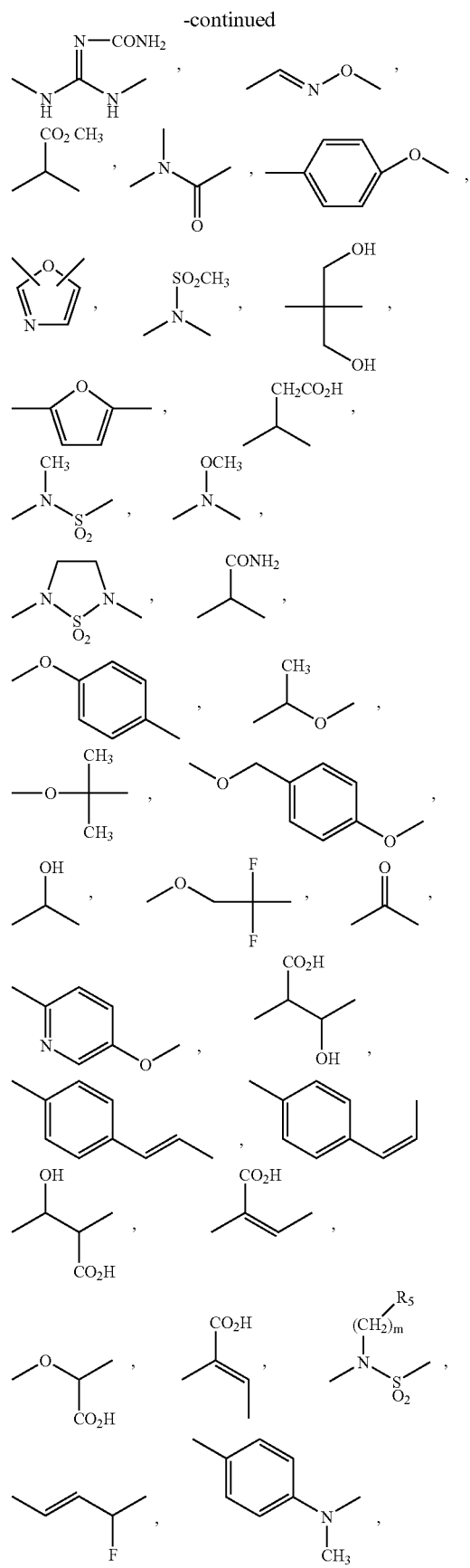

-continued

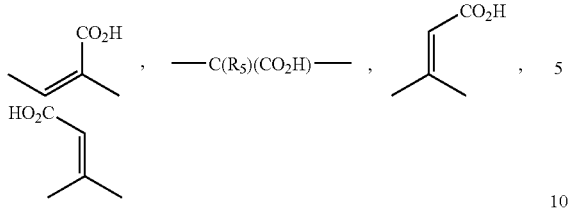

wherein
  m, $m_1$ and $m_2$ independently of one another represent an integer of 0 to 15, and
  $R_5$ is defined as above.

2. The compound of claim 1, wherein
X represents S,
$R_1$ represents hydroxy,
$R_2$ represents phenyl which is optionally substituted by one or two substituents selected from a group consisting of hydroxy, lower alkyl and halogen; or represents 6-membered unsaturated heterocycle containing nitrogen as the hetero atom,
$R_3$ represents lower alkyl, provided that $R_3$ does not exist when ----- is a double bond,
$R_4$ represents hydrogen,
A represents a group selected from the following formulae (a) to (e), (k) and (l);

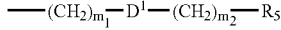 (a)

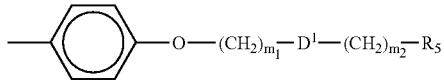 (b)

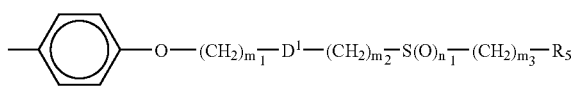 (c)

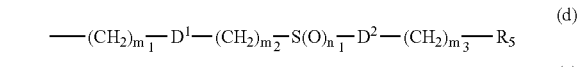 (d)

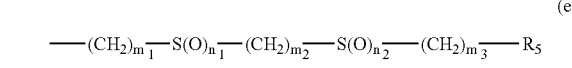 (e)

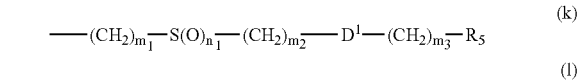 (k)

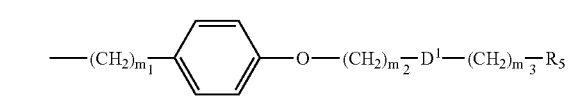 (l)

in the above formulae (a) to (e), (k) and (l)
  $m_1$ to $m_3$ independently of one another represent an integer of 0 to 15,
  $n_1$ to $n_2$ independently of one another represent an integer of 0, 1 or 2,
  $R_5$ represents alkyl; halogenoalkyl; alkoxy; hydroxy; carboxy; phenyl which is optionally substituted by one or two straight-chain or branched alkyl; or dialkylamino,
  $D^1$ and $D^2$ independently of one another represent a direct bond, or a group selected from the following:

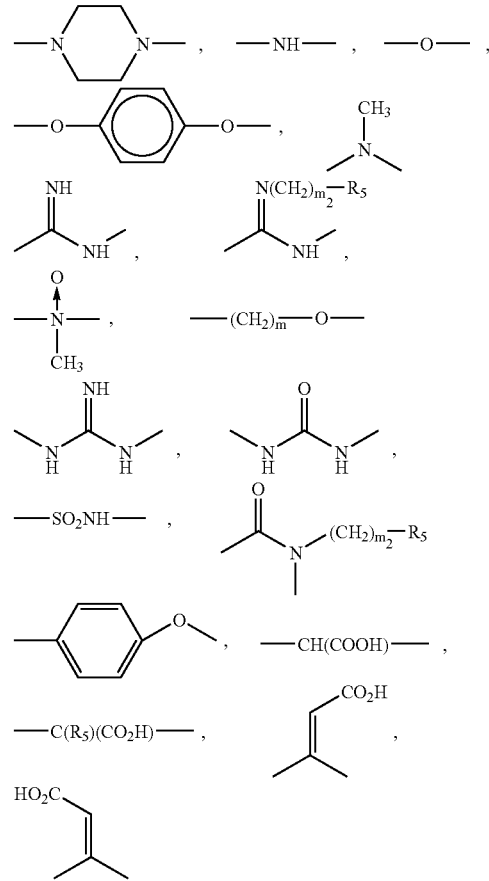

wherein
  $m_1$, and $m_2$ independently of one another represent an integer of 0 to 15, and
  $R_5$ is defined as above.

3. The compound of claim 2, which is selected from the group consisting of:
  6-{(3RS,4RS)-{9-[7-hydroxy-3-(4-hydroxyphenyl)-3-methylthiochroman-4-yl]nonylsulfinyl}hexanoic acid;
  (3RS,4RS)-7-hydroxy-3-(4-hydroxyphenyl)-3-methyl-4-{9-[2-(2-methoxyethoxy)ethylsulfinyl]nonyl}thiochroman;
  (3RS,4RS)-7-hydroxy-3-(4-hydroxyphenyl)-3-methyl-4-{9-[2-(2-hydroxyethoxy)ethylsulfinyl]nonyl}thiochroman;
  (3RS,4RS)-7-hydroxy-3-(2-methylphenyl)-3-methyl-4-[9-(4,4,5,5,5-pentafluoropentyl)sulfinylnonyl]thiochroman;
  (3RS,4RS)-7-hydroxy-3-(4-hydroxyphenyl)-3-methyl-4-[9-(4,4,5,5,5-pentafluoropentylsulfonylamino)nonyl]thiochroman;
  (3RS,4RS)-3-(4-fluorophenyl)-7-hydroxy-3-methyl-4-[9-(4,4,5,5,5-pentafluoropentylsulfinyl)nonyl]thiochroman;
  (3RS,4RS)-3-(3-fluorophenyl)-7-hydroxy-3-methyl-4-[9-(4,4,5,5,5-pentafluoropentylsulfinyl)nonyl]thiochroman;
  (3RS,4RS)-7-hydroxy-3-(4-hydroxyphenyl)-3-methyl-4-{3-{4-[2-(4,4,5,5,5-pentafluoropentylsulfinyl)ethoxy]phenoxy)propyl}thiochroman;

(3RS,4RS)-7-hydroxy-3-(4-hydroxyphenyl)-3-methyl-4-[4-oxa-9-(4,4,5,5,5-pentafluoropentylsulfinyl)nonyl]thiochroman;

(3'RS,4'RS)-10-[7-hydroxy-3-(4-hydroxyphenyl)-3-methylthiochroman-4-yl]-2-(4,4,5,5,5-pentafluoropentyl)decanoic acid;

(3'RS,4'RS)-{8-[7-hydroxy-3-(4-hyroxyphenyl)-3-methylthiochroman-4-yl]octyl}4,4,5,5,5-pentafluoropentyl)methane-1,1-dicarboxylic acid;

methyl-(3'RS,4'RS)-10-[7-hydroxy-3-(4-hydroxyphenyl)-3-methylthiochroman-4-yl]-2-(4,4,5,5,5-pentafluoropentyl)decanoate;

(3'RS,4'RS)-2-{8-[7-hydroxy-3-(4-hydroxyphenyl)-3-methylthiochroman-4-yl]octyl)-2-(4,4,5,5,5-pentafluoropentyl)propane-1,3-diol;

(3RS,4RS)-7-hydroxy-3-(4-hydroxyphenyl)-3-methyl-4-(9-(2-aza-2-carbonyl-1-(4,4,5,5,5-pentafluoropentylamino)ethenyl)aminononyl)thiochroman;

(3RS,4RS)-7-hydroxy-3-(4-hydroxyphenyl)-3-methyl-4-(9-(1-((4,4,5,5,5-pentafluoropentyl)amino)-2-nitroethenyl)amino)nonyl)thiochroman;

(3RS,4RS)-7-hydroxy-3-(4-hydroxyphenyl)-3-methyl-4-[9-(N-cyano-N-pentylcarbonyl)aminononyl]thiochroman;

(3RS,4RS)-4-allyl-7-methoxy-3-(4-methoxyphenyl)-3-methylthiochroman;

(3RS,4RS)-7-hydroxy-3-(4-hydroxyphenyl)-3-methyl-4-{9-[2-(2,2,2-trifluoroethoxy)ethylsulfinyl]nonyl}thiochroman;

(3'RS,4'RS)-8-[7-hydroxy-3-(4-hydroxyphenyl)-3-methylthiochroman-4-yl]octanoic acid;

(3'RS,4'RS)-6-[7-hydroxy-3-(4-hydroxyphenyl)-3-methylthiochroman-4-yl]hexanoic acid;

(3'RS,4'RS)-7-[7-hydroxy-3-(4-hydroxyphenyl)-3-methylthiochroman-4-yl]heptanoic acid;

(3RS,4RS)-4-[4,7-dioxa-9-(4,4,5,5,5-pentafluoropentylsulfinyl)nonyl]-7-hydroxy-3-(4-hydroxyphenyl)-3-methylthiochroman;

(3RS,4RS)-7-hydroxy-3-(4-hydroxyphenyl)-3-methyl-4-[6-oxa-9-(4,4,5,5,5-pentafluoropentylsulfinyl)nonyl]thiochroman;

(3RS,4RS)-7-hydroxy-3-(4-hydroxyphenyl)-3-methyl-4-[7-oxa-9-(4,4,5,5,5-pentafluoropentylsulfinyl)nonyl]thiochroman;

(3RS,4RS)-7-hydroxy-3-(4-hydroxyphenyl)-3-methyl-4-[5-oxa-9-(4,4,5,5,5-pentafluoropentylsulfinyl)nonyl]thiochroman;

(3'RS,4'RS)-9-[7-hydroxy-3-(4-hydroxyphenyl)-3-methylthiochroman-4-yl]nonanoic acid;

(3'RS,4'RS)-10-[7-hydroxy-3-(4-hydroxyphenyl)-3-methylthiochroman-4-yl]decanoic acid;

(3'RS,4'RS)-(E)-3-[7-hydroxy-3-(4-hydoxyphenyl)thiochroman-4-yl]phenylacrylic acid;

(3RS,4RS)-4-[9-(4-cyanobutylsulfinyl)nonyl]-7-hydroxy-3-(4-hydroxyphenyl)-3-methylthiochroman;

(3RS,4RS)-(E)-3-{4-[7-hydroxy-3-(4-hydroxyphenyl)thiochromen-4-yl]phenyl)propenoic acid;

(3RS,4RS)-(E)-3-{4-[7-hydroxy-3-(4-hydroxyphenyl)thiochroman-4-yl]phenyl}propenoic acid;

(3'RS,4'RS)-(E)-3-{4-[7-hydroxy-3-(4-hydroxyphenyl)-3-methylthiochroman-4-yl]phenyl)propenoic acid;

(3RS,4RS)-9-(7-hydroxy-3-(4-hydroxyphenyl)-3-thiochroman-4-(4,4,5,5,5-pentafluoropentyl)nonanoic acid;

(3RS,4RS)-7-hydroxy-3-(4-hydroxyphenyl)-4-{[11-carboxyl-11-(4,4,5,5,5-pentafluoropentyl)]undecyl)-3-methylthiochroman;

9-{4-[(3RS,4RS)-7-hydroxy-3-(4-hydroxyphenyl)-3-methylthiochroman-4-yl]phenoxy}-2-(4,4,5,5,5-pentafluoropentyl)nonanoic acid;

8-{4-[(3RS,4RS)-7-hydroxy-3-(4-hydroxyphenyl)-3-methylthiochroman-4-yl]phenoxy}-2-(4,4,5,5,5-pentafluoropentyl)octanoic acid;

7-{4-[(3RS,4RS)-7-hydroxy-3-(4-hydroxyphenyl)-3-methylthiochroman-4-yl]phenoxy}-2-(4,4,5,5,5-pentafluoropentyl)heptanoic acid;

6-{4-[(3RS,4RS)-7-hydroxy-3-(4-hydroxyphenyl)-3-methylthiochroman-4-yl]phenoxy}-2-(4,4,5,5,5-pentafluoropentyl)hexanoic acid;

5-{4-[(3RS,4RS)-7-hydroxy-3-(4-hydroxyphenyl)-3-methylthiochroman-4-yl]phenoxy}-2-(4,4,5,5,5-pentafluoropentyl)pentanoic acid;

(3'RS,4'RS)-11-[7-hydroxy-3-(4-hydroxyphenyl)-3-methylthiochroman-4-yl]-2-(4,4,5,5,5-pentafluoropentyl)undecanoic acid;

(3'RS,4'RS)-12-[7-hydroxy-3-(4-hydroxyphenyl)-3-methylthiochroman-4-yl]-2-(4,4,5,5,5-pentafluoropentyl)dodecanoic acid;

(3'RS,4'RS)-9-[7-hydroxy-3-(4-hydroxyphenyl)-3-methylthiochroman-4-yl]-2-(4,4,5,5,5-pentafluoropentyl)nonanoic acid;

(3'RS,4'RS)-10-[7-hydroxy-3-(4-hydroxyphenyl)-3-methylthiochroman-4-yl]-2-(4,4,5,5,5-pentafluoropentyl)decanoic acid;

(3'RS,4'RS)-10-[7-hydroxy-3-(4-hydroxyphenyl)-3-methylthiochroman-4-yl]-2-3,3,4,4,4-pentafluorobutyl)decanoic acid;

(3'RS,4'RS)-10-[7-hydroxy-3-(4-hydroxyphenyl)-3-methylthiochroman-4-yl]-2-(5,5,6,6,6-pentafluorohexyl)decanoic acid;

(3'RS,4'RS)-10-[7-hydroxy-3-(4-hydroxyphenyl)-3-methylthiochroman-4-(4-yl]-2-(6,6,7,7,7-pentafluoroheptyl)decanoic acid;

(3'RS,4'-RS)-11-[7-hydroxy-3-(4-hydroxyphenyl)-3-methylthiochroman-4-yl]-2-(3,3,4,4,4-pentafluorobutyl)undecanoic acid;

(3'RS,4'RS)-11-[7-hydroxy-3-(4-hydroxyphenyl)-3-methylthiochroman-4-yl]-2-(5,5,6,6,6-pentafluorohexyl)undecanoic acid;

(3'RS,4'RS)-11-[7-hydroxy-3-(4-hydroxyphenyl)-3-methylthiochroman-4-yl]-2-(6,6,7,7,7-pentafluoroheptyl)undecanoic acid;

(3'RS,4'RS)-11-[7-hydroxy-3-(4-hydroxyphenyl)-3-methylthiochroman-4-yl]-2-methyl-2-(4,4,5,5,5-pentafluoropentyl)undecanoic acid;

(3'RS,4'RS)-10-[7-hydroxy-3-(4-hydroxyphenyl)-3-methylthiochroman-4-yl]-2-methyl-2-(4,4,5,5,5-pentafluoropentyl)decanoic acid;

(3'RS,4'RS)-11-[7-hydroxy-3-(4-hydroxyphenyl)-3-methylthiochroman-4-yl]-2-ethyl-2-(4,4,5,5,5-pentafluoropentyl)undecanoic acid;

(3'RS,4'RS)-10-[7-hydroxy-3-(4-hydroxyphenyl)-3-methylthiochroman-4-yl]-2-ethyl-2-(4,4,5,5,5-pentafluoropentyl)decanoic acid;

(3'RS,4'RS)-11-[7-hydroxy-3-(4-hydroxyphenyl)-3-methylthiochroman-4-yl]-2-methyl -2-(5,5,6,6,6-pentafluorohexyl)undecanoic acid;

(3'RS,4'RS)-11-[7-hydroxy-3-(4-hydroxyphenyl)-3-methylthiochroman-4-yl]-2-methyl-2-(6,6,7,7,7-pentafluoroheptyl)undecanoic acid;

(3'RS,4'RS)-11-[7-hydroxy-3-(4-hydroxyphenyl)-3-methylthiochroman-4-yl]-2-ethyl -2-(5,5,6,6,6-pentafluorohexyl)undecanoic acid;

(3'RS,4'RS)-11-[7-hydroxy-3-(4-hydroxyphenyl)-3-methylthiochroman-4-yl]-2-ethyl-2-(6,6,7,7,7-pentafluoroheptyl)undecanoic acid;
(3'RS,4'RS)-10-[7-hydroxy-3-(4-hydroxyphenyl)-3-methylthiochroman-4-yl]-2-methyl-2-(5,5,6,6,6-pentafluorohexyl)decanoic acid;
(3'RS,4'RS)-10-[7-hydroxy-3-(4-hydroxyphenyl)-3-methylthiochroman-4-yl]-2-methyl-2-(6,6,7,7,7-pentafluoroheptyl)decanoic acid;
(3'RS,4'RS)-10-[7-hydroxy-3-(4-hydroxyphenyl)-3-methylthiochroman-4-yl]-2-ethyl-2-(5,5,6,6,6-pentafluorohexyl)decanoic acid;
(3'RS,4'RS)-10-[7-hydroxy-3-(4-hydroxyphenyl)-3-methylthiochroman-4-yl]-2-ethyl-2-(6,6,7,7,7-pentafluoroheptyl)decanoic acid.

4. A compound represented by the following formula (17aa):

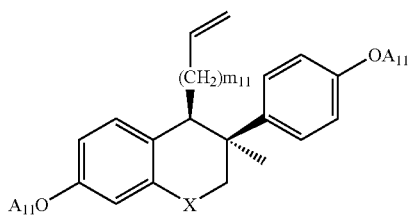

(17aa)

pharmaceutically acceptable salt or stereoisomer thereof, in which
X is defined as claim 1,
$A_{11}$ is a protecting group selected from a group consisting of t-butyldimethylsilyl, triisopropylsily, triethylsilyl, t-buthyldiphenylmethylsilyl, methoxymethyl, tertahydropyrany and methyl,
$m_{11}$ is an integer of 0 to 10.

5. A process for preparing the compound of formula (1a):

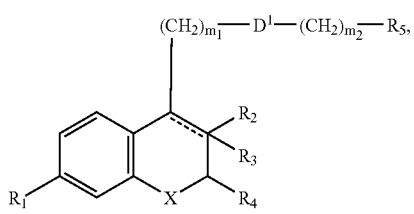

(1a)

pharmaceutically acceptable salt or stereoisomer thereof, wherein X, $R_1$, $R_2$, $R_3$, $R_4$, $R_5$, $m_1$, $m_2$ and $D^1$ are defined as claim 1, characterized in that
(a) a compound of formula (13):

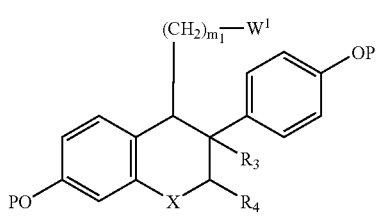

(13)

wherein X, $R_3$, $R_4$ and $m_1$ are defined as claim 1, P represents a hydroxy-protecting group, and $W^1$ represents a leaving group, is reacted with a compound of formula (14):

$$D^1H_2 \qquad (14)$$

wherein $D^1$ is defined as claim 1, to produce a compound of formula (15):

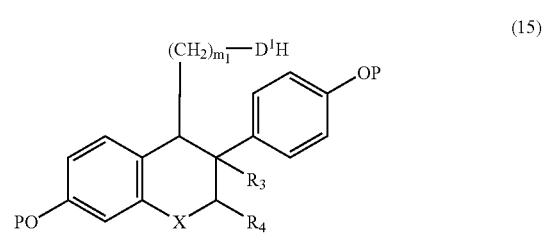

(15)

wherein X, $R_3$, $R_4$, $D^1$ and $m_1$ are defined as claim 1, and P is defined as above, the resulting compound of formula (15) is reacted with a compound of formula (16):

$$W^2-(CH_2)_{m_2}-R_5 \qquad (16)$$

wherein $R_5$ and $m_2$ are defined as claim 1, and $W^2$ represents a leaving group selected from a group consisting of acyl and hydrogen, and then deprotected to produce a compound of formula (1aa):

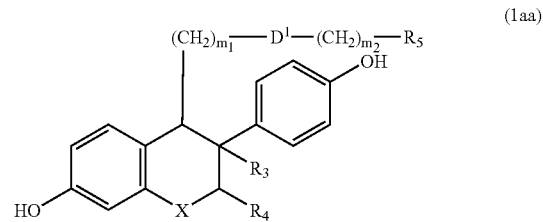

(1aa)

wherein X, $R_3$, $R_4$, $R_5$, $m_1$, $m_2$ and $D^1$ are defined as claim 1, or (b) the compound of formula (13) is reacted with sodium cyanide to produce a compound of formula (17):

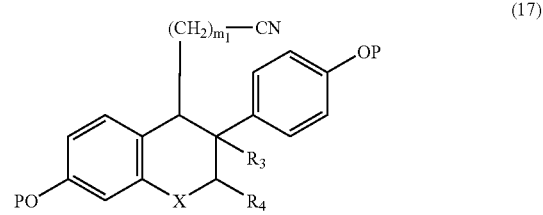

(17)

wherein X, $R_3$, $R_4$ and $m_1$ are defined as claim 1, and P is defined as above, the resulting compound of formula (17) is reacted with a compound of formula (18):

$$H_2N-(CH_2)_{m_2}-R_5 \qquad (18)$$

wherein $R_5$ and $m_2$ are defined as claim 1, in the presence of a Lewis acid to produce a compound of formula (1ab) or (1ac):

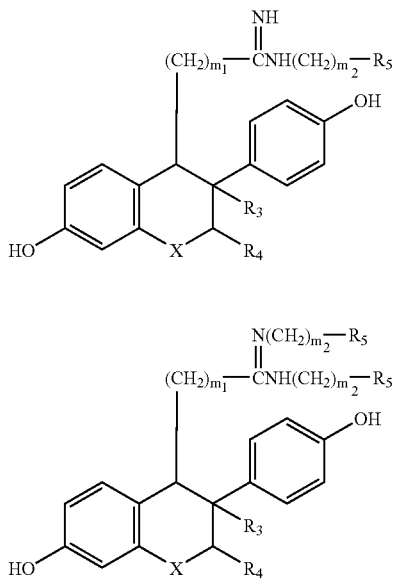

(1ab)

(1ac)

wherein X, $R_3$, $R_4$, $R_5$, $m_1$ and $m_2$ are defined as claim 1.

6. A process for preparing the compound of formula (1b):

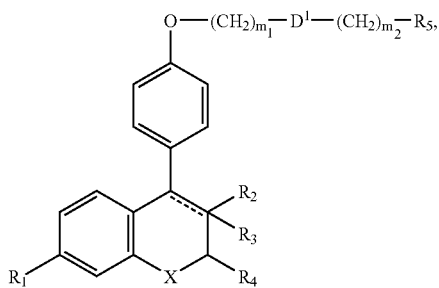

(1b)

pharmaceutically acceptable salt or stereoisomer thereof, wherein X, $R_1$, $R_2$, $R_3$, $R_4$, $R_5$, $m_1$, $m_2$ and $D^1$ are defined as claim 1, characterized in that a compound of formula (19):

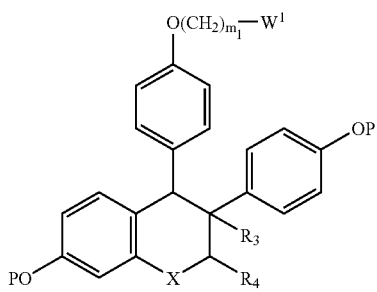

(19)

wherein X, $R_3$, $R_4$ and $m_1$, are defined as claim 1, P represents a hydroxy-protecting group, and $W^1$ represents a leaving group, is reacted with a compound of formula (20):

$$HD^1\text{-}(CH_2)_{m_2}\text{—}R_5 \qquad (20)$$

wherein $R_5$, $m_2$ and $D^1$ are defined as claim 1, and then deprotected to produce a compound of formula (1ba):

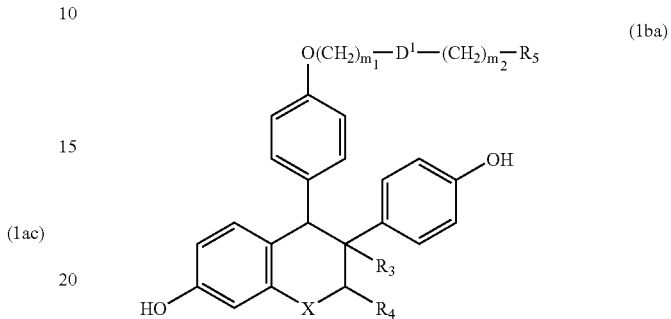

(1ba)

wherein X, $R_3$, $R_4$, $R_5$, $m_1$, $m_2$ and $D^1$ are defined as claim 1.

7. A process for preparing the compound of formula (1c):

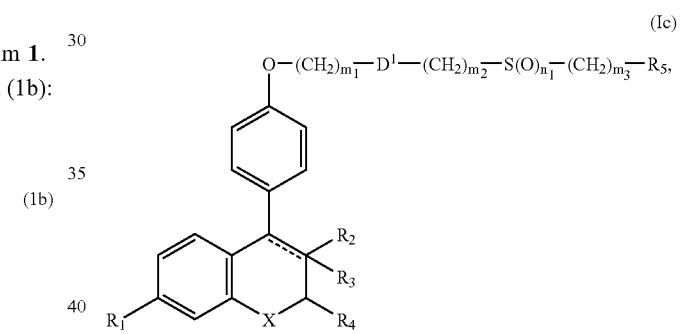

(1c)

pharmaceutically acceptable salt or stereoisomer thereof, wherein X $R_1$, $R_2$, $R_3$, $R_4$, $R_5$, $m_1$, $m_2$, $m_3$, $n_1$, and $D^1$ are defined as claim 1, characterized in that a compound of formula (21):

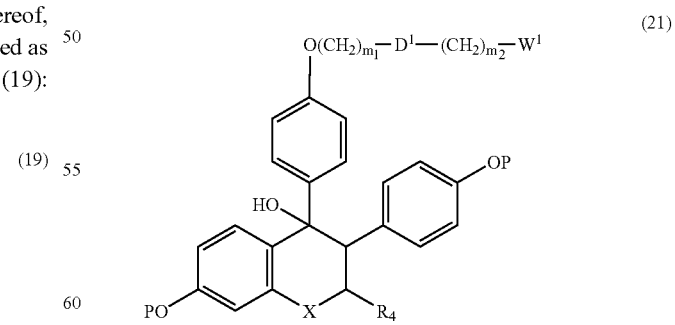

(21)

wherein X, $R_4$, $m_1$, $m_2$ and $D^1$ are defined as claim 1, P represents a hydroxy-protecting group, and $W^1$ represents a leaving group, is reacted with a compound of formula (22):

$$W^2\text{—}S\text{—}(CH_2)_{m_3}\text{—}R_5 \qquad (22)$$

wherein $R_5$ and $m_3$ are defined as claim 1, and $W^2$ represents a leaving group selected from a group consisting of acyl and hydrogen, to produce a compound of formula (23):

(23)

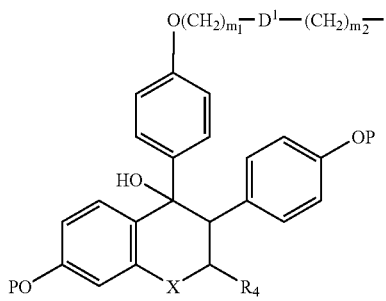

wherein X, $R_4$, $R_5$, $m_1$, $m_2$, $m_3$ and $D^1$ are defined as claim 1, and P is defined as above, the resulting compound of formula (23) is deprotected and dehydrated to produce a compound of formula (24):

(24)

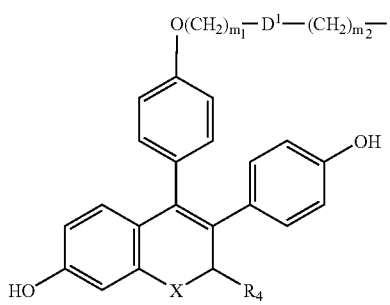

wherein X, $R_4$, $R_5$, $m_1$, $m_2$, $m_3$, and $D^1$ are defined as claim 1, which is then oxidized to produce a compound of formula (1ca):

(Ica)

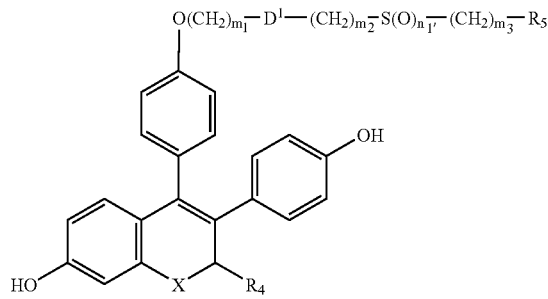

wherein X, $R_5$, $R_5$, $m_1$, $m_2$, $m_3$; and $D^1$ are defined as claim 1, and $n_1'$ represents 1 or 2.

8. A process for preparing the compound of formula (1d):

(Id)

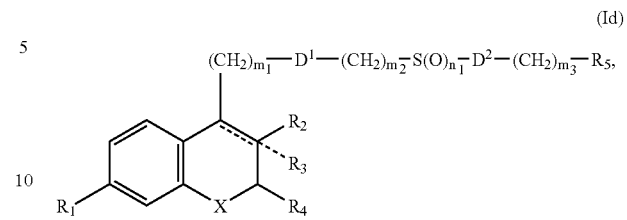

pharmaceutically acceptable salt or stereoisomer thereof, wherein X, $R_1$, $R_2$, $R_3$, $R_4$, $R_5$, $m_1$, $m_2$, $m_3$, $n_1$, $D^1$ and $D^2$ are defined as claim 1, characterized in that (a) a compound of formula (13):

(13)

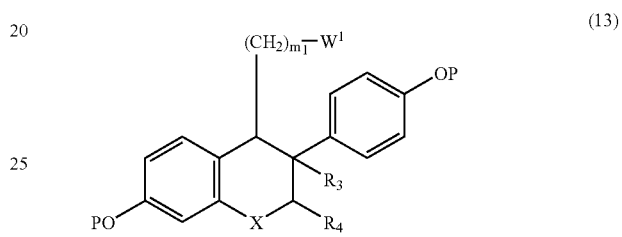

wherein X, $R_3$, $R_4$ and $m_1$ are defined as claim 1, P represents a hydroxy-protecting group, and $W^1$ represents a leaving group, is reacted with a compound of formula (25):

$$HD^1\text{-}(CH_2)_{m_2}\text{---}S(O)_{n_1}\text{---}(CH_2)_{m_3}\text{---}R_5 \qquad (25)$$

wherein $R_5$, $m_2$, $m_3$, $n_1$, and $D^1$ are defined as claim 1, and then deprotected to produce a compound of formula (1da):

(1da)

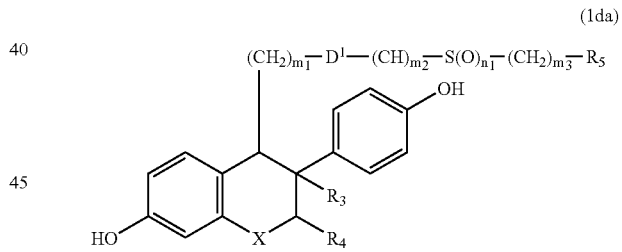

wherein X, $R_3$, $R_4$, $R_5$, $m_1$, $m_2$, $m_3$, n, and $D^1$ are defined as claim 1, (b) a compound of formula (15):

(15)

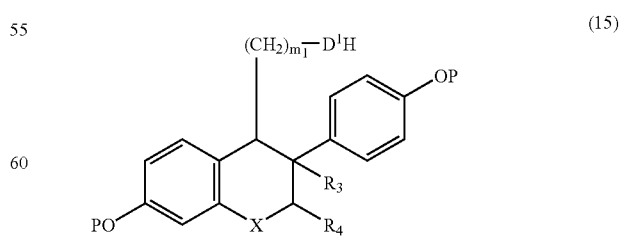

wherein X, $R_3$, $R_4$, $D^1$ and $m_1$ are defined as claim 1, and P is defined as above, is reacted with a compound of formula (26):

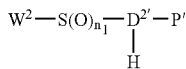  (26)

wherein $n_1$ is defined as claim 1, P' represents a hydroxy-protecting group, $W^2$ represents a leaving group selected from a group consisting of acyl and hydrogen, and $D^{2'}$ is the same with $D^2$, provided that 1 or 2 hydrogen atoms are excluded therefrom, to produce a compound of formula (27):

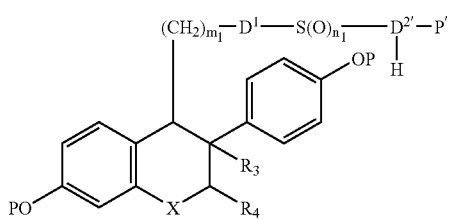  (27)

wherein X, $R_3$, $R_4$, $m_1$, $n_1$ and $D^1$ are defined as claim 1, and $D^{2'}$, P and P' are defined as above, the resulting compound of formula (27) is condensed with a compound of formula (28):

  (28)

wherein $R_5$ and $m_2$ are defined as claim 1, and then deprotected to produce a compound of formula (1db):

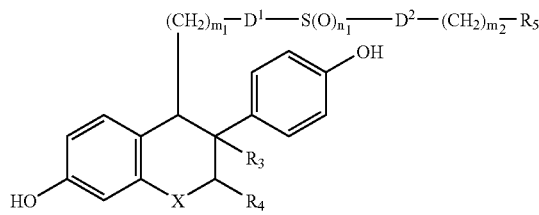  (1db)

wherein X, $R_3$, $R_4$, $R_5$, $m_1$, $m_2$, $n_1$, $D^1$ and $D^2$ are defined as claim 1, (c) the compound of formula (13) is reacted with a compound of formula (29):

  (29)

wherein $R_5$, $m_3$ and $D^2$ are defined as claim 1, and $W^2$ are defined as above, to produce a compound of formula (30):

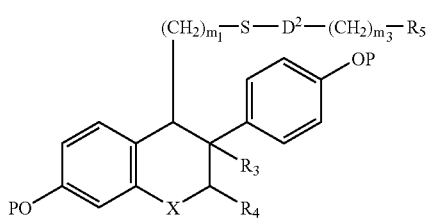  (30)

wherein X, $R_3$, $R_4$, $R_5$, $m_1$, $m_3$ and $D^2$ are defined as claim 1, and P are defined as above, the resulting compound of formula (30) is then deprotected and oxidized to produce a compound of formula (1dc):

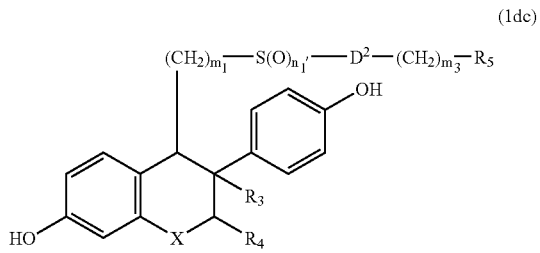  (1dc)

wherein X, $R_3$, $R_4$, $R_5$, $m_1$, $m_3$ and $D^2$ are -defined as claim 1, and $n_1'$ represents 1 or 2, (d) the compound of formula (13) is reacted with a compound of formula (29a):

  (29a)

wherein $m_3$ and $D^2$ are defined as claim 1, P' and $W^2$ are defined as above, and $R_5'$ is the same with $R_5$, provided that 1 or 2 hydrogen atoms are excluded therefrom, to produce a compound of formula (30a):

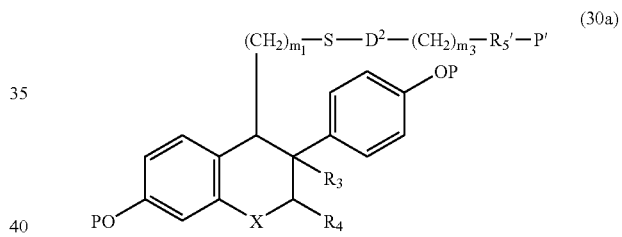  (30a)

wherein X, $R_3$, $R_4$, $m_1$, $m_3$ and $D^2$ are defined as claim 1, and P, P' and $R_5'$ are defined as above, the resulting compound of formula (30a) is then deprotected and oxidized to produce the compound of formula (1dc), (e) the compound of formula (13) is reacted with sodium azide and then reduced to produce a compound of formula (31):

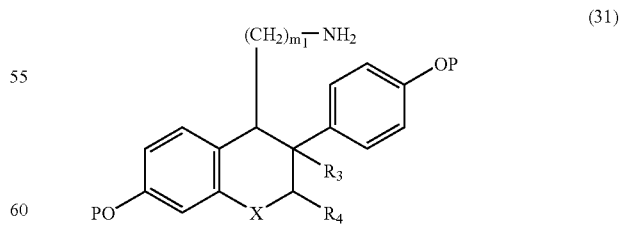  (31)

wherein X, $R_3$, $R_4$ and $m_1$ are defined as claim 1, and P is defined as above, the resulting compound of formula (31) is reacted with a compound of formula (32):

  (32)

wherein $R_5$ and $m_3$ are defined as claim 1, and $W^2$ is defined as above, and then deprotected to produce a compound of formula (1dd):

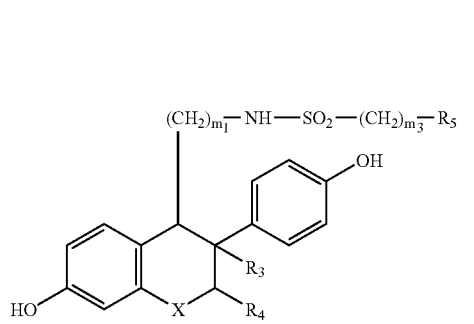
(1dd)

wherein X, $R_3$, $R_4$, R, $m_1$ and $m_3$ are defined as claim 1, (f) the compound of formula (31) is reacted with a compound of formula (32a):

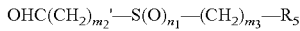
(32a)

wherein $R_5$, $m_3$ and $n_1$ are defined as claim 1, and $m_2'$ equals $m_2-1$, and then deprotected to produce a compound of formula (1de):

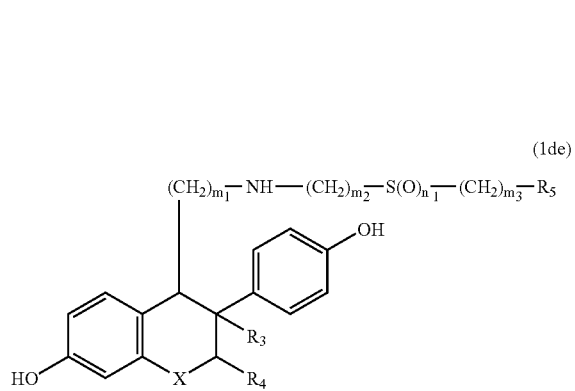
(1de)

wherein X, $R_3$, $R_4$, $R_5$, $m_1$, $m_2$, $m_3$ and $n_1$ are defined as claim 1, (g) a compound of formula (33):

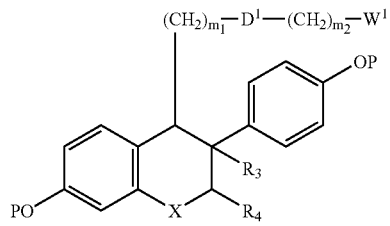
(33)

wherein X, $R_3$, $R_4$, $m_1$, $m_2$ and $D^1$ are defined as claim 1, and $W^1$ and P are defined as above, is reacted with the compound of formula (22):

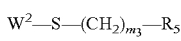
(22)

wherein $R_5$ and $m_3$ are defined as claim 1, and $W^2$ is defined as above, to produce a compound of formula (34):

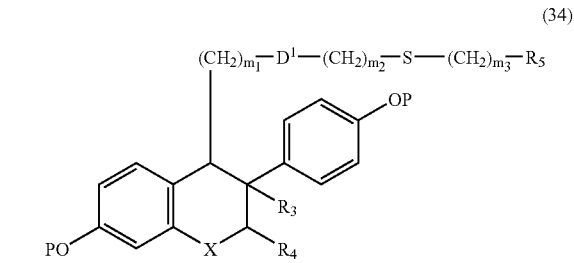
(34)

wherein X, $R_3$, $P_4$, $R_5$, $m_1$, $m_2$, $m_3$ and $D^1$ are defined as claim 1, and P is defined as above, the resulting compound of formula (34) is then deprotected and oxidized to produce a compound of formula (1df):

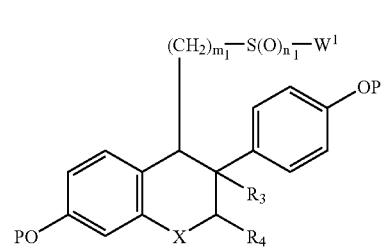
(1df)

wherein X, $R_3$, $R_4$, $R_5$, $m_1$, $m_2$, $m_3$ and $D^1$ are defined as claim 1, or (h) a compound of formula (35):

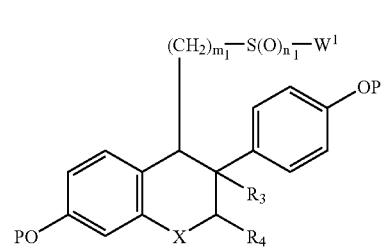
(35)

wherein X, $R_3$, $R_4$, $m_1$ and $n_1$ are defined as claim 1, and $W^1$ and P are defined as above, is reacted with a compound of formula (36):

(36)

wherein $R_5$, $m_3$ and $D^2$ are defined as claim 1, and P' is defined as above, and then deprotected to produce a compound of formula (1dg):

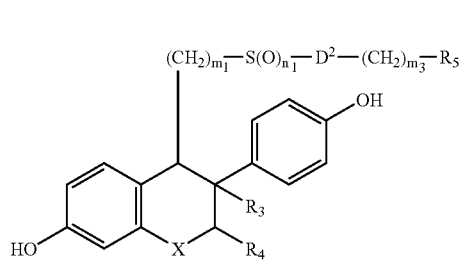

wherein X, $R_3$, $R_4$, $R_5$, $m_1$, $m_3$, $n_1$ and $D^2$ are defined as claim 1.

9. A process for preparing the compound of formula (1e):

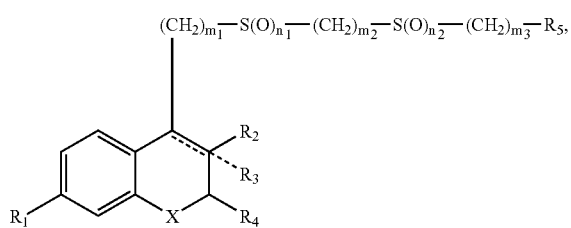

pharmaceutically -acceptable salt or stereoisomer thereof, wherein X, $R_1$, $R_2$, $R_3$, $R_4$, $R_5$, $m_1$, $m_2$, $m_3$, $n_1$ and $n_2$ are defined as claim 1, characterized in that a compound of formula (13):

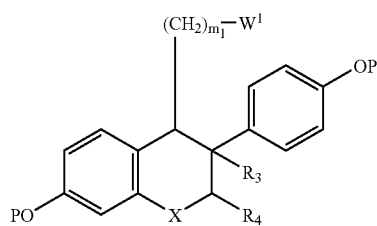

wherein X, $R_3$, $R_4$ and $m_1$ are defined as claim 1, P represents a hydroxy-protecting group, and $W^1$ represents a leaving group, is reacted with a compound of formula (37):

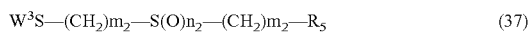

wherein $R_5$, $m_2$, $m_3$ and $n_2$ are defined as claim 1, and $W^3$ represents acyl group, and the resulting compound is then deprotected and oxidized to produce a compound of formula (1ea):

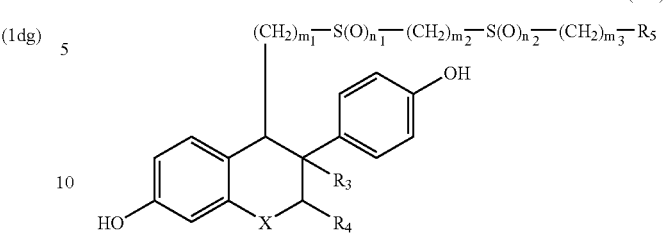

wherein X, $R_3$, $R_4$, $R_5$, $m_1$, $m_2$, $m_3$, $n_1$ and $n_2$ are defined as claim 1.

10. A process for preparing the compound of formula (1k):

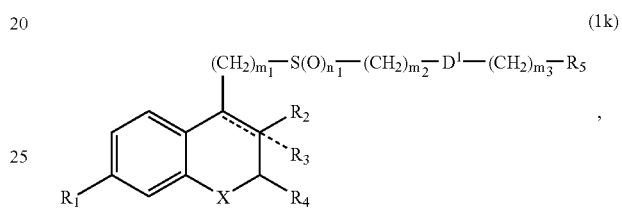

pharmaceutically acceptable salt or stereoisomer thereof, wherein X, $R_1$, $R_2$, $R_3$, $R_4$, $R_5$, $m_1$, $m_2$, $m_3$, $n_1$ and $D^1$ are defined as claim 1, can be prepared by a process characterized in that a compound of formula (13):

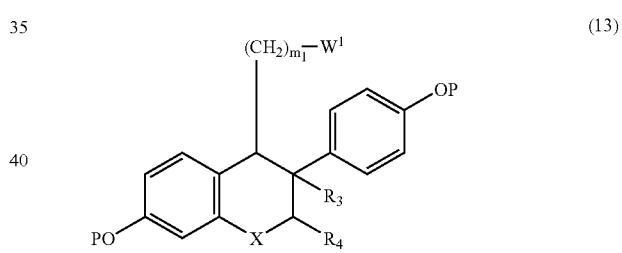

wherein X, $R_3$, $R_4$ and $m_1$ are defined as claim 1, P is represents a hydroxy-protecting group, and $W^1$ represents a leaving group, is reacted with a compound of formula (44):

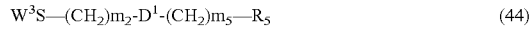

wherein $R_5$, $m_2$, $m_3$ and $D^1$ are defined as claim 1, and $W^3$ represents acyl group, and the resulting compound is then deprotected and oxidized to produce a compound of formula (1ka):

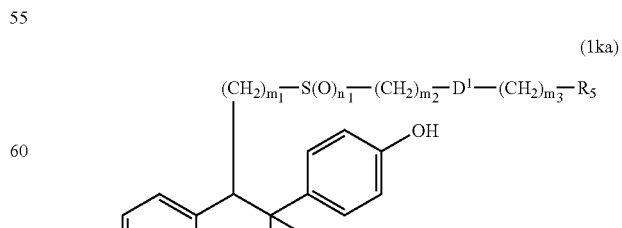

wherein X, $R_3$, $R_4$, $R_5$, $m_1$, $m_2$, $m_3$, $n_1$ and $D^1$ are defined as claim 1.

11. A process for preparing the compound of formula (11):

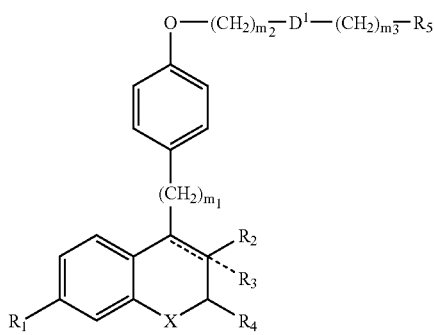
(11)

pharmaceutically acceptable salt or stereoisomer thereof, wherein X, $R_1$, $R_2$, $R_3$, $R_4$, $R_5$, $m_1$, $m_2$, $m_3$ and $D^1$ are defined as claim 1, can be prepared by a process characterized in that a compound of formula (45):

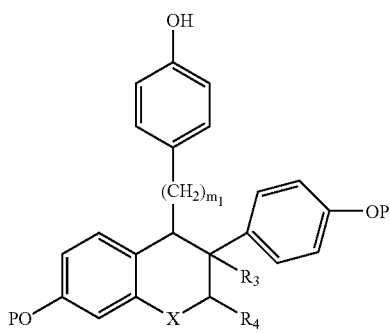
(45)

wherein X, $R_3$, $R_4$, and $m_1$ are defined as claim 1, and P represents a hydroxy-protecting group, is reacted with a compound of formula (46):

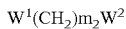
(46)

wherein $m_2$ is defined as claim 1, $W^1$ represents a leaving group, and $W^2$ represents a leaving group selected from a group consisting of acyl and hydrogen, to produce a compound of formula (47):

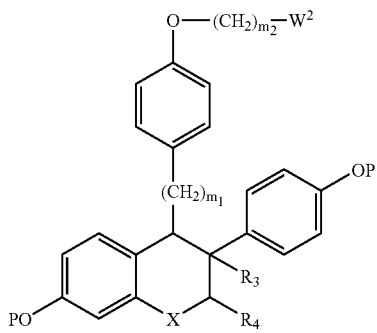
(47)

wherein X, $R_3$, $R_4$, $m_1$, and $m_2$ are defined as claim 1, and $W^2$ and P is defined as above, the resulting compound of formula (47) is reacted with a compound of formula (14):

(14)

wherein $D^1$ is defined as claim 1, to produce a compound of formula (48):

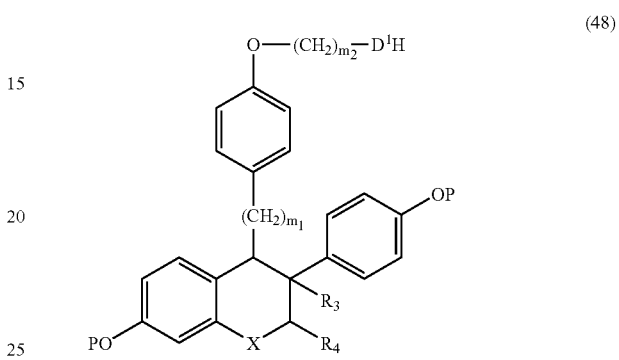
(48)

wherein X, $R_3$, $R_4$, $m_1$, $m_2$ and $D^1$ are defined as claim 1, and P is defined as above, the resulting compound of formula (48) is reacted with a compound of formula (16a):

(16a)

wherein $R_5$ and $m_3$ are defined as claim 1, and $W^5$ represents a leaving group and then deprotected to produce a compound of formula (11a):

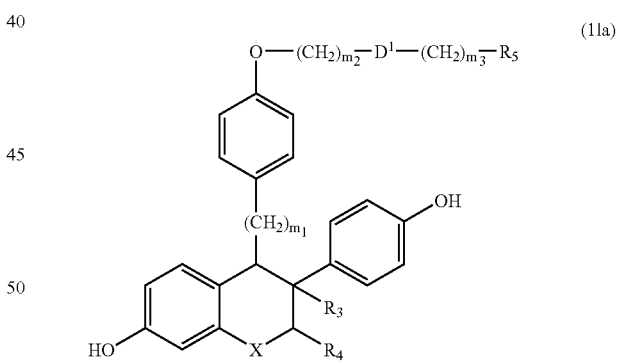
(11a)

wherein X, $R_3$, $R_4$, $R_5$, $m_1$, $m_2$, $m_3$ and $D^1$ are defined as claim 1.

12. An anti-estrogenic pharmaceutical composition containing as an active component the compound of formula (1), pharmaceutically acceptable salt or stereoisomer thereof according to anyone of claim 1 to 3 together with a pharmaceutically acceptable carrier.

13. The anti-estrogenic composition of claim 12 which is used for the treatment of breast cancer.

* * * * *